(12) United States Patent
Chiu et al.

(10) Patent No.: US 12,037,412 B2
(45) Date of Patent: Jul. 16, 2024

(54) ANTI-KLK5 ANTIBODIES AND METHODS OF USE

(71) Applicant: Genentech, Inc., South San Francisco, CA (US)

(72) Inventors: Cecilia P. C. Chiu, Redwood City, CA (US); Hilda Y. Hernandez-Barry, Martinez, CA (US); David B. Iaea, San Mateo, CA (US); Moulay Hicham Alaoui-Ismaili, San Mateo, CA (US); James T. Koerber, San Mateo, CA (US); Wei Yu Lin, Millbrae, CA (US); Kelly Loyet, South San Francisco, CA (US); Yonglian Sun, Foster City, CA (US); Benjamin T. Walters, South San Francisco, CA (US); Jawahar Sudhamsu, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 309 days.

(21) Appl. No.: 16/950,418

(22) Filed: Nov. 17, 2020

(65) Prior Publication Data

US 2021/0301032 A1 Sep. 30, 2021

Related U.S. Application Data

(63) Continuation of application No. 16/352,619, filed on Mar. 13, 2019, now abandoned.

(60) Provisional application No. 62/643,034, filed on Mar. 14, 2018.

(51) Int. Cl.
*C07K 16/40* (2006.01)
*A61K 47/68* (2017.01)

(52) U.S. Cl.
CPC .......... *C07K 16/40* (2013.01); *A61K 47/6871* (2017.08); *C07K 2317/24* (2013.01); *C07K 2317/34* (2013.01); *C07K 2317/55* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,834,290 A | 11/1998 | Egelrud et al. |
| 8,088,376 B2 | 1/2012 | Chamberlain et al. |
| 8,318,907 B2 | 11/2012 | Chamberlain et al. |
| 8,324,351 B2 | 12/2012 | Chamberlain et al. |
| 8,329,867 B2 | 12/2012 | Lazar et al. |
| 8,338,574 B2 | 12/2012 | Chamberlain et al. |
| 8,362,210 B2 | 1/2013 | Lazar et al. |
| 8,367,805 B2 | 2/2013 | Chamberlain et al. |
| 8,394,925 B2 | 3/2013 | Chamberlain et al. |
| 8,435,517 B2 | 5/2013 | Desjarlais |
| 8,546,543 B2 | 10/2013 | Lazar et al. |
| 8,629,113 B2 | 1/2014 | Lazar et al. |
| 8,802,820 B2 | 8/2014 | Chamberlain et al. |
| 8,852,586 B2 | 10/2014 | Chamberlain et al. |
| 8,883,973 B2 | 11/2014 | Chamberlain et al. |
| 9,062,117 B2 | 6/2015 | Desjarlais et al. |
| 9,200,079 B2 | 12/2015 | Chamberlain et al. |
| 9,221,916 B2 | 12/2015 | Desjarlais et al. |
| 9,266,966 B2 | 2/2016 | Desjarlais et al. |
| 9,371,397 B2 | 6/2016 | Lazar et al. |
| 9,475,881 B2 | 10/2016 | Lazar et al. |
| 9,493,578 B2 | 11/2016 | Lazar et al. |
| 9,540,451 B2 | 1/2017 | Desjarlais et al. |
| 9,617,348 B2 | 4/2017 | Desjarlais et al. |
| 9,803,023 B2 | 10/2017 | Chamberlain et al. |
| 10,155,800 B2 | 12/2018 | Lazar et al. |
| 10,336,818 B2 | 7/2019 | Chamberlain et al. |
| 10,821,094 B2 | 11/2020 | Azouz et al. |
| 2007/0135620 A1 | 6/2007 | Chamberlain et al. |
| 2009/0018033 A1 | 1/2009 | Morgan et al. |
| 2010/0098730 A1 | 4/2010 | Lowman et al. |
| 2010/0234575 A1 | 9/2010 | Chamberlain et al. |
| 2011/0189178 A1 | 8/2011 | Desjarlais et al. |
| 2014/0212435 A1 | 7/2014 | Moore et al. |
| 2014/0294810 A1 | 10/2014 | Lowman et al. |
| 2015/0071948 A1 | 3/2015 | Lazar et al. |
| 2015/0099863 A1 | 4/2015 | Chamberlain et al. |
| 2017/0058053 A1 | 3/2017 | Lazar et al. |
| 2017/0166655 A1 | 6/2017 | Lazar et al. |
| 2017/0335013 A1 | 11/2017 | Desjarlais et al. |
| 2018/0360981 A1 | 12/2018 | Lazar et al. |
| 2019/0127437 A1 | 5/2019 | Lazar et al. |
| 2019/0183989 A1 | 6/2019 | Deperthes et al. |
| 2020/0040103 A1 | 2/2020 | Chiu et al. |

(Continued)

FOREIGN PATENT DOCUMENTS

| | | |
|---|---|---|
| JP | 2007-500744 A | 1/2007 |
| JP | 2008-508862 A | 3/2008 |

(Continued)

OTHER PUBLICATIONS

Mateu et al. (Mateu MG, et al. Eur J Immunol. Jun. 1992;22(6):1385-9.) (Year: 1992).*
Greenspan et al. (Greenspan NS, Di Cera E. Defining epitopes: It's not as easy as it seems. Nat Biotechnol. Oct. 1999;17(10): 936-7.) (Year: 1999).*
Vajdos et al. (J Mol Biol. Jul. 5, 2002;320(2):415-28) (Year: 2002).*
Brown et al. (J Immunol. May 1996;156(9):3285-91) (Year: 1996).*
Wu et al.(Proc Natl Acad Sci. Dec. 11, 2007;104(50):19784-9) (Year: 2007).*
Anonymous, "Human Kallikrein 7 Antibody," rndsystems.com, Feb. 7, 2018, retrieved from https://resources.rndsystems.com/pdfs/datasheets/mab2624.pdf, 1 page.

(Continued)

*Primary Examiner* — Brian Gangle
*Assistant Examiner* — Andrea K McCollum
(74) *Attorney, Agent, or Firm* — Lawrence S. Graham

(57) ABSTRACT

The invention provides anti-kallikrein-related peptidase 5 (KLK5) antibodies and methods of using the same.

13 Claims, 69 Drawing Sheets

Specification includes a Sequence Listing.

(56) References Cited

U.S. PATENT DOCUMENTS

| | | |
|---|---|---|
| 2020/0123274 A1 | 4/2020 | Lazar et al. |
| 2021/0032313 A1 | 2/2021 | Nishimiya et al. |
| 2021/0162029 A1 | 6/2021 | Sampson |
| 2021/0163577 A1 | 6/2021 | Lazar |
| 2021/0163627 A1 | 6/2021 | Moore et al. |
| 2021/0171608 A1 | 6/2021 | Moore et al. |

FOREIGN PATENT DOCUMENTS

| | | | |
|---|---|---|---|
| JP | 2010-518039 A | 5/2010 | |
| JP | 2012-110324 A | 6/2012 | |
| WO | WO 95/00651 A1 | 1/1995 | |
| WO | WO 01/64747 A1 | 9/2001 | |
| WO | WO 02/44736 A2 | 6/2002 | |
| WO | WO 02/062135 A2 | 8/2002 | |
| WO | WO 2004/075723 A2 | 9/2004 | |
| WO | WO 2005/001025 A2 | 1/2005 | |
| WO | WO 2005/030250 A2 | 4/2005 | |
| WO | 2005/078123 A1 | 8/2005 | |
| WO | WO 2005/075667 A1 | 8/2005 | |
| WO | WO-2005078123 A1 * | 8/2005 | ........... C12N 9/6445 |
| WO | WO 2006/000448 A2 | 1/2006 | |
| WO | WO 2008/098720 A1 | 8/2008 | |
| WO | WO 2009/000878 A1 | 12/2008 | |
| WO | WO 2009/024527 A1 | 2/2009 | |
| WO | WO 2009/024528 A1 | 2/2009 | |
| WO | WO 2009/093119 A2 | 7/2009 | |
| WO | WO 2010/097066 A1 | 9/2010 | |
| WO | WO 2011/050276 A1 | 4/2011 | |
| WO | WO 2012/083385 A1 | 6/2012 | |
| WO | WO 2012/174569 A2 | 12/2012 | |
| WO | 2015/061441 A1 | 4/2015 | |
| WO | WO 2015/112079 A1 | 7/2015 | |
| WO | WO 2015/112081 A1 | 7/2015 | |
| WO | WO 2015/114144 A1 | 8/2015 | |
| WO | WO 2018/195472 A1 | 10/2018 | |
| WO | WO-2018195472 A1 * | 10/2018 | ............ A61K 38/00 |
| WO | WO 2019/178316 A1 | 9/2019 | |
| WO | WO 2019/234075 A1 | 12/2019 | |
| WO | WO 2020/095921 A1 | 5/2020 | |
| WO | WO 2021/009204 A1 | 1/2021 | |
| WO | WO 2021/055577 A2 | 3/2021 | |
| WO | WO 2021/067335 A1 | 4/2021 | |
| WO | WO 2021/092050 A1 | 5/2021 | |
| WO | WO 2021/226695 A1 | 11/2021 | |

OTHER PUBLICATIONS

Arron et al., "Noninvasive Biomarkers That Predict Treatment Benefit from Biologic Therapies in Asthma," Ann. Am. Thorac. Soc., 10(Supplement):S206-S213 (2013).

Arron et al., "Stratified medicine in inflammatory disorders: From theory to practice," Clinical Immunology, 161: 11-22 (2015).

Auton et al., "A global reference for human genetic variation," Nature, 526: 68-74 (2015).

Birben et al., "The role of SPINK5 in asthma related physiological events in the airway epithelium," Respiratory Medicine, 106: 349-355 (2012).

Bobrova, "Human Kallikrein Gene Family: Biology and the role in development of ovarian cancer and other diseases," Bulletin of RONTS im. N. N. Blokhin Rams, 17(4): 3-11 (2006).

Bønnelykke et al., "Leveraging gene-environment interactions and endotypes for asthma gene discovery," J. Allergy Clin. Immunol., 137: 667-679 (2016).

Church et al., "I am atopic, but why don't I develop allergy? The association between atopy and clinical expression of allergic disease," Clinical Experimental Allergy Reviews, 5(1): 12-15 (2005).

Corren et al., "Lebrikizumab Treatment in Adults with Asthma," N. Engl. J. Med., 365(12): 1088-1098 (2011).

Gudbjartsson et al., "Sequence variants affecting eosinophil Nos. associate with asthma and myocardial infarction," Nat. Genet., 41(3): 342-347 (2009).

Janeway et al., "The interaction of the antibody molecule with specific antigen," Immunobiology: The Immune System in Health and Disease, 5th Ed., New York: Garland Science, 5 pages (2001).

Jia et al., "Periostin is a systemic biomarker of eosinophilic airway inflammation in asthmatic patients," J. Allergy Clin. Immunol., 130: 647-654 (2012).

Judge et al., "A clinical and immunological study of Netherton's syndrome," British Journal of Dermatology, 131: 615-621 (1994).

Komatsu et al., "Aberrant human tissue kallikrein levels in the stratum corneum and serum of patients with psoriasis: dependence on phenotype, severity and therapy," Br. J. Dermatol., 156: 875-883 (2007).

Laureano et al., "Generation of recombinant antibodies against human tissue kallikrein 7 to treat skin diseases," Bioorganic Med. Chem. Letters, 30: 127626 (5 pages) (2020).

Manolio et al., "Finding the missing heritability of complex diseases," Nature, 461: 747-753 (2009).

Morizane et al., "Kallikrein Expression and Cathelicidin Processing Are Independently Controlled in Keratinocytes by Calcium, Vitamin D3, and Retinoic Acid," J. Invest. Dermatol., 130(5): 1297-1306 (2010).

Myers et al., "Further replication studies of the EVE Consortium meta-analysis identifies 2 asthma risk loci in European Americans," J. Allergy Clin. Immunol., 130: 1294-1301 (2012).

Myers et al., "Epistasis between serine protease inhibitor Kazal-type 5 (SPINK5) and thymic stromal lymphopoietin (TSLP) genes contributes to childhood asthma," J Allergy Clin Immunol 134(4): 891-899 (2014).

Redelfs et al., "The serine protease inhibitor of Kazal-type 9 (SPINK9) is expressed in lichen simplex chronicus, actinic keratosis and squamous cell carcinoma," Arch. Dermatol. Res., 308: 133-137 (2016).

Schechter et al., "Inhibition of human kallikreins 5 and 7 by the serine protease inhibitor lympho-epithelial Kazal-type inhibitor (LEKTI)," Biol. Chem., 386: 1173-1184 (2005).

Sun et al., "Inhibition of the kinase ITK in a mouse model of asthma reduces cell death and fails to inhibit the inflammatory response," Sci. Signal., 8(405):ra122 (13 pages) (2015).

Takayama et al., "Periostin: A novel component of subepithelial fibrosis of bronchial asthma downstream of IL-4 and IL-13 signals," J. Allergy Clin. Immunol., 118: 98-104 (2006).

Thibaut et al., "Topical Treatment of Rosacea with Ivermectin Inhibits Gene Expression of Cathelicidin Innate Immune Mediators, LL-37 and KLK5, in Reconstructed and Ex Vivo Skin Models," Dermatol. Ther. (Heidelb), 7: 213-225 (2017).

Wan et al., "Biomarkers in Severe Asthma," Immunol Allergy Clin. N. Am., 36: 547-557 (2016).

Wu et al., "Development and evaluation of an ELISA method for the measurement of kallikrein-related peptidase 5 (KLK5) in human serum," Open J. Clin. Diag., 3:159-166 (2013).

Wu et al., "BioGPS: building your own mash-up of gene annotations and expression profiles," Nucleic Acids Research, 44: D313-D316 (2016).

Zhu et al., "Persistent kallikrein 5 activation induces atopic dermatitis-like skin architecture independent of PAR2 activity," J. Allergy Clin. Immunol., 140(5): 1310-1322, 1322e1-5 (2017).

International Search Report and Written Opinion for PCT Application No. PCT/US2020/051233, dated Mar. 24, 2021, 26 pages.

International Search Report and Written Opinion for PCT Application No. PCT/US2019/022192, dated Jul. 8, 2019, 20 pages.

International Search Report and Written Opinion for PCT Application No. PCT/US2022/019912, dated Aug. 19, 2022, 21 pages.

International Search Report and Written Opinion for International Patent Application No. PCT/US2018/028637, dated Jul. 6, 2018, 10 pages.

Bitoun et al., "Netherton syndrome: disease expression and spectrum of SPINK5 mutations in 21 families," J. Invest. Dermatol. 118(2):352-61 (Feb. 2002).

Bønnelykke et al., "A genome-wide association study identifies CDHR3 as a susceptibility locus for early childhood asthma with severe exacerbations," Nat. Genet. 46:51-55 (2014).

(56) References Cited

OTHER PUBLICATIONS

Briot et al., "Kallikrein 5 induces atopic dermatitis-like lesions through PAR2-mediated thymic stromal lymphopoietin expression in Netherton syndrome," J. Exp. Med. 206:1135-1147 (2009).
Debela et al., "Structural basis of the zinc inhibition of human tissue kallikrein 5," J. Mol. Biol. 273(4):1017-31 (Nov. 2, 2007).
Debela et al., "Structures and specificity of the human kallikrein-related peptidases KLK 4, 5, 6, and 7," Biol. Chem. 389(6):623-32 (2008).
Deraison et al., "LEKTI Fragments Specifically Inhibit KLK5, KLK7, and KLK14 and Control Desquamation through a pH-dependent Interaction," Mol. Biol. Cell, 18: 3607-3619 (2007).
Descargues et al., "Spink5-deficient mice mimic Netherton syndrome," Nat. Genet. 37:56-65 (2005).
Fahy et al., "Type 2 inflammation in asthma—present in most, absent in many," Nat. Rev. Immunol. 15(1):57-65 (Jan. 2015).
Furio et al., "KLK5 Inactivation Reverses Cutaneous Hallmarks of Netherton Syndrome," PLoS Genet. 11(9):e1005389 (Sep. 21, 2015).
Furio et al., "Transgenic kallikrein 5 mice reproduce major cutaneous and systemic hallmarks of Netherton syndrome," J. Exp. Med. 211:499-513 (2014).
Hovnanian et al., "Netherton syndrome: skin inflammation and allergy by loss," Cell Tissue Res. 351:289-300 (2013).
Kasparek et al., "KLK5 and KLK7 Ablation Fully Rescues Lethality of Netherton Syndrome-Like Phenotype," PLoS Genet. 13(1):e1006566 (Jan. 17, 2017).
Meyer-Hoffert et al., "Identification of lympho-epithelial Kazal-type inhibitor 2 in human skin as a kallikrein-related peptidase 5-specific protease inhibiton," PLoS One 4(2):e4372 (2009).
Tan et al., "Toward the first class of suicide inhibitors of kallikreins involved in skin diseases," J. Med. Chem. 58(2):598-612 (Jan. 22, 2015).
Ullemar et al., "Heritability and confirmation of genetic association," Allergy 71:230-238 (2016).
Wang et al., "SPINK5 knockdown in organotypic human skin culture as a model system for Netherton syndrome: effect of genetic inhibition of serine proteases kallikrein 5 and kallikrein 7," Exp. Dermatol. 23(7):524-6 (Jul. 2014).
Wu et al., "Structural insight into distinct mechanisms of protease inhibition by antibodies," Proc. Nat'l Acad. Sci. USA 104(50):19784-19789 (Dec. 11, 2007).
Yousef et al., "Human kallikrein 5: a potential novel serum biomarker for breast and ovarian cancer," Cancer Res. 63(14):3958-65 (Jul. 15, 2003).
Laureano, A. et al., "Generation of soluble antibodies against human tissue kallikrein 7 and the evaluation of their biopharmaceutical use with a poloxamer-based hydrogel drug delivery system" (2020), retrieved from the internet: https://d197for5662m48.cloudfront.net/documents/publicationstatus/29066/preprint_pdf/acfa6b3a2c882a5171b04c31255fea06.pdf.
Weber, C. et al., "P017: Characterization of the protease inhibitor SPINK7 in human skin" Experimental Dermatology 23( SUPPL P017):e4 (2014).
Wu, Y., et al., "Development and evaluation of an ELISA method for the measurement of kallikrein-related peptidase 5 (KLK5) in human serum" Open J Clin Diagnostics 3(4):159-166 (Dec. 1, 2013).

* cited by examiner

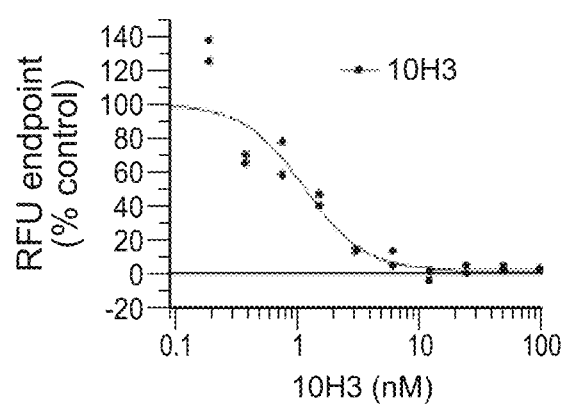
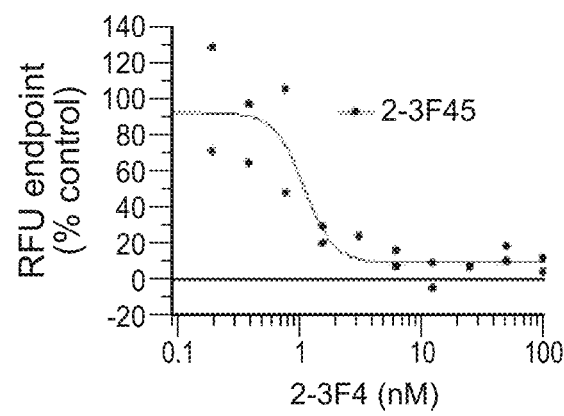
FIG. 2M
FIG. 2N

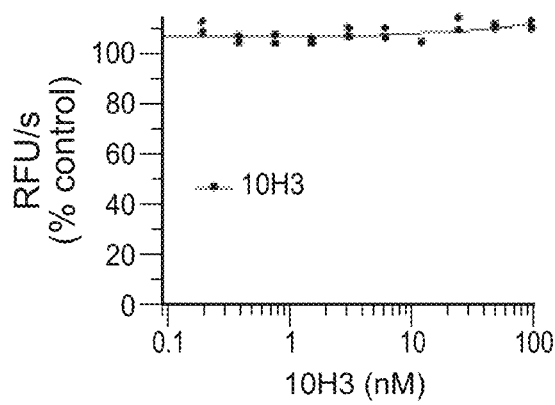
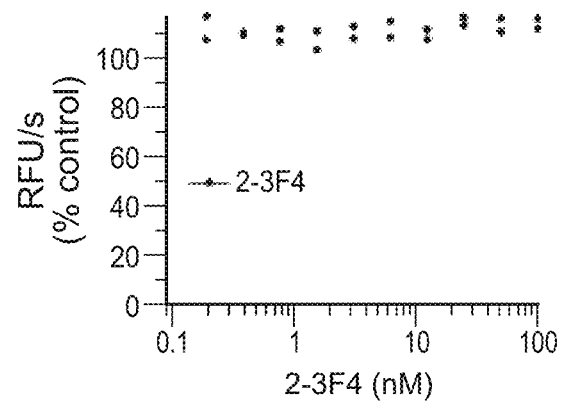
FIG. 6M  FIG. 6N

|  | Column | 1 | 2 | 3 | 4 | 5 | 6 | 7 | 8 | 9 | 10 |
|---|---|---|---|---|---|---|---|---|---|---|---|
|  |  | IC50 (nM) | | | | | | | | | Kiapp (nM) |
|  | Clone | Direct Assay (5nM KLK5) | Pro-KLK7 Coupled (5nM KLK5) | Pro-KLK1 Coupled (0.5nM KLK5) | MS Pro-KLK7 (5nM KLK5) | MS Pro-KLK1 (0.5nM KLK5) | KLK7 (5nM) | KLK1 (3nM) | KLK4 (2nM) | Trypsin (0.25 nM) | KLK5 (0.5-0.0625nM) |
| Group1 | 8B7 | 1.1 | 0.92 | 0.125 | 1.29 | 0.09 | >100 | >100 | >100 | >100 | 0.32 |
|  | 9B6 | 1.17 | 0.95 | 0.074 | 1.42 | 0.12 | >100 | >100 | >100 | >100 | 0.185 |
|  | 9F2 | 1.01 | 0.93 | 0.137 | 1.26 | 0.14 | >100 | >100 | >100 | >100 | 0.43 |
|  | 9H3 | 1.08 | 1.05 | 0.12 | 1.05 | 0.09 | >100 | >100 | >100 | >100 | 0.07 |
|  | 9H5 | 1.08 | 0.87 | 0.139 | 1.68 | 0.19 | >100 | >100 | >100 | >100 | 0.425 |
|  | 10C8 | 0.89 | 1.16 | 0.151 | 1.8 | 0.14 | >100 | >100 | >100 | >100 | 0.265 |
| Group2 | 8F5 | 1.15 | 0.76 | 0.149 | 1.31 | 0.16 | >100 | >100 | >100 | >100 | 1.91 |
|  | 10C5 | 0.98 | 0.58 | 0.111 | 0.31 | 0.08 | >100 | >100 | >100 | >100 | 0.15 |
|  | 2B11 | 1.29 | 0.86 | 0.17 | 1.72 | 0.48 | >100 | >100 | >100 | >100 | 6.35 |
|  | *10H3 | 1.09 | 1.17 | 0.122 | 0.97 | 0.08 | >100 | >100 | >100 | >100 | 0.51 |
|  | **2-3F4 | 1.02 | 1.1 | 0.129 | 0.38 | 0.09 | >100 | >100 | >100 | >100 | 1.14 |
|  | 3-3F5 | 1.32 | 1.53 | 0.14 | 1.44 | 0.15 | >100 | >100 | >100 | >100 | <0.01 |
|  | Spink9 | 1.23 | 2.07 | 0.325 | 1.13 | 0.58 | >100 | >100 | >100 | >100 | 1.28 |
|  | mAb1108 | partial | 1.84 | partial | partial | 0.34 | >100 | >100 | >100 | >100 | 1.53 |

| Kabat number | 85 | 86 | 87 | 88 | 89 | 90 | 91 | 92 | 93 | 94 | 95 | 95a | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|---|---|---|---|
| 14C8  | I | Y | F | C | H | Q | Y | G | L | S | F | P | . | . | Y | T | F | G | A | G | T | K | L | E | L | K |
| 14E12 | T | Y | F | C | Q | Q | Y | H | D | Y | P | . | . | Y | T | F | G | A | G | T | K | L | E | L | K |
| 8E11  | T | Y | Y | C | Q | Q | A | T | A | Y | G | S | S | G | N | A | F | G | G | G | T | E | L | V | V | K |
| 8G10  | T | Y | Y | C | Q | Q | A | T | A | Y | G | S | S | G | N | A | F | G | G | G | T | E | V | V | V | K |
| 9B6   | T | Y | Y | C | H | Q | D | Y | T | S | N | D | V | E | N | T | F | G | G | G | T | E | V | V | V | K |
| 2.3F4 | T | Y | Y | C | Q | Q | D | Y | T | G | N | V | D | N | T | F | G | G | G | T | E | V | V | V | K |
| 10C5  | T | Y | Y | C | H | Q | G | F | G | S | S | G | V | E | N | V | F | G | G | G | T | E | V | V | V | K |
| 2B11  | T | Y | Y | C | A | Q | G | Y | S | S | N | V | D | N | I | F | G | G | G | T | E | V | V | I | V | K |
| 10H3  | T | Y | Y | C | H | Q | D | Y | T | W | N | N | V | D | N | T | F | G | G | G | T | E | V | V | V | K |
| 9H3   | T | Y | Y | C | H | Q | D | Y | T | S | N | N | V | D | N | T | F | G | G | G | T | E | V | V | V | K |
| 8B7   | T | Y | Y | C | H | Q | D | Y | T | S | S | N | V | D | N | T | F | G | G | G | T | E | V | V | V | K |
| 9H5   | T | Y | Y | C | Q | Q | G | F | S | S | S | G | V | E | N | V | F | G | G | G | T | E | V | V | V | K |
| 9F2   | T | Y | Y | C | A | Q | G | D | S | H | N | N | V | D | N | I | F | G | G | G | T | E | V | V | V | K |
| 10C8  | T | Y | Y | C | Q | Q | D | Y | S | R | S | N | I | V | V | F | G | G | G | T | E | V | V | V | K |
| 8F5   | T | Y | Y | C | Q | Q | D | Y | S | S | G | V | E | N | V | F | G | G | G | T | E | V | V | V | K |
| 3.3F5 | T | Y | Y | C | Q | Q | G | Y | S | G | S | S | F | G | G | G | T | E | V | V | V | K |
| 9E3   | T | Y | Y | C | Q | Q | G | Y | S | G | S | N | V | E | N | T | F | G | G | G | T | E | V | V | V | K |
| 10D10 | T | Y | Y | C | Q | Q | G | Y | S | G | S | N | V | E | N | T | F | G | G | G | T | E | V | V | V | K |
| 12B3  | T | Y | Y | C | Q | Q | G | Y | S | G | S | N | V | E | N | T | F | G | G | G | T | E | V | V | V | K |
| 1D10  | T | Y | Y | C | Q | Q | G | Y | S | G | S | N | V | E | N | T | F | G | G | G | T | E | V | V | V | K |

Heavy chain variable region

CDR H1 – Contact (positions 30-35)
CDR H1 – Kabat (positions 31-35b)

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 35a | 35b | 35c | 35d | 36 | 37 | 38 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 14C8  | E | V | Q | L | V | E | S | G | G | G | L | V | Q | P | G | R | S | L | K | L | S | C | T | A | S | G | F | T | F | S | D | Y | N | M | A | . | . | . | . | W | V | R |
| 14E12 | E | V | Q | L | V | E | S | G | G | G | L | V | R | P | G | R | S | L | R | L | S | C | A | A | S | G | F | T | F | S | D | Y | Y | M | A | . | . | . | . | W | V | R |
| 8E11  | Q | E | Q | L | E | E | S | G | G | D | L | V | K | P | E | G | S | L | T | L | T | C | T | V | S | G | F | S | F | S | S | S | Y | W | I | C | . | . | . | W | V | R |
| 8G10  | Q | S | L | E | E | S | G | G | D | L | V | K | P | E | G | S | L | T | L | T | C | T | V | S | G | F | S | F | S | S | T | S | Y | W | I | C | . | . | . | W | V | R |
| 9B6   | Q | S | V | K | E | E | S | R | G | G | L | F | - | K | P | T | D | T | L | T | L | T | C | T | V | S | G | F | S | L | S | N | Y | G | V | T | . | . | . | W | V | R |
| 2.3F4 | Q | S | V | E | E | S | E | G | G | L | F | - | K | P | T | D | T | L | T | L | T | C | T | V | S | G | F | S | L | S | N | Y | G | V | S | . | . | . | . | W | V | R |
| 10C5  | Q | S | V | V | E | S | E | G | G | L | F | V | K | P | T | D | T | L | T | L | T | C | T | V | S | G | F | S | L | I | S | T | F | A | I | N | . | . | . | W | V | R |
| 2B11  | Q | S | V | K | E | E | S | E | G | G | L | F | - | K | P | T | D | T | L | T | L | T | C | T | V | S | G | F | S | L | S | G | Y | G | V | S | . | . | . | W | V | R |
| 10H3  | Q | S | V | K | E | E | S | E | G | G | L | F | V | K | P | T | D | N | L | T | L | T | C | T | V | S | G | F | S | L | S | N | Y | G | V | T | . | . | . | W | V | R |
| 9H3   | Q | S | V | K | E | E | S | E | G | G | L | F | V | K | P | T | D | T | L | T | L | T | C | T | V | S | G | F | S | L | S | S | Y | G | V | S | . | . | . | W | V | R |
| 8B7   | Q | S | V | K | E | E | S | E | G | G | L | F | V | K | P | T | D | T | L | T | L | T | C | T | V | S | G | F | S | L | S | G | Y | G | V | S | . | . | . | W | V | R |
| 9H5   | Q | S | V | K | E | E | S | E | G | G | L | F | V | K | P | T | D | N | L | T | L | T | C | T | V | S | G | F | S | L | S | N | Y | G | V | S | . | . | . | W | V | R |
| 9F2   | Q | S | V | K | E | E | S | E | G | G | L | F | V | K | P | T | D | T | L | T | L | T | C | T | V | S | G | F | S | L | S | S | Y | G | V | S | . | . | . | W | V | R |
| 10C8  | Q | S | V | K | E | E | S | E | G | G | L | F | V | K | P | T | D | T | L | T | L | T | C | T | V | S | G | F | S | L | S | S | Y | P | I | S | . | . | . | W | V | R |
| 8F5   | Q | S | L | E | E | S | G | G | G | L | V | V | K | P | G | A | S | L | T | L | T | C | T | V | S | G | F | S | L | N | D | Y | G | V | S | . | . | . | . | W | V | R |
| 3.3F5 | Q | S | L | E | E | S | G | G | G | L | V | V | K | P | G | A | S | L | T | L | T | C | T | V | S | G | F | S | L | T | N | Y | N | V | N | F | V | M | C | W | V | R |
| 9E3   | Q | E | Q | L | V | E | S | G | G | G | L | V | V | K | P | G | G | T | L | T | L | T | C | K | A | S | G | F | S | L | T | D | N | Y | V | M | S | . | . | W | V | R |
| 10D10 | Q | E | Q | L | E | E | S | G | G | G | L | V | V | K | P | G | G | T | L | T | L | T | C | T | A | S | G | F | D | F | N | G | G | G | I | Y | . | . | . | W | V | R |
| 12B3  | . | . | . | . | . | . | . | . | . | . | . | . | . | . | . | . | . | . | . | . | . | . | . | . | . | . | . | . | . | . | . | . | . | . | . | . | . | . | . | . | . | . |
| 1D10  | Q | S | L | E | E | S | G | G | G | L | V | V | K | P | G | G | T | L | T | L | T | C | T | A | S | G | F | D | F | D | F | N | G | G | G | I | Y | . | . | W | V | R |

CDR H3 - Contact
CDR H3 - Kabat

| Kabat number | 82a 82b 82c 83 84 85 86 87 88 89 90 91 92 93 94 95 96 97 98 99 100 100a 100b 100c 100d 100e 100f 100g 100h 101 102 103 104 105 106 107 108 |
|---|---|
| 14C8   | L Q M D S L R S E D T A T Y Y C A T G I F N Y G T D Y F . . . . D Y W G Q G V M V |
| 14E12  | L Q M D S L R S D D T A N Y Y C . . . . . . . . . . . . . . . A Y W G Q G T L V |
| 8E11   | L Q V T S L T A A D T A T Y Y C A R G G G S A D F G F . . . . D L W G P G T L V |
| 8G10   | L K M T S L T A A D T A T Y Y C A R G G G S A D F G F . . . . D L W G P G T L V |
| 9B6    | L Q M T S L T A A D T A T Y Y C A R D D V G G K S L . . . . . D I W G P G T L V |
| 2.3F4  | L K M T S L T A A D T A T Y Y C A R L C V D C A D A L . . . . D S W G P G T L V |
| 10C5   | L K M T R P T A A D T A T Y Y C A R E N P D Y G Y A Y . . . . D A W G P G T L V |
| 2B11   | L K M T S L T A A D T A T Y Y C A R E N A G S G W E L . . . . D I W G P G T L V |
| 10H3   | L K M T S L T A A D T A T Y Y C A R D N V G G D M S L . . . . D I W G P G T L V |
| 9H3    | L K M T S L T A A D T A T Y Y C A R D D D V G G G K S L . . . . D V W G P G T L V |
| 8B7    | L K M T S L T A A D T A T Y Y C A R D D D V G G G K S L . . . . D I W G P G T L V |
| 9H5    | L K M A S L T A A D T A T Y Y C A R D D D V G G R S L . . . . D I W G P G T L V |
| 9F2    | L Q V T S L T A A D T A T Y Y C V R E N P T Y G Y A Y . . . . D A W G P G T L V |
| 10C8   | L O V T S L T A A D T A T Y Y C A R D R D Y G Y R A D D A T S G M D L W G P G T L V |
| 8F5    | L K M T S L T A A D T A T Y Y C A R G D A G T S Y S F . . . . N F W G P G T L V |
| 3.3F5  | L Q V T S L T A A D T A T Y Y C A R G D A A S Y . . . . . . . N F W G P G T L V |
| 9E3    | L O L T S L T A A D T A T Y Y C A R E S G G S Y Y . . . . . . . . . |
| 10D10  | L Q M T S L T V A D T A T Y Y C A R E T G G S W Y . . . . . D L W G P G T L V |
| 12B3   |  |
| 1D10   |  |

| Kabat number | 110 | 111 | 112 | 113 |
|---|---|---|---|---|
| 14C8 | T | V | S | S |
| 14E12 | T | V | S | S |
| 8E11 | T | V | S | S |
| 8G10 | T | V | S | S |
| 9B6 | T | V | S | S |
| 2.3F4 | T | V | S | S |
| 10C5 | T | V | S | S |
| 2B11 | T | V | S | S |
| 10H3 | T | V | S | S |
| 9H3 | T | V | S | S |
| 8B7 | T | V | S | S |
| 9H5 | T | V | S | S |
| 9F2 | T | V | S | S |
| 10C8 | T | V | S | S |
| 8F5 | T | V | S | S |
| 3.3F5 | T | V | S | S |
| 9E3 | T | V | S | S |
| 10D10 | T | V | S | S |
| 12B3 | T | V | S | S |
| 1D10 | T | V | S | S |

ANTI-KLK5 ANTIBODIES AND METHODS OF USE

CROSS-REFERENCE TO RELATED APPLICATIONS

This application is a continuation of U.S. patent application Ser. No. 16/352,619, filed Mar. 13, 2019, which claims benefit under 35 U.S.C. § 119(e) to U.S. Provisional Application No. 62/643,034, filed Mar. 14, 2018, the entire contents of which are incorporated herein by reference.

SEQUENCE LISTING

The instant application contains a Sequence Listing submitted via EFS-Web and hereby incorporated by reference in its entirety. Said ASCII copy, created on Nov. 10, 2020, is named 2020-11-10_01146-0101-01US_SL_ST25.txt, and is 425,984 bytes in size.

FIELD OF THE INVENTION

The present invention relates to anti-KLK5 antibodies and methods of using the same.

BACKGROUND

Human kallikrein-related peptidases (KLKs) are (chymo)-trypsin-like serine proteases that are expressed in a variety of tissues such as prostate, ovary, breast, testis, brain, and skin. KLKs belong to a subgroup of the chymotrypsin-like serine protease family S1A of clan PA(S). The 15 human KLK genes are located on chromosome 19q13.4 and constitute the largest contiguous serine protease cluster in the human genome. These genes, generally composed of five coding exons and in some cases one or two 5' non-coding exons, encode the kallikrein-related peptidases KLK1 to KLK15. All KLK genes encode single-chain pre-pro-proteins containing a chymotrypsin- or trypsin-like catalytic domain of 224-237 residues with an amino acid sequence identity of approximately 40% among KLK4 to KLK15. KLK1 and its close homologs KLK2 and KLK3 form a clade of their own, KLK4, 5, and 7 belong to another subgroup, whereas KLK6 shares more similarity with KLK13 and KLK14. See Debela et al., *Biol Chem* 389, 623-632 (2008).

KLK5 appears to be most abundantly expressed in human skin, specifically in the upper spinous and granular layers of the skin, where keratinocytes undergo terminal differentiation and are transformed into flattened brick-like structures that form the stratum corneum, the outermost epidermal layer and the barrier to the outside environment. See Debela et al., *J Mol Biol*, 373, 1017-1031 (2007); and Tan et al., J Med Chem. 2015 Jan. 22; 58(2):598-612 (2014). KLK5 is described to play pathological roles in skin disorders such as Netherton Syndrome. See Furio et al., *PLOS Genet* 11(9), e1005389 (2015). Netherton Syndrome is caused by loss-of-function mutations in the SPINK5 gene, encoding the serine protease inhibitor Kazal-type 5 (SPINK5). See Descargues et al., Nat Genet. 2005 January; 37(1):56-65 (2004). SPINK5 has been shown to inhibit several members of the KLK serine protease family (e.g. KLK5 and KLK7). See Wang et al., Exp Dermatol. July; 23(7):524-6 (2014). The absence of SPINK5 in Netherton Syndrome results in unopposed KLKs activities. KLK5 hyperactivity is thought to be a key element in the pathophysiology of Netherton Syndrome as KLK5 is a regulator of proteolysis in the epidermis. Ablation of KLK5 and KLK7 rescues lethality of Netherton Syndrome-like phenotype. See Briot et al., J Exp Med. May 11; 206(5):1135-47 (2009); Furio et al., J Exp Med. March 10; 211(3):499-513 (2014); and Kasparek et al., PLoS Genet. 2017 Jan. 17; 13(1):e1006566 (2017). Netherton Syndrome is a complex systemic disease with multiple effects for which currently no satisfactory treatment is available.

Asthma is a clinically heterogeneous disorder associated with both genetic and environmental risk factors. Estimates of heritability from asthma twin studies vary from 35% to 80%, indicating an important role for genetic risk. See e.g., Ullemar et al., *Allergy* 71, 230-238 (2016). Several large scale GWAS have been performed for asthma and asthma related phenotypes, and many of the loci identified such as those near ORMDL3, IL13, IL1RL1 and TSLP genes have been confirmed in multiple study populations. See e.g., Bonnelykke et al., *Nat Genet* 46, 51-55 (2014). Recent studies identified a SNP at the KLK4/5 locus which is protective for the risk regarding periostin low, or type 2 low inflammation asthma. In the same study, KLK5 levels were found to be elevated in bronchoalveolar lavage of severe asthma patients supporting the hypothesis that KLK5 plays a role in bronchial obstruction and asthma pathogenesis.

Despite the advances in the field of diseases such as Netherton Syndrome and asthma, there remains a need to identify targets and develop means that can supplement or enhance the efficacy of existing therapies.

SUMMARY

Provided herein are anti-KLK5 antibodies and methods of using the same.

Further provided herein is an isolated antibody that binds to KLK5, wherein the antibody comprises (a) HVR-H1 comprising the amino acid sequence of SEQ ID NO:28; (b) HVR-H2 comprising the amino acid sequence selected from the group consisting of SEQ ID NO:38, SEQ ID NO:45, and SEQ ID NO:54; (c) HVR-H3 comprising the amino acid sequence selected from the group consisting of SEQ ID NO:65, SEQ ID NO:69, and SEQ ID NO:72; (d) HVR-L1 comprising the amino acid sequence of SEQ ID NO:96; (e) HVR-L2 comprising the amino acid sequence of SEQ ID NO:109; and (f) HVR-L3 comprising the amino acid sequence of SEQ ID NO:127.

In some embodiments, the antibody comprises (a) HVR-H1 comprising the amino acid sequence selected from the group consisting of SEQ ID NO:17, SEQ ID NO:22, and SEQ ID NO:24; (b) HVR-H2 comprising the amino acid sequence selected from the group consisting of SEQ ID NO:35, SEQ ID NO:36, SEQ ID NO:37, SEQ ID NO:42, SEQ ID NO:43, SEQ ID NO:44, SEQ ID NO:48, SEQ ID NO:49, SEQ ID NO:50, SEQ ID NO:51, SEQ ID NO:52, and SEQ ID NO:53; (c) HVR-H3 comprising the amino acid sequence selected from the group consisting of SEQ ID NO:65, SEQ ID NO:69, and SEQ ID NO:72; (d) HVR-L1 comprising the amino acid sequence selected from the group consisting of SEQ ID NO:82, SEQ ID NO:87, and SEQ ID NO:91; (e) HVR-L2 comprising the amino acid sequence selected from the group consisting of SEQ ID NO:99, SEQ ID NO:101, and SEQ ID NO:105; and (f) HVR-L3 comprising the amino acid sequence selected from the group consisting of SEQ ID NO:115, SEQ ID NO:119, and SEQ ID NO:122.

In some embodiments of any of the antibodies, the antibody comprises (i) (a) HVR-H1 comprising the amino acid sequence of SEQ ID NO:17; (b) HVR-H2 comprising the amino acid sequence of SEQ ID NO:35; (c) HVR-H3 comprising the amino acid sequence of SEQ ID NO:65; (d) HVR-L1 comprising the amino acid sequence of SEQ ID NO:82; (e) HVR-L2 comprising the amino acid sequence of SEQ ID NO:101; and (f) HVR-L3 comprising the amino acid sequence of SEQ ID NO:115; (ii) (a) HVR-H1 comprising the amino acid sequence of SEQ ID NO:22; (b) HVR-H2 comprising the amino acid sequence of SEQ ID NO:42; (c) HVR-H3 comprising the amino acid sequence of SEQ ID NO:69; (d) HVR-L1 comprising the amino acid sequence of SEQ ID NO:87; (e) HVR-L2 comprising the amino acid sequence of SEQ ID NO:105; and (f) HVR-L3 comprising the amino acid sequence of SEQ ID NO:119; or (iii) (a) HVR-H1 comprising the amino acid sequence of SEQ ID NO:24; (b) HVR-H2 comprising the amino acid sequence of SEQ ID NO:52; (c) HVR-H3 comprising the amino acid sequence of SEQ ID NO:72; (d) HVR-L1 comprising the amino acid sequence of SEQ ID NO:91; (e) HVR-L2 comprising the amino acid sequence of SEQ ID NO:99; and (f) HVR-L3 comprising the amino acid sequence of SEQ ID NO:122.

In some embodiments of any of the antibodies, the antibody comprises a) a VH sequence of SEQ ID NO:202 and a VL sequence of SEQ ID NO:140; b) a VH sequence of SEQ ID NO:225 and a VL sequence of SEQ ID NO:151; or c) a VH sequence of SEQ ID NO:257 and a VL sequence of SEQ ID NO:162.

In some embodiments of any of the antibodies, the antibody comprises a) a VH sequence of SEQ ID NO:201 and a VL sequence of SEQ ID NO:139; b) a VH sequence of SEQ ID NO:221 and a VL sequence of SEQ ID NO:149; or c) a VH sequence of SEQ ID NO:248 or SEQ ID NO:254, and a VL sequence of SEQ ID NO:160.

Further provided herein is an isolated antibody that binds to KLK5, wherein the antibody comprises a) a VH sequence having at least 95% sequence identity to the amino acid sequence of SEQ ID NO:201 and a VL sequence having at least 95% sequence identity to the amino acid sequence of SEQ ID NO:139; b) a VH sequence having at least 95% sequence identity to the amino acid sequence of SEQ ID NO:221 and a VL sequence having at least 95% sequence identity to the amino acid sequence of SEQ ID NO:149; or c) a VH sequence having at least 95% sequence identity to the amino acid sequence of SEQ ID NO:248 or SEQ ID NO:254, and a VL sequence having at least 95% sequence identity to the amino acid sequence of SEQ ID NO:160.

Further provided herein is an isolated antibody that binds to KLK5, wherein the antibody comprises (i) (a) HVR-H1 comprising the amino acid sequence of SEQ ID NO:14; (b) HVR-H2 comprising the amino acid sequence of SEQ ID NO:32; (c) HVR-H3 comprising the amino acid sequence of SEQ ID NO:62; (d) HVR-L1 comprising the amino acid sequence of SEQ ID NO:79; (e) HVR-L2 comprising the amino acid sequence of SEQ ID NO:99; and (f) HVR-L3 comprising the amino acid sequence of SEQ ID NO:112; (ii) (a) HVR-H1 comprising the amino acid sequence of SEQ ID NO:15; (b) HVR-H2 comprising the amino acid sequence of SEQ ID NO:33; (c) HVR-H3 comprising the amino acid sequence of SEQ ID NO:63; (d) HVR-L1 comprising the amino acid sequence of SEQ ID NO:80; (e) HVR-L2 comprising the amino acid sequence of SEQ ID NO:100; and (f) HVR-L3 comprising the amino acid sequence of SEQ ID NO:113; (iii) (a) HVR-H1 comprising the amino acid sequence of SEQ ID NO:16; (b) HVR-H2 comprising the amino acid sequence of SEQ ID NO:34; (c) HVR-H3 comprising the amino acid sequence of SEQ ID NO:64; (d) HVR-L1 comprising the amino acid sequence of SEQ ID NO:81; (e) HVR-L2 comprising the amino acid sequence of SEQ ID NO:99; and (f) HVR-L3 comprising the amino acid sequence of SEQ ID NO:114; (iv) (a) HVR-H1 comprising the amino acid sequence of SEQ ID NO:18; (b) HVR-H2 comprising the amino acid sequence of SEQ ID NO:39; (c) HVR-H3 comprising the amino acid sequence of SEQ ID NO:66; (d) HVR-L1 comprising the amino acid sequence of SEQ ID NO:83; (e) HVR-L2 comprising the amino acid sequence of SEQ ID NO:102; and (f) HVR-L3 comprising the amino acid sequence of SEQ ID NO:116; (v) (a) HVR-H1 comprising the amino acid sequence of SEQ ID NO:19; (b) HVR-H2 comprising the amino acid sequence of SEQ ID NO:40; (c) HVR-H3 comprising the amino acid sequence of SEQ ID NO:67; (d) HVR-L1 comprising the amino acid sequence of SEQ ID NO:84; (e) HVR-L2 comprising the amino acid sequence of SEQ ID NO:103; and (f) HVR-L3 comprising the amino acid sequence of SEQ ID NO:117; (vi) (a) HVR-H1 comprising the amino acid sequence of SEQ ID NO:20; (b) HVR-H2 comprising the amino acid sequence of SEQ ID NO:33; (c) HVR-H3 comprising the amino acid sequence of SEQ ID NO:68; (d) HVR-L1 comprising the amino acid sequence of SEQ ID NO:85; (e) HVR-L2 comprising the amino acid sequence of SEQ ID NO:103; and (f) HVR-L3 comprising the amino acid sequence of SEQ ID NO:118; (vii) (a) HVR-H1 comprising the amino acid sequence of SEQ ID NO:21; (b) HVR-H2 comprising the amino acid sequence of SEQ ID NO:41; (c) HVR-H3 comprising the amino acid sequence of SEQ ID NO:69; (d) HVR-L1 comprising the amino acid sequence of SEQ ID NO:86; (e) HVR-L2 comprising the amino acid sequence of SEQ ID NO:104; and (f) HVR-L3 comprising the amino acid sequence of SEQ ID NO:118; (viii) (a) HVR-H1 comprising the amino acid sequence of SEQ ID NO:22; (b) HVR-H2 comprising the amino acid sequence of SEQ ID NO:46; (c) HVR-H3 comprising the amino acid sequence of SEQ ID NO:69; (d) HVR-L1 comprising the amino acid sequence of SEQ ID NO:88; (e) HVR-L2 comprising the amino acid sequence of SEQ ID NO:105; and (f) HVR-L3 comprising the amino acid sequence of SEQ ID NO:120; (ix) (a) HVR-H1 comprising the amino acid sequence of SEQ ID NO:22; (b) HVR-H2 comprising the amino acid sequence of SEQ ID NO:42; (c) HVR-H3 comprising the amino acid sequence of SEQ ID NO:70; (d) HVR-L1 comprising the amino acid sequence of SEQ ID NO:89; (e) HVR-L2 comprising the amino acid sequence of SEQ ID NO:105; and (f) HVR-L3 comprising the amino acid sequence of SEQ ID NO:118; or (x) (a) HVR-H1 comprising the amino acid sequence of SEQ ID NO:23; (b) HVR-H2 comprising the amino acid sequence of SEQ ID NO:47; (c) HVR-H3 comprising the amino acid sequence of SEQ ID NO:71; (d) HVR-L1 comprising the amino acid sequence of SEQ ID NO:90; (e) HVR-L2 comprising the amino acid sequence of SEQ ID NO:106; and (f) HVR-L3 comprising the amino acid sequence of SEQ ID NO:121.

In some embodiments, the antibody comprises a VH sequence selected from the group consisting of SEQ ID NO:170, SEQ ID NO:171, SEQ ID NO:172, SEQ ID NO:203, SEQ ID NO:204, SEQ ID NO:205, SEQ ID NO:206, SEQ ID NO:226, SEQ ID NO:227, and SEQ ID NO:228, and a VL sequence selected from the group consisting of SEQ ID NO:131, SEQ ID NO:132, SEQ ID NO:133, SEQ ID NO:141, SEQ ID NO:142, SEQ ID NO:143, SEQ ID NO:144, SEQ ID NO:152, SEQ ID NO:153, and SEQ ID NO:154.

In some embodiments, the antibody comprises (a) a VH sequence of SEQ ID NO:170 and a VL sequence of SEQ ID NO:131; (b) a VH sequence of SEQ ID NO:171 and a VL sequence of SEQ ID NO:132; (c) a VH sequence of SEQ ID NO:172 and a VL sequence of SEQ ID NO:133; (d) a VH sequence of SEQ ID NO:203 and a VL sequence of SEQ ID NO:141; (e) a VH sequence of SEQ ID NO:204 and a VL sequence of SEQ ID NO:142; (f) a VH sequence of SEQ ID NO:205 and a VL sequence of SEQ ID NO:143; (g) a VH sequence of SEQ ID NO:206 and a VL sequence of SEQ ID NO:144; (h) a VH sequence of SEQ ID NO:226 and a VL sequence of SEQ ID NO:152; (i) a VH sequence of SEQ ID NO:227 and a VL sequence of SEQ ID NO:153; or (j) a VH sequence of SEQ ID NO:228 and a VL sequence of SEQ ID NO:154.

Further provided herein is an isolated antibody that binds to KLK5, wherein the antibody comprises (a) a VH sequence having at least 95% sequence identity to the amino acid sequence of SEQ ID NO:170 and a VL sequence having at least 95% sequence identity to the amino acid sequence of SEQ ID NO:131; (b) a VH sequence having at least 95% sequence identity to the amino acid sequence of SEQ ID NO:171 and a VL sequence having at least 95% sequence identity to the amino acid sequence of SEQ ID NO:132; (c) a VH sequence having at least 95% sequence identity to the amino acid sequence of SEQ ID NO:172 and a VL sequence having at least 95% sequence identity to the amino acid sequence of SEQ ID NO:133; (d) a VH sequence having at least 95% sequence identity to the amino acid sequence of SEQ ID NO:203 and a VL sequence having at least 95% sequence identity to the amino acid sequence of SEQ ID NO:141; (e) a VH sequence having at least 95% sequence identity to the amino acid sequence of SEQ ID NO:204 and a VL sequence having at least 95% sequence identity to the amino acid sequence of SEQ ID NO:142; (f) a VH sequence having at least 95% sequence identity to the amino acid sequence of SEQ ID NO:205 and a VL sequence having at least 95% sequence identity to the amino acid sequence of SEQ ID NO:143; (g) a VH sequence having at least 95% sequence identity to the amino acid sequence of SEQ ID NO:206 and a VL sequence having at least 95% sequence identity to the amino acid sequence of SEQ ID NO:144; (h) a VH sequence having at least 95% sequence identity to the amino acid sequence of SEQ ID NO:226 and a VL sequence having at least 95% sequence identity to the amino acid sequence of SEQ ID NO:152; (i) a VH sequence having at least 95% sequence identity to the amino acid sequence of SEQ ID NO:227 and a VL sequence having at least 95% sequence identity to the amino acid sequence of SEQ ID NO:153; or (j) a VH sequence having at least 95% sequence identity to the amino acid sequence of SEQ ID NO:228 and a VL sequence having at least 95% sequence identity to the amino acid sequence of SEQ ID NO:154.

In some embodiments of any of the antibodies, the antibody is an IgG1 or IgG4.

In some embodiments of any of the antibodies, the antibody inhibits the biological activity of KLK5 by at least 50% as measured by one or more methods as described in the Examples herein below. In some embodiments, the one or more methods is selected from the group consisting of a recombinant KLK5 direct activity assay, coupled pro-KLK1 fluorescent peptide assay, a coupled pro-KLK7 fluorescent peptide assay, a pro-KLK1 LC/MS assay, a pro-KLK7 LC/MS assay, and a $K_{i(app)}$ assay. In some embodiments, the biological activity is the serine protease activity of KLK5.

In some embodiments of any of the antibodies, the antibody is a monoclonal antibody.

In some embodiments of any of the antibodies, the antibody is a human, humanized, or chimeric antibody.

In some embodiments of any of the antibodies, the antibody is an antibody fragment that binds KLK5.

Further provided herein is an antibody that forms a thermodynamic epitope when bound to KLK5 comprising one or more of the sequences selected from the group consisting of SEQ ID NO:316, SEQ ID NO:317, SEQ ID NO:318, and SEQ ID NO:319 as measured by hydrogen exchange mass spectrometry.

Further provided herein is an antibody that competes for binding with any of the antibodies described herein.

Further provided herein is an antibody that binds to the same epitope as any of the antibodies described herein.

Further provided herein is an isolated nucleic acid encoding any of the antibodies described herein.

Further provided herein is a host cell comprising the nucleic acid described herein.

Further provided herein is a method of producing an antibody comprising culturing the host cell described herein so that the antibody is produced.

Further provided herein is an immunoconjugate comprising the antibody described herein.

Further provided herein is a pharmaceutical formulation comprising the antibody described herein and a pharmaceutically acceptable carrier.

Further provided herein is the antibody as described herein for use as a medicament.

Further provided herein is the antibody as described herein for use in treating a disease selected from the group consisting of Netherton Syndrome, asthma, atopic dermatitis, psoriasis, and rosacea. In some embodiments, the disease is selected from the group consisting of Netherton Syndrome, asthma, atopic dermatitis, psoriasis, rosacea and eosinophilic esophagitis. In some embodiments, the asthma is selected from the group consisting of atopic asthma, allergic asthma, non-allergic asthma, exercise-induced asthma, aspirin sensitive/exacerbated asthma, mild asthma, moderate to severe asthma, corticosteroid naïve asthma, chronic asthma, corticosteroid resistant asthma, corticosteroid refractory asthma, newly diagnosed and untreated asthma, asthma due to smoking, asthma uncontrolled on corticosteroids, T helper lymphocyte type 2 (Th2) or type 2 (Th2) high, or Type 2 (T2)-driven asthma, eosinophilic asthma, periostin-high asthma, eosinophil-high asthma, Th2-low asthma or nonTh2-driven asthma, periostin-low asthma, and eosinophil-low asthma. In some embodiments, the asthma is TH2-low asthma.

Further provided is the antibody as described herein for use in inhibiting the biological activity of KLK5.

Further provided is the use of the antibody as described herein in the manufacture of a medicament. In some embodiments, the medicament is for treating a disease selected from the group consisting of Netherton Syndrome, asthma, atopic dermatitis, psoriasis, and rosacea. In some embodiments, the disease is selected from the group consisting of Netherton Syndrome, asthma, atopic dermatitis, psoriasis, rosacea and eosinophilic esophagitis. In some embodiments, the asthma is selected from the group consisting of atopic asthma, allergic asthma, non-allergic asthma, exercise-induced asthma, aspirin sensitive/exacerbated asthma, mild asthma, moderate to severe asthma, corticosteroid naïve asthma, chronic asthma, corticosteroid resistant asthma, corticosteroid refractory asthma, newly diagnosed and untreated asthma, asthma due to smoking, asthma uncontrolled on corticosteroids, T helper lymphocyte type 2 (Th2) or type 2 (Th2) high, or Type 2 (T2)-driven asthma, eosinophilic asthma, periostin-high asthma, eosinophil-high asthma, Th2-low asthma or nonTh2-driven asthma, periostin-low asthma, and eosinophil-low asthma. In some embodiments, the asthma is TH2-low asthma.

Further provided is the use of the antibody described herein in the manufacture of a medicament for inhibiting the biological activity of KLK5.

Further provided is a method of treating an individual having a disease, wherein the disease is selected from the group consisting of Netherton Syndrome, asthma, atopic dermatitis, psoriasis, and rosacea comprising administering to the individual an effective amount of the antibody described herein. In some embodiments, the disease is selected from the group consisting of Netherton Syndrome, asthma, atopic dermatitis, psoriasis, rosacea and eosinophilic esophagitis. In some embodiments, the asthma is selected from the group consisting of atopic asthma, allergic asthma, non-allergic asthma, exercise-induced asthma, aspirin sensitive/exacerbated asthma, mild asthma, moderate to severe asthma, corticosteroid naïve asthma, chronic asthma, corticosteroid resistant asthma, corticosteroid refractory asthma, newly diagnosed and untreated asthma, asthma due to smoking, asthma uncontrolled on corticosteroids, T helper lymphocyte type 2 (Th2) or type 2 (Th2) high, or Type 2 (T2)-driven asthma, eosinophilic asthma, periostin-high asthma, eosinophil-high asthma, Th2-low asthma or nonTh2-driven asthma, periostin-low asthma, and eosinophil-low asthma. In some embodiments, the asthma is Th2-low asthma.

Further provided is a method of inhibiting the biological activity of KLK5 in an individual comprising administering to the individual an effective amount of the antibody described herein to inhibit the biological activity of KLK5.

Further provided herein is an antibody that specifically binds to human KLK5, wherein the antibody binds to an epitope on human KLK5 comprising one or more amino acid residues selected from the group consisting of Pro130, Ser131, Ala132, Gly133, Val162, Leu163, Ser164, Gln165, Lys166, Arg167, Glu169, Asp170, Ala171, Tyr172, Pro173, Arg174, Gln174A, Ile176, Asp177, Asp178, Gly184, Asp185, Lys186, Ala186A, Arg188, Asn223, Arg224, Pro225, and Lys233 according to standard protease numbering. In some embodiments, the antibody binds to an epitope on human KLK5 comprising one or more amino acid residues selected from the group consisting of Pro130, Ser131, Ala132, Val162, Leu163, Ser164, Gln165, Lys166, Arg167, Glu169, Asp170, Ala171, Tyr172, Pro173, Arg174, Gln174A, Ile176, Asp177, Asp178, Arg224, and Lys233 according to standard protease numbering. In some embodiments, the antibody binds to an epitope on human KLK5 comprising one or more amino acid residues selected from the group consisting of Pro130, Ser131, Ala132, Gly133, Val162, Leu163, Ser164, Gln165, Lys166, Arg167, Glu169, Asp170, Ala171, Tyr172, Pro173, Arg174, Gln174A, Ile176, Asp177, and Lys233 according to standard protease numbering. In some embodiments, the antibody binds to an epitope on human KLK5 comprising one or more amino acid residues selected from the group consisting of Ser131, Ala132, Gly133, Leu163, Ser164, Gln165, Lys166, Arg167, Glu169, Asp170, Ala171, Pro173, Arg174, Gly184, Asp185, Lys186, Ala186A, Arg188, Asn223, Arg224, and Pro225 according to standard protease numbering.

Further provided herein is an antibody when bound to human KLK5 results in a conformational change of human KLK5, wherein the conformational change allosterically results in the disruption of the substrate binding site and/or the active site of human KLK5.

BRIEF DESCRIPTION OF THE FIGURES

FIG. 1A: Spink9.SRE.Fc (Spink9), FIG. 1N: 2-3F4.

FIG. 2A: Spink9.SRE.Fc, FIG. 2I: 8B7, FIG. 2N: 2-3F4.

FIG. 3A: Spink9.SRE.Fc, FIG. 3N: 2-3F4.

FIG. 4A: SPINK9.SRE.Fc, FIG. 4N: 9H5.

FIG. 5A: SPINK9.SRE.Fc, FIG. 5N: 9H5.

FIG. 6A-6N shows the Specificity of KLK5 inhibitors on KLK7 activity. 5 nM recombinant human KLK7 and 0.19-100 nM anti-KLK5 inhibitors were pre-incubated for 30 minutes prior to addition of 100 µM suc-LLVY-AMC. Plates were examined every 102 s for 75 minutes using a PHERAstar® Plus reader using a 340 nm excitation/460 nm emission module. $IC_{50}$ values are summarized in Table 6.

The results for the KLK5 inhibitors are depicted as follows: FIG. 6A: Spink9.SRE.Fc, FIG. 6M: 10H3 and FIG. 6N: 2-3F4.

FIG. 7A: Spink9.SRE.Fc, FIG. 7N: 2-3F4.

FIG. 8A: Spink9.SRE.Fc, FIG. 8N: 2-3F4.

FIG. 9A: Spink9.SRE.Fc, FIG. 9N: 2-3F4.

FIG. 10A and FIG. 10B: Spink9.SRE.Fc.

FIG. 11 shows a table summarizing the $IC_{50}$ values as evaluated and shown in FIGS. 1-10.

FIG. 12A (depicting human KLK5 used in HDX experiments as SEQ ID NO: 353) shows sequence regions that are identified by hydrogen exchange measurements to be affected when in complex with each antibody, these sequence regions (underlined) are: region 1 (56-68, $pH_{exp}$ 8.0), region 2 (107-124, $pH_{exp}$ 6.0), region 3 (184-195, $pH_{exp}$ 8.0), region 4 (232-246, $pH_{exp}$ 6.0), effective time correction uses $pH_{ref}$=7.5. FIG. 12B shows the actual hydrogen exchange data for a representative peptide for each sequence region underlined in FIG. 12A.

Figure 13A-1:
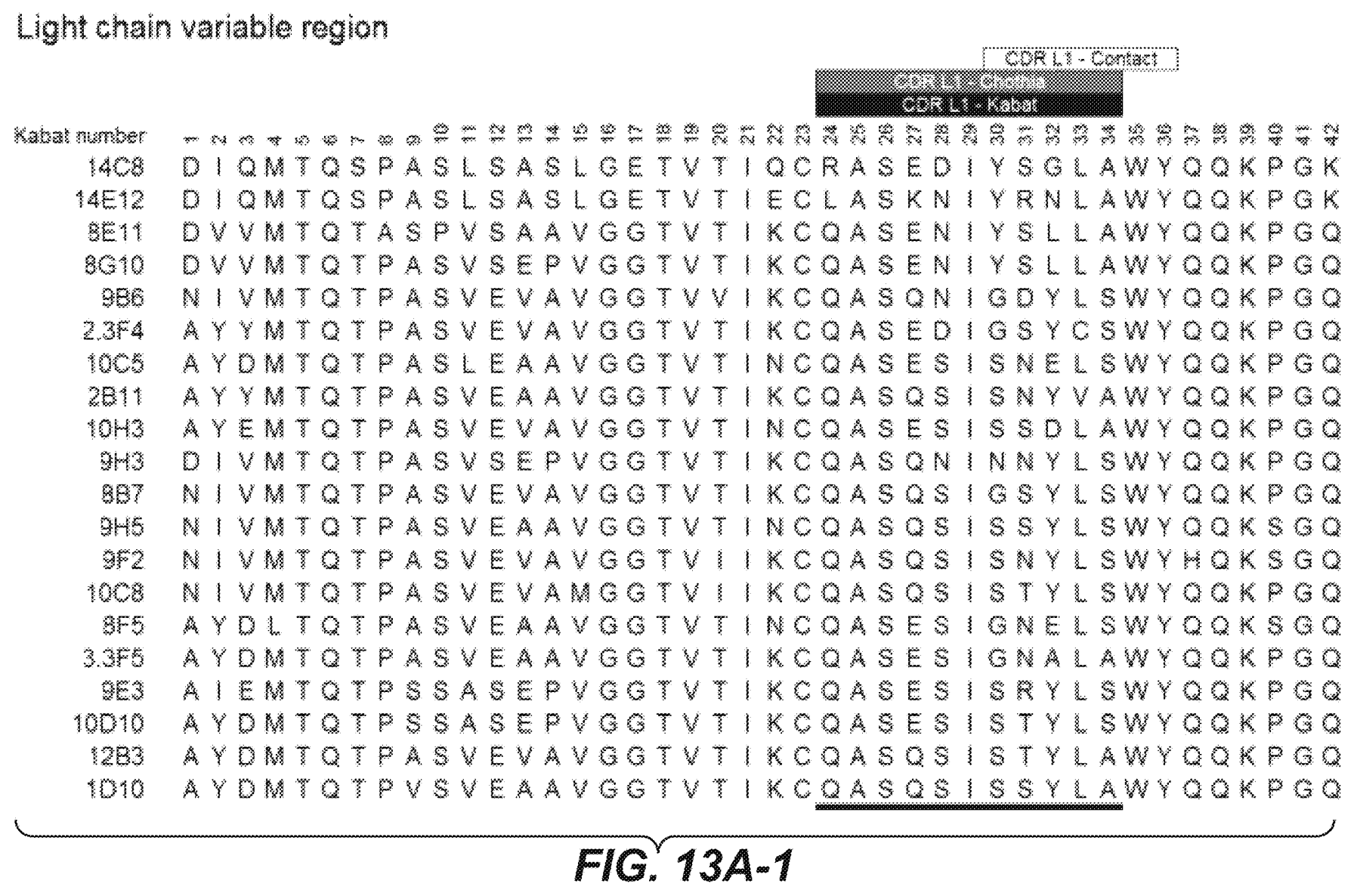
Figure 13A-2:
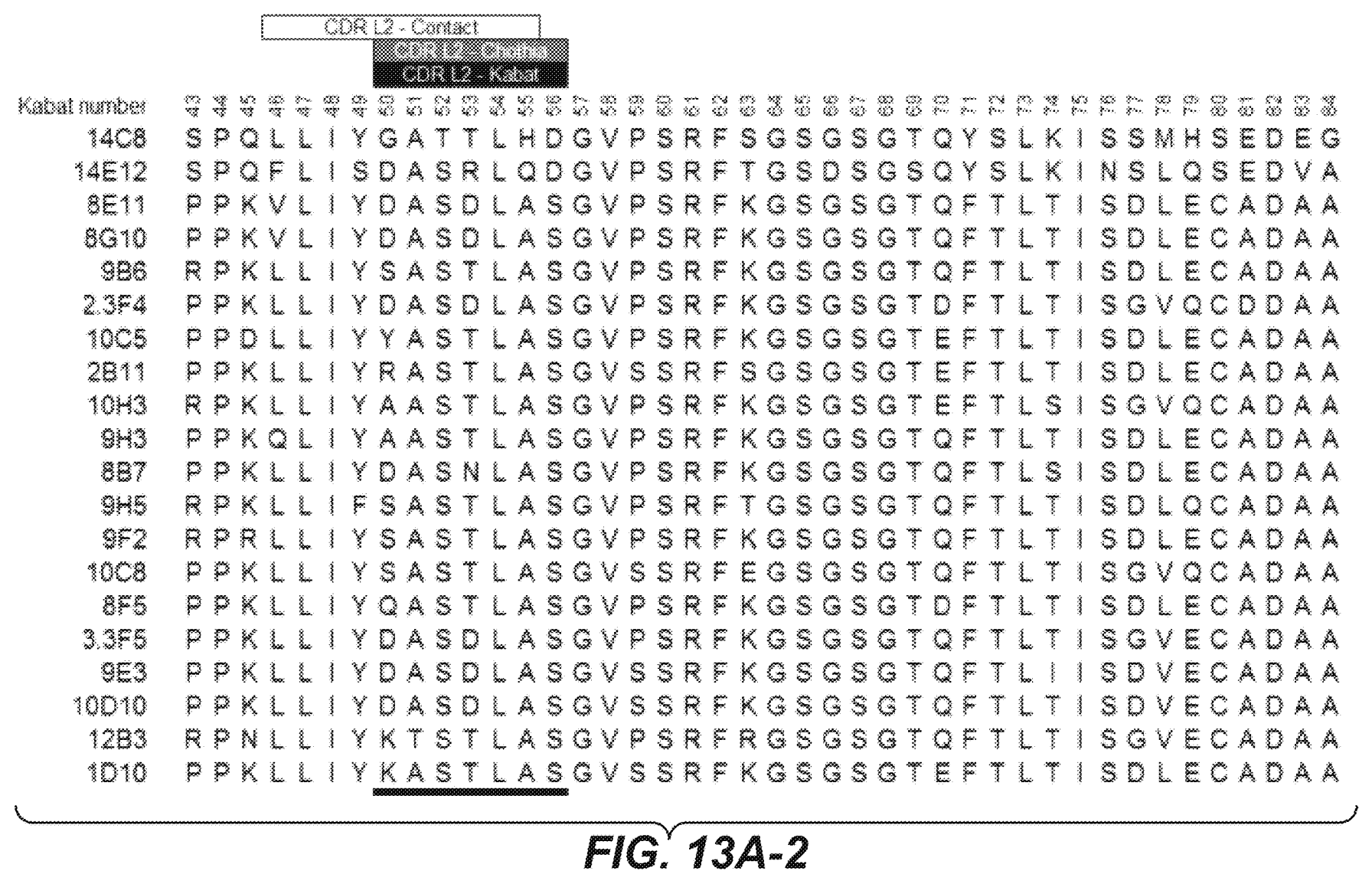
Figure 13B-2:
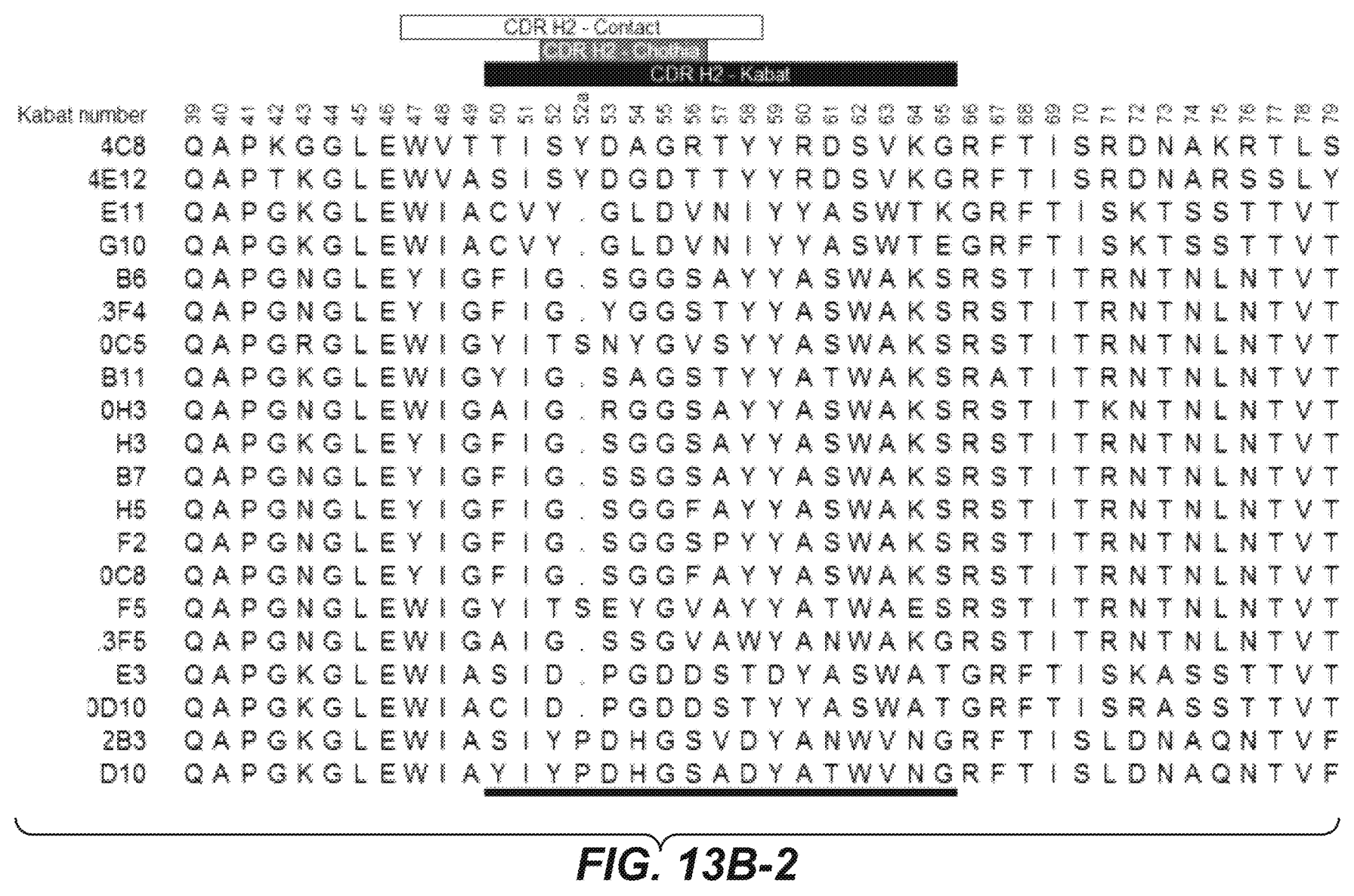

FIGS. 13A and 13B. FIG. 13A shows alignment of the light chain variable sequences of anti-KLK5 antibody clones 14C8 (SEQ ID NO: 128), 14E12 (SEQ ID NO: 129), 8E11 (SEQ ID NO: 130), 8G10 (SEQ ID NO: 131), 9B6 (SEQ ID NO: 132), 2-3F4 (SEQ ID NO: 133), 10C5 (SEQ ID NO: 134), 2B11 (SEQ ID NO: 141), 10H3 (SEQ ID NO: 142), 9H3 (SEQ ID NO: 143), 8B7 (SEQ ID NO: 144), 9H5 (SEQ ID NO: 145), 9F2 (SEQ ID NO: 152), 10C8 (SEQ ID NO: 153), 8F5 (SEQ ID NO: 154), 3-3F5 (SEQ ID NO: 155), 9E3 (SEQ ID NO: 163), 10D10 (SEQ ID NO: 164), 12B3 (SEQ ID NO: 165), 1D10 (SEQ ID NO: 166). FIG. 13B shows alignment of the heavy chain variable sequences of anti-KLK5 antibody clones 14C8 (SEQ ID NO: 167), 14E12 (SEQ ID NO: 168), 8E11 (SEQ ID NO: 169), 8G10 (SEQ ID NO: 170), 9B6 (SEQ ID NO: 171), 2-3F4 (SEQ ID NO: 172), 10C5 (SEQ ID NO: 173), 2B11 (SEQ ID NO: 203), 10H3 (SEQ ID NO: 204), 9H3 (SEQ ID NO: 205), 8B7 (SEQ ID NO: 206), 9H5 (SEQ ID NO: 207), 9F2 (SEQ ID NO: 226), 10C8 (SEQ ID NO: 227), 8F5 (SEQ ID NO: 228), 3-3F5 (SEQ ID NO: 229), 9E3 (SEQ ID NO: 258), 10D10 (SEQ ID NO: 259), 12B3 (SEQ ID NO: 260), 1D10 (SEQ ID NO: 261). Shown are also the CDR regions according to Kabat numbering.

FIGS. 14A and 14B. FIG. 14A shows alignment of the light chain variable sequences of the anti-KLK5 antibody clone 10C5 (SEQ ID NO: 134) and six humanized 10C5 clones (hu10C5-L1 (SEQ ID NO: 135), hu10C5-L2 (SEQ ID NO: 136), hu10C5-L3 (SEQ ID NO: 137), hu10C5-L4 (SEQ ID NO: 138), hu10C5-L5 (SEQ ID NO: 139), and hu10C5-L6 (SEQ ID NO: 321)). FIG. 14B shows alignment of the heavy chain variable sequences of the anti-KLK5 antibody clone 10C5 (SEQ ID NO: 173) and 28 humanized 10C5 clones (hu10C5-H1 (SEQ ID NO: 174), hu10C5-H2 (SEQ ID NO: 175), hu10C5-H3 (SEQ ID NO: 176), hu10C5-H4 (SEQ ID NO: 177), hu10C5-H5 (SEQ ID NO: 178), hu10C5-H6 (SEQ ID NO: 179), hu10C5-H7 (SEQ ID NO: 180), hu10C5-H8 (SEQ ID NO: 181), hu10C5-H9 (SEQ ID NO: 182), hu10C5-H10 (SEQ ID NO: 183), hu10C5-H11 (SEQ ID NO: 184), hu10C5-H12 (SEQ ID NO: 185), hu10C5-H13 (SEQ ID NO: 186), hu10C5-H14 (SEQ ID NO: 187), hu10C5-H15 (SEQ ID NO: 188), hu10C5-H16 (SEQ ID NO: 189), hu10C5-H17 (SEQ ID NO: 190), hu10C5-H18 (SEQ ID NO: 191), hu10C5-H19 (SEQ ID NO: 192), hu10C5-H20 (SEQ ID NO: 193), hu10C5-H21 (SEQ ID NO: 194), hu10C5-H22 (SEQ ID NO: 194), hu10C5-H23 (SEQ ID NO: 196), hu10C5-H24 (SEQ ID NO: 197), hu10C5-H25 (SEQ ID NO: 198), hu10C5-H26 (SEQ ID NO: 199), hu10C5-H27 (SEQ ID NO: 200), and hu10C5-H26 (SEQ ID NO: 201). The amino acid residues highlighted in black are the residues which were changed. Shown are also the CDR regions according to Kabat numbering.

FIGS. 15A and 15B. FIG. 15A shows alignment of the light chain variable sequences of the anti-KLK5 antibody clone 9H5 (SEQ ID NO: 145) and four humanized 9H5 clones (hu9H5-L1 (SEQ ID NO: 146), hu9H5-L2 (SEQ ID NO: 147), hu9H5-L3 (SEQ ID NO: 148), and hu9H5-L4

(SEQ ID NO: 149)). FIG. 15B shows alignment of the heavy chain variable sequences of the anti-KLK5 antibody clone 9H5 (SEQ ID NO: 207) and 17 humanized 9H5 clones (hu9H5-H1 (SEQ ID NO: 208), hu9H5-H2 (SEQ ID NO: 209), hu9H5-H3 (SEQ ID NO: 210), hu9H5-H4 (SEQ ID NO: 211), hu9H5-H5 (SEQ ID NO: 212), hu9H5-H6 (SEQ ID NO: 213), hu9H5-H7 (SEQ ID NO: 214), hu9H5-H8 (SEQ ID NO: 215), hu9H5-H9 (SEQ ID NO: 216), hu9H5-H10 (SEQ ID NO: 217), hu9H5-H11 (SEQ ID NO: 218), hu9H5-H12 (SEQ ID NO: 219), hu9H5-H13 (SEQ ID NO: 220), hu9H5-H14 (SEQ ID NO: 221), hu9H5-H15 (SEQ ID NO: 222), hu9H5-H16 (SEQ ID NO: 223), and hu9H5-H17 (SEQ ID NO: 224). The amino acid residues highlighted in black are the residues which were changed. Shown are also the CDR regions according to Kabat numbering.

FIGS. 16A and 16B. FIG. 16A shows alignment of the light chain variable sequences of the anti-KLK5 antibody clone 3-3F5 (SEQ ID NO: 155) and five humanized 3-3F5 clones (hu3-3F5-L1 (SEQ ID NO: 156), hu3-3F5-L2 (SEQ ID NO: 157), hu3-3F5-L3 (SEQ ID NO: 158), hu3-3F5-L4 (SEQ ID NO: 159), and hu3-3F5-L5 (SEQ ID NO: 160)). FIG. 16B shows alignment of the heavy chain variable sequences of the anti-KLK5 antibody clone 3-3F5 (SEQ ID NO: 229) and 27 humanized 3-3F5 clones (hu3-3F5-H1 (SEQ ID NO: 230), hu3-3F5-H2 (SEQ ID NO: 231), hu3-3F5-H3 (SEQ ID NO: 232), hu3-3F5-H4 (SEQ ID NO: 233), hu3-3F5-H5 (SEQ ID NO: 234), hu3-3F5-H6 (SEQ ID NO: 235), hu3-3F5-H7 (SEQ ID NO: 236), hu3-3F5-H8 (SEQ ID NO: 237), hu3-3F5-H9 (SEQ ID NO: 238), hu3-3F5-H10 (SEQ ID NO: 239), hu3-3F5-H11 (SEQ ID NO: 240), hu3-3F5-H12 (SEQ ID NO: 241), hu3-3F5-H13 (SEQ ID NO: 242), hu3-3F5-H14 (SEQ ID NO: 243), hu3-3F5-H15 (SEQ ID NO: 244), hu3-3F5-H16 (SEQ ID NO: 245), hu3-3F5-H17 (SEQ ID NO: 246), hu3-3F5-H18 (SEQ ID NO: 247), hu3-3F5-H19 (SEQ ID NO: 248), hu3-3F5-H20 (SEQ ID NO: 249), hu3-3F5-H21 (SEQ ID NO: 250), hu3-3F5-H22 (SEQ ID NO: 251), hu3-3F5-H23 (SEQ ID NO: 252), hu3-3F5-H24 (SEQ ID NO: 253), hu3-3F5-H25 (SEQ ID NO: 254), hu3-3F5-H26 (SEQ ID NO: 255), and hu3-3F5-H27 (SEQ ID NO: 256)). The amino acid residues highlighted in black are the residues which were changed. Shown are also the CDR regions according to Kabat numbering.

FIG. 18A shows an overlay of human KLK5 with KLK5-10C5 Fab complex. FIG. 18B shows the interface between human KLK5 and 10C5 Fab. The numbering of the amino acid residues of human KLK5 is based on the standard numbering for proteases. See Debela et al., *J Mol Biol*, 373, 1017-1031 (2007). The numbering of the amino acid residues of the Fab fragments is based on Kabat.

FIG. 19A shows an overlay of human KLK5 with KLK5-9H5 Fab complex. FIG. 19B shows the interface between human KLK5 and 9H5 Fab. The numbering of the amino acid residues of human KLK5 is based on the standard numbering for proteases. The numbering of the amino acid residues of the Fab fragments is based on Kabat.

FIG. 20A shows an overlay of human KLK5 with KLK5-3-3F5 Fab complex. FIG. 20B shows the interface between human KLK5 and 3-3F5 Fab. The numbering of the amino acid residues of human KLK5 is based on the standard numbering for proteases. The numbering of the amino acid residues of the Fab fragments is based on Kabat.

DETAILED DESCRIPTION OF EMBODIMENTS OF THE INVENTION

I. Definitions

Figure 1A:
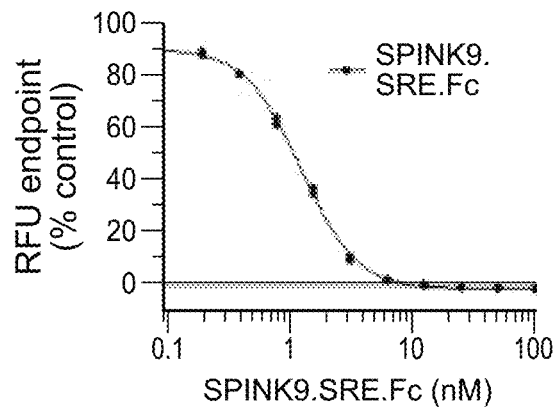
FIG. 1A-1N show the evaluation of each of the KLK5 inhibitors using fluorescent peptide substrate in the direct assay. 5 nM recombinant human KLK5 and 0.19-100 nM KLK5 inhibitors were pre-incubated for 30 minutes prior to addition of 50 µM Boc-VPR-AMC. Plates were examined every 102 s for 30-60 minute using a PHERAstar® Plus reader using a 340 nm excitation/460 nm emission module. The results for the KLK5 inhibitors are depicted as follows.

The terms "anti-KLK5 antibody" and "an antibody that binds to KLK5" refer to an antibody that is capable of binding KLK5 with sufficient affinity such that the antibody is useful as a diagnostic and/or therapeutic agent in targeting KLK5. In some embodiments, the extent of binding of an anti-KLK5 antibody to an unrelated polypeptide (polypeptide other than KLK5) is less than about 10% of the binding of the antibody to KLK5 as measured, e.g., by a radioimmunoassay (RIA). In some embodiments, an antibody that binds to KLK5 has a dissociation constant (Kd) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M). In some embodiments, an antibody that binds to KLK5 has an $IC_{50}$ value (concentration of an inhibitor, e.g. an antibody or fragment thereof, required to reduce the rate of an enzymatic reaction by 50%) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M). In some embodiments, an anti-KLK5 antibody binds to a binding region (e.g. an epitope) of KLK5 that is conserved among different species of KLK polypeptides.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

The term "isolated" as used in reference to antibody, binding polypeptide, polynucleotide or small molecule is one which has been separated from a component of its natural environment. In some embodiments, an antibody, binding polypeptide, polynucleotide or small molecule is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

The term "monoclonal antibody" as used herein refers to an antibody obtained from a population of substantially homogeneous antibodies, i.e., the individual antibodies comprising the population are identical and/or bind the same binding region (e.g., epitope), except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies described herein may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies.

A "blocking antibody" or an "antagonist antibody" is one which inhibits or reduces biological activity of the antigen it binds. Preferred blocking antibodies or antagonist antibodies substantially or completely inhibit the biological activity of the antigen.

The term "chimeric" antibody refers to an antibody in which a portion of the heavy and/or light chain is derived from a particular source or species, while the remainder of the heavy and/or light chain is derived from a different source or species.

The terms "full length antibody," "intact antibody," and "whole antibody" are used herein interchangeably to refer to an antibody (e.g., an anti-KLK5 antibody) having a structure substantially similar to a native antibody structure or having heavy chains that contain an Fc region.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In some embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" or an "antibody that binds to the same binding region" as a reference antibody refers to an antibody that blocks binding of the reference antibody to its binding partner (e.g., an antigen) in a competition assay by 50% or more, and conversely, the reference antibody blocks binding of the antibody to its binding partner in a competition assay by 50% or more.

The term "thermodynamic epitope", e.g. in the context of epitope mapping using hydrogen exchange mass spectrometry, refers to those portions of a protein whose backbone structural dynamics or local free energy of unfolding is altered in response to a specific binding event such as becoming bound by an antibody. The structural epitope may or may not be partially or entirely contained within the thermodynamic epitope.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest,* 5th Ed. Public Health Service, National Institutes of Health, Bethesda, MD (1991));

(c) antigen contacts occurring at amino acid residues 27c-36 (L1), 46-55 (L2), 89-96 (L3), (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra, e.g. as set out in FIGS. 13-16 as well as in the Table of Sequences herein below. Unless otherwise indicated, the CDRs are determined according to Kabat et al., supra.

The term "variable region" or "variable domain" refers to the domain of an antibody heavy or light chain that is involved in binding the antibody to an antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology,* 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, M D, 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda MD (1991), vols. 1-3. In one embodiment, for the VL, the subgroup is subgroup kappa I as in Kabat et al., supra. In one embodiment, for the VH, the subgroup is subgroup III as in Kabat et al., supra.

"Affinity" or "Binding Affinity" refers to the strength of the sum total of noncovalent interactions between a single binding site of a molecule (e.g., antibody, binding polypeptide, polynucleotide, small molecule) and its binding partner (e.g., an antigen). Unless indicated otherwise, as used herein, "binding affinity" refers to intrinsic binding affinity which reflects a 1:1 interaction between members of a binding pair (e.g., either of antibody, binding polypeptide, polynucleotide, small molecule and the antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

A "binding region" is the portion of the binding partner (e.g., an antigen) to which a KLK5 antibody selectively binds. For a binding polypeptide binding partner, a linear binding region can be a peptide portion of about 4-15 (e.g., 4, 5, 6, 7, 8, 9, 10, 11, 12, 13, 14 or 15) amino acid residues. A non-linear, conformational binding region may comprise residues of a polypeptide sequence brought to close vicinity in the three-dimensional (3D) structure of the binding polypeptide binding partner.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The terms "KLK5" and "Kallikrein-5," as used herein, refers to any native KLK5 from any vertebrate source, including mammals such as primates (e.g., humans) and rodents (e.g., mice and rats), unless otherwise indicated. The term encompasses "full-length," unprocessed KLK5 as well as any form of KLK5 that results from processing in the cell. The term also encompasses naturally occurring variants of KLK5, e.g., splice variants or allelic variants. In some embodiments, the amino acid sequence of an exemplary human KLK5 is UNIPROT Q9Y337. In some embodiments, the amino acid sequence of an exemplary human KLK5 is selected from the group consisting of SEQ ID NO:1, SEQ ID NO:2, SEQ ID NO:3, SEQ ID NO:4, SEQ ID NO:5, SEQ ID NO:6, SEQ ID NO:7, and SEQ ID NO:8. In some embodiments, the amino acid sequence of an exemplary human KLK5 is amino acid residues 23-293 (minus signal peptide) of UNIPROT Q9Y337 (G55, D153 variant) and is shown in SEQ ID NO:2. In some embodiments, the amino acid sequence of an exemplary human KLK5 is amino acid residues 23-293 (minus signal peptide) of the G55, N153 variant shown in SEQ ID NO:4. In some embodiments, the amino acid sequence of an exemplary human KLK5 is amino acid residues 23-293 (minus signal peptide) of the R55, N153 variant shown in SEQ ID NO:6. In some embodiments, the amino acid sequence of an exemplary human KLK5 is amino acid residues 23-293 (minus signal peptide) of the R55, D153 variant shown in SEQ ID NO:8.

The numbering in this paragraph below, relates to full-length unprocessed KLK5. In some embodiments, the amino acid sequence of the human KLK5 comprises the amino acid N at position 153. In some embodiments, the amino acid sequence of the human KLK5 comprises the amino acid D at position 153. In some embodiments, the amino acid sequence of the human KLK5 comprises the amino acid G at position 55. In some embodiments, the amino acid sequence of the human KLK5 comprises the amino acid R at position 55. In some embodiments, the amino acid sequence of the human KLK5 comprises the amino acid G at position 55 and the amino acid N at position 153. In some embodiments, the amino acid sequence of the human KLK5 comprises the amino acid G at position 55 and the amino acid D at position 153. In some embodiments, the amino acid sequence of the human KLK5 comprises the amino acid R at position 55 and the amino acid N at position 153. In some embodiments, the amino acid sequence of the human KLK5 comprises the amino acid R at position 55 and the amino acid D at position 153.

The numbering in this paragraph below, relates to full-length unprocessed KLK5. In some embodiments, the nucleic acid sequence of the human KLK5 comprises a sequence encoding an N at position 153. In some embodiments, the nucleic acid sequence of the human KLK5 comprises a sequence encoding a D at position 153. In some embodiments, the nucleic acid sequence of the human KLK5 comprises a sequence encoding a G at position 55. In some embodiments, the nucleic acid sequence of the human KLK5 comprises a sequence encoding an R at position 55. In some embodiments, the nucleic acid sequence of the human KLK5 comprises a sequence encoding a G at position 55 and an N at position 153. In some embodiments, the nucleic acid sequence of the human KLK5 comprises a sequence encoding G at position 55 and a D at position 153. In some embodiments, the nucleic acid sequence of the human KLK5 comprises a sequence encoding R at position 55 and an N at position 153. In some embodiments, the nucleic acid sequence of the human KLK5 comprises a sequence encoding an R at position 55 and a D at position 153.

The terms "SPINK5" and "Serine protease inhibitor Kazal-type 5," as used herein, refers to any native SPINK5 from any vertebrate source, including mammals such as primates (e.g., humans) and rodents (e.g., mice and rats), unless otherwise indicated. The term encompasses "full-length," unprocessed SPINK5 as well as any form of SPINK5 that result from processing in the cell. The term also encompasses naturally occurring variants of SPINK5, e.g., splice variants or allelic variants. In some embodiments, the amino acid sequence of an exemplary human SPINK5 is UNIPROT Q9NQ38 and is shown in SEQ ID NO:9. In some embodiments, the amino acid sequence of an exemplary human SPINK5 is amino acid residues 23-1064 (minus signal peptide) of UNIPROT Q9NQ38 and is shown in SEQ ID NO:10.

The term "SPINK fusion polypeptide" as used herein refers to a fusion polypeptide in which a SPINK polypeptide or a fragment thereof (e.g., certain domains of the SPINK polypeptide (e.g., SPINK5 and/or SPINK9) is linked, directly or indirectly, to another polypeptide (e.g., non-SPINK polypeptide).

The term "SPINK Fc fusion polypeptide" as used herein refers to a fusion polypeptide in which a SPINK polypeptide or a fragment thereof (e.g., certain domains of the SPINK polypeptide (e.g., SPINK5 and/or SPINK9) is linked, directly or indirectly, to an Fc region. In some embodiments, the Fc region is selected from the group consisting of an IgG1 Fc region, IgG2a Fc region and IgG4 Fc region. In some embodiments, the Fc region is an IgG2a Fc region. In some embodiments, the IgG2a Fc region is a mouse IgG2a Fc region. In some embodiments, the Fc region is an IgG1 Fc region. In some embodiments, the IgG1 Fc region is a human IgG1 Fc region. In some embodiments, the Fc region is an IgG4 Fc region. In some embodiments, the IgG4 Fc region is a human IgG4 Fc region. In some embodiments, the SPINK polypeptide or a fragment thereof is a human SPINK polypeptide or a fragment thereof. In some embodiments, the SPINK polypeptide or a fragment thereof is a mouse SPINK polypeptide or a fragment thereof. It is understood that minor sequence variations such as insertions, deletions, substitutions, especially conservative amino acid substitutions of the SPINK polypeptide, the SPINK domains or the Fc that do not affect the function and/or activity of the SPINK polypeptide, the SPINK domains or the SPINK Fc fusion polypeptide are provided herein. In some embodiments, the SPINK Fc fusion polypeptide provided herein can bind to KLK5, which can lead to inhibition of KLK5. In some embodiments, the SPINK polypeptide or a fragment thereof is SPINK 9. In some embodiments, the SPINK Fc fusion polypeptide is SPINK9.SRE.Fc (SEQ ID NO:320).

The term "polypeptide" as used herein, refers to any native polypeptide of interest (e.g., KLK5, or SPINK5) from any vertebrate source, including mammals such as primates (e.g., humans) and rodents (e.g., mice and rats), unless otherwise indicated. The term encompasses "full-length," unprocessed polypeptide as well as any form of the polypeptide that results from processing in the cell. The term also encompasses naturally occurring variants of the polypeptide, e.g., splice variants or allelic variants.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, a-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

An "isolated" polynucleotide or nucleic acid refers to a molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-KLK5 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "KLK5 genomic sequence" as used herein, refers to either the cDNA and/or the genomic form of the KLK5 gene, which may include introns as well as upstream and downstream regulatory sequences.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

A "reference sample", "reference cell", "reference tissue", "control sample", "control cell", or "control tissue", as used herein, refers to a sample, cell, tissue, standard, or level that is used for comparison purposes. In one embodiment, a reference sample, reference cell, reference tissue, control sample, control cell, or control tissue is obtained from a healthy and/or non-diseased part of the body (e.g., tissue or cells) of the same subject. For example, healthy and/or non-diseased cells or tissue adjacent to the diseased cells or tissue (e.g., cells or tissue adjacent to a tumor). In another embodiment, a reference sample is obtained from an untreated tissue and/or cell of the body of the same subject. In yet another embodiment, a reference sample, reference cell, reference tissue, control sample, control cell, or control tissue is obtained from a healthy and/or non-diseased part of the body (e.g., tissues or cells) of another subject. In even another embodiment, a reference sample, reference cell, reference tissue, control sample, control cell, or control tissue is obtained from an untreated tissue and/or cell of the body of another subject.

The term "sample," as used herein, refers to a formulation that is obtained or derived from a subject of interest that contains a cellular and/or other molecular entity that is to be characterized and/or identified, for example based on physical, biochemical, chemical and/or physiological characteristics. For example, the phrase "disease sample" and variations thereof refers to any sample obtained from a subject of interest that would be expected or is known to contain the cellular and/or molecular entity that is to be characterized. Samples include, but are not limited to, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, blood-derived cells, urine, cerebrospinal fluid, saliva, sputum, tears, perspiration, mucus, tumor lysates, and tissue culture medium, tissue extracts such as homogenized tissue, tumor tissue, cellular extracts, and combinations thereof.

By "tissue sample" or "cell sample" is meant a collection of similar cells obtained from a tissue of a subject. The source of the tissue or cell sample may be solid tissue as from a fresh, frozen and/or preserved organ, tissue sample, biopsy, and/or aspirate; blood or any blood constituents such as plasma; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like.

An "effective amount" of an agent, e.g., a pharmaceutical formulation, refers to an amount effective, at dosages and for periods of time necessary, to achieve the desired therapeutic result.

A "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In some embodiments, the subject is a human.

The term "patient" as used herein, refers to an animal, such as a mammal. In one embodiment, patient refers to a human.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "Th2-high asthma" as used herein, refers to asthma that exhibits high levels of one or more Th2 cell-related cytokines, for example, IL13, IL4, IL9, IL5, or that exhibits Th2 cytokine-associated inflammation. In some embodiments, the term Th2-high asthma may be used interchangeably with eosinophil-high asthma. In some embodiments, the Th2-high asthma is Th2 driven asthma. In some embodiments, the asthma patient has been determined to be Eosinophilic Inflammation Positive (EIP). See, e.g., International Patent Application Publication No. WO 2015/061441, which is incorporated by reference herein in its entirety. In some embodiments, the subject has been determined to have elevated levels of at least one of the eosinophilic signature genes as compared to a control or reference level. See WO2015/061441. In some embodiments, the Th2-high asthma is periostin-high asthma. In some embodiments, the subject has high serum periostin. In some embodiments, the subject is eighteen years or older. In some embodiments, the subject has been determined to have an elevated level of serum periostin as compared to a control or reference level. In some embodiments, the control or reference level is the median level of periostin in a population. In some embodiments, the subject has been determined to have 20 ng/ml or higher serum periostin. In some embodiments, the subject has been determined to have 25 ng/ml or higher serum periostin. In some embodiments, the subject has been determined to have ng/ml or higher serum periostin. In some embodiments, the control or reference level of serum periostin is 20 ng/ml, 25 ng/ml, or 50 ng/ml. In some embodiments, the asthma is eosinophil-high asthma. In some embodiments, the subject has been determined to have an elevated eosinophil count as compared to a control or reference level. In some embodiments, the control or reference level is the median level of a population. In some embodiments, the subject has been determined to have 150 or higher eosinophil count/µl blood. In some embodiments, the subject has been determined to have 200 or higher eosinophil count/µl blood. In some embodiments, the subject has been determined to have 250 or higher eosinophil count/µl blood. In some embodiments, the subject has been determined to have 300 or higher eosinophil count/µl blood. In some embodiments, the subject has been determined to have 350 or higher eosinophil count/µl blood. In some embodiments, the subject has been determined to have 400 or higher eosinophil count/µl blood. In some embodiments, the subject has been determined to have 450 or higher eosinophil count/µl blood. In some embodiments, the subject has been determined to have 500 or higher eosinophil count/µl blood. In some preferred embodiments, the subject has been determined to have 300 or higher eosinophil count/µl blood. In some embodiments, the eosinophils are peripheral blood eosinophils. In some embodiments, the eosinophils are sputum eosinophils. In some embodiments, the subject exhibits elevated level of FeNO (fractional exhaled nitric acid) and/or elevated level of IgE. For example, in some instances, the subject exhibits a FeNO level above any of about 5 ppb (parts per billion), 10 ppb, 15 ppb, 20 ppb, 25 ppb, 30 ppb, 35 ppb, 40 ppb, 45 ppb, 50 ppb, 60 ppb, 70 ppb, 80 ppb, 90 ppb and 100 ppb. In some instances, the subject has an IgE level that is above 50 IU/ml.

The term "Th2-low asthma", "non-Th2-high asthma", "type 2-low asthma", "T2-low asthma", "non-eosinophilic asthma", pauci-granulocytic asthma", or "pauci-inflammatory asthma", as used herein, refers to asthma that exhibits low levels of one or more Th2 cell-related cytokines, for example, IL13, IL4, IL9, IL5, or exhibits non-Th2 cytokine-associated inflammation. In some embodiments, the term Th2-low asthma may be used interchangeably with eosinophil-low asthma. In some embodiments, the asthma patient has been determined to be Eosinophilic Inflammation Negative (EIN). See, e.g., WO 2015/061441. In some embodiments, the Th2-low asthma is Th17-driven asthma. In some embodiments, the Th2-low asthma is periostin-low asthma. In some embodiments, the subject is eighteen years or older. In some embodiments, the subject has been determined to have a reduced level of serum periostin as compared to a control or reference level. In some embodiments, the control or reference level is the median level of periostin in a population. In some embodiments, the subject has been determined to have less than 20 ng/ml serum periostin. In some embodiments, the asthma is eosinophil-low asthma. In some embodiments, the subject has been determined to have a reduced eosinophil count as compared to a control or reference level. In some embodiments, the control or reference level is the medium level of a population. In some embodiments, the subject has been determined to have less than 150 eosinophil count/µl blood. In some embodiments, the subject has been determined to have less than 100 eosinophil count/µl blood. In certain preferred embodiments, the subject has been determined to have less than 300 eosinophil count/µl blood.

"Treatment" (and variations such as "treat" or "treating") refers to clinical intervention in an attempt to alter the natural course of the subject or cell being treated. Desirable effects of treatment include one or more of preventing occurrence or recurrence of disease, alleviation of symptoms, diminishment of any direct or indirect pathological consequences of the disease, stabilized (i.e., not worsening) state of disease, decreasing the rate of disease progression, amelioration or palliation of the disease state, prolonging survival as compared to expected survival if not receiving treatment and improved prognosis.

The term "package insert" is used to refer to instructions customarily included in commercial packages of therapeutic products, that contain information about the indications, usage, dosage, administration, combination therapy, contraindications and/or warnings concerning the use of such therapeutic products.

The use of the terms "a" and "an" and "the" and similar terms in the context of describing embodiments herein are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. It is understood that aspects and embodiments provided herein include "consisting" and/or "consisting essentially of" aspects and embodiments.

As is understood by one skilled in the art, reference to "about" a value or parameter herein includes (and describes) embodiments that are directed to that value or parameter per se. For example, description referring to "about X" includes description of "X".

The phrase "substantially different," refers to a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values may be, for example, greater than about 10%, greater than about 20%, greater than about 30%, greater than about 40%, and/or greater than about 50% as a function of the value for the reference/comparator molecule.

II. Compositions and Methods

In one aspect, the invention is based, in part, on the discovery of KLK5 antibodies that inhibit the biological activity of KLK5. In some embodiments, antibodies that bind to KLK5 are provided. In some embodiments, an isolated antibody that binds to KLK5 is provided, i.e. an anti-KLK5 antibody. In some embodiments, the anti-KLK5 antibody inhibits the biological activity of KLK5. In some embodiments, the anti-KLK5 antibody substantially or completely inhibits the biological activity of KLK5. In some embodiments, the biological activity of KLK5 is serine protease activity. In some embodiments, the biological activity of KLK5 is tryptic-like serine protease activity. In some embodiments, the biological activity of KLK5 is KLK5 promoted human smooth muscle cell proliferation and contraction. In some embodiments, the biological activity of KLK5 is KLK5 induced epithelial expression of inflammatory cytokines, chemokines, and adhesion molecules. In some embodiments, the biological activity of KLK5 is KLK5 induced epithelium production of neutrophil chemotactic cytokines and neutrophil influx into the lung tissues. In some embodiments, the biological activity of KLK5 is inhibited by at least about any of 40%, 50%, 60%, 70%, 80%, 90% and/or more. In some embodiments, the biological activity of the KLK5 is inhibited by about any of 40%, 50%, 60%, 70%, 80%, 90% and/or more. In some embodiments, the biological activity of the KLK5 is inhibited by between any of 40-50%, 50-60%, 60-70%, 70-80%, 80-90%, and/or 90-100%.

In some embodiments of any of the anti-KLK5 antibodies, the anti-KLK5 antibody substantially or completely inhibits binding of SPINK5 to KLK5. In some embodiments, binding of SPINK5 to KLK5 is inhibited by at least about any of 40%, 50%, 60%, 70%, 80%, 90% and/or more. In some embodiments, binding of SPINK5 to KLK5 is inhibited by about any of 40%, 50%, 60%, 70%, 80%, 90% and/or more. In some embodiments, binding of SPINK5 to KLK5 is inhibited by between any of 40-50%, 50-60%, 60-70%, 70-80%, 80-90%, and/or 90-100%.

In some embodiments of any of the anti-KLK5 antibodies, the anti-KLK5 antibody has an $IC_{50}$ value of less than about any of 1000 nM, 500 nM, 100 nM, 50 nM, 10 nM, 5 nM, 1 nM, 500 pM, 100 pM, 50 pM, 10 pM, 5 pM, and/or 1 pM. In some embodiments, the anti-KLK5 antibody has an $IC_{50}$ value of less than any of 1000 nM, 500 nM, 100 nM, 50 nM, 10 nM, 5 nM, 1 nM, 500 pM, 100 pM, 50 pM, 10 pM, 5 pM, and/or 1 pM. In some embodiments, the anti-KLK5 antibody has an $IC_{50}$ value of between about any of 50 μM-1 μM, 1 μM-500 nM, 500 nM-100 nM, 100 nM-10 nM, 10 nM-1 nM, 1000 pM-500 pM, 500 pM-200 pM, 200 pM-150 pM, 150 pM-100 pM, 100 pM-10 pM, and/or 10 pM-1 pM.

Antibodies provided herein are useful, e.g., for the diagnosis or treatment of disease selected from the group consisting of Netherton Syndrome, asthma, atopic dermatitis, psoriasis, and rosacea. In some embodiments, the disease is selected from the group consisting of Netherton Syndrome, asthma, atopic dermatitis, psoriasis, rosacea and eosinophilic esophagitis. In some embodiments, the asthma is persistent chronic severe asthma with acute events of worsening symptoms (exacerbations or flares) that can be life threatening. In some embodiments, the asthma is atopic (also known as allergic) asthma, non-allergic asthma (e.g., often triggered by infection with a respiratory virus (e.g., influenza, parainfluenza, rhinovirus, human metapneumovirus, and respiratory syncytial virus) or inhaled irritant (air pollutants, smog, diesel particles, volatile chemicals and gases indoors or outdoors, or even by cold dry air). In some embodiments, the asthma is intermittent or exercise-induced, asthma due to acute or chronic primary or secondhand exposure to "smoke" (typically cigarettes, cigars, pipes), inhaling or "vaping" (tobacco, marijuana or other such substances), or asthma triggered by recent ingestion of aspirin or related NSAIDS. In some embodiments, the asthma is mild, or corticosteroid naïve asthma, newly diagnosed and untreated asthma, or not previously requiring chronic use of inhaled topical or systemic steroids to control the symptoms (cough, wheeze, shortness of breath/breathlessness, or chest pain). In some embodiments, the asthma is chronic, corticosteroid resistant asthma, corticosteroid refractory asthma, asthma uncontrolled on corticosteroids or other chronic asthma controller medications. In some embodiments, the asthma is moderate to severe asthma. In some embodiments, the asthma is Th2-high asthma. In some embodiments, the asthma is severe asthma. In some embodiments, the asthma is atopic asthma, allergic asthma, non-allergic asthma (e.g., due to infection and/or respiratory syncytial virus (RSV)), exercise-induced asthma, aspirin sensitive/exacerbated asthma, mild asthma, moderate to severe asthma, corticosteroid naïve asthma, chronic asthma, corticosteroid resistant asthma, corticosteroid refractory asthma, newly diagnosed and untreated asthma, asthma due to smoking, asthma uncontrolled on corticosteroids. In some embodiments, the asthma is T helper lymphocyte type 2 (Th2) or type 2 (Th2) high, or Type 2 (T2)-driven asthma. In some embodiments, the asthma is eosinophilic asthma. In some embodiments, the asthma is allergic asthma. In some embodiments, the subject has been determined to be Eosinophilic Inflammation Positive (EIP). See WO2015/061441. In some embodiments, the asthma is periostin-high asthma (e.g., having periostin level at least about any of 20 ng/mL, 25 ng/mL, or 50 ng/mL serum). In some embodiments, the asthma is eosinophil-high asthma (e.g., at least about any of 150, 200, 250, 300, 350, 400 eosinophil counts/ml blood). In some embodiments, the asthma is Th2-low asthma or nonTh2-driven asthma. In some embodiments, the subject has been determined to be Eosinophilic Inflammation Negative (EIN). See WO2015/061441. In some embodiments, the asthma is periostin-low asthma (e.g., having periostin level less than about 20 ng/mL serum). In some embodiments, the asthma is eosinophil-low asthma (e.g., less than about 150 eosinophil counts/1A blood or less than about 100 eosinophil counts/1A blood).

A. Exemplary Anti-KLK5 Antibodies

Provided herein are isolated antibodies that bind to KLK5. In one embodiment, the antibody inhibits the biological activity of KLK5 by at least 50%. KLK5 is a (chymo)-trypsin-like serine proteases that is expressed in human skin, specifically in the upper spinous and granular layers of the skin. KLK5 is known to play pathological roles in skin disorders such as Netherton Syndrome.

An exemplary naturally occurring human KLK5 precursor protein sequence, with signal peptide (amino acids 1-22) is provided in SEQ ID NO:1. The corresponding mature KLK5 protein sequence corresponding to amino acids 23-293 of SEQ ID NO:1 is provided in SEQ ID NO:2. Exemplary variants of human KLK5 precursor proteins with signal peptides containing either one or both of the amino acid exchanges R55 and N153 are provided in SEQ ID NO:3, SEQ ID NO:4, SEQ ID NO:5, SEQ ID NO:6, SEQ ID NO:7 and SEQ ID NO:8, respectively.

In certain embodiments, an anti-KLK5 antibody has one or more of the following characteristics, in any combination:
a) inhibits the biological activity of KLK5 by at least 50%, at least 60%, at least 70%, at least 80%, at least 90%, or 100%;
b) inhibits the serine protease activity of KLK5;
c) binds specifically to human KLK5;
d) has an $IC_{50}$ value of less than 10 nM, less than 5 nM, less than 3 nM, less than 2 nM, less than 1 nM, less than 0.5 nM, less than 0.1 nM; and/or
e) has an $IC_{50}$ value of less than 500 pM, less than 200 pM, less than 100 pM, less than 50 pM, less than 25 pM, less than 10 pM, less than 5 pM, less than 1 pM.

Antibody 8G10, 9B6, 2-3F4, 10C5, 2B11, 10H3, 9H3, 8B7, 9H5, 9F2, 10C8, 8F5, 3-3F5 and Other Embodiments In one aspect, an anti-KLK5 antibody is provided comprising at least one, two, three, four, five, or six HVRs selected from (a) HVR-H1 comprising the amino acid sequence selected from any one of SEQ ID NOs:14-24; (b) HVR-H2 comprising the amino acid sequence selected from any one of SEQ ID NOs:32-53; (c) HVR-H3 comprising the amino acid sequence selected from any one of SEQ ID NOs:62-72; (d) HVR-L1 comprising the amino acid sequence selected from any one of SEQ ID NOs:79-91; (e) HVR-L2 comprising the amino acid sequence selected from any one of SEQ ID NOs:99-106; and (f) HVR-L3 comprising the amino acid sequence selected from any one of SEQ ID NOs:112-122.

In one aspect, an anti-KLK5 antibody is provided comprising at least one, at least two, or all three VH HVR sequences selected from (a) HVR-H1 comprising the amino acid sequence selected from any one of SEQ ID NOs:14-24; (b) HVR-H2 comprising the amino acid sequence selected from any one of SEQ ID NOs:32-53; (c) HVR-H3 comprising the amino acid sequence selected from any one of SEQ ID NOs:62-72. In one embodiment, the antibody comprises HVR-H3 comprising the amino acid sequence selected from any one of SEQ ID NOs:62-72. In another embodiment, the antibody comprises HVR-H3 comprising the amino acid sequence selected from any one of SEQ ID NOs:62-72 and HVR-L3 comprising the amino acid sequence selected from any one of SEQ ID NOs:112-122. In a further embodiment, the antibody comprises HVR-H3 comprising the amino acid sequence selected from any one of SEQ ID NOs:62-72, HVR-L3 comprising the amino acid sequence selected from any one of SEQ ID NOs:112-122, and HVR-H2 comprising the amino acid sequence selected from any one of SEQ ID NOs:32-53. In a further embodiment, the antibody comprises (a) HVR-H1 comprising the amino acid sequence selected from any one of SEQ ID NOs:14-24; (b) HVR-H2 comprising the amino acid sequence selected from any one of SEQ ID NOs:32-53; and (c) HVR-H3 comprising the amino acid sequence selected from any one of SEQ ID NOs:62-72.

In another aspect, an anti-KLK5 antibody is provided comprising at least one, at least two, or all three VL HVR sequences selected from (a) HVR-L1 comprising the amino acid sequence selected from any one of SEQ ID NOs:79-91; (b) HVR-L2 comprising the amino acid sequence selected from any one of SEQ ID NOs:99-106; and (c) HVR-L3 comprising the amino acid sequence selected from any one of SEQ ID NOs:112-122. In one embodiment, the antibody comprises (a) HVR-L1 comprising the amino acid sequence selected from any one of SEQ ID NOs:79-91; (b) HVR-L2 comprising the amino acid sequence selected from any one of SEQ ID NOs:99-106; and (c) HVR-L3 comprising the amino acid sequence selected from any one of SEQ ID NOs:112-122.

In another aspect, an anti-KLK5 antibody is provided comprises (a) a VH domain comprising at least one, at least two, or all three VH HVR sequences selected from (i) HVR-H1 comprising the amino acid sequence selected from any one of SEQ ID NOs:14-24, (ii) HVR-H2 comprising the amino acid sequence selected from any one of SEQ ID NOs:32-53, and (iii) HVR-H3 comprising the amino acid sequence selected from any one of SEQ ID NOs:62-72; and (b) a VL domain comprising at least one, at least two, or all three VL HVR sequences selected from (i) HVR-L1 comprising the amino acid sequence selected from any one of SEQ ID NOs:79-91, (ii) HVR-L2 comprising the amino acid sequence selected from any one of SEQ ID NOs:99-106, and (c) HVR-L3 comprising the amino acid sequence selected from any one of SEQ ID NOs:112-122.

In another aspect, an anti-KLK5 antibody is provided comprising (a) HVR-H1 comprising the amino acid sequence selected from any one of SEQ ID NOs:14-24; (b) HVR-H2 comprising the amino acid sequence selected from any one of SEQ ID NOs:32-53; (c) HVR-H3 comprising the amino acid sequence selected from any one of SEQ ID NOs:62-72; (d) HVR-L1 comprising the amino acid sequence selected from any one of SEQ ID NOs:79-91; (e) HVR-L2 comprising the amino acid sequence selected from any one of SEQ ID NOs:99-106; and (f) HVR-L3 comprising the amino acid sequence selected from any one of SEQ ID NOs:112-122.

In any of the above embodiments, an anti-KLK5 antibody is humanized. In one embodiment, an anti-KLK5 antibody comprises HVRs as in any of the above embodiments, and further comprises an acceptor human framework, e.g. a human immunoglobulin framework or a human consensus framework.

In another aspect, an anti-KLK5 antibody is provided comprising a heavy chain variable domain (VH) sequence having at least any of 90%, 91%, 92%, 93%, 94%, 95%, 96%, 97%, 98%, 99%, or 100% sequence identity to the amino acid sequence selected from any one of SEQ ID NO:170-257. In certain embodiments, a VH sequence having at least any of 90%, 91%, 92%, 93%, 94%, 95%, 96%, 97%, 98%, or 99% identity to the amino acid sequence selected from any one of SEQ ID NO:170-257 contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in any one of SEQ ID NO:170-257. In certain embodiments, substitutions, insertions, or deletions occur in regions outside the HVRs (i.e., in the FRs). Optionally, the anti-KLK5 antibody comprises the VH sequence selected from any one of SEQ ID NO:170-257, including post-translational modifications of that sequence. In a particular embodiment, the VH comprises one, two or three HVRs selected from: (a) HVR-H1 comprising the amino acid sequence selected from any one of SEQ ID NOs:14-24; (b) HVR-H2 comprising the amino acid sequence selected from any one of SEQ ID NOs:32-53; (c) HVR-H3 comprising the amino acid sequence selected from any one of SEQ ID NOs:62-72.

In another aspect, an anti-KLK5 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence selected from any one of SEQ ID NO:131-161. In certain embodiments, a VL sequence having at least 90%, 91%, 92%, 93%, 94%, 95%, 96%, 97%, 98%, or 99% identity to the amino acid sequence selected from any one of SEQ ID NO:131-162 contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in the amino acid sequence selected from any one of SEQ ID NO:131-162. In certain embodiments, the substitutions, insertions, or deletions occur in regions outside the HVRs (i.e., in the FRs). Optionally, the anti-KLK5 antibody comprises the VL sequence of the amino acid sequence selected from any one of SEQ ID NO:131-162, including post-translational modifications of that sequence. In a particular embodiment, the VL comprises one, two or three HVRs selected from (a) HVR-L1 comprising the amino acid sequence selected from any one of SEQ ID NOs:79-91; (b) HVR-L2 comprising the amino acid sequence selected from any one of SEQ ID NOs:99-106; and (c) HVR-L3 comprising the amino acid sequence selected from any one of SEQ ID NOs:112-122.

In another aspect, an anti-KLK5 antibody is provided, wherein the antibody comprises a VH as in any of the embodiments provided above, and a VL as in any of the embodiments provided above. In one embodiment, the antibody comprises the VH and VL sequences in SEQ ID NO:170 and SEQ ID NO:131, respectively, including post-translational modifications of those sequences. In one embodiment, the antibody comprises the VH and VL sequences in SEQ ID NO:171 and SEQ ID NO:132, respectively, including post-translational modifications of those sequences. In one embodiment, the antibody comprises the VH and VL sequences in SEQ ID NO:172 and SEQ ID NO:133, respectively, including post-translational modifications of those sequences. In one embodiment, the antibody comprises the VH and VL sequences in SEQ ID NO:201 and SEQ ID NO:139, respectively, including post-translational modifications of those sequences. In one embodiment, the antibody comprises the VH and VL sequences in SEQ ID NO:203 and SEQ ID NO:141, respectively, including post-translational modifications of those sequences. In one embodiment, the antibody comprises the VH and VL sequences in SEQ ID NO:204 and SEQ ID NO:142, respectively, including post-translational modifications of those sequences. In one embodiment, the antibody comprises the VH and VL sequences in SEQ ID NO:205 and SEQ ID NO:143, respectively, including post-translational modifications of those sequences. In one embodiment, the antibody comprises the VH and VL sequences in SEQ ID NO:206 and SEQ ID NO:144, respectively, including post-translational modifications of those sequences. In one embodiment, the antibody comprises the VH and VL sequences in SEQ ID NO:221 and SEQ ID NO:149, respectively, including post-translational modifications of those sequences. In one embodiment, the antibody comprises the VH and VL sequences in SEQ ID NO:226 and SEQ ID NO:152, respectively, including post-translational modifications of those sequences. In one embodiment, the antibody comprises the VH and VL sequences in SEQ ID NO:227 and SEQ ID NO:153, respectively, including post-translational modifications of those sequences. In one embodiment, the antibody comprises the VH and VL sequences in SEQ ID NO:228 and SEQ ID NO:154, respectively, including post-translational modifications of those sequences. In one embodiment, the antibody comprises the VH and VL sequences in SEQ ID NO:248 and SEQ ID NO:160, respectively, including post-translational modifications of those sequences.

In a further aspect, an anti-KLK5 antibody is provided that binds to the same epitope as an anti-KLK5 antibody provided herein. For example, in certain embodiments, an antibody is provided that binds to the same epitope as an anti-KLK5 antibody comprising a VH sequence of the amino acid sequence selected from any one of SEQ ID NO:170-257. In certain embodiments, an antibody is provided that, when bound to KLK5 results in a thermodynamic epitope comprising one or more of the sequences selected from the group consisting of SEQ ID NO:316, SEQ ID NO:317, SEQ ID NO:318, and SEQ ID NO:319 as measured by hydrogen exchange mass spectrometry.

In another aspect, an anti-KLK5 antibody is provided, wherein the antibody comprises a HC sequence of the amino acid sequence selected from any one of SEQ ID NO:288-306. In another aspect, an anti-KLK5 antibody is provided, wherein the antibody comprises a LC sequence of the amino acid sequence selected from any one of SEQ ID NO:265-280.

In one embodiment, the antibody comprises the HC and LC sequences in SEQ ID NO:288 and SEQ ID NO:265, respectively, including post-translational modifications of those sequences. In one embodiment, the antibody comprises the HC and LC sequences in SEQ ID NO:289 and SEQ ID NO:266, respectively, including post-translational modifications of those sequences. In one embodiment, the antibody comprises the HC and LC sequences in SEQ ID NO:290 and SEQ ID NO:267, respectively, including post-translational modifications of those sequences. In one embodiment, the antibody comprises the HC and LC sequences in SEQ ID NO:292 and SEQ ID NO:269, respectively, including post-translational modifications of those sequences. In one embodiment, the antibody comprises the HC and LC sequences in SEQ ID NO:293 and SEQ ID NO:269, respectively, including post-translational modifications of those sequences. In one embodiment, the antibody comprises the HC and LC sequences in SEQ ID NO:294 and SEQ ID NO:270, respectively, including post-translational modifications of those sequences. In one embodiment, the antibody comprises the HC and LC sequences in SEQ ID NO:295 and SEQ ID NO:271, respectively, including post-translational modifications of those sequences. In one embodiment, the antibody comprises the HC and LC sequences in SEQ ID NO:296 and SEQ ID NO:272, respectively, including post-translational modifications of those sequences. In one embodiment, the antibody comprises the HC and LC sequences in SEQ ID NO:297 and SEQ ID NO:273, respectively, including post-translational modifications of those sequences. In one embodiment, the antibody comprises the HC and LC sequences in SEQ ID NO:299 and SEQ ID NO:275, respectively, including post-translational modifications of those sequences. In one embodiment, the antibody comprises the HC and LC sequences in SEQ ID NO:300 and SEQ ID NO:275, respectively, including post-translational modifications of those sequences. In one embodiment, the antibody comprises the HC and LC sequences in SEQ ID NO:301 and SEQ ID NO:276, respectively, including post-translational modifications of those sequences. In one embodiment, the antibody comprises the HC and LC sequences in SEQ ID NO:302 and SEQ ID NO:277, respectively, including post-translational modifications of those sequences. In one embodiment, the antibody comprises the HC and LC sequences in SEQ ID NO:303 and SEQ ID NO:278, respectively, including post-translational modifications of those sequences. In one embodiment, the antibody comprises the HC and LC sequences in SEQ ID NO:305 and SEQ ID NO:280, respectively, including post-translational modifications of those sequences. In one embodiment, the antibody comprises the HC and LC sequences in SEQ ID NO:306 and SEQ ID NO:280, respectively, including post-translational modifications of those sequences.

Figure 14A:
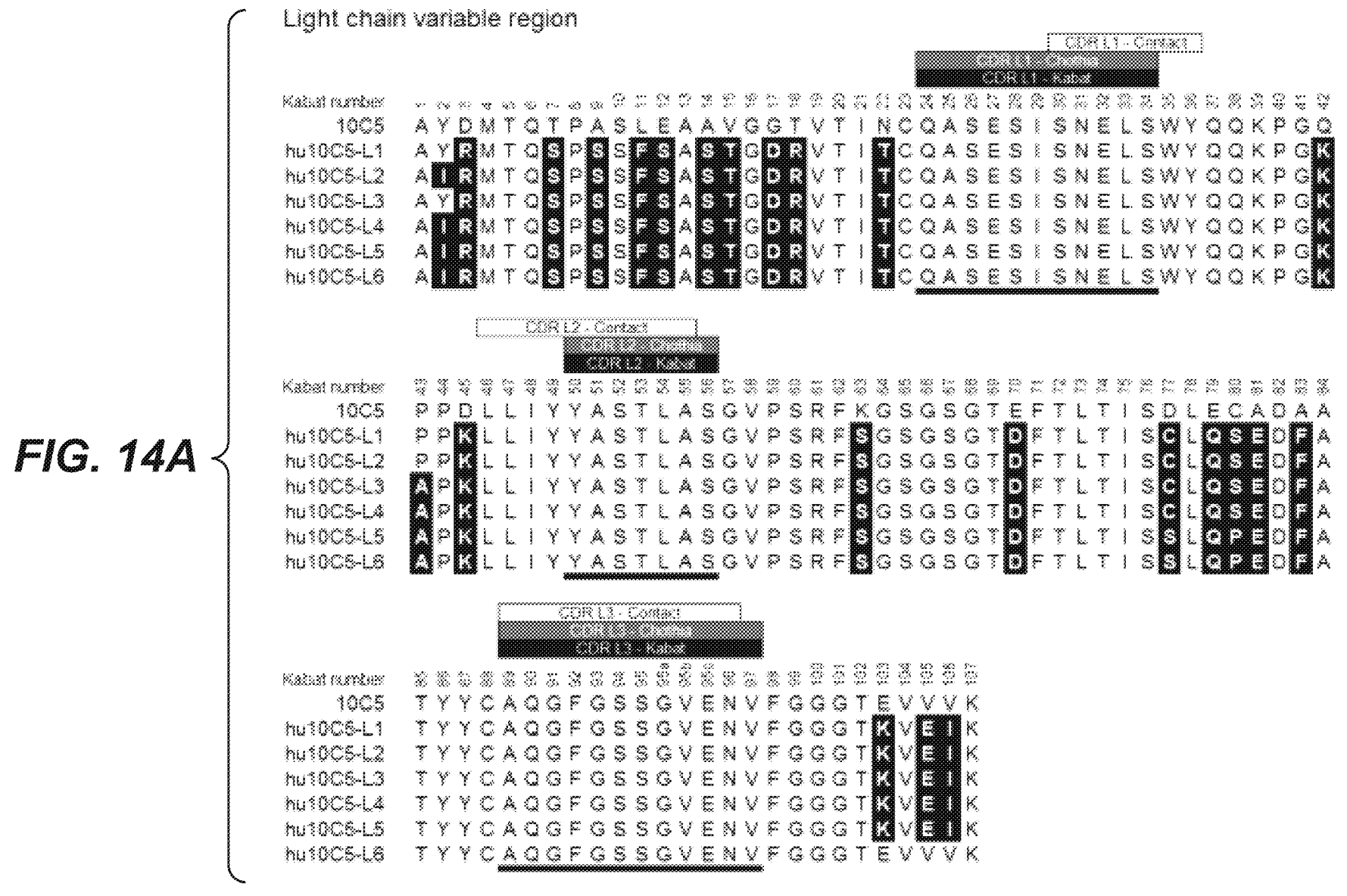
Figure 15A:
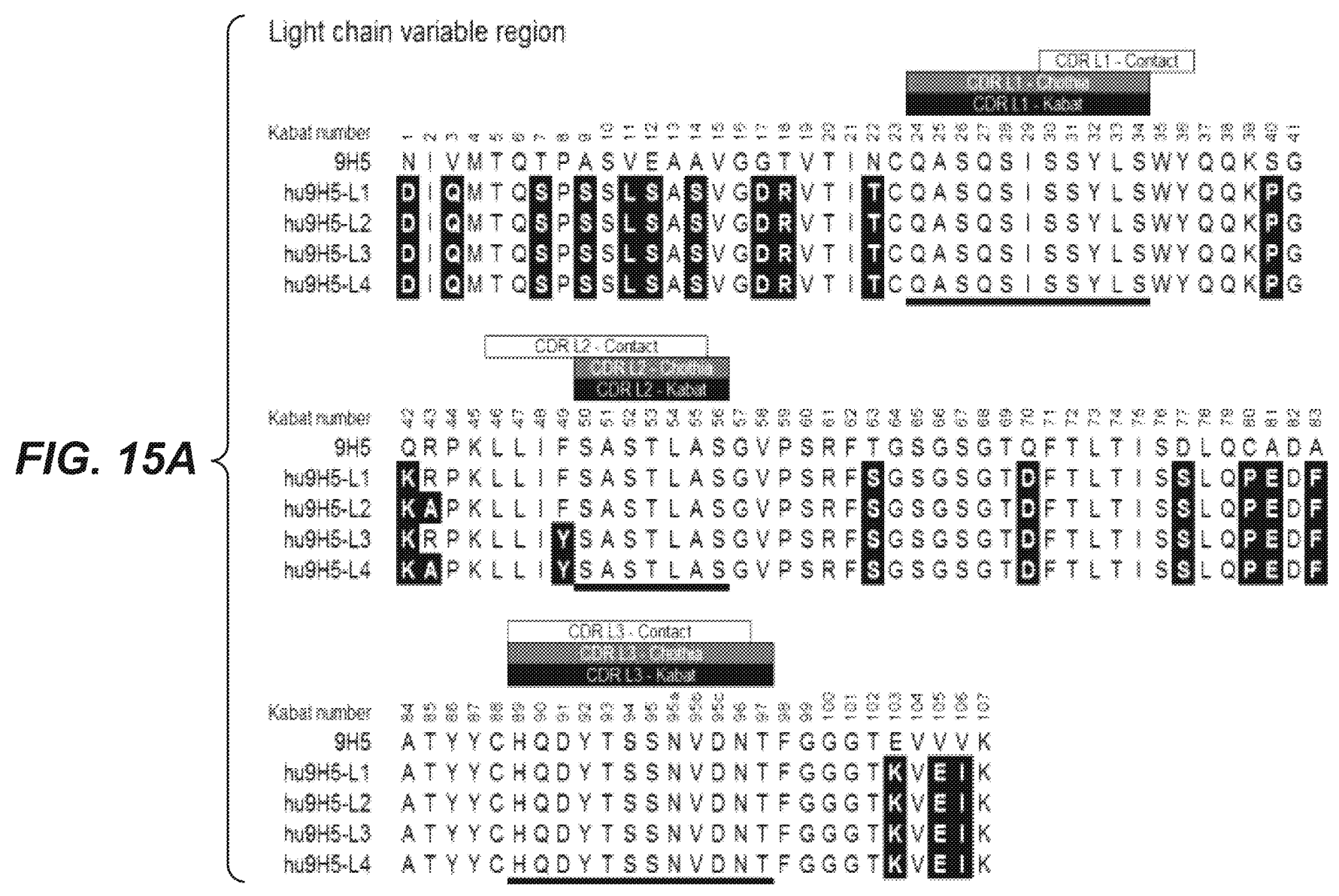
Figures 2, 14B:
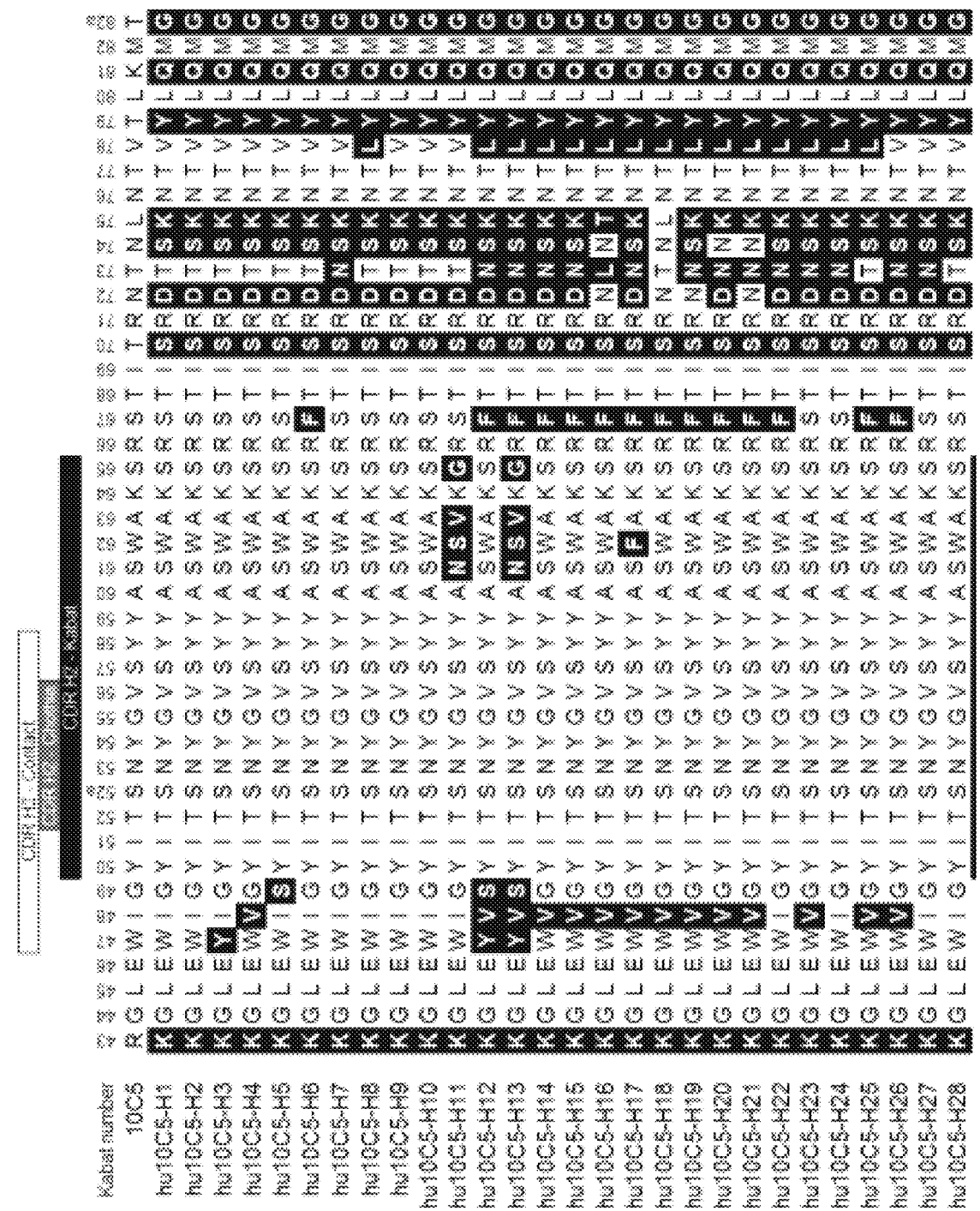
Figures 1, 15B:
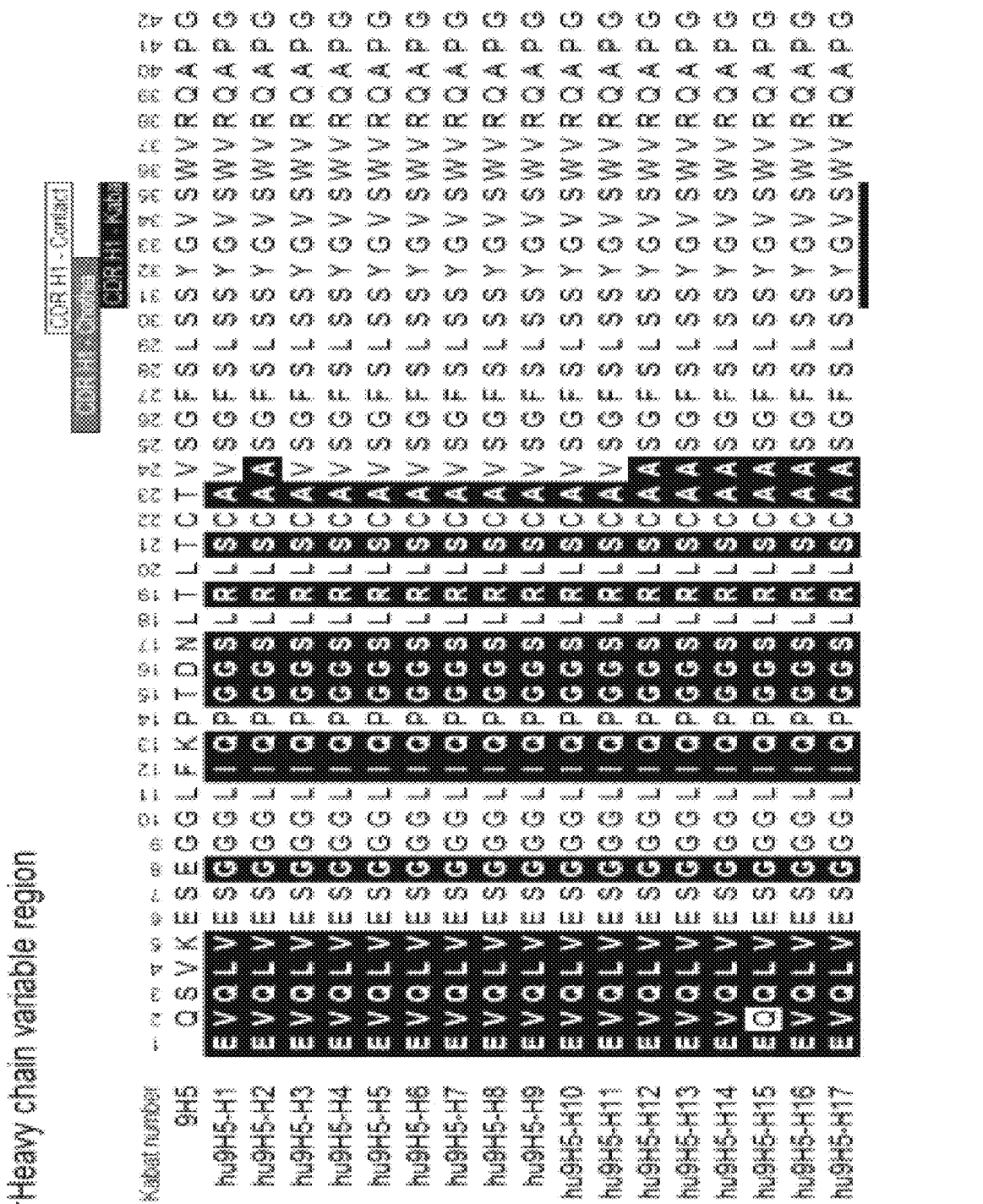

Provided herein are antibodies comprising a light chain variable domain comprising the HVR1-LC, HVR2-LC and HVR3-LC sequence according to Kabat numbering as depicted in FIGS. 14A, 15A and/or 16A and a heavy chain variable domain comprising the HVR1-HC, HVR2-HC and HVR3-HC sequence according to Kabat numbering as depicted in FIGS. 14B, 15B and/or 16B. In some embodiments, the antibody comprises a light chain variable domain comprising the HVR1-LC, HVR2-LC and/or HVR3-LC sequence, and the FR1-LC, FR2-LC, FR3-LC and/or FR4-LC sequence as depicted in FIGS. 14A, 15A and/or 16A. In some embodiments, the antibody comprises a heavy chain variable domain comprising the HVR1-HC, HVR2-HC and/or HVR3-HC sequence, and the FR1-HC, FR2-HC, FR3-HC and/or FR4-HC sequence as depicted in FIGS. 14B, 15B and/or 16B.

In a further aspect, an anti-KLK5 antibody is provided that binds to the same epitope as an anti-KLK5 antibody provided herein.

In a further aspect, an anti-KLK5 antibody is provided that, when bound to KLK5 results in a thermodynamic epitope comprising one or more of the sequences selected from the group consisting of SEQ ID NO:316, SEQ ID NO:317, SEQ ID NO:318, and SEQ ID NO:319 as measured by hydrogen exchange mass spectrometry.

In a further aspect, an anti-KLK5 antibody according to any of the above embodiments is a monoclonal antibody, including a chimeric, humanized or human antibody. In one embodiment, an anti-KLK5 antibody is humanized. In one embodiment, an anti-KLK5 antibody comprises HVRs as in any of the above embodiments, and further comprises an acceptor human framework, e.g. a human immunoglobulin framework or a human consensus framework. In one embodiment, an anti-KLK5 antibody is an antibody fragment, e.g., a Fv, Fab, Fab', scFv, diabody, or F(ab')$_2$ fragment. In another embodiment, the antibody is a full length antibody, e.g an intact IgG1 antibody or an intact IgG4 antibody or other antibody class or isotype as defined herein.

In a further aspect, an anti-KLK5 antibody according to any of the above embodiments may incorporate any of the features, singly or in combination, as described below.

Antibody 10C5, 9H5, 3-3F5 and Other Embodiments

In one aspect, an anti-KLK5 antibody is provided comprising at least one, two, three, four, five, or six HVRs selected from (a) HVR-H1 comprising the amino acid sequence of SEQ ID NO:28; (b) HVR-H2 comprising the amino acid sequence of SEQ ID NO:38, SEQ ID NO:45, or SEQ ID NO:54; (c) HVR-H3 comprising the amino acid sequence of SEQ ID NO:65, SEQ ID NO:69, or SEQ ID NO:72; (d) HVR-L1 comprising the amino acid sequence of SEQ ID NO:96; (e) HVR-L2 comprising the amino acid sequence of SEQ ID NO:109; and (f) HVR-L3 comprising the amino acid sequence of SEQ ID NO:127.

In one aspect, an anti-KLK5 antibody is provided comprising at least one, two, three, four, five, or six HVRs selected from (a) HVR-H1 comprising the amino acid sequence of SEQ ID NO:17, SEQ ID NO:22, or SEQ ID NO:24; (b) HVR-H2 comprising the amino acid sequence of SEQ ID NO:35, SEQ ID NO:36, SEQ ID NO:37, SEQ ID NO:42, SEQ ID NO:43, SEQ ID NO:44, SEQ ID NO:48, SEQ ID NO:49, SEQ ID NO:50, SEQ ID NO:51, SEQ ID NO:52, or SEQ ID NO:53; (c) HVR-H3 comprising the amino acid sequence of SEQ ID NO:65, SEQ ID NO:69, or SEQ ID NO:72; (d) HVR-L1 comprising the amino acid sequence of SEQ ID NO:82, SEQ ID NO:87, or SEQ ID NO:91; (e) HVR-L2 comprising the amino acid sequence of SEQ ID NO:99, SEQ ID NO:101, or SEQ ID NO:105; and (f) HVR-L3 comprising the amino acid sequence of SEQ ID NO:115, SEQ ID NO:119, or SEQ ID NO:122.

In one aspect, an anti-KLK5 antibody is provided comprising at least one, at least two, or all three VH HVR sequences selected from (a) HVR-H1 comprising the amino acid sequence of SEQ ID NO:17, SEQ ID NO:22, or SEQ ID NO:24; (b) HVR-H2 comprising the amino acid sequence of SEQ ID NO:35, SEQ ID NO:36, SEQ ID NO:37, SEQ ID NO:42, SEQ ID NO:43, SEQ ID NO:44, SEQ ID NO:48, SEQ ID NO:49, SEQ ID NO:50, SEQ ID NO:51, SEQ ID NO:52, or SEQ ID NO:53; and (c) HVR-H3 comprising the amino acid sequence of SEQ ID NO:65, SEQ ID NO:69, or SEQ ID NO:72. In one embodiment, the antibody comprises HVR-H3 comprising the amino acid sequence of SEQ ID NO:65, SEQ ID NO:69, or SEQ ID NO:72. In another embodiment, the antibody comprises HVR-H3 comprising the amino acid sequence of SEQ ID NO:65, SEQ ID NO:69, or SEQ ID NO:72 and HVR-L3 comprising the amino acid sequence of SEQ ID NO:115, SEQ ID NO:119, or SEQ ID NO:122. In a further embodiment, the antibody comprises HVR-H3 comprising the amino acid sequence of SEQ ID NO:65, SEQ ID NO:69, or SEQ ID NO:72, HVR-L3 comprising the amino acid sequence of SEQ ID NO:115, SEQ ID NO:119, or SEQ ID NO:122, and HVR-H2 comprising the amino acid sequence of SEQ ID NO:35, SEQ ID NO:36, SEQ ID NO:37, SEQ ID NO:42, SEQ ID NO:43, SEQ ID NO:44, SEQ ID NO:48, SEQ ID NO:49, SEQ ID NO:50, SEQ ID NO:51, SEQ ID NO:52, or SEQ ID NO:53. In a further embodiment, the antibody comprises (a) HVR-H1 comprising the amino acid sequence of SEQ ID NO:17, SEQ ID NO:22, or SEQ ID NO:24; (b) HVR-H2 comprising the amino acid sequence of SEQ ID NO:35, SEQ ID NO:36, SEQ ID NO:37, SEQ ID NO:42, SEQ ID NO:43, SEQ ID NO:44, SEQ ID NO:48, SEQ ID NO:49, SEQ ID NO:50, SEQ ID NO:51, SEQ ID NO:52, or SEQ ID NO:53; and (c) HVR-H3 comprising the amino acid sequence of SEQ ID NO:65, SEQ ID NO:69, or SEQ ID NO:72.

In another aspect, an anti-KLK5 antibody is provided comprising at least one, at least two, or all three VL HVR sequences selected from (a) HVR-L1 comprising the amino acid sequence of SEQ ID NO:82, SEQ ID NO:87, or SEQ ID NO:91; (b) HVR-L2 comprising the amino acid sequence of SEQ ID NO:99, SEQ ID NO:101, or SEQ ID NO:105; and (c) HVR-L3 comprising the amino acid sequence of SEQ ID NO:115, SEQ ID NO:119, or SEQ ID NO:122.

In another aspect, an anti-KLK5 antibody is provided comprises (a) a VH domain comprising at least one, at least two, or all three VH HVR sequences selected from (i) HVR-H1 comprising the amino acid sequence of SEQ ID NO:17, (ii) HVR-H2 comprising the amino acid sequence of SEQ ID NO:35, and (iii) HVR-H3 comprising the amino acid sequence of SEQ ID NO:65; and (b) a VL domain comprising at least one, at least two, or all three VL HVR sequences selected from (i) HVR-L1 comprising the amino acid sequence of SEQ ID NO:82, (ii) HVR-L2 comprising the amino acid sequence of SEQ ID NO:101, and (c) HVR-L3 comprising the amino acid sequence of SEQ ID NO:115.

In another aspect, an anti-KLK5 antibody is provided comprising (a) HVR-H1 comprising the amino acid sequence of SEQ ID NO:17; (b) HVR-H2 comprising the amino acid sequence of SEQ ID NO:35; (c) HVR-H3 comprising the amino acid sequence of SEQ ID NO:65; (d) HVR-L1 comprising the amino acid sequence of SEQ ID NO:82; (e) HVR-L2 comprising the amino acid sequence of SEQ ID NO:101; and (f) HVR-L3 comprising the amino acid sequence of SEQ ID NO:115.

In another aspect, an anti-KLK5 antibody is provided comprises (a) a VH domain comprising at least one, at least two, or all three VH HVR sequences selected from (i) HVR-H1 comprising the amino acid sequence of SEQ ID NO:22, (ii) HVR-H2 comprising the amino acid sequence of SEQ ID NO:42, and (iii) HVR-H3 comprising the amino acid sequence of SEQ ID NO:69; and (b) a VL domain comprising at least one, at least two, or all three VL HVR sequences selected from (i) HVR-L1 comprising the amino acid sequence of SEQ ID NO:87, (ii) HVR-L2 comprising the amino acid sequence of SEQ ID NO:105, and (c) HVR-L3 comprising the amino acid sequence of SEQ ID NO:119.

In another aspect, an anti-KLK5 antibody is provided comprising (a) HVR-H1 comprising the amino acid sequence of SEQ ID NO:22; (b) HVR-H2 comprising the amino acid sequence of SEQ ID NO:42; (c) HVR-H3 comprising the amino acid sequence of SEQ ID NO:69; (d) HVR-L1 comprising the amino acid sequence of SEQ ID NO:87; (e) HVR-L2 comprising the amino acid sequence of SEQ ID NO:105; and (f) HVR-L3 comprising the amino acid sequence of SEQ ID NO:119.

In another aspect, an anti-KLK5 antibody is provided comprises (a) a VH domain comprising at least one, at least two, or all three VH HVR sequences selected from (i) HVR-H1 comprising the amino acid sequence of SEQ ID NO:24, (ii) HVR-H2 comprising the amino acid sequence of SEQ ID NO:52, and (iii) HVR-H3 comprising the amino acid sequence of SEQ ID NO:72; and (b) a VL domain comprising at least one, at least two, or all three VL HVR sequences selected from (i) HVR-L1 comprising the amino acid sequence of SEQ ID NO:91, (ii) HVR-L2 comprising the amino acid sequence of SEQ ID NO:99, and (c) HVR-L3 comprising the amino acid sequence of SEQ ID NO:122.

In another aspect, an anti-KLK5 antibody is provided comprising (a) HVR-H1 comprising the amino acid sequence of SEQ ID NO:24; (b) HVR-H2 comprising the amino acid sequence of SEQ ID NO:52; (c) HVR-H3 comprising the amino acid sequence of SEQ ID NO:72; (d) HVR-L1 comprising the amino acid sequence of SEQ ID NO:91; (e) HVR-L2 comprising the amino acid sequence of SEQ ID NO:99; and (f) HVR-L3 comprising the amino acid sequence of SEQ ID NO:122.

In another aspect, an anti-KLK5 antibody is provided comprising a heavy chain variable domain (VH) sequence having SEQ ID NO:202. In another aspect, an anti-KLK5 antibody is provided comprising a light chain variable domain (VL) sequence having SEQ ID NO:140.

In another aspect, an anti-KLK5 antibody is provided comprising a heavy chain variable domain (VH) sequence selected from any one of SEQ ID NOs:173-201. In another aspect, an anti-KLK5 antibody is provided comprising a light chain variable domain (VL) sequence selected from any one of SEQ ID NOs:134-139 and SEQ ID NO:321.

In another aspect, an anti-KLK5 antibody is provided comprising a heavy chain variable domain (VH) sequence having at least any of 90%, 91%, 92%, 93%, 94%, 95%, 96%, 97%, 98%, 99%, or 100% sequence identity to the amino acid sequence of SEQ ID NO:201. In certain embodiments, a VH sequence having at least any of 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:201. In certain embodiments, substitutions, insertions, or deletions occur in regions outside the HVRs (i.e., in the FRs). Optionally, the anti-KLK5 antibody comprises the VH sequence in SEQ ID NO:201, including post-translational modifications of that sequence. In a particular embodiment, the VH comprises one, two or three HVRs selected from: (a) HVR-H1 comprising the amino acid sequence of SEQ ID NO:17, (b) HVR-H2 comprising the amino acid sequence of SEQ ID NO:35, and (c) HVR-H3 comprising the amino acid sequence of SEQ ID NO:65.

In another aspect, an anti-KLK5 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:139. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:139. In certain embodiments, the substitutions, insertions, or deletions occur in regions outside the HVRs (i.e., in the FRs). Optionally, the anti-KLK5 antibody comprises the VL sequence in SEQ ID NO:139, including post-translational modifications of that sequence. In a particular embodiment, the VL comprises one, two or three HVRs selected from (a) HVR-L1 comprising the amino acid sequence of SEQ ID NO:82; (b) HVR-L2 comprising the amino acid sequence of SEQ ID NO:101; and (c) HVR-L3 comprising the amino acid sequence of SEQ ID NO:115.

In another aspect, an anti-KLK5 antibody is provided, wherein the antibody comprises a VH as in any of the embodiments provided above, and a VL as in any of the embodiments provided above. In one embodiment, the antibody comprises the VH and VL sequences in SEQ ID NO:201 and SEQ ID NO:139, respectively, including post-translational modifications of those sequences.

In a further aspect, an anti-KLK5 antibody is provided that binds to the same epitope as an anti-KLK5 antibody provided herein. For example, in certain embodiments, an antibody is provided that binds to the same epitope as an anti-KLK5 antibody comprising a VH sequence of SEQ ID NO:201 and a VL sequence of SEQ ID NO:139. In certain embodiments, an antibody is provided that, when bound to KLK5 results in a thermodynamic epitope comprising one or more of the sequences selected from the group consisting of SEQ ID NO:316, SEQ ID NO:317, SEQ ID NO:318, and SEQ ID NO:319 as measured by hydrogen exchange mass spectrometry.

In another aspect, an anti-KLK5 antibody is provided comprising a heavy chain variable domain (VH) sequence having SEQ ID NO:225. In another aspect, an anti-KLK5 antibody is provided comprising a light chain variable domain (VL) sequence having SEQ ID NO:151.

In another aspect, an anti-KLK5 antibody is provided comprising a heavy chain variable domain (VH) sequence selected from any one of SEQ ID NOs:207-224. In another aspect, an anti-KLK5 antibody is provided comprising a light chain variable domain (VL) sequence selected from any one of SEQ ID NOs:145-150.

In another aspect, an anti-KLK5 antibody is provided comprising a heavy chain variable domain (VH) sequence having at least any of 90%, 91%, 92%, 93%, 94%, 95%, 96%, 97%, 98%, 99%, or 100% sequence identity to the amino acid sequence of SEQ ID NO:221. In certain embodiments, a VH sequence having at least any of 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:221. In certain embodiments, substitutions, insertions, or deletions occur in regions outside the HVRs (i.e., in the FRs). Optionally, the anti-KLK5 antibody comprises the VH sequence in SEQ ID NO:221, including post-translational modifications of that sequence. In a particular embodiment, the VH comprises one, two or three HVRs selected from: (a) HVR-H1 comprising the amino acid sequence of SEQ ID NO:22, (b) HVR-H2 comprising the amino acid sequence of SEQ ID NO:42, and (c) HVR-H3 comprising the amino acid sequence of SEQ ID NO:69.

In another aspect, an anti-KLK5 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:149. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:149. In certain embodiments, the substitutions, insertions, or deletions occur in regions outside the HVRs (i.e., in the FRs). Optionally, the anti-KLK5 antibody comprises the VL sequence in SEQ ID NO:149, including post-translational modifications of that sequence. In a particular embodiment, the VL comprises one, two or three HVRs selected from (a) HVR-L1 comprising the amino acid sequence of SEQ ID NO:87; (b) HVR-L2 comprising the amino acid sequence of SEQ ID NO:105; and (c) HVR-L3 comprising the amino acid sequence of SEQ ID NO:119.

In another aspect, an anti-KLK5 antibody is provided, wherein the antibody comprises a VH as in any of the embodiments provided above, and a VL as in any of the embodiments provided above. In one embodiment, the antibody comprises the VH and VL sequences in SEQ ID NO:221 and SEQ ID NO:149, respectively, including post-translational modifications of those sequences.

In a further aspect, an anti-KLK5 antibody is provided that binds to the same epitope as an anti-KLK5 antibody provided herein. For example, in certain embodiments, an antibody is provided that binds to the same epitope as an anti-KLK5 antibody comprising a VH sequence of SEQ ID NO:221 and a VL sequence of SEQ ID NO:149. In certain embodiments, an antibody is provided that, when bound to KLK5 results in a thermodynamic epitope comprising one or more of the sequences selected from the group consisting of SEQ ID NO:316, SEQ ID NO:317, SEQ ID NO:318, and SEQ ID NO:319 as measured by hydrogen exchange mass spectrometry.

In another aspect, an anti-KLK5 antibody is provided comprising a heavy chain variable domain (VH) sequence having SEQ ID NO:257. In another aspect, an anti-KLK5 antibody is provided comprising a light chain variable domain (VL) sequence having SEQ ID NO:162.

In another aspect, an anti-KLK5 antibody is provided comprising a heavy chain variable domain (VH) sequence selected from any one of SEQ ID NOs:229-256. In another aspect, an anti-KLK5 antibody is provided comprising a light chain variable domain (VL) sequence selected from any one of SEQ ID NOs:155-161.

In another aspect, an anti-KLK5 antibody is provided comprising a heavy chain variable domain (VH) sequence having at least any of 90%, 91%, 92%, 93%, 94%, 95%, 96%, 97%, 98%, 99%, or 100% sequence identity to the amino acid sequence of SEQ ID NO:248. In certain embodiments, a VH sequence having at least any of 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:248. In certain embodiments, substitutions, insertions, or deletions occur in regions outside the HVRs (i.e., in the FRs). Optionally, the anti-KLK5 antibody comprises the VH sequence in SEQ ID NO:248, including post-translational modifications of that sequence.

In a particular embodiment, the VH comprises one, two or three HVRs selected from: (a) HVR-H1 comprising the amino acid sequence of SEQ ID NO:24, (b) HVR-H2 comprising the amino acid sequence of SEQ ID NO:52, and (c) HVR-H3 comprising the amino acid sequence of SEQ ID NO:72.

In another aspect, an anti-KLK5 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:160. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:160. In certain embodiments, the substitutions, insertions, or deletions occur in regions outside the HVRs (i.e., in the FRs). Optionally, the anti-KLK5 antibody comprises the VL sequence in SEQ ID NO:160, including post-translational modifications of that sequence. In a particular embodiment, the VL comprises one, two or three HVRs selected from (a) HVR-L1 comprising the amino acid sequence of SEQ ID NO:91; (b) HVR-L2 comprising the amino acid sequence of SEQ ID NO:99; and (c) HVR-L3 comprising the amino acid sequence of SEQ ID NO:122.

In another aspect, an anti-KLK5 antibody is provided, wherein the antibody comprises a VH as in any of the embodiments provided above, and a VL as in any of the embodiments provided above. In one embodiment, the antibody comprises the VH and VL sequences in SEQ ID NO:248 and SEQ ID NO:160, respectively, including post-translational modifications of those sequences.

In a further aspect, an anti-KLK5 antibody is provided that binds to the same epitope as an anti-KLK5 antibody provided herein. For example, in certain embodiments, an antibody is provided that binds to the same epitope as an anti-KLK5 antibody comprising a VH sequence of SEQ ID NO:248 and a VL sequence of SEQ ID NO:160.

Provided herein are antibodies comprising a light chain variable domain comprising the HVR1-LC, HVR2-LC and HVR3-LC sequence according to Kabat numbering as depicted in FIGS. 14A, 15A and/or 16A and a heavy chain variable domain comprising the HVR1-HC, HVR2-HC and HVR3-HC sequence according to Kabat numbering as depicted in FIGS. 14B, 15B and/or 16B. In some embodiments, the antibody comprises a light chain variable domain comprising the HVR1-LC, HVR2-LC and/or HVR3-LC sequence, and the FR1-LC, FR2-LC, FR3-LC and/or FR4-LC sequence as depicted in FIGS. 14A, 15A and/or 16A. In some embodiments, the antibody comprises a heavy chain variable domain comprising the HVR1-HC, HVR2-HC and/or HVR3-HC sequence, and the FR1-HC, FR2-HC, FR3-HC and/or FR4-HC sequence as depicted in FIGS. 14B, 15B and/or 16B.

In a further aspect, an anti-KLK5 antibody according to any of the above embodiments is a monoclonal antibody, including a chimeric, humanized or human antibody. In one embodiment, an anti-KLK5 antibody is humanized. In one embodiment, an anti-KLK5 antibody comprises HVRs as in any of the above embodiments, and further comprises an acceptor human framework, e.g. a human immunoglobulin framework or a human consensus framework.

In one embodiment, an anti-KLK5 antibody is an antibody fragment, e.g., a Fv, Fab, Fab', scFv, diabody, or F(ab')$_2$ fragment. In another embodiment, the antibody is a full length antibody, e.g an intact IgG1 antibody or an intact IgG4 antibody or other antibody class or isotype as defined herein.

Further provided herein is an antibody that specifically binds to human KLK5, wherein the antibody binds to an epitope on human KLK5 comprising one or more amino acid residues selected from the group consisting of Pro130, Ser131, Ala132, Gly133, Val162, Leu163, Ser164, Gln165, Lys166, Arg167, Glu169, Asp170, Ala171, Tyr172, Pro173, Arg174, Gln174A, Ile176, Asp177, Asp178, Gly184, Asp185, Lys186, Ala186A, Arg188, Asn223, Arg224, Pro225, and Lys233 according to standard protease numbering. In some embodiments, the antibody binds to an epitope on human KLK5 comprising one or more amino acid residues selected from the group consisting of Pro130, Ser131, Ala132, Val162, Leu163, Ser164, Gln165, Lys166, Arg167, Glu169, Asp170, Ala171, Tyr172, Pro173, Arg174, Gln174A, Ile176, Asp177, Asp178, Arg224, and Lys233 according to standard protease numbering. In some embodiments, the antibody binds to an epitope on human KLK5 comprising one or more amino acid residues selected from the group consisting of Pro130, Ser131, Ala132, Gly133, Val162, Leu163, Ser164, Gln165, Lys166, Arg167, Glu169, Asp170, Ala171, Tyr172, Pro173, Arg174, Gln174A, Ile176, Asp177, and Lys233 according to standard protease numbering. In some embodiments, the antibody binds to an epitope on human KLK5 comprising one or more amino acid residues selected from the group consisting of Ser131, Ala132, Gly133, Leu163, Ser164, Gln165, Lys166, Arg167, Glu169, Asp170, Ala171, Pro173, Arg174, Gly184, Asp185, Lys186, Ala186A, Arg188, Asn223, Arg224, and Pro225 according to standard protease numbering.

Further provided herein is an antibody when bound to human KLK5 results in a conformational change of human KLK5, wherein the conformational change allosterically results in the disruption of the substrate binding site and/or the active site of human KLK5.

In a further aspect, an anti-KLK5 antibody according to any of the above embodiments may incorporate any of the features, singly or in combination, as described below.

Antibody 8G10 and Other Embodiments

In one aspect, an anti-KLK5 antibody is provided comprising at least one, two, three, four, five, or six HVRs selected from (a) HVR-H1 comprising the amino acid sequence of SEQ ID NO:14; (b) HVR-H2 comprising the amino acid sequence of SEQ ID NO:32; (c) HVR-H3 comprising the amino acid sequence of SEQ ID NO:62; (d) HVR-L1 comprising the amino acid sequence of SEQ ID NO:79; (e) HVR-L2 comprising the amino acid sequence of SEQ ID NO:99; and (f) HVR-L3 comprising the amino acid sequence of SEQ ID NO:112.

In one aspect, an anti-KLK5 antibody is provided comprising at least one, at least two, or all three VH HVR sequences selected from (a) HVR-H1 comprising the amino acid sequence of SEQ ID NO:14; (b) HVR-H2 comprising the amino acid sequence of SEQ ID NO:32; and (c) HVR-H3 comprising the amino acid sequence of SEQ ID NO:62. In one embodiment, the antibody comprises HVR-H3 comprising the amino acid sequence of SEQ ID NO:62. In another embodiment, the antibody comprises HVR-H3 comprising the amino acid sequence of SEQ ID NO:62 and HVR-L3 comprising the amino acid sequence of SEQ ID NO:112. In a further embodiment, the antibody comprises HVR-H3 comprising the amino acid sequence of SEQ ID NO:62, HVR-L3 comprising the amino acid sequence of SEQ ID NO:112, and HVR-H2 comprising the amino acid sequence of SEQ ID NO:32. In a further embodiment, the antibody comprises (a) HVR-H1 comprising the amino acid sequence of SEQ ID NO:14; (b) HVR-H2 comprising the amino acid sequence of SEQ ID NO:32; and (c) HVR-H3 comprising the amino acid sequence of SEQ ID NO:62.

In another aspect, an anti-KLK5 antibody is provided comprising at least one, at least two, or all three VL HVR sequences selected from (a) HVR-L1 comprising the amino acid sequence of SEQ ID NO:79; (b) HVR-L2 comprising the amino acid sequence of SEQ ID NO:99; and (c) HVR-L3 comprising the amino acid sequence of SEQ ID NO:112. In one embodiment, the antibody comprises (a) HVR-L1 comprising the amino acid sequence of SEQ ID NO:79; (b) HVR-L2 comprising the amino acid sequence of SEQ ID NO:99; and (c) HVR-L3 comprising the amino acid sequence of SEQ ID NO:112.

In another aspect, an anti-KLK5 antibody is provided comprises (a) a VH domain comprising at least one, at least two, or all three VH HVR sequences selected from (i) HVR-H1 comprising the amino acid sequence of SEQ ID NO:14, (ii) HVR-H2 comprising the amino acid sequence of SEQ ID NO:32, and (iii) HVR-H3 comprising the amino acid sequence of SEQ ID NO:62; and (b) a VL domain comprising at least one, at least two, or all three VL HVR sequences selected from (i) HVR-L1 comprising the amino acid sequence of SEQ ID NO:79, (ii) HVR-L2 comprising the amino acid sequence of SEQ ID NO:99, and (c) HVR-L3 comprising the amino acid sequence of SEQ ID NO:112.

In another aspect, an anti-KLK5 antibody is provided comprising (a) HVR-H1 comprising the amino acid sequence of SEQ ID NO:14; (b) HVR-H2 comprising the amino acid sequence of SEQ ID NO:32; (c) HVR-H3 comprising the amino acid sequence of SEQ ID NO:62; (d) HVR-L1 comprising the amino acid sequence of SEQ ID NO:79; (e) HVR-L2 comprising the amino acid sequence of SEQ ID NO:99; and (f) HVR-L3 comprising the amino acid sequence of SEQ ID NO:112.

In another aspect, an anti-KLK5 antibody is provided comprising a heavy chain variable domain (VH) sequence having at least any of 90%, 91%, 92%, 93%, 94%, 95%, 96%, 97%, 98%, 99%, or 100% sequence identity to the amino acid sequence of SEQ ID NO:170. In certain embodiments, a VH sequence having at least any of 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:170. In certain embodiments, substitutions, insertions, or deletions occur in regions outside the HVRs (i.e., in the FRs). Optionally, the anti-KLK5 antibody comprises the VH sequence in SEQ ID NO:170, including post-translational modifications of that sequence. In a particular embodiment, the VH comprises one, two or three HVRs selected from: (a) HVR-H1 comprising the amino acid sequence of SEQ ID NO:14, (b) HVR-H2 comprising the amino acid sequence of SEQ ID NO:32, and (c) HVR-H3 comprising the amino acid sequence of SEQ ID NO:62.

In another aspect, an anti-KLK5 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:131. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:131. In certain embodiments, the substitutions, insertions, or deletions occur in regions outside the HVRs (i.e., in the FRs). Optionally, the anti-KLK5 antibody comprises the VL sequence in SEQ ID NO:131, including post-translational modifications of that sequence. In a particular embodiment, the VL comprises one, two or three HVRs selected from (a) HVR-L1 comprising the amino acid sequence of SEQ ID NO:79; (b) HVR-L2 comprising the amino acid sequence of SEQ ID NO:99; and (c) HVR-L3 comprising the amino acid sequence of SEQ ID NO:112.

In another aspect, an anti-KLK5 antibody is provided, wherein the antibody comprises a VH as in any of the embodiments provided above, and a VL as in any of the embodiments provided above. In one embodiment, the antibody comprises the VH and VL sequences in SEQ ID NO:170 and SEQ ID NO:131, respectively, including post-translational modifications of those sequences.

In a further aspect, an anti-KLK5 antibody is provided that binds to the same epitope as an anti-KLK5 antibody provided herein. For example, in certain embodiments, an antibody is provided that binds to the same epitope as an anti-KLK5 antibody comprising a VH sequence of SEQ ID NO:170 and a VL sequence of SEQ ID NO:131.

In a further aspect, an anti-KLK5 antibody according to any of the above embodiments is a monoclonal antibody, including a chimeric, humanized or human antibody. In one embodiment, an anti-KLK5 antibody is humanized. In one embodiment, an anti-KLK5 antibody comprises HVRs as in any of the above embodiments, and further comprises an acceptor human framework, e.g. a human immunoglobulin framework or a human consensus framework.

In one embodiment, an anti-KLK5 antibody is an antibody fragment, e.g., a Fv, Fab, Fab', scFv, diabody, or F(ab')$_2$ fragment. In another embodiment, the antibody is a full length antibody, e.g an intact IgG1 antibody or an intact IgG4 antibody or other antibody class or isotype as defined herein.

In a further aspect, an anti-KLK5 antibody according to any of the above embodiments may incorporate any of the features, singly or in combination, as described below.

Antibody 9B6 and Other Embodiments

In one aspect, an anti-KLK5 antibody is provided comprising at least one, two, three, four, five, or six HVRs selected from (a) HVR-H1 comprising the amino acid sequence of SEQ ID NO:15; (b) HVR-H2 comprising the amino acid sequence of SEQ ID NO:33; (c) HVR-H3 comprising the amino acid sequence of SEQ ID NO:63; (d) HVR-L1 comprising the amino acid sequence of SEQ ID NO:80; (e) HVR-L2 comprising the amino acid sequence of SEQ ID NO:100; and (f) HVR-L3 comprising the amino acid sequence of SEQ ID NO:113.

In one aspect, an anti-KLK5 antibody is provided comprising at least one, at least two, or all three VH HVR sequences selected from (a) HVR-H1 comprising the amino acid sequence of SEQ ID NO:15; (b) HVR-H2 comprising the amino acid sequence of SEQ ID NO:33; and (c) HVR-H3 comprising the amino acid sequence of SEQ ID NO:63. In one embodiment, the antibody comprises HVR-H3 comprising the amino acid sequence of SEQ ID NO:63. In another embodiment, the antibody comprises HVR-H3 comprising the amino acid sequence of SEQ ID NO:63 and HVR-L3 comprising the amino acid sequence of SEQ ID NO:113. In a further embodiment, the antibody comprises HVR-H3 comprising the amino acid sequence of SEQ ID NO:63, HVR-L3 comprising the amino acid sequence of SEQ ID NO:113, and HVR-H2 comprising the amino acid sequence of SEQ ID NO:33. In a further embodiment, the antibody comprises (a) HVR-H1 comprising the amino acid sequence of SEQ ID NO:15; (b) HVR-H2 comprising the amino acid sequence of SEQ ID NO:33; and (c) HVR-H3 comprising the amino acid sequence of SEQ ID NO:63.

In another aspect, an anti-KLK5 antibody is provided comprising at least one, at least two, or all three VL HVR sequences selected from (a) HVR-L1 comprising the amino acid sequence of SEQ ID NO:80; (b) HVR-L2 comprising the amino acid sequence of SEQ ID NO:100; and (c) HVR-L3 comprising the amino acid sequence of SEQ ID NO:113. In one embodiment, the antibody comprises (a) HVR-L1 comprising the amino acid sequence of SEQ ID NO:80; (b) HVR-L2 comprising the amino acid sequence of SEQ ID NO:100; and (c) HVR-L3 comprising the amino acid sequence of SEQ ID NO:113.

In another aspect, an anti-KLK5 antibody is provided comprises (a) a VH domain comprising at least one, at least two, or all three VH HVR sequences selected from (i) HVR-H1 comprising the amino acid sequence of SEQ ID NO:15, (ii) HVR-H2 comprising the amino acid sequence of SEQ ID NO:33, and (iii) HVR-H3 comprising the amino acid sequence of SEQ ID NO:63; and (b) a VL domain comprising at least one, at least two, or all three VL HVR sequences selected from (i) HVR-L1 comprising the amino acid sequence of SEQ ID NO:80, (ii) HVR-L2 comprising the amino acid sequence of SEQ ID NO:100, and (c) HVR-L3 comprising the amino acid sequence of SEQ ID NO:113.

In another aspect, an anti-KLK5 antibody is provided comprising (a) HVR-H1 comprising the amino acid sequence of SEQ ID NO:15; (b) HVR-H2 comprising the amino acid sequence of SEQ ID NO:33; (c) HVR-H3 comprising the amino acid sequence of SEQ ID NO:63; (d) HVR-L1 comprising the amino acid sequence of SEQ ID NO:80; (e) HVR-L2 comprising the amino acid sequence of SEQ ID NO:100; and (f) HVR-L3 comprising the amino acid sequence of SEQ ID NO:113.

In another aspect, an anti-KLK5 antibody is provided comprising a heavy chain variable domain (VH) sequence having at least any of 90%, 91%, 92%, 93%, 94%, 95%, 96%, 97%, 98%, 99%, or 100% sequence identity to the amino acid sequence of SEQ ID NO:171. In certain embodiments, a VH sequence having at least any of 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:171. In certain embodiments, substitutions, insertions, or deletions occur in regions outside the HVRs (i.e., in the FRs). Optionally, the anti-KLK5 antibody comprises the VH sequence in SEQ ID NO:171, including post-translational modifications of that sequence. In a particular embodiment, the VH comprises one, two or three HVRs selected from: (a) HVR-H1 comprising the amino acid sequence of SEQ ID NO:15, (b) HVR-H2 comprising the amino acid sequence of SEQ ID NO:33, and (c) HVR-H3 comprising the amino acid sequence of SEQ ID NO:63.

In another aspect, an anti-KLK5 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:132. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:132. In certain embodiments, the substitutions, insertions, or deletions occur in regions outside the HVRs (i.e., in the FRs). Optionally, the anti-KLK5 antibody comprises the VL sequence in SEQ ID NO:132, including post-translational modifications of that sequence. In a particular embodiment, the VL comprises one, two or three HVRs selected from (a) HVR-L1 comprising the amino acid sequence of SEQ ID NO:80; (b) HVR-L2 comprising the amino acid sequence of SEQ ID NO:100; and (c) HVR-L3 comprising the amino acid sequence of SEQ ID NO:113.

In another aspect, an anti-KLK5 antibody is provided, wherein the antibody comprises a VH as in any of the embodiments provided above, and a VL as in any of the embodiments provided above. In one embodiment, the antibody comprises the VH and VL sequences in SEQ ID NO:171 and SEQ ID NO:132, respectively, including post-translational modifications of those sequences.

In a further aspect, an anti-KLK5 antibody is provided that binds to the same epitope as an anti-KLK5 antibody provided herein. For example, in certain embodiments, an antibody is provided that binds to the same epitope as an anti-KLK5 antibody comprising a VH sequence of SEQ ID NO:171 and a VL sequence of SEQ ID NO:132.

In a further aspect, an anti-KLK5 antibody according to any of the above embodiments is a monoclonal antibody, including a chimeric, humanized or human antibody. In one embodiment, an anti-KLK5 antibody is humanized. In one embodiment, an anti-KLK5 antibody comprises HVRs as in any of the above embodiments, and further comprises an acceptor human framework, e.g. a human immunoglobulin framework or a human consensus framework.

In one embodiment, an anti-KLK5 antibody is an antibody fragment, e.g., a Fv, Fab, Fab', scFv, diabody, or F(ab')$_2$ fragment. In another embodiment, the antibody is a full length antibody, e.g an intact IgG1 antibody or an intact IgG4 antibody or other antibody class or isotype as defined herein.

In a further aspect, an anti-KLK5 antibody according to any of the above embodiments may incorporate any of the features, singly or in combination, as described below.

Antibody 2-3F4 and Other Embodiments

In one aspect, an anti-KLK5 antibody is provided comprising at least one, two, three, four, five, or six HVRs selected from (a) HVR-H1 comprising the amino acid sequence of SEQ ID NO:16; (b) HVR-H2 comprising the amino acid sequence of SEQ ID NO:34; (c) HVR-H3 comprising the amino acid sequence of SEQ ID NO:64; (d) HVR-L1 comprising the amino acid sequence of SEQ ID NO:81; (e) HVR-L2 comprising the amino acid sequence of SEQ ID NO:99; and (f) HVR-L3 comprising the amino acid sequence of SEQ ID NO:114.

In one aspect, an anti-KLK5 antibody is provided comprising at least one, at least two, or all three VH HVR sequences selected from (a) HVR-H1 comprising the amino acid sequence of SEQ ID NO:16; (b) HVR-H2 comprising the amino acid sequence of SEQ ID NO:34; and (c) HVR-H3 comprising the amino acid sequence of SEQ ID NO:64. In one embodiment, the antibody comprises HVR-H3 comprising the amino acid sequence of SEQ ID NO:64. In another embodiment, the antibody comprises HVR-H3 comprising the amino acid sequence of SEQ ID NO:64 and HVR-L3 comprising the amino acid sequence of SEQ ID NO:114. In a further embodiment, the antibody comprises HVR-H3 comprising the amino acid sequence of SEQ ID NO:64, HVR-L3 comprising the amino acid sequence of SEQ ID NO:114, and HVR-H2 comprising the amino acid sequence of SEQ ID NO:34. In a further embodiment, the antibody comprises (a) HVR-H1 comprising the amino acid sequence of SEQ ID NO:16; (b) HVR-H2 comprising the amino acid sequence of SEQ ID NO:34; and (c) HVR-H3 comprising the amino acid sequence of SEQ ID NO:64.

In another aspect, an anti-KLK5 antibody is provided comprising at least one, at least two, or all three VL HVR sequences selected from (a) HVR-L1 comprising the amino acid sequence of SEQ ID NO:81; (b) HVR-L2 comprising the amino acid sequence of SEQ ID NO:99; and (c) HVR-L3 comprising the amino acid sequence of SEQ ID NO:114. In one embodiment, the antibody comprises (a) HVR-L1 comprising the amino acid sequence of SEQ ID NO:81; (b) HVR-L2 comprising the amino acid sequence of SEQ ID NO:99; and (c) HVR-L3 comprising the amino acid sequence of SEQ ID NO:114.

In another aspect, an anti-KLK5 antibody is provided comprises (a) a VH domain comprising at least one, at least two, or all three VH HVR sequences selected from (i) HVR-H1 comprising the amino acid sequence of SEQ ID NO:16, (ii) HVR-H2 comprising the amino acid sequence of SEQ ID NO:34, and (iii) HVR-H3 comprising the amino acid sequence of SEQ ID NO:64; and (b) a VL domain comprising at least one, at least two, or all three VL HVR sequences selected from (i) HVR-L1 comprising the amino acid sequence of SEQ ID NO:81, (ii) HVR-L2 comprising the amino acid sequence of SEQ ID NO:99, and (c) HVR-L3 comprising the amino acid sequence of SEQ ID NO:114.

In another aspect, an anti-KLK5 antibody is provided comprising (a) HVR-H1 comprising the amino acid sequence of SEQ ID NO:16; (b) HVR-H2 comprising the amino acid sequence of SEQ ID NO:34; (c) HVR-H3 comprising the amino acid sequence of SEQ ID NO:64; (d) HVR-L1 comprising the amino acid sequence of SEQ ID NO:81; (e) HVR-L2 comprising the amino acid sequence of SEQ ID NO:99; and (f) HVR-L3 comprising the amino acid sequence of SEQ ID NO:114.

In another aspect, an anti-KLK5 antibody is provided comprising a heavy chain variable domain (VH) sequence having at least any of 90%, 91%, 92%, 93%, 94%, 95%, 96%, 97%, 98%, 99%, or 100% sequence identity to the amino acid sequence of SEQ ID NO:172. In certain embodiments, a VH sequence having at least any of 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:172. In certain embodiments, substitutions, insertions, or deletions occur in regions outside the HVRs (i.e., in the FRs). Optionally, the anti-KLK5 antibody comprises the VH sequence in SEQ ID NO:172, including post-translational modifications of that sequence. In a particular embodiment, the VH comprises one, two or three HVRs selected from: (a) HVR-H1 comprising the amino acid sequence of SEQ ID NO:16, (b) HVR-H2 comprising the amino acid sequence of SEQ ID NO:34, and (c) HVR-H3 comprising the amino acid sequence of SEQ ID NO:64.

In another aspect, an anti-KLK5 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:133. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:133. In certain embodiments, the substitutions, insertions, or deletions occur in regions outside the HVRs (i.e., in the FRs). Optionally, the anti-KLK5 antibody comprises the VL sequence in SEQ ID NO:133, including post-translational modifications of that sequence. In a particular embodiment, the VL comprises one, two or three HVRs selected from (a) HVR-L1 comprising the amino acid sequence of SEQ ID NO:81; (b) HVR-L2 comprising the amino acid sequence of SEQ ID NO:99; and (c) HVR-L3 comprising the amino acid sequence of SEQ ID NO:114.

In another aspect, an anti-KLK5 antibody is provided, wherein the antibody comprises a VH as in any of the embodiments provided above, and a VL as in any of the embodiments provided above. In one embodiment, the antibody comprises the VH and VL sequences in SEQ ID NO:172 and SEQ ID NO:133, respectively, including post-translational modifications of those sequences.

In a further aspect, an anti-KLK5 antibody is provided that binds to the same epitope as an anti-KLK5 antibody provided herein. For example, in certain embodiments, an antibody is provided that binds to the same epitope as an anti-KLK5 antibody comprising a VH sequence of SEQ ID NO:172 and a VL sequence of SEQ ID NO:133.

In a further aspect, an anti-KLK5 antibody according to any of the above embodiments is a monoclonal antibody, including a chimeric, humanized or human antibody. In one embodiment, an anti-KLK5 antibody is humanized. In one embodiment, an anti-KLK5 antibody comprises HVRs as in any of the above embodiments, and further comprises an acceptor human framework, e.g. a human immunoglobulin framework or a human consensus framework.

In one embodiment, an anti-KLK5 antibody is an antibody fragment, e.g., a Fv, Fab, Fab', scFv, diabody, or F(ab')$_2$ fragment. In another embodiment, the antibody is a full length antibody, e.g an intact IgG1 antibody or an intact IgG4 antibody or other antibody class or isotype as defined herein.

In a further aspect, an anti-KLK5 antibody according to any of the above embodiments may incorporate any of the features, singly or in combination, as described below.

Antibody 10C5 and Other Embodiments

In one aspect, an anti-KLK5 antibody is provided comprising at least one, two, three, four, five, or six HVRs selected from (a) HVR-H1 comprising the amino acid sequence of SEQ ID NO:17; (b) HVR-H2 comprising the amino acid sequence of SEQ ID NO:35; (c) HVR-H3 comprising the amino acid sequence of SEQ ID NO:65; (d) HVR-L1 comprising the amino acid sequence of SEQ ID NO:82; (e) HVR-L2 comprising the amino acid sequence of SEQ ID NO:101; and (f) HVR-L3 comprising the amino acid sequence of SEQ ID NO:115.

In one aspect, an anti-KLK5 antibody is provided comprising at least one, at least two, or all three VH HVR sequences selected from (a) HVR-H1 comprising the amino acid sequence of SEQ ID NO:17; (b) HVR-H2 comprising the amino acid sequence of SEQ ID NO:35; and (c) HVR-H3 comprising the amino acid sequence of SEQ ID NO:65. In one embodiment, the antibody comprises HVR-H3 comprising the amino acid sequence of SEQ ID NO:65. In another embodiment, the antibody comprises HVR-H3 comprising the amino acid sequence of SEQ ID NO:65 and HVR-L3 comprising the amino acid sequence of SEQ ID NO:115. In a further embodiment, the antibody comprises HVR-H3 comprising the amino acid sequence of SEQ ID NO:65, HVR-L3 comprising the amino acid sequence of SEQ ID NO:115, and HVR-H2 comprising the amino acid sequence of SEQ ID NO:35. In a further embodiment, the antibody comprises (a) HVR-H1 comprising the amino acid sequence of SEQ ID NO:17; (b) HVR-H2 comprising the amino acid sequence of SEQ ID NO:35; and (c) HVR-H3 comprising the amino acid sequence of SEQ ID NO:65.

In another aspect, an anti-KLK5 antibody is provided comprising at least one, at least two, or all three VL HVR sequences selected from (a) HVR-L1 comprising the amino acid sequence of SEQ ID NO:82; (b) HVR-L2 comprising the amino acid sequence of SEQ ID NO:101; and (c) HVR-L3 comprising the amino acid sequence of SEQ ID NO:115. In one embodiment, the antibody comprises (a) HVR-L1 comprising the amino acid sequence of SEQ ID NO:82; (b) HVR-L2 comprising the amino acid sequence of SEQ ID NO:101; and (c) HVR-L3 comprising the amino acid sequence of SEQ ID NO:115.

In another aspect, an anti-KLK5 antibody is provided comprises (a) a VH domain comprising at least one, at least two, or all three VH HVR sequences selected from (i) HVR-H1 comprising the amino acid sequence of SEQ ID NO:17, (ii) HVR-H2 comprising the amino acid sequence of SEQ ID NO:35, and (iii) HVR-H3 comprising the amino acid sequence of SEQ ID NO:65; and (b) a VL domain comprising at least one, at least two, or all three VL HVR sequences selected from (i) HVR-L1 comprising the amino acid sequence of SEQ ID NO:82, (ii) HVR-L2 comprising the amino acid sequence of SEQ ID NO:101, and (c) HVR-L3 comprising the amino acid sequence of SEQ ID NO:115.

In another aspect, an anti-KLK5 antibody is provided comprising (a) HVR-H1 comprising the amino acid sequence of SEQ ID NO:17; (b) HVR-H2 comprising the amino acid sequence of SEQ ID NO:35; (c) HVR-H3 comprising the amino acid sequence of SEQ ID NO:65; (d) HVR-L1 comprising the amino acid sequence of SEQ ID NO:82; (e) HVR-L2 comprising the amino acid sequence of SEQ ID NO:101; and (f) HVR-L3 comprising the amino acid sequence of SEQ ID NO:115.

In another aspect, an anti-KLK5 antibody is provided comprising a heavy chain variable domain (VH) sequence having at least any of 90%, 91%, 92%, 93%, 94%, 95%, 96%, 97%, 98%, 99%, or 100% sequence identity to the amino acid sequence of SEQ ID NO:201. In certain embodiments, a VH sequence having at least any of 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:201. In certain embodiments, substitutions, insertions, or deletions occur in regions outside the HVRs (i.e., in the FRs). Optionally, the anti-KLK5 antibody comprises the VH sequence in SEQ ID NO:201, including post-translational modifications of that sequence. In a particular embodiment, the VH comprises one, two or three HVRs selected from: (a) HVR-H1 comprising the amino acid sequence of SEQ ID NO:17, (b) HVR-H2 comprising the amino acid sequence of SEQ ID NO:35, and (c) HVR-H3 comprising the amino acid sequence of SEQ ID NO:65.

In another aspect, an anti-KLK5 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:139. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:139. In certain embodiments, the substitutions, insertions, or deletions occur in regions outside the HVRs (i.e., in the FRs). Optionally, the anti-KLK5 antibody comprises the VL sequence in SEQ ID NO:139, including post-translational modifications of that sequence. In a particular embodiment, the VL comprises one, two or three HVRs selected from (a) HVR-L1 comprising the amino acid sequence of SEQ ID NO:82; (b) HVR-L2 comprising the amino acid sequence of SEQ ID NO:101; and (c) HVR-L3 comprising the amino acid sequence of SEQ ID NO:115.

In another aspect, an anti-KLK5 antibody is provided, wherein the antibody comprises a VH as in any of the embodiments provided above, and a VL as in any of the embodiments provided above. In one embodiment, the antibody comprises the VH and VL sequences in SEQ ID NO:201 and SEQ ID NO:139, respectively, including post-translational modifications of those sequences.

In a further aspect, an anti-KLK5 antibody is provided that binds to the same epitope as an anti-KLK5 antibody provided herein. For example, in certain embodiments, an antibody is provided that binds to the same epitope as an anti-KLK5 antibody comprising a VH sequence of SEQ ID NO:201 and a VL sequence of SEQ ID NO:139. In certain embodiments, an antibody is provided that, when bound to KLK5 results in a thermodynamic epitope comprising one or more of the sequences selected from the group consisting of SEQ ID NO:316, SEQ ID NO:317, SEQ ID NO:318, and SEQ ID NO:319 as measured by hydrogen exchange mass spectrometry.

In a further aspect, an anti-KLK5 antibody according to any of the above embodiments is a monoclonal antibody, including a chimeric, humanized or human antibody. In one embodiment, an anti-KLK5 antibody is humanized. In one embodiment, an anti-KLK5 antibody comprises HVRs as in any of the above embodiments, and further comprises an acceptor human framework, e.g. a human immunoglobulin framework or a human consensus framework.

In one embodiment, the anti-KLK5 antibody comprises a VH domain comprising one or more heavy chain framework sequences selected from (a) a heavy chain frame work region 1 (HC-FR1) of SEQ ID NO:333, (b) a heavy chain frame work region 2 (HC-FR2) of SEQ ID NO:334, (c) a heavy chain frame work region 3 (HC-FR3) of SEQ ID NO:335, and (d) a heavy chain frame work region 4 (HC-FR4) of SEQ ID NO:336.

In one embodiment, the anti-KLK5 antibody comprises a VH domain comprising a HC-FR1 of SEQ ID NO:333. In one embodiment, the anti-KLK5 antibody comprises a VH domain comprising a HC-FR2 of SEQ ID NO:334. In one embodiment, the anti-KLK5 antibody comprises a VH domain comprising a HC-FR3 of SEQ ID NO:335. In one embodiment, the anti-KLK5 antibody comprises a VH domain comprising a HC-FR4 of SEQ ID NO:336.

In one embodiment, the anti-KLK5 antibody comprises a VL domain comprising one or more light chain framework sequences selected from (a) a light chain frame work region 1 (LC-FR1) of SEQ ID NO:329, (b) a light chain frame work region 2 (LC-FR2) of SEQ ID NO:330, (c) a light chain frame work region 3 (LC-FR3) of SEQ ID NO:331, and (d) a light chain frame work region 4 (LC-FR4) of SEQ ID NO:332.

In one embodiment, the anti-KLK5 antibody comprises a VL domain comprising a LC-FR1 of SEQ ID NO:329. In one embodiment, the anti-KLK5 antibody comprises a VL domain comprising a LC-FR2 of SEQ ID NO:330. In one embodiment, the anti-KLK5 antibody comprises a VL domain comprising a LC-FR3 of SEQ ID NO:331. In one embodiment, the anti-KLK5 antibody comprises a VL domain comprising a LC-FR4 of SEQ ID NO:332.

In one embodiment, an anti-KLK5 antibody is an antibody fragment, e.g., a Fv, Fab, Fab', scFv, diabody, or F(ab')$_2$ fragment. In another embodiment, the antibody is a full length antibody, e.g an intact IgG1 antibody or an intact IgG4 antibody or other antibody class or isotype as defined herein.

Further provided herein is an antibody that specifically binds to human KLK5, wherein the antibody binds to an epitope on human KLK5 comprising one or more amino acid residues selected from the group consisting of Pro130, Ser131, Ala132, Val162, Leu163, Ser164, Gln165, Lys166, Arg167, Glu169, Asp170, Ala171, Tyr172, Pro173, Arg174, Gln174A, Ile176, Asp177, Asp178, Arg224, and Lys233 according to standard protease numbering. In one embodiment, the antibody comprises (a) HVR-H1 comprising the amino acid sequence of SEQ ID NO:17; (b) HVR-H2 comprising the amino acid sequence of SEQ ID NO:35; (c) HVR-H3 comprising the amino acid sequence of SEQ ID NO:65; (d) HVR-L1 comprising the amino acid sequence of SEQ ID NO:82; (e) HVR-L2 comprising the amino acid sequence of SEQ ID NO:101; and (f) HVR-L3 comprising the amino acid sequence of SEQ ID NO:115. In one embodiment, the antibody comprises the VH and VL sequences in SEQ ID NO:201 and SEQ ID NO:139

Further provided herein is an antibody when bound to human KLK5 results in a conformational change of human KLK5, wherein the conformational change allosterically results in the disruption of the substrate binding site and/or the active site of human KLK5. In one embodiment, the antibody comprises (a) HVR-H1 comprising the amino acid sequence of SEQ ID NO:17; (b) HVR-H2 comprising the amino acid sequence of SEQ ID NO:35; (c) HVR-H3 comprising the amino acid sequence of SEQ ID NO:65; (d) HVR-L1 comprising the amino acid sequence of SEQ ID NO:82; (e) HVR-L2 comprising the amino acid sequence of SEQ ID NO:101; and (f) HVR-L3 comprising the amino acid sequence of SEQ ID NO:115. In one embodiment, the antibody comprises the VH and VL sequences in SEQ ID NO:201 and SEQ ID NO:139.

In a further aspect, an anti-KLK5 antibody according to any of the above embodiments may incorporate any of the features, singly or in combination, as described below.

Antibody 2B11 and Other Embodiments

In one aspect, an anti-KLK5 antibody is provided comprising at least one, two, three, four, five, or six HVRs selected from (a) HVR-H1 comprising the amino acid sequence of SEQ ID NO:18; (b) HVR-H2 comprising the amino acid sequence of SEQ ID NO:39; (c) HVR-H3 comprising the amino acid sequence of SEQ ID NO:66; (d) HVR-L1 comprising the amino acid sequence of SEQ ID NO:83; (e) HVR-L2 comprising the amino acid sequence of SEQ ID NO:102; and (f) HVR-L3 comprising the amino acid sequence of SEQ ID NO:116.

In one aspect, an anti-KLK5 antibody is provided comprising at least one, at least two, or all three VH HVR sequences selected from (a) HVR-H1 comprising the amino acid sequence of SEQ ID NO:18; (b) HVR-H2 comprising the amino acid sequence of SEQ ID NO:39; and (c) HVR-H3 comprising the amino acid sequence of SEQ ID NO:66. In one embodiment, the antibody comprises HVR-H3 comprising the amino acid sequence of SEQ ID NO:66. In another embodiment, the antibody comprises HVR-H3 comprising the amino acid sequence of SEQ ID NO:66 and HVR-L3 comprising the amino acid sequence of SEQ ID NO:116. In a further embodiment, the antibody comprises HVR-H3 comprising the amino acid sequence of SEQ ID NO:66, HVR-L3 comprising the amino acid sequence of SEQ ID NO:116, and HVR-H2 comprising the amino acid sequence of SEQ ID NO:39. In a further embodiment, the antibody comprises (a) HVR-H1 comprising the amino acid sequence of SEQ ID NO:18; (b) HVR-H2 comprising the amino acid sequence of SEQ ID NO:39; and (c) HVR-H3 comprising the amino acid sequence of SEQ ID NO:66.

In another aspect, an anti-KLK5 antibody is provided comprising at least one, at least two, or all three VL HVR sequences selected from (a) HVR-L1 comprising the amino acid sequence of SEQ ID NO:83; (b) HVR-L2 comprising the amino acid sequence of SEQ ID NO:102; and (c) HVR-L3 comprising the amino acid sequence of SEQ ID NO:116. In one embodiment, the antibody comprises (a) HVR-L1 comprising the amino acid sequence of SEQ ID NO:83; (b) HVR-L2 comprising the amino acid sequence of SEQ ID NO:102; and (c) HVR-L3 comprising the amino acid sequence of SEQ ID NO:116.

In another aspect, an anti-KLK5 antibody is provided comprises (a) a VH domain comprising at least one, at least two, or all three VH HVR sequences selected from (i) HVR-H1 comprising the amino acid sequence of SEQ ID NO:18, (ii) HVR-H2 comprising the amino acid sequence of SEQ ID NO:39, and (iii) HVR-H3 comprising the amino acid sequence of SEQ ID NO:66; and (b) a VL domain comprising at least one, at least two, or all three VL HVR sequences selected from (i) HVR-L1 comprising the amino acid sequence of SEQ ID NO:83, (ii) HVR-L2 comprising the amino acid sequence of SEQ ID NO:102, and (c) HVR-L3 comprising the amino acid sequence of SEQ ID NO:116.

In another aspect, an anti-KLK5 antibody is provided comprising (a) HVR-H1 comprising the amino acid sequence of SEQ ID NO:18; (b) HVR-H2 comprising the amino acid sequence of SEQ ID NO:39; (c) HVR-H3 comprising the amino acid sequence of SEQ ID NO:66; (d) HVR-L1 comprising the amino acid sequence of SEQ ID NO:83; (e) HVR-L2 comprising the amino acid sequence of SEQ ID NO:102; and (f) HVR-L3 comprising the amino acid sequence of SEQ ID NO:116.

In another aspect, an anti-KLK5 antibody is provided comprising a heavy chain variable domain (VH) sequence having at least any of 90%, 91%, 92%, 93%, 94%, 95%, 96%, 97%, 98%, 99%, or 100% sequence identity to the amino acid sequence of SEQ ID NO:203. In certain embodiments, a VH sequence having at least any of 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:203. In certain embodiments, substitutions, insertions, or deletions occur in regions outside the HVRs (i.e., in the FRs). Optionally, the anti-KLK5 antibody comprises the VH sequence in SEQ ID NO:203, including post-translational modifications of that sequence. In a particular embodiment, the VH comprises one, two or three HVRs selected from: (a) HVR-H1 comprising the amino acid sequence of SEQ ID NO:18, (b) HVR-H2 comprising the amino acid sequence of SEQ ID NO:39, and (c) HVR-H3 comprising the amino acid sequence of SEQ ID NO:66.

In another aspect, an anti-KLK5 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:141. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:141. In certain embodiments, the substitutions, insertions, or deletions occur in regions outside the HVRs (i.e., in the FRs). Optionally, the anti-KLK5 antibody comprises the VL sequence in SEQ ID NO:141, including post-translational modifications of that sequence. In a particular embodiment, the VL comprises one, two or three HVRs selected from (a) HVR-L1 comprising the amino acid sequence of SEQ ID NO:83; (b) HVR-L2 comprising the amino acid sequence of SEQ ID NO:102; and (c) HVR-L3 comprising the amino acid sequence of SEQ ID NO:116.

In another aspect, an anti-KLK5 antibody is provided, wherein the antibody comprises a VH as in any of the embodiments provided above, and a VL as in any of the embodiments provided above. In one embodiment, the antibody comprises the VH and VL sequences in SEQ ID NO:203 and SEQ ID NO:141, respectively, including post-translational modifications of those sequences.

In a further aspect, an anti-KLK5 antibody is provided that binds to the same epitope as an anti-KLK5 antibody provided herein. For example, in certain embodiments, an antibody is provided that binds to the same epitope as an anti-KLK5 antibody comprising a VH sequence of SEQ ID NO:203 and a VL sequence of SEQ ID NO:141.

In a further aspect, an anti-KLK5 antibody according to any of the above embodiments is a monoclonal antibody, including a chimeric, humanized or human antibody. In one embodiment, an anti-KLK5 antibody is humanized. In one embodiment, an anti-KLK5 antibody comprises HVRs as in any of the above embodiments, and further comprises an acceptor human framework, e.g. a human immunoglobulin framework or a human consensus framework.

In one embodiment, an anti-KLK5 antibody is an antibody fragment, e.g., a Fv, Fab, Fab', scFv, diabody, or F(ab')$_2$ fragment. In another embodiment, the antibody is a full length antibody, e.g an intact IgG1 antibody or an intact IgG4 antibody or other antibody class or isotype as defined herein.

In a further aspect, an anti-KLK5 antibody according to any of the above embodiments may incorporate any of the features, singly or in combination, as described below.

Antibody 10H3 and Other Embodiments

In one aspect, an anti-KLK5 antibody is provided comprising at least one, two, three, four, five, or six HVRs selected from (a) HVR-H1 comprising the amino acid sequence of SEQ ID NO:19; (b) HVR-H2 comprising the amino acid sequence of SEQ ID NO:40; (c) HVR-H3 comprising the amino acid sequence of SEQ ID NO:67; (d) HVR-L1 comprising the amino acid sequence of SEQ ID NO:84; (e) HVR-L2 comprising the amino acid sequence of SEQ ID NO:103; and (f) HVR-L3 comprising the amino acid sequence of SEQ ID NO:117.

In one aspect, an anti-KLK5 antibody is provided comprising at least one, at least two, or all three VH HVR sequences selected from (a) HVR-H1 comprising the amino acid sequence of SEQ ID NO:19; (b) HVR-H2 comprising the amino acid sequence of SEQ ID NO:40; and (c) HVR-H3 comprising the amino acid sequence of SEQ ID NO:67. In one embodiment, the antibody comprises HVR-H3 comprising the amino acid sequence of SEQ ID NO:67. In another embodiment, the antibody comprises HVR-H3 comprising the amino acid sequence of SEQ ID NO:67 and HVR-L3 comprising the amino acid sequence of SEQ ID NO:117. In a further embodiment, the antibody comprises HVR-H3 comprising the amino acid sequence of SEQ ID NO:67, HVR-L3 comprising the amino acid sequence of SEQ ID NO:117, and HVR-H2 comprising the amino acid sequence of SEQ ID NO:40. In a further embodiment, the antibody comprises (a) HVR-H1 comprising the amino acid sequence of SEQ ID NO:22; (b) HVR-H2 comprising the amino acid sequence of SEQ ID NO:40; and (c) HVR-H3 comprising the amino acid sequence of SEQ ID NO:67.

In another aspect, an anti-KLK5 antibody is provided comprising at least one, at least two, or all three VL HVR sequences selected from (a) HVR-L1 comprising the amino acid sequence of SEQ ID NO:84; (b) HVR-L2 comprising the amino acid sequence of SEQ ID NO:103; and (c) HVR-L3 comprising the amino acid sequence of SEQ ID NO:117. In one embodiment, the antibody comprises (a) HVR-L1 comprising the amino acid sequence of SEQ ID NO:84; (b) HVR-L2 comprising the amino acid sequence of SEQ ID NO:103; and (c) HVR-L3 comprising the amino acid sequence of SEQ ID NO:117.

In another aspect, an anti-KLK5 antibody is provided comprises (a) a VH domain comprising at least one, at least two, or all three VH HVR sequences selected from (i) HVR-H1 comprising the amino acid sequence of SEQ ID NO:19, (ii) HVR-H2 comprising the amino acid sequence of SEQ ID NO:40, and (iii) HVR-H3 comprising the amino acid sequence of SEQ ID NO:67; and (b) a VL domain comprising at least one, at least two, or all three VL HVR sequences selected from (i) HVR-L1 comprising the amino acid sequence of SEQ ID NO:84, (ii) HVR-L2 comprising the amino acid sequence of SEQ ID NO:103, and (c) HVR-L3 comprising the amino acid sequence of SEQ ID NO:117.

In another aspect, an anti-KLK5 antibody is provided comprising (a) HVR-H1 comprising the amino acid sequence of SEQ ID NO:19; (b) HVR-H2 comprising the amino acid sequence of SEQ ID NO:40; (c) HVR-H3 comprising the amino acid sequence of SEQ ID NO:67; (d) HVR-L1 comprising the amino acid sequence of SEQ ID NO:84; (e) HVR-L2 comprising the amino acid sequence of SEQ ID NO:103; and (f) HVR-L3 comprising the amino acid sequence of SEQ ID NO:117.

In another aspect, an anti-KLK5 antibody is provided comprising a heavy chain variable domain (VH) sequence having at least any of 90%, 91%, 92%, 93%, 94%, 95%, 96%, 97%, 98%, 99%, or 100% sequence identity to the amino acid sequence of SEQ ID NO:204. In certain embodiments, a VH sequence having at least any of 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:204. In certain embodiments, substitutions, insertions, or deletions occur in regions outside the HVRs (i.e., in the FRs). Optionally, the anti-KLK5 antibody comprises the VH sequence in SEQ ID NO:204, including post-translational modifications of that sequence. In a particular embodiment, the VH comprises one, two or three HVRs selected from: (a) HVR-H1 comprising the amino acid sequence of SEQ ID NO:19, (b) HVR-H2 comprising the amino acid sequence of SEQ ID NO:40, and (c) HVR-H3 comprising the amino acid sequence of SEQ ID NO:67.

In another aspect, an anti-KLK5 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:142. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:142. In certain embodiments, the substitutions, insertions, or deletions occur in regions outside the HVRs (i.e., in the FRs). Optionally, the anti-KLK5 antibody comprises the VL sequence in SEQ ID NO:142, including post-translational modifications of that sequence. In a particular embodiment, the VL comprises one, two or three HVRs selected from (a) HVR-L1 comprising the amino acid sequence of SEQ ID NO:84; (b) HVR-L2 comprising the amino acid sequence of SEQ ID NO:103; and (c) HVR-L3 comprising the amino acid sequence of SEQ ID NO:117.

In another aspect, an anti-KLK5 antibody is provided, wherein the antibody comprises a VH as in any of the embodiments provided above, and a VL as in any of the embodiments provided above. In one embodiment, the antibody comprises the VH and VL sequences in SEQ ID NO:204 and SEQ ID NO:142, respectively, including post-translational modifications of those sequences.

In a further aspect, an anti-KLK5 antibody is provided that binds to the same epitope as an anti-KLK5 antibody provided herein. For example, in certain embodiments, an antibody is provided that binds to the same epitope as an anti-KLK5 antibody comprising a VH sequence of SEQ ID NO:204 and a VL sequence of SEQ ID NO:142. In certain embodiments, an antibody is provided that, when bound to KLK5 results in a thermodynamic epitope comprising one or more of the sequences selected from the group consisting of SEQ ID NO:316, SEQ ID NO:317, SEQ ID NO:318, and SEQ ID NO:319 as measured by hydrogen exchange mass spectrometry.

In a further aspect, an anti-KLK5 antibody according to any of the above embodiments is a monoclonal antibody, including a chimeric, humanized or human antibody. In one embodiment, an anti-KLK5 antibody is humanized. In one embodiment, an anti-KLK5 antibody comprises HVRs as in any of the above embodiments, and further comprises an acceptor human framework, e.g. a human immunoglobulin framework or a human consensus framework.

In one embodiment, an anti-KLK5 antibody is an antibody fragment, e.g., a Fv, Fab, Fab', scFv, diabody, or F(ab')$_2$ fragment. In another embodiment, the antibody is a full length antibody, e.g an intact IgG1 antibody or an intact IgG4 antibody or other antibody class or isotype as defined herein.

In a further aspect, an anti-KLK5 antibody according to any of the above embodiments may incorporate any of the features, singly or in combination, as described below.

Antibody 9H3 and Other Embodiments

In one aspect, an anti-KLK5 antibody is provided comprising at least one, two, three, four, five, or six HVRs selected from (a) HVR-H1 comprising the amino acid sequence of SEQ ID NO:20; (b) HVR-H2 comprising the amino acid sequence of SEQ ID NO:33; (c) HVR-H3 comprising the amino acid sequence of SEQ ID NO:68; (d) HVR-L1 comprising the amino acid sequence of SEQ ID NO:85; (e) HVR-L2 comprising the amino acid sequence of SEQ ID NO:103; and (f) HVR-L3 comprising the amino acid sequence of SEQ ID NO:118.

In one aspect, an anti-KLK5 antibody is provided comprising at least one, at least two, or all three VH HVR sequences selected from (a) HVR-H1 comprising the amino acid sequence of SEQ ID NO:20; (b) HVR-H2 comprising the amino acid sequence of SEQ ID NO:33; and (c) HVR-H3 comprising the amino acid sequence of SEQ ID NO:68. In one embodiment, the antibody comprises HVR-H3 comprising the amino acid sequence of SEQ ID NO:68. In another embodiment, the antibody comprises HVR-H3 comprising the amino acid sequence of SEQ ID NO:68 and HVR-L3 comprising the amino acid sequence of SEQ ID NO:118. In a further embodiment, the antibody comprises HVR-H3 comprising the amino acid sequence of SEQ ID NO:68, HVR-L3 comprising the amino acid sequence of SEQ ID NO:118, and HVR-H2 comprising the amino acid sequence of SEQ ID NO:33. In a further embodiment, the antibody comprises (a) HVR-H1 comprising the amino acid sequence of SEQ ID NO:20; (b) HVR-H2 comprising the amino acid sequence of SEQ ID NO:33; and (c) HVR-H3 comprising the amino acid sequence of SEQ ID NO:68.

In another aspect, an anti-KLK5 antibody is provided comprising at least one, at least two, or all three VL HVR sequences selected from (a) HVR-L1 comprising the amino acid sequence of SEQ ID NO:85; (b) HVR-L2 comprising the amino acid sequence of SEQ ID NO:103; and (c) HVR-L3 comprising the amino acid sequence of SEQ ID NO:118. In one embodiment, the antibody comprises (a) HVR-L1 comprising the amino acid sequence of SEQ ID NO:85; (b) HVR-L2 comprising the amino acid sequence of SEQ ID NO:103; and (c) HVR-L3 comprising the amino acid sequence of SEQ ID NO:118.

In another aspect, an anti-KLK5 antibody is provided comprises (a) a VH domain comprising at least one, at least two, or all three VH HVR sequences selected from (i) HVR-H1 comprising the amino acid sequence of SEQ ID NO:20, (ii) HVR-H2 comprising the amino acid sequence of SEQ ID NO:33, and (iii) HVR-H3 comprising the amino acid sequence of SEQ ID NO:68; and (b) a VL domain comprising at least one, at least two, or all three VL HVR sequences selected from (i) HVR-L1 comprising the amino acid sequence of SEQ ID NO:85, (ii) HVR-L2 comprising the amino acid sequence of SEQ ID NO:103, and (c) HVR-L3 comprising the amino acid sequence of SEQ ID NO:118.

In another aspect, an anti-KLK5 antibody is provided comprising (a) HVR-H1 comprising the amino acid sequence of SEQ ID NO:20; (b) HVR-H2 comprising the amino acid sequence of SEQ ID NO:33; (c) HVR-H3 comprising the amino acid sequence of SEQ ID NO:68; (d) HVR-L1 comprising the amino acid sequence of SEQ ID NO:85; (e) HVR-L2 comprising the amino acid sequence of SEQ ID NO:103; and (f) HVR-L3 comprising the amino acid sequence of SEQ ID NO:118.

In another aspect, an anti-KLK5 antibody is provided comprising a heavy chain variable domain (VH) sequence having at least any of 90%, 91%, 92%, 93%, 94%, 95%, 96%, 97%, 98%, 99%, or 100% sequence identity to the amino acid sequence of SEQ ID NO:205. In certain embodiments, a VH sequence having at least any of 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:205. In certain embodiments, substitutions, insertions, or deletions occur in regions outside the HVRs (i.e., in the FRs). Optionally, the anti-KLK5 antibody comprises the VH sequence in SEQ ID NO:205, including post-translational modifications of that sequence. In a particular embodiment, the VH comprises one, two or three HVRs selected from: (a) HVR-H1 comprising the amino acid sequence of SEQ ID NO:20, (b) HVR-H2 comprising the amino acid sequence of SEQ ID NO:33, and (c) HVR-H3 comprising the amino acid sequence of SEQ ID NO:68.

In another aspect, an anti-KLK5 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:143. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:143. In certain embodiments, the substitutions, insertions, or deletions occur in regions outside the HVRs (i.e., in the FRs). Optionally, the anti-KLK5 antibody comprises the VL sequence in SEQ ID NO:143, including post-translational modifications of that sequence. In a particular embodiment, the VL comprises one, two or three HVRs selected from (a) HVR-L1 comprising the amino acid sequence of SEQ ID NO:85; (b) HVR-L2 comprising the amino acid sequence of SEQ ID NO:103; and (c) HVR-L3 comprising the amino acid sequence of SEQ ID NO:118.

In another aspect, an anti-KLK5 antibody is provided, wherein the antibody comprises a VH as in any of the embodiments provided above, and a VL as in any of the embodiments provided above. In one embodiment, the antibody comprises the VH and VL sequences in SEQ ID NO:205 and SEQ ID NO:1143, respectively, including post-translational modifications of those sequences.

In a further aspect, an anti-KLK5 antibody is provided that binds to the same epitope as an anti-KLK5 antibody provided herein. For example, in certain embodiments, an antibody is provided that binds to the same epitope as an anti-KLK5 antibody comprising a VH sequence of SEQ ID NO:205 and a VL sequence of SEQ ID NO:143.

In a further aspect, an anti-KLK5 antibody according to any of the above embodiments is a monoclonal antibody, including a chimeric, humanized or human antibody. In one embodiment, an anti-KLK5 antibody is humanized. In one embodiment, an anti-KLK5 antibody comprises HVRs as in any of the above embodiments, and further comprises an acceptor human framework, e.g. a human immunoglobulin framework or a human consensus framework.

In one embodiment, an anti-KLK5 antibody is an antibody fragment, e.g., a Fv, Fab, Fab', scFv, diabody, or F(ab')$_2$ fragment. In another embodiment, the antibody is a full length antibody, e.g an intact IgG1 antibody or an intact IgG4 antibody or other antibody class or isotype as defined herein.

In a further aspect, an anti-KLK5 antibody according to any of the above embodiments may incorporate any of the features, singly or in combination, as described below.

Antibody 8B7 and Other Embodiments

In one aspect, an anti-KLK5 antibody is provided comprising at least one, two, three, four, five, or six HVRs selected from (a) HVR-H1 comprising the amino acid sequence of SEQ ID NO:21; (b) HVR-H2 comprising the amino acid sequence of SEQ ID NO:41; (c) HVR-H3 comprising the amino acid sequence of SEQ ID NO:69; (d) HVR-L1 comprising the amino acid sequence of SEQ ID NO:86; (e) HVR-L2 comprising the amino acid sequence of SEQ ID NO:104; and (f) HVR-L3 comprising the amino acid sequence of SEQ ID NO:118.

In one aspect, an anti-KLK5 antibody is provided comprising at least one, at least two, or all three VH HVR sequences selected from (a) HVR-H1 comprising the amino acid sequence of SEQ ID NO:21; (b) HVR-H2 comprising the amino acid sequence of SEQ ID NO:41; and (c) HVR-H3 comprising the amino acid sequence of SEQ ID NO:69. In one embodiment, the antibody comprises HVR-H3 comprising the amino acid sequence of SEQ ID NO:69. In another embodiment, the antibody comprises HVR-H3 comprising the amino acid sequence of SEQ ID NO:69 and HVR-L3 comprising the amino acid sequence of SEQ ID NO:118. In a further embodiment, the antibody comprises HVR-H3 comprising the amino acid sequence of SEQ ID NO:68, HVR-L3 comprising the amino acid sequence of SEQ ID NO:118, and HVR-H2 comprising the amino acid sequence of SEQ ID NO:41. In a further embodiment, the antibody comprises (a) HVR-H1 comprising the amino acid sequence of SEQ ID NO:21; (b) HVR-H2 comprising the amino acid sequence of SEQ ID NO:41; and (c) HVR-H3 comprising the amino acid sequence of SEQ ID NO:69.

In another aspect, an anti-KLK5 antibody is provided comprising at least one, at least two, or all three VL HVR sequences selected from (a) HVR-L1 comprising the amino acid sequence of SEQ ID NO:86; (b) HVR-L2 comprising the amino acid sequence of SEQ ID NO:104; and (c) HVR-L3 comprising the amino acid sequence of SEQ ID NO:118. In one embodiment, the antibody comprises (a) HVR-L1 comprising the amino acid sequence of SEQ ID NO:86; (b) HVR-L2 comprising the amino acid sequence of SEQ ID NO:104; and (c) HVR-L3 comprising the amino acid sequence of SEQ ID NO:118.

In another aspect, an anti-KLK5 antibody is provided comprises (a) a VH domain comprising at least one, at least two, or all three VH HVR sequences selected from (i) HVR-H1 comprising the amino acid sequence of SEQ ID NO:21, (ii) HVR-H2 comprising the amino acid sequence of SEQ ID NO:41, and (iii) HVR-H3 comprising the amino acid sequence of SEQ ID NO:69; and (b) a VL domain comprising at least one, at least two, or all three VL HVR sequences selected from (i) HVR-L1 comprising the amino acid sequence of SEQ ID NO:86, (ii) HVR-L2 comprising the amino acid sequence of SEQ ID NO:104, and (c) HVR-L3 comprising the amino acid sequence of SEQ ID NO:118.

In another aspect, an anti-KLK5 antibody is provided comprising (a) HVR-H1 comprising the amino acid sequence of SEQ ID NO:21; (b) HVR-H2 comprising the amino acid sequence of SEQ ID NO:41; (c) HVR-H3 comprising the amino acid sequence of SEQ ID NO:69; (d) HVR-L1 comprising the amino acid sequence of SEQ ID NO:86; (e) HVR-L2 comprising the amino acid sequence of SEQ ID NO:104; and (f) HVR-L3 comprising the amino acid sequence of SEQ ID NO:118.

In another aspect, an anti-KLK5 antibody is provided comprising a heavy chain variable domain (VH) sequence having at least any of 90%, 91%, 92%, 93%, 94%, 95%, 96%, 97%, 98%, 99%, or 100% sequence identity to the amino acid sequence of SEQ ID NO:206. In certain embodiments, a VH sequence having at least any of 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:206. In certain embodiments, substitutions, insertions, or deletions occur in regions outside the HVRs (i.e., in the FRs). Optionally, the anti-KLK5 antibody comprises the VH sequence in SEQ ID NO:206, including post-translational modifications of that sequence. In a particular embodiment, the VH comprises one, two or three HVRs selected from: (a) HVR-H1 comprising the amino acid sequence of SEQ ID NO:21, (b) HVR-H2 comprising the amino acid sequence of SEQ ID NO:41, and (c) HVR-H3 comprising the amino acid sequence of SEQ ID NO:69.

In another aspect, an anti-KLK5 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:144. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:144. In certain embodiments, the substitutions, insertions, or deletions occur in regions outside the HVRs (i.e., in the FRs). Optionally, the anti-KLK5 antibody comprises the VL sequence in SEQ ID NO:144, including post-translational modifications of that sequence. In a particular embodiment, the VL comprises one, two or three HVRs selected from (a) HVR-L1 comprising the amino acid sequence of SEQ ID NO:86; (b) HVR-L2 comprising the amino acid sequence of SEQ ID NO:104; and (c) HVR-L3 comprising the amino acid sequence of SEQ ID NO:118.

In another aspect, an anti-KLK5 antibody is provided, wherein the antibody comprises a VH as in any of the embodiments provided above, and a VL as in any of the embodiments provided above. In one embodiment, the antibody comprises the VH and VL sequences in SEQ ID NO:206 and SEQ ID NO:144, respectively, including post-translational modifications of those sequences.

In a further aspect, an anti-KLK5 antibody is provided that binds to the same epitope as an anti-KLK5 antibody provided herein. For example, in certain embodiments, an antibody is provided that binds to the same epitope as an anti-KLK5 antibody comprising a VH sequence of SEQ ID NO:206 and a VL sequence of SEQ ID NO:144.

In a further aspect, an anti-KLK5 antibody according to any of the above embodiments is a monoclonal antibody, including a chimeric, humanized or human antibody. In one embodiment, an anti-KLK5 antibody is humanized. In one embodiment, an anti-KLK5 antibody comprises HVRs as in any of the above embodiments, and further comprises an acceptor human framework, e.g. a human immunoglobulin framework or a human consensus framework.

In one embodiment, an anti-KLK5 antibody is an antibody fragment, e.g., a Fv, Fab, Fab', scFv, diabody, or F(ab')$_2$ fragment. In another embodiment, the antibody is a full length antibody, e.g an intact IgG1 antibody or an intact IgG4 antibody or other antibody class or isotype as defined herein.

In a further aspect, an anti-KLK5 antibody according to any of the above embodiments may incorporate any of the features, singly or in combination, as described below.

Antibody 9H5 and Other Embodiments

In one aspect, an anti-KLK5 antibody is provided comprising at least one, two, three, four, five, or six HVRs selected from (a) HVR-H1 comprising the amino acid sequence of SEQ ID NO:22; (b) HVR-H2 comprising the amino acid sequence of SEQ ID NO:42; (c) HVR-H3 comprising the amino acid sequence of SEQ ID NO:69; (d) HVR-L1 comprising the amino acid sequence of SEQ ID NO:87; (e) HVR-L2 comprising the amino acid sequence of SEQ ID NO:105; and (f) HVR-L3 comprising the amino acid sequence of SEQ ID NO:119.

In one aspect, an anti-KLK5 antibody is provided comprising at least one, at least two, or all three VH HVR sequences selected from (a) HVR-H1 comprising the amino acid sequence of SEQ ID NO:22; (b) HVR-H2 comprising the amino acid sequence of SEQ ID NO:42; and (c) HVR-H3 comprising the amino acid sequence of SEQ ID NO:69. In one embodiment, the antibody comprises HVR-H3 comprising the amino acid sequence of SEQ ID NO:69. In another embodiment, the antibody comprises HVR-H3 comprising the amino acid sequence of SEQ ID NO:69 and HVR-L3 comprising the amino acid sequence of SEQ ID NO:119. In a further embodiment, the antibody comprises HVR-H3 comprising the amino acid sequence of SEQ ID NO:69, HVR-L3 comprising the amino acid sequence of SEQ ID NO:119, and HVR-H2 comprising the amino acid sequence of SEQ ID NO:42. In a further embodiment, the antibody comprises (a) HVR-H1 comprising the amino acid sequence of SEQ ID NO:22; (b) HVR-H2 comprising the amino acid sequence of SEQ ID NO:42; and (c) HVR-H3 comprising the amino acid sequence of SEQ ID NO:69.

In another aspect, an anti-KLK5 antibody is provided comprising at least one, at least two, or all three VL HVR sequences selected from (a) HVR-L1 comprising the amino acid sequence of SEQ ID NO:87; (b) HVR-L2 comprising the amino acid sequence of SEQ ID NO:105; and (c) HVR-L3 comprising the amino acid sequence of SEQ ID NO:119. In one embodiment, the antibody comprises (a) HVR-L1 comprising the amino acid sequence of SEQ ID NO:87; (b) HVR-L2 comprising the amino acid sequence of SEQ ID NO:105; and (c) HVR-L3 comprising the amino acid sequence of SEQ ID NO:119.

In another aspect, an anti-KLK5 antibody is provided comprises (a) a VH domain comprising at least one, at least two, or all three VH HVR sequences selected from (i) HVR-H1 comprising the amino acid sequence of SEQ ID NO:22, (ii) HVR-H2 comprising the amino acid sequence of SEQ ID NO:42, and (iii) HVR-H3 comprising the amino acid sequence of SEQ ID NO:69; and (b) a VL domain comprising at least one, at least two, or all three VL HVR sequences selected from (i) HVR-L1 comprising the amino acid sequence of SEQ ID NO:87, (ii) HVR-L2 comprising the amino acid sequence of SEQ ID NO:105, and (c) HVR-L3 comprising the amino acid sequence of SEQ ID NO:119.

In another aspect, an anti-KLK5 antibody is provided comprising (a) HVR-H1 comprising the amino acid sequence of SEQ ID NO:22; (b) HVR-H2 comprising the amino acid sequence of SEQ ID NO:42; (c) HVR-H3 comprising the amino acid sequence of SEQ ID NO:69; (d) HVR-L1 comprising the amino acid sequence of SEQ ID NO:87; (e) HVR-L2 comprising the amino acid sequence of SEQ ID NO:105; and (f) HVR-L3 comprising the amino acid sequence of SEQ ID NO:119.

In another aspect, an anti-KLK5 antibody is provided comprising a heavy chain variable domain (VH) sequence having at least any of 90%, 91%, 92%, 93%, 94%, 95%, 96%, 97%, 98%, 99%, or 100% sequence identity to the amino acid sequence of SEQ ID NO:221. In certain embodiments, a VH sequence having at least any of 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:221. In certain embodiments, substitutions, insertions, or deletions occur in regions outside the HVRs (i.e., in the FRs). Optionally, the anti-KLK5 antibody comprises the VH sequence in SEQ ID NO:221, including post-translational modifications of that sequence. In a particular embodiment, the VH comprises one, two or three HVRs selected from: (a) HVR-H1 comprising the amino acid sequence of SEQ ID NO:22, (b) HVR-H2 comprising the amino acid sequence of SEQ ID NO:42, and (c) HVR-H3 comprising the amino acid sequence of SEQ ID NO:69.

In another aspect, an anti-KLK5 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:149. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:149. In certain embodiments, the substitutions, insertions, or deletions occur in regions outside the HVRs (i.e., in the FRs). Optionally, the anti-KLK5 antibody comprises the VL sequence in SEQ ID NO:149, including post-translational modifications of that sequence. In a particular embodiment, the VL comprises one, two or three HVRs selected from (a) HVR-L1 comprising the amino acid sequence of SEQ ID NO:87; (b) HVR-L2 comprising the amino acid sequence of SEQ ID NO:105; and (c) HVR-L3 comprising the amino acid sequence of SEQ ID NO:119.

In another aspect, an anti-KLK5 antibody is provided, wherein the antibody comprises a VH as in any of the embodiments provided above, and a VL as in any of the embodiments provided above. In one embodiment, the antibody comprises the VH and VL sequences in SEQ ID NO:221 and SEQ ID NO:149, respectively, including post-translational modifications of those sequences.

In a further aspect, an anti-KLK5 antibody is provided that binds to the same epitope as an anti-KLK5 antibody provided herein. For example, in certain embodiments, an antibody is provided that binds to the same epitope as an anti-KLK5 antibody comprising a VH sequence of SEQ ID NO:221 and a VL sequence of SEQ ID NO:149. In certain embodiments, an antibody is provided that, when bound to KLK5 results in a thermodynamic epitope comprising one or more of the sequences selected from the group consisting of SEQ ID NO:316, SEQ ID NO:317, SEQ ID NO:318, and SEQ ID NO:319 as measured by hydrogen exchange mass spectrometry.

In a further aspect, an anti-KLK5 antibody according to any of the above embodiments is a monoclonal antibody, including a chimeric, humanized or human antibody. In one embodiment, an anti-KLK5 antibody is humanized. In one embodiment, an anti-KLK5 antibody comprises HVRs as in any of the above embodiments, and further comprises an acceptor human framework, e.g. a human immunoglobulin framework or a human consensus framework.

In one embodiment, the anti-KLK5 antibody comprises a VH domain comprising one or more heavy chain framework sequences selected from (a) a heavy chain frame work region 1 (HC-FR1) of SEQ ID NO:341, (b) a heavy chain frame work region 2 (HC-FR2) of SEQ ID NO:342, (c) a heavy chain frame work region 3 (HC-FR3) of SEQ ID NO:343, and (d) a heavy chain frame work region 4 (HC-FR4) of SEQ ID NO:344.

In one embodiment, the anti-KLK5 antibody comprises a VH domain comprising a HC-FR1 of SEQ ID NO:341. In one embodiment, the anti-KLK5 antibody comprises a VH domain comprising a HC-FR2 of SEQ ID NO:342. In one embodiment, the anti-KLK5 antibody comprises a VH domain comprising a HC-FR3 of SEQ ID NO:343. In one embodiment, the anti-KLK5 antibody comprises a VH domain comprising a HC-FR4 of SEQ ID NO:344.

In one embodiment, the anti-KLK5 antibody comprises a VL domain comprising one or more light chain framework sequences selected from (a) a light chain frame work region 1 (LC-FR1) of SEQ ID NO:337, (b) a light chain frame work region 2 (LC-FR2) of SEQ ID NO:338, (c) a light chain frame work region 3 (LC-FR3) of SEQ ID NO:339, and (d) a light chain frame work region 4 (LC-FR4) of SEQ ID NO:340.

In one embodiment, the anti-KLK5 antibody comprises a VL domain comprising a LC-FR1 of SEQ ID NO:337. In one embodiment, the anti-KLK5 antibody comprises a VL domain comprising a LC-FR2 of SEQ ID NO:338. In one embodiment, the anti-KLK5 antibody comprises a VL domain comprising a LC-FR3 of SEQ ID NO:339. In one embodiment, the anti-KLK5 antibody comprises a VL domain comprising a LC-FR4 of SEQ ID NO:340.

In one embodiment, an anti-KLK5 antibody is an antibody fragment, e.g., a Fv, Fab, Fab', scFv, diabody, or F(ab')$_2$ fragment. In another embodiment, the antibody is a full length antibody, e.g an intact IgG1 antibody or an intact IgG4 antibody or other antibody class or isotype as defined herein.

Further provided herein is an antibody that specifically binds to human KLK5, wherein the antibody binds to an epitope on human KLK5 comprising one or more amino acid residues selected from the group consisting of Pro130, Ser131, Ala132, Gly133, Val162, Leu163, Ser164, Gln165, Lys166, Arg167, Glu169, Asp170, Ala171, Tyr172, Pro173, Arg174, Gln174A, Ile176, Asp177, and Lys233 according to standard protease numbering. In one embodiment, the antibody comprises (a) HVR-H1 comprising the amino acid sequence of SEQ ID NO:22; (b) HVR-H2 comprising the amino acid sequence of SEQ ID NO:42; (c) HVR-H3 comprising the amino acid sequence of SEQ ID NO:69; (d) HVR-L1 comprising the amino acid sequence of SEQ ID NO:87; (e) HVR-L2 comprising the amino acid sequence of SEQ ID NO:105; and (f) HVR-L3 comprising the amino acid sequence of SEQ ID NO:119. In one embodiment, the antibody comprises the VH and VL sequences in SEQ ID NO:221 and SEQ ID NO:149.

Further provided herein is an antibody when bound to human KLK5 results in a conformational change of human KLK5, wherein the conformational change allosterically results in the disruption of the substrate binding site and/or the active site of human KLK5. In one embodiment, the antibody comprises (a) HVR-H1 comprising the amino acid sequence of SEQ ID NO:22; (b) HVR-H2 comprising the amino acid sequence of SEQ ID NO:42; (c) HVR-H3 comprising the amino acid sequence of SEQ ID NO:69; (d) HVR-L1 comprising the amino acid sequence of SEQ ID NO:87; (e) HVR-L2 comprising the amino acid sequence of SEQ ID NO:105; and (f) HVR-L3 comprising the amino acid sequence of SEQ ID NO:119. In one embodiment, the antibody comprises the VH and VL sequences in SEQ ID NO:221 and SEQ ID NO:149.

In a further aspect, an anti-KLK5 antibody according to any of the above embodiments may incorporate any of the features, singly or in combination, as described below.

Antibody 9F2 and Other Embodiments

In one aspect, an anti-KLK5 antibody is provided comprising at least one, two, three, four, five, or six HVRs selected from (a) HVR-H1 comprising the amino acid sequence of SEQ ID NO:22; (b) HVR-H2 comprising the amino acid sequence of SEQ ID NO:46; (c) HVR-H3 comprising the amino acid sequence of SEQ ID NO:69; (d) HVR-L1 comprising the amino acid sequence of SEQ ID NO:88; (e) HVR-L2 comprising the amino acid sequence of SEQ ID NO:105; and (f) HVR-L3 comprising the amino acid sequence of SEQ ID NO:120.

In one aspect, an anti-KLK5 antibody is provided comprising at least one, at least two, or all three VH HVR sequences selected from (a) HVR-H1 comprising the amino acid sequence of SEQ ID NO:22; (b) HVR-H2 comprising the amino acid sequence of SEQ ID NO:46; and (c) HVR-H3 comprising the amino acid sequence of SEQ ID NO:69.

In one embodiment, the antibody comprises HVR-H3 comprising the amino acid sequence of SEQ ID NO:69. In another embodiment, the antibody comprises HVR-H3 comprising the amino acid sequence of SEQ ID NO:69 and HVR-L3 comprising the amino acid sequence of SEQ ID NO:120. In a further embodiment, the antibody comprises HVR-H3 comprising the amino acid sequence of SEQ ID NO:69, HVR-L3 comprising the amino acid sequence of SEQ ID NO:120, and HVR-H2 comprising the amino acid sequence of SEQ ID NO:46. In a further embodiment, the antibody comprises (a) HVR-H1 comprising the amino acid sequence of SEQ ID NO:22; (b) HVR-H2 comprising the amino acid sequence of SEQ ID NO:46; and (c) HVR-H3 comprising the amino acid sequence of SEQ ID NO:69.

In another aspect, an anti-KLK5 antibody is provided comprising at least one, at least two, or all three VL HVR sequences selected from (a) HVR-L1 comprising the amino acid sequence of SEQ ID NO:88; (b) HVR-L2 comprising the amino acid sequence of SEQ ID NO:105; and (c) HVR-L3 comprising the amino acid sequence of SEQ ID NO:120. In one embodiment, the antibody comprises (a) HVR-L1 comprising the amino acid sequence of SEQ ID NO:88; (b) HVR-L2 comprising the amino acid sequence of SEQ ID NO:105; and (c) HVR-L3 comprising the amino acid sequence of SEQ ID NO:120.

In another aspect, an anti-KLK5 antibody is provided comprises (a) a VH domain comprising at least one, at least two, or all three VH HVR sequences selected from (i) HVR-H1 comprising the amino acid sequence of SEQ ID NO:22, (ii) HVR-H2 comprising the amino acid sequence of SEQ ID NO:46, and (iii) HVR-H3 comprising the amino acid sequence of SEQ ID NO:69; and (b) a VL domain comprising at least one, at least two, or all three VL HVR sequences selected from (i) HVR-L1 comprising the amino acid sequence of SEQ ID NO:88, (ii) HVR-L2 comprising the amino acid sequence of SEQ ID NO:105, and (c) HVR-L3 comprising the amino acid sequence of SEQ ID NO:120.

In another aspect, an anti-KLK5 antibody is provided comprising (a) HVR-H1 comprising the amino acid sequence of SEQ ID NO:22; (b) HVR-H2 comprising the amino acid sequence of SEQ ID NO:46; (c) HVR-H3 comprising the amino acid sequence of SEQ ID NO:69; (d) HVR-L1 comprising the amino acid sequence of SEQ ID NO:88; (e) HVR-L2 comprising the amino acid sequence of SEQ ID NO:105; and (f) HVR-L3 comprising the amino acid sequence of SEQ ID NO:120.

In another aspect, an anti-KLK5 antibody is provided comprising a heavy chain variable domain (VH) sequence having at least any of 90%, 91%, 92%, 93%, 94%, 95%, 96%, 97%, 98%, 99%, or 100% sequence identity to the amino acid sequence of SEQ ID NO:226. In certain embodiments, a VH sequence having at least any of 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:226. In certain embodiments, substitutions, insertions, or deletions occur in regions outside the HVRs (i.e., in the FRs). Optionally, the anti-KLK5 antibody comprises the VH sequence in SEQ ID NO:226, including post-translational modifications of that sequence. In a particular embodiment, the VH comprises one, two or three HVRs selected from: (a) HVR-H1 comprising the amino acid sequence of SEQ ID NO:22, (b) HVR-H2 comprising the amino acid sequence of SEQ ID NO:46, and (c) HVR-H3 comprising the amino acid sequence of SEQ ID NO:69.

In another aspect, an anti-KLK5 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:152. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:152. In certain embodiments, the substitutions, insertions, or deletions occur in regions outside the HVRs (i.e., in the FRs). Optionally, the anti-KLK5 antibody comprises the VL sequence in SEQ ID NO:152, including post-translational modifications of that sequence. In a particular embodiment, the VL comprises one, two or three HVRs selected from (a) HVR-L1 comprising the amino acid sequence of SEQ ID NO:88; (b) HVR-L2 comprising the amino acid sequence of SEQ ID NO:105; and (c) HVR-L3 comprising the amino acid sequence of SEQ ID NO:120.

In another aspect, an anti-KLK5 antibody is provided, wherein the antibody comprises a VH as in any of the embodiments provided above, and a VL as in any of the embodiments provided above. In one embodiment, the antibody comprises the VH and VL sequences in SEQ ID NO:226 and SEQ ID NO:152, respectively, including post-translational modifications of those sequences.

In a further aspect, an anti-KLK5 antibody is provided that binds to the same epitope as an anti-KLK5 antibody provided herein. For example, in certain embodiments, an antibody is provided that binds to the same epitope as an anti-KLK5 antibody comprising a VH sequence of SEQ ID NO:226 and a VL sequence of SEQ ID NO:152.

In a further aspect, an anti-KLK5 antibody according to any of the above embodiments is a monoclonal antibody, including a chimeric, humanized or human antibody. In one embodiment, an anti-KLK5 antibody is humanized. In one embodiment, an anti-KLK5 antibody comprises HVRs as in any of the above embodiments, and further comprises an acceptor human framework, e.g. a human immunoglobulin framework or a human consensus framework.

In one embodiment, an anti-KLK5 antibody is an antibody fragment, e.g., a Fv, Fab, Fab', scFv, diabody, or F(ab')$_2$ fragment. In another embodiment, the antibody is a full length antibody, e.g an intact IgG1 antibody or an intact IgG4 antibody or other antibody class or isotype as defined herein.

In a further aspect, an anti-KLK5 antibody according to any of the above embodiments may incorporate any of the features, singly or in combination, as described below.

Antibody 10C8 and Other Embodiments

In one aspect, an anti-KLK5 antibody is provided comprising at least one, two, three, four, five, or six HVRs selected from (a) HVR-H1 comprising the amino acid sequence of SEQ ID NO:22; (b) HVR-H2 comprising the amino acid sequence of SEQ ID NO:42; (c) HVR-H3 comprising the amino acid sequence of SEQ ID NO:70; (d) HVR-L1 comprising the amino acid sequence of SEQ ID NO:89; (e) HVR-L2 comprising the amino acid sequence of SEQ ID NO:105; and (f) HVR-L3 comprising the amino acid sequence of SEQ ID NO:118.

In one aspect, an anti-KLK5 antibody is provided comprising at least one, at least two, or all three VH HVR sequences selected from (a) HVR-H1 comprising the amino acid sequence of SEQ ID NO:22; (b) HVR-H2 comprising the amino acid sequence of SEQ ID NO:42; and (c) HVR-H3 comprising the amino acid sequence of SEQ ID NO:70. In one embodiment, the antibody comprises HVR-H3 comprising the amino acid sequence of SEQ ID NO:70. In another embodiment, the antibody comprises HVR-H3 comprising the amino acid sequence of SEQ ID NO:70 and HVR-L3 comprising the amino acid sequence of SEQ ID NO:118. In a further embodiment, the antibody comprises HVR-H3 comprising the amino acid sequence of SEQ ID NO:70, HVR-L3 comprising the amino acid sequence of SEQ ID NO:118, and HVR-H2 comprising the amino acid sequence of SEQ ID NO:42. In a further embodiment, the antibody comprises (a) HVR-H1 comprising the amino acid sequence of SEQ ID NO:22; (b) HVR-H2 comprising the amino acid sequence of SEQ ID NO:42; and (c) HVR-H3 comprising the amino acid sequence of SEQ ID NO:70.

In another aspect, an anti-KLK5 antibody is provided comprising at least one, at least two, or all three VL HVR sequences selected from (a) HVR-L1 comprising the amino acid sequence of SEQ ID NO:89; (b) HVR-L2 comprising the amino acid sequence of SEQ ID NO:105; and (c) HVR-L3 comprising the amino acid sequence of SEQ ID NO:118. In one embodiment, the antibody comprises (a) HVR-L1 comprising the amino acid sequence of SEQ ID NO:89; (b) HVR-L2 comprising the amino acid sequence of SEQ ID NO:105; and (c) HVR-L3 comprising the amino acid sequence of SEQ ID NO:118.

In another aspect, an anti-KLK5 antibody is provided comprises (a) a VH domain comprising at least one, at least two, or all three VH HVR sequences selected from (i) HVR-H1 comprising the amino acid sequence of SEQ ID NO:22, (ii) HVR-H2 comprising the amino acid sequence of SEQ ID NO:42, and (iii) HVR-H3 comprising the amino acid sequence of SEQ ID NO:70; and (b) a VL domain comprising at least one, at least two, or all three VL HVR sequences selected from (i) HVR-L1 comprising the amino acid sequence of SEQ ID NO:89, (ii) HVR-L2 comprising the amino acid sequence of SEQ ID NO:105, and (c) HVR-L3 comprising the amino acid sequence of SEQ ID NO:118.

In another aspect, an anti-KLK5 antibody is provided comprising (a) HVR-H1 comprising the amino acid sequence of SEQ ID NO:22; (b) HVR-H2 comprising the amino acid sequence of SEQ ID NO:42; (c) HVR-H3 comprising the amino acid sequence of SEQ ID NO:70; (d) HVR-L1 comprising the amino acid sequence of SEQ ID NO:89; (e) HVR-L2 comprising the amino acid sequence of SEQ ID NO:105; and (f) HVR-L3 comprising the amino acid sequence of SEQ ID NO:118.

In another aspect, an anti-KLK5 antibody is provided comprising a heavy chain variable domain (VH) sequence having at least any of 90%, 91%, 92%, 93%, 94%, 95%, 96%, 97%, 98%, 99%, or 100% sequence identity to the amino acid sequence of SEQ ID NO:227. In certain embodiments, a VH sequence having at least any of 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:227. In certain embodiments, substitutions, insertions, or deletions occur in regions outside the HVRs (i.e., in the FRs). Optionally, the anti-KLK5 antibody comprises the VH sequence in SEQ ID NO:227, including post-translational modifications of that sequence. In a particular embodiment, the VH comprises one, two or three HVRs selected from: (a) HVR-H1 comprising the amino acid sequence of SEQ ID NO:22, (b) HVR-H2 comprising the amino acid sequence of SEQ ID NO:42, and (c) HVR-H3 comprising the amino acid sequence of SEQ ID NO:70.

In another aspect, an anti-KLK5 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:153. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:153. In certain embodiments, the substitutions, insertions, or deletions occur in regions outside the HVRs (i.e., in the FRs). Optionally, the anti-KLK5 antibody comprises the VL sequence in SEQ ID NO:153, including post-translational modifications of that sequence. In a particular embodiment, the VL comprises one, two or three HVRs selected from (a) HVR-L1 comprising the amino acid sequence of SEQ ID NO:89; (b) HVR-L2 comprising the amino acid sequence of SEQ ID NO:105; and (c) HVR-L3 comprising the amino acid sequence of SEQ ID NO:118.

In another aspect, an anti-KLK5 antibody is provided, wherein the antibody comprises a VH as in any of the embodiments provided above, and a VL as in any of the embodiments provided above. In one embodiment, the antibody comprises the VH and VL sequences in SEQ ID NO:227 and SEQ ID NO:153, respectively, including post-translational modifications of those sequences.

In a further aspect, an anti-KLK5 antibody is provided that binds to the same epitope as an anti-KLK5 antibody provided herein. For example, in certain embodiments, an antibody is provided that binds to the same epitope as an anti-KLK5 antibody comprising a VH sequence of SEQ ID NO:227 and a VL sequence of SEQ ID NO:153.

In a further aspect, an anti-KLK5 antibody according to any of the above embodiments is a monoclonal antibody, including a chimeric, humanized or human antibody. In one embodiment, an anti-KLK5 antibody is humanized. In one embodiment, an anti-KLK5 antibody comprises HVRs as in any of the above embodiments, and further comprises an acceptor human framework, e.g. a human immunoglobulin framework or a human consensus framework.

In one embodiment, an anti-KLK5 antibody is an antibody fragment, e.g., a Fv, Fab, Fab', scFv, diabody, or F(ab')$_2$ fragment. In another embodiment, the antibody is a full length antibody, e.g an intact IgG1 antibody or an intact IgG4 antibody or other antibody class or isotype as defined herein.

In a further aspect, an anti-KLK5 antibody according to any of the above embodiments may incorporate any of the features, singly or in combination, as described below.

Antibody 8F5 and Other Embodiments

In one aspect, an anti-KLK5 antibody is provided comprising at least one, two, three, four, five, or six HVRs selected from (a) HVR-H1 comprising the amino acid sequence of SEQ ID NO:23; (b) HVR-H2 comprising the amino acid sequence of SEQ ID NO:47; (c) HVR-H3 comprising the amino acid sequence of SEQ ID NO:71; (d) HVR-L1 comprising the amino acid sequence of SEQ ID NO:90; (e) HVR-L2 comprising the amino acid sequence of SEQ ID NO:106; and (f) HVR-L3 comprising the amino acid sequence of SEQ ID NO:121.

In one aspect, an anti-KLK5 antibody is provided comprising at least one, at least two, or all three VH HVR sequences selected from (a) HVR-H1 comprising the amino acid sequence of SEQ ID NO:23; (b) HVR-H2 comprising the amino acid sequence of SEQ ID NO:47; and (c) HVR-H3 comprising the amino acid sequence of SEQ ID NO:71. In one embodiment, the antibody comprises HVR-H3 comprising the amino acid sequence of SEQ ID NO:71. In another embodiment, the antibody comprises HVR-H3 comprising the amino acid sequence of SEQ ID NO:71 and HVR-L3 comprising the amino acid sequence of SEQ ID NO:121. In a further embodiment, the antibody comprises HVR-H3 comprising the amino acid sequence of SEQ ID NO:70, HVR-L3 comprising the amino acid sequence of SEQ ID NO:121, and HVR-H2 comprising the amino acid sequence of SEQ ID NO:47. In a further embodiment, the antibody comprises (a) HVR-H1 comprising the amino acid sequence of SEQ ID NO:23; (b) HVR-H2 comprising the amino acid sequence of SEQ ID NO:47; and (c) HVR-H3 comprising the amino acid sequence of SEQ ID NO:71.

In another aspect, an anti-KLK5 antibody is provided comprising at least one, at least two, or all three VL HVR sequences selected from (a) HVR-L1 comprising the amino acid sequence of SEQ ID NO:90; (b) HVR-L2 comprising the amino acid sequence of SEQ ID NO:106; and (c) HVR-L3 comprising the amino acid sequence of SEQ ID NO:121. In one embodiment, the antibody comprises (a) HVR-L1 comprising the amino acid sequence of SEQ ID NO:90; (b) HVR-L2 comprising the amino acid sequence of SEQ ID NO:106; and (c) HVR-L3 comprising the amino acid sequence of SEQ ID NO:121.

In another aspect, an anti-KLK5 antibody is provided comprises (a) a VH domain comprising at least one, at least two, or all three VH HVR sequences selected from (i) HVR-H1 comprising the amino acid sequence of SEQ ID NO:23, (ii) HVR-H2 comprising the amino acid sequence of SEQ ID NO:47, and (iii) HVR-H3 comprising the amino acid sequence of SEQ ID NO:71; and (b) a VL domain comprising at least one, at least two, or all three VL HVR sequences selected from (i) HVR-L1 comprising the amino acid sequence of SEQ ID NO:90, (ii) HVR-L2 comprising the amino acid sequence of SEQ ID NO:106, and (c) HVR-L3 comprising the amino acid sequence of SEQ ID NO:121.

In another aspect, an anti-KLK5 antibody is provided comprising (a) HVR-H1 comprising the amino acid sequence of SEQ ID NO:23; (b) HVR-H2 comprising the amino acid sequence of SEQ ID NO:47; (c) HVR-H3 comprising the amino acid sequence of SEQ ID NO:71; (d) HVR-L1 comprising the amino acid sequence of SEQ ID NO:90; (e) HVR-L2 comprising the amino acid sequence of SEQ ID NO:106; and (f) HVR-L3 comprising the amino acid sequence of SEQ ID NO:121.

In another aspect, an anti-KLK5 antibody is provided comprising a heavy chain variable domain (VH) sequence having at least any of 90%, 91%, 92%, 93%, 94%, 95%, 96%, 97%, 98%, 99%, or 100% sequence identity to the amino acid sequence of SEQ ID NO:228. In certain embodiments, a VH sequence having at least any of 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:228. In certain embodiments, substitutions, insertions, or deletions occur in regions outside the HVRs (i.e., in the FRs). Optionally, the anti-KLK5 antibody comprises the VH sequence in SEQ ID NO:228, including post-translational modifications of that sequence. In a particular embodiment, the VH comprises one, two or three HVRs selected from: (a) HVR-H1 comprising the amino acid sequence of SEQ ID NO:23, (b) HVR-H2 comprising the amino acid sequence of SEQ ID NO:47, and (c) HVR-H3 comprising the amino acid sequence of SEQ ID NO:71.

In another aspect, an anti-KLK5 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:154. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:154. In certain embodiments, the substitutions, insertions, or deletions occur in regions outside the HVRs (i.e., in the FRs). Optionally, the anti-KLK5 antibody comprises the VL sequence in SEQ ID NO:154, including post-translational modifications of that sequence. In a particular embodiment, the VL comprises one, two or three HVRs selected from (a) HVR-L1 comprising the amino acid sequence of SEQ ID NO:90; (b) HVR-L2 comprising the amino acid sequence of SEQ ID NO:106; and (c) HVR-L3 comprising the amino acid sequence of SEQ ID NO:121.

In another aspect, an anti-KLK5 antibody is provided, wherein the antibody comprises a VH as in any of the embodiments provided above, and a VL as in any of the embodiments provided above. In one embodiment, the antibody comprises the VH and VL sequences in SEQ ID NO:228 and SEQ ID NO:154, respectively, including post-translational modifications of those sequences.

In a further aspect, an anti-KLK5 antibody is provided that binds to the same epitope as an anti-KLK5 antibody provided herein. For example, in certain embodiments, an antibody is provided that binds to the same epitope as an anti-KLK5 antibody comprising a VH sequence of SEQ ID NO:228 and a VL sequence of SEQ ID NO:154.

In a further aspect, an anti-KLK5 antibody according to any of the above embodiments is a monoclonal antibody, including a chimeric, humanized or human antibody. In one embodiment, an anti-KLK5 antibody is humanized. In one embodiment, an anti-KLK5 antibody comprises HVRs as in any of the above embodiments, and further comprises an acceptor human framework, e.g. a human immunoglobulin framework or a human consensus framework.

In one embodiment, an anti-KLK5 antibody is an antibody fragment, e.g., a Fv, Fab, Fab', scFv, diabody, or F(ab')$_2$ fragment. In another embodiment, the antibody is a full length antibody, e.g an intact IgG1 antibody or an intact IgG4 antibody or other antibody class or isotype as defined herein.

In a further aspect, an anti-KLK5 antibody according to any of the above embodiments may incorporate any of the features, singly or in combination, as described below.

Antibody 3-3F5 and Other Embodiments

In one aspect, an anti-KLK5 antibody is provided comprising at least one, two, three, four, five, or six HVRs selected from (a) HVR-H1 comprising the amino acid sequence of SEQ ID NO:24; (b) HVR-H2 comprising the amino acid sequence of SEQ ID NO:52; (c) HVR-H3 comprising the amino acid sequence of SEQ ID NO:72; (d) HVR-L1 comprising the amino acid sequence of SEQ ID NO:91; (e) HVR-L2 comprising the amino acid sequence of SEQ ID NO:99; and (f) HVR-L3 comprising the amino acid sequence of SEQ ID NO:122.

In one aspect, an anti-KLK5 antibody is provided comprising at least one, at least two, or all three VH HVR sequences selected from (a) HVR-H1 comprising the amino acid sequence of SEQ ID NO:24; (b) HVR-H2 comprising the amino acid sequence of SEQ ID NO:52; and (c) HVR-H3 comprising the amino acid sequence of SEQ ID NO:72. In one embodiment, the antibody comprises HVR-H3 comprising the amino acid sequence of SEQ ID NO:72. In another embodiment, the antibody comprises HVR-H3 comprising the amino acid sequence of SEQ ID NO:72 and HVR-L3 comprising the amino acid sequence of SEQ ID NO:122. In a further embodiment, the antibody comprises HVR-H3 comprising the amino acid sequence of SEQ ID NO:72, HVR-L3 comprising the amino acid sequence of SEQ ID NO:122, and HVR-H2 comprising the amino acid sequence of SEQ ID NO:52. In a further embodiment, the antibody comprises (a) HVR-H1 comprising the amino acid sequence of SEQ ID NO:24; (b) HVR-H2 comprising the amino acid sequence of SEQ ID NO:52; and (c) HVR-H3 comprising the amino acid sequence of SEQ ID NO:72.

In another aspect, an anti-KLK5 antibody is provided comprising at least one, at least two, or all three VL HVR sequences selected from (a) HVR-L1 comprising the amino acid sequence of SEQ ID NO:91; (b) HVR-L2 comprising the amino acid sequence of SEQ ID NO:99; and (c) HVR-L3 comprising the amino acid sequence of SEQ ID NO:122. In one embodiment, the antibody comprises (a) HVR-L1 comprising the amino acid sequence of SEQ ID NO:91; (b) HVR-L2 comprising the amino acid sequence of SEQ ID NO:99; and (c) HVR-L3 comprising the amino acid sequence of SEQ ID NO:122.

In another aspect, an anti-KLK5 antibody is provided comprises (a) a VH domain comprising at least one, at least two, or all three VH HVR sequences selected from (i) HVR-H1 comprising the amino acid sequence of SEQ ID NO:24, (ii) HVR-H2 comprising the amino acid sequence of SEQ ID NO:52, and (iii) HVR-H3 comprising the amino acid sequence of SEQ ID NO:72; and (b) a VL domain comprising at least one, at least two, or all three VL HVR sequences selected from (i) HVR-L1 comprising the amino acid sequence of SEQ ID NO:91, (ii) HVR-L2 comprising the amino acid sequence of SEQ ID NO:99, and (c) HVR-L3 comprising the amino acid sequence of SEQ ID NO:122.

In another aspect, an anti-KLK5 antibody is provided comprising (a) HVR-H1 comprising the amino acid sequence of SEQ ID NO:24 (b) HVR-H2 comprising the amino acid sequence of SEQ ID NO:52; (c) HVR-H3 comprising the amino acid sequence of SEQ ID NO:72; (d) HVR-L1 comprising the amino acid sequence of SEQ ID NO:91; (e) HVR-L2 comprising the amino acid sequence of SEQ ID NO:99; and (f) HVR-L3 comprising the amino acid sequence of SEQ ID NO:122.

In another aspect, an anti-KLK5 antibody is provided comprising a heavy chain variable domain (VH) sequence having at least any of 90%, 91%, 92%, 93%, 94%, 95%, 96%, 97%, 98%, 99%, or 100% sequence identity to the amino acid sequence of SEQ ID NO:248. In certain embodiments, a VH sequence having at least any of 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:248. In certain embodiments, substitutions, insertions, or deletions occur in regions outside the HVRs (i.e., in the FRs). Optionally, the anti-KLK5 antibody comprises the VH sequence in SEQ ID NO:248, including post-translational modifications of that sequence. In a particular embodiment, the VH comprises one, two or three HVRs selected from: (a) HVR-H1 comprising the amino acid sequence of SEQ ID NO:24, (b) HVR-H2 comprising the amino acid sequence of SEQ ID NO:52, and (c) HVR-H3 comprising the amino acid sequence of SEQ ID NO:72.

In another aspect, an anti-KLK5 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:160. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-KLK5 antibody comprising that sequence retains the ability to bind to KLK5. In certain embodiments, a total of 1 to 10 amino acids have been substituted, inserted and/or deleted in SEQ ID NO:160. In certain embodiments, the substitutions, insertions, or deletions occur in regions outside the HVRs (i.e., in the FRs). Optionally, the anti-KLK5 antibody comprises the VL sequence in SEQ ID NO:160, including post-translational modifications of that sequence. In a particular embodiment, the VL comprises one, two or three HVRs selected from (a) HVR-L1 comprising the amino acid sequence of SEQ ID NO:91; (b) HVR-L2 comprising the amino acid sequence of SEQ ID NO:99; and (c) HVR-L3 comprising the amino acid sequence of SEQ ID NO:122.

In another aspect, an anti-KLK5 antibody is provided, wherein the antibody comprises a VH as in any of the embodiments provided above, and a VL as in any of the embodiments provided above. In one embodiment, the antibody comprises the VH and VL sequences in SEQ ID NO:248 and SEQ ID NO:160, respectively, including post-translational modifications of those sequences.

In a further aspect, an anti-KLK5 antibody is provided that binds to the same epitope as an anti-KLK5 antibody provided herein. For example, in certain embodiments, an antibody is provided that binds to the same epitope as an anti-KLK5 antibody comprising a VH sequence of SEQ ID NO:248 and a VL sequence of SEQ ID NO:160.

In a further aspect, an anti-KLK5 antibody according to any of the above embodiments is a monoclonal antibody, including a chimeric, humanized or human antibody. In one embodiment, an anti-KLK5 antibody is humanized. In one embodiment, an anti-KLK5 antibody comprises HVRs as in any of the above embodiments, and further comprises an acceptor human framework, e.g. a human immunoglobulin framework or a human consensus framework.

In one embodiment, the anti-KLK5 antibody comprises a VH domain comprising one or more heavy chain framework sequences selected from (a) a heavy chain frame work region 1 (HC-FR1) of SEQ ID NO:349, (b) a heavy chain frame work region 2 (HC-FR2) of SEQ ID NO:350, (c) a heavy chain frame work region 3 (HC-FR3) of SEQ ID NO:351, and (d) a heavy chain frame work region 4 (HC-FR4) of SEQ ID NO:352.

In one embodiment, the anti-KLK5 antibody comprises a VH domain comprising a HC-FR1 of SEQ ID NO:349. In one embodiment, the anti-KLK5 antibody comprises a VH domain comprising a HC-FR2 of SEQ ID NO:350. In one embodiment, the anti-KLK5 antibody comprises a VH domain comprising a HC-FR3 of SEQ ID NO:351. In one embodiment, the anti-KLK5 antibody comprises a VH domain comprising a HC-FR4 of SEQ ID NO:352.

In one embodiment, the anti-KLK5 antibody comprises a VL domain comprising one or more light chain framework sequences selected from (a) a light chain frame work region 1 (LC-FR1) of SEQ ID NO:345, (b) a light chain frame work region 2 (LC-FR2) of SEQ ID NO:346, (c) a light chain frame work region 3 (LC-FR3) of SEQ ID NO:347, and (d) a light chain frame work region 4 (LC-FR4) of SEQ ID NO:348.

In one embodiment, the anti-KLK5 antibody comprises a VL domain comprising a LC-FR1 of SEQ ID NO:345. In one embodiment, the anti-KLK5 antibody comprises a VL domain comprising a LC-FR2 of SEQ ID NO:346. In one embodiment, the anti-KLK5 antibody comprises a VL domain comprising a LC-FR3 of SEQ ID NO:347. In one embodiment, the anti-KLK5 antibody comprises a VL domain comprising a LC-FR4 of SEQ ID NO:348.

In one embodiment, an anti-KLK5 antibody is an antibody fragment, e.g., a Fv, Fab, Fab', scFv, diabody, or F(ab')$_2$ fragment. In another embodiment, the antibody is a full length antibody, e.g an intact IgG1 antibody or an intact IgG4 antibody or other antibody class or isotype as defined herein.

Further provided herein is an antibody that specifically binds to human KLK5, wherein the antibody binds to an epitope on human KLK5 comprising one or more amino acid residues selected from the group consisting of Ser131, Ala132, Gly133, Leu163, Ser164, Gln165, Lys166, Arg167, Glu169, Asp170, Ala171, Pro173, Arg174, Gly184, Asp185, Lys186, Ala186A, Arg188, Asn223, Arg224, and Pro225 according to standard protease numbering. In one embodiment, the antibody comprises (a) HVR-H1 comprising the amino acid sequence of SEQ ID NO:24 (b) HVR-H2 comprising the amino acid sequence of SEQ ID NO:52; (c) HVR-H3 comprising the amino acid sequence of SEQ ID NO:72; (d) HVR-L1 comprising the amino acid sequence of SEQ ID NO:91; (e) HVR-L2 comprising the amino acid sequence of SEQ ID NO:99; and (f) HVR-L3 comprising the amino acid sequence of SEQ ID NO:122. In one embodiment, the antibody comprises the VH and VL sequences in SEQ ID NO:248 and SEQ ID NO:160.

Further provided herein is an antibody when bound to human KLK5 results in a conformational change of human KLK5, wherein the conformational change allosterically results in the disruption of the substrate binding site and/or the active site of human KLK5. In one embodiment, the antibody comprises (a) HVR-H1 comprising the amino acid sequence of SEQ ID NO:24 (b) HVR-H2 comprising the amino acid sequence of SEQ ID NO:52; (c) HVR-H3 comprising the amino acid sequence of SEQ ID NO:72; (d) HVR-L1 comprising the amino acid sequence of SEQ ID NO:91; (e) HVR-L2 comprising the amino acid sequence of SEQ ID NO:99; and (f) HVR-L3 comprising the amino acid sequence of SEQ ID NO:122. In one embodiment, the antibody comprises the VH and VL sequences in SEQ ID NO:248 and SEQ ID NO:160.

In a further aspect, an anti-KLK5 antibody according to any of the above embodiments may incorporate any of the features, singly or in combination, as described below.

2. Antibody Affinity

In some embodiments of any of the anti-KLK5 antibodies, the anti-KLK5 antibody has a binding affinity (dissociation constant Kd) to KLK5 of $\leq 1$ µM, $\leq 100$ nM, $\leq 10$ nM, $\leq 1$ nM, $\leq 0.1$ nM, $\leq 0.01$ nM, or $\leq 0.001$ nM (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIA-CORE®-3000 (BIAcore, Inc., Piscataway, NJ) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds 106 M-1 s-1 by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

3. Antibody Fragments

In some embodiments, the anti-KLK5 antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthun, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516 B 1).

Antibody fragments can be made by various techniques, including but not limited to proteolytic digestion of an intact antibody as well as production by recombinant host cells (e.g. *E. coli* or phage), as described herein.

4. Chimeric and Humanized Antibodies

In some embodiments, the anti-KLK5 antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

5. Human Antibodies

In some embodiments, the anti-KLK5 antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

6. Library-Derived Antibodies

Anti-KLK5 antibodies may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, NJ, 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, NJ, 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In some embodiments, the anti-KLK5 antibody provided herein is a multispecific antibody, e.g. a bispecific antibody. Multispecific antibodies are monoclonal antibodies that have binding specificities for at least two different sites. In certain embodiments, one of the binding specificities is for KLK5 and the other is for any other antigen. In certain embodiments, bispecific antibodies may bind to two different epitopes of KLK5. Bispecific antibodies may also be used to localize cytotoxic agents to cells which express KLK5. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (sFv) dimers (see, e.g. Gruber et al., *J. Immunol.*, 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to KLK5 as well as another, different antigen (see, US 2008/0069820, for example).

7. Antibody Variants

In some embodiments, amino acid sequence variants of the anti-KLK5 antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In some embodiments, anti-KLK5 antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, the anti-KLK5 antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In some embodiments, anti-KLK5 antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.,* 94(4):680-688 (2006); and WO2003/085107).

Anti-KLK5 antibody variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In some embodiments, one or more amino acid modifications may be introduced into the Fc region of the anti-KLK5 antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In some embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability.

The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103: 2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

d) Cysteine Engineered Antibody Variants

In some embodiments, it may be desirable to create cysteine engineered anti-KLK5 antibodies, e.g., THIO-MAB™ antibodies in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In some embodiments, the anti-KLK5 antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In some embodiments, conjugates of the anti-KLK5 antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Anti-KLK5 antibodies may be produced using recombinant methods and compositions, e.g., as described in U.S. Pat. No. 4,816,567. In one embodiment, isolated nucleic acid encoding an anti-KLK5 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-KLK5 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-KLK5 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology, Vol.* 248 (B. K. C. Lo, ed., Humana Press, Totowa, N J, 2003), pp. 245-254, describing expression of antibody fragments in *E. coli.*). After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, NJ), pp. 255-268 (2003).

C. Assays

Anti-KLK5 antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, BIACore®, FACS, or Western blot, etc.

In another aspect, competition assays may be used to identify an antibody that competes with any of the antibodies described herein for binding to KLK5. In certain embodiments, such a competing antibody binds to the same epitope (e.g., a linear or a conformational epitope) that is bound by any of the antibodies described herein. Detailed exemplary methods for mapping an epitope to which an antibody binds are provided in Morris (1996) "Epitope Mapping Protocols," in *Methods in Molecular Biology* vol. 66 (Humana Press, Totowa, NJ).

In an exemplary competition assay, immobilized KLK5 is incubated in a solution comprising a first labeled antibody that binds to KLK5 (e.g., any of the antibodies described herein) and a second unlabeled antibody that is being tested for its ability to compete with the first antibody for binding to KLK5. The second antibody may be present in a hybridoma supernatant. As a control, immobilized KLK5 is incubated in a solution comprising the first labeled antibody but not the second unlabeled antibody. After incubation under conditions permissive for binding of the first antibody to KLK5, excess unbound antibody is removed, and the amount of label associated with immobilized KLK5 is measured. If the amount of label associated with immobilized KLK5 is substantially reduced in the test sample relative to the control sample, then that indicates that the second antibody is competing with the first antibody for binding to KLK5. See Harlow and Lane (1988) *Antibodies: A Laboratory Manual* ch. 14 (Cold Spring Harbor Laboratory, Cold Spring Harbor, NY).

2. Activity Assays

In one aspect, assays are provided for identifying anti-KLK5 antibodies having biological activity. Biological activity may include, e.g. inhibition of KLK5. In one embodiment, the anti-KLK5 antibodies inhibit the serine protease activity of KLK5. Antibodies having such biological activity in vivo and/or in vitro are also provided.

In some embodiments, the anti-KLK5 antibodies are tested for such biological activity. In some embodiments, the biological activity is tested by one or more methods selected from the group consisting of a direct activity assay, fluorescent peptide assay, an LC/MS assay, and a $K_{i(app)}$ assay. In some embodiments, the biological activity is measured by one or more methods selected from the group consisting of a recombinant KLK5 direct activity assay, coupled pro-KLK1 fluorescent peptide assay, a coupled pro-KLK7 fluorescent peptide assay, a pro-KLK1 LC/MS assay, a pro-KLK7 LC/MS assay, and a $K_{i(app)}$ assay. In some embodiments, the $IC_{50}$ values are measured by the assays described herein above and in detail in the Examples below.

D. Immunoconjugates

The invention also provides immunoconjugates comprising an anti-KLK5 antibody provided herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL, U.S.A).

E. Methods and Compositions for Diagnostics and Detection

In some embodiments, any of the anti-KLK5 antibodies provided herein is useful for detecting the presence of KLK5 in a biological sample. The term "detecting" as used herein encompasses quantitative or qualitative detection. In some embodiments, a biological sample comprises a cell or tissue, such as skin epidermis, lung parenchyma, bronchial subepithelium. In some embodiments, a biological sample comprises bronchial alveolar lavage.

In one embodiment, an anti-KLK5 antibody for use in a method of diagnosis or detection is provided. In a further aspect, a method of detecting the presence of KLK5 in a biological sample is provided. In certain embodiments, the method comprises contacting the biological sample with an anti-KLK5 antibody as described herein under conditions permissive for binding of the anti-KLK5 antibody to KLK5, and detecting whether a complex is formed between the anti-KLK5 antibody and KLK5. Such method may be an in vitro or in vivo method. In one embodiment, an anti-KLK5 antibody is used to select subjects eligible for therapy with an anti-KLK5 antibody, e.g. where KLK5 is a biomarker for selection of patients.

Exemplary disorders that may be diagnosed using an anti-KLK5 antibody of the invention include Netherton Syndrome, asthma, atopic dermatitis, psoriasis, and rosacea. In some embodiments, the disease is selected from the group consisting of Netherton Syndrome, asthma, atopic dermatitis, psoriasis, rosacea and eosinophilic esophagitis. In some embodiments, the asthma is selected from the group consisting of atopic asthma, allergic asthma, non-allergic asthma, exercise-induced asthma, aspirin sensitive/exacerbated asthma, mild asthma, moderate to severe asthma, corticosteroid naïve asthma, chronic asthma, corticosteroid resistant asthma, corticosteroid refractory asthma, newly diagnosed and untreated asthma, asthma due to smoking, asthma uncontrolled on corticosteroids, T helper lymphocyte type 2 (Th2) or type 2 (Th2) high, or Type 2 (T2)-driven asthma, eosinophilic asthma, periostin-high asthma, eosinophil-high asthma, Th2-low asthma or nonTh2-driven asthma, periostin-low asthma, and eosinophil-low asthma. In some embodiments, the asthma is TH2-low asthma.

In certain embodiments, labeled anti-KLK5 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-KLK5 antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-KLK5 antibodies provided herein may be used in therapeutic methods.

In one aspect, an anti-KLK5 antibody for use as a medicament is provided. In further aspects, an anti-KLK5 antibody is provided for use in treating a disease selected from the group consisting of Netherton Syndrome, asthma, atopic dermatitis, psoriasis, and rosacea. In some embodiments, the disease is selected from the group consisting of Netherton Syndrome, asthma, atopic dermatitis, psoriasis, rosacea and eosinophilic esophagitis. In some embodiments, the asthma is selected from the group consisting of atopic asthma, allergic asthma, non-allergic asthma, exercise-induced asthma, aspirin sensitive/exacerbated asthma, mild asthma, moderate to severe asthma, corticosteroid naïve asthma, chronic asthma, corticosteroid resistant asthma, corticosteroid refractory asthma, newly diagnosed and untreated asthma, asthma due to smoking, asthma uncontrolled on corticosteroids, T helper lymphocyte type 2 (Th2) or type 2 (Th2) high, or Type 2 (T2)-driven asthma, eosinophilic asthma, periostin-high asthma, eosinophil-high asthma, Th2-low asthma or nonTh2-driven asthma, periostin-low asthma, and eosinophil-low asthma. In some embodiments, the asthma is TH2-low asthma.

In certain embodiments, an anti-KLK5 antibody for use in a method of treatment is provided. In certain embodiments, the invention provides an anti-KLK5 antibody for use in a method of treating an individual having a disease, wherein the disease is selected from the group consisting of Netherton Syndrome, asthma, atopic dermatitis, psoriasis, and rosacea comprising administering to the individual an effective amount of the anti-KLK5 antibody. In one such embodiment, the method further comprises administering to the individual an effective amount of at least one additional therapeutic agent, e.g., as described below. In some embodiments, provided is an anti-KLK5 antibody for use in inhibiting the biological activity of KLK5. In some embodiments, provided is an anti-KLK5 antibody for use in a method of inhibiting the biological activity of KLK5 in an individual comprising administering to the individual an effective of the anti-KLK5 antibody to inhibit the biological activity of KLK5. An "individual" according to any of the above embodiments is preferably a human. In some embodiments, the disease is selected from the group consisting of Netherton Syndrome, asthma, atopic dermatitis, psoriasis, rosacea and eosinophilic esophagitis. In some embodiments, the asthma is selected from the group consisting of atopic asthma, allergic asthma, non-allergic asthma, exercise-induced asthma, aspirin sensitive/exacerbated asthma, mild asthma, moderate to severe asthma, corticosteroid naïve asthma, chronic asthma, corticosteroid resistant asthma, corticosteroid refractory asthma, newly diagnosed and untreated asthma, asthma due to smoking, asthma uncontrolled on corticosteroids, T helper lymphocyte type 2 (Th2) or type 2 (Th2) high, or Type 2 (T2)-driven asthma, eosinophilic asthma, periostin-high asthma, eosinophil-high asthma, Th2-low asthma or nonTh2-driven asthma, periostin-low asthma, and eosinophil-low asthma. In some embodiments, the asthma is TH2-low asthma.

In a further aspect, the invention provides for the use of an anti-KLK5 antibody in the manufacture or preparation of a medicament. In one embodiment, the medicament is for treatment a disease, wherein the disease is selected from the group consisting of Netherton Syndrome, asthma, atopic dermatitis, psoriasis, and rosacea. In a further embodiment, the medicament is for use in a method of treating a disease, wherein the disease is selected from the group consisting of Netherton Syndrome, asthma, atopic dermatitis, psoriasis, and rosacea comprising administering to an individual having said disease an effective amount of the medicament. In one such embodiment, the method further comprises administering to the individual an effective amount of at least one additional therapeutic agent, e.g., as described below. In a further embodiment, the medicament is for inhibiting the biological activity of KLK5. In a further embodiment, the medicament is for use in a method of inhibiting the biological activity of KLK5 in an individual comprising administering to the individual an amount effective of the medicament to inhibiting the biological activity of KLK5. An "individual" according to any of the above embodiments may be a human. In some embodiments, the disease is selected from the group consisting of Netherton Syndrome, asthma, atopic dermatitis, psoriasis, rosacea and eosinophilic esophagitis. In some embodiments, the asthma is selected from the group consisting of atopic asthma, allergic asthma, non-allergic asthma, exercise-induced asthma, aspirin sensitive/exacerbated asthma, mild asthma, moderate to severe asthma, corticosteroid naïve asthma, chronic asthma, corticosteroid resistant asthma, corticosteroid refractory asthma, newly diagnosed and untreated asthma, asthma due to smoking, asthma uncontrolled on corticosteroids, T helper lymphocyte type 2 (Th2) or type 2 (Th2) high, or Type 2 (T2)-driven asthma, eosinophilic asthma, periostin-high asthma, eosinophil-high asthma, Th2-low asthma or nonTh2-driven asthma, periostin-low asthma, and eosinophil-low asthma. In some embodiments, the asthma is TH2-low asthma.

In a further aspect, the invention provides a method for treating a disease, wherein the disease is selected from the group consisting of Netherton Syndrome, asthma, atopic dermatitis, psoriasis, and rosacea. In some embodiments, the disease is selected from the group consisting of Netherton Syndrome, asthma, atopic dermatitis, psoriasis, rosacea and eosinophilic esophagitis. In one embodiment, the method comprises administering to an individual having such Netherton Syndrome, asthma, atopic dermatitis, psoriasis, or rosacea an effective amount of an anti-KLK5 antibody. In one such embodiment, the method further comprises administering to the individual an effective amount of at least one additional therapeutic agent, as described below. An "individual" according to any of the above embodiments may be a human. In some embodiments, the asthma is selected from the group consisting of atopic asthma, allergic asthma, non-allergic asthma, exercise-induced asthma, aspirin sensitive/exacerbated asthma, mild asthma, moderate to severe asthma, corticosteroid naïve asthma, chronic asthma, corticosteroid resistant asthma, corticosteroid refractory asthma, newly diagnosed and untreated asthma, asthma due to smoking, asthma uncontrolled on corticosteroids, T helper lymphocyte type 2 (Th2) or type 2 (Th2) high, or Type 2 (T2)-driven asthma, eosinophilic asthma, periostin-high asthma, eosinophil-high asthma, Th2-low asthma or nonTh2-driven asthma, periostin-low asthma, and eosinophil-low asthma. In some embodiments, the asthma is TH2-low asthma.

In a further aspect, the invention provides a method for inhibiting the biological activity of KLK5 in an individual. In one embodiment, the method comprises administering to the individual an effective amount of an anti-KLK5 antibody to inhibiting the biological activity of KLK5. In one embodiment, an "individual" is a human.

In a further aspect, the invention provides pharmaceutical formulations comprising any of the anti-KLK5 antibodies provided herein, e.g., for use in any of the above therapeutic methods. In one embodiment, a pharmaceutical formulation comprises any of the anti-KLK5 antibodies provided herein and a pharmaceutically acceptable carrier. In another embodiment, a pharmaceutical formulation comprises any of the anti-KLK5 antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent. In some embodiments, the additional therapeutic agent is an IL-13 axis binding antagonist, an IL-5 axis binding antagonist, an IL-33 axis binding antagonist, an M1 prime antagonist, an IgE antagonist, a TRPA1 antagonist, a CRTH2 antagonist, a bronchodilator or asthma symptom controller medication, an immunomodulator, a corticosteroid, a Th2 pathway inhibitor, a tyrosine kinase inhibitor, or a phosphodiesterase inhibitor. In some embodiments, the IL-13 axis binding antagonist is an anti-IL-13 antibody. In some embodiments, the anti-IL-13 antibody is lebrikizumab. In some embodiments, the IL-5 axis binding antagonist is an IL-5 binding antagonist or an IL-5 receptor binding antagonist. In some embodiments, the IL-33 axis binding antagonist is an IL-33 binding antagonist or an ST2 binding antagonist. In some embodiments, the IL-33 binding antagonist is an anti-IL-33 antibody. In some embodiments, the M1 prime antagonist is quilizumab.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-KLK5 antibody and administration of an additional therapeutic agent occur within about one month, or within about one, two or three weeks, or within about one, two, three, four, five, or six days, of each other. Antibodies of the invention can also be used in combination with radiation therapy.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered.

It is understood that any of the above formulations or therapeutic methods may be carried out using an immunoconjugate of the invention in place of or in addition to an anti-KLK5 antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-KLK5 antibody.

III. Examples

The following are examples of methods and compositions of the invention. It is understood that various other embodiments may be practiced, given the general description provided above.

Example 1—Material and Methods

Generation of Anti-KLK5 Antibodies

New Zealand White rabbits were immunized with human KLK5 and single B cells were isolated using a modified protocol related to published literature, e.g. see Offner et al., *PLoS ONE* 9(2), 2014. This modified workflow included direct FACS sorting of IgG+ huKLK5+ B cells into single wells. The B cell culture supernatants were assayed by ELISA for binding to human KLK5 and an irrelevant control protein. KLK5 specific B cells were lysed and immediately frozen in −80° C. for storage until molecular cloning. Variable regions (VH and VL) of each monoclonal antibody from rabbit B cells were cloned into expression vectors from extracted mRNA as previously described, e.g. see Offner et al., *PLoS ONE* 9(2), 2014. Individual recombinant rabbit antibodies were expressed in Expi293 cells and subsequently purified with protein A. Purified anti-KLK5 antibodies were then subjected to functional activity assays and kinetic screening.

Rats were immunized in a similar manner and hybridomas were generated using a modified fusion partner (e.g. see Price et al., *J Immunol Methods* 31; 343(1):28-41 (2009)). Various conditions were optimized to enable sorting of individual IgG+ huKLK5+ hybridomas into single wells followed by additional culturing after sorting. The resulting hybridoma supernatants were assayed by ELISA and positive samples were purified using protein A for subsequent functional and kinetic characterization.

BIAcore™ Experiments

The binding affinity of the antibodies in this section was determined by BIAcore™ T200 machine. Briefly, BIAcore™ research grade CM5 chips were activated with 1-ethyl-3-(3-dimethylaminopropyl) carbodiimide (EDC) and N-hydroxysuccinimide (NHS) reagents according to the supplier's instructions. Goat anti-human Fc IgGs were coupled to the chips to achieve approximately 10,000 response units (RU) in each flow cell. Unreacted coupling groups were blocked with 1M ethanolamine. For kinetics measurements, antibodies were captured to achieve approximately 300 RU. Ten-fold serial dilutions of human KLK5 were injected in HBS-P buffer at 37° C. with a flow rate of 30 μL/min. Association rates (ka) and dissociation rates (kd) were calculated using a 1:1 Langmuir binding model (BIAcore™ T200 Evaluation Software version 2.0). The equilibrium dissociation constant (KD) was calculated as the ratio kd/ka.

Assays for Determination of KLK5 Inhibition

The inhibition of human KLK5 by anti-KLK5 antibodies was measured using a recombinant KLK5 direct activity assay. Recombinant human KLK5 (Genentech) was diluted to 5 nM in direct assay buffer (75 mM Tris (pH 8.0), 150 mM NaCl and 0.01% TWEEN® 20) and combined with anti-KLK5 antibodies in 384-well assay plate (384 Well Low Volume, Black, Round Bottom, Corning, Catalog No. 4514). Antibodies were supplied in either phosphate sample buffer (70 mM sodium phosphate (pH 6), 200 mM NaCl and 0.01% TWEEN® 20) or citrate/Tris sample buffer (10 mM citric acid, 30 mM Tris (pH 6) and 0.01% TWEEN® 20). Antibody dilutions were made in the appropriate sample buffer or in direct assay buffer. Plates were incubated for 30 minutes at ambient temperature. Fluorescent peptide substrate, Boc-VPR-AMC (Bachem, Part No. 1-1120) was added directly to the assay plate. Final in-well concentrations were μM Boc-VPR-AMC, 5 nM recombinant human KLK5, and 0.19-100 nM anti-KLK5 antibodies. Plates were examined every 102 s for 30-60 minute using a PHERAstar® Plus reader using a 340 nm excitation/460 nm emission module. The Reaction rate (expressed as RFU) was calculated by linear regression of readings in the linear range, typically beginning at 204 s and continuing until the end of the assay. Buffer alone and 100 nM final SPINK9.SRE.Fc (Genentech) were used as 100% and 0% activity controls, respectively. The $IC_{50}$ value of the anti-KLK5 antibodies were determined from a four-parameter fit for their respective curves.

The inhibition of human KLK5 by anti-KLK5 antibodies was measured using a coupled pro-KLK7 fluorescent peptide assay. Recombinant human KLK5 (Genentech) was diluted to 5 nM in pro-KLK7 citrate/Tris coupled buffer (50 mM Tris (pH 7.5), 150 mM NaCl and 0.01% TWEEN® 20) if antibody samples were in citrate/Tris sample buffer or pro-KLK7 phosphate coupled buffer (50 mM Tris (pH 8.0), 150 mM NaCl and 0.01% TWEEN® 20) if antibody samples were in phosphate sample buffer. Diluted KLK5 was then combined with anti-KLK5 antibodies in 384-well assay plate (384 Well Low Volume, Black, Round Bottom, Corning, Catalog No. 4514). Antibody dilutions were made as described for the direct KLK5 assay. Plates were incubated for minutes at ambient temperature. Fluorescent peptide substrate, suc-LLVY-AMC (Bachem, Part No. 1-1395) and pro-KLK7 (Genentech) were added directly to the assay plate and incubated at ambient temperature. Final in-well concentrations were 100 μM suc-LLVY-AMC, 125 nM pro-KLK7, 5 nM recombinant human KLK5, and 0.19-100 nM anti-KLK5 antibodies. After 24 hours, fluorescent readings were made every 102 s for 30-60 min and the RFU endpoint value was calculated by averaging the last 5 readings. Buffer alone and 100 nM final SPINK9.SRE.Fc (Genentech) were used as 100% and 0% activity controls, respectively. The $IC_{50}$ value of the anti-KLK5 antibodies were determined from a four-parameter fit for their respective curves.

$IC_{50}$ value of the anti-KLK5 antibodies was determined using a pro-KLK7 Assay by KLK5-derived cleavage peptide detection using LC/MS (pro-KLK7 LC/MS assay). The product peptide EEAQGDK from reaction between the enzyme KLK5 and substrate proKLK7 was detected by mass spectrometry coupled to liquid chromatography. All compounds were diluted with 50 mM ammonium bicarbonate buffer (Powder/Certified, Fisher Chemical, A643-500) with final concentrations in the assay at 5 nM KLK5 (Genentech) and antibodies ranging from 0.02 to nM, diluted in 96-well plates (Bio-Rad, Hard-Shell 96-Well PCR Plates, low profile, thin wall, skirted, blue/clear #HSP9631). Plates were incubated at room temperature for 30 minutes. Afterward, 15 nM of substrate proKLK7 (Genentech) was added to the enzyme plus inhibitors. After 2 hours, the reaction was quenched using 0.5 μL of Formic Acid (99.5+%, Optima™ LC/MS Grade, Fisher Chemical, A117-10X1AMP). Peptide was detected using the combination of the following masses: Q1, 388.7 m/z and Q3, 319.0 m/z, in a QTRAP® 6500 LC-MS/MS mass spectrometer (Sciex, Framingham, MA). Quantitation of generated peptide was measured using a synthetic KLK7 peptide calibration curve. The $IC_{50}$ values were determined using Prism 6 Software (GraphPad Software, La Jolla, CA).

The inhibition of human KLK5 by anti-KLK5 antibodies was measured using a coupled pro-KLK1 fluorescent peptide assay. Recombinant human KLK5 (Genentech) was diluted to 0.5 nM in pro-KLK1 coupled assay buffer (100 mM Tris (pH 8.5) and 0.01% TWEEN® 20) and combined with anti-KLK5 antibodies in 384-well assay plate (384 Well Low Volume, Black, Round Bottom, Corning, Catalog No. 4514). Antibody dilutions were made as described for the direct KLK5 assay. Plates were incubated for 30 minutes at ambient temperature. Fluorescent peptide substrate, PFR-AMC (Bachem, Part No. 1-1295) and pro-KLK1 (Genentech) were added directly to the assay plate and incubated at ambient temperature. Final in-well concentrations were μM PFR-AMC, 31.25 nM pro-KLK1, 0.5 nM recombinant human KLK5, and 0.19-100 nM anti-KLK5 antibodies. Plates were examined every 102 s for 120 minute using a PHERAstar® Plus reader using a 340 nm excitation/460 nm emission module. The endpoint RFU values were calculated by averaging readings around a time dictated by the inflection point of a plot of RFU versus time for the no inhibitor controls. Buffer alone and 100 nM final SPINK9.SRE.Fc (Genentech) was used as 100% and 0% activity controls, respectively. The $IC_{50}$ values of the anti-KLK5 antibodies were determined from a four-parameter fit for their respective curves.

$IC_{50}$ values of the anti-KLK5 antibodies was determined using a pro-KLK1 Assay by KLK5-derived cleavage peptide detection using LC/MS (pro-KLK1 LC/MS Assay). The product peptide APPIQSR from reaction between the enzyme KLK5 and substrate proKLK1 was detected by mass spectrometry coupled to liquid chromatography. All compounds were diluted with 50 mM ammonium bicarbonate buffer (Powder/Certified, Fisher Chemical, A643-500) with final concentrations in the assay at 0.5 nM KLK5 (Genentech) and antibodies ranging from 0.01 to 29 nM, diluted in 96-well plates (Bio-Rad, Hard-Shell 96-Well PCR Plates, low profile, thin wall, skirted, blue/clear #HSP9631). Plates were incubated at room temperature for 60 minutes. Afterward, 300 nM of substrate proKLK1 (Genentech) was added to the enzyme plus inhibitors. After 20 minutes, the reaction was quenched using 0.5 µL of Formic Acid (99.5+ %, Optima™ LC/MS Grade, Fisher Chemical, A117-10X1AMP). Peptide was detected using the combination of the following masses: Q1, 384.7 m/z and Q3, 600.3 m/z, in a QTRAP® 6500 LC-MS/MS mass spectrometer (Sciex, Framingham, MA). $IC_{50}$ value were determined using peak areas and Prism 6 Software (GraphPad Software, La Jolla, CA).

$K_{i(app)}$ assay using Z-VPR-pNA as substrate was performed at room temperature in a 96-well half-area plate (white with clear, flat bottom, Corning #3884). Inhibitor samples were diluted to 3× final concentration in assay buffer (100 mM Tris, pH 8.0, 100 mM NaCl, 0.01% TWEEN® 20). Buffer alone and 100 nM final SPINK9.SRE.Fc (Genentech) were used as 100% and 0% activity controls, respectively. Inhibitor or control samples (20 µL) were added to the plate followed by 20 µL KLK5 (Genentech) in assay buffer at final concentrations of 0.5, 0.25, 0.125, and 0.0625 nM. After 30 minutes, 20 µL of Z-VPR-pNA substrate (California Peptide, #876-08, prepared as a 30 mM stock solution in DMSO) in assay buffer was added at a final concentration of 300 µM. In some initial assays the final DMSO concentration was increased to 10% by making an initial dilution of the substrate to 3 mM in DMSO before diluting to 900 µM (i.e., 3× final) in assay buffer. After addition of substrate, the plate was read in a Versamax tunable microplate reader with measurements at 405 nm taken every 102 seconds for 3 hours. Reaction rates (expressed as µAU/s) were calculated by linear regression in the range 4182-10710 seconds. Reaction rates were normalized to the values of the 0% and 100% activity controls and fit with a 4-parameter equation to calculate $IC_{50}$ values. In the case of a bivalent inhibitor, the raw $IC_{50}$ value was multiplied by two. The $IC_{50}$ value was then plotted versus KLK5 enzyme concentration, yielding the Ki(app) from the y-intercept value. In addition, if the inhibitor was potent enough, the combined purity of both enzyme and inhibitor could be judged by comparing the slope of the plot to the theoretical value of 0.5.

Assays for Determination of Antibody Selectivity

KLK1 selectivity assay was performed at room temperature in a 384-well plate (black, low-volume round bottom, Corning #4514) with a final reaction volume of 15 µL. Inhibitor samples were diluted to 3× final concentration in assay buffer (75 mM Tris, pH 8.0, 150 mM NaCl, 0.01% TWEEN® 20). Reactions lacking inhibitor and reactions lacking enzyme were used as 100% and 0% activity controls, respectively. Inhibitor or control samples (5 µL) were added to the plate followed by 5 µL KLK1 (R&D Systems, 2337-SE, Lot NLY0315111, activated according to R&D systems protocol) in assay buffer at a final concentration of 3 nM. After 30 minutes, 5 µL of H-Pro-Phe-Arg-AMC acetate salt (Bachem I-1295, 10 mM stock solution in water) in assay buffer was added at a final concentration of 100 µM. After addition of substrate, the plate was read in PHERAstar® microplate reader using optic module FI 340 460 with the gain set to 85%. Measurements were taken every 102 seconds for 1 hour. Reaction rates (expressed as RFU/s) were calculated by linear regression in the range 204-918 seconds. Reaction rates were normalized to the values of the 0% and 100% activity controls and fit with a 4-parameter equation to calculate $IC_{50}$ values. In the case of bivalent inhibitors, the raw $IC_{50}$ value was multiplied by two.

KLK4 selectivity assay was performed at room temperature in a 384-well plate (black, low-volume round bottom, Corning #4514) with a final reaction volume of 15 µL. Inhibitor samples were diluted to 3× final concentration in assay buffer (75 mM Tris, pH 8.0, 150 mM NaCl, 0.01% TWEEN® 20). Reactions lacking inhibitor and reactions lacking enzyme were used as 100% and 0% activity controls, respectively. Inhibitor or control samples (5 µL) were added to the plate followed by 5 µL KLK4 (R&D Systems, 1719-SE, Lot MSY0116011, activated according to R&D systems protocol) in assay buffer at a final concentration of 2 nM. After 30 minutes, 5 µL of Boc-Val-Pro-Arg-AMC (Bachem I-1120, 31.3 mM stock solution in water) in assay buffer was added at a final concentration of 50 µM. After addition of substrate, the plate was read in PHERAstar® microplate reader using optic module FI 340 460 with the gain set to 85%. Measurements were taken every 102 seconds for 1 hour. Reaction rates (expressed as RFU/s) were calculated by linear regression in the range 510-3570 seconds. Reaction rates were normalized to the values of the 0% and 100% activity controls and fit with a 4-parameter equation to calculate $IC_{50}$ values. In the case of bivalent inhibitors, the raw $IC_{50}$ value was multiplied by two.

Trypsin selectivity assay was performed at room temperature in a 384-well plate (black, low-volume round bottom, Corning #4514) with a final reaction volume of 15 µL. Inhibitor samples were diluted to 3× final concentration in assay buffer (75 mM Tris, pH 8.0, 150 mM NaCl, 0.01% TWEEN® 20). Reactions lacking inhibitor and reactions lacking enzyme were used as 100% and 0% activity controls, respectively. Inhibitor or control samples (5 µL) were added to the plate followed by 5 µL trypsin (Sigma Aldrich T8003, Lot SLBM2321V, 42.0 µM stock solution in 1 mM HCl) in assay buffer at a final concentration of 0.25 nM. After 30 minutes, 5 µL of Boc-Val-Pro-Arg-AMC (Bachem I-1120, 31.3 mM stock solution in water) in assay buffer was added at a final concentration of 50 µM. After addition of substrate, the plate was read in PHERAstar® microplate reader using optic module FI 340 460 with the gain set to 85%. Measurements were taken every 102 seconds for 1 hour. Reaction rates (expressed as RFU/s) were calculated by linear regression in the range 204-3570 seconds. Reaction rates were normalized to the values of the 0% and 100% activity controls and fit with a 4-parameter equation to calculate $IC_{50}$ values. In the case of bivalent inhibitors, the raw $IC_{50}$ value was multiplied by two.

KLK7 selectivity assay was performed at room temperature in a 384-well plate (black, low-volume round bottom, Corning #4514) with a final reaction volume of 15 µL. Inhibitor samples were diluted to 3× final concentration in assay buffer (75 mM Tris, pH 8.0, 150 mM NaCl, 0.01% TWEEN® 20). Reactions lacking inhibitor and reactions lacking enzyme were used as 100% and 0% activity controls, respectively. Inhibitor or control samples (5 µL) were added to the plate followed by 5 µL KLK7 (Genentech) in assay buffer at a final concentration of 5 nM. After 30 min, 5 µL of Suc-Leu-Leu-Val-Tyr-AMC (Bachem I-1395, 25 mM stock solution in water) in assay buffer was added at a final concentration of 100 µM. After addition of substrate, the plate was read in PHERAstar® microplate reader using optic module FI 340 460 (AMC Module) with the gain set to 85%. Measurements were taken every 102 seconds for 1 hour 15 minute. Reaction rates (expressed as RFU/s) were calculated by linear regression in the range 2040-4488 seconds. Reaction rates were normalized to the values of the 0% and 100% activity controls and fit with a 4-parameter equation to calculate $IC_{50}$ values.

PHERAstar® Experiments

Pre MCA PHERAstar® Module: After 30 min, 5 µL of Suc-Leu-Leu-Val-Tyr-AMC (Bachem I-1395, 25 mM stock solution in water) in assay buffer was added at a final concentration of 100 µM. After addition of substrate, the plate was read in PHERAstar® microplate reader using optic module FI 340 460 (AMC Module) with the gain set to 85%. Measurements were taken every 102 seconds for 1 hour 15 minute. Reaction rates (expressed as RFU/s) were calculated by linear regression in the range 2040-4488 seconds. Reaction rates were normalized to the values of the 0% and 100% activity controls and fit with a 4-parameter equation to calculate $IC_{50}$ values.

Post MCA PHERAstar® Module: After 30 min, 5 µL of Mca-RPKPVE-Nval-WRK(Dnp)-NH2 Fluorogenic MMP Substrate (R&D Systems ES002, 4.3 mM stock solution in DMSO) in assay buffer was added at a final concentration of 10 µM. After addition of substrate, the plate was read in PHERAstar® microplate reader using optic module FI 320 405 (MCA Module) with the gain set to 85%. Measurements were taken every 102 seconds for 1 hour 15 minute. Reaction rates (expressed as RFU/s) were calculated by linear regression in the range 204-1020 seconds. Reaction rates were normalized to the values of the 0% and 100% activity controls and fit with a 4-parameter equation to calculate $IC_{50}$ values.

Wasatch Experiments

An array-based SPR imaging system (Carterra™, USA) was used to epitope bin a panel of 288 monoclonal antibodies. Purified antibodies were diluted at 10 µg/ml in 10 mM sodium acetate buffer pH 4.5. Using amine coupling, antibodies were directly immobilized onto a SPR sensorprism CMD 200M chip (XanTec Bioanalytics GmbH, Germany) using a Continuous Flow Microspotter (Carterra™, USA) to create an array of 288 antibodies. For analysis, the IBIS MX96 SPRi (Carterra™, USA) was used to evaluate analytes binding to the immobilized ligands. For kinetic analyses, human, cyno and murine KLK5 were injected for 3 minutes from 0 to 300 nM at 3-fold dilution followed by a dissociation period of 10 minutes. Human KLK1, KLK4, and KLK7 were injected at a single concentration of 500 nM to ensure the specificities of the antibodies. For epitope binning against SPINK9-Fc-SRE, human KLK5 was first injected for 4 minute at 100 nM and was followed by a second 4 minute injection of SPINK9-Fc-SRE at 10 µg/ml. The surface was regenerated with 10 mM glycine pH1.5 between cycles. The experiment was performed at 25° C. in a running buffer of HBS-T buffer (0.01M HEPES pH 7.4, 0.15M NaCl, surfactant P20). The kinetic data was processed using Scrubber 2.0 (BioLogic™ Software) and the epitope binning data was processed using Wasatch binning software tool (Carterra™ USA).

Hydrogen Exchange Mass Spectrometry

Experimental starting material compositions are listed in Table 2. Two labeling solutions were prepared with $^2H_2O$ (heavy water) having a pH of either 6.0 or 8.0, and consisting of a mixture of anhydrous monobasic sodium phosphate and dibasic sodium phosphate dehydrate combined in an appropriate ratio to achieve the stated deuterium activity at a total concentration 10 mM with 140 mM NaCl. Starting materials (Table 2) were diluted approximately 1:10 with labeling solutions using a leap robotics platform and incubated for various times before being diluted 1:1 with quench buffer (4M GdmCl, 0.5 M TCEP, 200 mM Citric acid), to a final pH of 2.5, and then prepared quickly for mass measurement. Quenched material was injected into an online flow system where it was digested using pepsin, buffer exchanged while bound to a trap column, separated by reversed-phase chromatography, and introduced into the gas phase by electrospray where individual peptides are assessed for the amount of carried deuterium.

TABLE 2

| Sample | Mab:KLK5 Ratio | Starting Material Exp. Composition | |
|---|---|---|---|
| | | [Mab] µM | [KLK5] µM |
| KLK5.10C5 | 0.70 | 23.10 | 33.00 |
| KLK5.10H3 | 0.65 | 20.98 | 33.00 |
| KLK5.9H5 | 0.55 | 18.07 | 33.00 |
| KLK5 | 0.00 | 0.00 | 33.00 |

At either pH 6.0 or 8.0, samples were labeled for 0.5, 5.0, 56.0, and 600.0 minutes. Independent experimental replicates were included; on plots shown, error bars represent the range of measurements, whose average shown by markers in FIG. 12B. Feature abstraction and data analysis involved custom in-house software.

Figures 12A, 12B:
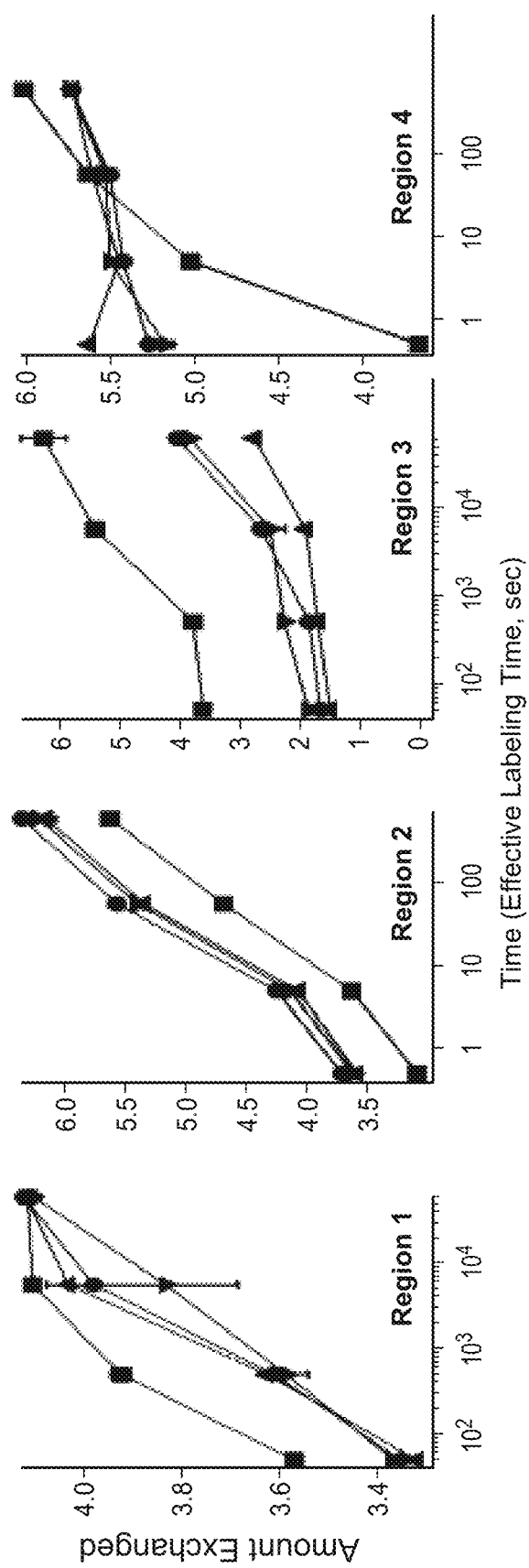
FIGS. 12A and 12B.

Effective labeling time at a reference pH was defined by both experimental pH and actual labeling time: $t_{eff}=t_{exp}*10^{(pH_{ref}-pH_{exp})}$. The reference pH in FIG. 12B is 6.0. To correct for a well-known proton activity offset that occurs as a result of $^2H_2O$, the following relationship connects pH measurements with pH values referred herein:

$$pH=pH_{measure}+([^2H_2O/^2H_2O+{}^1H_2O]*0.4).$$

The sequence and retention time of experimental peptides derived from KLK5 was determined in initial experiments where the same procedural workflow described above was followed but with a labeling buffer in $^1H_2O$ solvent. This provides a starting mass from which the amount of deuterium contained in each peptide during the labeling experiments may be determined; additionally, these experiments utilize tandem-MS for de novo sequencing by MS.

IL-8 Secretion Assay

IL-8 is secreted by several cell types in response to inflammatory stimuli. KLK5 stimulates A459 cells, resulting in the secretion of IL-8. Adenocarcinomic human alveolar basal epithelial cells constitute the A549 cell-line. A549 cells were cultured with media containing RPMI, 10% FBS, L-glutamine, and supplemented with penicillin and streptomycin. Cells were plated into TC-treated 96-well plates (Corning, Cat. #3997) at 50,000 cells per well and starved of serum for 18 hours before KLK5 challenge. Human KLK5 was first incubated with KLK5 inhibitors or starvation media for 1 hour at room temperature prior to addition to plate (200 nM in-well concentration) for 24 hr at 37° C. in a humid environment in the presence of 5% CO2. Endotoxin inhibitor (1 µM) was also added to each well. After incubation, the cell supernatants were collected and either analyzed immediately or stored at −20° C. Cell supernatants were serially diluted in sample diluent (PBS/0.5% BSA/0.05% polysorbate-20/5 mM EDTA/0.25% CHAPS/0.2% BGG/10 ppM Proclin) for analysis in an IL-8 sandwich ELISA using a standard protocol with mouse anti-human IL-8 monoclonal antibody for capture (R&D Systems, Cat #MAB208) and biotinylated mouse anti-human IL-8 monoclonal antibody for detection (R&D Systems, Cat #BAF208). The cell stimulation activity of KLK5 was analyzed by normalizing the IL-8 concentrations to 100% for KLK5 treatment alone and to 0% for starvation media alone treatment. $IC_{50}$ values were determined using a 4-parameter fit with GraphPad Prism software.

KLK5 and Fab Expression, Purification and Crystallization

Recombinant human KLK5 residues I67-S293 (SEQ ID NO:328) was expressed in a Baculovirus expression system as a C-terminal fusion of ubiquitin with an Enterokinase cleavage site engineered between ubiquitin and KLK5. Sf9 cells were coexpressed with EndoH with 1 mg/mL of Kifunensine. Protein was purified on a HiTrap™ Heparin column. The column was washed with 25 mM TRIS pH 7.5 for 5 CV (column volumes), and then eluted with 0-750 mM NaCl over a gradient of 20 CV. Resultant protein pool was then further purified over 5200 by SEC in 25 mM Tris pH 7.5, 300 mM NaCl. The Ubiquitin was then cleaved using Enterokinase, and sample further purified by SEC again. Mass spectrometry and SDS PAGE revealed a pure KLK5 sample, which was confirmed to be active. Fab fragments including heavy and light chains were expressed and purified as described. See Carter et al., *Biotechnology* 10(2), 163-167 (1992). KLK5 was then mixed with each of the Fabs separately, 10C5, 9H5, and 3-3F5, and the complex was purified by SEC in 25 mM HEPES pH 7.2, 100 mM NaCl. The crystallization conditions for the 3 Fab-KLK5 complexes were as follows: 3-3F5 complex—15% PEG 4K, 0.1 M MgCl2, 0.1 M Na Citrate pH 5.0; 10C5 Complex: 20% PEG4K, 0.2M Ammonium Sulfate, 25% Glycerol; 9H5 Complex: 15% PEG4K, 10% Isopropanol, 0.1M HEPES pH 7.5. Crystal for the 10C5 and 9H5 complexes were only obtained when the lysine residues in the protein complexes were methylated. See Walter et al., *Structure*, 14(11), 1617-1622 (2006).

Data Collection and Structure Solution

X-ray diffraction data was collected under cryo-cooled conditions at 100 Kelvin using various synchrotron X-ray radiation at the Advanced Light Source (Berkeley, CA) or Advanced Photon Source (Argonne, IL) according to standard methods. Diffraction images were processed and reduced using the data processing software XDS. See Kabsch W, *Acta Crystallogr D Biol Crystallogr*, 66(Pt 2), 125-132 (2010). Models were generated using the molecular replacement technique with the program PHASER. The structure of human TIGIT (see Debala et al., *J Mol Biol*, 373:1017-1031 (2007)) and Fab antibody model (See Nakamura et al., *Cell Host Microbe*, 14(1), 93-103 (2013)) were used as search models. The structures underwent iterative rounds of model adjustment using the program COOT and refinement using the Phenix.refine or BUSTER programs. Models were refined to acceptable R and R free values and Ramachandran statistics (calculated by Molprobity). The crystal structures of KLK5 complexed with each of the Fabs, 10C5, 9H5 and 3-3F5 as well as the details of interactions and epitopes can be found in FIGS. 18-20 and Tables 5-13.

Example 2—Humanization of Anti-KLK5 Antibodies

By immunization of animals with human KLK5 as described herein above, as set of 540 monoclonal anti-KLK5 antibodies was obtained. As this set contained anti-KLK5 antibodies with highly variable characteristics, the antibodies were screened for desired characteristics, such as a certain $IC_{50}$ values and selectivity to human KLK5. This screening revealed a large number of antibodies with low affinity to human KLK5, no selectivity with respect to human KLK5, and/or insufficient functional activity. For example, some of the obtained anti-KLK5 antibodies were partial inhibitors, i.e. inhibition by ≤50% (e.g. clones 12B3, 1D10) or inhibition by ≤90% (e.g. clones 14C8, 14E12, 8E11). Some of the obtained anti-KLK5 antibodies inhibited human KLK5 only in one of the assays described herein (e.g. clones 9E3, 10D10). Only 13 anti-KLK5 antibodies were selected based on their characteristics (clones 8G10, 9B6, 2-3F4, 10C5, 2B11, 9H3, 8B7, 9H5, 9F2, 10C8, 8F5, 3-3F5). The three anti-KLK5 antibodies with the highest inhibitory activities (clones 9H5, 10C5, 3-3F5) were then selected for humanization.

Rabbit monoclonal antibodies 9H5, 10C5, and 3-3F5 were humanized as described below. Residue numbers are according to Kabat et al., Sequences of proteins of immunological interest, 5th Ed., Public Health Service, National Institutes of Health, Bethesda, Md. (1991).

Figure 16A:
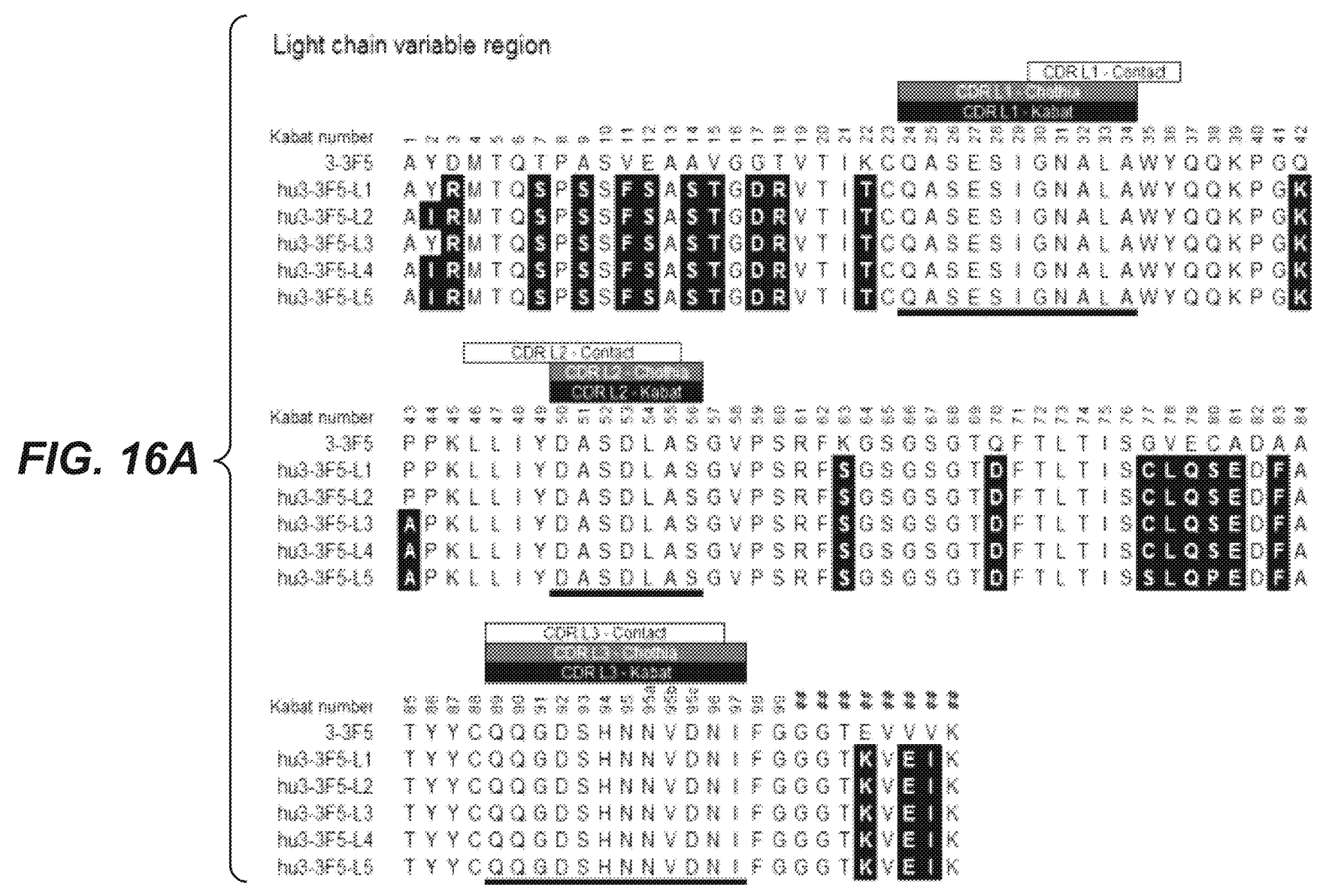
Figures 2, 16B:
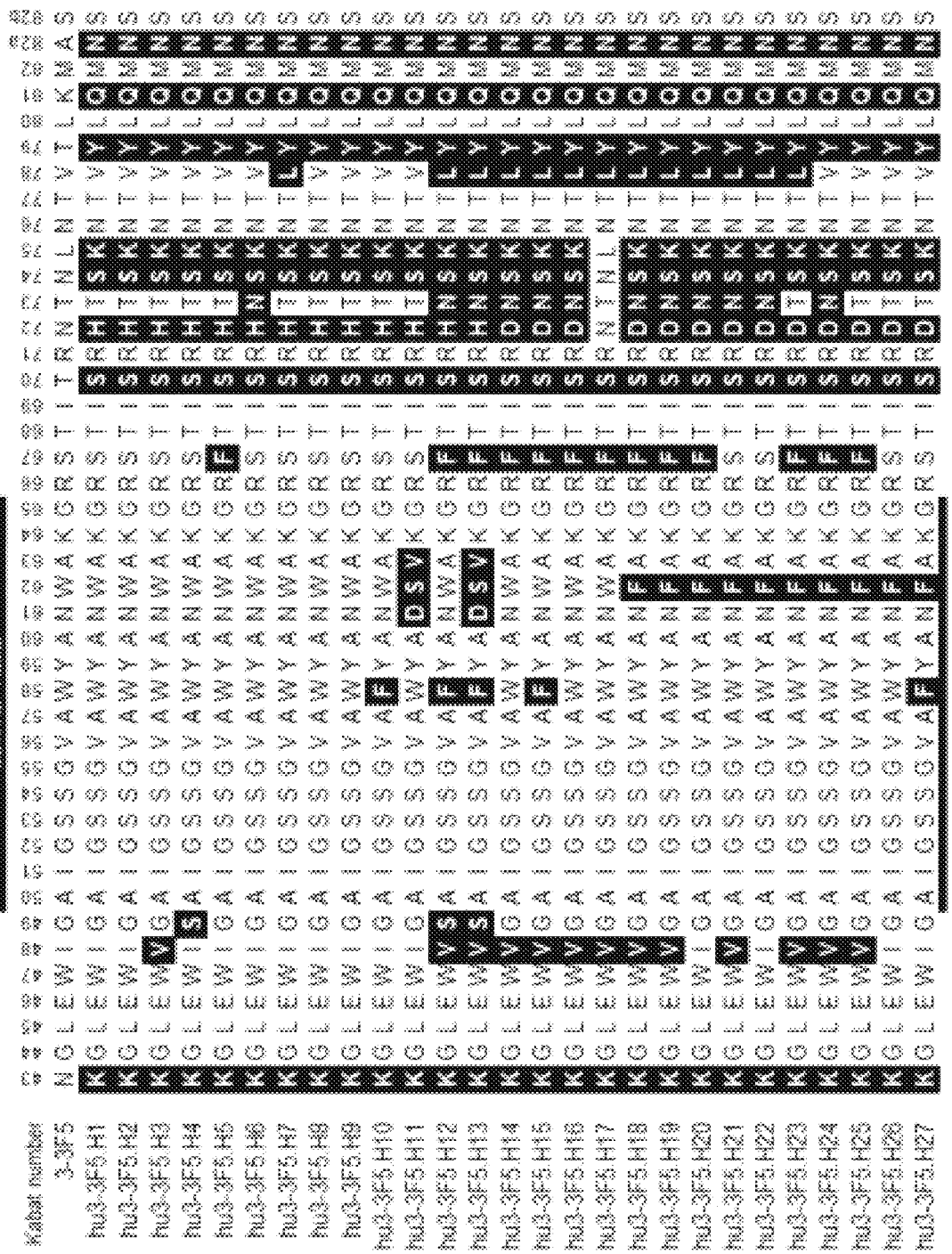

Variants constructed during the humanization of 9H5, 10C5, and 3-3F5 were assessed in the form of human IgG1. Hypervariable regions from each of the rabbit antibodies (namely positions 24-34 (L1), 50-56 (L2) and 89-97 (L3) in VL domain, and 26-35 (H1), 50-65 (H2) and (H3) in VH domain) were grafted into various acceptor frameworks. Specifically, for 9H5, VL CDRs were grafted into KV1D-39*01 and VH CDRs were grafted into HV3-53*01. For 10C5, VL CDRs were grafted into KV1-8*01 and VH CDRs were grafted into HV3-64*01. For 3-3F5, VL CDRs were grafted into KV1-8*01 and VH CDRs were grafted into HV3-23*01. All VL and VH Vernier positions from rabbit antibodies were also grafted into their respective human germline frameworks. The grafts with all rabbit amino acids in Vernier positions are referred to as L1H1 (hu9H5.L1H1, hu10C5.L1H1 and hu3-3F5.L1H1) (FIGS. 14-16).

The binding affinity of the antibodies in this section was determined using BIAcore™ T200 as described herein above. The binding affinity of humanized 9H5, 10C5 and 3-3F5 version L1H1 (hu9H5.L1H1, hu10C5.L1H1 and hu3-3F5.L1H1) antibodies were compared to their chimeric parental clones. Rabbit Vernier positions of version L1H1 antibodies were converted back to human residues to evaluate the contribution of each rabbit Vernier positions to binding affinity to hKLK5.

For 9H5, three additional light chains (L2: L1+Ala43, L3: L1+Tyr49, and L4: L1+Ala43+Tyr49 (CDR graft)) and sixteen additional heavy chains (H2: H1+Ala24, H3: H1+Trp47, H4: H1+Val48, H5: H1+Ser49, H6: H1+Phe67, H7: H1+Asn73, H8: H1+Leu78, H9: H1+Tyr91, H10: H1+Gln105, H11: no rabbit residues in Vernier positions (CDR graft), H12: H1+Asp61+Ser62+Val63+Gly65, H13: CDR graft+Asp61+Ser62+Val63+Gly65, H14: CDR graft+Tyr47+Gly49, H15: H14+Gln2, H16: H14+Asn72+Thr73+Asn74+Leu75, and H17: H14+Phe62) were made (FIG. 15). Tyr47 and Gly49 on the heavy chain (H14) were determined to be the key rabbit Vernier residues based on binding affinity evaluation of the variant antibodies described above (data not shown). Chimeric 9H5 bound with a KD of $1.9E^{-10}$ M, while hu9H5.L4H14, bound with a KD of $6.9E^{-10}$ M.

For 10C5, four additional light chain variants L2-L5 (L2: L1+Ile2, L3: L1+Ala43, L4: L1+Ile2+Ala43 (CDR graft), L5: CDR graft+Ser77+Pro80, L6: CDR graft+Ser77+Pro80+Glu103+Val105+Val106) and twenty-seven additional heavy chain variants H2 to H28 (H2: H1+Ala24, H3: H1+Tyr47, H4: H1+Val48, H5: H1+Ser49, H6: H1+Phe67, H7: H1+Asn73, H8: H1+Leu78, H9: H1+Tyr91, H10: H1+Gln105, H11: H1+Asn61+Ser62+Val63+Gly65, H12: no rabbit residues in Vernier positions (CDR graft), H13: CDR graft+Asn61+Ser62+Val63+Gly65, H14: CDR graft+Trp47+Gly49, H15: H14+Gln2, H16: H14+Asn72+Leu73+Asn74+Thr75, H17: H14+Phe62, H18: H14+Asn72+Thr73+Asn74+Leu75, H19: H14+Asn72, H20: H14+Asn74, H21: H14+Asn72+Asn74, H22: H14+Ile48, H23: H14+Ser67, H24: H22+Ser67, H25: H14+Thr73, H26:

H14+Thr78, H27: H25+Thr78, H28: H22+Ser67+Thr73+Thr78) were made (FIG. 14). Trp47, Ile48, Gly49, Ser67, Thr73, and Val78 on the heavy chain (H28) were determined to be the key rabbit Vernier residues based on binding affinity evaluation of the variant antibodies described above (data not shown). Chimeric 10C5 bound with a KD of $1.65E^{-11}$ M, while hu10C5.L5H28, bound with a KD of $5.70E^{-11}$ M.

For 3-3F5, four additional light chain variants L2-L5 (L2: L1+Ile2, L3: L1+Ala43, L4: L1+Ile2+Ala43 (CDR graft), L5: CDR graft+Ser77+Pro80) and twenty-six additional heavy chain variants H2 to H27 (H2: H1+Ala24, H3: H1+Val48, H4: H1+Ser49, H5: H1+Phe67, H6: H1+Asn73, H7: H1+Leu78, H8: H1+Tyr91, H9: H1+Arg105, H10: H1+Phe58, H11: H1+Asp61+Ser62+Val63, H12: CDR graft+Phe58, H13: CDR graft+Phe58+Asp61+Ser62+Val63, H14: CDR graft+Gly49, H15: H14+Phe58, H16: H14+Gln2, H17: H14+Asn72+Thr73+Asn74+Leu75, H18: H14+Phe62, H19: H18+Val24, H20: H18+Ile48, H21: H18+Ser67, H22: H18+Ile48+Ser67, H23: H18+Thr73, H24: H18+Val78, H25: H18+Thr73+Val78, H26: H18+I148+Ser67+Thr73+Val78, H27: CDRs graft+Ala24+Ile48+Gly49+Phe58+Phe62+Ser67, H28: H19+Phe58+Thr73+Thr78) were made (FIG. 16). Val24, Gly49, Thr73, and Val78 on the heavy chain (H28) were determined to be the key rabbit Vernier residues based on binding affinity evaluation of the variant antibodies described above (data not shown). Chimeric 3-3F5 bound with a KD of $<1E^{-12}$ M (KD is below the detection limit of $10E^{-6}$ $s^{-1}$ for the instrument), while hu3-3F5.L5H19 bound with a KD of $4.1E^{-12}$ M and hu3-3F5.L5H25 bound with a KD of $9.1E^{-12}$ M.

The hu9H5.L4H14, hu10C5.L5H28, hu3-3F5.L5H19, hu3-3F5.L5H25 and their chimeric counterparts were tested for their ability to bind human KLK5 as described herein above. Binding properties for the humanized antibodies are shown in Table 3.

TABLE 3

| Ligand | Sample | ka (1/Ms) | kd (1/s) | KD (M) |
|---|---|---|---|---|
| human KLK5 | 9H5 | $7.05E^{+5}$ | $1.37E^{-4}$ | $1.93E^{-10}$ |
|  | hu9H5.L4H14 | $8.10E^{+5}$ | $5.62E^{-4}$ | $6.94E^{-10}$ |
| human KLK5 | 10C5 | $1.78E^{+7}$ | $2.92E^{-4}$ | $1.65E^{-11}$ |
|  | hu10C5.L5H28 | $1.90E^{+7}$ | $1.08E^{-3}$ | $5.70E^{-11}$ |
| human KLK5 | 3-3F5 | $2.93E^{+7}$ | $<1.00E^{-5}$ | $<1.00E^{-12}$ |
|  | hu3-3F5.L5H19 | $4.84E^{+7}$ | $2.01E^{-4}$ | $4.14E^{-12}$ |
|  | hu3-3F5.L5H25 | $2.57E^{+7}$ | $2.35E^{-4}$ | $9.14E^{-12}$ |

Example 3—Evaluation of IC 50 Values and Specificity of Anti-KLK5 Antibodies

Figure 1B:
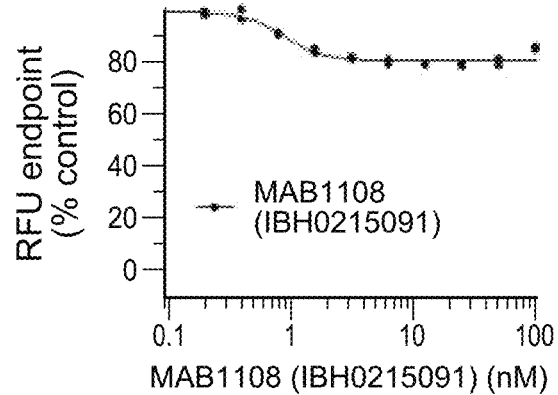
FIG. 1B: mAb1108.
Figure 1C:
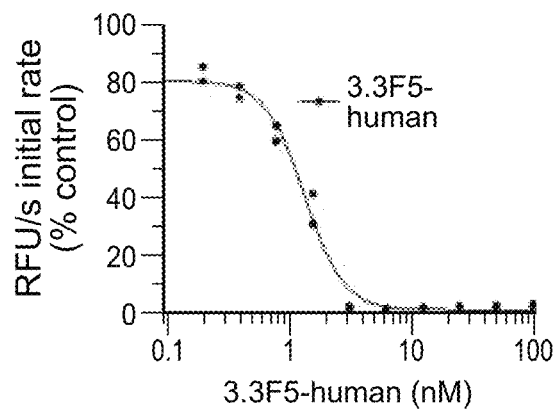
FIG. 1C: 3-3F5.
Figure 1D:
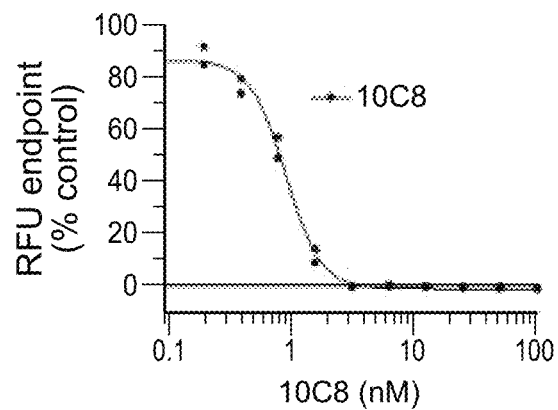
FIG. 1D: 10C8.
Figure 1E:
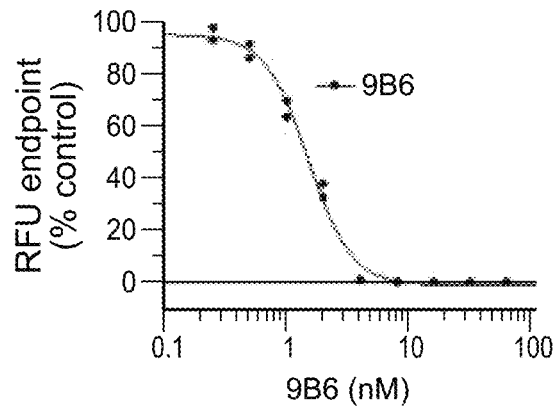
FIG. 1E: 9B6.
Figure 1F:
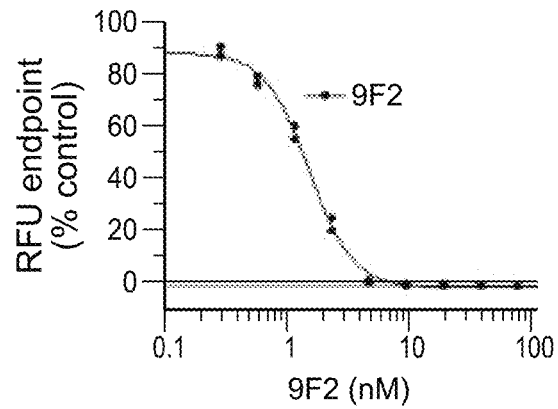
FIG. 1F: 9F2.
Figure 1G:
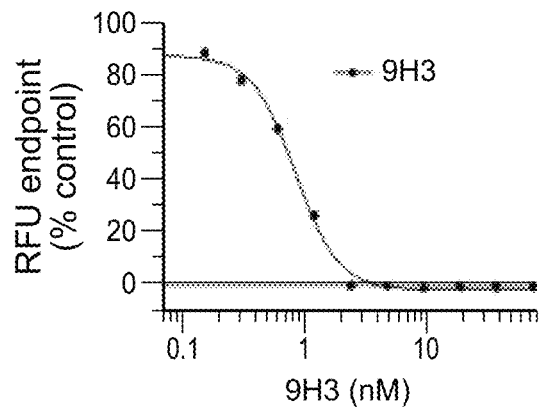
FIG. 1G: 9H3.
Figure 1H:
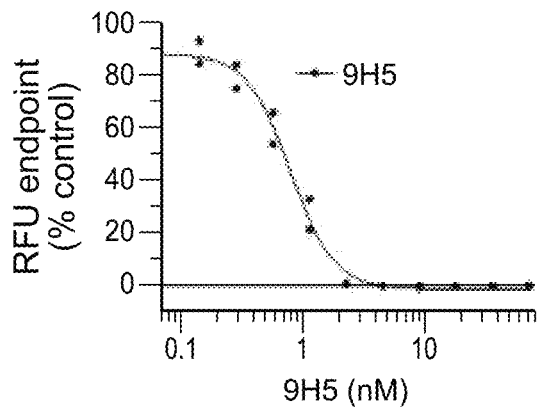
FIG. 1H: 9H5.
Figure 1I:
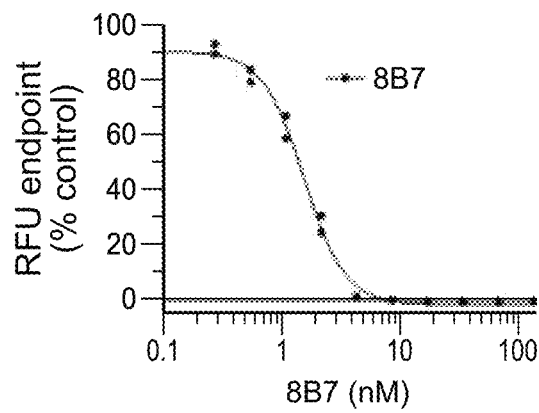
FIG. 1I: 8B7.
Figure 1J:
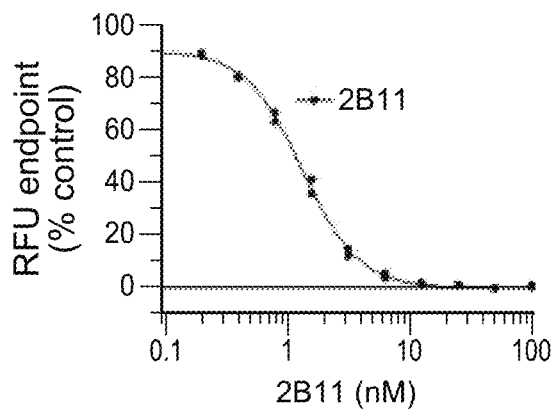
FIG. 1J: 2B11.
Figure 1K:
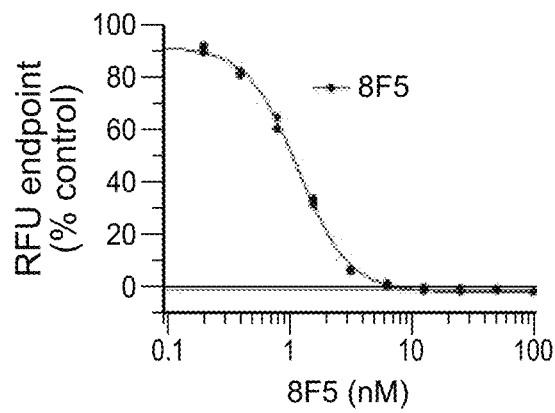
FIG. 1K: 8F5.
Figure 1L:
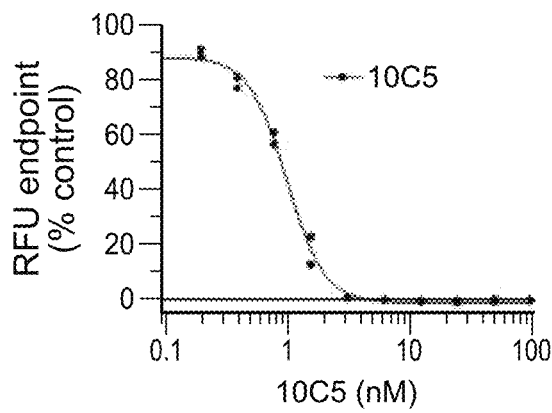
FIG. 1L: 10C5.
Figure 1M:
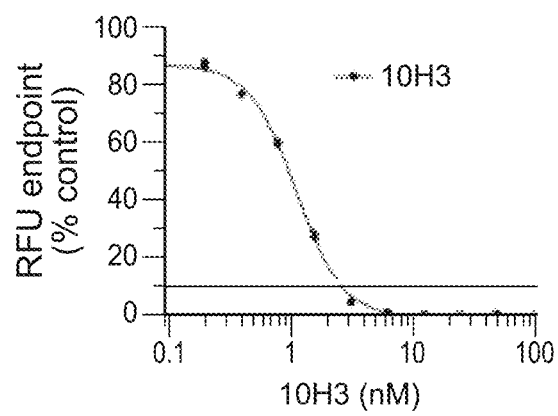
FIG. 1M: 10H3.
Figure 1N:
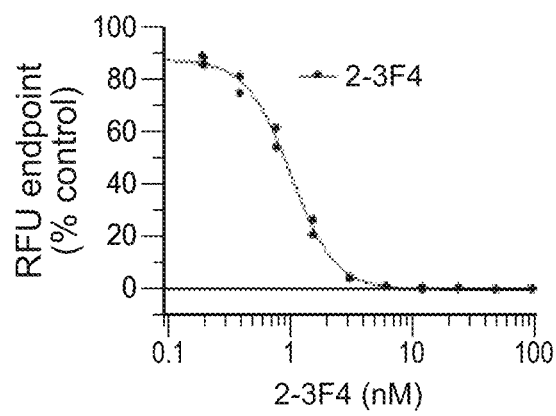

Evaluation of KLK5 Inhibitor $IC_{50}$ Values Using Fluorescent Peptide Substrates The ability of Spink9.SRE.Fc, mAb1108 or 12 selected antibodies to inhibit the proteolysis of the substrate, Boc-VPR-AMC, by human KLK5 was assessed using an enzymatic assay. In this assay the three-mer fluorogenic peptide substrate contains a highly fluorescent 7-amino4-methylcoumarin (AMC) group that is quenched by resonance energy transfer to the t-Butyloxycarbonyl (Boc). The cleavage of the peptide substrate by human KLK5 resulted in an increased fluorescent signal and the inhibition or absence of KLK5 resulted in a quenched fluorescent signal. The results were expressed as a percentage of maximum KLK5 activity (% control). The results of a single experiment run in duplicate are shown in FIG. 1. The calculated $IC_{50}$ value for Spink9.SRE.Fc (FIG. 1A) was 1.23 nM and the range of $IC_{50}$ values for the 12 selected antibodies (FIG. 1 C-N) was 0.89 to 1.32 nM. Spink0.SRE.Fc as well as all 12 selected antibodies fully inhibited KLK5 activity, although mAb1108 (FIG. 1B) only demonstrated ~20% inhibition of KLK5 activity. The $IC_{50}$ values from the curve fittings are presented in FIG. 11 (Column 1).

Evaluation of KLK5 Inhibitor $IC_{50}$ Values Using Coupled Macromolecular Substrate Activity As demonstrated in FIG. 1, Spink9.SRE.Fc as well as the identified 12 anti-KLK5 antibodies are potent inhibitors of KLK5 activity as monitored using a peptide based substrate. To further evaluate the inhibitory profiles of these inhibitors, two assays were developed utilizing macromolecular substrates, pro-KLK7 (FIG. 2) and pro-KLK1 (FIG. 3), in combination with KLK specific fluorescent peptide substrates.

In FIG. 2, the ability of Spink9.SRE.Fc, mAb1108 or 12 selected anti-KLK5 antibodies to inhibit KLK5 mediated activation of pro-KLK7 was assessed using a coupled enzymatic assay. In this assay, human KLK5 is incubated with human pro-KLK7 resulting in cleavage, release of the KLK7 pro-domain and activation of KLK7. Activated human KLK7 can proteolyze a KLK7 specific substrate, Suc-LLVY-AMC, resulting in an increased fluorescent signal. The cleavage of pro-KLK7 by human KLK5 results in active KLK7 and an increased fluorescent signal whereas the inhibition or absence of KLK5 resulted in a quenched fluorescent signal. The results were expressed as a percentage of maximum human KLK5 activity (% control). The results of a single experiment run in duplicate are shown in FIG. 2.

Figure 2A:
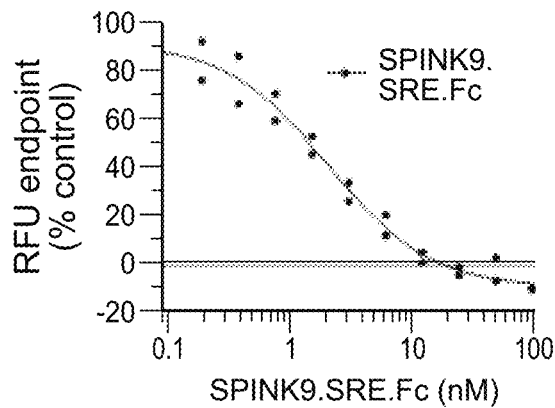
FIG. 2A-2N show the evaluation of KLK5 inhibitors in pro-KLK7 coupled assay. 5 nM recombinant human KLK5 and 0.19-100 nM anti-KLK5 inhibitors were pre-incubated for 30 minutes prior to addition of 125 nM pro-KLK7 and 100 µM suc-LLVY-AMC. After 24 hours, fluorescent readings were made every 102 s for 30-60 min and the RFU endpoint value was calculated by averaging the last 5 readings. The results for the KLK5 inhibitors are depicted as follows.
Figure 2B:
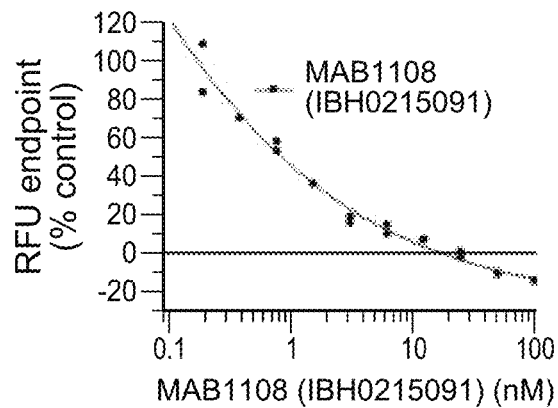
FIG. 2B: mAb1108.
Figure 2C:
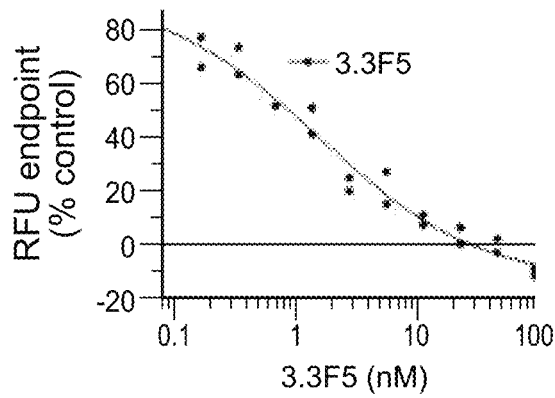
FIG. 2C: 3-3F5.
Figure 2D:
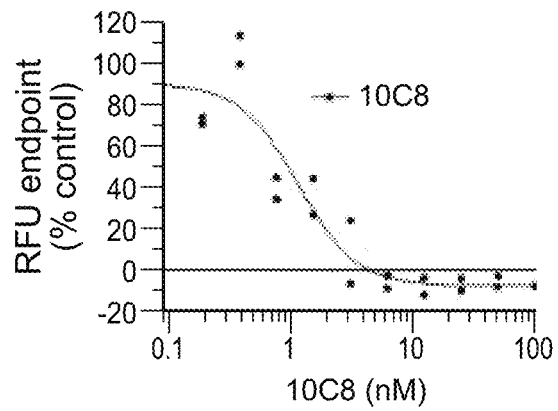
FIG. 2D: 10C8.
Figure 2E:
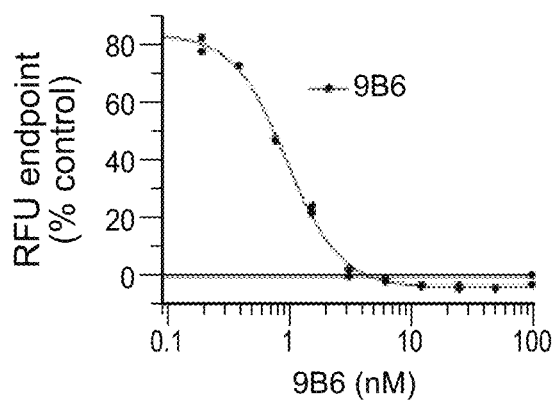
FIG. 2E: 9B6.
Figure 2F:
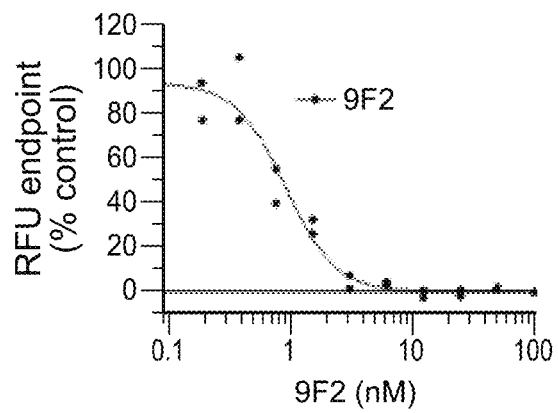
FIG. 2F: 9F2.
Figure 2G:
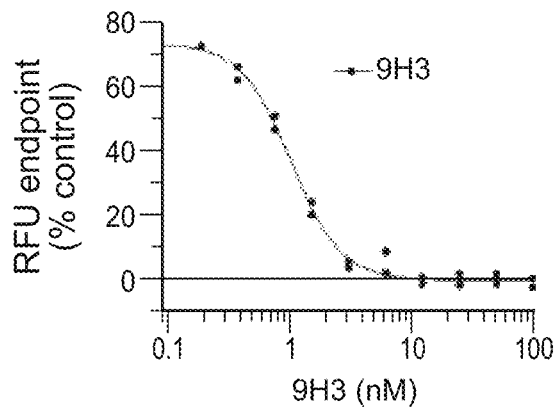
FIG. 2G: 9H3.
Figure 2H:
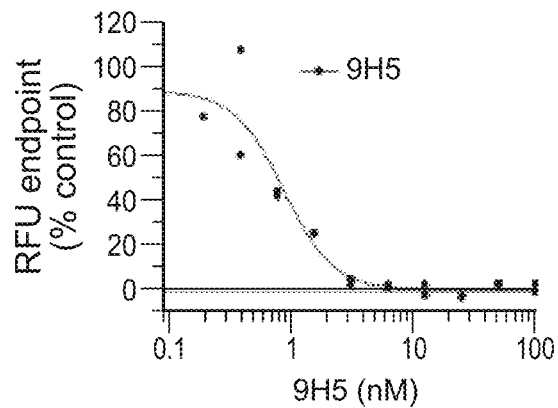
FIG. 2I: 9H5.
FIG. 2J: 2B11.
FIG. 2K: 8F5.
FIG. 2L: 10C5.
FIG. 2M: 10H3.
Figure 2I:
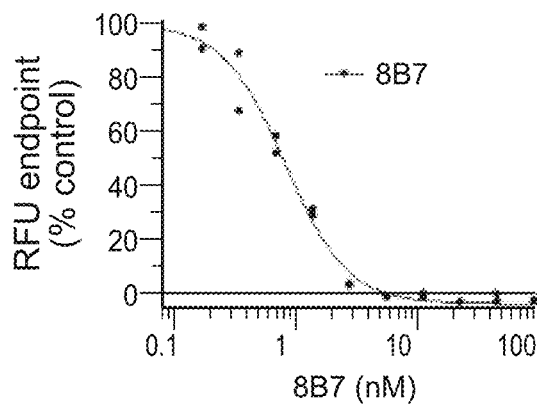
Figure 2J:
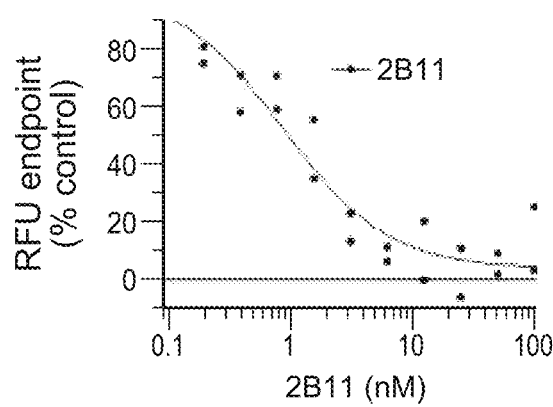
Figure 2K:
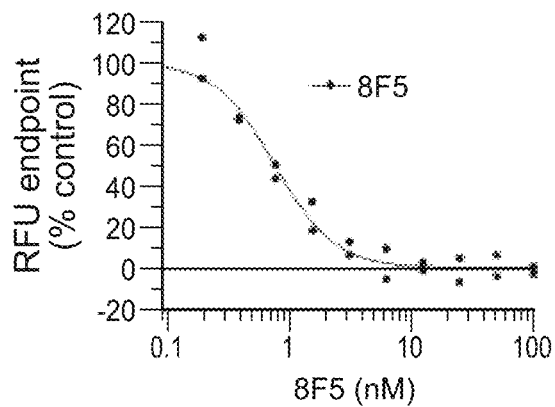
Figure 2L:
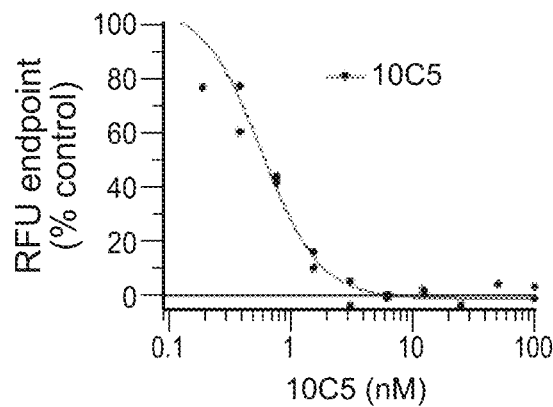

Similar to data using the peptide-based substrate (FIG. 1), Spink9.SRE.Fc (FIG. 2A) was a potent inhibitor of KLK5 activation of pro-KLK7 with an $IC_{50}$ value of 2.07 nM. Additionally, mAb1108 (FIG. 2B) had an $IC_{50}$ value of 1.21 nM whereas the range of $IC_{50}$ values for the 12 selected anti-KLK5 antibodies (FIG. 2 C-N) was 0.58 to 1.53 nM. In the KLK5 pro-KLK7 coupled assay all of inhibitors, Spink9.SRE.Fc as well as antibodies, fully inhibited KLK5 activity. The $IC_{50}$ values from the curve fittings are presented in FIG. 11 (Column 2).

Figure 3A:
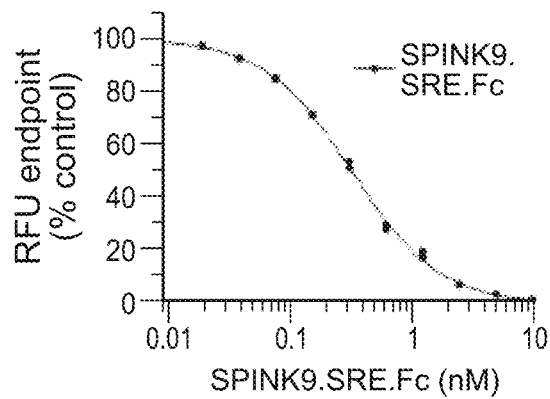
FIG. 3A-3N show the evaluation of KLK5 inhibitors in pro-KLK1 coupled assay. 0.5 nM recombinant human KLK5 and 0.019-10 nM KLK5 inhibitors were pre-incubated for 30 minutes prior to addition of 31.25 nM pro-KLK1 and 50 µM PFR-AMC. Plates were examined every 102 s for 120 minute using a PHERAstar® Plus reader using a 340 nm excitation/460 nm emission module. The results for the KLK5 inhibitors are depicted as follows.
Figure 3B:
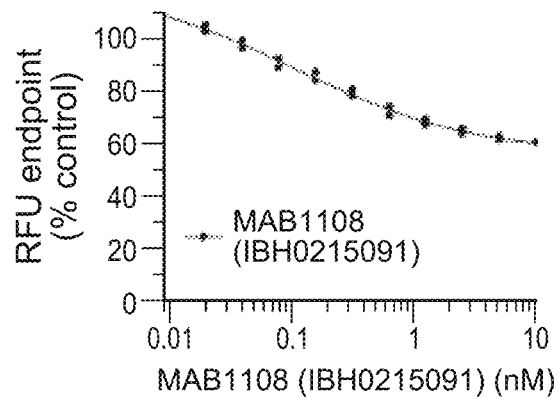
FIG. 3B: mAb1108.
Figure 3C:
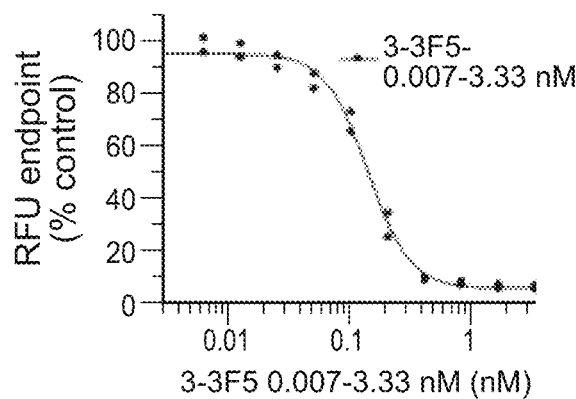
FIG. 3C: 3-3F5.
Figure 3D:
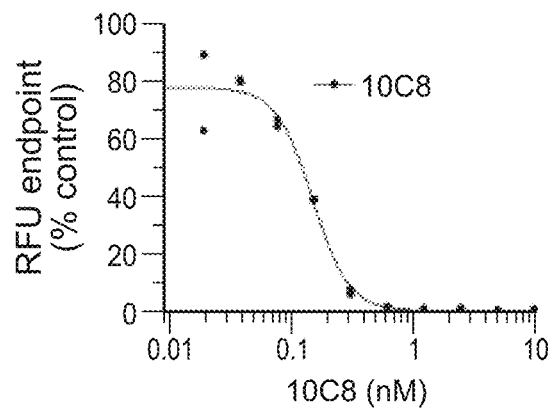
FIG. 3D: 10C8.
Figure 3E:
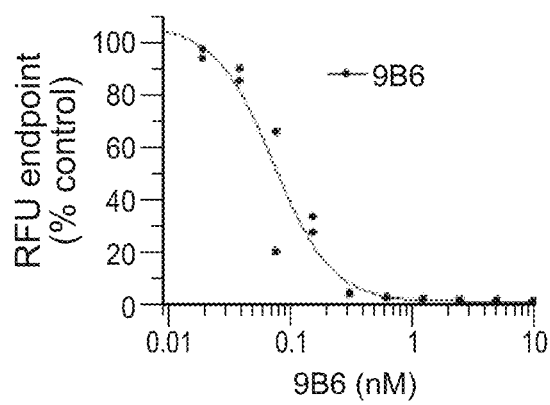
FIG. 3E: 9B6.
Figure 3F:
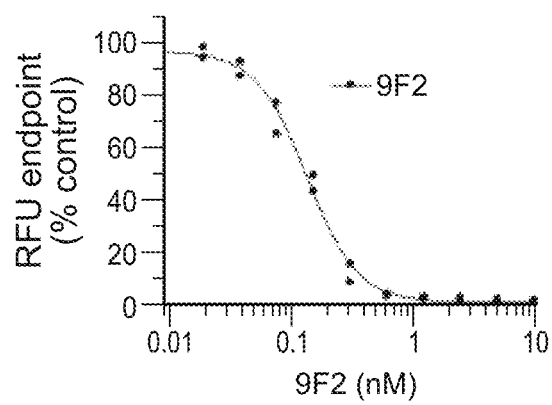
FIG. 3F: 9F2.
Figure 3G:
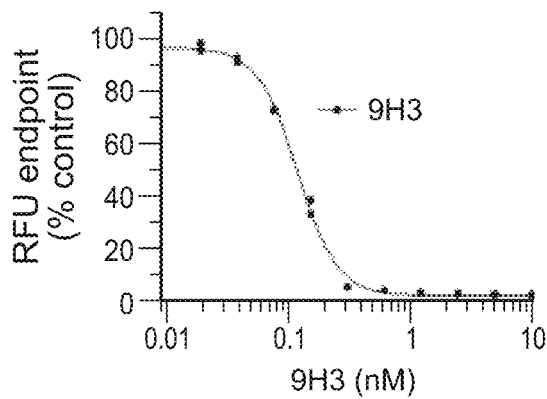
FIG. 3G: 9H3.
Figure 3H:
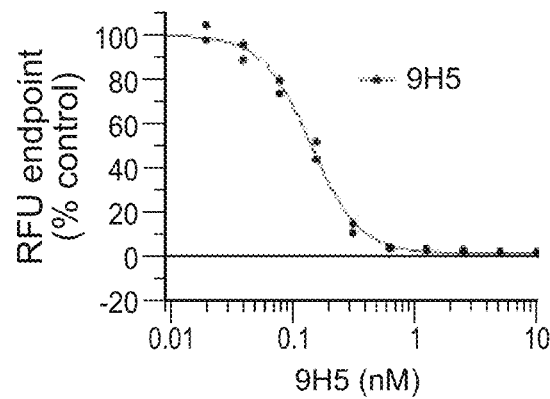
FIG. 3H: 9H5.
Figure 3I:
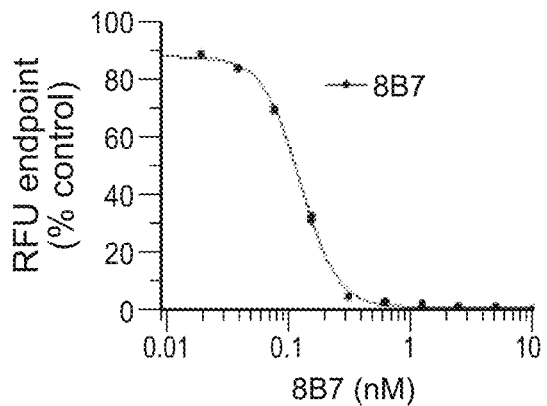
FIG. 3I: 8B7.
Figure 3J:
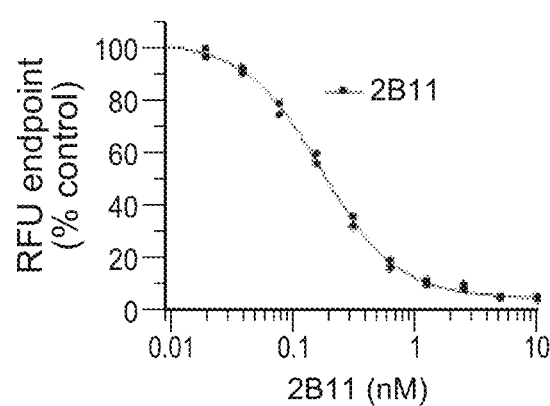
FIG. 3J: 2B11.
Figure 3K:
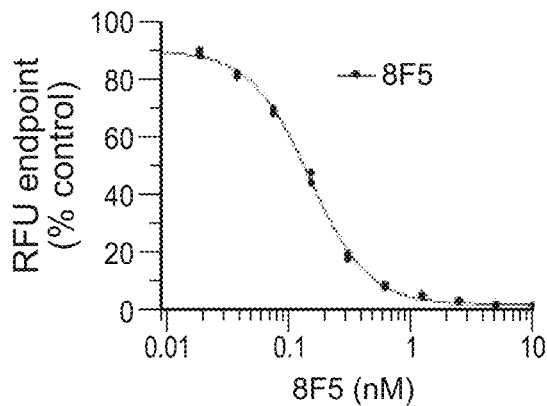
FIG. 3K: 8F5.
Figure 3L:
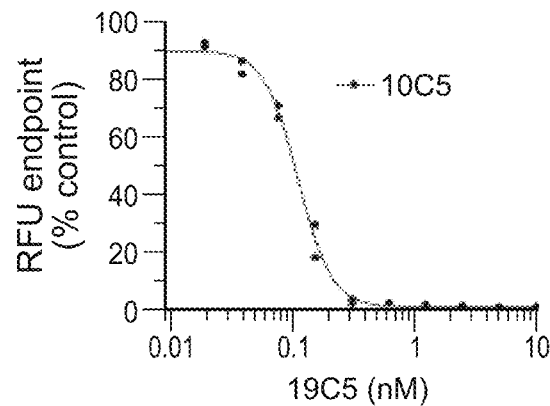
FIG. 3L: 10C5.
Figure 3M:
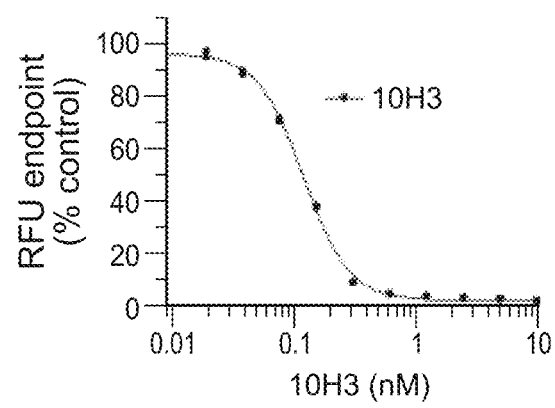
FIG. 3M.
Figure 3N:
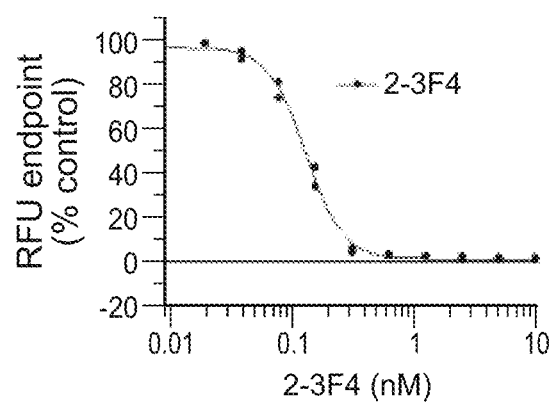
Figure 4A:
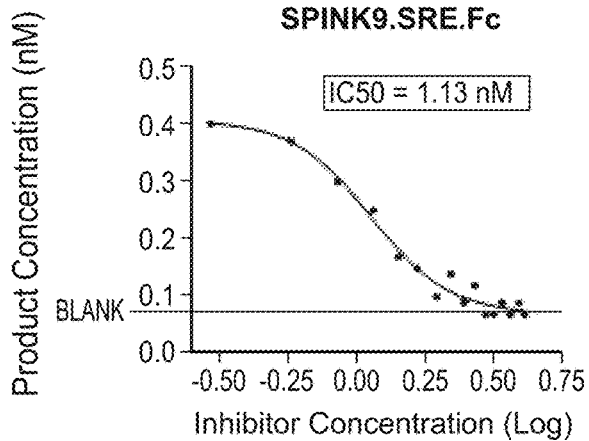
FIG. 4A-4N shows the results of an LC/MS assay measuring the inhibition of proteolysis of pro-KLK7 by recombinant KLK5 by monitoring the KLK5-derived cleavage product peptides. A pre-incubation of SPINK9.SRE.Fc, mAb1108 and the 12 selected antibodies and KLK5 preceded a two-hour incubation of 5 nM KLK5 with 15 nM pro-KLK7. The results for the KLK5 inhibitors are depicted as follows.
Figure 4B:
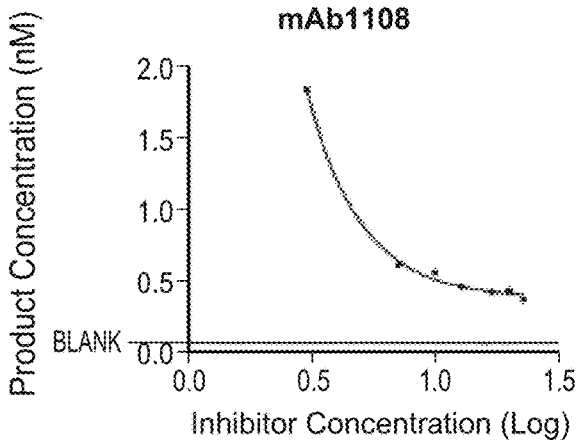
FIG. 4B: mAb1108.
Figure 4C:
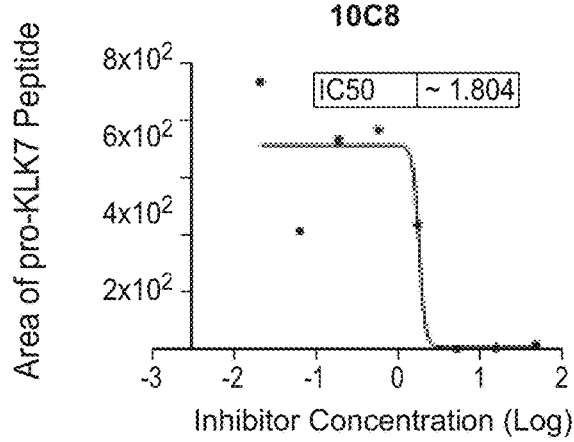
FIG. 4C: 10C8.
Figure 4D:
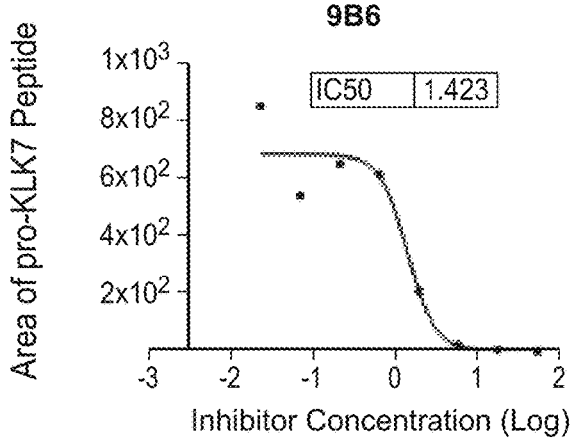
FIG. 4D: 9B6.
Figure 4E:
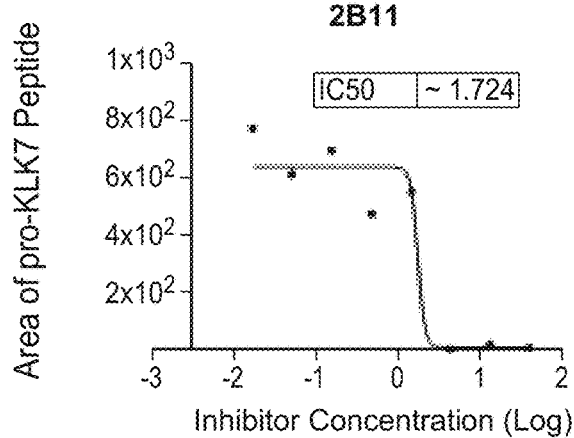
FIG. 4E: 2B11.
Figure 4F:
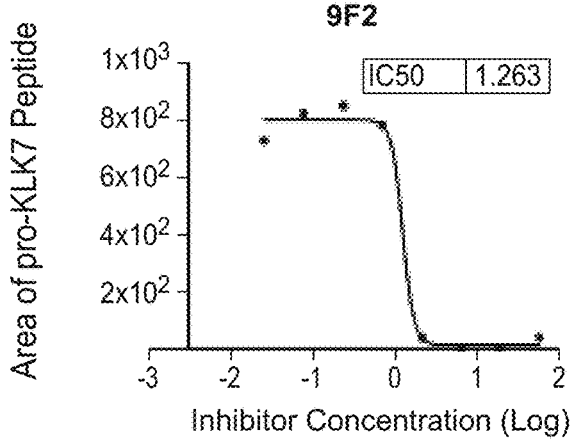
FIG. 4F: 9F2.
Figure 4G:
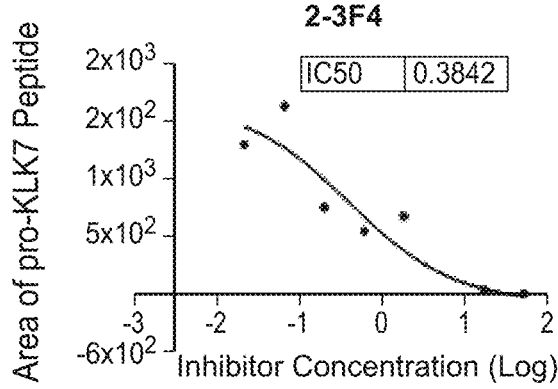
FIG. 4G: 2-3F4.
Figure 4H:
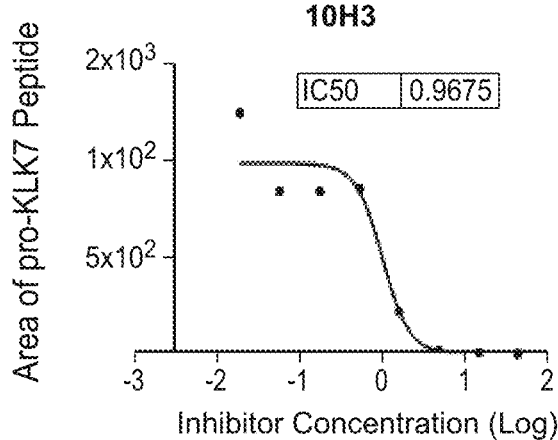
FIG. 4H: 10H3.
Figure 4I:
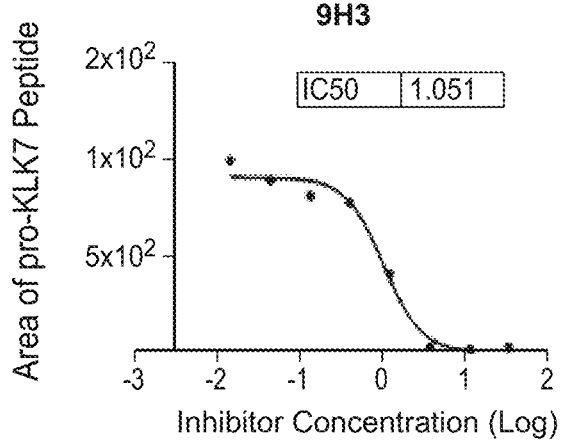
FIG. 4I: 9H3.
Figure 4J:
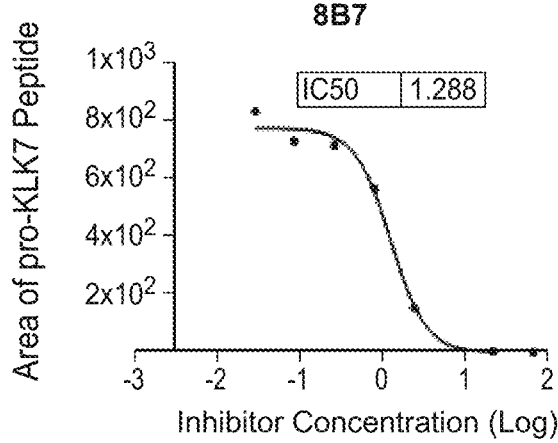
FIG. 4J: 8B7.
Figure 4K:
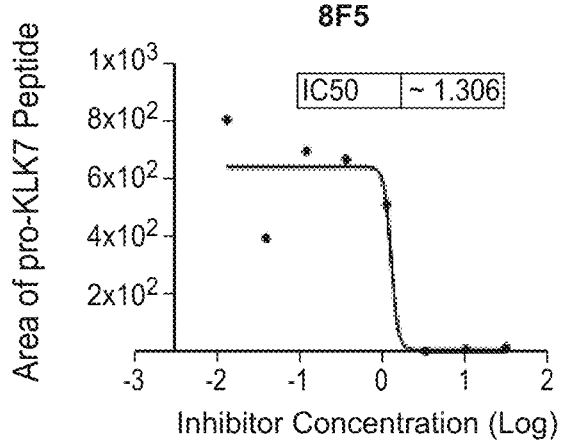
FIG. 4K: 8F5.
Figure 4L:
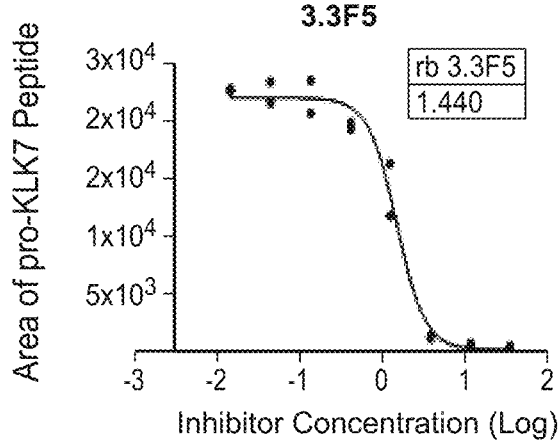
FIG. 4L: 3-3F5.
Figure 4M:
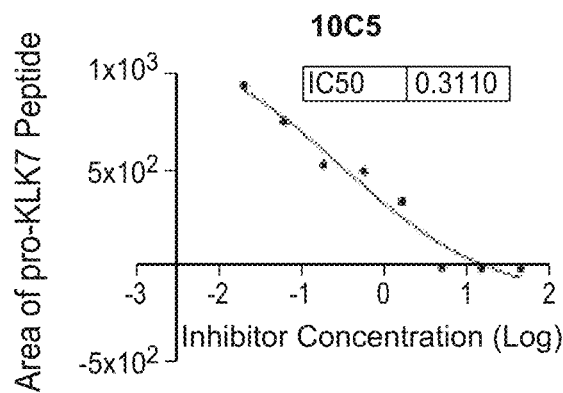
FIG. 4M: 10C5.
Figure 4N:
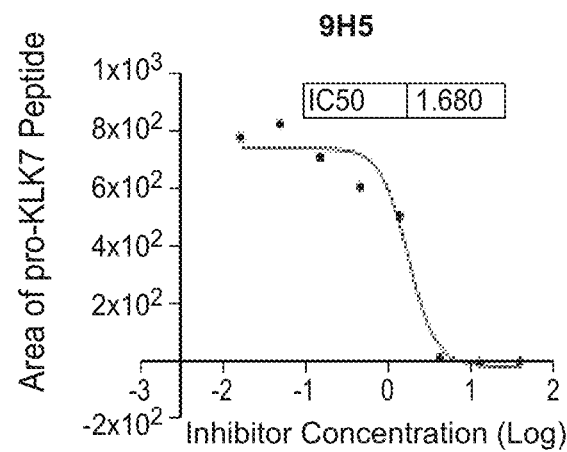
Figure 5A:
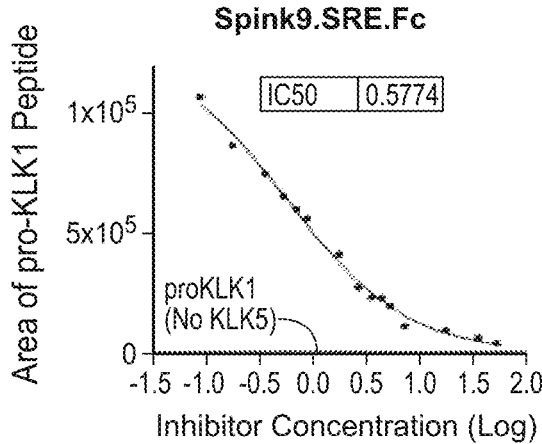
FIG. 5A-5N shows the results of an LC/MS assay measuring the inhibition of proteolysis of pro-KLK1 by recombinant KLK5 by monitoring the KLK5-derived cleavage product peptides. A pre-incubation of SPINK9.SRE.Fc, mAb1108 and 12 selected antibodies and KLK5 preceded a 20 minute incubation of 0.5 nM KLK5 with 300 nM pro-KLK1 (FIG. 5A-N). The results for the KLK5 inhibitors are depicted as follows.
Figure 5B:
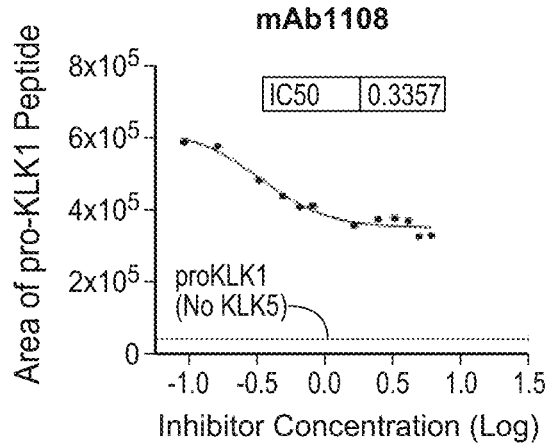
FIG. 5B: mAb1108.
Figure 5C:
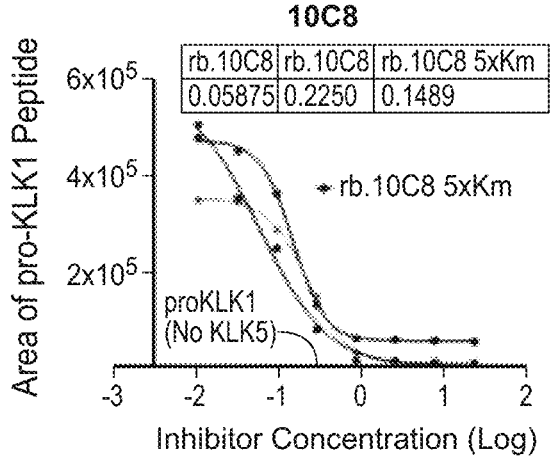
FIG. 5C: 10C8.
Figure 5D:
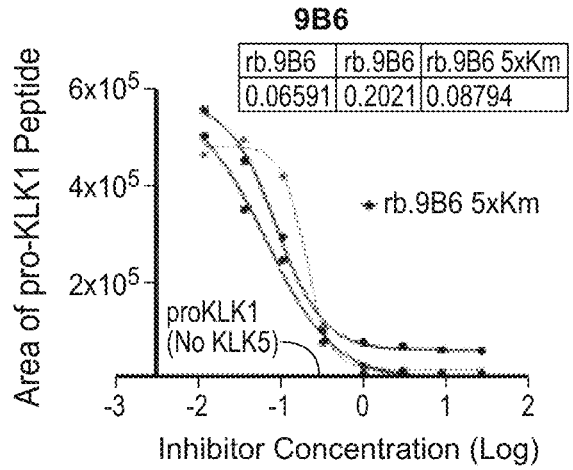
FIG. 5D: 9B6.
Figure 5E:
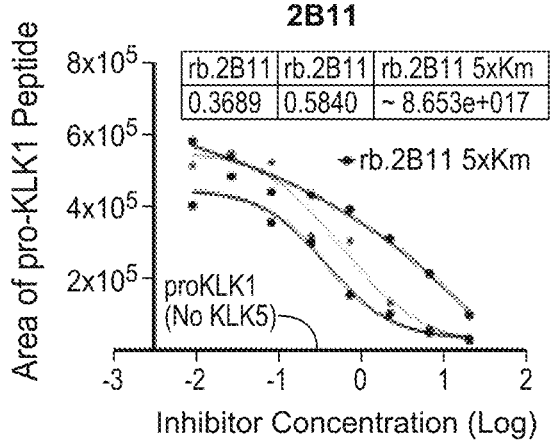
FIG. 5E: 2B11.
Figure 5F:
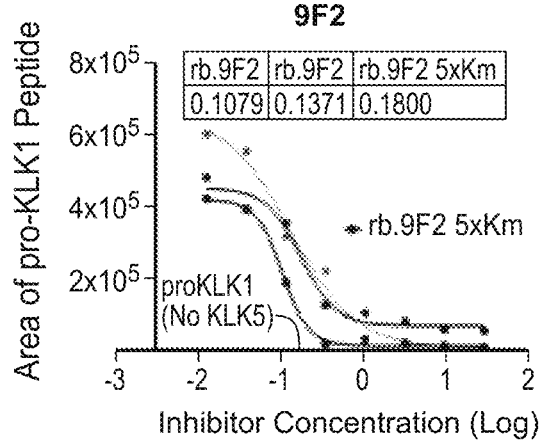
FIG. 5F: 9F2.
Figure 5G:
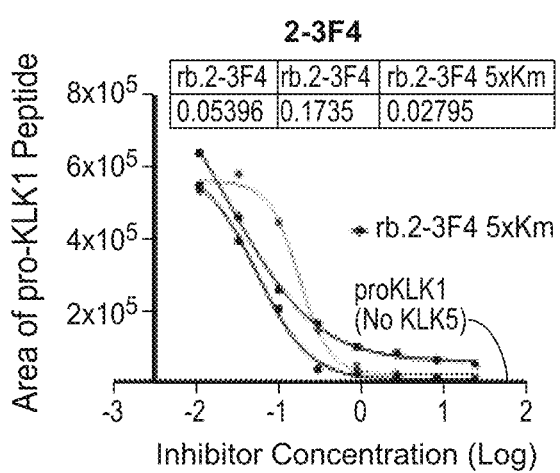
FIG. 5G: 2-3F4.
Figure 5H:
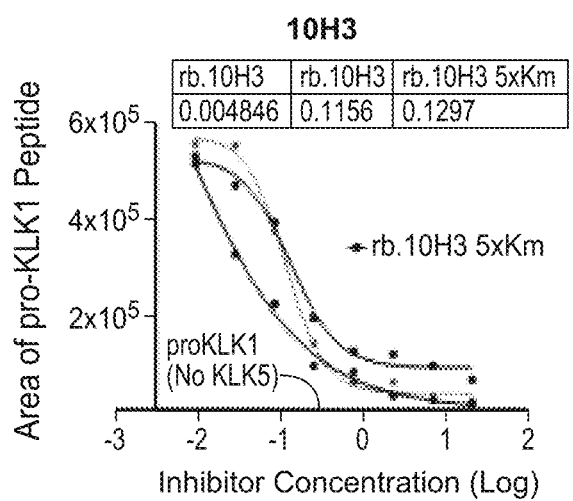
FIG. 5H.
Figure 5I:
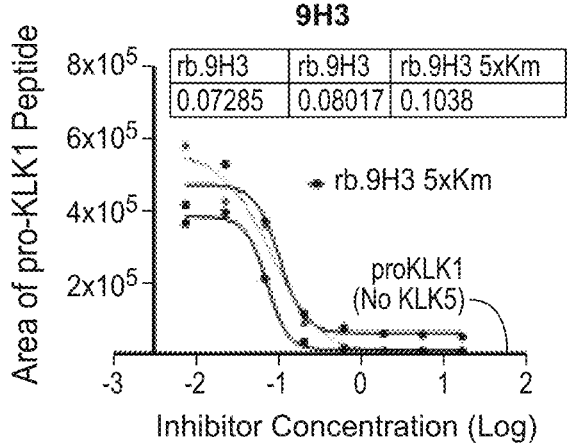
FIG. 5I: 9H3.
Figure 5J:
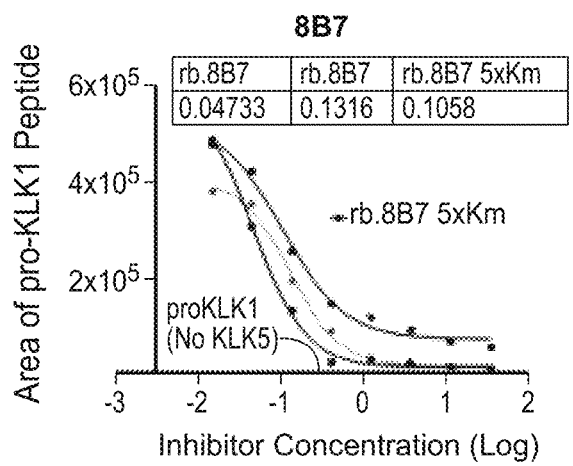
FIG. 5J: 8B7.
Figure 5K:
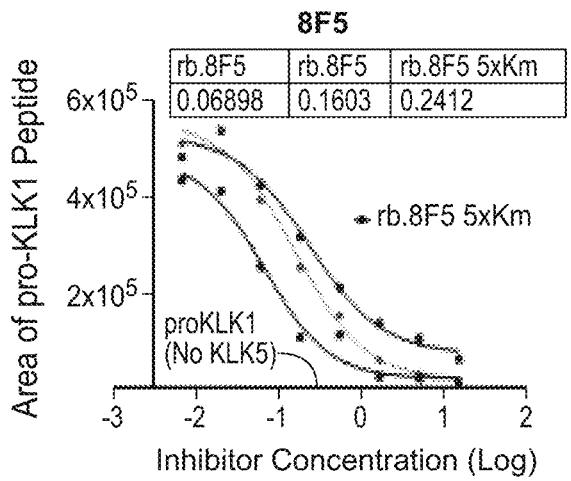
FIG. 5K: 8F5.
Figure 5L:
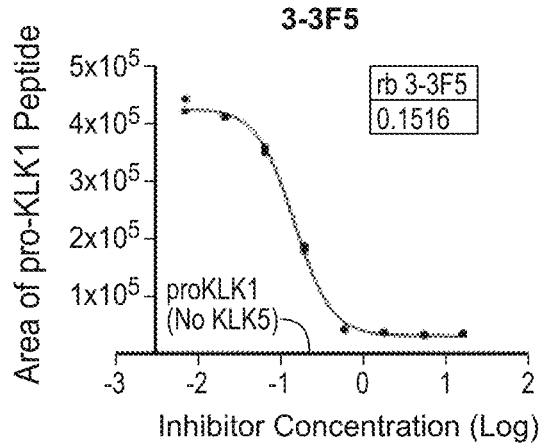
FIG. 5L: 3-3F5.
Figure 5M:
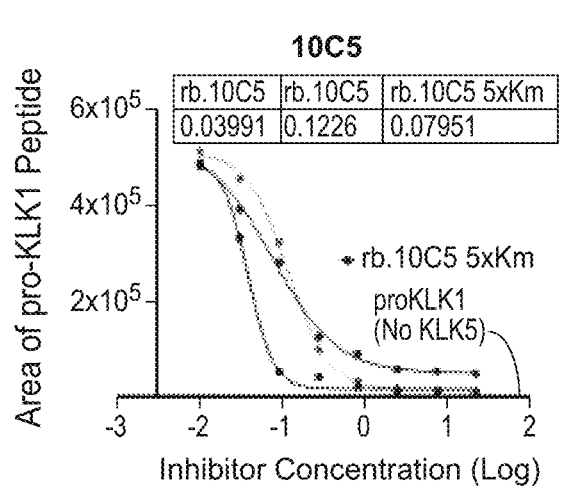
FIG. 5M: 10C5.
Figure 5N:
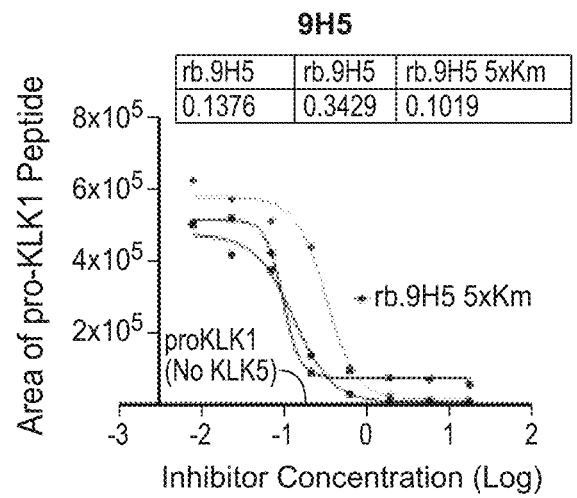
Figure 6A:
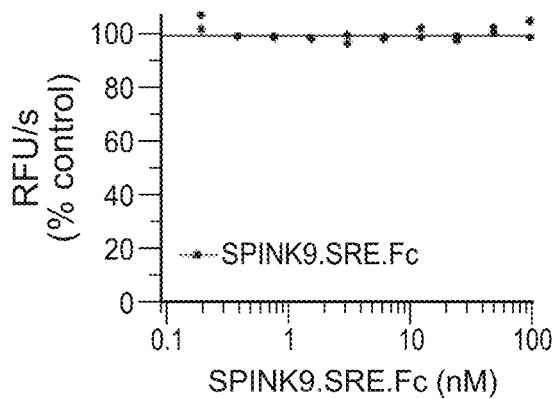
Figure 6B:
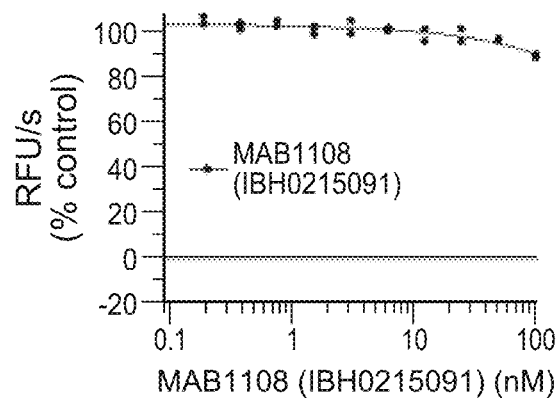
FIG. 6B: mAb1108.
Figure 6C:
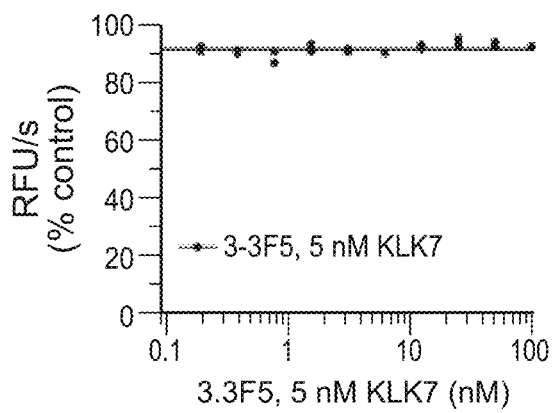
FIG. 6C: 3-3F5.
Figure 6D:
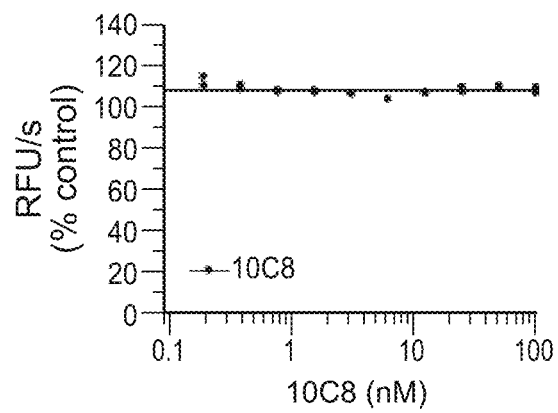
FIG. 6D: 10C8.
Figure 6E:
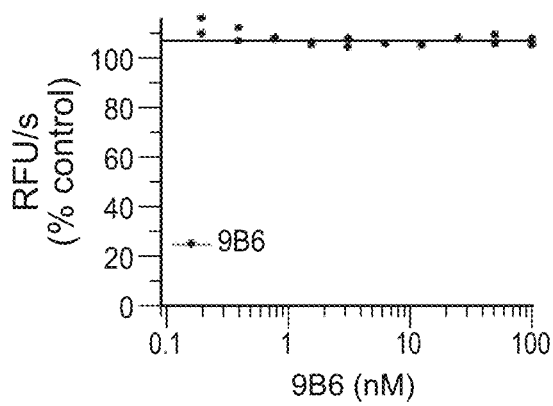
FIG. 6E: 9B6.
Figure 6F:
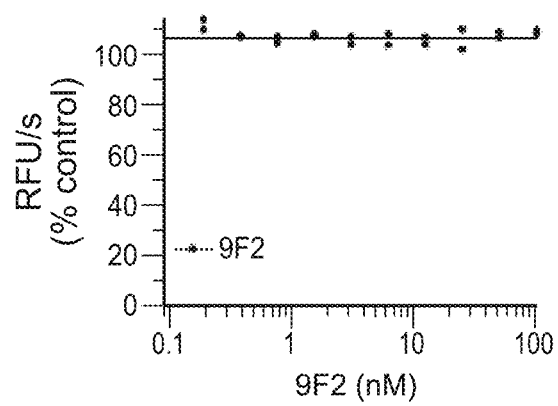
FIG. 6F: 9F2.
Figure 6G:
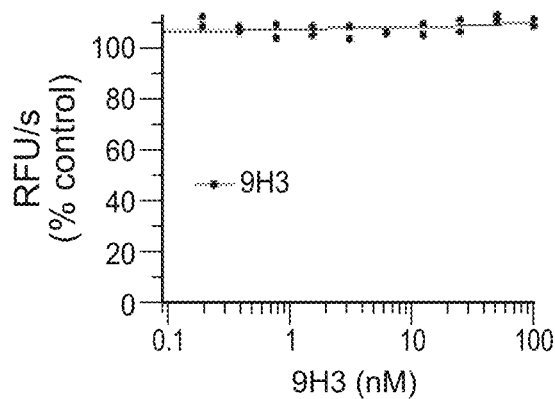
FIG. 6G: 9H3.
Figure 6H:
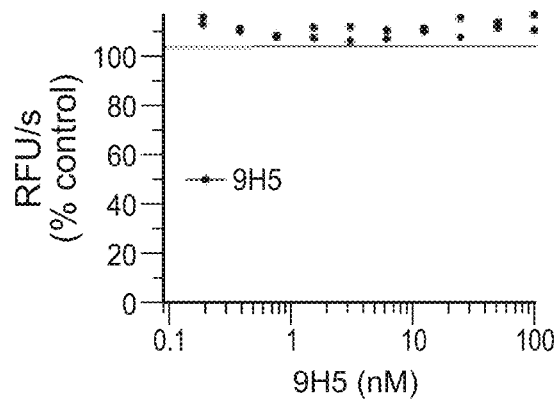
FIG. 6H: 9H5.
Figure 6I:
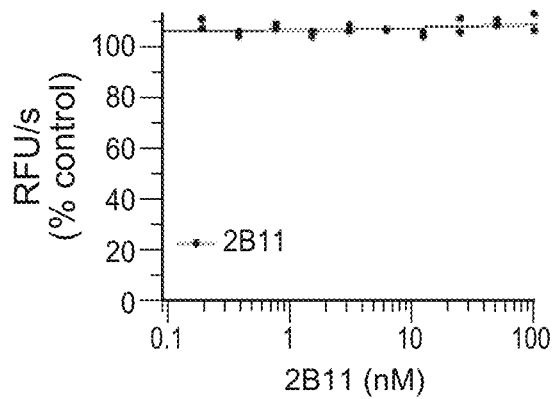
FIG. 6I: 2B11.
Figure 6J:
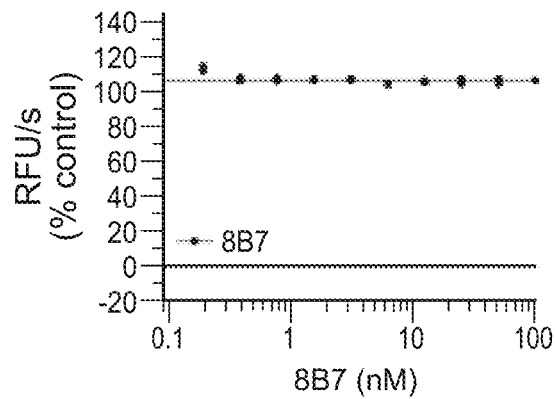
FIG. 6J: 8B7.
Figure 6K:
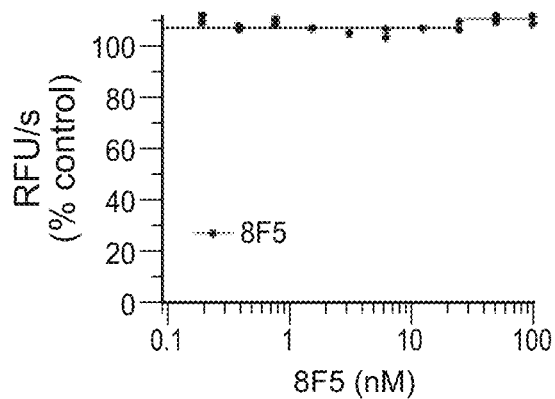
FIG. 6K: 8F5.
Figure 6L:
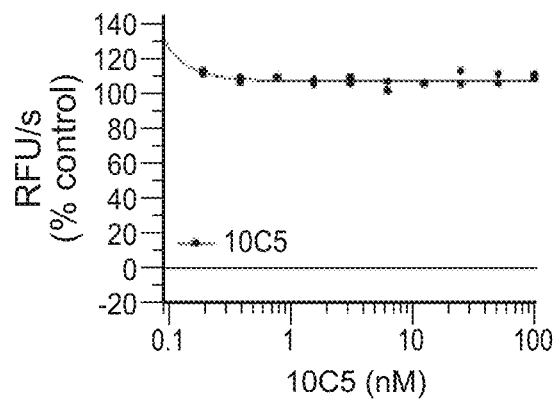
FIG. 6L: 10C5.
Figure 7A:
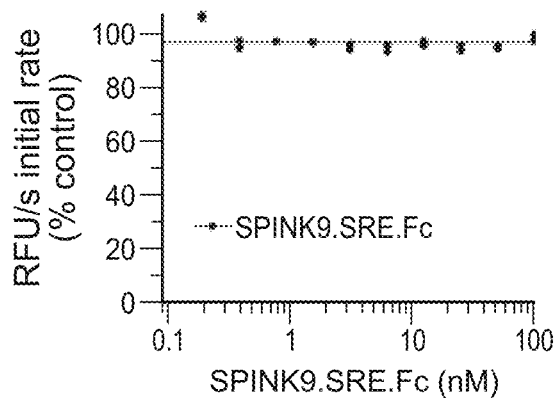
FIG. 7A-7N shows the specificity of KLK5 inhibitors on KLK1 activity. 3 nM recombinant human KLK1 and 0.19-100 nM anti-KLK5 inhibitors were pre-incubated for 30 minutes prior to addition of 100 µM PFR-AMC. Plates were examined every 102 s for 60 minutes using a PHERAstar® Plus reader using a 340 nm excitation/460 nm emission module. $IC_{50}$ values are summarized in Table 7. The results for the KLK5 inhibitors are depicted as follows.
Figure 7B:
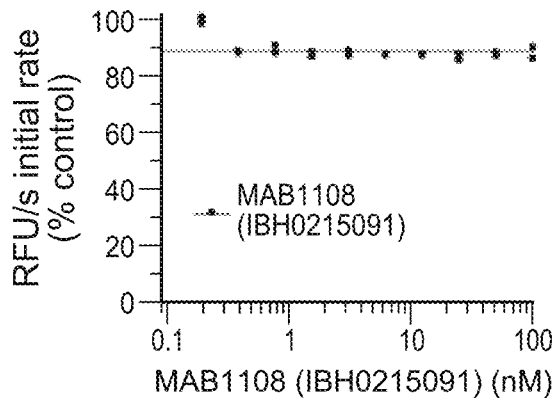
FIG. 7B: mAb1108.
Figure 7C:
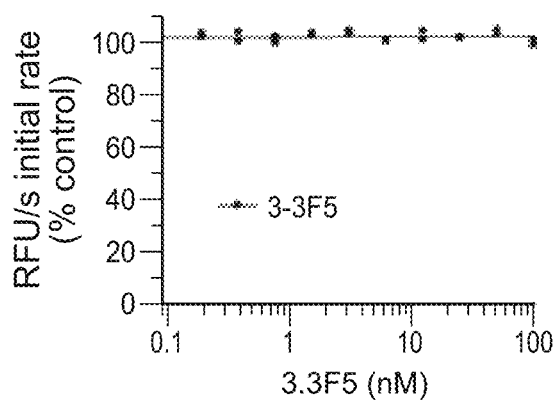
FIG. 7C: 3-3F5.
Figure 7D:
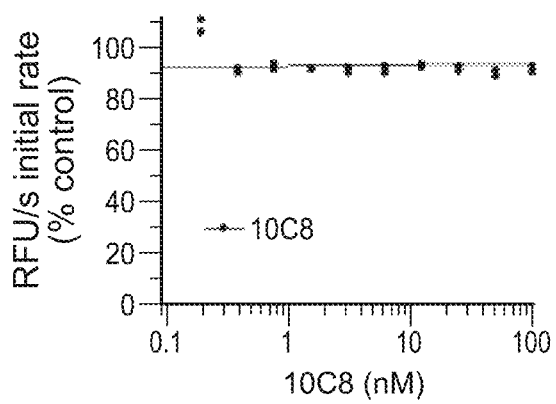
FIG. 7D: 10C8.
Figure 7E:
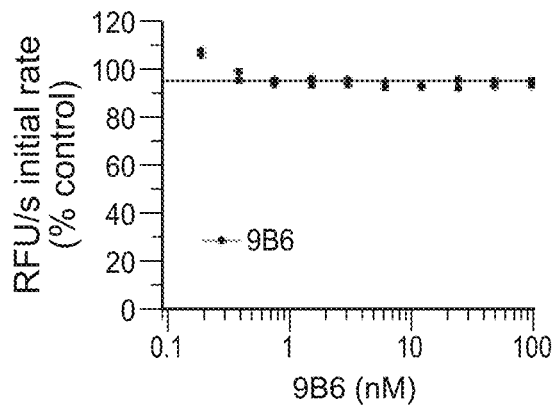
FIG. 7E: 9B6.
Figure 7F:
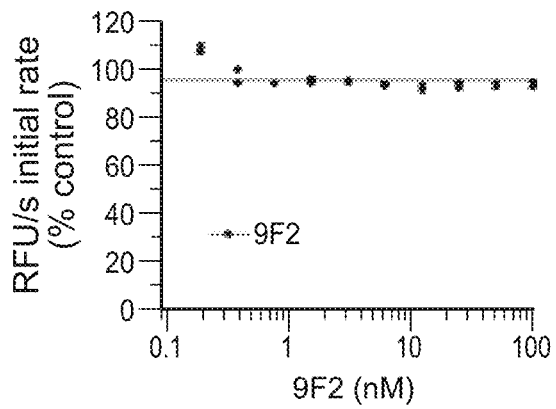
FIG. 7F: 9F2.
Figure 7G:
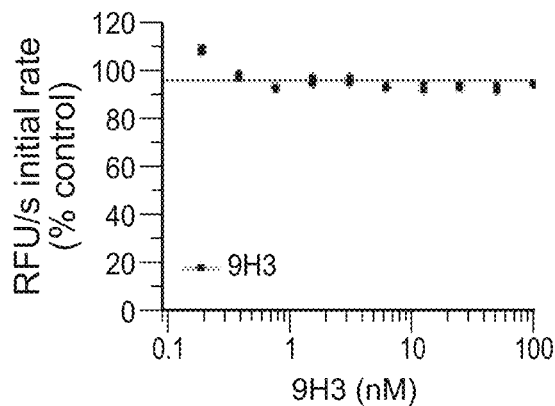
FIG. 7G: 9H3.
Figure 7H:
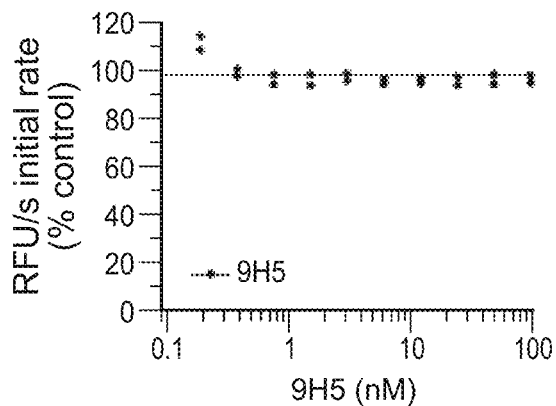
FIG. 7H: 9H5.
Figure 7I:
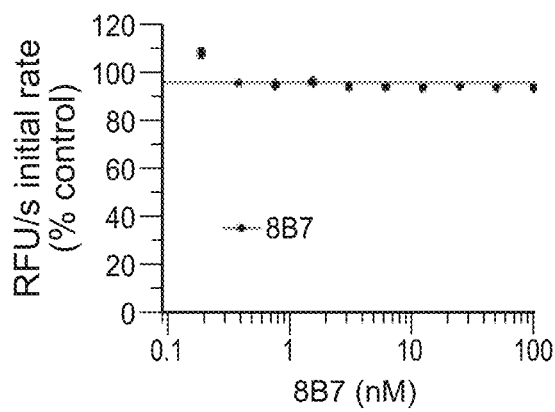
FIG. 7I: 8B7.
Figure 7J:
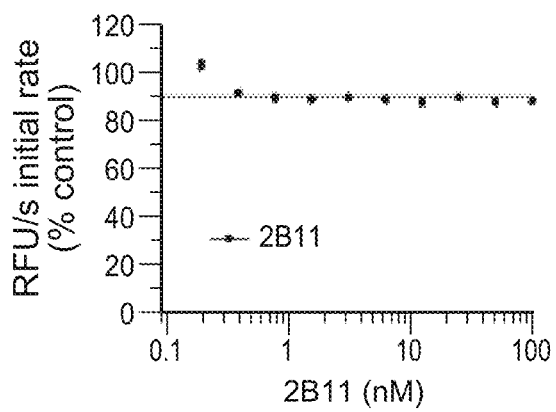
FIG. 7J: 2B11.
Figure 7K:
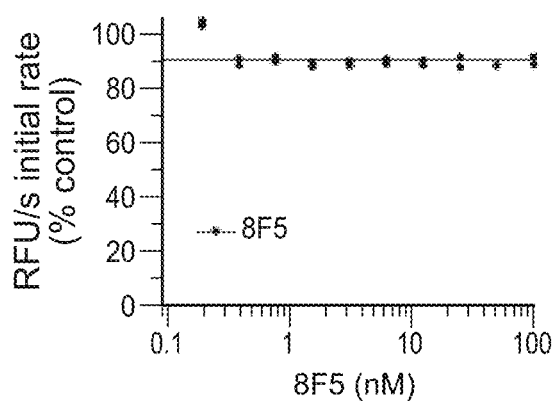
FIG. 7K: 8F5.
Figure 7L:
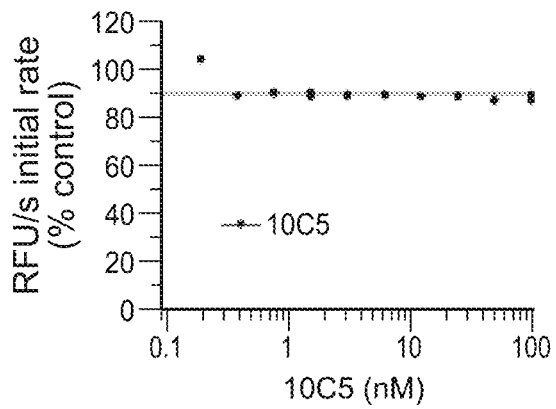
FIG. 7L: 10C5.
Figure 7M:
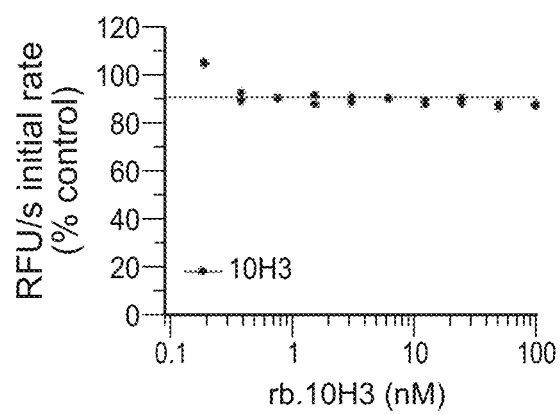
FIG. 7M.
Figure 7N:
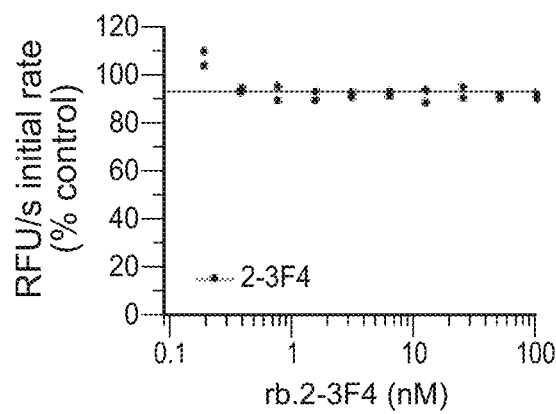
Figure 8A:
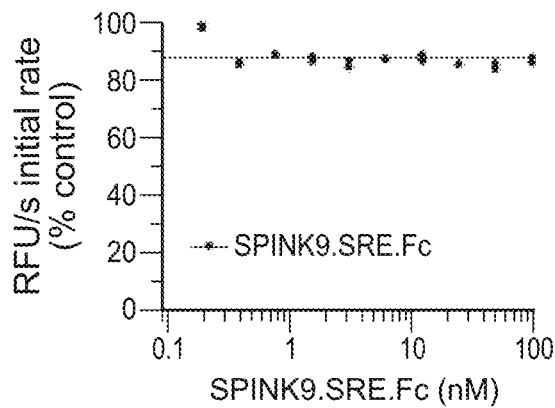
FIG. 8A-8N shows the specificity of KLK5 inhibitors on KLK4 activity. 2 nM recombinant human KLK4 and 0.19-100 nM anti-KLK5 inhibitors were pre-incubated for 30 minutes prior to addition of 50 µM Boc-VPR-AMC. Plates were examined every 102 s for 60 minutes using a PHERAstar® Plus reader using a 340 nm excitation/460 nm emission module. $IC_{50}$ values are summarized in Table 8. The results for the KLK5 inhibitors are depicted as follows.
Figure 8B:
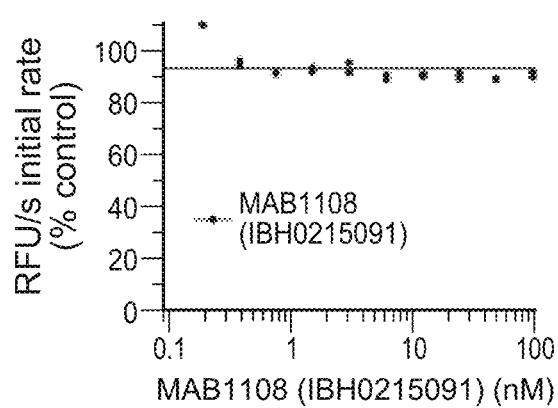
FIG. 8B: mAb1108.
Figure 8C:
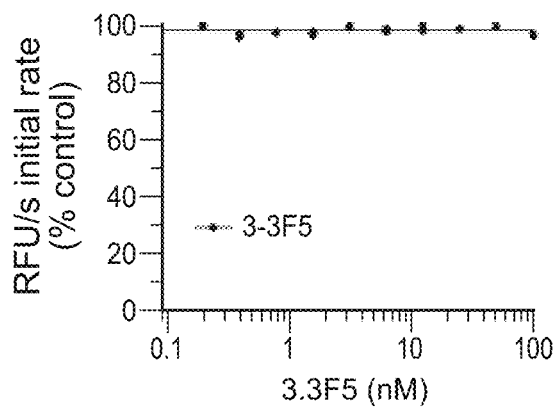
FIG. 8C: 3-3F5.
Figure 8D:
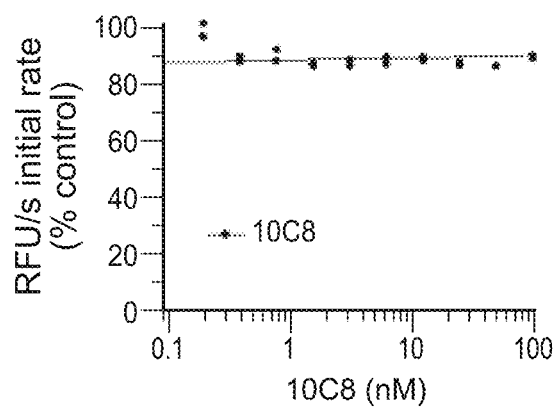
FIG. 8D: 10C8.
Figure 8E:
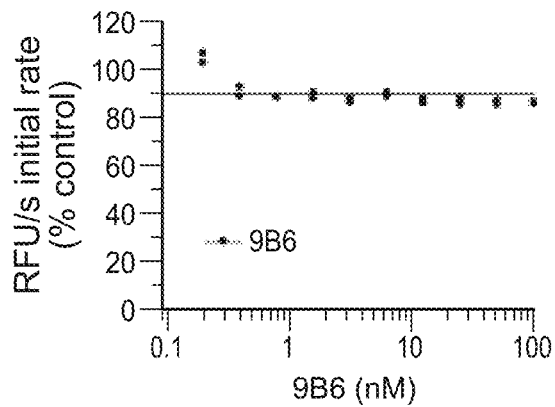
FIG. 8E: 9B6.
Figure 8F:
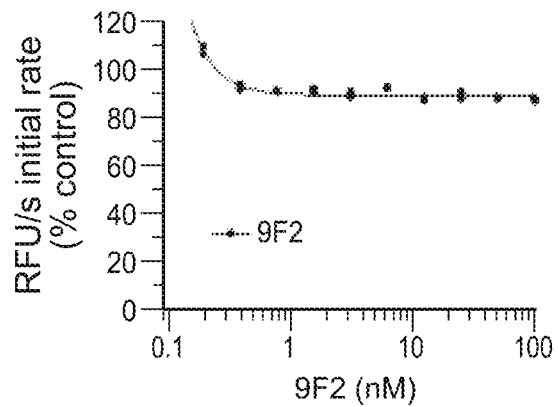
FIG. 8F: 9F2.
Figure 8G:
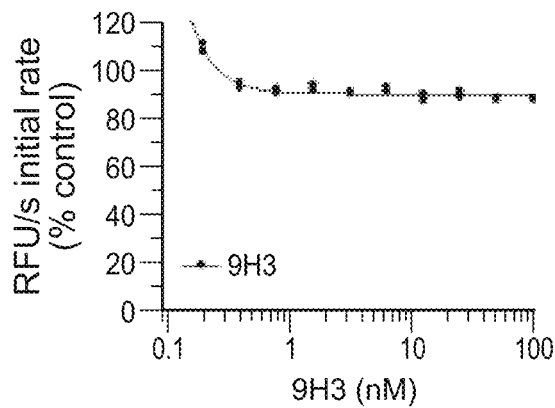
FIG. 8G: 9H3.
Figure 8H:
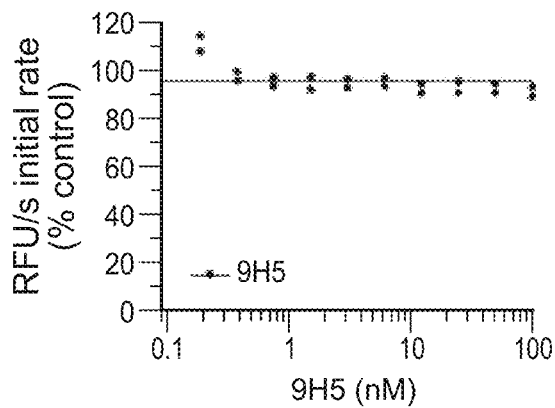
FIG. 8H: 9H5.
Figure 8I:
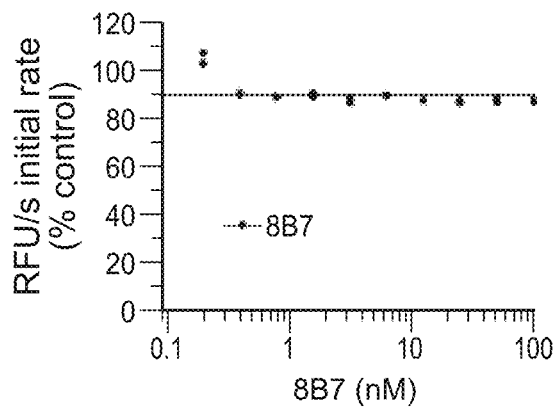
FIG. 8I: 8B7.
Figure 8J:
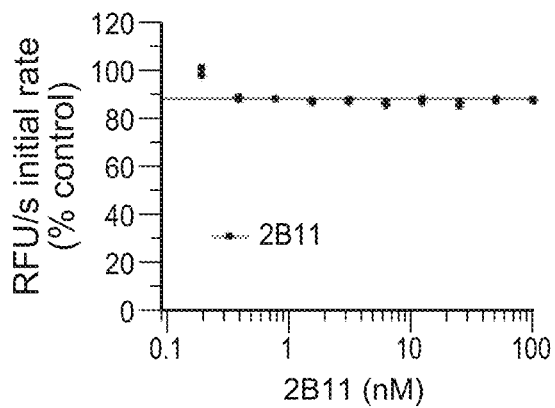
FIG. 8J: 2B11.
Figure 8K:
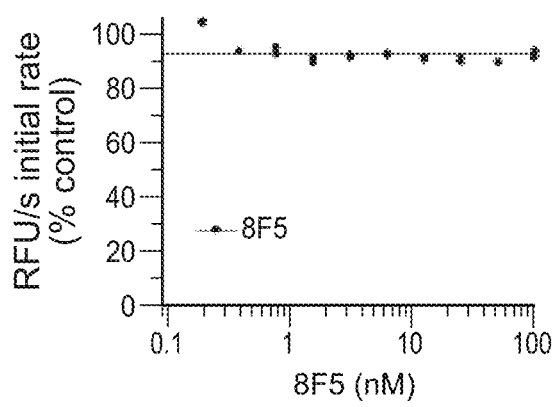
FIG. 8K: 8F5.
Figure 8L:
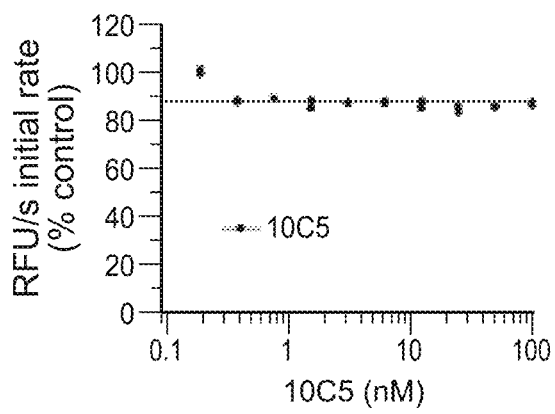
FIG. 8L: 10C5.
Figure 8M:
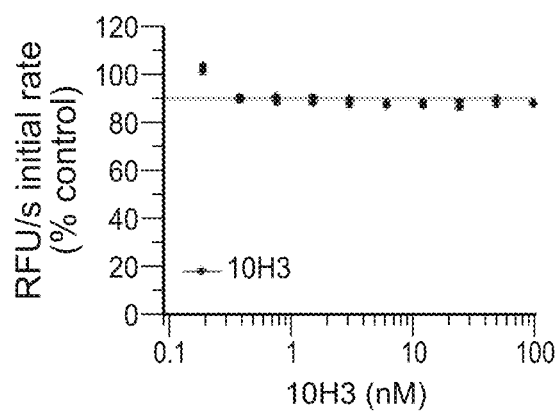
FIG. 8M: 10H3
Figure 8N:
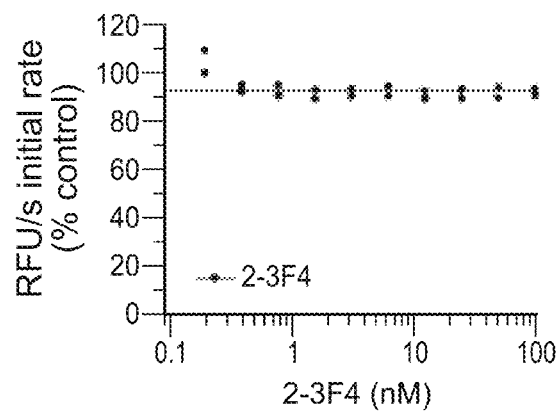
Figure 9A:
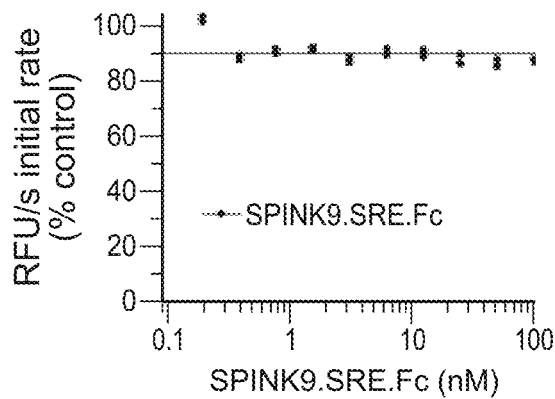
FIG. 9A-9N shows the specificity of KLK5 inhibitors on Trypsin activity. 0.25 nM trypsin isolated from bovine pancreas and 0.19-100 nM anti-KLK5 inhibitors were pre-incubated for 30 minutes prior to addition of 50 µM Boc-VPR-AMC. Plates were examined every 102 s for minutes using a PHERAstar® Plus reader using a 340 nm excitation/460 nm emission module. $IC_{50}$ values for selected antibodies (FIG. 9C-N) are summarized in Table 9. The results for the KLK5 inhibitors are depicted as follows.
Figure 9B:
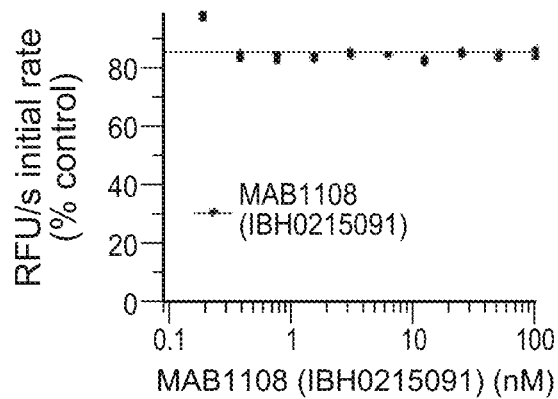
FIG. 9B: mAb1108.
Figure 9C:
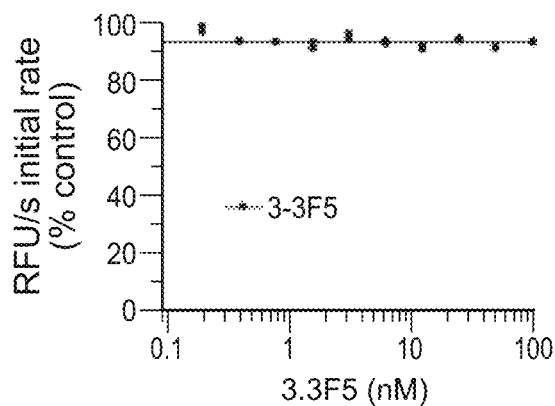
FIG. 9C: 3-3F5.
Figure 9D:
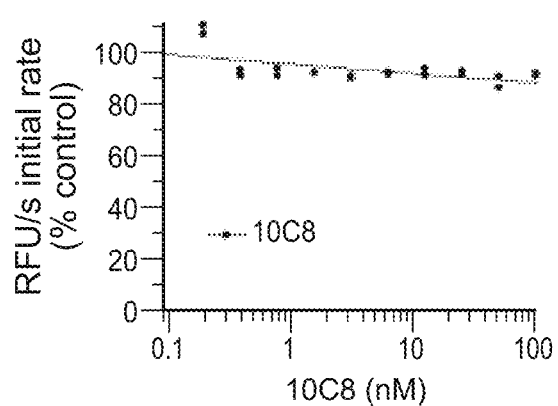
FIG. 9D: 10C8.
Figure 9E:
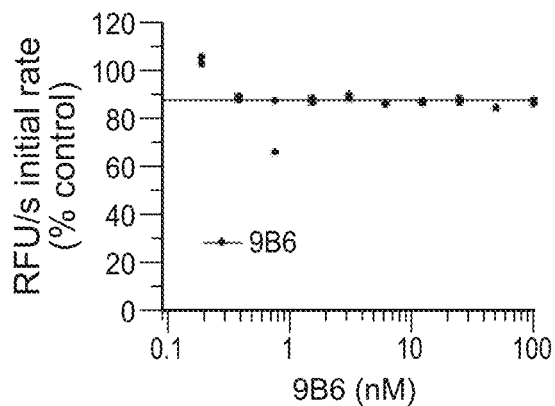
FIG. 9E: 9B6.
Figure 9F:
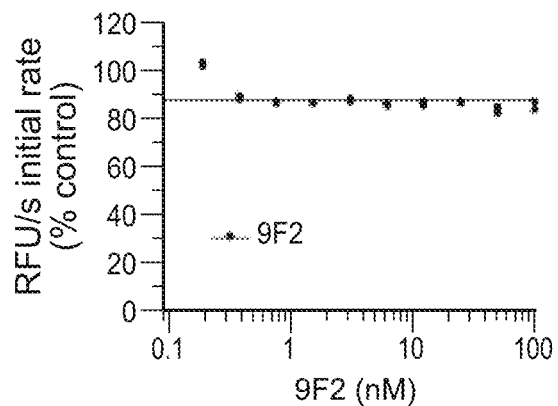
FIG. 9F: 9F2.
Figure 9G:
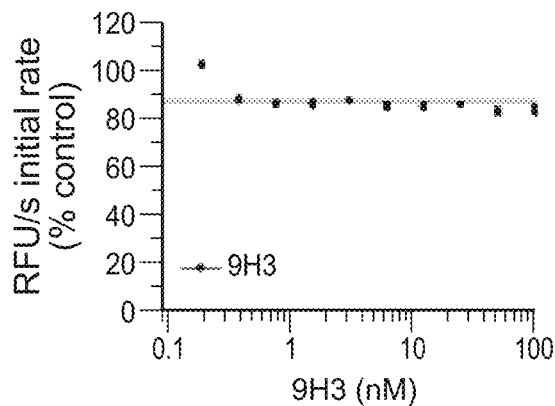
FIG. 9G: 9H3.
Figure 9H:
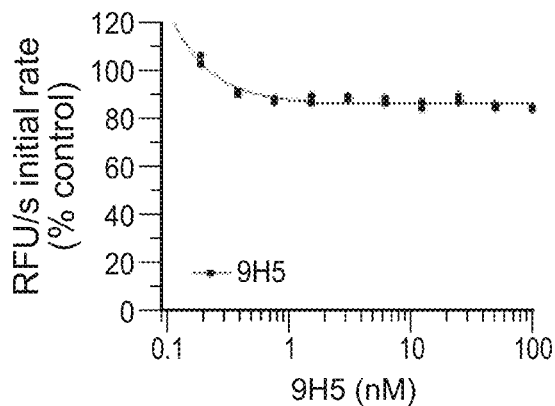
FIG. 9H: 9H5.
Figure 9I:
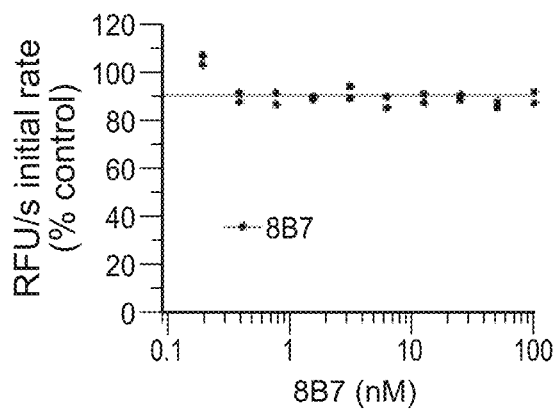
FIG. 9I: 8B7.
Figure 9J:
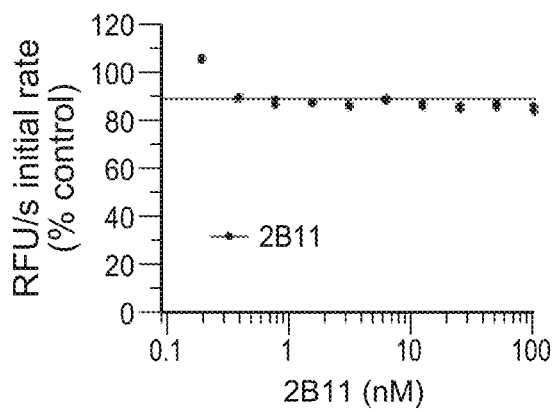
FIG. 9J: 2B11.
Figure 9K:
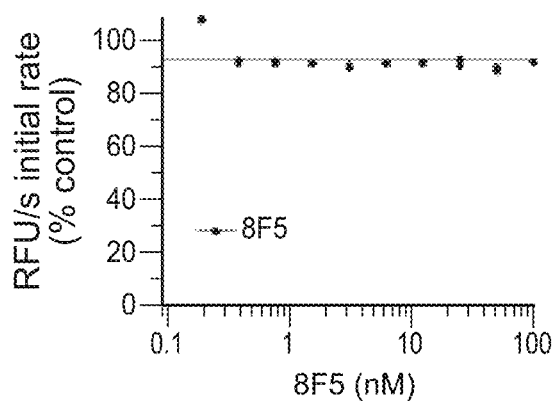
FIG. 9K: 8F5.
Figure 9L:
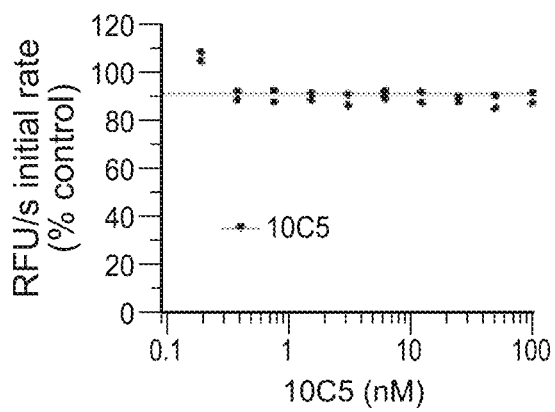
FIG. 9L: 10C5.
Figure 9M:
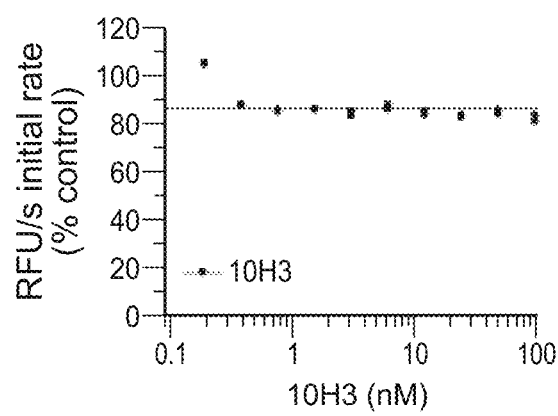
FIG. 9M: 10H3
Figure 9N:
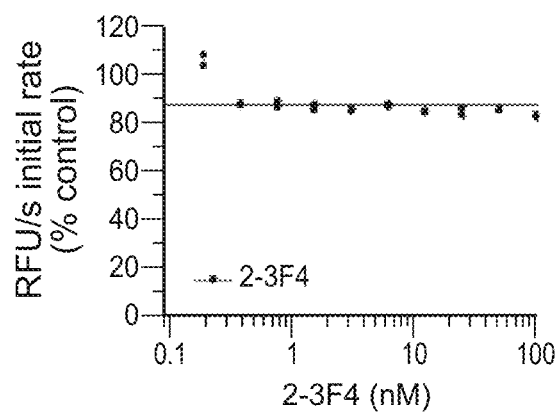
Figure 10A:
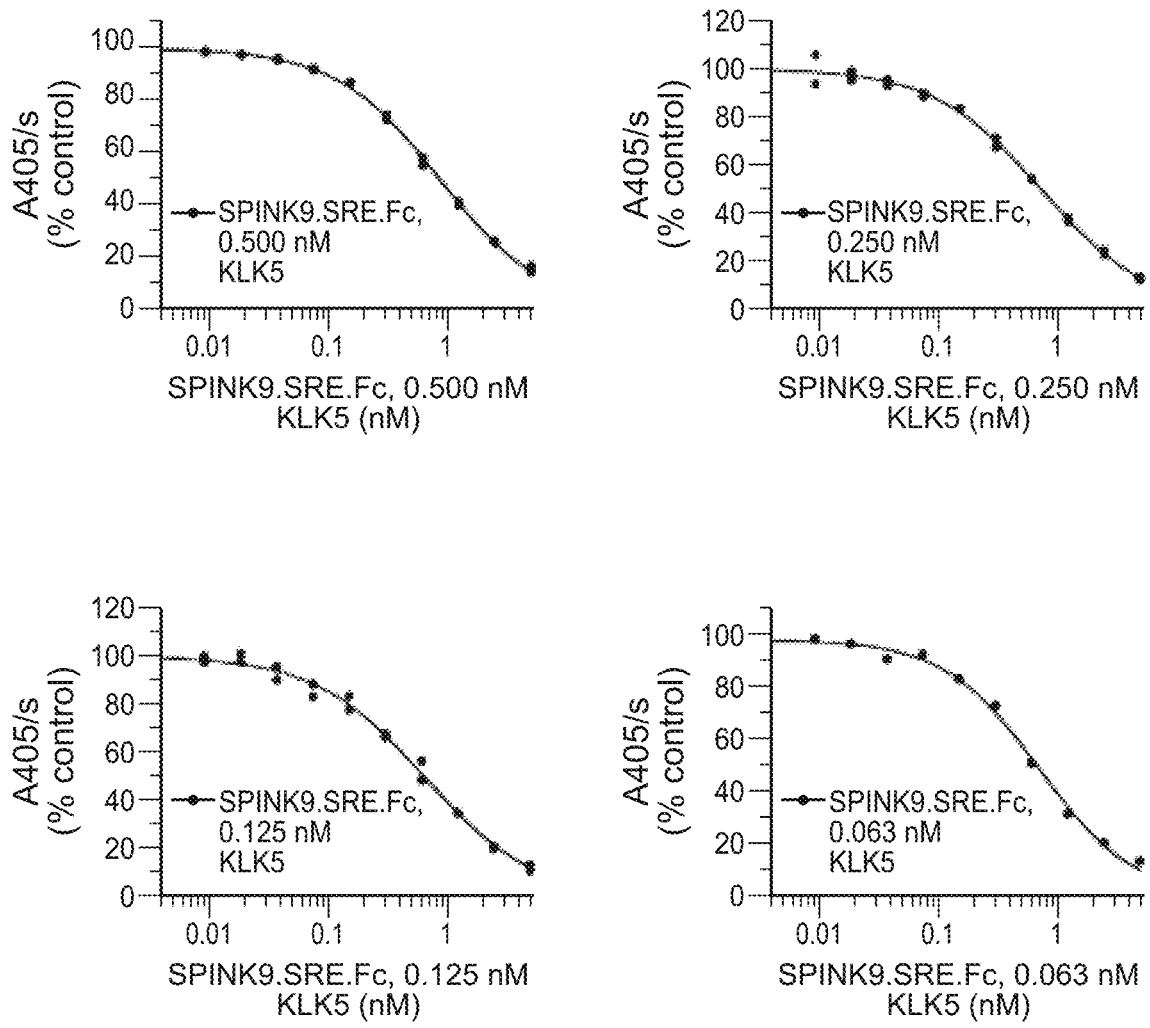
FIG. 10A-10AB shows the analysis of KLK5 inhibitor potency by determination of $Ki_{app}$. KLK5 at various concentrations (0.5, 0.25, 0.125, and 0.0625 nM) and 0.0019-10 nM anti-KLK5 inhibitors were pre-incubated for 30 minutes prior to addition of 300 µM Z-VPR-pNA. Plates were read in a Versamax tunable microplate reader with measurements at 405 nm taken every 102 seconds for 3 hours. The derived $Ki_{app}$ values are summarized in Table 10. The results for the KLK5 inhibitors are depicted as follows (respective left panels show $IC_{50}$ values of KLK5 inhibitors at various KLK5 concentrations (0.5, 0.25, 0.125, and 0.0625 nM); respective right panels show $IC_{50}$ values determined and plotted as a function of KLK5 concentration)
Figure 10B:
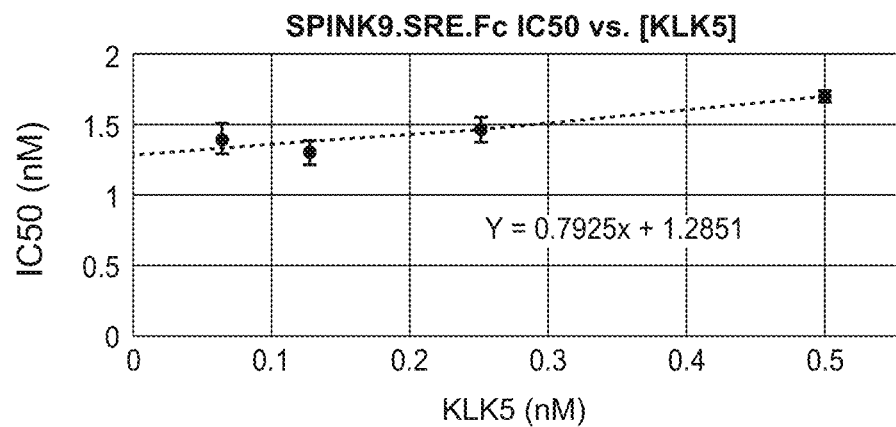
Figure 10C:
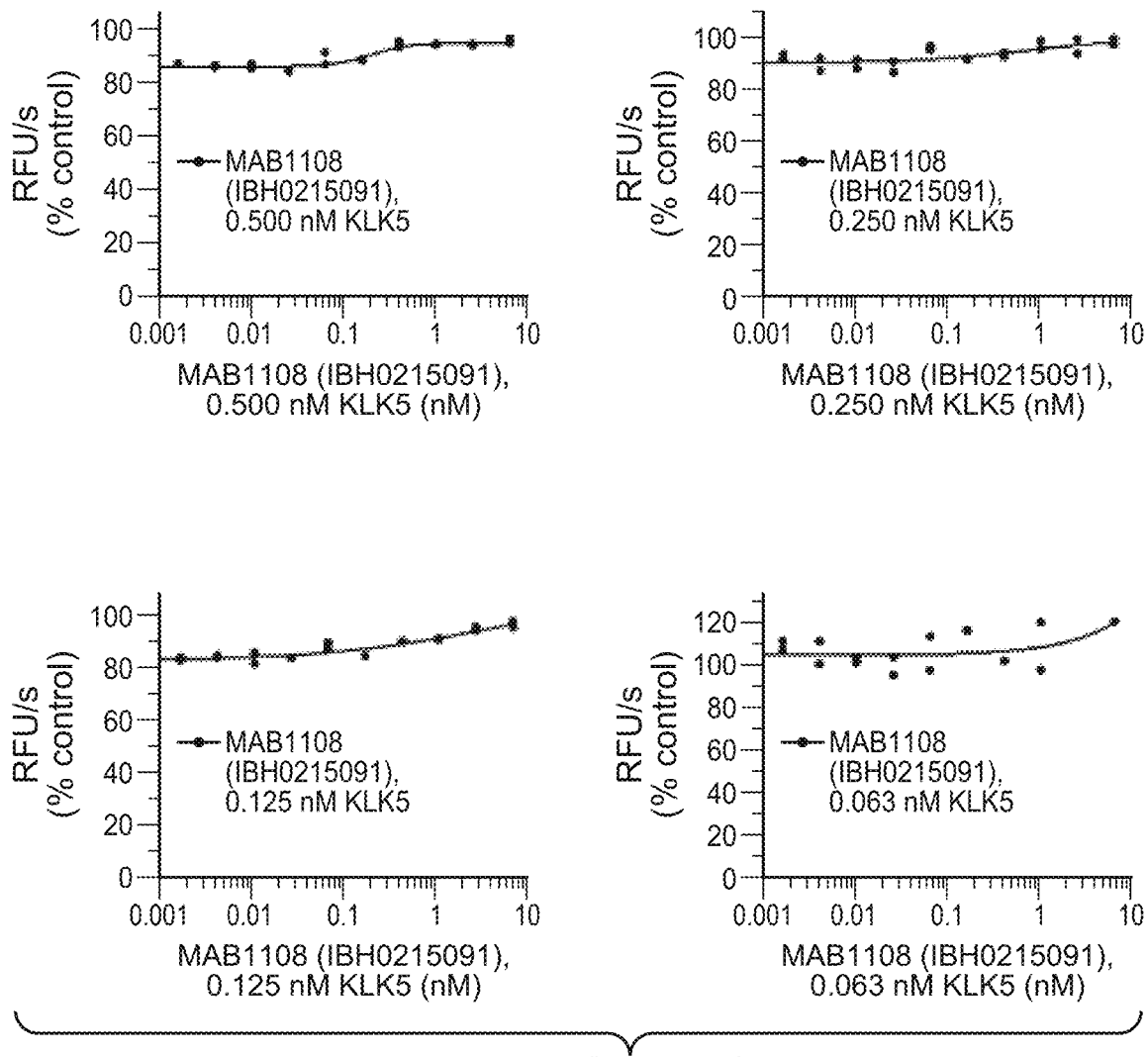
FIG. 10C and FIG. 10D: mAb1108.
Figure 10D:
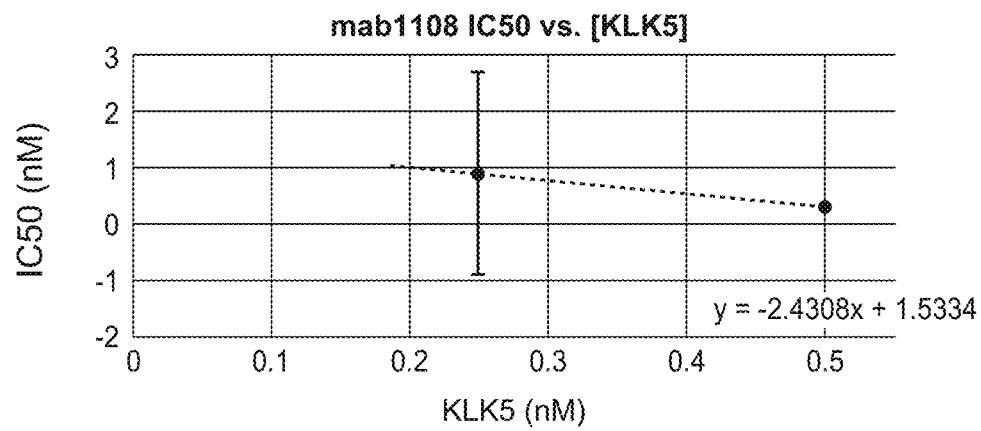
Figure 10E:
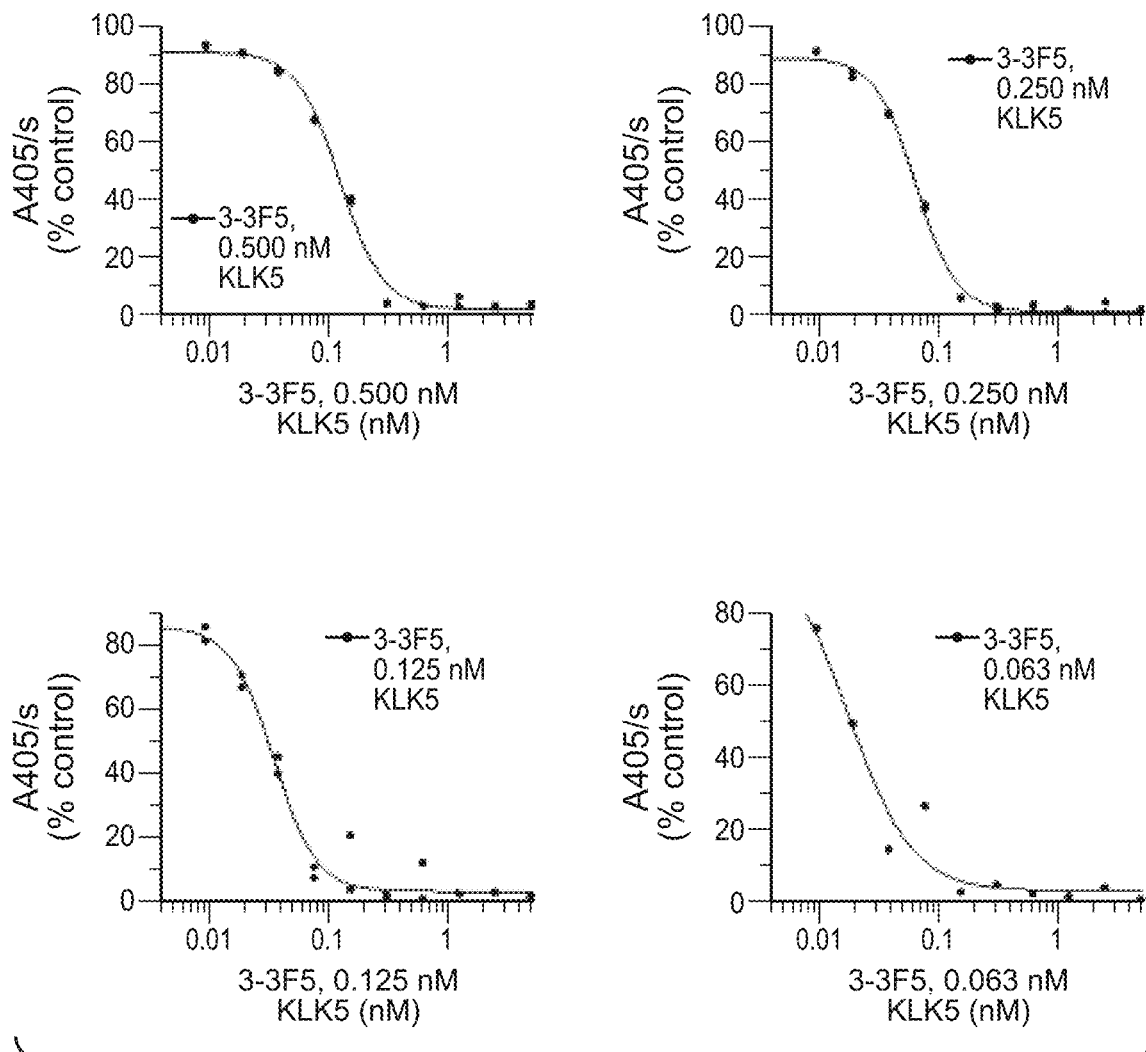
FIG. 10E and FIG. 10F: 3-3F5.
Figure 10F:
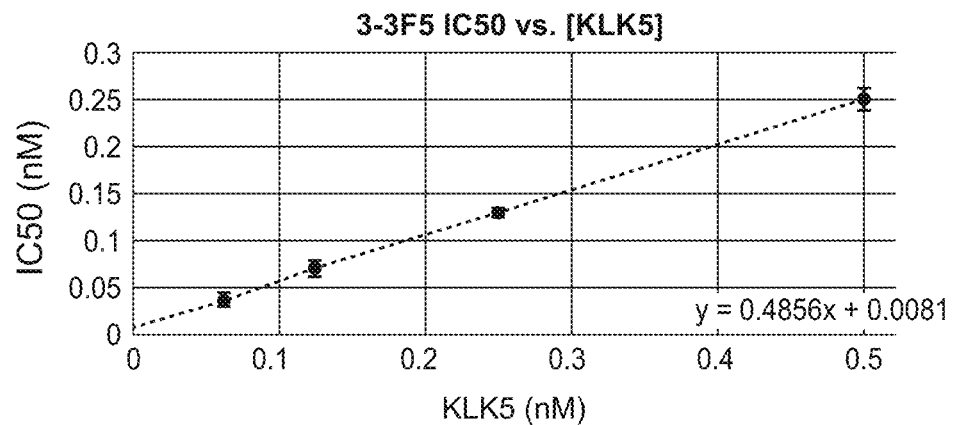
Figure 10G:
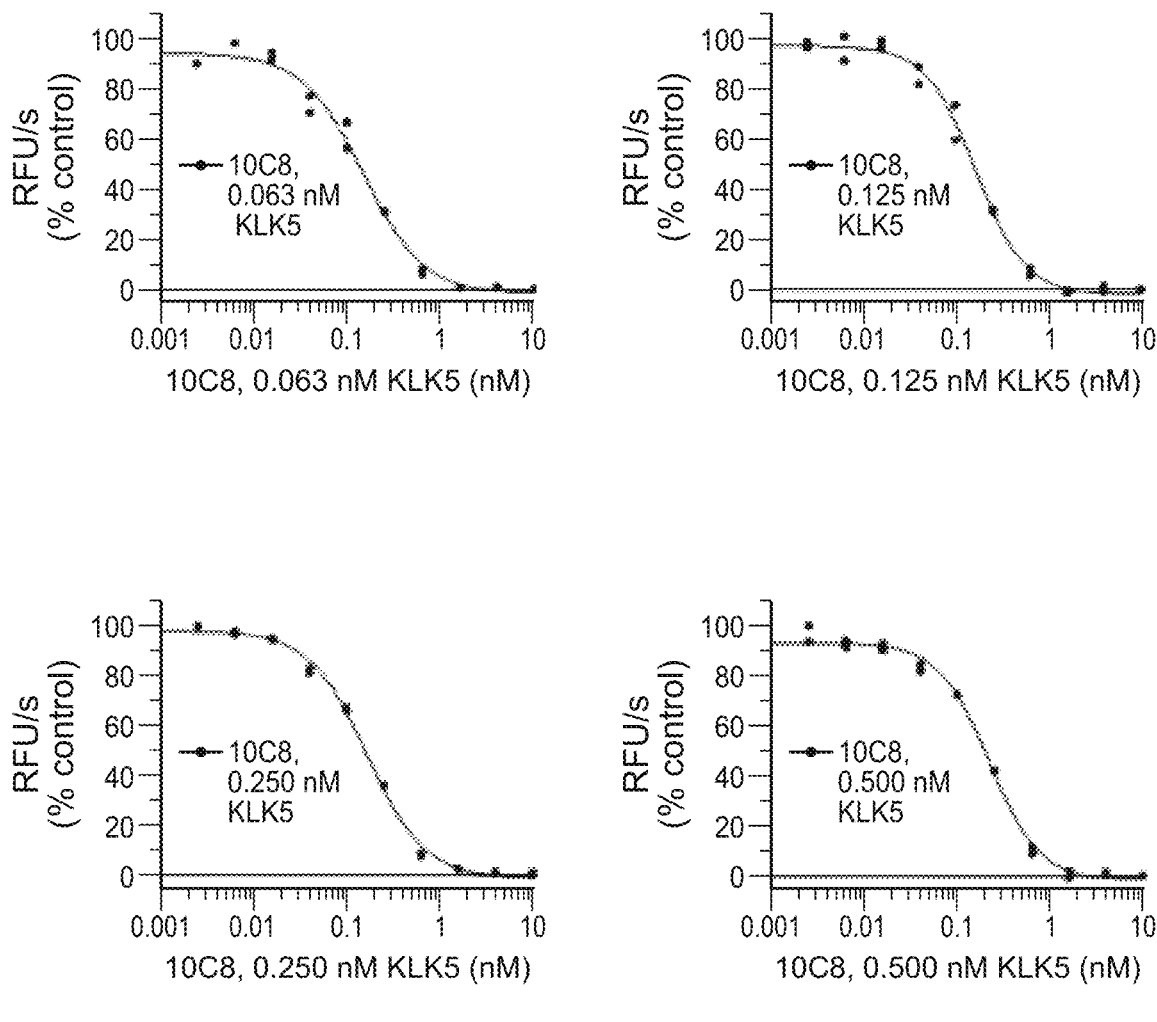
FIG. 10G and FIG. 10H: 10C8.
Figure 10H:
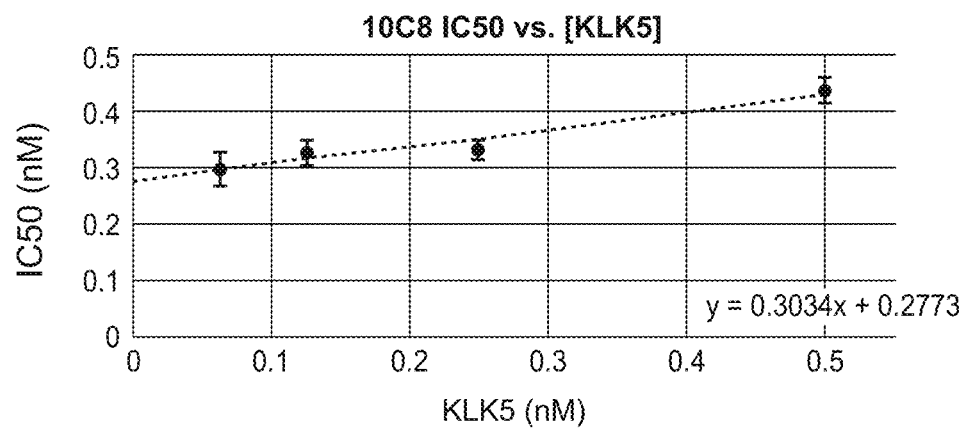
Figure 10I:
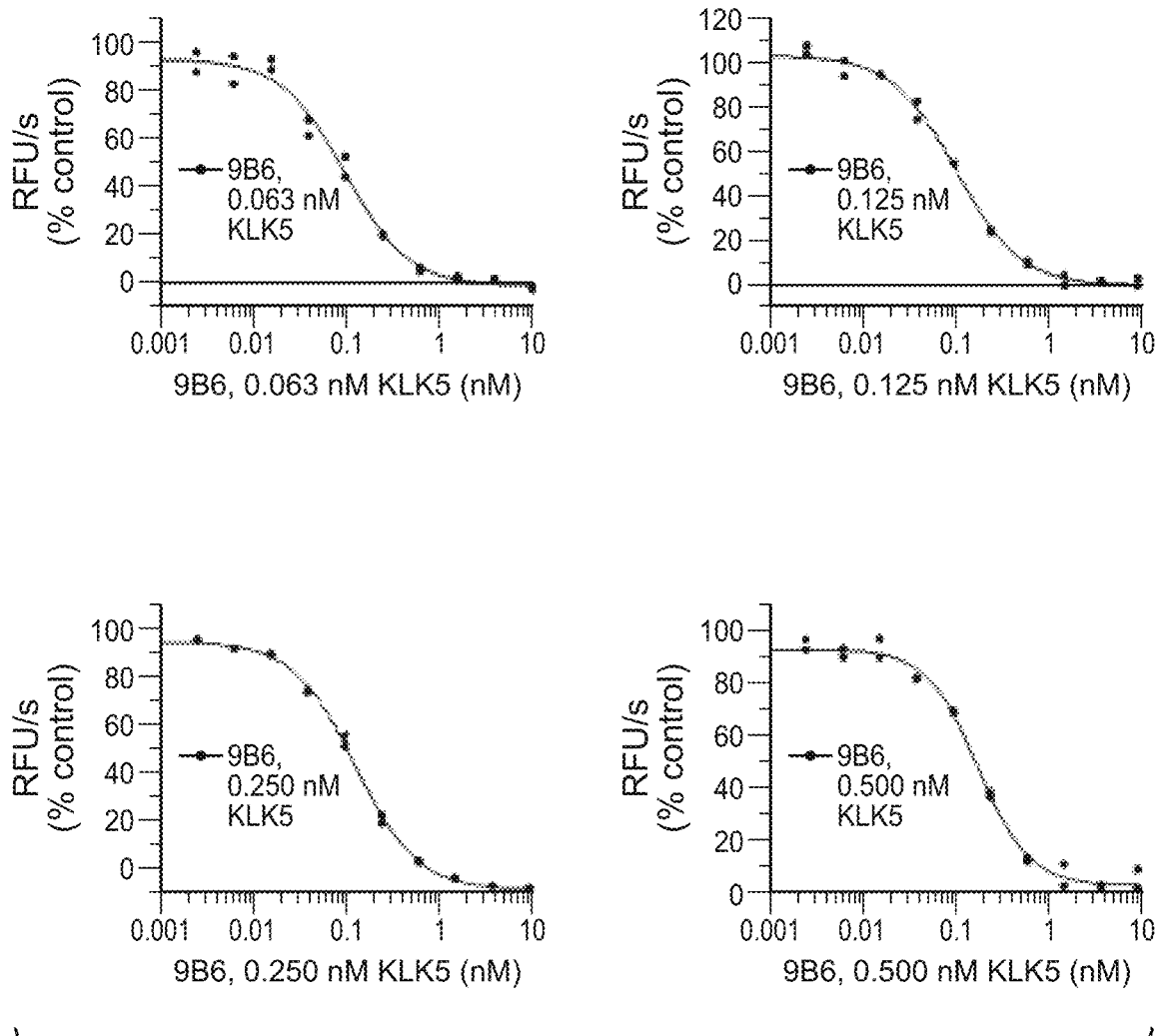
FIG. 10I and FIG. 10J: 9B6.
Figure 10J:
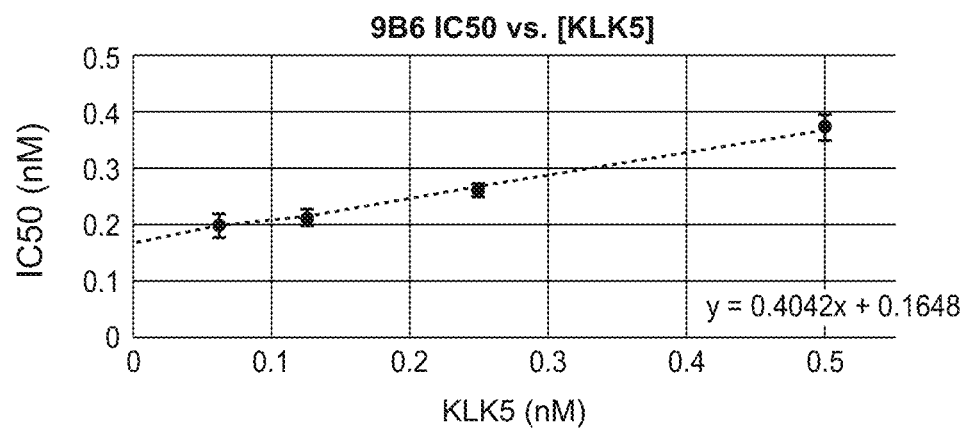
Figure 10K:
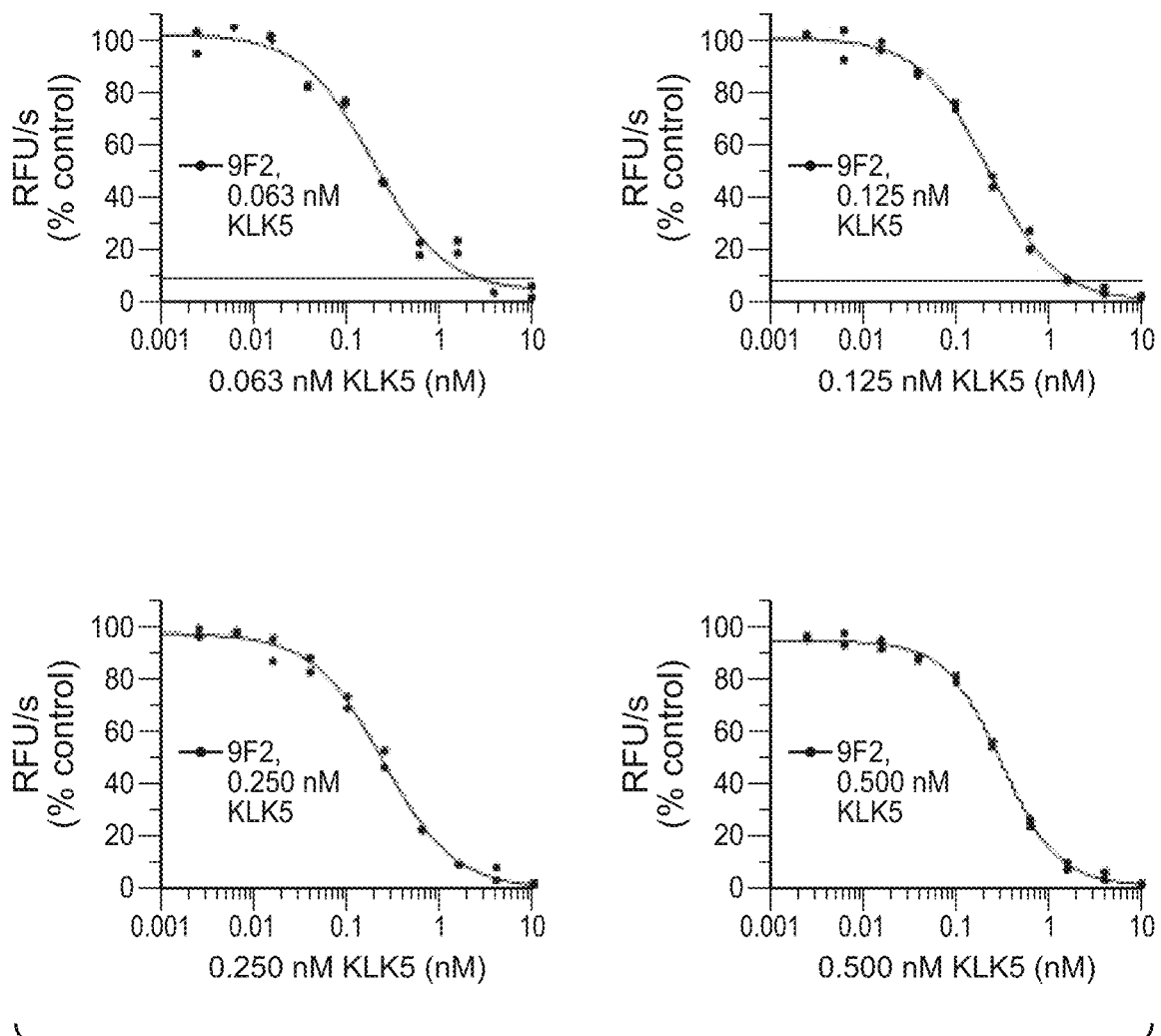
FIG. 10K and FIG. 10L: 9F2.
Figure 10L:
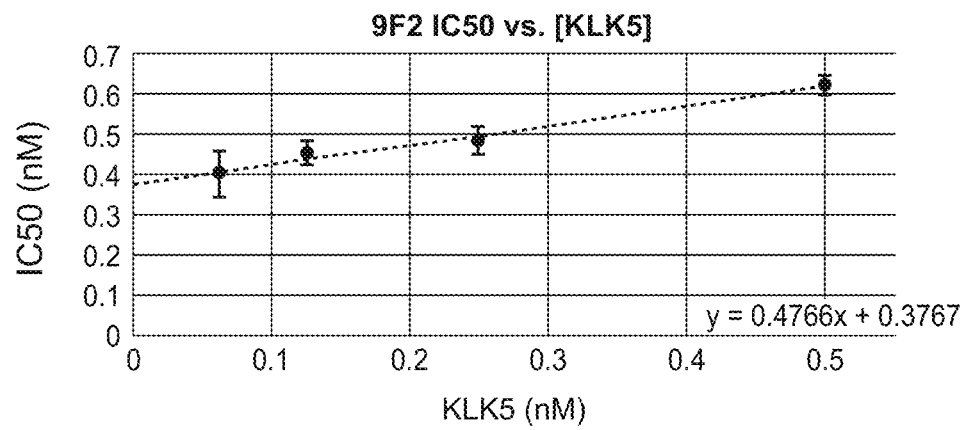
Figure 10M:
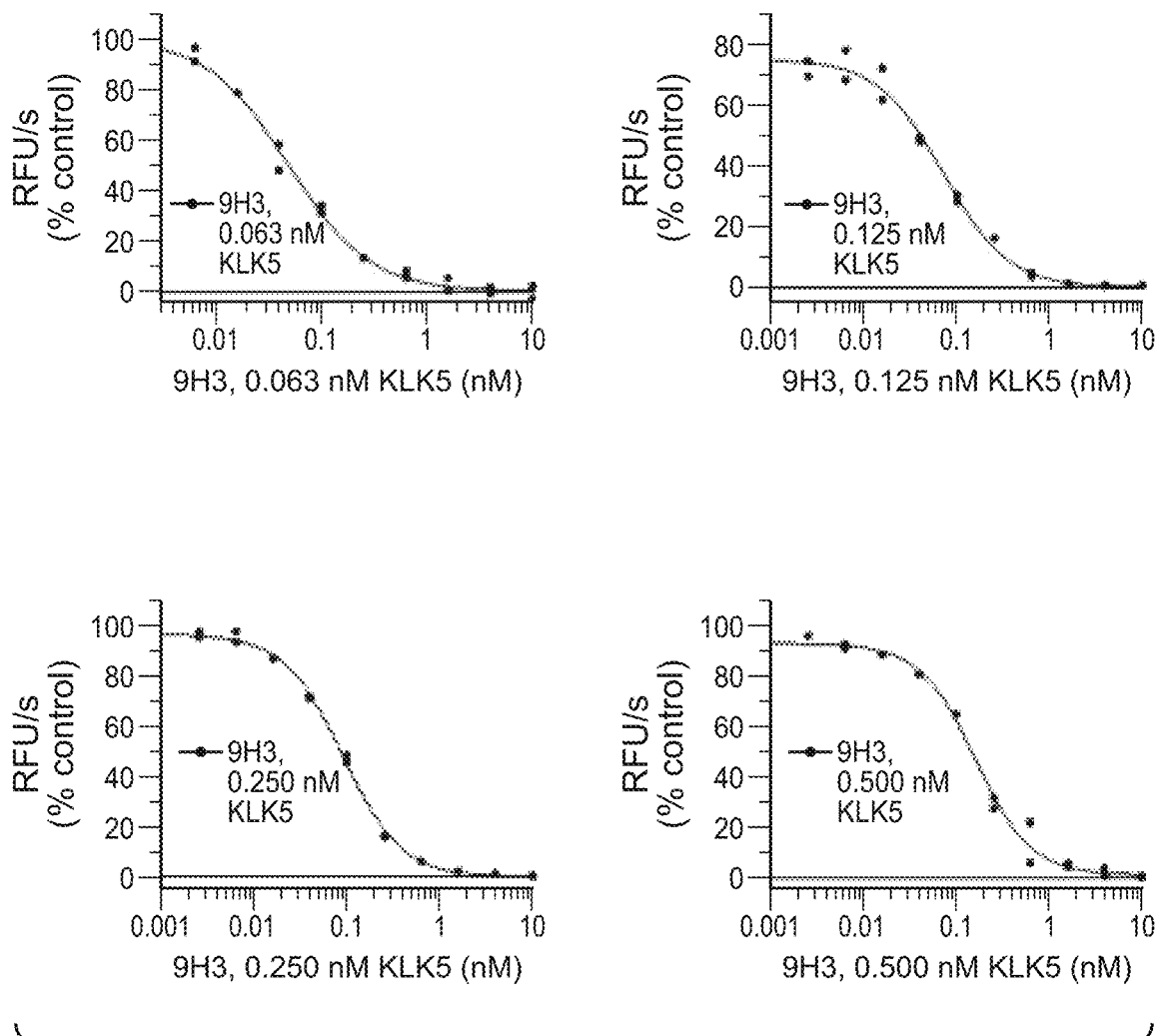
FIG. 10M and FIG. 10N: 9H3.
Figure 10N:
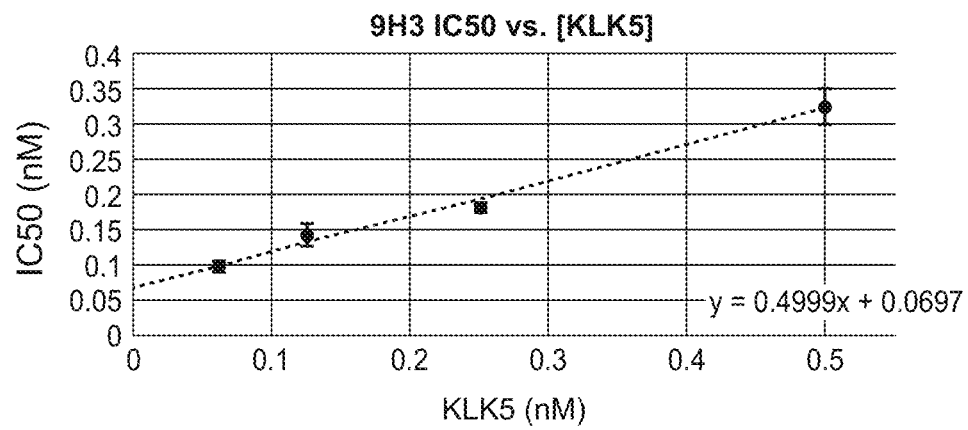
Figure 10O:
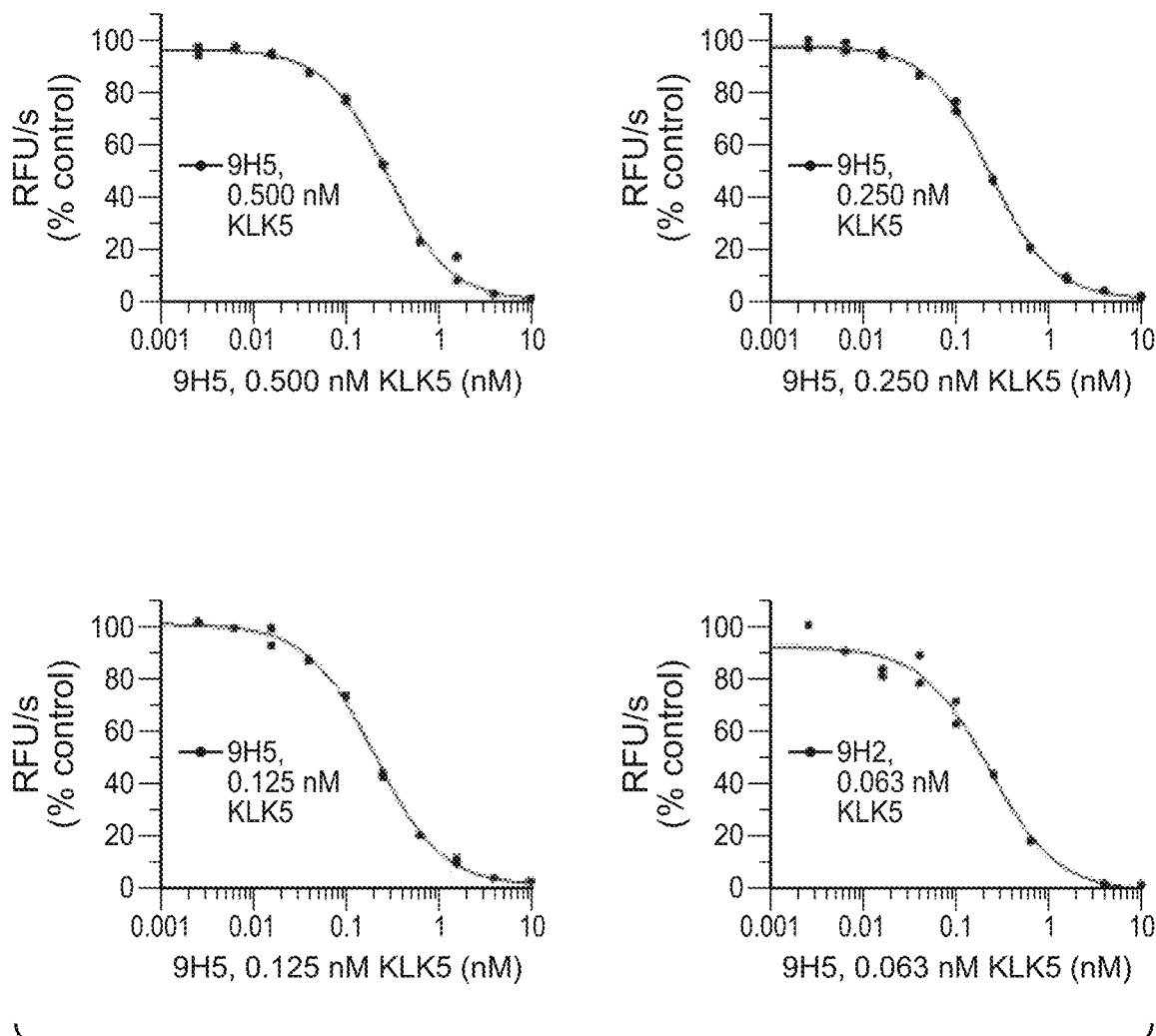
FIG. 10O and FIG. 10P: 9H5.
Figure 10P:
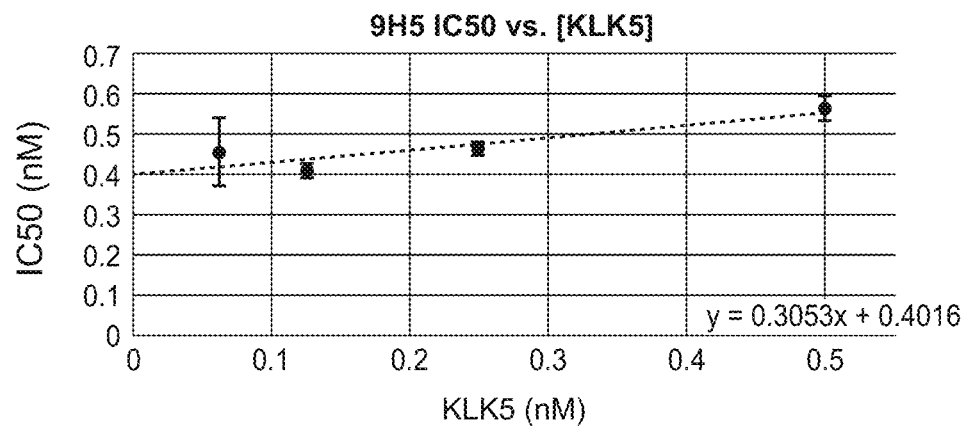
Figure 10Q:
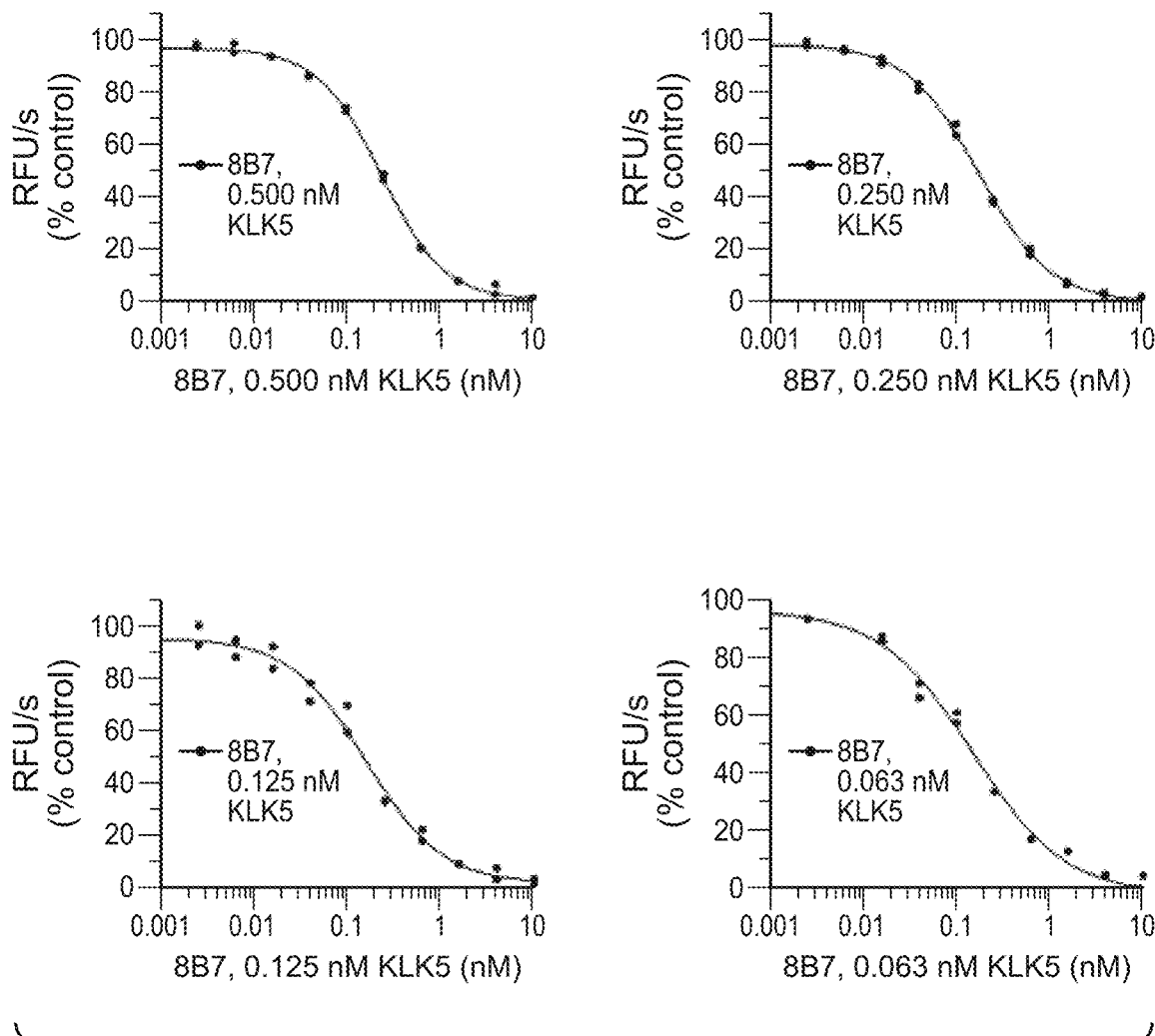
FIG. 10Q and FIG. 10R: 8B7.
Figure 10R:
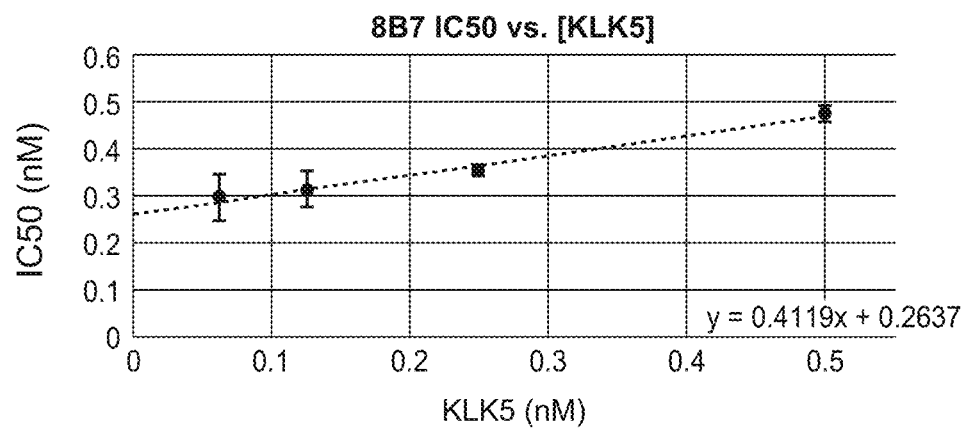
Figure 10S:
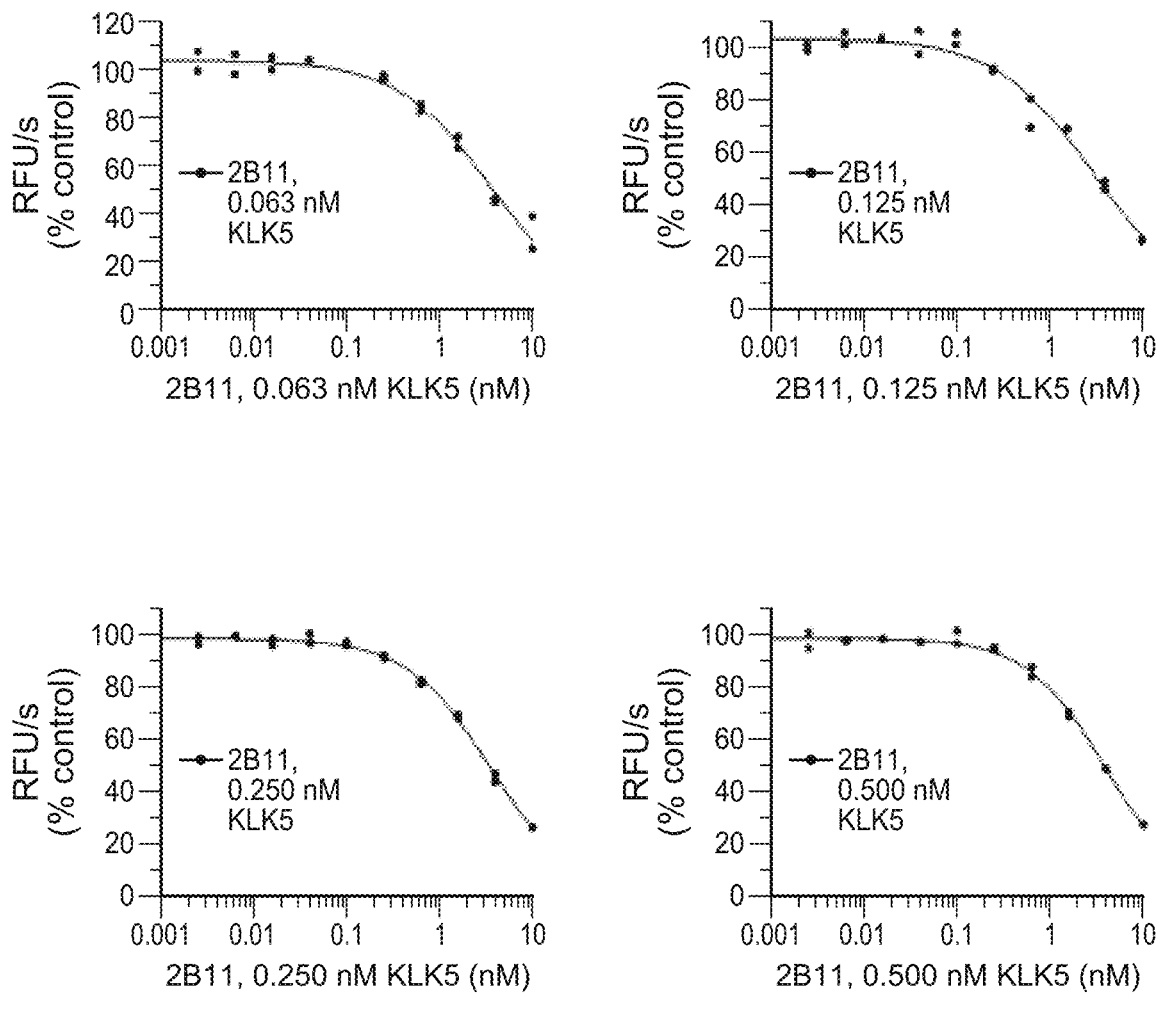
FIG. 10S and FIG. 10T: 2B11.
Figure 10T:
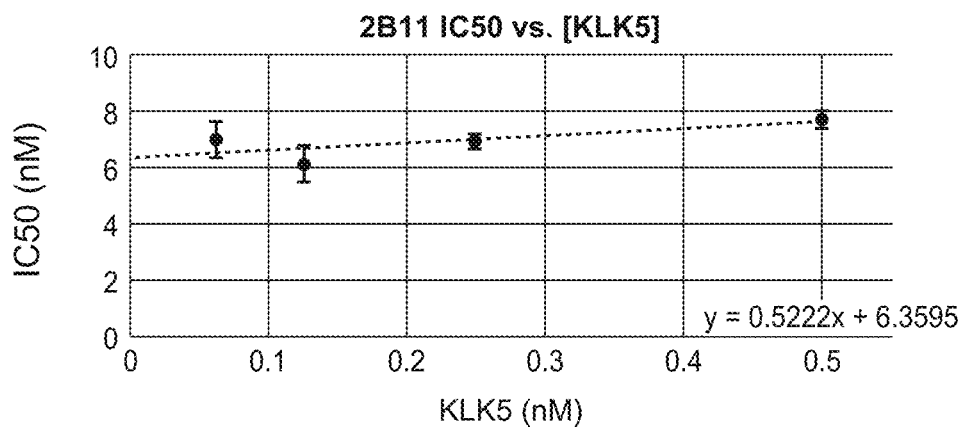
Figure 10U:
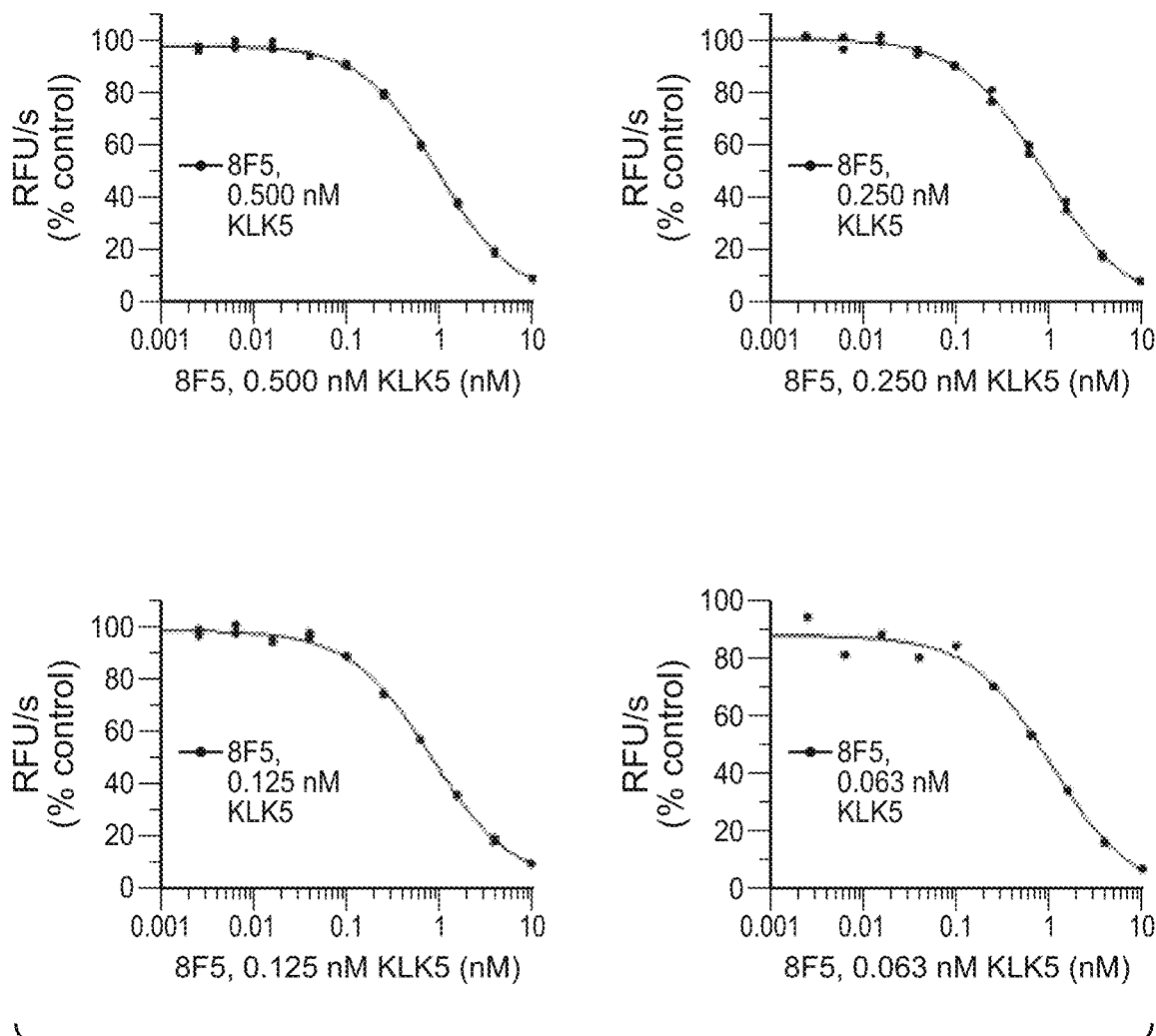
FIG. 10U and FIG. 10V: 8F5.
Figure 10V:
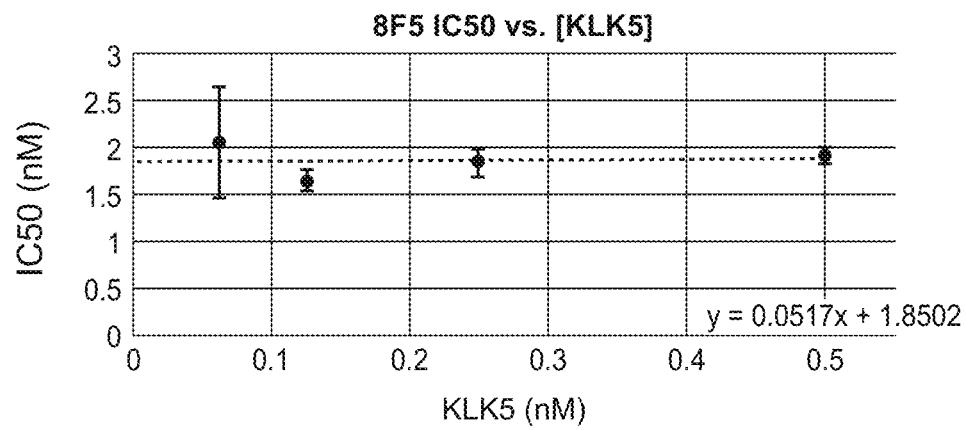
Figure 10W:
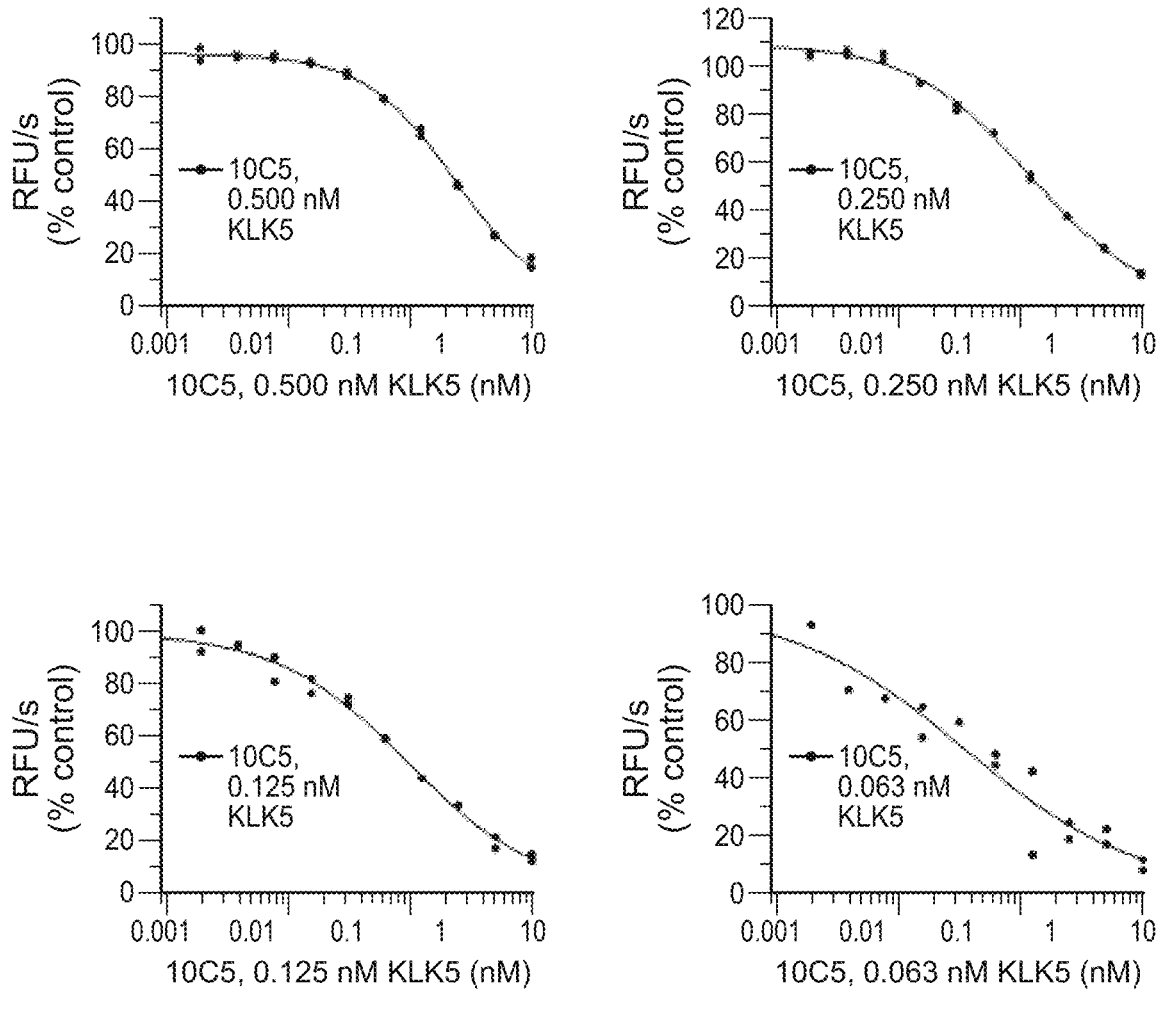
FIG. 10W and FIG. 10X: 10C5.
Figure 10X:
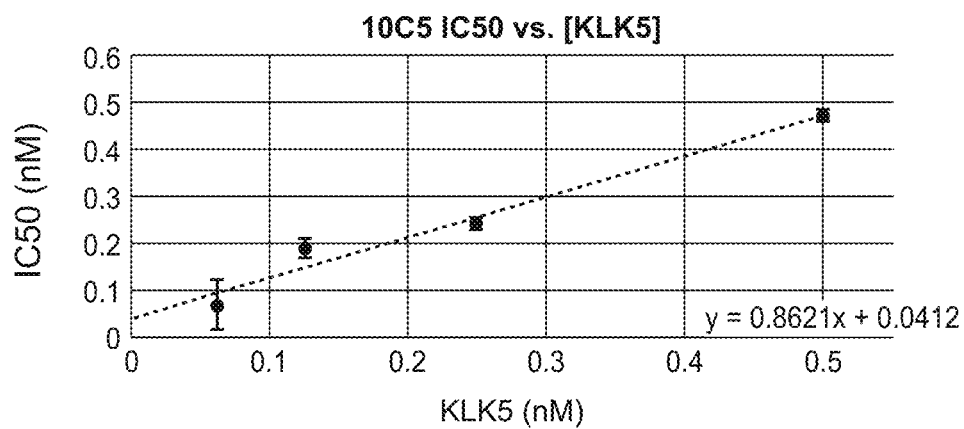
Figure 10Y:
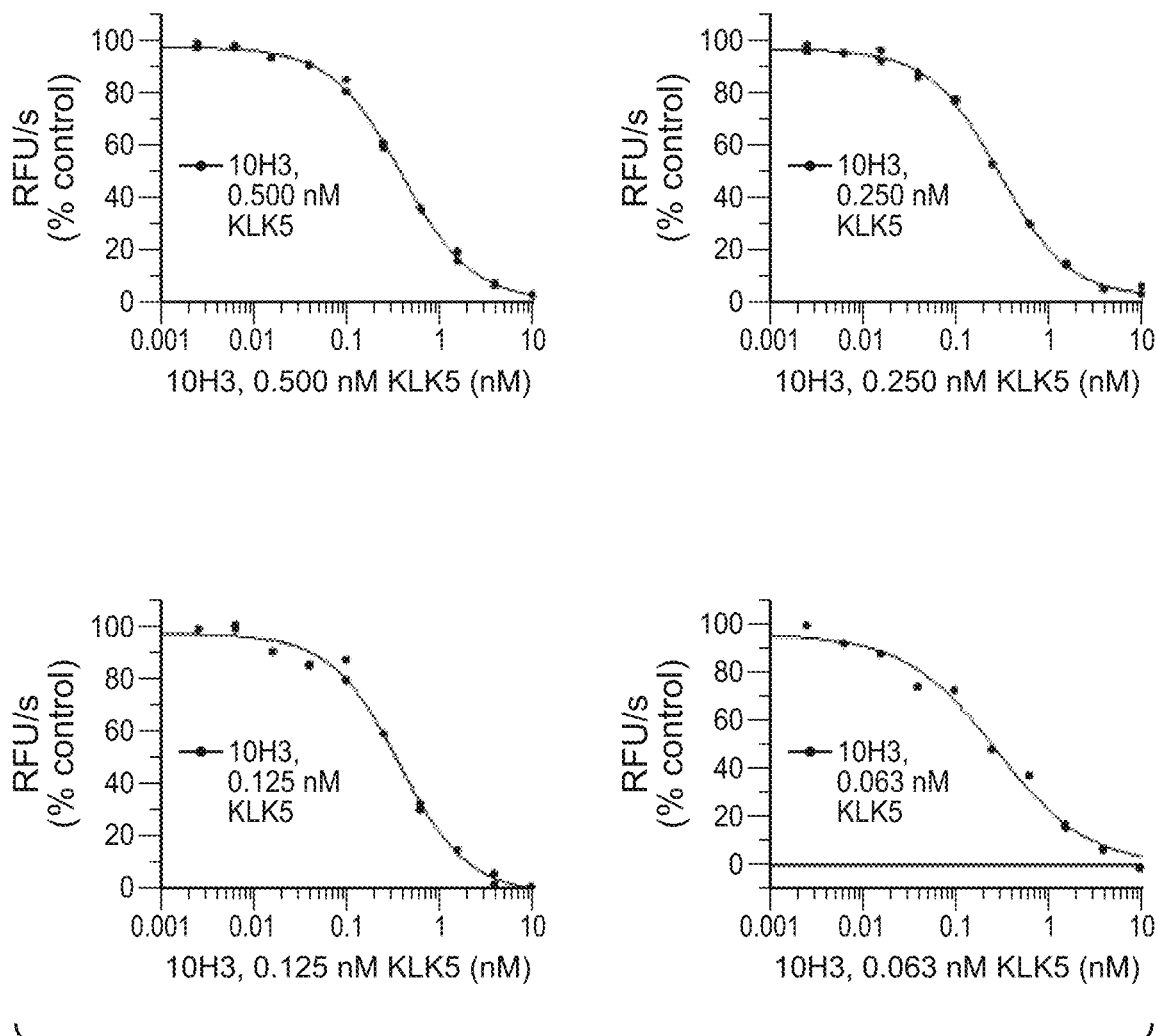
FIG. 10Y and FIG. 10Z: 10H3, FIG. 10AA and FIG. 10AB: 2-3F4.
Figure 10Z:
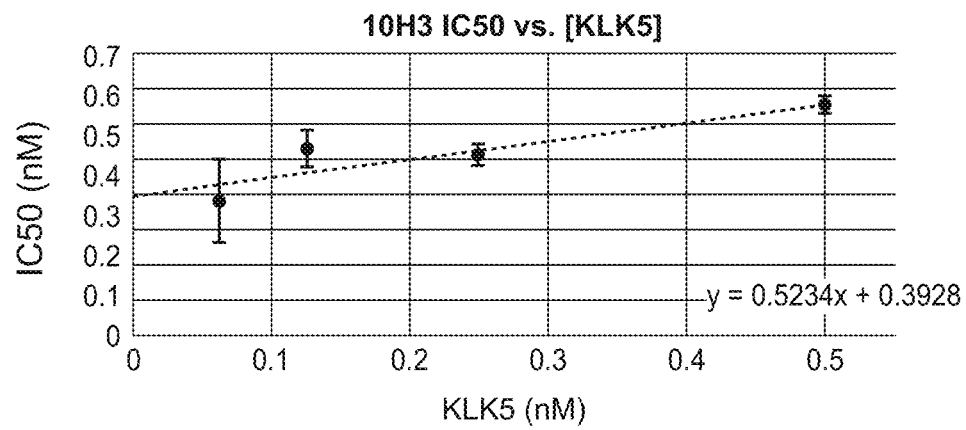
Figure 10A:
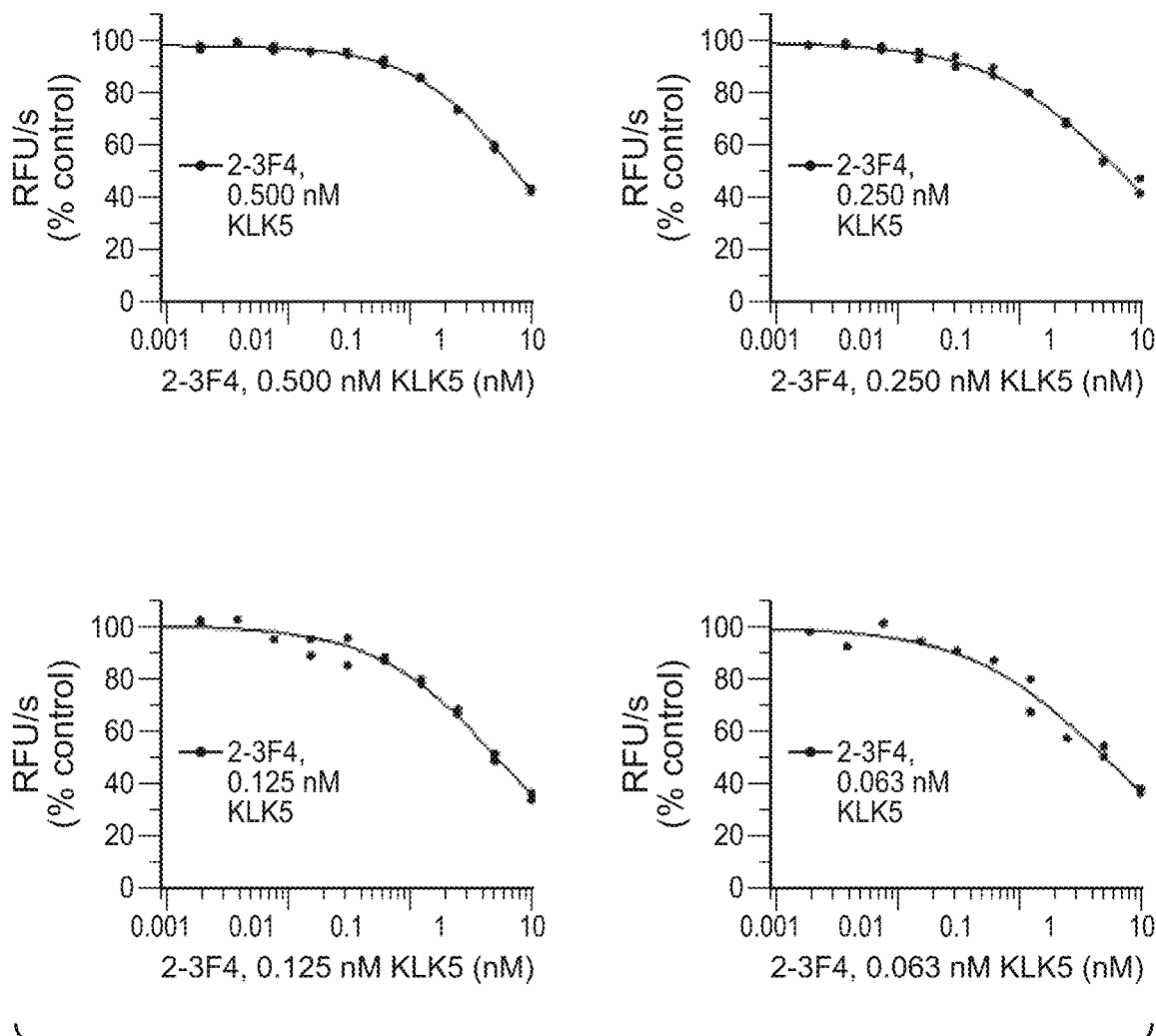
Figure 10A:
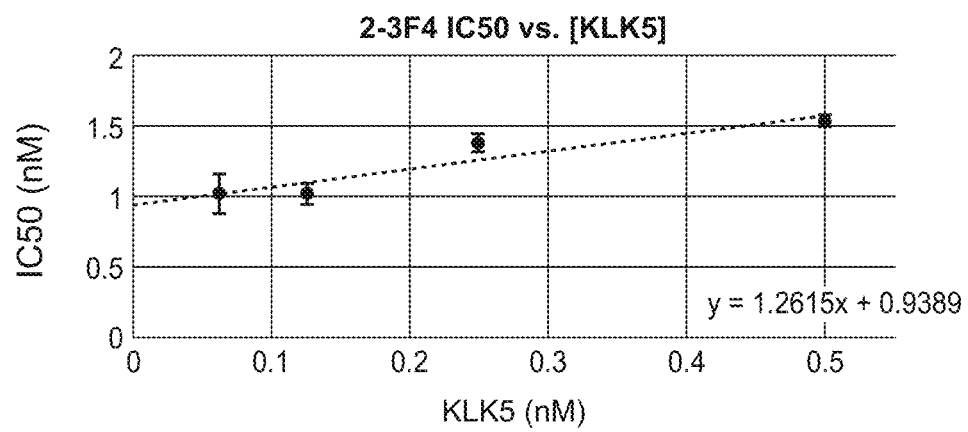
Figures 3, 16B:
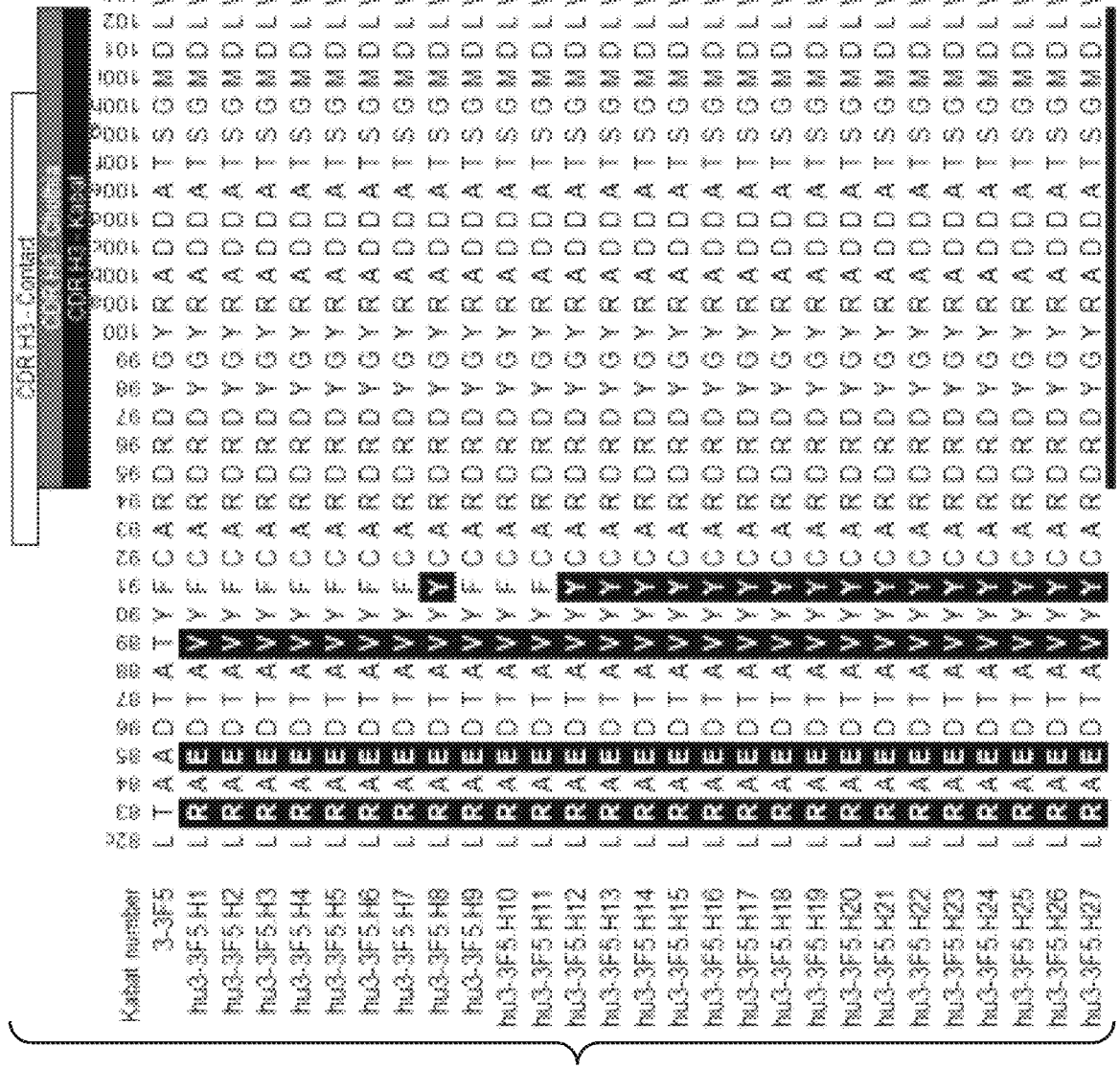

In FIG. 3, the ability of Spink9.SRE.Fc, mAb1108 or 12 selected anti-KLK5 antibodies to inhibit KLK5 mediated activation of pro-KLK1 was assessed using a coupled enzymatic assay. In this assay, human KLK5 is incubated with human pro-KLK1 resulting in cleavage, release of the KLK7 pro-domain and activation of KLK1. Activated human KLK1 can proteolyze a KLK1 specific substrate, PFR-AMC, resulting in an increased fluorescent signal. The cleavage of pro-KLK1 by human KLK5 results in active KLK1 and an increased fluorescent signal whereas the inhibition or absence of KLK5 resulted in a quenched fluorescent signal. The results were expressed as a percentage of maximum human KLK5 activity (% control). The results of a single experiment run in duplicate are shown in FIG. 3. The $IC_{50}$ value for Spink9.SRE.Fc (FIG. 3A) was nM and the range of $IC_{50}$ for the 12 selected anti-KLK5 antibodies (FIG. 2 C-N) was 0.074 to 0.151 nM. Spink0.SRE.Fc as well as all 12 selected anti-KLK5 antibodies fully inhibited KLK5 activity, although mAb1108 (FIG. 1B) only demonstrated ~40% inhibition of KLK5 activity. The $IC_{50}$ values from the curve fittings are presented in FIG. 11 (Column 3).

KLK5-Derived Cleavage Peptide Detection by LC/MS for $IC_{50}$ Value Determination The ability of Spink9.SRE.Fc, mAb1108 or 12 selected anti-KLK5 antibodies to inhibit proteolysis of pro-KLK7 or pro-KLK1 by recombinant KLK5 was assessed using an LC/MS assay that monitors the KLK5-derived cleavage product peptides. For both assays, the cleavage of the pro-peptide KLK7 or KLK1 by human KLK5 results in a specific MS signal and the inhibition of KLK5 activity results in a measurable decrease of the peptide signal. The results of a single experiment for pro-KLK7 are shown in FIG. 4 and they are expressed as area of pro-peptide KLK7. The calculated $IC_{50}$ value for Spink9.SRE.Fc (FIG. 4A) was 1.13 nM, for MAb1108 (FIG. 4B) was 1.86 nM and the range of $IC_{50}$ values for the 12 selected anti-KLK5 antibodies (FIG. 4 C-N) was 0.31 to 1.72 nM. Spink9.SRE.Fc as well as all 12 selected anti-KLK5 antibodies fully inhibited KLK5 activity, and mAb1108 (FIG. 4B) demonstrated ~80% inhibition of KLK5 activity. The $IC_{50}$ values from the curve fittings are presented in FIG. 11 (Column 4). FIG. 5 shows the results of three experiments for pro-KLK1 and they are expressed as area of pro-peptide KLK1. The $IC_{50}$ value for Spink0.SRE.Fc (FIG. 5A) was 0.58 nM, for MAb1108 (FIG. 5B) was 0.34 nM and the range of $IC_{50}$ values for the 12 selected anti-KLK5 antibodies (FIG. 5 C-N) was 0.08 to nM. Spink9.SRE.Fc as well as all 12 selected anti-KLK5 antibodies fully inhibited KLK5 activity, although mAb1108 (FIG. 5B) demonstrated ~40% inhibition of KLK5 activity. The $IC_{50}$ values from the curve fittings are presented in FIG. 11 (Column 5).

Specificity of KLK5 Antibodies

To evaluate the specificity the anti-KLK5 antibodies characterized in FIGS. 1-5, the 12 anti-KLK5 antibodies were assayed against activated human KLK7 (FIG. 6), human KLK1 (FIG. 7), human KLK4 (FIG. 8) and trypsin (FIG. 9) monitored by the cleavage of specific fluorescent peptide substrates. As these 12 anti-KLK5 antibodies were generated to selectively interact with KLK5, it was anticipated that these molecules should not inhibit other KLKs (FIGS. 6-9) or trypsin (FIG. 9).

In FIG. 6, the ability of Spink9.SRE.Fc, mAb1108 or 12 selected anti-KLK5 antibodies to inhibit the proteolysis of the substrate, Suc-LLVY-AMC, by human KLK7 was assessed using an enzymatic assay. The cleavage of the peptide substrate by human KLK7 resulted in an increased fluorescent signal and the inhibition or absence of KLK7 resulted in a quenched fluorescent signal. The results were expressed as a percentage of maximum KLK7 activity (% control). The results of a single experiment run in duplicate are shown in FIG. 6. Spink9.SRE.Fc (FIG. 6A) and mAb1108 (FIG. 6B) did not inhibit KLK7 up to 100 nM. As seen in FIG. 6, the 12 selected anti-KLK5 antibodies (FIGS. 6C-N) also do not inhibit KLK7 activity up to 100 nM. The $IC_{50}$ values from the curve fittings are presented in FIG. 11 (Column 6).

In FIG. 7, the ability of Spink9.SRE.Fc, mAb1108 or 12 selected anti-KLK5 antibodies to inhibit the proteolysis of the substrate, PFR-AMC, by human KLK1 was assessed using an enzymatic assay. The cleavage of the peptide substrate by human KLK1 resulted in an increased fluorescent signal and the inhibition or absence of KLK1 resulted in a quenched fluorescent signal. The results were expressed as a percentage of maximum KLK1activity (% control). The results of a single experiment run in duplicate are shown in FIG. 7. Spink9.SRE.Fc (FIG. 7A) and mAb1108 (FIG. 7B) did not inhibit KLK1 up to 100 nM. As seen in FIG. 7, the 12 selected anti-KLK5 antibodies (FIGS. 7C-N) also do not inhibit KLK1 activity up to 100 nM. The $IC_{50}$ values from the curve fittings are presented in FIG. 11 (Column 7).

In FIG. 8, the ability of Spink9.SRE.Fc, mAb1108 or 12 selected anti-KLK5 antibodies to inhibit the proteolysis of the substrate, Boc-VPR-AMC, by human KLK4 was assessed using an enzymatic assay. The cleavage of the peptide substrate by human KLK4 resulted in an increased fluorescent signal and the inhibition or absence of KLK4 resulted in a quenched fluorescent signal. The results were expressed as a percentage of maximum KLK4 activity (% control). The results of a single experiment run in duplicate are shown in FIG. 8. Spink9.SRE.Fc (FIG. 8A) and mAb1108 (FIG. 8B) did not inhibit KLK4 up to 100 nM. As seen in FIG. 8, the 12 selected anti-KLK5 antibodies (FIGS. 8C-N) also do not inhibit KLK4 activity up to 100 nM. The $IC_{50}$ values from the curve fittings are presented in FIG. 11 (Column 8).

In FIG. 9, the ability of Spink9.SRE.Fc, mAb1108 or 12 selected antibodies to inhibit the proteolysis of the substrate, Boc-VPR-AMC, by bovine trypsin was assessed using an enzymatic assay. The cleavage of the peptide substrate by trypsin resulted in an increased fluorescent signal and the inhibition or absence of trypsin resulted in a quenched fluorescent signal. The results were expressed as a percentage of maximum trypsin activity (% control). The results of a single experiment run in duplicate are shown in FIG. 9. Spink9.SRE.Fc (FIG. 9A) and mAb1108 (FIG. 9B) did not inhibit trypsin up to 100 nM. As seen in FIG. 9, the 12 selected antibodies (FIGS. 9C-N) also do not inhibit trypsin activity up to 100 nM. The $IC_{50}$ values from the curve fittings are presented in FIG. 11 (Column 9).

Taken together, these studies using KLK7 (FIG. 6 and Table 6), KLK1 (FIG. 7 and Table 7), KLK4 (FIG. 8 and Table 8) and trypsin (FIG. 9 and Table 9) show that Spink9.SRE.Fc, mAb1108 or the 12 selected antibodies specifically interact and inhibit only KLK5 activity.

Ranking of Antibodies by $Ki_{app}$

In characterizing the 12 selected antibodies in either the direct (FIG. 1) or coupled assays (FIGS. 2-5), it was observed that the selected antibodies have similar or greater inhibitory potency than Spink9.SRE.Fc for KLK5. However, several of the antibodies have similar $IC_{50}$ values in each of the assays (Tables 1-5) making it difficult to rank the potency of the antibodies.

In FIG. 10, the ability of Spink9.SRE.Fc, mAb1108 or 12 selected antibodies to inhibit the proteolysis of the substrate, z-VPR-pNA, by human KLK5 at various concentrations was assessed using an enzymatic assay. In this assay the three-mer chromogenic peptide substrate contains a p-nitroanilide (pNA) group that is quenched by the terminal amino acid. The cleavage of the chromogenic peptide substrate by KLK5 resulted in an increased absorbance at 405 nm and the inhibition or absence of KLK5 resulted in a low absorbance 405 nm. The results were expressed as a percentage of maximum KLK5 activity (% control).

The $IC_{50}$ values of Spink9. SRE.Fc at various KLK5 concentrations (FIG. 10A) is determined and plotted as a function of KLK5 concentration (FIG. 10B) where the $Ki_{app}$ value is determined as the y-intercept. From this analysis, the $Ki_{app}$ value for Spink9.SRE.Fc is 1.28 nM. This analysis was also performed for mAb1108 (FIG. 10 C-D) that has a $Ki_{app}$ value of 1.53 nM as well as the 12 selected antibodies (FIG. 10 E-AB), which have a range of $Ki_{app}$ values of less than 0.01 nM to 6.35 nM. The $Ki_{app}$ values from this analysis are presented in FIG. 11 (Column 10).

Example 4—Kinetic Analysis and Epitope Binning with Wasatch

The results of the epitope binning and off-rates against human KLK5 for a subset of the most potent antibodies are shown in Table 4. Variable levels of binding were observed to mouse and cyno KLK5. Importantly, no binding was observed to human KLK1, human KLK4, or human KLK7, confirming that these antibodies are specific. Most clones, except for 8E11 and 8G10, compete with SPINK9 for binding to human KLK5, suggesting that they either bind the same epitope (i.e., the active site) at SPINK9 or allosterically alter human KLK5 so that SPINK9 can no longer bind.

TABLE 4

| Clone ID | SPINK9 competition (Y/N) | human KLK5 kd (1/s) |
| --- | --- | --- |
| 14C8 | Y | $3.76E^{-04}$ |
| 14E12 | Y | $4.14E^{-04}$ |
| 2B11 | Y | $5.74E^{-04}$ |
| 8B7 | Y | $5.47E^{-04}$ |
| 8E11 | N | $2.02E^{-04}$ |
| 8F5 | Y | $3.16E^{-04}$ |
| 8G10 | N | $2.45E^{-04}$ |
| 9B6 | Y | $1.78E^{-04}$ |
| 9F2 | Y | $3.39E^{-04}$ |
| 9H3 | Y | $1.43E^{-04}$ |
| 9H5 | Y | $3.67E^{-04}$ |
| 10C5 | Y | $1.26E^{-04}$ |
| 10C8 | Y | $6.16E^{-05}$ |
| 10H3 | Y | $5.89E^{-04}$ |
| 2.3F4 | Y | $1.84E^{-04}$ |
| SPINK9-SRE-Fc | Y | $4.70E^{-04}$ |

Example 5—Epitope Mapping by Hydrogen Exchange Mass Spectrometry

Hydrogen exchange measurements as completed herein measure the exchange of protons bound to backbone amide residues with those bound to molecules of the solvent. When a protiated ($^1H$) sample is diluted into deuterated solvent, difference in mass between a proton and deuteron can be measured by mass spectrometry. Upon a series of increasing incubation times in deuterated solvent ($^2H_2O$), rate of exchange can be measured. In this way, KLK 5 (SEQ ID NO:353) complexed to one of three anti-KLK5 antibodies (10C5, 10H3 and 9H5) over three separate experiments was measured and then compared to results obtained from performing the experiment on KLK5 alone. A differential analysis of mass differences was then performed and overlapping peptides utilized to narrow in on a common thermodynamic epitope shared between all three anti-KLK5 antibodies (10C5, 10H3 and 9H5) (FIG. 12A). The term "thermodynamic epitope" refers to those portions of a protein whose backbone structural dynamics, or local free energy of unfolding is altered in response to a specific binding event such as becoming bound by an antibody. The structural epitope may be contained within the thermodynamic epitope.

Interpretation of data used the rule of N-2 whereby each peptide cannot carry deuterium on the first two sites due to back exchange. In addition, when there are many unique overlapping peptides, this information may be used to narrow in on those affected residues within each peptide. The four sequence regions of KLK5 identified to comprise a common thermodynamic epitope between are LRPNQL (FIG. 12 B, Region 1), QGVKSI (FIG. 12 B, Region 2), KRCEDAYPRQIDDT (FIG. 12 B, Region 3), and DYPCARPNRPGVY (FIG. 12 B, Region 4), a common structural epitope between all three antibodies tested is contained within these regions.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Figure 17:
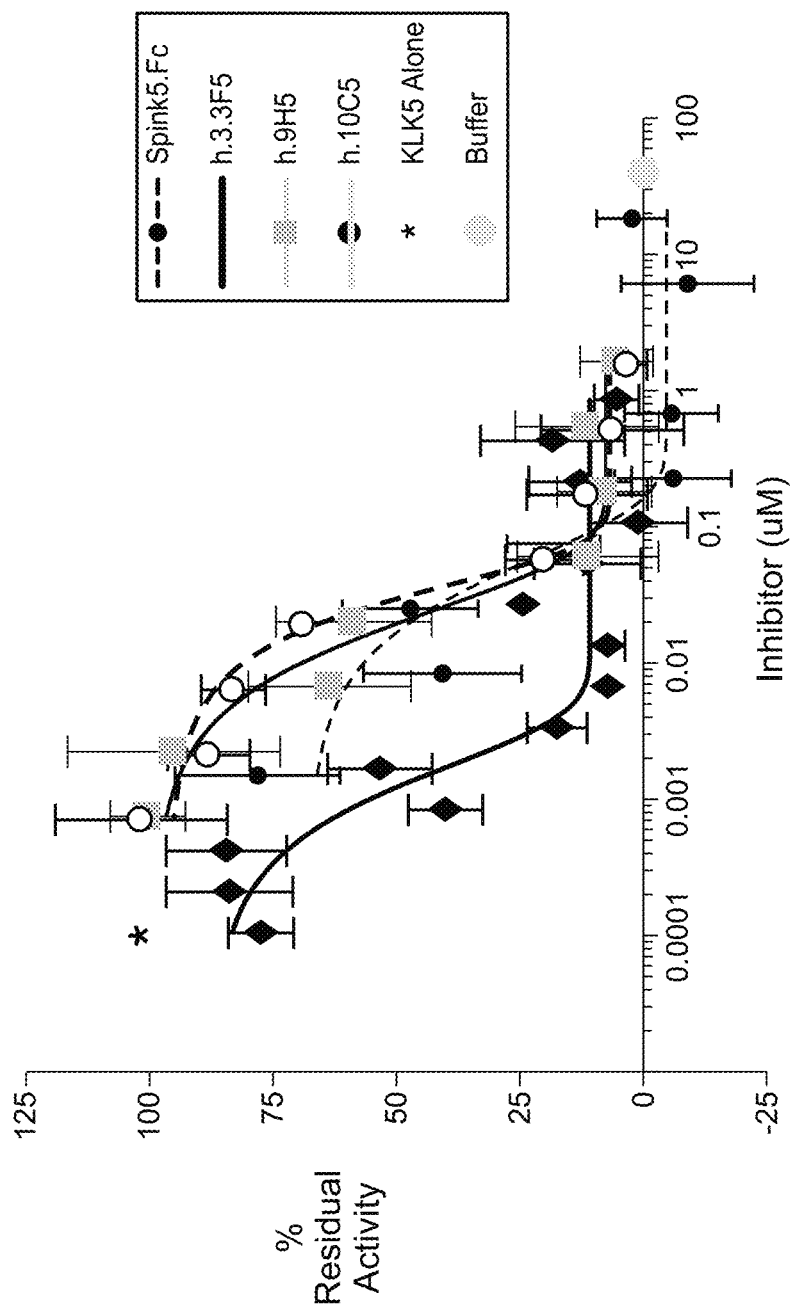
FIG. 17 shows the evaluation of KLK5 inhibitors in the A549 cell-based IL-8 secretion assay. The KLK5-induced IL-8 secretion level (gray star) was set at 100% residual activity while the buffer (starvation media) alone (gray circle) was set at 0% residual activity. Dose response curves are shown for Spink5.Fc (black circle and dotted black line), humanized 3.3F5 (black diamond and solid black line) anti-KLK5 antibody, humanized 9H5 anti-KLK5 antibody (open gray square and solid gray line), and humanized 10C5 anti-KLK5 antibody (black open circle and dotted gray line). The data shown are the mean±standard deviation of at least three independent experiments.

Example 6—Evaluation of KLK5 Inhibitor IC50 Values in a Cell-Based IL-8 Secretion Assay KLK5 stimulates A549 cells to secrete IL-8. The ability of Spink5.Fc, Spink9.SRE.Fc, or humanized anti-KLK5 antibodies 3-3F5, 9H5, or 10C5, to inhibit KLK5-induced IL-8 secretion was evaluated in the A549 cell-based IL-8 secretion assay. In this assay, serum-starved A549 cells were stimulated with 200 nM KLK5 for 24 hr (KLK5 alone or KLK5 pre-incubated with inhibitors for 1 hour). The IL-8 concentration was measured with a sandwich ELISA and IC50s of the inhibitors were determined. The results were expressed as a percentage of maximum KLK5 activity and the averages±standard deviations of at least three independent experiments are shown in FIG. 17. All inhibitors fully inhibited KLK5-induced IL-8 secretion to within 5% of the level of buffer alone (starvation media), which was within the error of the assay. All inhibitors showed potent inhibition of KLK5-induced IL-8 secretion and the average IC50s for at least three independent experiments were as follows: Spink5.Fc (21 nM); 10C5 (28 nM); 9H5 (15 nM); 3-3F5 (1.2 nM). The residual activity observed when KLK5 is incubated with 360 nM Spink9.SRE.Fc is 2% (data not shown).

Example 7—Structure of 10C5, 9H5 and 3-3F5 Bound to Human KLK5

For crystal structure experiments described herein, human KLK5 residues I67-S293 (SEQ ID NO:328) were used. The numbering of the amino acid residues of human KLK5 used in this Example 7 and as shown in corresponding FIGS. 18-20 and Tables 5-13 is based on the standard numbering for proteases. See Debela et al., *J Mol Biol*, 373, 1017-1031 (2007). The numbering of the amino acid residues of the Fab fragments used in this Example 7 and as shown in corresponding FIGS. 18-20 and Tables 5-13 is based on Kabat.

The Structure of 10C5 Bound to Human KLK5

Figure 18A:
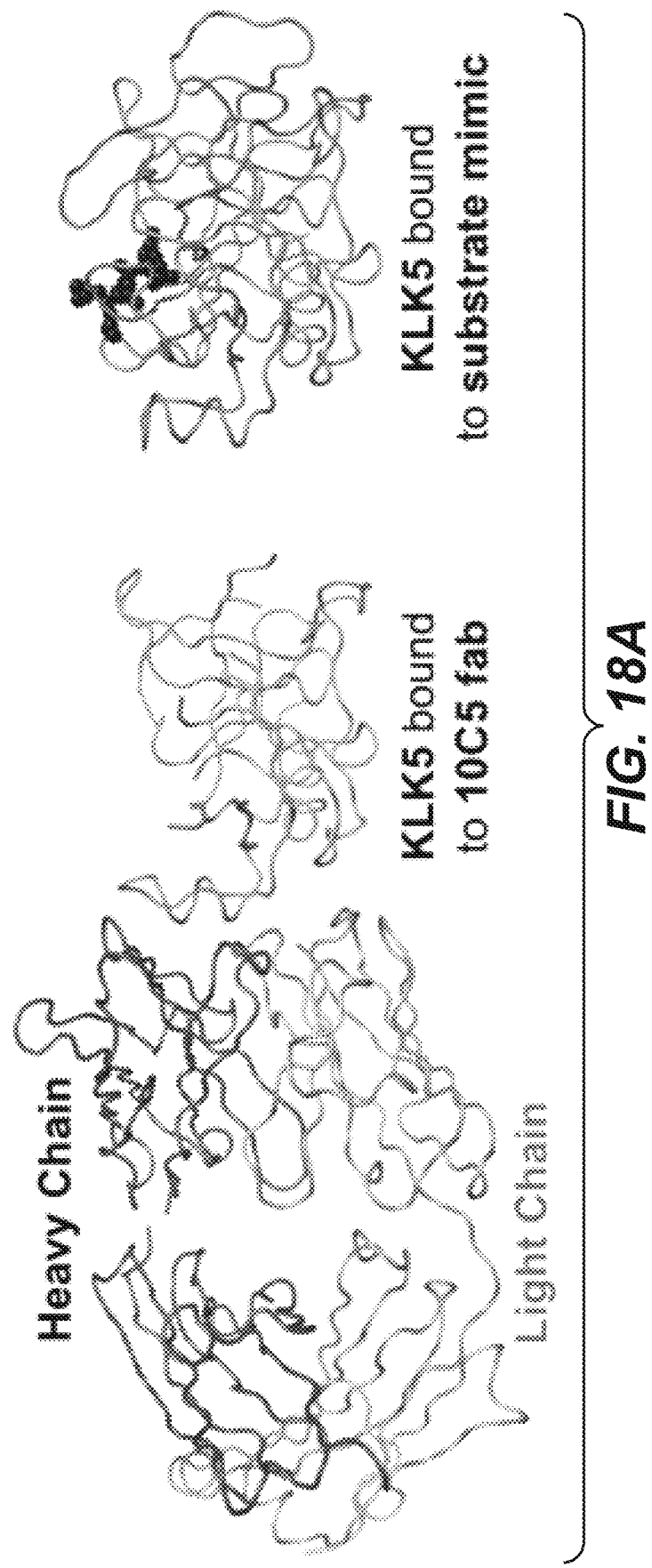
FIGS. 18A and 18B.
Figure 18B:
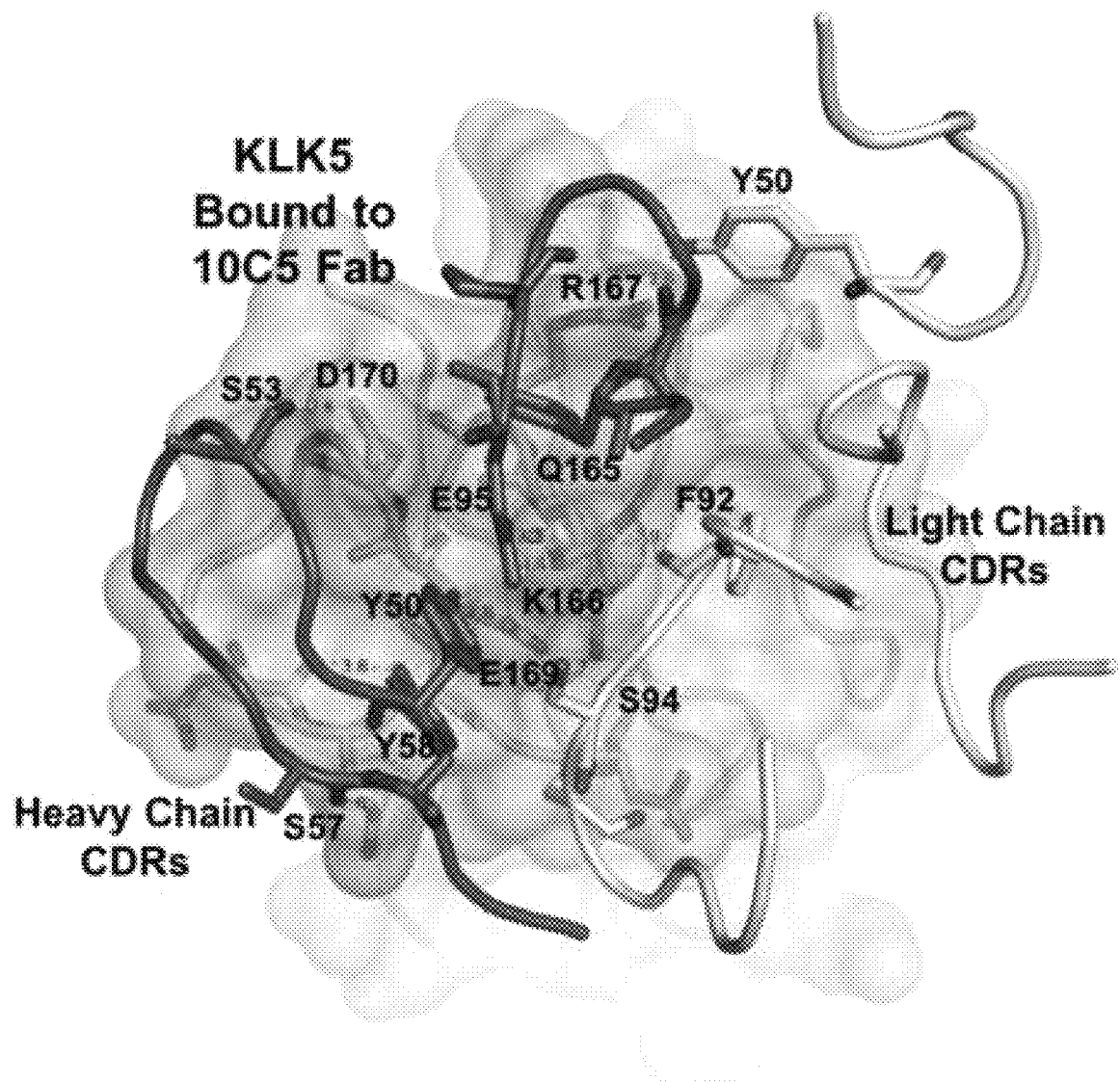

The 10C5 Fab/KLK5 complex structure shows that the binding of 10C5 to KLK5 results in conformational changes that allosterically result in disruption of the substrate binding site as well as the active site of KLK5, including the catalytic triad, rendering the protease unable to bind substrates and losing activity. The most distinct element of KLK5 that is recognized by the 10C5 fab is the helix encompassing residues 163-174A. The loop/turn immediately following the helix, made up by the residues 173-174A is flipped up by the antibody binding which results in a steric clash with residues in the 220s loop as well as the 90s loop (standard protease convention), that are important for substrate binding as well as positioning of the catalytic triad in the active site that cleaves peptides (FIG. 18A).

The buried surface area between KLK5 and 10C5 Fab is ~860 Å$^2$. In the 10C5 fab light chain, CDR-L1, residues Q24-S34 contact residues S131, A132, S164 and R167 in KLK5; Y50 from CDR-L2 contacts R167 in KLK5; CDR-L3 contacts A132, L163, S164, Q165, K166, E169, I176, D177 and D178 in KLK5. In the 10C5 heavy chain, CDRH1, residues S31-T35 contact only D170 in KLK5; CDRH2, residues Y50-A63, contacts residues K166, E169, D170, A171, Y172, P173, R174, Q174A and I176 in KLK5; CDRH3, E95-Y100c contacts residues S164, K166, R167 and D170 in KLK5 (Tables 5-7, FIG. 18B).

The sequences of the 10C5 Fab HC and LC used for the crystallization with human KLK5 is depicted in SEQ ID NO:322 and SEQ ID NO:323, respectively.

TABLE 5

| Interface residues in 10C5 Heavy Chain (Kabat Numbering) | Interface residues in KLK5 (Standard Protease Numbering) | Interface residues in 10C5 Light Chain (Kabat Numbering) | Interface residues in KLK5 (Standard Protease Numbering) |
| --- | --- | --- | --- |
| Ser 31 | Ser 164 | Glu 27 | Pro 130 |
| Gly 33 | Lys 166 | Ser 28 | Ser 131 |
| Tyr 50 | Arg 167 | Ser 30 | Ala 132 |
| Thr 52 | Glu 169 | Glu 32 | Val 162 |
| Ser 52A | Asp 170 | Tyr 50 | Leu 163 |
| Asn 53 | Ala 171 | Gly 91 | Ser 164 |
| Tyr 54 | Tyr 172 | Phe 92 | Gln 165 |
| Val 56 | Pro 173 | Gly 93 | Lys 166 |
| Ser 57 | Arg 174 | Ser 94 | Arg 167 |
| Tyr 58 | Gln 174A | Ser 95 | Glu 169 |
| Tyr 59 | Ile 176 | Val 97 | Gln 174A |
| Lys 64 | Arg 224 | | Ile 176 |
| Glu 95 | | | Asp 177 |
| Pro 97 | | | Asp 178 |
| Gly 100 | | | Lys 233 |
| Tyr 100A | | | |
| Tyr 100C | | | |

TABLE 6

Hydrogen Bonds

| Heavy Chain Residue | Bond Length (Angstrom) | KLK5 residue | Light Chain Residue | Bond Length (Angstrom) | KLK5 residue |
| --- | --- | --- | --- | --- | --- |
| Tyr 50 [OH] | 2.8 | Glu 169 [OE2] | Tyr 50 [OH] | 2.6 | Arg 167 [NH1] |
| Ser 52A [OG] | 2.6 | Asp 170 [OD1] | Phe 92 [O] | 2.9 | Gln 165 [N] |
| Ser 52A [N] | 3.4 | Asp 170 [OD2] | Phe 92 [O] | 3.2 | Lys 166 [N] |
| Tyr 58 [OH] | 3.8 | Arg 174 [O] | Ser 95 [OG] | 3.7 | Asp 178 [N] |
| Ser 57 [O] | 2.6 | Gln 174A [NE2] | Ser 94 [N] | 2.7 | Glu 169 [OE1] |
| Tyr 58 [OH] | 3.0 | Ile 176 [N] | | | |

TABLE 7

Salt Bridges

| Heavy Chain Residue | Bond Length (Angstrom) | KLK5 residue |
| --- | --- | --- |
| Glu 95 [OE1] | 2.3 | Lys 166 [NZ] |
| Glu 95 [OE1] | 3.4 | Lys 166 [NZ] |

The Structure of 9H5 Bound to Human KLK5

Figure 19A:
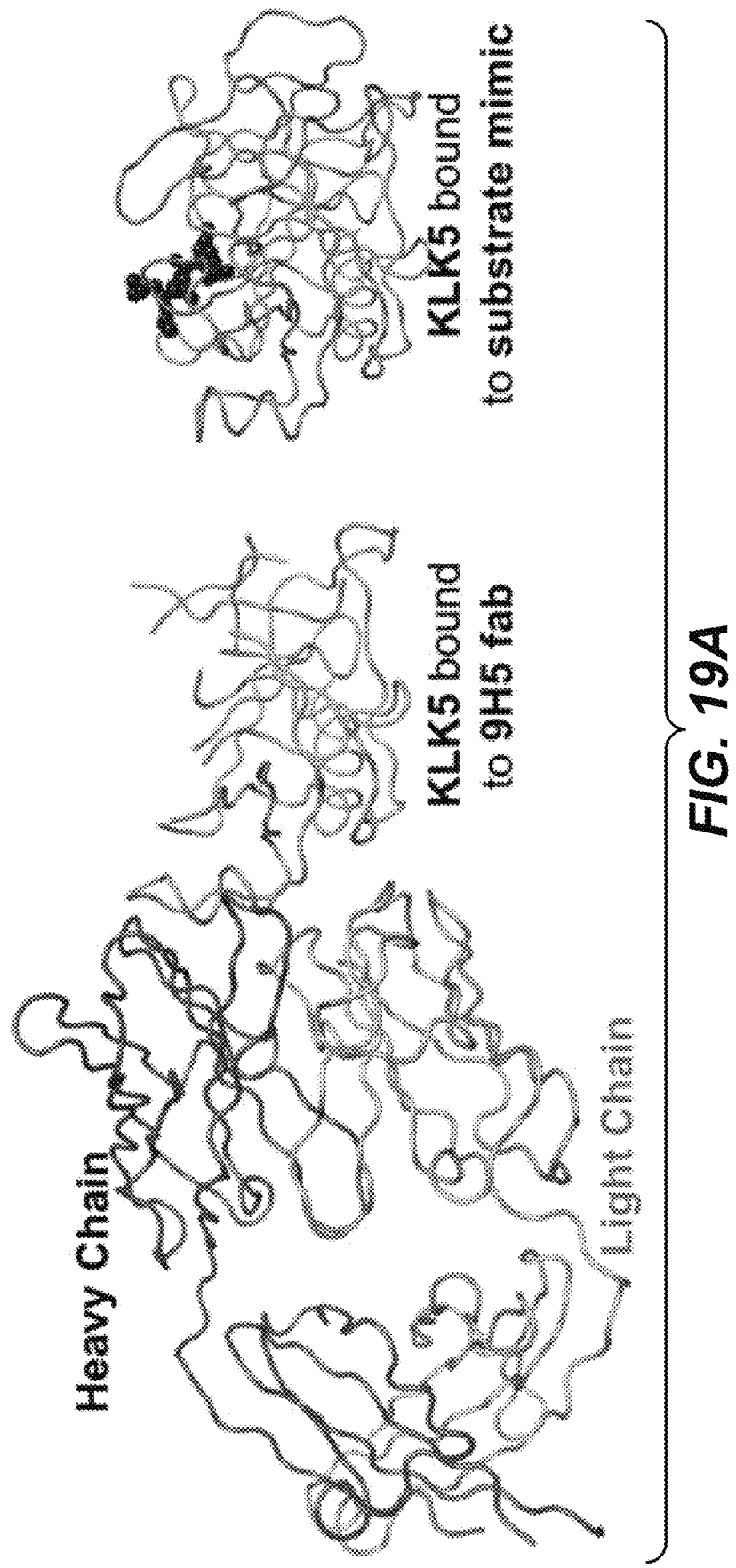
FIGS. 19A and 19B.
Figure 19B:
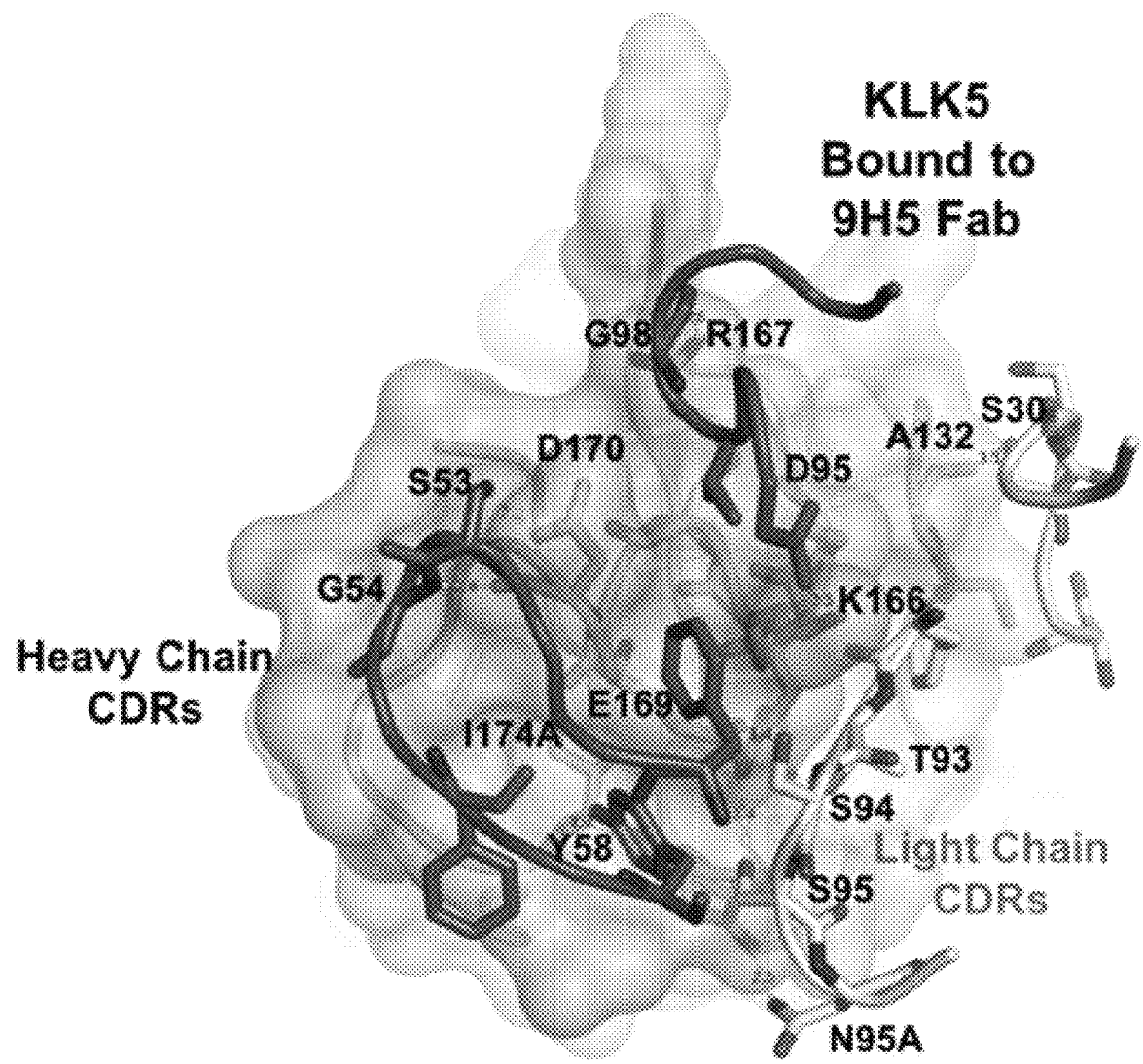

The 9H5 Fab/KLK5 complex structure shows that the binding of 9H5 to KLK5 results in conformational changes, similar to 10C5 fab, result in allosteric disruption of the substrate binding site as well as the active site of KLK5, including the catalytic triad, rendering the protease unable to bind substrates and losing activity. The most distinct element of KLK5 that is recognized by the 9H5 fab is the helix encompassing residues 163-174A. The loop/turn immediately following the helix, made up by the residues 173-174A is flipped up by the antibody binding which results in a steric clash with residues in the 220s loop as well as the 90s loop (standard protease convention), that are important for substrate binding as well as positioning of the catalytic triad in the active site that cleaves peptides. Overall, more of the KLK5 protein is disordered in the 9H5:KLK5 complex crystal structure, compared to 10C5 bound KLK5, and is likely a direct result of the Fab binding and the induced conformational changes (FIG. 19A).

The buried surface area between KLK5 and 9H5 Fab is 805 Å$^2$. In the 9H5 light chain, CDRL1, residues Q24-S34 contacts residues S131, A132, G133, L163, S164, R167 in KLK5; CDRL2, residues S50-S56, does not contact any residues in KLK5; CDRL3, residues H89-T97 contact residues A132, S164, Q165, K166, E169, Q174A, I176 and D177 in KLK5. In the 9H5 heavy chain, CDRH1, residues S31-S35 do not contact KLK5; CDRH2, residues F50-A63 contacts residues K166, E169, D170, Y172, P173, R174, Q174A and I176 in KLK5; CDRH3, residues D95-I102 contacts residues K166, R167 and D170 in KLK5 (Tables 8-10, FIG. 19B).

The sequences of the 9H5 Fab HC and LC used for the crystallization with human KLK5 is depicted in SEQ ID NO:324 and SEQ ID NO:325, respectively.

TABLE 8

| Interface residues in 9H5 Heavy Chain (Kabat Numbering) | Interface residues in KLK5 (Standard Protease Numbering) | Interface residues in 9H5 Light Chain (Kabat Numbering) | Interface residues in KLK5 (Standard Protease Numbering) |
| --- | --- | --- | --- |
| Ser 31 | Ser 164 | Gln 27 | Pro 130 |
| Gly 33 | Lys 166 | Ser 28 | Ser 131 |
| Ser 35 | Arg 167 | Ser 30 | Ala 132 |
| Phe 50 | Glu 169 | Tyr 32 | Gly 133 |
| Gly 52 | Asp 170 | His 89 | Val 162 |
| Ser 53 | Ala 171 | Gln 90 | Leu 163 |
| Gly 54 | Tyr 172 | Asp 91 | Ser 164 |
| Phe 56 | Pro 173 | Tyr 92 | Gln 165 |
| Tyr 58 | Arg 174 | Thr 93 | Lys 166 |
| Lys 64 | Gln 174A | Ser 94 | Arg 167 |
| Asp 95 | Ile 176 | Ser 95 | Glu 169 |
| Val 97 | Asp 177 | Asn 95A | Gln 174A |
| Gly 98 | | Thr 97 | Ile 176 |
| Ser 100B | | | Asp 177 |
| Leu 100C | | | Lys 233 |

TABLE 9

| Hydrogen Bonds | | | | | |
|---|---|---|---|---|---|
| Heavy Chain Residue | Bond Length (Angstrom) | KLK5 residue | Light Chain Residue | Bond Length (Angstrom) | KLK5 residue |
| Ser 53 [N] | 2.3 | Asp 170 [OD2] | Tyr 92 [O] | 3.2 | Gln 165 [N] |
| Ser 53 [N] | 3.5 | Asp 170 [O] | Tyr 92 [O] | 2.8 | Lys 166 [N] |
| Ser 53 [OG] | 2.2 | Asp 170 [OD2] | Ser 30 [OG] | 3.1 | Ala 132 [O] |
| Ser 53 [OG] | 3.7 | Asp 170 [O] | Thr 93 [OG1] | 2.9 | Glu 169 [OE1] |
| Gly 54 [N] | 3.5 | Asp 170 [OD2] | Ser 95 [OG] | 3.4 | Glu 169 [OE1] |
| Gly 54 [N] | 2.8 | Asp 170 [O] | Ser 94 [N] | 3.0 | Glu 169 [OE2] |
| Tyr 58 [OH] | 3.1 | Ile 176 [O] | Ser 95 [OG] | 3.6 | Ile 176 [O] |
| Gly 98 [O] | 3.6 | Arg 167 [NH2] | Asn 95A [ND2] | 2.5 | Asp 177 [OD1] |
| Tyr 58 [OH] | 2.7 | Ile 176 [N] | | | |

TABLE 10

| Salt Bridges | | |
|---|---|---|
| Heavy Chain Residue | Bond Length (Angstrom) | KLK5 residue |
| Asp 95 [OD1] | 2.5 | Lys 166 [NZ] |
| Asp 95 [OD2] | 3.7 | Lys 166 [NZ] |

The Structure of 3F5.5 Fab Bound to Human KLK5

Figure 20A:
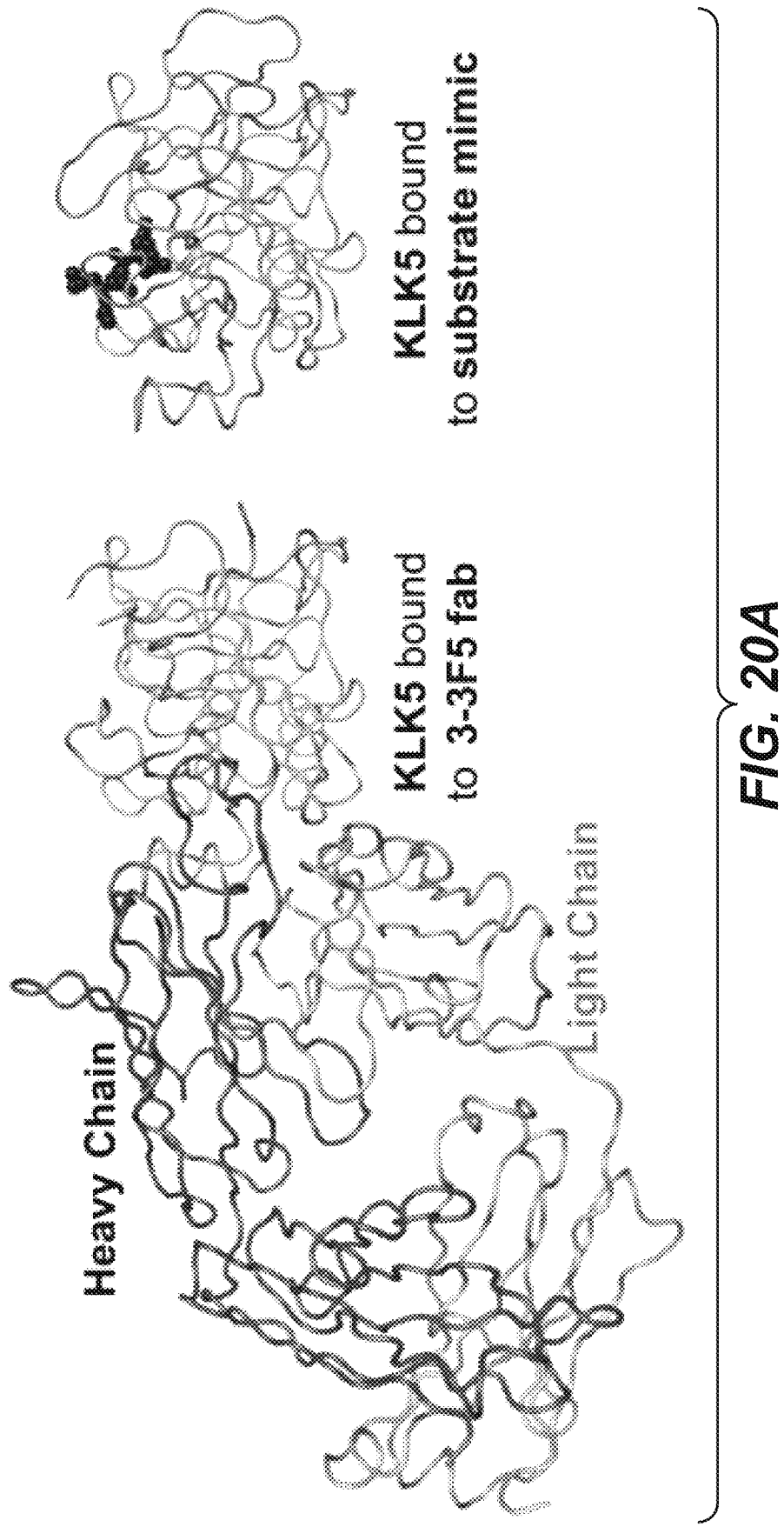
FIGS. 20A and 20B.
Figure 20B:
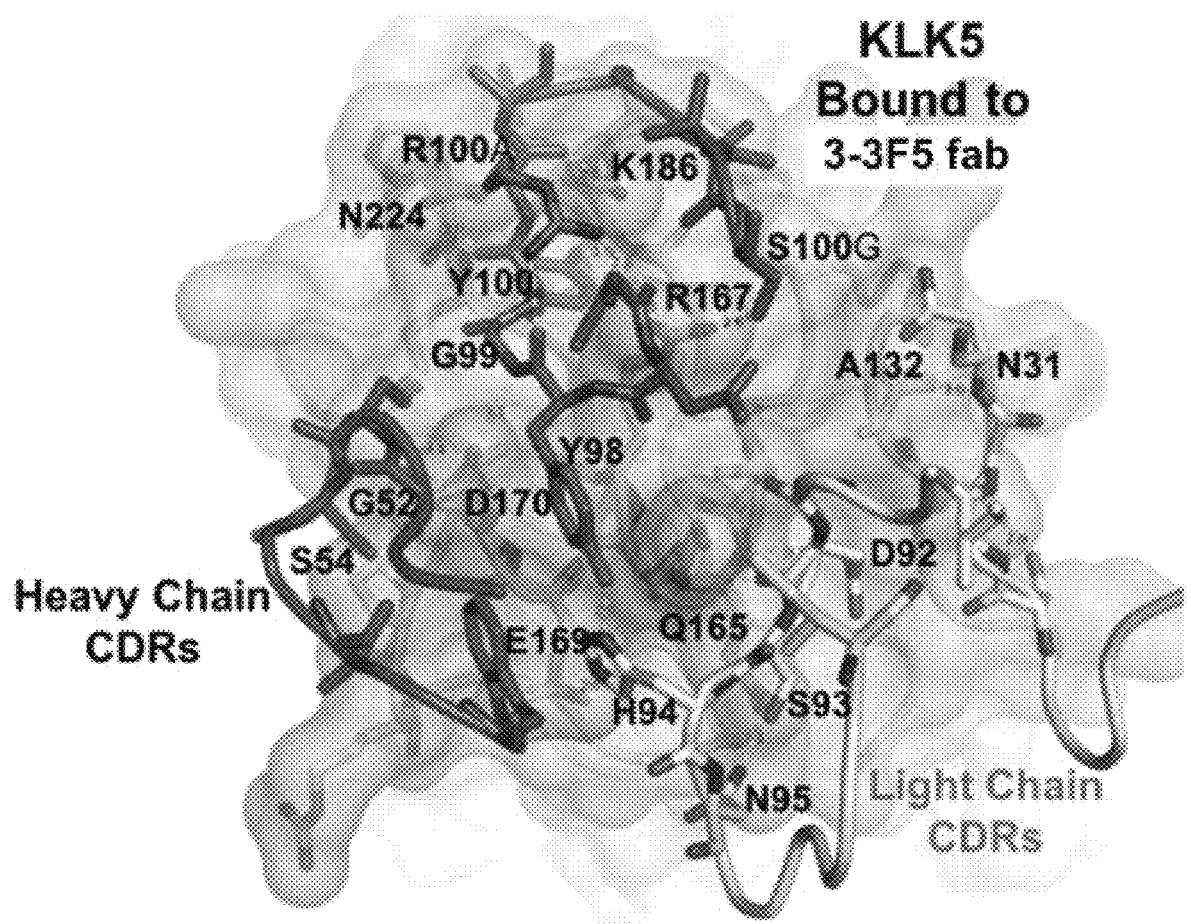

The 3-3F5 Fab/KLK5 complex structure shows that the binding of the 3-3F5 to KLK5 results in slight conformational changes, although not as drastic as observed with the 10C5 or the 9H5 complexes with KLK5. The substrate recognition pocket is altered, where the Asp 189 in KLK5, (which forms a salt bridge and thereby recognizing positively charged P1-residue (Arg/Lys) before proteolysis) becomes disordered. The catalytic triad in KLK5 appears intact, although the fab binding renders the catalytic pocket more open, resulting in KLK5 losing catalytic activity. The 140s loop and 70s loop are disordered in the crystal structure (FIG. 20A).

The buried surface area between KLK5 and 3F5.5 Fab is 956 Å$^2$. In the 3-3F5 light chain, CDRL1, residues Q24-A34 contact S131, A132 and G133 in KLK5; CDRL2, residues D50-S56 does not contact any residues in KLK5; CDRL3, residues Q89-I97 contact residues S164, Q165, K166 and E169 in KLK5. In the 3F5.5 heavy chain, CDRH1 residues D31-E46 does not interact with KLK5 at all, neither does CDRH2; CDRH3, residues D95-G100i contact residues L163, S164, K166, R167, D170, G184, D185, K186, A187, N224, R225 and P225 in KLK5 (Tables 11-13, FIG. 20B).

The sequences of the 3-3F5 Fab HC and LC used for the crystallization with human KLK5 is depicted in SEQ ID NO:326 and SEQ ID NO:327, respectively.

TABLE 11

| Interface residues in 3-3F5 Heavy Chain (Kabat Numbering) | Interface residues in KLK5 (Standard Protease Numbering) | Interface residues in 3-3F5 Light Chain (Kabat Numbering) | Interface residues in KLK5 (Standard Protease Numbering) |
|---|---|---|---|
| Asp 31 | Leu 163 | Ile 2 | Ser 131 |
| Trp 47 | Ser 164 | Ser 28 | Ala 132 |
| Gly 52 | Lys 166 | Ile 29 | Gly 133 |
| Ser 53 | Arg 167 | Gly 30 | Ser 164 |
| Ser 54 | Glu 169 | Asn 31 | Gln 165 |
| Val 56 | Asp 170 | Ala 32 | Lys 166 |
| Trp 58 | Ala 171 | Asp 50 | Arg 167 |
| Asp 95 | Pro 173 | Gly 68 | Glu 169 |
| Arg 96 | Arg 174 | Gln 89 | Asp 170 |
| Asp 97 | Gly 184 | Gln 90 | |
| Tyr 98 | Asp 185 | Gly 91 | |
| Gly 99 | Lys 186 | Asp 92 | |
| Tyr 100 | Ala 186A | Ser 93 | |
| Arg 100A | Arg 188 | His 94 | |
| Ala 100B | Asn 223 | Asn 95 | |
| Asp 100C | Arg 224 | Ile 97 | |
| Ala 100E | Pro 225 | | |
| Thr 100F | | | |
| Ser 100G | | | |
| Met 100I | | | |

TABLE 12

| Hydrogen Bonds | | | | | |
|---|---|---|---|---|---|
| Heavy Chain Residue | Bond Length (Angstrom) | KLK5 residue | Light Chain Residue | Bond Length (Angstrom) | KLK5 residue |
| Ser 53 [N] | 3.0 | Asp 170 [OD1] | Ser 28 [OG] | 2.9 | Ser 131 [OG] |
| Ser 54 [N] | 3.0 | Asp 170 [OD1] | Asp 92 [OD1] | 3.7 | Gln 165 [N] |
| Ser 54 [OG] | 2.8 | Asp 170 [OD1] | Asp 92 [O] | 3.1 | Gln 165 [N] |
| Gly 99 [N] | 3.1 | Asp 170 [OD2] | Asp 92 [O] | 3.0 | Lys 166 [N] |
| Ser 53 [N] | 3.1 | Asp 170 [OD2] | Asn 31 [N] | 3.6 | Ala 132 [O] |
| Ser 53 [OG] | 3.0 | Asp 170 [OD2] | Asn 95 [ND2] | 3.1 | Gln 165 [OE] |
| Ala 100B [N] | 2.8 | Asn 223 [OD1] | | | |
| Thr 100F [O] | 3.9 | Arg 167 [NH1] | | | |

TABLE 12-continued

Hydrogen Bonds

| Heavy Chain Residue | Bond Length (Angstrom) | KLK5 residue | Light Chain Residue | Bond Length (Angstrom) | KLK5 residue |
|---|---|---|---|---|---|
| Arg 96 [O] | 2.8 | Arg 167 [NH1] | | | |
| Ser 100G [OG] | 2.8 | Arg 167 [NH2] | | | |
| Tyr 100 [OH] | 2.9 | Asp 185 [N] | | | |
| Tyr 100 [OH] | 3.7 | Lys 186 [N] | | | |
| Arg 100A [O] | 2.8 | Lys 186 [NZ] | | | |
| Tyr 100 [O] | 3.0 | Asn 223 [ND2] | | | |

TABLE 13

Salt Bridges

| Heavy Chain Residue | Bond Length (Angstrom) | KLK5 residue |
|---|---|---|
| His 94 [NE2] | 2.8 | Glu 169 [OE1] |
| His 94 [NE2] | 3.9 | Glu 169 [OE2] |

Table of Sequences

| NAME | SEQUENCE | SEQ ID NO |
|---|---|---|
| Human KLK5 Q9Y337 G55, D153 (incl. signal peptide (underlined)) | MATARPPWMWVLCALITALLLGVTEHVLANNDVSCDHPSNTVPSGSNQDLGAGAGE DARSDDSSSRIINGSDCDMHTQPWQAALLLRPNQLYCGAVLVHPQWLLTAAHCRKK VFRVRLGHYSLSPVYESGQQMFQGVKSIPHPGYSHPGHSNDLMLIKLNRRIRPTKD VRPINVSSHCPSAGTKCLVSGWGTTKSPQVHFPKVLQCLNISVLSQKRCEDAYPRQ IDDTMFCAGDKAGRDSCQGDSGGPVVCNGSLQGLVSWGDYPCARPNRPGVYTNLCK FTKWIQETIQANS | 1 |
| Human KLK5 G55, D153 (mature form) | VTEHVLANNDVSCDHPSNTVPSGSNQDLGAGAGEDARSDDSSSRIINGSDCDMHTQ PWQAALLLRPNQLYCGAVLVHPQWLLTAAHCRKKVFRVRLGHYSLSPVYESGQQMF QGVKSIPHPGYSHPGHSNDLMLIKLNRRIRPTKDVRPINVSSHCPSAGTKCLVSGW GTTKSPQVHFPKVLQCLNISVLSQKRCEDAYPRQIDDTMFCAGDKAGRDSCQGDSG GPVVCNGSLQGLVSWGDYPCARPNRPGVYTNLCKFTKWIQETIQANS | 2 |
| Human KLK5 G55, N153 (incl. signal peptide (underlined)) | MATARPPWMWVLCALITALLLGVTEHVLANNDVSCDHPSNTVPSGSNQDLGAGAGE DARSDDSSSRIINGSDCDMHTQPWQAALLLRPNQLYCGAVLVHPQWLLTAAHCRKK VFRVRLGHYSLSPVYESGQQMFQGVKSIPHPGYSHPGHSNNLMLIKLNRRIRPTKD VRPINVSSHCPSAGTKCLVSGWGTTKSPQVHFPKVLQCLNISVLSQKRCEDAYPRQ IDDTMFCAGDKAGRDSCQGDSGGPVVCNGSLQGLVSWGDYPCARPNRPGVYTNLCK FTKWIQETIQANS | 3 |
| Human KLK5 G55, N153 (mature form) | VTEHVLANNDVSCDHPSNTVPSGSNQDLGAGAGEDARSDDSSSRIINGSDCDMHTQ PWQAALLLRPNQLYCGAVLVHPQWLLTAAHCRKKVFRVRLGHYSLSPVYESGQQMF QGVKSIPHPGYSHPGHSNNLMLIKLNRRIRPTKDVRPINVSSHCPSAGTKCLVSGW GTTKSPQVHFPKVLQCLNISVLSQKRCEDAYPRQIDDTMFCAGDKAGRDSCQGDSG GPVVCNGSLQGLVSWGDYPCARPNRPGVYTNLCKFTKWIQETIQANS | 4 |
| Human KLK5 R55, N153 (incl. signal peptide (underlined)) | MATARPPWMWVLCALITALLLGVTEHVLANNDVSCDHPSNTVPSGSNQDLGAGARE DARSDDSSSRIINGSDCDMHTQPWQAALLLRPNQLYCGAVLVHPQWLLTAAHCRKK VFRVRLGHYSLSPVYESGQQMFQGVKSIPHPGYSHPGHSNNLMLIKLNRRIRPTKD VRPINVSSHCPSAGTKCLVSGWGTTKSPQVHFPKVLQCLNISVLSQKRCEDAYPRQ IDDTMFCAGDKAGRDSCQGDSGGPVVCNGSLQGLVSWGDYPCARPNRPGVYTNLCK FTKWIQETIQANS | 5 |
| Human KLK5 R55, N153 (mature form) | VTEHVLANNDVSCDHPSNTVPSGSNQDLGAGAREDARSDDSSSRIINGSDCDMHTQ PWQAALLLRPNQLYCGAVLVHPQWLLTAAHCRKKVFRVRLGHYSLSPVYESGQQMF QGVKSIPHPGYSHPGHSNNLMLIKLNRRIRPTKDVRPINVSSHCPSAGTKCLVSGW GTTKSPQVHFPKVLQCLNISVLSQKRCEDAYPRQIDDTMFCAGDKAGRDSCQGDSG GPVVCNGSLQGLVSWGDYPCARPNRPGVYTNLCKFTKWIQETIQANS | 6 |
| Human KLK5 R55, D153 (incl. signal peptide (underlined)) | MATARPPWMWVLCALITALLLGVTEHVLANNDVSCDHPSNTVPSGSNQDLGAGARE DARSDDSSSRIINGSDCDMHTQPWQAALLLRPNQLYCGAVLVHPQWLLTAAHCRKK VFRVRLGHYSLSPVYESGQQMFQGVKSIPHPGYSHPGHSNDLMLIKLNRRIRPTKD VRPINVSSHCPSAGTKCLVSGWGTTKSPQVHFPKVLQCLNISVLSQKRCEDAYPRQ IDDTMFCAGDKAGRDSCQGDSGGPVVCNGSLQGLVSWGDYPCARPNRPGVYTNLCK FTKWIQETIQANS | 7 |

| | Table of Sequences | |
|---|---|---|
| NAME | SEQUENCE | SEQ ID NO |
| Human KLK5 R55, D153 (mature form) | VTEHVLANNDVSCDHPSNTVPSGSNQDLGAGAREDARSDDSSSRIINGSDCDMHTQ PWQAALLLRPNQLYCGAVLVHPQWLLTAAHCRKKVFRVRLGHYSLSPVYESGQQMF QGVKSIPHPGYSHPGHSNDLMLIKLNRRIRPTKDVRPINVSSHCPSAGTKCLVSGW GTTKSPQVHFPKVLQCLNISVLSQKRCEDAYPRQIDDTMFCAGDKAGRDSCQGDSG GPVVCNGSLQGLVSWGDYPCARPNRPGVYTNLCKFTKWIQETIQANS | 8 |
| Human SPINK5 Q9NQ38 (incl. signal peptide (underlined)) | MKIATVSVLLPLALCLIQDAASKNEDQEMCHEFQAFMKNGKLFCPQDKKFFQSLDG IMFINKCATCKMILEKEAKSQKRARHLARAPKATAPTELNCDDFKKGERDGDFICP DYYEAVCGTDGKTYDNRCALCAENAKTGSQIGVKSEGECKSSNPEQDVCSAFRPFV RDGRLGCTRENDPVLGPDGKTHGNKCAMCAELFLKEAENAKREGETRIRRNAEKDF CKEYEKQVRNGRLFCTRESDPVRGPDGRMHGNKCALCAEIFKQRFSEENSKTDQNL GKAEEKTKVKREIVKLCSQYQNQAKNGILFCTRENDPIRGPDGKMHGNLCSMCQAY FQAENEEKKKAEARARNKRESGKATSYAELCSEYRKLVRNGKLACTRENDPIQGPD GKVHGNTCSMCEVFFQAEEEEKKKKEGKSRNKRQSKSTASFEELCSEYRKSRKNGR LFCTRENDPIQGPDKMHGNTCSMCEAFFQQEERARAKAKREAAKEICSEFRDQVR NGTLICTREHNPVRGPDKMHGNKCAMCASVFKLEEEEKKNDKEEKGKVEAEKVKR EAVQELCSEYRHYVRNGRLPCTRENDPIEGLDGKIHGNTCSMCEAFFQQEAKEKER AEPRAKVKREAEKETCDEFRRLLQNGKLFCTRENDPVRGPDGKTHGNKCAMCKAVF QKENEERKRKEEEDQRNAAGHGSSGGGGGNTQDECAEYREQMKNGRLSCTRESDPV RDADGKSYNNQCTMCKAKLEREAERKNEYSRSRSNGTGSESGKDTCDEFRSQMKNG KLICTRESDPVRGPDGKTHGNKCTMCKEKLEREAAEKKKKEDEDRSNTGERSNTGE RSNDKEDLCREFRSMQRNGKLICTRENNPVRGPYGKMHINKCAMCQSIFDREANER KKKDEEKSSSKPSNNAKDECSEFRNYIRNNELICPRENDPVHGADGKFYTNKCYMC RAVFLTEALERAKLQEKPSHVRASQEEDSPDSFSSLDSEMCKDYRVLPRIGYLCPK DLKPVCGDDGQTYNNPCMLCHENLIRQTNTHIRSTGKCEESSTPGTTAASMPPSDE | 9 |
| Human SPINK5 (mature form) | KNEDQEMCHEFQAFMKNGKLFCPQDKKFFQSLDGIMFINKCATCKMILEKEAKSQK RARHLARAPKATAPTELNCDDFKKGERDGDFICPDYYEAVCGTDGKTYDNRCALCA ENAKTGSQIGVKSEGECKSSNPEQDVCSAFRPFVRDGRLGCTRENDPVLGPDGKTH GNKCAMCAELFLKEAENAKREGETRIRRNAEKDFCKEYEKQVRNGRLFCTRESDPV RGPDGRMHGNKCALCAEIFKQRFSEENSKTDQNLGKAEEKTKVKREIVKLCSQYQN QAKNGILFCTRENDPIRGPDGKMHGNLCSMCQAYFQAENEEKKKAEARARNKRESG KATSYAELCSEYRKLVRNGKLACTRENDPIQGPDGKVHGNTCSMCEVFFQAEEEEK KKKEGKSRNKRQSKSTASFEELCSEYRKSRKNGRLFCTRENDPIQGPDKMHGNTC SMCEAFFQQEERARAKAKREAAKEICSEFRDQVRNGTLICTREHNPVRGPDKMHG NKCAMCASVFKLEEEEKKNDKEEKGKVEAEKVKREAVQELCSEYRHYVRNGRLPCT RENDPIEGLDGKIHGNTCSMCEAFFQQEAKEKERAEPRAKVKREAEKETCDEFRRL LQNGKLFCTRENDPVRGPDGKTHGNKCAMCKAVFQKENEERKRKEEEDQRNAAGHG SSGGGGGNTQDECAEYREQMKNGRLSCTRESDPVRDADGKSYNNQCTMCKAKLERE AERKNEYSRSRSNGTGSESGKDTCDEFRSQMKNGKLICTRESDPVRGPDGKTHGNK CTMCKEKLEREAAEKKKKEDEDRSNTGERSNTGERSNDKEDLCREFRSMQRNGKLI CTRENNPVRGPYGKMHINKCAMCQSIFDREANERKKKDEEKSSSKPSNNAKDECSE FRNYIRNNELICPRENDPVHGADGKFYTNKCYMCRAVELTEALERAKLQEKPSHVR ASQEEDSPDSFSSLDSEMCKDYRVLPRIGYLCPKDLKPVCGDDGQTYNNPCMLCHE NLIRQTNTHIRSTGKCEESSTPGTTAASMPPSDE | 10 |
| HVR-H1 Sequences | | |
| HVR-H1 14C8 | DYNMA | 11 |
| HVR-H1 14E12 | DYYMA | 12 |
| HVR-H1 8E11 | SSYWIC | 13 |
| HVR-H1 8G10 | TSYWIC | 14 |
| HVR-H1 9B6 | NYGVT | 15 |
| HVR-H1 2.3F4 | NYGVS | 16 |
| HVR-H1 10C5, hu10C5-H1 to hu10C5-H28 | SYGVT | 17 |
| HVR-H1 2B11 | NYGVS | 18 |

Table of Sequences

| NAME | SEQUENCE | SEQ ID NO |
|---|---|---|
| HVR-H1 10H3 | TFAIN | 19 |
| HVR-H1 9H3 | GYGVS | 20 |
| HVR-H1 8B7 | NYGVT | 21 |
| HVR-H1 9F2, 10C8, 9H5, hu9H5-H1 to hu9H5-H17 | SYGVS | 22 |
| HVR-H1 8F5 | SYPIS | 23 |
| HVR-H1 3-3F5, hu3-3F5-H1 to hu3-3F5-H27 | DYGVS | 24 |
| HVR-H1 9E3 | NNYVNFVMC | 25 |
| HVR-H1 10D10 | DNYVMS | 26 |
| HVR-H1 12B3, 1D10 | GGGIY | 27 |
| HVR-H1 10C5, hu10C5-H1 to hu10C5-H28, 9H5, hu9H5-H1 to hu9H5-H17, 3-3F5, hu3-3F5-H1 to hu3-3F5-H27 (consensus) | $X_1$YGV$X_2$ wherein $X_1$ is S or D, $X_2$ is T or S | 28 |
| HVR-H2 Sequences | | |
| HVR-H2 14C8 | TISYDAGRTYYRDSVKG | 29 |
| HVR-H2 14E12 | SISYDGDTTYYRDSVKG | 30 |
| HVR-H2 8E11 | CVYGLDVNIYYASWTK | 31 |
| HVR-H2 8G10 | CVYGLDVNIYYASWTE | 32 |
| HVR-H2 9B6, 9H3 | FIGSGGSAYYASWAKS | 33 |
| HVR-H2 2.3F4 | FIGYGGSTYYASWAKS | 34 |

-continued

Table of Sequences

| NAME | SEQUENCE | SEQ ID NO |
|---|---|---|
| HVR-H2 10C5, hu10C5-H1 to hu10C5-H10, hu10C5-H12, hu10C5-H14 to hu10C5-H16, hu10C5-H18 to hu10C5-H28 | YITSNYGVSYYASWAKS | 35 |
| HVR-H2 hu10C5-H11 hu10C5-H13 | YITSNYGVSYYANSVKG | 36 |
| HVR-H2 hu10C5-H17 | YITSNYGVSYYASFAKS | 37 |
| HVR-H2 hu10C5-H1 to hu10C5-H28 (consensus) | YITSNYGVSYYAX$_1$X$_2$X$_3$KX$_4$ wherein X$_1$ is S or N, X$_2$ is W, S or F, X$_3$ is A or V, X$_4$ is S or G | 38 |
| HVR-H2 2B11 | YIGSAGSTYYATWAKS | 39 |
| HVR-H2 10H3 | AIGRGGSAYYASWAKS | 40 |
| HVR-H2 8B7 | FIGSSGSAYYASWAKS | 41 |
| HVR-H2 10C8, 9H5, hu9H5-H1 to hu9H5-H10, hu9H5-H12, hu9H5-H14 to hu9H5-H16 | FIGSGGFAYYASWAKS | 42 |
| HVR-H2 hu9H5-H11, hu9H5-H13 | FIGSGGFAYYADSVKG | 43 |
| HVR-H2 hu9H5-H17 | FIGSGGFAYYASFAKS | 44 |
| HVR-H2 hu9H5-H1 to hu9H5-H17 (consensus) | FIGSGGFAYYAX$_1$X$_2$X$_3$KX$_4$ wherein X$_1$ is S or D, X$_2$ is W, S or F, X$_3$ is A or V, X$_4$ is S or G | 45 |
| HVR-H2 9F2 | FIGSGGSPYYASWAKS | 46 |
| HVR-H2 8F5 | YITSEYGVAYYATWAES | 47 |
| HVR-H2 3-3F5, hu3-3F5-H1 to hu3-3F5-H9, hu3-3F5-H14, hu3-3F5-H16, hu3-3F5-H17 | AIGSSGVAWYANWAKG | 48 |
| HVR-H2 hu3-3F5-H10, hu3-3F5-H12, hu3-3F5-H15 | AIGSSGVAFYANWAKG | 49 |
| HVR-H2 hu3-3F5-H11, | AIGSSGVAWYADSVKG | 50 |

Table of Sequences

| NAME | SEQUENCE | SEQ ID NO |
|---|---|---|
| HVR-H2 hu3-3F5-H13 | AIGSSGVAFYADSVKG | 51 |
| HVR-H2 hu3-3F5-H18 to hu3-3F5-H26 | AIGSSGVAWYANFAKG | 52 |
| HVR-H2 hu3-3F5-H27 | AIGSSGVAFYANFAKG | 53 |
| HVR-H2 hu3-3F5-H1 to hu3-3F5-H27 (consensus) | AIGSSGVAX$_1$YAX$_2$X$_3$X$_4$KG wherein X$_1$ is W or F, X$_2$ is N or D, X$_3$ is W, S or F, X$_4$ is A or V | 54 |
| HVR-H2 9E3 | SIDPGDDSTDYASWAT | 55 |
| HVR-H2 10D10 | CIDPGDDSTYYASWAT | 56 |
| HVR-H2 12B3 | SIYPDHGSVDYANWVNG | 57 |
| HVR-H2 1D10 | YIYPDHGSADYATWVNG | 58 |
| HVR-H2 9H5, hu9H5-H1 to hu9H5-H17, 3-3F5, hu3-3F5-H1 to hu3-3F5-H27 (consensus) | X$_1$IGSX$_2$GX$_3$AX$_4$YAX$_5$X$_6$X$_7$KX$_8$ wherein X$_1$ is F or A, X$_2$ is G or S, X$_3$ is F or V, X$_4$ is Y, W, or F, X$_5$ is S, D, or N, X$_6$ is W, S, or F, X$_7$ is A or V, X$_8$ is S or G | 59 |

HVR-H3 Sequences

| NAME | SEQUENCE | SEQ ID NO |
|---|---|---|
| HVR-H3 14C8 | GIFNYGTDYFDY | 60 |
| HVR-H3 14E12 | DGTIPAGSWFAY | 61 |
| HVR-H3 8E11, 8G10 | GGGSADFGFDL | 62 |
| HVR-H3 9B6 | DDVGGGKSLDI | 63 |
| HVR-H3 2.3F4 | LCGVDCADALDS | 64 |
| HVR-H3 10C5 hu10C5-H1 to hu10C5-H28 | ENPDYGYAYDA | 65 |
| HVR-H3 2B11 | AAYSAGSADAEDI | 66 |
| HVR-H3 10H3 | ENAGSGWGELDI | 67 |
| HVR-H3 9H3 | DNVGGDMSLDI | 68 |

-continued

Table of Sequences

| NAME | SEQUENCE | SEQ ID NO |
|---|---|---|
| HVR-H3 8B7, 9F2, 9H5 hu9H5-H1 to hu9H5-H17 | DDVGGGKSLDI | 69 |
| HVR-H3 10C8 | DDVGGGRSLDI | 70 |
| HVR-H3 8F5 | ENPTYGYAYDA | 71 |
| HVR-H3 3-3F5, hu3-3F5-H1 to hu3-3F5-H27 | DRDYGYRADDATSGMDL | 72 |
| HVR-H3 9E3 | GDAGTSYSFNF | 73 |
| HVR-H3 10D10 | GDAAASYSFNF | 74 |
| HVR-H3 12B3 | ESGGSYYDL | 75 |
| HVR-H3 1D10 | ETGGSWYDL | 76 |

HVR-L1 Sequences

| NAME | SEQUENCE | SEQ ID NO |
|---|---|---|
| HVR-L1 14C8 | RASEDIYSGLA | 77 |
| HVR-L1 14E12 | LASKNIYRNLA | 78 |
| HVR-L1 8E11, 8G10 | QASENIYSLLA | 79 |
| HVR-L1 9B6 | QASQNIGDYLS | 80 |
| HVR-L1 2.3F4 | QASEDIGSYCS | 81 |
| HVR-L1 10C5, hu10C5-L1 to hu10C5-L6 | QASESISNELS | 82 |
| HVR-L1 2B11 | QASQSISNYVA | 83 |
| HVR-L1 10H3 | QASESISSDLA | 84 |
| HVR-L1 9H3 | QASQNINNYLS | 85 |
| HVR-L1 8B7 | QASQSIGSYLS | 86 |
| HVR-L1 9H5, hu9H5-L1 to hu9H5-L4 | QASQSISSYLS | 87 |
| HVR-L1 9F2 | QASQSISNYLS | 88 |

-continued

Table of Sequences

| NAME | SEQUENCE | SEQ ID NO |
|---|---|---|
| HVR-L1 10C8 | QASQSISTYLS | 89 |
| HVR-L1 8F5 | QASESIGNELS | 90 |
| HVR-L1 3-3F5, hu3-3F5-L1 to hu3-3F5-L5 | QASESIGNALA | 91 |
| HVR-L1 9E3 | QASESISRYLS | 92 |
| HVR-L1 10D10 | QASESISTYLS | 93 |
| HVR-L1 12B3 | QASQSISTYLA | 94 |
| HVR-L1 1D10 | QASQSISSYLA | 95 |
| HVR-L1 10C5, hu10C5-L1 to hu10C5-L6, 9H5, hu9H5-L1 to hu9H5-L4, 3-3F5, hu3-3F5-L1 to hu3-3F5-L5 (consensus) | QASX$_1$SIX$_2$X$_3$X$_4$LX$_5$ wherein X$_1$ is E or Q, X$_2$ is S or G, X$_3$ is N or S, X$_4$ is E, Y or A, X$_5$ is S or A | 96 |
| HVR-L2 Sequences | | |
| HVR-L2 14C8 | GATTLHD | 97 |
| HVR-L2 14E12 | DASRLQD | 98 |
| HVR-L2 8E11, 8G10, 2.3F4, 9E3, 10D10, 3-3F5, hu3-3F5-L1 to hu3-3F5-L5 | DASDLAS | 99 |
| HVR-L2 9B6 | SASTLAS | 100 |
| HVR-L2 10C5, hu10C5-L1 to hu10C5-L6 | YASTLAS | 101 |
| HVR-L2 2B11 | RASTLAS | 102 |
| HVR-L2 10H3, 9H3 | AASTLAS | 103 |
| HVR-L2 8B7 | DASNLAS | 104 |

-continued

Table of Sequences

| NAME | SEQUENCE | SEQ ID NO |
|---|---|---|
| HVR-L2 9F2 10C8 9H5, hu9H5-L1 to hu9H5-L4 | SASTLAS | 105 |
| HVR-L2 8F5 | QASTLAS | 106 |
| HVR-L2 12B3 | KTSTLAS | 107 |
| HVR-L2 1D10 | KASTLAS | 108 |
| HVR-L2 10C5, hu10C5-L1 to hu10C5-L6 9H5, hu9H5-L1 to hu9H5-L4, 3-3F5, hu3-3F5-L1 to hu3-3F5-L5 (consensus) | $X_1$AS$X_2$LAS wherein $X_1$ is Y, S or D, $X_2$ is T or D | 109 |

HVR-L3 Sequences

| NAME | SEQUENCE | SEQ ID NO |
|---|---|---|
| HVR-L3 14C8 | HQGLSFPYT | 110 |
| HVR-L3 14E12 | QQYHDYPYT | 111 |
| HVR-L3 8E11, 8G10 | QATAYGSSGNA | 112 |
| HVR-L3 9B6 | HQDYTSNDVENT | 113 |
| HVR-L3 2.3F4 | QQDYTGNNVDNT | 114 |
| HVR-L3 10C5, hu10C5-L1 to hu10C5-L6 | AQGFGSSGVENV | 115 |
| HVR-L3 2B11 | HQGYSSSNVDNI | 116 |
| HVR-L3 10H3 | QQGYTWNNVDNV | 117 |
| HVR-L3 9H3, 8B7, 10C8 | HQDYTSNNVDNT | 118 |
| HVR-L3 9H5, hu9H5-L1 to hu9H5-L4 | HQDYTSSNVDNT | 119 |
| HVR-L3 9F2 | HQDYTSNSVDNT | 120 |
| HVR-L3 8F5 | AQGFSSSGVENV | 121 |

Table of Sequences

| NAME | SEQUENCE | SEQ ID NO |
|---|---|---|
| HVR-L3 3-3F5, hu3-3F5-L1 to hu3-3F5-L5 | QQGDSHNNVDNI | 122 |
| HVR-L3 9E3 | QQDYSRSNIVNS | 123 |
| HVR-L3 10D10 | QQDYSSSNIVNS | 124 |
| HVR-L3 12B3 | QQGYSGSSVENT | 125 |
| HVR-L3 1D10 | QQGYSGSNVENT | 126 |
| HVR-L3 10C5, hu10C5-L1 to hu10C5-L6 9H5, hu9H5-L1 to hu9H5-L4, 3-3F5, hu3-3F5-L1 to hu3-3F5-L5 (consensus) | $X_1QX_2X_3X_4X_5X_6X_7VX_8NX_9$ wherein $X_1$ is A, H or Q, $X_2$ is G or D, $X_3$ is F, Y or D, $X_4$ is G, T or S, $X_5$ is S or H, $X_6$ is S or N, $X_7$ is G or N, $X_8$ is E or D, $X_9$ is V, T or I | 127 |

VL Sequences (HVRs underlined)

| NAME | SEQUENCE | SEQ ID NO |
|---|---|---|
| VL 14C8 | DIQMTQSPASLSASLGETVTIQC<u>RASEDIYSGLA</u>WYQQKPGKSPQLLIY<u>GATTLHD</u>GVPSRFSGSGSGTQYSLKISSMHSEDEGIYFC<u>HQGLSFPYT</u>FGAGTKLELK | 128 |
| VL 14E12 | DIQMTQSPASLSASLGETVTIEC<u>LASKNIYRNLA</u>WYQQKPGKSPQFLIS<u>DASRLQD</u>GVPSRFTGSDSGSQYSLKINSLQSEDVATYFC<u>QQYHDYPYT</u>FGAGTKLELK | 129 |
| VL 8E11 | DVVMTQTASPVSAAVGGTVTIKC<u>QASENIYSLLA</u>WYQQKPGQPPKVLIY<u>DASDLAS</u>GVPSRFKGSGSGTQFTLTISDLECADAATYYC<u>QATAYGSSGNAF</u>GGGTEVVVK | 130 |
| VL 8G10 | DVVMTQTPASVSEPVGGTVTIKC<u>QASENIYSLLA</u>WYQQKPGQPPKVLIY<u>DASDLAS</u>GVPSRFKGSGSGTQFTLTISDLECADAATYYC<u>QATAYGSSGNAF</u>GGGTEVVVK | 131 |
| VL 9B6 | NIVMTQTPASVEVAVGGTVVIKC<u>QASQNIGDYLS</u>WYQQKPGQRPKLLIY<u>SASTLAS</u>GVPSRFKGSGSGTQFTLTISDLECADAATYYC<u>HQDYTSNDVENT</u>FGGGTEVVVK | 132 |
| VL 2.3F4 | AYYMTQTPASVEVAVGGTVTIKC<u>QASEDIGSYCS</u>WYQQKPGQPPKLLIY<u>DASDLAS</u>GVPSRFKGSGSGTDFTLTISGVQCDDAATYYC<u>QQDYTGNNVDNT</u>FGGGSEVVVK | 133 |
| VL 10C5 | AYDMTQTPASLEAAVGGTVTINC<u>QASESISNELS</u>WYQQKPGQPPDLLIY<u>YASTLAS</u>GVPSRFKGSGSGTEFTLTISDLECADAATYYC<u>AQGFGSSGVENV</u>FGGGTEVVVK | 134 |
| VL hu10C5-L1 | AYRMTQSPSSFSASTGDRVTITC<u>QASESISNELS</u>WYQQKPGKPPKLLIY<u>YASTLAS</u>GVPSRFSGSGSGTDFTLTISCLQSEDFATYYC<u>AQGFGSSGVENV</u>FGGGTKVEIK | 135 |
| VL hu10C5-L2 | AIRMTQSPSSFSASTGDRVTITC<u>QASESISNELS</u>WYQQKPGKPPKLLIY<u>YASTLAS</u>GVPSRFSGSGSGTDFTLTISCLQSEDFATYYC<u>AQGFGSSGVENV</u>FGGGTKVEIK | 136 |
| VL hu10C5-L3 | AYRMTQSPSSFSASTGDRVTITC<u>QASESISNELS</u>WYQQKPGKAPKLLIY<u>YASTLAS</u>GVPSRFSGSGSGTDFTLTISCLQSEDFATYYC<u>AQGFGSSGVENV</u>FGGGTKVEIK | 137 |
| VL hu10C5-L4 | AIRMTQSPSSFSASTGDRVTITC<u>QASESISNELS</u>WYQQKPGKAPKLLIY<u>YASTLAS</u>GVPSRFSGSGSGTDFTLTISCLQSEDFATYYC<u>AQGFGSSGVENV</u>FGGGTKVEIK | 138 |
| VL hu10C5-L5 | AIRMTQSPSSFSASTGDRVTITC<u>QASESISNELS</u>WYQQKPGKAPKLLIY<u>YASTLAS</u>GVPSRFSGSGSGTDFTLTISSLQPEDFATYYC<u>AQGFGSSGVENV</u>FGGGTKVEIK | 139 |
| VL 10C5, hu10C5-L1 to hu10C5-L6 (consensus) | $AX_1RMTQSPSSFSASTGDRVTITC$<u>$QASESISNELS$</u>$WYQQKPGKX_2PKLLIY$<u>$YASTLA$</u>$SGVPSRFSGSGSGTDFTLTISX_3LQX_4EDFATYYC$<u>$AQGFGSSGVENV$</u>$FGGGTX_5VX_6X_7K$ wherein $X_1$ is Y or I, $X_2$ is P or A, $X_3$ is C or S, $X_4$ is S or P, $X_5$ is E or K, $X_6$ is E or V, $X_7$ is I or V | 140 |

-continued

Table of Sequences

| NAME | SEQUENCE | SEQ ID NO |
|------|----------|-----------|
| VL 2B11 | AYYMTQTPASVEAAVGGTVTIKCQASQSISNYVAWYQQKPGQPPKLLIYRASTLAS GVSSRFSGSGSGTEFTLTISDLECADAATYYCHQGYSSSNVDNIFGGGTEVVVK | 141 |
| VL 10H3 | AYEMTQTPASVEVAVGGTVTINCQASESISSDLAWYQQKPGQRPKLLIYAASTLAS GVPSRFKGSGSGTEFTLSISGVQCADAATYYCQQGYTWNNVDNVFGGGTEVVVK | 142 |
| VL 9H3 | DIVMTQTPASVSEPVGGTVTIKCQASQNINNYLSWYQQKPGQPPKQLIYAASTLAS GVPSRFKGSGSGTQFTLTISDLECADAATYYCHQDYTSNNVDNTFGGGTEVVVK | 143 |
| VL 8B7 | NIVMTQTPASVEVAVGGTVTIKCQASQSIGSYLSWYQQKPGQPPKLLIYDASNLAS GVPSRFKGSGSGTQFTLSISDLECADAATYYCHQDYTSNNVDNTFGGGTEVVIK | 144 |
| VL 9H5 | NIVMTQTPASVEAVGGTVTINCQASQSISSYLSWYQQKSGQRPKLLIFSASTLAS GVPSRFTGSGSGTQFTLTISDLQCADAATYYCHQDYTSSNVDNTFGGGTEVVVK | 145 |
| VL hu9H5-L1 | DIQMTQSPSSLSASVGDRVTITCQASQSISSYLSWYQQKPGKRPKLLIFSASTLAS GVPSRFSGSGSGTDFTLTISSLQPEDFATYYCHQDYTSSNVDNTFGGGTKVEIK | 146 |
| VL hu9H5-L2 | DIQMTQSPSSLSASVGDRVTITCQASQSISSYLSWYQQKPGKAPKLLIFSASTLAS GVPSRFSGSGSGTDFTLTISSLQPEDFATYYCHQDYTSSNVDNTFGGGTKVEIK | 147 |
| VL hu9H5-L3 | DIQMTQSPSSLSASVGDRVTITCQASQSISSYLSWYQQKPGKRPKLLIYSASTLAS GVPSRFSGSGSGTDFTLTISSLQPEDFATYYCHQDYTSSNVDNTFGGGTKVEIK | 148 |
| VL hu9H5-L4 | DIQMTQSPSSLSASVGDRVTITCQASQSISSYLSWYQQKPGKAPKLLIYSASTLAS GVPSRFSGSGSGTDFTLTISSLQPEDFATYYCHQDYTSSNVDNTFGGGTKVEIK | 149 |
| VL hu9H5-L5 | DIQMTQSPSSLSASVGDRVTITCQASQSISSYLSWYQQKPGKAPKLLIYSASTLAS GVPSRFSGSGSGTDFTLTISSLQPEDFATYYCHQDYTSSNVDNTFGGGTEVVVK | 150 |
| VL 9H5, hu9H5-L1 to hu9H5-L5 (consensus) | DIQMTQSPSSLSASVGDRVTITCQASQSISSYLSWYQQKPGKX$_1$PKLLIX$_2$SASTLA SGVPSRFSGSGSGTDFTLTISSLQPEDFATYYCHQDYTSSNVDNTFGGGTX$_3$VX$_4$X$_5$K wherein X$_1$ is R or A, X$_2$ is F or Y, X$_3$ is E or K, X$_4$ is E or V, X$_5$ is V or I | 151 |
| VL 9F2 | NIVMTQTPASVEVAVGGTVIIKCQASQSISNYLSWYHQKSGQRPRLLIYSASTLAS GVPSRFKGSGSGTQFTLTISDLECADAATYYCHQDYTSNSVDNTFGGGTEVVVK | 152 |
| VL 10C8 | NIVMTQTPASVEVAMGGTVIIKCQASQSISTYLSWYQQKPGQPPKLLIYSASTLAS GVSSRFEGSGSGTQFTLTISGVQCADAATYYCHQDYTSNNVDNTFGGGTEVVVK | 153 |
| VL 8F5 | AYDLTQTPASVEAVGGTVTINCQASESIGNELSWYQQKSGQPPKLLIYQASTLAS GVPSRFKGSGSGTDFTLTISDLECADAATYYCAQGFSSSGVENVFGGGTEVVVK | 154 |
| VL 3-3F5 | AYDMTQTPASVEAAVGGTVTIKCQASESIGNALAWYQQKPGQPPKLLIYDASDLAS GVPSRFKGSGSGTQFTLTISGVECADAATYYCQQGDSHNNVDNIFGGGTEVVVK | 155 |
| VL hu3-3F5-L1 | AYRMTQSPSSFSASTGDRVTITCQASESIGNALAWYQQKPGKPPKLLIYDASDLAS GVPSRFSGSGSGTDFTLTISCLQSEDFATYYCQQGDSHNNVDNIFGGGTKVEIK | 156 |
| VL hu3-3F5-L2 | AIRMTQSPSSFSASTGDRVTITCQASESIGNALAWYQQKPGKPPKLLIYDASDLAS GVPSRFSGSGSGTDFTLTISCLQSEDFATYYCQQGDSHNNVDNIFGGGTKVEIK | 157 |
| VL hu3-3F5-L3 | AYRMTQSPSSFSASTGDRVTITCQASESIGNALAWYQQKPGKAPKLLIYDASDLAS GVPSRFSGSGSGTDFTLTISCLQSEDFATYYCQQGDSHNNVDNIFGGGTKVEIK | 158 |
| VL hu3-3F5-L4 | AIRMTQSPSSFSASTGDRVTITCQASESIGNALAWYQQKPGKAPKLLIYDASDLAS GVPSRFSGSGSGTDFTLTISCLQSEDFATYYCQQGDSHNNVDNIFGGGTKVEIK | 159 |
| VL hu3-3F5-L5 | AIRMTQSPSSFSASTGDRVTITCQASESIGNALAWYQQKPGKAPKLLIYDASDLAS GVPSRFSGSGSGTDFTLTISSLQPEDFATYYCQQGDSHNNVDNIFGGGTKVEIK | 160 |
| VL hu3-3F5-L6 | AIRMTQSPSSFSASTGDRVTITCQASESIGNALAWYQQKPGKAPKLLIYDASDLAS GVPSRFSGSGSGTDFTLTISSLQPEDFATYYCQQGDSHNNVDNIFGGGTEVVVK | 161 |
| VL 3-3F5, hu3-3F5-L1 to hu3-3F5-L6 (consensus) | AX$_1$RMTQSPSSFSASTGDRVTITCQASESIGNALAWYQQKPGKX$_2$PKLLIYDASDLA SGVPSRFSGSGSGTDFTLTISX$_3$LQX$_4$EDFATYYCQQGDSHNNVDNIFGGGTX$_5$VX$_6$X$_7$K wherein X$_1$ is Y or I, X$_2$ is P or A, X$_3$ is C or S, X$_4$ is S or P X$_5$ is E or K, X$_6$ is E or V, X$_7$ is V or I | 162 |

-continued

Table of Sequences

| NAME | SEQUENCE | SEQ ID NO |
|---|---|---|
| VL 9E3 | AIEMTQTPSSASEPVGGTVTIKCQASESISRYLSWYQQKPGQPPKLLIYDASDLAS GVSSRFKGSGSGTQFTLIIISDVECADAATYYCQQDYSRSNIVNSFGGGTEVVVK | 163 |
| VL 10D10 | AYDMTQTPSSASEPVGGTVTIKCQASESISTYLSWYQQKPGQPPKLLIYDASDLAS GVSSRFKGSGSGTQFTLTISDVECADAATYYCQQDYSSSNIVNSFGGGTEVVVK | 164 |
| VL 12B3 | AYDMTQTPASVEVAVGGTVTIKCQASQSISTYLAWYQQKPGQRPNLLIYKTSTLAS GVPSRFRGSGSGTQFTLTISGVECADAATYYCQQGYSGSSVENTFGGGTEVVVK | 165 |
| VL 1D10 | AYDMTQTPVSVEAAVGGTVTIKCQASQSISSYLAWYQQKPGQPPKLLIYKASTLAS GVSSRFKGSGSGTEFTLTISDLECADAATYYCQQGYSGSNVENTFGGGTEVVVK | 166 |
| VH Sequences (HVRs underlined) | | |
| VH 14C8 | EVQLVESGGGLVQPGRSLKLSCTASGFTFSDYNMAWVRQAPKGGLEWVTTISYDAG RTYYRDSVKGRFTISRDNAKRTLSLQMDSLRSEDTATYYCATGIFNYGTDYFDYWG QGVMVTVSS | 167 |
| VH 14E12 | EVQLVESGGGLVRPGRSLRLSCAASGFTFSDYYMAWVRQAPTKGLEWVASISYDGD TTYYRDSVKGRFTISRDNARSSLYLQMDSLRSDDTANYFCTTDGTIPAGSWFAYWG QGTLVTVSS | 168 |
| VH 8E11 | QEQLEESGGDLVKPEGSLTLTCTASGFSFSSSYWICWVRQAPGKGLEWIACVYGLD VNIYYASWTKGRFTISKTSSTTVTLQMTSLTAADTATYFCARGGGSADFGFDLWGP GTLVTVSS | 169 |
| VH 8G10 | QSLEESGGDLVKPEGSLTLTCTASGFSFSTSYWICWVRQAPGKGLEWIACVYGLDV NIYYASWTEGRFTISKTSSTTVTLQVTSLTAADTATYFCARGGGSADFGFDLWGPG TLVTVSS | 170 |
| VH 9B6 | QSVKESEGGLFKPTDNLTLTCTVSGFSLSNYGVTWVRQAPGNGLEYIGFIGSGGSA YYASWAKSRSTITRNTNLNTVTLKMTSLTAADTATYFCARDDVGGGKSLDIWGPGT LVTVSS | 171 |
| VH 2.3F4 | QSVEESRGGLIKPTDTLTLTCTASGFSLSNYGVSWVRQAPGNGLEYIGFIGYGGST YYASWAKSRSTITRNTNLNTVTLQMTSLTAADTATYFCARLCGVDCADALDSWGPG TLVTVSS | 172 |
| VH 10C5 | QSLEESGGGLVKPTDTLTLTCTVSGFSLSSYGVTWVRQAPGRGLEWIGYITSNYGV SYYASWAKSRSTITRNTNLNTVTLKMTSLTAADTATYFCARENPDYGYAYDAWGPG TLVTVSV | 173 |
| VH hu10C5-H1 | EVQLVESGGGLVQPGGSLRLSCAVSGFSLSSYGVTWVRQAPGKGLEWIGYITSNYG VSYYASWAKSRSTISRDTSKNTVYLQMGSLRAEDMAVYFCARENPDYGYAYDAWGP GTTVTVSS | 174 |
| VH hu10C5-H2 | EVQLVESGGGLVQPGGSLRLSCAASGFSLSSYGVTWVRQAPGKGLEWIGYITSNYG VSYYASWAKSRSTISRDTSKNTVYLQMGSLRAEDMAVYFCARENPDYGYAYDAWGP GTTVTVSS | 175 |
| VH hu10C5-H3 | EVQLVESGGGLVQPGGSLRLSCAVSGFSLSSYGVTWVRQAPGKGLEYIGYITSNYG VSYYASWAKSRSTISRDTSKNTVYLQMGSLRAEDMAVYFCARENPDYGYAYDAWGP GTTVTVSS | 176 |
| VH hu10C5-H4 | EVQLVESGGGLVQPGGSLRLSCAVSGFSLSSYGVTWVRQAPGKGLEWVGYITSNYG VSYYASWAKSRSTISRDTSKNTVYLQMGSLRAEDMAVYFCARENPDYGYAYDAWGP GTTVTVSS | 177 |
| VH hu10C5-H5 | EVQLVESGGGLVQPGGSLRLSCAVSGFSLSSYGVTWVRQAPGKGLEWISYITSNYG VSYYASWAKSRSTISRDTSKNTVYLQMGSLRAEDMAVYFCARENPDYGYAYDAWGP GTTVTVSS | 178 |
| VH hu10C5-H6 | EVQLVESGGGLVQPGGSLRLSCAVSGFSLSSYGVTWVRQAPGKGLEWIGYITSNYG VSYYASWAKSRFTISRDTSKNTVYLQMGSLRAEDMAVYFCARENPDYGYAYDAWGP GTTVTVSS | 179 |
| VH hu10C5-H7 | EVQLVESGGGLVQPGGSLRLSCAVSGFSLSSYGVTWVRQAPGKGLEWIGYITSNYG VSYYASWAKSRSTISRDNSKNTVYLQMGSLRAEDMAVYFCARENPDYGYAYDAWGP GTTVTVSS | 180 |
| VH hu10C5-H8 | EVQLVESGGGLVQPGGSLRLSCAVSGFSLSSYGVTWVRQAPGKGLEWIGYITSNYG VSYYASWAKSRSTISRDTSKNTLYLQMGSLRAEDMAVYFCARENPDYGYAYDAWGP GTTVTVSS | 181 |

Table of Sequences

| NAME | SEQUENCE | SEQ ID NO |
|---|---|---|
| VH hu10C5-H9 | EVQLVESGGGLVQPGGSLRLSCAVSGFSLSSYGVTWVRQAPGKGLEWIGYITSNYGVSYYASWAKSRSTISRDTSKNTVYLQMGSLRAEDMAVYYCARENPDYGYAYDAWGPGTTVTVSS | 182 |
| VH hu10C5-H10 | EVQLVESGGGLVQPGGSLRLSCAVSGFSLSSYGVTWVRQAPGKGLEWIGYITSNYGVSYYASWAKSRSTISRDTSKNTVYLQMGSLRAEDMAVYFCARENPDYGYAYDAWGQGTTVTVSS | 183 |
| VH hu10C5-H11 | EVQLVESGGGLVQPGGSLRLSCAVSGFSLSSYGVTWVRQAPGKGLEWIGYITSNYGVSYYANSVKGRSTISRDTSKNTVYLQMGSLRAEDMAVYFCARENPDYGYAYDAWGPGTTVTVSS | 184 |
| VH hu10C5-H12 | EVQLVESGGGLVQPGGSLRLSCAASGFSLSSYGVTWVRQAPGKGLEYVSYITSNYGVSYYASWAKSRFTISRDNSKNTLYLQMGSLRAEDMAVYYCARENPDYGYAYDAWGQGTTVTVSS | 185 |
| VH hu10C5-H13 | EVQLVESGGGLVQPGGSLRLSCAASGFSLSSYGVTWVRQAPGKGLEYVSYITSNYGVSYYANSVKGRFTISRDNSKNTLYLQMGSLRAEDMAVYYCARENPDYGYAYDAWGQGTTVTVSS | 186 |
| VH hu10C5-H14 | EVQLVESGGGLVQPGGSLRLSCAASGFSLSSYGVTWVRQAPGKGLEWVGYITSNYGVSYYASWAKSRFTISRDNSKNTLYLQMGSLRAEDMAVYYCARENPDYGYAYDAWGQGTTVTVSS | 187 |
| VH hu10C5-H15 | EQQLVESGGGLVQPGGSLRLSCAASGFSLSSYGVTWVRQAPGKGLEWVGYITSNYGVSYYASWAKSRFTISRDNSKNTLYLQMGSLRAEDMAVYYCARENPDYGYAYDAWGQGTTVTVSS | 188 |
| VH hu10C5-H16 | EVQLVESGGGLVQPGGSLRLSCAASGFSLSSYGVTWVRQAPGKGLEWVGYITSNYGVSYYASWAKSRFTISRNLNTNTLYLQMGSLRAEDMAVYYCARENPDYGYAYDAWGQGTTVTVSS | 189 |
| VH hu10C5-H17 | EVQLVESGGGLVQPGGSLRLSCAASGFSLSSYGVTWVRQAPGKGLEWVGYITSNYGVSYYASFAKSRFTISRDNSKNTLYLQMGSLRAEDMAVYYCARENPDYGYAYDAWGQGTTVTVSS | 190 |
| VH hu10C5-H18 | EVQLVESGGGLVQPGGSLRLSCAASGFSLSSYGVTWVRQAPGKGLEWVGYITSNYGVSYYASWAKSRFTISRNTNLNTLYLQMGSLRAEDMAVYYCARENPDYGYAYDAWGQGTTVTVSS | 191 |
| VH hu10C5-H19 | EVQLVESGGGLVQPGGSLRLSCAASGFSLSSYGVTWVRQAPGKGLEWVGYITSNYGVSYYASWAKSRFTISRNNSKNTLYLQMGSLRAEDMAVYYCARENPDYGYAYDAWGQGTTVTVSS | 192 |
| VH hu10C5-H20 | EVQLVESGGGLVQPGGSLRLSCAASGFSLSSYGVTWVRQAPGKGLEWVGYITSNYGVSYYASWAKSRFTISRDNNKNTLYLQMGSLRAEDMAVYYCARENPDYGYAYDAWGQGTTVTVSS | 193 |
| VH hu10C5-H21 | EVQLVESGGGLVQPGGSLRLSCAASGFSLSSYGVTWVRQAPGKGLEWVGYITSNYGVSYYASWAKSRFTISRNNNKNTLYLQMGSLRAEDMAVYYCARENPDYGYAYDAWGQGTTVTVSS | 194 |
| VH hu10C5-H22 | EVQLVESGGGLVQPGGSLRLSCAASGFSLSSYGVTWVRQAPGKGLEWIGYITSNYGVSYYASWAKSRFTISRDNSKNTLYLQMGSLRAEDMAVYYCARENPDYGYAYDAWGQGTTVTVSS | 195 |
| VH hu10C5-H23 | EVQLVESGGGLVQPGGSLRLSCAASGFSLSSYGVTWVRQAPGKGLEWVGYITSNYGVSYYASWAKSRSTISRDNSKNTLYLQMGSLRAEDMAVYYCARENPDYGYAYDAWGQGTTVTVSS | 196 |
| VH hu10C5-H24 | EVQLVESGGGLVQPGGSLRLSCAASGFSLSSYGVTWVRQAPGKGLEWIGYITSNYGVSYYASWAKSRSTISRDNSKNTLYLQMGSLRAEDMAVYYCARENPDYGYAYDAWGQGTTVTVSS | 197 |
| VH hu10C5-H25 | EVQLVESGGGLVQPGGSLRLSCAASGFSLSSYGVTWVRQAPGKGLEWVGYITSNYGVSYYASWAKSRFTISRDTSKNTLYLQMGSLRAEDMAVYYCARENPDYGYAYDAWGQGTTVTVSS | 198 |
| VH hu10C5-H26 | EVQLVESGGGLVQPGGSLRLSCAASGFSLSSYGVTWVRQAPGKGLEWVGYITSNYGVSYYASWAKSRFTISRDNSKNTVYLQMGSLRAEDMAVYYCARENPDYGYAYDAWGQGTTVTVSS | 199 |

-continued

Table of Sequences

| NAME | SEQUENCE | SEQ ID NO |
|------|----------|-----------|
| VH hu10C5-H27 | EVQLVESGGGLVQPGGSLRLSCAASGFSLSSYGVTWVRQAPGKGLEWIGYITSNYG VSYYASWAKSRSTISRDNSKNTVYLQMGSLRAEDMAVYYCARENPDYGYAYDAWGQ GTTVTVSS | 200 |
| VH hu10C5-H28 | EVQLVESGGGLVQPGGSLRLSCAASGFSLSSYGVTWVRQAPGKGLEWIGYITSNYG VSYYASWAKSRSTISRDTSKNTVYLQMGSLRAEDMAVYYCARENPDYGYAYDAWGQ GTTVTVSS | 201 |
| VH 10C5, hu10C5-H1 to hu10C5-H28 (consensus) | EX$_1$QLVESGGGLVQPGGSLRLSCAX$_2$SGFSLSSYGVTWVRQAPGKGLEX$_3$X$_4$X$_5$YITS NYGVSYYAX$_6$X$_7$X$_8$KX$_9$RX$_{10}$TISRX$_{11}$X$_{12}$X$_{13}$X$_{14}$NTX$_{15}$YLQMGSLRAEDMAVYX$_{16}$CA RENPDYGYAYDAWGX$_{17}$GTTVTVSS<br>wherein X$_1$ is V or Q, X$_2$ is V or A, X$_3$ is W or Y, X$_4$ is I or V, X$_5$ is G or S, X$_6$ is S or N, X$_7$ is W, S or F, X$_8$ is A or V, X$_9$ is S or G, X$_{10}$ is S or F, X$_{11}$ is D or N, X$_{12}$ is T, L or N, X$_{13}$ is S or N, X$_{14}$ is K, T or L, X$_{15}$ is V or L, X$_{16}$ is F or Y, X$_{17}$ is P or Q | 202 |
| VH 2B11 | QSVKESEGGLFKPTDTLTLTCTVSGFSLINYGVSWVRQAPGKGLEWIGYIGSAGST YYATWAKSRATITRNTNLNTVTLKMTSLTAADTATYFCARAAYSAGSADAEDIWGP GTLVTVSS | 203 |
| VH 10H3 | QSVKESEGGLIKPTDTLTLTCTVSGFSLSTFAINWVRQAPGNGLEWIGAIGRGGSA YYASWAKSRSTITKNTNLNTVTLKMTRPTAADTATYFCARENAGSGWGELDIWGPG TLVTVSS | 204 |
| VH 9H3 | QSVKESEGGLFKPTDTLTLTCTVSGFSLSGYGVSWVRQAPGKGLEYIGFIGSGGSA YYASWAKSRSTITRNTNLNTVTLKMTRLTAADTATYFCARDNVGGDMSLDIWGPGT LVTVSS | 205 |
| VH 8B7 | QSVKESEGGLFKPTDNLTLTCTVSGFSLSNYGVTWVRQAPGNGLEYIGFIGSSGSA YYASWAKSRSTITRNTNLNTVTLKMTSLTAADTATYFCARDDVGGGKSLDIWGPGT LVTVSS | 206 |
| VH 9H5 | QSVKESEGGLFKPTDNLTLTCTVSGFSLSSYGVSWVRQAPGNGLEYIGFIGSGGFA YYASWAKSRSTITRNTNLNTVTLKMTSLTAADTATYFCARDDVGGGKSLDIWGPGT VVTVSV | 207 |
| VH hu9H5-H1 | EVQLVESGGGLIQPGGSLRLSCAVSGFSLSSYGVSWVRQAPGKGLEYIGFIGSGGF AYYASWAKSRSTISRDTSKNTVYLQMNSLRAEDTAVYFCARDDVGGGKSLDIWGPG TLVTVSS | 208 |
| VH hu9H5-H2 | EVQLVESGGGLIQPGGSLRLSCAASGFSLSSYGVSWVRQAPGKGLEYIGFIGSGGF AYYASWAKSRSTISRDTSKNTVYLQMNSLRAEDTAVYFCARDDVGGGKSLDIWGPG TLVTVSS | 209 |
| VH hu9H5-H3 | EVQLVESGGGLIQPGGSLRLSCAVSGFSLSSYGVSWVRQAPGKGLEWIGFIGSGGF AYYASWAKSRSTISRDTSKNTVYLQMNSLRAEDTAVYFCARDDVGGGKSLDIWGPG TLVTVSS | 210 |
| VH hu9H5-H4 | EVQLVESGGGLIQPGGSLRLSCAVSGFSLSSYGVSWVRQAPGKGLEYVGFIGSGGF AYYASWAKSRSTISRDTSKNTVYLQMNSLRAEDTAVYFCARDDVGGGKSLDIWGPG TLVTVSS | 211 |
| VH hu9H5-H5 | EVQLVESGGGLIQPGGSLRLSCAVSGFSLSSYGVSWVRQAPGKGLEYISFIGSGGF AYYASWAKSRSTISRDTSKNTVYLQMNSLRAEDTAVYFCARDDVGGGKSLDIWGPG TLVTVSS | 212 |
| VH hu9H5-H6 | EVQLVESGGGLIQPGGSLRLSCAVSGFSLSSYGVSWVRQAPGKGLEYIGFIGSGGF AYYASWAKSRFTISRDTSKNTVYLQMNSLRAEDTAVYFCARDDVGGGKSLDIWGPG TLVTVSS | 213 |
| VH hu9H5-H7 | EVQLVESGGGLIQPGGSLRLSCAVSGFSLSSYGVSWVRQAPGKGLEYIGFIGSGGF AYYASWAKSRSTISRDNSKNTVYLQMNSLRAEDTAVYFCARDDVGGGKSLDIWGPG TLVTVSS | 214 |
| VH hu9H5-H8 | EVQLVESGGGLIQPGGSLRLSCAVSGFSLSSYGVSWVRQAPGKGLEYIGFIGSGGF AYYASWAKSRSTISRDTSKNTLYLQMNSLRAEDTAVYFCARDDVGGGKSLDIWGPG TLVTVSS | 215 |
| VH hu9H5-H9 | EVQLVESGGGLIQPGGSLRLSCAVSGFSLSSYGVSWVRQAPGKGLEYIGFIGSGGF AYYASWAKSRSTISRDTSKNTVYLQMNSLRAEDTAVYYCARDDVGGGKSLDIWGPG TLVTVSS | 216 |

Table of Sequences

| NAME | SEQUENCE | SEQ ID NO |
|---|---|---|
| VH hu9H5-H10 | EVQLVESGGGLIQPGGSLRLSCAVSGFSLSSYGVSWVRQAPGKGLEYIGFIGSGGF AYYASWAKSRSTISRDTSKNTVYLQMNSLRAEDTAVYFCARDDVGGGKSLDIWGQG TLVTVSS | 217 |
| VH hu9H5-H11 | EVQLVESGGGLIQPGGSLRLSCAVSGFSLSSYGVSWVRQAPGKGLEYIGFIGSGGF AYYADSVKGRSTISRDTSKNTVYLQMNSLRAEDTAVYFCARDDVGGGKSLDIWGPG TLVTVSS | 218 |
| VH hu9H5-H12 | EVQLVESGGGLIQPGGSLRLSCAASGFSLSSYGVSWVRQAPGKGLEWVSFIGSGGF AYYASWAKSRFTISRDNSKNTLYLQMNSLRAEDTAVYYCARDDVGGGKSLDIWGQG TLVTVSS | 219 |
| VH hu9H5-H13 | EVQLVESGGGLIQPGGSLRLSCAASGFSLSSYGVSWVRQAPGKGLEWVSFIGSGGF AYYADSVKGRFTISRDNSKNTLYLQMNSLRAEDTAVYYCARDDVGGGKSLDIWGQG TLVTVSS | 220 |
| VH hu9H5-H14 | EVQLVESGGGLIQPGGSLRLSCAASGFSLSSYGVSWVRQAPGKGLEYVGFIGSGGF AYYASWAKSRFTISRDNSKNTLYLQMNSLRAEDTAVYYCARDDVGGGKSLDIWGQG TLVTVSS | 221 |
| VH hu9H5-H15 | EQQLVESGGGLIQPGGSLRLSCAASGFSLSSYGVSWVRQAPGKGLEYVGFIGSGGF AYYASWAKSRFTISRDNSKNTLYLQMNSLRAEDTAVYYCARDDVGGGKSLDIWGQG TLVTVSS | 222 |
| VH hu9H5-H16 | EVQLVESGGGLIQPGGSLRLSCAASGFSLSSYGVSWVRQAPGKGLEYVGFIGSGGF AYYASWAKSRFTISRNTNLNTLYLQMNSLRAEDTAVYYCARDDVGGGKSLDIWGQG TLVTVSS | 223 |
| VH hu9H5-H17 | EVQLVESGGGLIQPGGSLRLSCAASGFSLSSYGVSWVRQAPGKGLEYVGFIGSGGF AYYASFAKSRFTISRDNSKNTLYLQMNSLRAEDTAVYYCARDDVGGGKSLDIWGQG TLVTVSS | 224 |
| VH 9H5, hu9H5-H1 to hu9H5-H17 (consensus) | EX$_1$QLVESGGGLIQPGGSLRLSCAX$_2$SGFSLSSYGVSWVRQAPGKGLEX$_3$X$_4$X$_5$FIGS GGFAYYAX$_6$X$_7$X$_8$KX$_9$RX$_{10}$TISRX$_{11}$X$_{12}$X$_{13}$X$_{14}$NTX$_{15}$YLQMNSLRAEDTAVYX$_{16}$CAR DDVGGGKSLDIWGX$_{17}$GTLVTVSS<br>wherein X$_1$ is V or Q, X$_2$ is V or A, X$_3$ is Y or W, X$_4$ is I or V, X$_5$ is G or S, X$_6$ is S or D, X$_7$ is W, S or F, X$_8$ is A or V, X$_9$ is S or G, X$_{10}$ is S or F, X$_{11}$ is D or N, X$_{12}$ is T or N, X$_{13}$ is S or N, X$_{14}$ is K or L, X$_{15}$ is V or L, X$_{16}$ is F or Y, X$_{17}$ is P or Q | 225 |
| VH 9F2 | QSVKESEGGLFKPTDNLTLTCTVSGFSLSSYGVSWVRQAPGNGLEYIGFIGSGGSP YYASWAKSRSTITRNTNLNTVTLKMTSLTAADTATYFCARDDVGGGKSLDIWGPGT LVTVSS | 226 |
| VH 10C8 | QSVKESEGGLFKPTDNLTLTCTVSGFSLSSYGVSWVRQAPGNGLEYIGFIGSGGFA YYASWAKSRSTITRNTNLNTVTLKMTSLTAADTATYFCARDDVGGGRSLDIWGPGT VVTVSS | 227 |
| VH 8F5 | QSVKESEGGLFKPTDTLTLTCTVSGFSLSSYPISWVRQAPGNGLEWIGYITSEYGV AYYATWAESRSTITRNTNLNTVTLKMTSLTAADTATYFCVRENPTYGYAYDAWGPG TLVTVSS | 228 |
| VH 3-3F5 | QSVKESEGGLFKPTDTLTLTCTVSGFSLNDYGVSWVRQAPGNGLEWIGAIGSSGVA WYANWAKGRSTITRNTNLNTVTLKMASLTAADTATYFCARDRDYGYRADDATSGMD LWGPGTLVTVSS | 229 |
| VH hu3-3F5-H1 | EVQLVESGGGLVQPGGSLRLSCAVSGFSLNDYGVSWVRQAPGKGLEWIGAIGSSGV AWYANWAKGRSTISRHTSKNTVYLQMNSLRAEDTAVYFCARDRDYGYRADDATSGM DLWGPGTLVTVSS | 230 |
| VH hu3-3F5-H2 | EVQLVESGGGLVQPGGSLRLSCAASGFSLNDYGVSWVRQAPGKGLEWIGAIGSSGV AWYANWAKGRSTISRHTSKNTVYLQMNSLRAEDTAVYFCARDRDYGYRADDATSGM DLWGPGTLVTVSS | 231 |
| VH hu3-3F5-H3 | EVQLVESGGGLVQPGGSLRLSCAVSGFSLNDYGVSWVRQAPGKGLEWVGAIGSSGV AWYANWAKGRSTISRHTSKNTVYLQMNSLRAEDTAVYFCARDRDYGYRADDATSGM DLWGPGTLVTVSS | 232 |
| VH hu3-3F5-H4 | EVQLVESGGGLVQPGGSLRLSCAVSGFSLNDYGVSWVRQAPGKGLEWISAIGSSGV AWYANWAKGRSTISRHTSKNTVYLQMNSLRAEDTAVYFCARDRDYGYRADDATSGM DLWGPGTLVTVSS | 233 |

-continued

Table of Sequences

| NAME | SEQUENCE | SEQ ID NO |
|---|---|---|
| VH hu3-3F5-H5 | EVQLVESGGGLVQPGGSLRLSCAVSGFSLNDYGVSWVRQAPGKGLEWIGAIGSSGV AWYANWAKGRFTISRHTSKNTVYLQMNSLRAEDTAVYFCARDRDYGYRADDATSGM DLWGPGTLVTVSS | 234 |
| VH hu3-3F5-H6 | EVQLVESGGGLVQPGGSLRLSCAVSGFSLNDYGVSWVRQAPGKGLEWIGAIGSSGV AWYANWAKGRSTISRHNSKNTVYLQMNSLRAEDTAVYFCARDRDYGYRADDATSGM DLWGPGTLVTVSS | 235 |
| VH hu3-3F5-H7 | EVQLVESGGGLVQPGGSLRLSCAVSGFSLNDYGVSWVRQAPGKGLEWIGAIGSSGV AWYANWAKGRSTISRHTSKNTLYLQMNSLRAEDTAVYFCARDRDYGYRADDATSGM DLWGPGTLVTVSS | 236 |
| VH hu3-3F5-H8 | EVQLVESGGGLVQPGGSLRLSCAVSGFSLNDYGVSWVRQAPGKGLEWIGAIGSSGV AWYANWAKGRSTISRHTSKNTVYLQMNSLRAEDTAVYYCARDRDYGYRADDATSGM DLWGPGTLVTVSS | 237 |
| VH hu3-3F5-H9 | EVQLVESGGGLVQPGGSLRLSCAVSGFSLNDYGVSWVRQAPGKGLEWIGAIGSSGV AWYANWAKGRSTISRHTSKNTVYLQMNSLRAEDTAVYFCARDRDYGYRADDATSGM DLWGRGTLVTVSS | 238 |
| VH hu3-3F5-H10 | EVQLVESGGGLVQPGGSLRLSCAVSGFSLNDYGVSWVRQAPGKGLEWIGAIGSSGV AFYANWAKGRSTISRHTSKNTVYLQMNSLRAEDTAVYFCARDRDYGYRADDATSGM DLWGPGTLVTVSS | 239 |
| VH hu3-3F5-H11 | EVQLVESGGGLVQPGGSLRLSCAVSGFSLNDYGVSWVRQAPGKGLEWIGAIGSSGV AWYADSVKGRSTISRHTSKNTVYLQMNSLRAEDTAVYFCARDRDYGYRADDATSGM DLWGPGTLVTVSS | 240 |
| VH hu3-3F5-H12 | EVQLVESGGGLVQPGGSLRLSCAASGFSLNDYGVSWVRQAPGKGLEWVSAIGSSGV AFYANWAKGRFTISRHNSKNTLYLQMNSLRAEDTAVYCARDRDYGYRADDATSGM DLWGRGTLVTVSS | 241 |
| VH hu3-3F5-H13 | EVQLVESGGGLVQPGGSLRLSCAASGFSLNDYGVSWVRQAPGKGLEWVSAIGSSGV AFYADSVKGRFTISRHNSKNTLYLQMNSLRAEDTAVYYCARDRDYGYRADDATSGM DLWGRGTLVTVSS | 242 |
| VH hu3-3F5-H14 | EVQLLESGGGLVQPGGSLRLSCAASGFSLNDYGVSWVRQAPGKGLEWVGAIGSSGV AWYANWAKGRFTISRDNSKNTLYLQMNSLRAEDTAVYYCARDRDYGYRADDATSGM DLWGRGTLVTVSS | 243 |
| VH hu3-3F5-H15 | EVQLLESGGGLVQPGGSLRLSCAASGFSLNDYGVSWVRQAPGKGLEWVGAIGSSGV AFYANWAKGRFTISRDNSKNTLYLQMNSLRAEDTAVYYCARDRDYGYRADDATSGM DLWGRGTLVTVSS | 244 |
| VH hu3-3F5-H16 | EQQLLESGGGLVQPGGSLRLSCAASGFSLNDYGVSWVRQAPGKGLEWVGAIGSSGV AWYANWAKGRFTISRDNSKNTLYLQMNSLRAEDTAVYYCARDRDYGYRADDATSGM DLWGRGTLVTVSS | 245 |
| VH hu3-3F5-H17 | EVQLLESGGGLVQPGGSLRLSCAASGFSLNDYGVSWVRQAPGKGLEWVGAIGSSGV AWYANWAKGRFTISRNTNLNTLYLQMNSLRAEDTAVYYCARDRDYGYRADDATSGM DLWGRGTLVTVSS | 246 |
| VH hu3-3F5-H18 | EVQLLESGGGLVQPGGSLRLSCAASGFSLNDYGVSWVRQAPGKGLEWVGAIGSSGV AWYANFAKGRFTISRDNSKNTLYLQMNSLRAEDTAVYYCARDRDYGYRADDATSGM DLWGRGTLVTVSS | 247 |
| VH hu3-3F5-H19 | EVQLLESGGGLVQPGGSLRLSCAVSGFSLNDYGVSWVRQAPGKGLEWVGAIGSSGV AWYANFAKGRFTISRDNSKNTLYLQMNSLRAEDTAVYYCARDRDYGYRADDATSGM DLWGRGTLVTVSS | 248 |
| VH hu3-3F5-H20 | EVQLLESGGGLVQPGGSLRLSCAASGFSLNDYGVSWVRQAPGKGLEWIGAIGSSGV AWYANFAKGRFTISRDNSKNTLYLQMNSLRAEDTAVYYCARDRDYGYRADDATSGM DLWGRGTLVTVSS | 249 |
| VH hu3-3F5-H21 | EVQLLESGGGLVQPGGSLRLSCAASGFSLNDYGVSWVRQAPGKGLEWVGAIGSSGV AWYARSTISRDNSKNTLYLQMNSLRAEDTAVYYCARDRDYGYRADDATSGM DLWGRGTLVTVSS | 250 |
| VH hu3-3F5-H22 | EVQLLESGGGLVQPGGSLRLSCAASGFSLNDYGVSWVRQAPGKGLEWIGAIGSSGV AWYANFAKGRSTISRDNSKNTLYLQMNSLRAEDTAVYYCARDRDYGYRADDATSGM DLWGRGTLVTVSS | 251 |

-continued

Table of Sequences

| NAME | SEQUENCE | SEQ ID NO |
|---|---|---|
| VH hu3-3F5-H23 | EVQLLESGGGLVQPGGSLRLSCAASGFSLN<u>DYGVS</u>WVRQAPGKGLEWVG<u>AIGSSGV AWYANFAKG</u>RFTISRDTSKNTLYLQMNSLRAEDTAVYYCAR<u>DRDYGYRADDATSGM DLW</u>GRGTLVTVSS | 252 |
| VH hu3-3F5-H24 | EVQLLESGGGLVQPGGSLRLSCAASGFSLN<u>DYGVS</u>WVRQAPGKGLEWVG<u>AIGSSGV AWYANFAKG</u>RFTISRDNSKNTVYLQMNSLRAEDTAVYYCAR<u>DRDYGYRADDATSGM DLW</u>GRGTLVTVSS | 253 |
| VH hu3-3F5-H25 | EVQLLESGGGLVQPGGSLRLSCAASGFSLN<u>DYGVS</u>WVRQAPGKGLEWVG<u>AIGSSGV AWYANFAKG</u>RFTISRDTSKNTVYLQMNSLR<u>A</u>EDTAVYYCAR<u>DRDYGYRADDATSGM DLW</u>GRGTLVTVSS | 254 |
| VH hu3-3F5-H26 | EVQLLESGGGLVQPGGSLRLSCAASGFSLN<u>DYGVS</u>WVRQAPGKGLEWIG<u>AIGSSGV AWYANFAKG</u>RSTISRDTSKNTVYLQMNSLR<u>A</u>EDTAVYYCAR<u>DRDYGYRADDATSGM DLW</u>GRGTLVTVSS | 255 |
| VH hu3-3F5-H27 | EVQLLESGGGLVQPGGSLRLSCAASGFSLN<u>DYGVS</u>WVRQAPGKGLEWIG<u>AIGSSGV AFYANFAKG</u>RSTISRDTSKNTVYLQMNSLR<u>A</u>EDTAVYYCAR<u>DRDYGYRADDATSGM DLW</u>GRGTLVTVSS | 256 |
| VH 3-3F5, hu3-3F5-H1 to hu3-3F5-H27 (consensus) | EX$_1$QLX$_2$ESGGGLVQPGGSLRLSCAX$_3$SGFSLN<u>DYGVS</u>WVRQAPGKGLEWX$_4$X$_5$<u>AIGS SGVAX$_6$YAX$_7$X$_8$X$_9$KGR</u>X$_{10}$TISRX$_{11}$X$_{12}$X$_{13}$X$_{14}$NTX$_{15}$YLQMNSLRAEDTAVYX$_{16}$CAR <u>DRDYGYRADDATSGMDLWG</u>X$_{17}$GTLVTVSS<br>wherein X$_1$ is V or Q, X$_2$ is V or L, X$_3$ is V or A, X$_4$ is I or V, X$_5$ is G or S, X$_6$ is W or F, X$_7$ is N or D, X$_8$ is W, S or F, X$_9$ is A or V, X$_{10}$ is S or F, X$_{11}$ is H, N or D, X$_{12}$ is T or N, X$_{13}$ is S or N, X$_{14}$ is K or L, X$_{15}$ is V or L, X$_{16}$ is F or Y, X$_{17}$ is P or R | 257 |
| VH 9E3 | QEQLEESGGGLVKPGASLTLTCTVSGFSLT<u>NNYVNFVMC</u>WVRQAPGKGLEWIA<u>SID PGDDSTDYASWATG</u>RFTISKASSTTVTLQVTSLTAADTATYFCAR<u>GDAGTSYSFNF WG</u>PGTLVTVS | 258 |
| VH 10D10 | QEQLVESGGGLVKPGASLTLTCTASGFSLT<u>DNYVMS</u>WVRQAPGKGLEWIA<u>CIDPGD DSTYYASWATG</u>RFTISRASSTTVTLQVTSLT<u>A</u>ADTATYFCAR<u>GDAAASYSFNFWGP</u>GTLVTVSS | 259 |
| VH 12B3 | QSLEESGGGLVKPGGTLTLTCKASGIDF<u>NGGGIYW</u>VRQAPGKGLEWIA<u>SIYPDHGS VDYANWVNG</u>RFTISLDNAQNTVFLQLTSLT<u>V</u>ADTATYFCAR<u>ESGGSYYDLWG</u>PGTL VTVSS | 260 |
| VH 1D10 | QSLEESGGGLVKPGGTLTLTCTASGFDF<u>NGGGIYW</u>VRQAPGKGLEWIA<u>YIYPDHGS ADYATWVNG</u>RFTISLDNAQNTVFLQMTSLT<u>V</u>ADTATYFCAR<u>ETGGSWYDLWG</u>PGTL VTVSS | 261 |
| LC Sequences | | |
| LC 14C8 | DIQMTQSPASLSASLGETVTIQCRASEDIYSGLAWYQQKPGKSPQLLIYGATTLHD GVPSRFSGSGSGTQYSLKISSMHSEDEGIYFCHQGLSFPYTFGAGTKLELKRADAA PTVSIFPPSSEQLTSGGASVVCFLNNFYPKDINVKWKIDGSERQNGVLNSWTDQDS KDSTYSMSSTLTLTKDEYERHNSYTCEATHKTSTSPIVKSFNRNEC | 262 |
| LC 14E12 | DIQMTQSPASLSASLGETVTIECLASKNIYRNLAWYQQKPGKSPQFLISDASRLQD GVPSRFTGSDSGSQYSLKINSLQSEDVATYFCQQYHDYPYTFGAGTKLELKRADAA PTVSIFPPSSEQLTSGGASVVCFLNNFYPKDINVKWKIDGSERQNGVLNSWTDQDS KDSTYSMSSTLTLTKDEYERHNSYTCEATHKTSTSPIVKSFNRNEC | 263 |
| LC 8E11 | DVVMTQTASPVSAAVGGTVTIKCQASENIYSLLAWYQQKPGQPPKVLIYDASDLAS GVPSRFKGSGSGTQFTLTISDLECADAATYYCQATAYGSSGNAFGGGTEVVVKRAD AAPTVSIFPPSSEQLTSGGASVVCFLNNFYPKDINVKWKIDGSERQNGVLNSWTDQ DSKDSTYSMSSTLTLTKDEYERHNSYTCEATHKTSTSPIVKSFNRNEC | 264 |
| LC 8G10 | DVVMTQTPASVSEPVGGTVTIKCQASENIYSLLAWYQQKPGQPPKVLIYDASDLAS GVPSRFKGSGSGTQFTLTISDLECADAATYYCQATAYGSSGNAFGGGTEVVVKRAD AAPTVSIFPPSSEQLTSGGASVVCFLNNFYPKDINVKWKIDGSERQNGVLNSWTDQ DSKDSTYSMSSTLTLTKDEYERHNSYTCEATHKTSTSPIVKSFNRNEC | 265 |
| LC 9B6 | NIVMTQTPASVEVAVGGTVVIKCQASQNIGDYLSWYQQKPGQRPKLLIYSASTLAS GVPSRFKGSGSGTQFTLTISDLECADAATYYCHQDYTSNDVENTFGGGTEVVVKRA DAAPTVSIFPPSSEQLTSGGASVVCFLNNFYPKDINVKWKIDGSERQNGVLNSWTD QDSKDSTYSMSSTLTLTKDEYERHNSYTCEATHKTSTSPIVKSFNRNEC | 266 |
| LC 2.3F4 | AYYMTQTPASVEVAVGGTVTIKCQASEDIGSYCSWYQQKPGQPPKLLIYDASDLAS GVPSRFKGSGSGTDFTLTISGVQCDDAATYYCQQDYTGNNVDNTFGGGSEVVVKRA | 267 |

Table of Sequences

| NAME | SEQUENCE | SEQ ID NO |
|---|---|---|
| | DAAPTVSIFPPSSEQLTSGGASVVCFLNNFYPKDINVKWKIDGSERQNGVLNSWTD<br>QDSKDSTYSMSSTLTLTKDEYERHNSYTCEATHKTSTSPIVKSFNRNEC | |
| LC<br>10C5 | AYDMTQTPASLEAAVGGTVTINCQASESISNELSWYQQKPGQPPDLLIYYASTLAS<br>GVPSRFKGSGSGTEFTLTISDLECADAATYYCAQGFGSSGVENVFGGGTEVVVKRA<br>DAAPTVSIFPPSSEQLTSGGASVVCFLNNFYPKDINVKWKIDGSERQNGVLNSWTD<br>QDSKDSTYSMSSTLTLTKDEYERHNSYTCEATHKTSTSPIVKSFNRNEC | 268 |
| LC<br>10C5-L5<br>huKappa | AIRMTQSPSSFSASTGDRVTITCQASESISNELSWYQQKPGKAPKLLIYYASTLAS<br>GVPSRFSGSGSGTDFTLTISSLQPEDFATYYCAQGFGSSGVENVFGGGTKVEIKRT<br>VAAPSVFIFPPSDEQLKSGTASVVCLLNNFYPREAKVQWKVDNALQSGNSQESVTE<br>QDSKDSTYSLSSTLTLSKADYEKHKVYACEVTHQGLSSPVTKSFNRGEC | 269 |
| LC<br>2B11 | AYYMTQTPASVEAAVGGTVTIKCQASQSISNYVAWYQQKPGQPPKLLIYRASTLAS<br>GVSSRFSGSGSGTEFTLTISDLECADAATYYCHQGYSSSNVDNIFGGGTEVVVKRA<br>DAAPTVSIFPPSSEQLTSGGASVVCFLNNFYPKDINVKWKIDGSERQNGVLNSWTD<br>QDSKDSTYSMSSTLTLTKDEYERHNSYTCEATHKTSTSPIVKSFNRNEC | 270 |
| LC<br>10H3 | AYEMTQTPASVEVAVGGTVTINCQASESISSDLAWYQQKPGQRPKLLIYAASTLAS<br>GVPSRFKGSGSGTEFTLSIGVQCADAATYYCQQGYTWNNVDNVFGGGTEVVVKRA<br>DAAPTVSIFPPSSEQLTSGGASVVCFLNNFYPKDINVKWKIDGSERQNGVLNSWTD<br>QDSKDSTYSMSSTLTLTKDEYERHNSYTCEATHKTSTSPIVKSFNRNEC | 271 |
| LC<br>9H3 | DIVMTQTPASVSEPVGGTVTIKCQASQNINNYLSWYQQKPGQPPKQLIYAASTLAS<br>GVPSRFKGSGSGTQFTLTISDLECADAATYYCHQDYTSNNVDNTFGGGTEVVVKRA<br>DAAPTVSIFPPSSEQLTSGGASVVCFLNNFYPKDINVKWKIDGSERQNGVLNSWTD<br>QDSKDSTYSMSSTLTLTKDEYERHNSYTCEATHKTSTSPIVKSFNRNEC | 272 |
| LC<br>8B7 | NIVMTQTPASVEVAVGGTVTIKCQASQSIGSYLSWYQQKPGQPPKLLIYDASNLAS<br>GVPSRFKGSGSGTQFTLSISDLECADAATYYCHQDYTSNNVDNTFGGGTEVVIKRA<br>DAAPTVSIFPPSSEQLTSGGASVVCFLNNFYPKDINVKWKIDGSERQNGVLNSWTD<br>QDSKDSTYSMSSTLTLTKDEYERHNSYTCEATHKTSTSPIVKSFNRNEC | 273 |
| LC<br>9H5 | NIVMTQTPASVEAAVGGTVTINCQASQSISSYLSWYQQKSGQRPKLLIFSASTLAS<br>GVPSRFTGSGSGTQFTLTISDLQCADAATYYCHQDYTSSNVDNTFGGGTEVVVKRA<br>DAAPTVSIFPPSSEQLTSGGASVVCFLNNFYPKDINVKWKIDGSERQNGVLNSWTD<br>QDSKDSTYSMSSTLTLTKDEYERHNSYTCEATHKTSTSPIVKSFNRNEC | 274 |
| LC<br>9H5-L4<br>huKappa | DIQMTQSPSSLSASVGDRVTITCQASQSISSYLSWYQQKPGKAPKLLIYSASTLAS<br>GVPSRFSGSGSGTDFTLTISSLQPEDFATYYCHQDYTSSNVDNTFGGGTKVEIKRT<br>VAAPSVFIFPPSDEQLKSGTASVVCLLNNFYPREAKVQWKVDNALQSGNSQESVTE<br>QDSKDSTYSLSSTLTLSKADYEKHKVYACEVTHQGLSSPVTKSFNRGEC | 275 |
| LC<br>9F2 | NIVMTQTPASVEVAVGGTVIIKCQASQSISNYLSWYHQKSGQRPRLLIYSASTLAS<br>GVPSRFKGSGSGTQFTLTISDLECADAATYYCHQDYTSNSVDNTFGGGTEVVVKRA<br>DAAPTVSIFPPSSEQLTSGGASVVCFLNNFYPKDINVKWKIDGSERQNGVLNSWTD<br>QDSKDSTYSMSSTLTLTKDEYERHNSYTCEATHKTSTSPIVKSFNRNEC | 276 |
| LC<br>10C8 | NIVMTQTPASVEVAMGGTVIIKCQASQSISTYLSWYQQKPGQPPKLLIYSASTLAS<br>GVSSRFEGSGSGTQFTLTISGVQCADAATYYCHQDYTSNNVDNTFGGGTEVVVKRA<br>DAAPTVSIFPPSSEQLTSGGASVVCFLNNFYPKDINVKWKIDGSERQNGVLNSWTD<br>QDSKDSTYSMSSTLTLTKDEYERHNSYTCEATHKTSTSPIVKSFNRNEC | 277 |
| LC<br>8F5 | AYDLTQTPASVEAAVGGTVTINCQASESIGNELSWYQQKSGQPPKLLIYQASTLAS<br>GVPSRFKGSGSGTDFTLTISDLECADAATYYCAQGFSSSGVENVFGGGTEVVVKRA<br>DAAPTVSIFPPSSEQLTSGGASVVCFLNNFYPKDINVKWKIDGSERQNGVLNSWTD<br>QDSKDSTYSMSSTLTLTKDEYERHNSYTCEATHKTSTSPIVKSFNRNEC | 278 |
| LC<br>3-3F5 | AYDMTQTPASVEAAVGGTVTIKCQASESIGNALAWYQQKPGQPPKLLIYDASDLAS<br>GVPSRFKGSGSGTQFTLTISGVECADAATYYCQQGDSHNNVDNIFGGGTEVVVKRA<br>DAAPTVSIFPPSSEQLTSGGASVVCFLNNFYPKDINVKWKIDGSERQNGVLNSWTD<br>QDSKDSTYSMSSTLTLTKDEYERHNSYTCEATHKTSTSPIVKSFNRNEC | 279 |
| LC<br>3-3F5-L5<br>huKappa | AIRMTQSPSSFSASTGDRVTITCQASESIGNALAWYQQKPGKAPKLLIYDASDLAS<br>GVPSRFSGSGSGTDFTLTISSLQPEDFATYYCQQGDSHNNVDNIFGGGTKVEIKRT<br>VAAPSVFIFPPSDEQLKSGTASVVCLLNNFYPREAKVQWKVDNALQSGNSQESVTE<br>QDSKDSTYSLSSTLTLSKADYEKHKVYACEVTHQGLSSPVTKSFNRGEC | 280 |
| LC<br>9E3 | AIEMTQTPSSASEPVGGTVTIKCQASESISRYLSWYQQKPGQPPKLLIYDASDLAS<br>GVSSRFKGSGSGTQFTLIISDVECADAATYYCQQDYSRSNIVNSFGGGTEVVVKRA<br>DAAPTVSIFPPSSEQLTSGGASVVCFLNNFYPKDINVKWKIDGSERQNGVLNSWTD<br>QDSKDSTYSMSSTLTLTKDEYERHNSYTCEATHKTSTSPIVKSFNRNEC | 281 |

Table of Sequences

| NAME | SEQUENCE | SEQ ID NO |
|---|---|---|
| LC 10D10 | AYDMTQTPSSASEPVGGTVTIKCQASESISTYLSWYQQKPGQPPKLLIYDASDLAS GVSSRFKGSGSGTQFTLTISDVECADAATYYCQQDYSSSNIVNSFGGGTEVVVKRA DAAPTVSIFPPSSEQLTSGGASVVCFLNNFYPKDINVKWKIDSERQNGVLNSWTD QDSKDSTYSMSSTLTLTKDEYERHNSYTCEATHKTSTSPIVKSFNRNEC | 282 |
| LC 12B3 | AYDMTQTPASVEVAVGGTVTIKCQASQSISTYLAWYQQKPGQRPNLLIYKTSTLAS GVPSRFRGSGSGTQFTLTISGVECADAATYYCQQGYSGSSVENTFGGGTEVVVKRA DAAPTVSIFPPSSEQLTSGGASVVCFLNNFYPKDINVKWKIDSERQNGVLNSWTD QDSKDSTYSMSSTLTLTKDEYERHNSYTCEATHKTSTSPIVKSFNRNEC | 283 |
| LC 1D10 | AYDMTQTPVSVEAAVGGTVTIKCQASQSISSYLAWYQQKPGQPPKLLIYKASTLAS GVSSRFKGSGSGTEFTLTISDLECADAATYYCQQGYSGSNVENTFGGGTEVVVKRA DAAPTVSIFPPSSEQLTSGGASVVCFLNNFYPKDINVKWKIDSERQNGVLNSWTD QDSKDSTYSMSSTLTLTKDEYERHNSYTCEATHKTSTSPIVKSFNRNEC | 284 |
| HC Sequences | | |
| HC 14C8 | EVQLVESGGGLVQPGRSLKLSCTASGFTFSDYNMAWVRQAPKGGLEWVTTISYDAG RTYYRDSVKGRFTISRDNAKRTLSLQMDSLRSEDTATYYCATGIFNYGTDYFDYWG QGVMVTSSASTKGPSVYPLAPVCGDTTGSSVTLGCLVKGYFPEPVTLTWNSGSLS SGVHTFPAVLQSDLYTLSSSVTVTSSTWPSQSITCNVAHPASSTKVDKKIEPRGPT IKPCPPCKCPAPNLLGGPSVFIFPPKIKDVLMISLSPIVTCVVVDVSEDDPDVQIS WFVNNVEVHTAQTQTHREDYNSTLRVVSALPIQHQDWMSGKEFKCKVNNKDLPAPI ERTISKPKGSVRAPQVYVLPPPEEEMTKKQVTLTCMVTDFMPEDIYVEWTNNGKTE LNYKNTEPVLDSDGSYFMYSKLRVEKKNWVERNSYSCSVVHEGLHNHHTTKSFSRT PGK | 285 |
| HC 14E12 | EVQLVESGGGLVRPGRSLRLSCAASGFTFSDYYMAWVRQAPTKGLEWVASISYDGD TTYYRDSVKGRFTISRDNARSSLYLQMDSLRSDDTANYFCTTDGTIPAGSWFAYWG QGTLVTVSSASTKGPSVYPLAPVCGDTTGSSVTLGCLVKGYFPEPVTLTWNSGSLS SGVHTFPAVLQSDLYTLSSSVTVTSSTWPSQSITCNVAHPASSTKVDKKIEPRGPT IKPCPPCKCPAPNLLGGPSVFIFPPKIKDVLMISLSPIVTCVVVDVSEDDPDVQIS WFVNNVEVHTAQTQTHREDYNSTLRVVSALPIQHQDWMSGKEFKCKVNNKDLPAPI ERTISKPKGSVRAPQVYVLPPPEEEMTKKQVTLTCMVTDFMPEDIYVEWTNNGKTE LNYKNTEPVLDSDGSYFMYSKLRVEKKNWVERNSYSCSVVHEGLHNHHTTKSFSRT PGK | 286 |
| HC 8E11 | QEQLEESGGDLVKPEGSLTLTCTASGFSFSSSYWICWVRQAPGKGLEWIACVYGLD VNIYYASWTKGRFTISKTSSTTVTLQMTSLTAADTATYYCARGGGSADFGFDLWGP GTLVTVSSASTKGPSVYPLAPVCGDTTGSSVTLGCLVKGYFPEPVTLTWNSGSLSS GVHTFPAVLQSDLYTLSSSVTVTSSTWPSQSITCNVAHPASSTKVDKKIEPRGPTI KPCPPCKCPAPNLLGGPSVFIFPPKIKDVLMISLSPIVTCVVVDVSEDDPDVQISW FVNNVEVHTAQTQTHREDYNSTLRVVSALPIQHQDWMSGKEFKCKVNNKDLPAPIE RTISKPKGSVRAPQVYVLPPPEEEMTKKQVTLTCMVTDFMPEDIYVEWTNNGKTEL NYKNTEPVLDSDGSYFMYSKLRVEKKNWVERNSYSCSVVHEGLHNHHTTKSFSRTP GK | 287 |
| HC 8G10 | QSLEESGGDLVKPEGSLTLTCTASGFSFSTSYWICWVRQAPGKGLEWIACVYGLDV NIYYASWTEGRFTISKTSSTTVTLQVTSLTAADTATYFCARGGGSADFGFDLWGPG TLVTVSSASTKGPSVYPLAPVCGDTTGSSVTLGCLVKGYFPEPVTLTWNSGSLSSG VHTFPAVLQSDLYTLSSSVTVTSSTWPSQSITCNVAHPASSTKVDKKIEPRGPTIK PCPPCKCPAPNLLGGPSVFIFPPKIKDVLMISLSPIVTCVVVDVSEDDPDVQISWF VNNVEVHTAQTQTHREDYNSTLRVVSALPIQHQDWMSGKEFKCKVNNKDLPAPIER TISKPKGSVRAPQVYVLPPPEEEMTKKQVTLTCMVTDFMPEDIYVEWTNNGKTELN YKNTEPVLDSDGSYFMYSKLRVEKKNWVERNSYSCSVVHEGLHNHHTTKSFSRTPG K | 288 |
| HC 9B6 | QSVKESEGGLFKPTDNLTLTCTVSGFSLSNYGVTWVRQAPGNGLEYIGFIGSGGSA YYASWAKSRSTITRNTNLNTVTLKMTSLTAADTATYFCARDDVGGGKSLDIWGPGT LVTVSSASTKGPSVYPLAPVCGDTTGSSVTLGCLVKGYFPEPVTLTWNSGSLSSGV HTFPAVLQSDLYTLSSSVTVTSSTWPSQSITCNVAHPASSTKVDKKIEPRGPTIKP CPPCKCPAPNLLGGPSVFIFPPKIKDVLMISLSPIVTCVVVDVSEDDPDVQISWFV NNVEVHTAQTQTHREDYNSTLRVVSALPIQHQDWMSGKEFKCKVNNKDLPAPIERT ISKPKGSVRAPQVYVLPPPEEEMTKKQVTLTCMVTDFMPEDIYVEWTNNGKTELNY KNTEPVLDSDGSYFMYSKLRVEKKNWVERNSYSCSVVHEGLHNHHTTKSFSRTPGK | 289 |
| HC 2.3F4 | QSVEESRGGLIKPTDTLTLTCTASGFSLSNYGVSWVRQAPGNGLEYIGFIGYGGST YYASWAKSRSTITRNTNLNTVTLQMTSLTAADTATYFCARLCGVDCADALDSWGPG TLVTVSSASTKGPSVYPLAPVCGDTTGSSVTLGCLVKGYFPEPVTLTWNSGSLSSG VHTFPAVLQSDLYTLSSSVTVTSSTWPSQSITCNVAHPASSTKVDKKIEPRGPTIK PCPPCKCPAPNLLGGPSVFIFPPKIKDVLMISLSPIVTCVVVDVSEDDPDVQISWF | 290 |

Table of Sequences

| NAME | SEQUENCE | SEQ ID NO |
|---|---|---|
| | VNNVEVHTAQTQTHREDYNSTLRVVSALPIQHQDWMSGKEFKCKVNNKDLPAPIER<br>TISKPKGSVRAPQVYVLPPPEEEMTKKQVTLTCMVTDFMPEDIYVEWTNNGKTELN<br>YKNTEPVLDSDGSYFMYSKLRVEKKNWVERNSYSCSVVHEGLHNHHTTKSFSRTPG<br>K | |
| HC 10C5 | QSLEESGGGLVKPTDTLTLTCTVSGFSLSSYGVTWVRQAPGRGLEWIGYITSNYGV<br>SYYASWAKSRSTITRNTNLNTVTLKMTSLTAADTATYFCARENPDYGYAYDAWGPG<br>TLVTVSSASTKGPSVYPLAPVCGDTTGSSVTLGCLVKGYFPEPVTLTWNSGSLSSG<br>VHTFPAVLQSDLYTLSSSVTVTSSTWPSQSITCNVAHPASSTKVDKKIEPRGPTIK<br>PCPPCKCPAPNLLGGPSVFIFPPKIKDVLMISLSPIVTCVVVDVSEDDPDVQISWF<br>VNNVEVHTAQTQTHREDYNSTLRVVSALPIQHQDWMSGKEFKCKVNNKDLPAPIER<br>TISKPKGSVRAPQVYVLPPPEEEMTKKQVTLTCMVTDFMPEDIYVEWTNNGKTELN<br>YKNTEPVLDSDGSYFMYSKLRVEKKNWVERNSYSCSVVHEGLHNHHTTKSFSRTPG<br>K | 291 |
| HC 10C5-H28 hIgG1 N297G | EVQLVESGGGLVQPGGSLRLSCAASGFSLSSYGVTWVRQAPGKGLEWIGYITSNYG<br>VSYYASWAKSRSTISRDTSKNTVYLQMGSLRAEDMAVYYCARENPDYGYAYDAWGQ<br>GTTVTVSSASTKGPSVFPLAPSSKSTSGGTAALGCLVKDYFPEPVTVSWNSGALTS<br>GVHTFPAVLQSSGLYSLSSVVTVPSSSLGTQTYICNVNHKPSNTKVDKKVEPKSCD<br>KTHTCPPCPAPELLGGPSVFLFPPKPKDTLMISRTPEVTCVVVDVSHEDPEVKFNW<br>YVDGVEVHNAKTKPREEQYGSTYRVVSVLTVLHQDWLNGKEYKCKVSNKALPAPIE<br>KTISKAKGQPREPQVYTLPPSREEMTKNQVSLTCLVKGFYPSDIAVEWESNGQPEN<br>NYKTTPPVLDSDGSFFLYSKLTVDKSRWQQGNVFSCSVMHEALHNHYTQKSLSLSP<br>GK | 292 |
| HC 10C5-H28 hIgG4 S228P | EVQLVESGGGLVQPGGSLRLSCAASGFSLSSYGVTWVRQAPGKGLEWIGYITSNYG<br>VSYYASWAKSRSTISRDTSKNTVYLQMGSLRAEDMAVYYCARENPDYGYAYDAWGQ<br>GTTVTVSSASTKGPSVFPLAPCSRSTSESTAALGCLVKDYFPEPVTVSWNSGALTS<br>GVHTFPAVLQSSGLYSLSSVVTVPSSSLGTKTYTCNVDHKPSNTKVDKRVESKYGP<br>PCPPCPAPEFLGGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTI<br>SKAKGQPREPQVYTLPPSQEEMTKNQVSLTCLVKGFYPSDIAVEWESNGQPENNYK<br>TTPPVLDSDGSFFLYSRLTVDKSRWQEGNVFSCSVMHEALHNHYTQKSLSLSLGK | 293 |
| HC 2B11 | QSVKESEGGLFKPTDTLTLTCTVSGFSLINYGVSWVRQAPGKGLEWIGYIGSAGST<br>YYATWAKSRATITRNTNLNTVTLKMTSLTAADTATYFCARAAYSAGSADAEDIWGP<br>GTLVTVSSASTKGPSVYPLAPVCGDTTGSSVTLGCLVKGYFPEPVTLTWNSGSLSS<br>GVHTFPAVLQSDLYTLSSSVTVTSSTWPSQSITCNVAHPASSTKVDKKIEPRGPTI<br>KPCPPCKCPAPNLLGGPSVFIFPPKIKDVLMISLSPIVTCVVVDVSEDDPDVQISW<br>FVNNVEVHTAQTQTHREDYNSTLRVVSALPIQHQDWMSGKEFKCKVNNKDLPAPIE<br>RTISKPKGSVRAPQVYVLPPPEEEMTKKQVTLTCMVTDFMPEDIYVEWTNNGKTEL<br>NYKNTEPVLDSDGSYFMYSKLRVEKKNWVERNSYSCSVVHEGLHNHHTTKSFSRTP<br>GK | 294 |
| HC 10H3 | QSVKESEGGLIKPTDTLTLTCTVSGFSLSTFAINWVRQAPGNGLEWIGAIGRGGSA<br>YYASWAKSRSTITRNTNLNTVTLKMTRPTAADTATYFCARENAGSGWGELDIWGPG<br>TLVTVSSASTKGPSVYPLAPVCGDTTGSSVTLGCLVKGYFPEPVTLTWNSGSLSSG<br>VHTFPAVLQSDLYTLSSSVTVTSSTWPSQSITCNVAHPASSTKVDKKIEPRGPTIK<br>PCPPCKCPAPNLLGGPSVFIFPPKIKDVLMISLSPIVTCVVVDVSEDDPDVQISWF<br>VNNVEVHTAQTQTHREDYNSTLRVVSALPIQHQDWMSGKEFKCKVNNKDLPAPIER<br>TISKPKGSVRAPQVYVLPPPEEEMTKKQVTLTCMVTDFMPEDIYVEWTNNGKTELN<br>YKNTEPVLDSDGSYFMYSKLRVEKKNWVERNSYSCSVVHEGLHNHHTTKSFSRTPG<br>K | 295 |
| HC 9H3 | QSVKESEGGLFKPTDTLTLTCTVSGFSLSGYGVSWVRQAPGKGLEYIGFIGSGGSA<br>YYASWAKSRSTITRNTNLNTVTLKMTRLTAADTATYFCARDNVGGDMSLDIWGPGT<br>LVTVSSASTKGPSVYPLAPVCGDTTGSSVTLGCLVKGYFPEPVTLTWNSGSLSSGV<br>HTFPAVLQSDLYTLSSSVTVTSSTWPSQSITCNVAHPASSTKVDKKIEPRGPTIKP<br>CPPCKCPAPNLLGGPSVFIFPPKIKDVLMISLSPIVTCVVVDVSEDDPDVQISWFV<br>NNVEVHTAQTQTHREDYNSTLRVVSALPIQHQDWMSGKEFKCKVNNKDLPAPIERT<br>ISKPKGSVRAPQVYVLPPPEEEMTKKQVTLTCMVTDFMPEDIYVEWTNNGKTELNY<br>KNTEPVLDSDGSYFMYSKLRVEKKNWVERNSYSCSVVHEGLHNHHTTKSFSRTPGK | 296 |
| HC 8B7 | QSVKESEGGLFKPTDNLTLTCTVSGFSLSNYGVTWVRQAPGNGLEYIGFIGSSGSA<br>YYASWAKSRSTITRNTNLNTVTLKMTSLTAADTATYFCARDDVGGGKSLDIWGPGT<br>LVTVSSASTKGPSVYPLAPVCGDTTGSSVTLGCLVKGYFPEPVTLTWNSGSLSSGV<br>HTFPAVLQSDLYTLSSSVTVTSSTWPSQSITCNVAHPASSTKVDKKIEPRGPTIKP<br>CPPCKCPAPNLLGGPSVFIFPPKIKDVLMISLSPIVTCVVVDVSEDDPDVQISWFV<br>NNVEVHTAQTQTHREDYNSTLRVVSALPIQHQDWMSGKEFKCKVNNKDLPAPIERT<br>ISKPKGSVRAPQVYVLPPPEEEMTKKQVTLTCMVTDFMPEDIYVEWTNNGKTELNY<br>KNTEPVLDSDGSYFMYSKLRVEKKNWVERNSYSCSVVHEGLHNHHTTKSFSRTPGK | 297 |
| HC 9H5 | QSVKESEGGLFKPTDNLTLTCTVSGFSLSSYGVSWVRQAPGNGLEYIGFIGSGGFA<br>YYASWAKSRSTITRNTNLNTVTLKMTSLTAADTATYFCARDDVGGGKSLDIWGPGT | 298 |

Table of Sequences

| NAME | SEQUENCE | SEQ ID NO |
|---|---|---|
| | VVTVSSASTKGPSVYPLAPVCGDTTGSSVTLGCLVKGYFPEPVTLTWNSGSLSSGV HTFPAVLQSDLYTLSSSVTVTSSTWPSQSITCNVAHPASSTKVDKKIEPRGPTIKP CPPCKCPAPNLLGGPSVFIFPPKIKDVLMISLSPIVTCVVVDVSEDDPDVQISWFV NNVEVHTAQTQTHREDYNSTLRVVSALPIQHQDWMSGKEFKCKVNNKDLPAPIERT ISKPKGSVRAPQVYVLPPPEEEMTKKQVTLTCMVTDFMPEDIYVEWTNNGKTELNY KNTEPVLDSDGSYFMYSKLRVEKKNWVERNSYSCSVVHEGLHNHHTTKSFSRTPGK | |
| HC 9H5-H14 hIgG1 N297G | EVQLVESGGGLIQPGGSLRLSCAASGFSLSSYGVSWVRQAPGKGLEYVGFIGSGGF AYYASWAKSRFTISRDNSKNTLYLQMNSLRAEDTAVYYCARDDVGGGKSLDIWGQG TLVTVSSASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKVEPKSCDK THTCPPCPAPELLGGPSVFLFPPKPKDTLMISRTPEVTCVVVDVSHEDPEVKFNWY VDGVEVHNAKTKPREEQYGSTYRVVSVLTVLHQDWLNGKEYKCKVSNKALPAPIEK TISKAKGQPREPQVYTLPPSREEMTKNQVSLTCLVKGFYPSDIAVEWESNGQPENN YKTTPPVLDSDGSFFLYSKLTVDKSRWQQGNVFSCSVMHEALHNHYTQKSLSLSPG K | 299 |
| HC 9H5-H14 hIgG4 S228P | EVQLVESGGGLIQPGGSLRLSCAASGFSLSSYGVSWVRQAPGKGLEYVGFIGSGGF AYYASWAKSRFTISRDNSKNTLYLQMNSLRAEDTAVYYCARDDVGGGKSLDIWGQG TLVTVSSASTKGPSVFPLAPCSRSTSESTAALGCLVKDYFPEPVTVSWNSGALTSG VHTFPAVLQSSGLYSLSSVVTVPSSSLGTKTYTCNVDHKPSNTKVDKRVESKYGPP CPPCPAPEFLGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEKTIS KAKGQPREPQVYTLPPSQEEMTKNQVSLTCLVKGFYPSDIAVEWESNGQPENNYKT TPPVLDSDGSFFLYSRLTVDKSRWQEGNVFSCSVMHEALHNHYTQKSLSLSLGK | 300 |
| HC 9F2 | QSVKESEGGLFKPTDNLTLTCTVSGFSLSSYGVSWVRQAPGNGLEYIGFIGSGGSP YYASWAKSRSTITRNTNLNTVTLKMTSLTAADTATYFCARDDVGGGKSLDIWGPGT LVTVSSASTKGPSVYPLAPVCGDTTGSSVTLGCLVKGYFPEPVTLTWNSGSLSSGV HTFPAVLQSDLYTLSSSVTVTSSTWPSQSITCNVAHPASSTKVDKKIEPRGPTIKP CPPCKCPAPNLLGGPSVFIFPPKIKDVLMISLSPIVTCVVVDVSEDDPDVQISWFV NNVEVHTAQTQTHREDYNSTLRVVSALPIQHQDWMSGKEFKCKVNNKDLPAPIERT ISKPKGSVRAPQVYVLPPPEEEMTKKQVTLTCMVTDFMPEDIYVEWTNNGKTELNY KNTEPVLDSDGSYFMYSKLRVEKKNWVERNSYSCSVVHEGLHNHHTTKSFSRTPGK | 301 |
| HC 10C8 | QSVKESEGGLFKPTDNLTLTCTVSGFSLSSYGVSWVRQAPGNGLEYIGFIGSGGFA YYASWAKSRSTITRNTNLNTVTLKMTSLTAADTATYFCARDDVGGGRSLDIWGPGT VVTVSSASTKGPSVYPLAPVCGDTTGSSVTLGCLVKGYFPEPVTLTWNSGSLSSGV HTFPAVLQSDLYTLSSSVTVTSSTWPSQSITCNVAHPASSTKVDKKIEPRGPTIKP CPPCKCPAPNLLGGPSVFIFPPKIKDVLMISLSPIVTCVVVDVSEDDPDVQISWFV NNVEVHTAQTQTHREDYNSTLRVVSALPIQHQDWMSGKEFKCKVNNKDLPAPIERT ISKPKGSVRAPQVYVLPPPEEEMTKKQVTLTCMVTDFMPEDIYVEWTNNGKTELNY KNTEPVLDSDGSYFMYSKLRVEKKNWVERNSYSCSVVHEGLHNHHTTKSFSRTPGK | 302 |
| HC 8F5 | QSVKESEGGLFKPTDTLTLTCTVSGFSLSSYPISWVRQAPGNGLEWIGYITSEYGV AYYATWAESRSTITRNTNLNTVTLKMTSLTAADTATYFCVRENPTYGYAYDAWGPG TLVTVSSASTKGPSVYPLAPVCGDTTGSSVTLGCLVKGYFPEPVTLTWNSGSLSSG VHTFPAVLQSDLYTLSSSVTVTSSTWPSQSITCNVAHPASSTKVDKKIEPRGPTIK PCPPCKCPAPNLLGGPSVFIFPPKIKDVLMISLSPIVTCVVVDVSEDDPDVQISWF VNNVEVHTAQTQTHREDYNSTLRVVSALPIQHQDWMSGKEFKCKVNNKDLPAPIER TISKPKGSVRAPQVYVLPPPEEEMTKKQVTLTCMVTDFMPEDIYVEWTNNGKTELN YKNTEPVLDSDGSYFMYSKLRVEKKNWVERNSYSCSVVHEGLHNHHTTKSFSRTPG K | 303 |
| HC 3-3F5 | QSVKESEGGLFKPTDTLTLTCTVSGFSLNDYGVSWVRQAPGNGLEWIGAIGSSGVA WYANWAKGRSTITRNTNLNTVTLKMASLTAADTATYFCARDRDYGYRADDATSGMD LWGPGTLVTVSSASTKGPSVYPLAPVCGDTTGSSVTLGCLVKGYFPEPVTLTWNSG SLSSGVHTFPAVLQSDLYTLSSSVTVTSSTWPSQSITCNVAHPASSTKVDKKIEPR GPTIKPCPPCKCPAPNLLGGPSVFIFPPKIKDVLMISLSPIVTCVVVDVSEDDPDV QISWFVNNVEVHTAQTQTHREDYNSTLRVVSALPIQHQDWMSGKEFKCKVNNKDLP APIERTISKPKGSVRAPQVYVLPPPEEEMTKKQVTLTCMVTDFMPEDIYVEWTNNG KTELNYKNTEPVLDSDGSYFMYSKLRVEKKNWVERNSYSCSVVHEGLHNHHTTKSF SRTPGK | 304 |
| HC 3-3F5-H19 hIgG1 N297G | EVQLLESGGGLVQPGGSLRLSCAVSGFSLNDYGVSWVRQAPGKGLEWVGAIGSSGV AWYANFAKGRFTISRDNSKNTLYLQMNSLRAEDTAVYYCARDRDYGYRADDATSGM DLWGRGTLVTVSSASTKGPSVFPLAPSSKSTSGGTAALGCLVKDYFPEPVTVSWNS GALTSGVHTFPAVLQSSGLYSLSSVVTVPSSSLGTQTYICNVNHKPSNTKVDKKVE PKSCDKTHTCPPCPAPELLGGPSVFLFPPKPKDTLMISRTPEVTCVVVDVSHEDPE VKFNWYVDGVEVHNAKTKPREEQYGSTYRVVSVLTVLHQDWLNGKEYKCKVSNKAL PAPIEKTISKAKGQPREPQVYTLPPSREEMTKNQVSLTCLVKGFYPSDIAVEWESN GQPENNYKTTPPVLDSDGSFFLYSKLTVDKSRWQQGNVFSCSVMHEALHNHYTQKS LSLSPGK | 305 |

-continued

Table of Sequences

| NAME | SEQUENCE | SEQ ID NO |
|---|---|---|
| HC 3-3F5-H19 hIgG4 S228P | EVQLLESGGGLVQPGGSLRLSCAVSGFSLNDYGVSWVRQAPGKGLEWVGAIGSSGV AWYANFAKGRFTISRDNSKNTLYLQMNSLRAEDTAVYYCARDRDYGYRADDATSGM DLWGRGTLVTVSSASTKGPSVFPLAPCSRSTSESTAALGCLVKDYFPEPVTVSWNS GALTSGVHTFPAVLQSSGLYSLSSVVTVPSSSLGTKTYTCNVDHKPSNTKVDKRVE SKYGPPCPPCPAPEFLGGPSVFLFPPKPKDTLMISRTPEVTCVVVDVSQEDPEVQF NWYVDGVEVHNAKTKPREEQFNSTYRVVSVLTVLHQDWLNGKEYKCKVSNKGLPSS IEKTISKAKGQPREPQVYTLPPSQEEMTKNQVSLTCLVKGFYPSDIAVEWESNGQP ENNYKTTPPVLDSDGSFFLYSRLTVDKSRWQEGNVFSCSVMHEALHNHYTQKSLSL SLGK | 306 |
| HC 9E3 | QEQLEESGGGLVKPGASLTLTCTVSGFSLTNNYVNFVMCWVRQAPGKGLEWIASID PGDDSTDYASWATGRFTISKASSTTVTLQVTSLTAADTATYFCARGDAGTSYSFNF WGPGTLVTVSSASTKGPSVYPLAPVCGDTTGSSVTLGCLVKGYFPEPVTLTWNSGS LSSGVHTFPAVLQSDLYTLSSSVTVTSSTWPSQSITCNVAHPASSTKVDKKIEPRG PTIKPCPPCKCPAPNLLGGPSVFIFPPKIKDVLMISLSPIVTCVVVDVSEDDPDVQ ISWFVNNVEVHTAQTQTHREDYNSTLRVVSALPIQHQDWMSGKEFKCKVNNKDLPA PIERTISKPKGSVRAPQVYVLPPPEEEMTKKQVTLTCMVTDFMPEDIYVEWTNNGK TELNYKNTEPVLDSDGSYFMYSKLRVEKKNWVERNSYSCSVVHEGLHNHHTTKSFS RTPGK | 307 |
| HC 10D10 | QEQLVESGGGLVKPGASLTLTCTASGFSLTDNYVMSWVRQAPGKGLEWIACIDPGD DSTYYASWATGRFTISRASSTTVTLQVTSLTAADTATYFCARGDAAASYSFNFWGP GTLVTVSSASTKGPSVYPLAPVCGDTTGSSVTLGCLVKGYFPEPVTLTWNSGSLSS GVHTFPAVLQSDLYTLSSSVTVTSSTWPSQSITCNVAHPASSTKVDKKIEPRGPTI KPCPPCKCPAPNLLGGPSVFIFPPKIKDVLMISLSPIVTCVVVDVSEDDPDVQISW FVNNVEVHTAQTQTHREDYNSTLRVVSALPIQHQDWMSGKEFKCKVNNKDLPAPIE RTISKPKGSVRAPQVYVLPPPEEEMTKKQVTLTCMVTDFMPEDIYVEWTNNGKTEL NYKNTEPVLDSDGSYFMYSKLRVEKKNWVERNSYSCSVVHEGLHNHHTTKSFSRTP GK | 308 |
| HC 12B3 | QSLEESGGGLVKPGGTLTLTCKASGIDFNGGGIYWVRQAPGKGLEWIASIYPDHGS VDYANWVNGRFTISLDNAQNTVFLQLTSLTVADTATYFCARESGGSYYDLWGPGTL VTVSSASTKGPSVYPLAPVCGDTTGSSVTLGCLVKGYFPEPVTLTWNSGSLSSGVH TFPAVLQSDLYTLSSSVTVTSSTWPSQSITCNVAHPASSTKVDKKIEPRGPTIKPC PPCKCPAPNLLGGPSVFIFPPKIKDVLMISLSPIVTCVVVDVSEDDPDVQISWFVN NVEVHTAQTQTHREDYNSTLRVVSALPIQHQDWMSGKEFKCKVNNKDLPAPIERTI SKPKGSVRAPQVYVLPPPEEEMTKKQVTLTCMVTDFMPEDIYVEWTNNGKTELNYK NTEPVLDSDGSYFMYSKLRVEKKNWVERNSYSCSVVHEGLHNHHTTKSFSRTPGK | 309 |
| HC 1D10 | QSLEESGGGLVKPGGTLTLTCTASGFDFNGGGIYWVRQAPGKGLEWIAYIYPDHGS ADYATWVNGRFTISLDNAQNTVFLQMTSLTVADTATYFCARETGGSWYDLWGPGTL VTVSSASTKGPSVYPLAPVCGDTTGSSVTLGCLVKGYFPEPVTLTWNSGSLSSGVH TFPAVLQSDLYTLSSSVTVTSSTWPSQSITCNVAHPASSTKVDKKIEPRGPTIKPC PPCKCPAPNLLGGPSVFIFPPKIKDVLMISLSPIVTCVVVDVSEDDPDVQISWFVN NVEVHTAQTQTHREDYNSTLRVVSALPIQHQDWMSGKEFKCKVNNKDLPAPIERTI SKPKGSVRAPQVYVLPPPEEEMTKKQVTLTCMVTDFMPEDIYVEWTNNGKTELNYK NTEPVLDSDGSYFMYSKLRVEKKNWVERNSYSCSVVHEGLHNHHTTKSFSRTPGK | 310 |
| Constant Regions | | |
| huKappa | RTVAAPSVFIFPPSDEQLKSGTASVVCLLNNFYPREAKVQWKVDNALQSGNSQESV TEQDSKDSTYSLSSTLTLSKADYEKHKVYACEVTHQGLSSPVTKSFNRGEC | 311 |
| hIgG1 N297 | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKKVEPKSCDKTHTCPPC PAPELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKG QPREPQVYTLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSPGK | 312 |
| hIgG1 G297 | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKKVEPKSCDKTHTCPPC PAPELLGGPSVFLFPPKPKDTLMISRTPEVTCVVVDVSHEDPEVKFNWYVDGVEVH NAKTKPREEQYGSTYRVVSVLTVLHQDWLNGKEYKCKVSNKALPAPIEKTISKAKG QPREPQVYTLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSPGK | 313 |
| hIgG4 S228 | ASTKGPSVFPLAPCSRSTSESTAALGCLVKDYFPEPVTVSWNSGALTSGVHTFPAV LQSSGLYSLSSVVTVPSSSLGTKTYTCNVDHKPSNTKVDKRVESKYGPPCPSCPAP EFLGGPSVFLFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTISKAKGQPR EPQVYTLPPSQEEMTKNQVSLTCLVKGFYPSDIAVEWESNGQPENNYKTTPPVLDS DGSFFLYSRLTVDKSRWQEGNVFSCSVMHEALHNHYTQKSLSLSLGK | 314 |

| NAME | SEQUENCE | SEQ ID NO |
|---|---|---|
| hIgG4 P228 | ASTKGPSVFPLAPCSRSTSESTAALGCLVKDYFPEPVTVSWNSGALTSGVHTFPAV LQSSGLYSLSSVVTVPSSSLGTKTYTCNVDHKPSNTKVDKRVESKYGPPCPPCPAP EFLGGPSVFLFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTISKAKGQPR EPQVYTLPPSQEEMTKNQVSLTCLVKGFYPSDIAVEWESNGQPENNYKTTPPVLDS DGSFFLYSRLTVDKSRWQEGNVFSCSVMHEALHNHYTQKSLSLSLGK | 315 |

Miscellaneous Sequences

| NAME | SEQUENCE | SEQ ID NO |
|---|---|---|
| KLK5 thermodynamic epitope Region 1 | LRPNQL | 316 |
| KLK5 thermodynamic epitope Region 2 | QGVKSI | 317 |
| KLK5 thermodynamic epitope Region 3 | KRCEDAYPRQIDDT | 318 |
| KLK5 thermodynamic epitope Region 4 | DYPCARPNRPGVY | 319 |
| Hu SPINK9 (I20-C86. C22S.H48R. M49E); Fc human IgG1 E356.M358 | IESAKQTKQMVDCSHYKKLPPGQQRFCHREYDPICGSDGKTYKNDCFFCSK VKKTDGTLKFVHFGKCGNSVTDKTHTCPPCPAPELLGGPSVFLFPPKPKDT LMISRTPEVTCVVVDVSHEDPEVKFNWYVDGVEVHNAKTKPREEQYNSTYR VVSVLTVLHQDWLNGKEYKCKVSNKALPAPIEKTISKAKGQPREPQVYTLP PSREEMTKNQVSLTCLVKGFYPSDIAVEWESNGQPENNYKTTPPVLDSDGS FFLYSKLTVDKSRWQQGNVFSCSVMHEALHNHYTQKSLSLSPGK | 320 |
| VL hu10C5-L6 | AIRMTQSPSSFSASTGDRVTITCQASESISNELSWYQQKPGKAPKLLIYYASTLAS GVPSRFSGSGSGTDFTLTISSLQPEDFATYYCAQGFGSSGVENVFGGGTEVVVK | 321 |
| Fab HC 10C5 Humanized | EVQLVESGGGLVQPGGSLRLSCAASGFSLSSYGVTWVRQAPGKGLEWIGYITSNYG VSYYASWAKSRSTISRDTSKNTVYLQMGSLRAEDMAVYYCARENPDYGYAYDAWGQ GTTVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSCD | 322 |
| Fab LC 10C5 Humanized | AIRMTQSPSSFSASTGDRVTITCQASESISNELSWYQQKPGKAPKLLIYYASTLAS GVPSRFSGSGSGTDFTLTISSLQPEDFATYYCAQGFGSSGVENVFGGGTKVEIKRT VAAPSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC | 323 |
| Fab HC 9H5 Humanized | EVQLVESGGGLIQPGGSLRLSCAASGFSLSSYGVSWVRQAPGKGLEYVGFIGSGGF AYYASWAKSRFTISRDNSKNTLYLQMNSLRAEDTAVYYCARDDVGGGKSLDIWGQG TLVTVSSASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKVEPKSCD | 324 |
| Fab LC 9H5 Humanized | DIQMTQSPSSLSASVGDRVTITCQASQSISSYLSWYQQKPGKAPKLLIYSASTLAS GVPSRFSGSGSGTDFTLTISSLQPEDFATYYCHQDYTSSNVDNTFGGGTKVEIKRT VAAPSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC | 325 |
| Fab HC 3-3F5 Humanized | EVQLLESGGGLVQPGGSLRLSCAVSGFSLNDYGVSWVRQAPGKGLEWVGAIGSSGV AWYANFAKGRFTISRDNSKNTLYLQMNSLRAEDTAVYYCARDRDYGYRADDATSGM DLWGRGTLVTVSSASTKGPSVFPLAPSSKSTSGGTAALGCLVKDYFPEPVTVSWNS GALTSGVHTFPAVLQSSGLYSLSSVVTVPSSSLGTQTYICNVNHKPSNT KVDKKVEPKSCD | 326 |
| Fab LC 3-3F5 Humanized | AIRMTQSPSSFSASTGDRVTITCQASESIGNALAWYQQKPGKAPKLLIYDASDLAS GVPSRFSGSGSGTDFTLTISSLQPEDFATYYCQQGDSHNNVDNIFGGGTKVEIKRT VAAPSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC | 327 |

-continued

Table of Sequences

| NAME | SEQUENCE | SEQ ID NO |
|---|---|---|
| Human KLK5 Crystal Structure Experiments | IINGSDCDMHTQPWQAALLLRPNQLYCGAVLVHPQWLLTAAHCRKKVFRVRLGHYS LSPVYESGQQMFQGVKSIPHPGYSHPGHSNDLMLIKLNRRIRPTKDVRPINVSSHC PSAGTKCLVSGWGTTKSPQVHFPKVLQCLNISVLSQKRCEDAYPRQIDDTMFCAGD KAGRDSCQGDSGGPVVCNGSLQGLVSWGDYPCARPNRPGVYTNLCKFTKWIQETIQ ANS | 328 |

Framework Sequences

| NAME | SEQUENCE | SEQ ID NO |
|---|---|---|
| FR-L1 10C5 (consensus) | AX$_1$RMTQSPSSFSASTGDRVTITC<br>wherein X$_1$ is Y or H | 329 |
| FR-L2 10C5 (consensus) | WYQQKPGKX$_1$PKLLIY<br>wherein X$_1$ is P or A | 330 |
| FR-L3 10C5 (consensus) | GVPSRFSGSGSGTDFTLTISX$_1$LQX$_2$EDFATYYC<br>wherein X$_1$ is C or S, X$_2$ is S or P | 331 |
| FR-L4 10C5 (consensus) | FGGGTX$_1$VX$_2$X$_3$K<br>wherein X$_1$ is E or K, X$_2$ is E or V, X$_3$ is I or V | 332 |
| FR-H1 10C5 (consensus) | EX$_1$QLVESGGGLVQPGGSLRLSCAX$_2$SGFSLS<br>wherein X$_1$ is V or Q, X$_2$ is V or A | 333 |
| FR-H2 10C5 (consensus) | WVRQAPGKGLEX$_1$X$_2$X$_3$<br>wherein X$_1$ is W or Y, X$_2$ is I or V, X$_3$ is G or S | 334 |
| FR-H3 10C5 (consensus) | RX$_1$TISRX$_2$X$_3$X$_4$X$_5$NTX$_6$YLQMGSLRAEDMAVYX$_7$CAR<br>wherein X$_1$ is S or F, X$_2$ is D or N, X$_3$ is T, L or N, X$_4$ is S or N, X$_5$ is K, T or L, X$_6$ is V or L, X$_7$ is F or Y | 335 |
| FR-H4 10C5 (consensus) | WGX$_1$GTTVTVSS<br>wherein X$_1$ is P or Q | 336 |
| FR-L1 9H5 | DIQMTQSPSSLSASVGDRVTITC | 337 |
| FR-L2 9H5 (consensus) | WYQQKPGKX$_1$PKLLIX$_2$<br>wherein X$_1$ is R or A, X$_2$ is F or Y | 338 |
| FR-L3 9H5 | GVPSRFSGSGSGTDFTLTISSLQPEDFATYYC | 339 |
| FR-L4 9H5 (consensus) | FGGGTX$_3$VX$_4$X$_5$K<br>wherein X$_3$ is E or K, X$_4$ is E or V, X$_5$ is V or I | 340 |
| FR-H1 9H5 (consensus) | EX$_1$QLVESGGGLIQPGGSLRLSCAX$_2$SGFSLS<br>wherein X$_1$ is V or Q, X$_2$ is V or A | 341 |
| FR-H2 9H5 (consensus) | WVRQAPGKGLEX$_1$X$_2$X$_3$<br>wherein X$_1$ is Y or W, X$_2$ is I or V, X$_3$ is G or S | 342 |
| FR-H3 9H5 (consensus) | RX$_1$TISRX$_2$X$_3$X$_4$X$_5$NTX$_6$YLQMNSLRAEDTAVYX$_7$CAR<br>wherein X$_1$ is S or F, X$_2$ is D or N, X$_3$ is T or N, X$_4$ is S or N, X$_5$ is K or L, X$_6$ is V or L, X$_7$ is F or Y | 343 |
| FR-H4 9H5 (consensus) | WGX$_1$GTLVTVSS<br>wherein X$_1$ is P or Q | 344 |
| FR-L1 3-3F5 (consensus) | AX$_1$RMTQSPSSFSASTGDRVTITC<br>wherein X$_1$ is Y or I | 345 |

-continued

| Table of Sequences | | |
|---|---|---|
| NAME | SEQUENCE | SEQ ID NO |
| FR-L2 3-3F5 (consensus) | WYQQKPGKX$_1$PKLLIY wherein X$_1$ is P or A | 346 |
| FR-L3 3-3F5 (consensus) | GVPSRFSGSGSGTDFTLTISX$_1$LQX$_2$EDFATYYC wherein X$_1$ is C or S, X$_2$ is S or P | 347 |
| FR-L4 3-3F5 (consensus) | FGGGTX$_1$VX$_2$X$_3$K wherein X$_1$ is E or K, X$_2$ is E or V, X$_3$ is V or I | 348 |
| FR-H1 3-3F5 (consensus) | EX$_1$QLX$_2$ESGGGLVQPGGSLRLSCAX$_3$SGFSLN wherein X$_1$ is V or Q, X$_2$ is V or L, X$_3$ is V or A | 349 |
| FR-H2 3-3F5 (consensus) | WVRQAPGKGLEWX$_1$X$_2$ wherein X$_1$ is I or V, X$_2$ is G or S | 350 |
| FR-H3 3-3F5 (consensus) | RX$_1$TISRX$_2$X$_3$X$_4$X$_5$NTX$_6$YLQMNSLRAEDTAVYX$_7$CAR wherein X$_1$ is S or F, X$_2$ is H, N or D, X$_3$ is T or N, X$_4$ is S or N, X$_5$ is K or L, X$_6$ is V or L, X$_7$ is F or Y | 351 |
| FR-H4 3-3F5 (consensus) | WGX$_1$GTLVTVSS wherein X$_1$ is P or R | 352 |
| Human KLK5 HDX Experiments | NNDVSCDHPSNTVPSGSNQDLGAGAGEDARSDDSSSRIINGSDCDMHTQPWQAALL LRPNQLYCGAVLVHPQWLLTAAHCRKKVFRVRLGHYSLSPVYESGQQMFQGVKSIP HPGYSHPGHSNDLMLIKLNRRIRPTKDVRPINVSSHCPSAGTKCLVSGWGTTKSPQ VHFPKVLQCLNISVLSQKRCEDAYPRQIDDTMFCAGDKAGRDSCQGDSGGPVVCNG SLQGLVSWGDYPCARPNRPGVYTNLCKFTKWIQETIQANSGNSDYKDDDDK | 353 |

What is claimed is:

1. An isolated antibody that binds to kallikrein-related peptidase 5 (KLK5), wherein the antibody comprises:
   (a) HVR-H1 comprising the amino acid sequence of SEQ ID NO:24; (b) HVR-H2 comprising the amino acid sequence selected from the group consisting of SEQ ID NO:48, SEQ ID NO:49, SEQ ID NO:50, SEQ ID NO:51, SEQ ID NO:52, and SEQ ID NO:53; (c) HVR-H3 comprising the amino acid sequence of SEQ ID NO:72; (d) HVR-L1 comprising the amino acid sequence of SEQ ID NO:91; (e) HVR-L2 comprising the amino acid sequence of SEQ ID NO:99; and (f) HVR-L3 comprising the amino acid sequence of SEQ ID NO:122.

2. The antibody of claim 1, wherein the antibody comprises:
   (a) HVR-H1 comprising the amino acid sequence of SEQ ID NO:24; (b) HVR-H2 comprising the amino acid sequence of SEQ ID NO:52; (c) HVR-H3 comprising the amino acid sequence of SEQ ID NO:72; (d) HVR-L1 comprising the amino acid sequence of SEQ ID NO:91; (e) HVR-L2 comprising the amino acid sequence of SEQ ID NO:99; and (f) HVR-L3 comprising the amino acid sequence of SEQ ID NO: 122.

3. The antibody of claim 1, wherein the antibody inhibits the biological activity of KLK5 by at least 50% as measured by one or more methods selected from the group consisting of a recombinant KLK5 direct activity assay, a coupled pro-kallikrein-related peptidase 1 (KLK1) fluorescent peptide assay, a coupled pro-KLK7 fluorescent peptide assay, a pro-KLK1 LC/MS assay, a pro-KLK7 LC/MS assay, and a $K_{i(app)}$ assay.

4. The antibody of claim 3, wherein the biological activity is the serine protease activity of KLK5.

5. The antibody of claim 1, wherein the antibody comprises a heavy chain variable domain (VH) having the amino acid sequence of SEQ ID NO: 257, and a light chain variable domain (VL) having the amino acid sequence of SEQ ID NO: 162.

6. The antibody of claim 1, wherein the antibody comprises a heavy chain variable domain (VH) having at least 95% sequence identity to the amino acid sequence of SEQ ID NO: 248, and a light chain variable domain (VL) having at least 95% sequence identity to the amino acid sequence of SEQ ID NO: 160.

7. The antibody of claim 1, wherein the antibody comprises a heavy chain variable domain (VH) having the amino acid sequence of SEQ ID NO: 248, and a light chain variable domain (VL) having the amino acid sequence of SEQ ID NO: 160.

8. The antibody of claim 1, wherein the antibody comprises a heavy chain (HC) having the amino acid sequence of SEQ ID NO: 305 or 306, and a light chain (LC) having the amino acid sequence of SEQ ID NO: 280.

9. A pharmaceutical formulation comprising the antibody of claim 1, and a pharmaceutically acceptable carrier.

10. An immunoconjugate comprising the antibody of claim 1.

11. An isolated nucleic acid encoding the antibody of claim 1.

12. An isolated host cell comprising the nucleic acid of claim 11.

13. A method of producing an antibody comprising culturing the isolated host cell of claim 12 so that the antibody is produced.

* * * * *

SEQUENCE LISTING

<160> NUMBER OF SEQ ID NOS: 356

<210> SEQ ID NO 1
<211> LENGTH: 293
<212> TYPE: PRT
<213> ORGANISM: Homo sapiens

<400> SEQUENCE: 1

```
Met Ala Thr Ala Arg Pro Pro Trp Met Trp Val Leu Cys Ala Leu Ile
1               5                   10                  15

Thr Ala Leu Leu Leu Gly Val Thr Glu His Val Leu Ala Asn Asn Asp
            20                  25                  30

Val Ser Cys Asp His Pro Ser Asn Thr Val Pro Ser Gly Ser Asn Gln
        35                  40                  45

Asp Leu Gly Ala Gly Ala Gly Glu Asp Ala Arg Ser Asp Asp Ser Ser
    50                  55                  60

Ser Arg Ile Ile Asn Gly Ser Asp Cys Asp Met His Thr Gln Pro Trp
65                  70                  75                  80

Gln Ala Ala Leu Leu Leu Arg Pro Asn Gln Leu Tyr Cys Gly Ala Val
                85                  90                  95

Leu Val His Pro Gln Trp Leu Leu Thr Ala Ala His Cys Arg Lys Lys
            100                 105                 110

Val Phe Arg Val Arg Leu Gly His Tyr Ser Leu Ser Pro Val Tyr Glu
        115                 120                 125

Ser Gly Gln Gln Met Phe Gln Gly Val Lys Ser Ile Pro His Pro Gly
```

-continued

```
                130                 135                 140
Tyr Ser His Pro Gly His Ser Asn Asp Leu Met Leu Ile Lys Leu Asn
145                 150                 155                 160

Arg Arg Ile Arg Pro Thr Lys Asp Val Arg Pro Ile Asn Val Ser Ser
                165                 170                 175

His Cys Pro Ser Ala Gly Thr Lys Cys Leu Val Ser Gly Trp Gly Thr
                180                 185                 190

Thr Lys Ser Pro Gln Val His Phe Pro Lys Val Leu Gln Cys Leu Asn
                195                 200                 205

Ile Ser Val Leu Ser Gln Lys Arg Cys Glu Asp Ala Tyr Pro Arg Gln
                210                 215                 220

Ile Asp Asp Thr Met Phe Cys Ala Gly Asp Lys Ala Gly Arg Asp Ser
225                 230                 235                 240

Cys Gln Gly Asp Ser Gly Gly Pro Val Val Cys Asn Gly Ser Leu Gln
                245                 250                 255

Gly Leu Val Ser Trp Gly Asp Tyr Pro Cys Ala Arg Pro Asn Arg Pro
                260                 265                 270

Gly Val Tyr Thr Asn Leu Cys Lys Phe Thr Lys Trp Ile Gln Glu Thr
                275                 280                 285

Ile Gln Ala Asn Ser
    290
```

```
<210> SEQ ID NO 2
<211> LENGTH: 271
<212> TYPE: PRT
<213> ORGANISM: Homo sapiens

<400> SEQUENCE: 2

Val Thr Glu His Val Leu Ala Asn Asn Asp Val Ser Cys Asp His Pro
1               5                   10                  15

Ser Asn Thr Val Pro Ser Gly Ser Asn Gln Asp Leu Gly Ala Gly Ala
                20                  25                  30

Gly Glu Asp Ala Arg Ser Asp Asp Ser Ser Arg Ile Ile Asn Gly
            35                  40                  45

Ser Asp Cys Asp Met His Thr Gln Pro Trp Gln Ala Ala Leu Leu Leu
    50                  55                  60

Arg Pro Asn Gln Leu Tyr Cys Gly Ala Val Leu Val His Pro Gln Trp
65                  70                  75                  80

Leu Leu Thr Ala Ala His Cys Arg Lys Lys Val Phe Arg Val Arg Leu
                85                  90                  95

Gly His Tyr Ser Leu Ser Pro Val Tyr Glu Ser Gly Gln Gln Met Phe
                100                 105                 110

Gln Gly Val Lys Ser Ile Pro His Pro Gly Tyr Ser His Pro Gly His
                115                 120                 125

Ser Asn Asp Leu Met Leu Ile Lys Leu Asn Arg Arg Ile Arg Pro Thr
130                 135                 140

Lys Asp Val Arg Pro Ile Asn Val Ser Ser His Cys Pro Ser Ala Gly
145                 150                 155                 160

Thr Lys Cys Leu Val Ser Gly Trp Gly Thr Thr Lys Ser Pro Gln Val
                165                 170                 175

His Phe Pro Lys Val Leu Gln Cys Leu Asn Ile Ser Val Leu Ser Gln
                180                 185                 190

Lys Arg Cys Glu Asp Ala Tyr Pro Arg Gln Ile Asp Asp Thr Met Phe
                195                 200                 205
```

```
Cys Ala Gly Asp Lys Ala Gly Arg Asp Ser Cys Gln Gly Asp Ser Gly
    210                 215                 220

Gly Pro Val Val Cys Asn Gly Ser Leu Gln Gly Leu Val Ser Trp Gly
225                 230                 235                 240

Asp Tyr Pro Cys Ala Arg Pro Asn Arg Pro Gly Val Tyr Thr Asn Leu
                245                 250                 255

Cys Lys Phe Thr Lys Trp Ile Gln Glu Thr Ile Gln Ala Asn Ser
            260                 265                 270
```

<210> SEQ ID NO 3
<211> LENGTH: 293
<212> TYPE: PRT
<213> ORGANISM: Homo sapiens

<400> SEQUENCE: 3

```
Met Ala Thr Ala Arg Pro Pro Trp Met Trp Val Leu Cys Ala Leu Ile
1               5                   10                  15

Thr Ala Leu Leu Leu Gly Val Thr Glu His Val Leu Ala Asn Asn Asp
            20                  25                  30

Val Ser Cys Asp His Pro Ser Asn Thr Val Pro Ser Gly Ser Asn Gln
        35                  40                  45

Asp Leu Gly Ala Gly Ala Gly Glu Asp Ala Arg Ser Asp Asp Ser Ser
    50                  55                  60

Ser Arg Ile Ile Asn Gly Ser Asp Cys Asp Met His Thr Gln Pro Trp
65                  70                  75                  80

Gln Ala Ala Leu Leu Leu Arg Pro Asn Gln Leu Tyr Cys Gly Ala Val
                85                  90                  95

Leu Val His Pro Gln Trp Leu Leu Thr Ala Ala His Cys Arg Lys Lys
            100                 105                 110

Val Phe Arg Val Arg Leu Gly His Tyr Ser Leu Ser Pro Val Tyr Glu
        115                 120                 125

Ser Gly Gln Gln Met Phe Gln Gly Val Lys Ser Ile Pro His Pro Gly
    130                 135                 140

Tyr Ser His Pro Gly His Ser Asn Asn Leu Met Leu Ile Lys Leu Asn
145                 150                 155                 160

Arg Arg Ile Arg Pro Thr Lys Asp Val Arg Pro Ile Asn Val Ser Ser
                165                 170                 175

His Cys Pro Ser Ala Gly Thr Lys Cys Leu Val Ser Gly Trp Gly Thr
            180                 185                 190

Thr Lys Ser Pro Gln Val His Phe Pro Lys Val Leu Gln Cys Leu Asn
        195                 200                 205

Ile Ser Val Leu Ser Gln Lys Arg Cys Glu Asp Ala Tyr Pro Arg Gln
    210                 215                 220

Ile Asp Asp Thr Met Phe Cys Ala Gly Asp Lys Ala Gly Arg Asp Ser
225                 230                 235                 240

Cys Gln Gly Asp Ser Gly Gly Pro Val Val Cys Asn Gly Ser Leu Gln
                245                 250                 255

Gly Leu Val Ser Trp Gly Asp Tyr Pro Cys Ala Arg Pro Asn Arg Pro
            260                 265                 270

Gly Val Tyr Thr Asn Leu Cys Lys Phe Thr Lys Trp Ile Gln Glu Thr
        275                 280                 285

Ile Gln Ala Asn Ser
    290
```

<210> SEQ ID NO 4

-continued

```
<211> LENGTH: 271
<212> TYPE: PRT
<213> ORGANISM: Homo sapiens

<400> SEQUENCE: 4

Val Thr Glu His Val Leu Ala Asn Asn Asp Val Ser Cys Asp His Pro
1               5                   10                  15

Ser Asn Thr Val Pro Ser Gly Ser Asn Gln Asp Leu Gly Ala Gly Ala
            20                  25                  30

Gly Glu Asp Ala Arg Ser Asp Ser Ser Arg Ile Ile Asn Gly
        35                  40                  45

Ser Asp Cys Asp Met His Thr Gln Pro Trp Gln Ala Ala Leu Leu Leu
50                  55                  60

Arg Pro Asn Gln Leu Tyr Cys Gly Ala Val Leu Val His Pro Gln Trp
65                  70                  75                  80

Leu Leu Thr Ala Ala His Cys Arg Lys Lys Val Phe Arg Val Arg Leu
                85                  90                  95

Gly His Tyr Ser Leu Ser Pro Val Tyr Glu Ser Gly Gln Gln Met Phe
            100                 105                 110

Gln Gly Val Lys Ser Ile Pro His Pro Gly Tyr Ser His Pro Gly His
            115                 120                 125

Ser Asn Asn Leu Met Leu Ile Lys Leu Asn Arg Arg Ile Arg Pro Thr
130                 135                 140

Lys Asp Val Arg Pro Ile Asn Val Ser Ser His Cys Pro Ser Ala Gly
145                 150                 155                 160

Thr Lys Cys Leu Val Ser Gly Trp Gly Thr Thr Lys Ser Pro Gln Val
                165                 170                 175

His Phe Pro Lys Val Leu Gln Cys Leu Asn Ile Ser Val Leu Ser Gln
            180                 185                 190

Lys Arg Cys Glu Asp Ala Tyr Pro Arg Gln Ile Asp Asp Thr Met Phe
            195                 200                 205

Cys Ala Gly Asp Lys Ala Gly Arg Asp Ser Cys Gln Gly Asp Ser Gly
210                 215                 220

Gly Pro Val Val Cys Asn Gly Ser Leu Gln Gly Leu Val Ser Trp Gly
225                 230                 235                 240

Asp Tyr Pro Cys Ala Arg Pro Asn Arg Pro Gly Val Tyr Thr Asn Leu
                245                 250                 255

Cys Lys Phe Thr Lys Trp Ile Gln Glu Thr Ile Gln Ala Asn Ser
            260                 265                 270

<210> SEQ ID NO 5
<211> LENGTH: 293
<212> TYPE: PRT
<213> ORGANISM: Homo sapiens

<400> SEQUENCE: 5

Met Ala Thr Ala Arg Pro Pro Trp Met Trp Val Leu Cys Ala Leu Ile
1               5                   10                  15

Thr Ala Leu Leu Leu Gly Val Thr Glu His Val Leu Ala Asn Asn Asp
            20                  25                  30

Val Ser Cys Asp His Pro Ser Asn Thr Val Pro Ser Gly Ser Asn Gln
        35                  40                  45

Asp Leu Gly Ala Gly Ala Arg Glu Asp Ala Arg Ser Asp Ser Ser
    50                  55                  60

Ser Arg Ile Ile Asn Gly Ser Asp Cys Asp Met His Thr Gln Pro Trp
65                  70                  75                  80
```

```
Gln Ala Ala Leu Leu Leu Arg Pro Asn Gln Leu Tyr Cys Gly Ala Val
                85                  90                  95

Leu Val His Pro Gln Trp Leu Leu Thr Ala Ala His Cys Arg Lys Lys
            100                 105                 110

Val Phe Arg Val Arg Leu Gly His Tyr Ser Leu Ser Pro Val Tyr Glu
        115                 120                 125

Ser Gly Gln Gln Met Phe Gln Gly Val Lys Ser Ile Pro His Pro Gly
    130                 135                 140

Tyr Ser His Pro Gly His Ser Asn Asn Leu Met Leu Ile Lys Leu Asn
145                 150                 155                 160

Arg Arg Ile Arg Pro Thr Lys Asp Val Arg Pro Ile Asn Val Ser Ser
                165                 170                 175

His Cys Pro Ser Ala Gly Thr Lys Cys Leu Val Ser Gly Trp Gly Thr
            180                 185                 190

Thr Lys Ser Pro Gln Val His Phe Pro Lys Val Leu Gln Cys Leu Asn
        195                 200                 205

Ile Ser Val Leu Ser Gln Lys Arg Cys Glu Asp Ala Tyr Pro Arg Gln
    210                 215                 220

Ile Asp Asp Thr Met Phe Cys Ala Gly Asp Lys Ala Gly Arg Asp Ser
225                 230                 235                 240

Cys Gln Gly Asp Ser Gly Gly Pro Val Val Cys Asn Gly Ser Leu Gln
                245                 250                 255

Gly Leu Val Ser Trp Gly Asp Tyr Pro Cys Ala Arg Pro Asn Arg Pro
            260                 265                 270

Gly Val Tyr Thr Asn Leu Cys Lys Phe Thr Lys Trp Ile Gln Glu Thr
        275                 280                 285

Ile Gln Ala Asn Ser
    290

<210> SEQ ID NO 6
<211> LENGTH: 271
<212> TYPE: PRT
<213> ORGANISM: Homo sapiens

<400> SEQUENCE: 6

Val Thr Glu His Val Leu Ala Asn Asn Asp Val Ser Cys Asp His Pro
1               5                   10                  15

Ser Asn Thr Val Pro Ser Gly Ser Asn Gln Asp Leu Gly Ala Gly Ala
            20                  25                  30

Arg Glu Asp Ala Arg Ser Asp Asp Ser Ser Arg Ile Ile Asn Gly
        35                  40                  45

Ser Asp Cys Asp Met His Thr Gln Pro Trp Gln Ala Ala Leu Leu Leu
    50                  55                  60

Arg Pro Asn Gln Leu Tyr Cys Gly Ala Val Leu Val His Pro Gln Trp
65                  70                  75                  80

Leu Leu Thr Ala Ala His Cys Arg Lys Lys Val Phe Arg Val Arg Leu
                85                  90                  95

Gly His Tyr Ser Leu Ser Pro Val Tyr Glu Ser Gly Gln Gln Met Phe
            100                 105                 110

Gln Gly Val Lys Ser Ile Pro His Pro Gly Tyr Ser His Pro Gly His
        115                 120                 125

Ser Asn Asn Leu Met Leu Ile Lys Leu Asn Arg Arg Ile Arg Pro Thr
    130                 135                 140

Lys Asp Val Arg Pro Ile Asn Val Ser Ser His Cys Pro Ser Ala Gly
```

```
                145                 150                 155                 160
        Thr Lys Cys Leu Val Ser Gly Trp Gly Thr Thr Lys Ser Pro Gln Val
                        165                 170                 175

His Phe Pro Lys Val Leu Gln Cys Leu Asn Ile Ser Val Leu Ser Gln
                        180                 185                 190

Lys Arg Cys Glu Asp Ala Tyr Pro Arg Gln Ile Asp Thr Met Phe
                        195                 200                 205

Cys Ala Gly Asp Lys Ala Gly Arg Asp Ser Cys Gln Gly Asp Ser Gly
                        210                 215                 220

Gly Pro Val Val Cys Asn Gly Ser Leu Gln Gly Leu Val Ser Trp Gly
        225                 230                 235                 240

Asp Tyr Pro Cys Ala Arg Pro Asn Arg Pro Gly Val Tyr Thr Asn Leu
                        245                 250                 255

Cys Lys Phe Thr Lys Trp Ile Gln Glu Thr Ile Gln Ala Asn Ser
                        260                 265                 270

<210> SEQ ID NO 7
<211> LENGTH: 293
<212> TYPE: PRT
<213> ORGANISM: Homo sapiens

<400> SEQUENCE: 7

Met Ala Thr Ala Arg Pro Pro Trp Met Trp Val Leu Cys Ala Leu Ile
        1               5                   10                  15

Thr Ala Leu Leu Leu Gly Val Thr Glu His Val Leu Ala Asn Asn Asp
                        20                  25                  30

Val Ser Cys Asp His Pro Ser Asn Thr Val Pro Ser Gly Ser Asn Gln
                        35                  40                  45

Asp Leu Gly Ala Gly Ala Arg Glu Asp Ala Arg Ser Asp Asp Ser Ser
                        50                  55                  60

Ser Arg Ile Ile Asn Gly Ser Asp Cys Asp Met His Thr Gln Pro Trp
        65                  70                  75                  80

Gln Ala Ala Leu Leu Leu Arg Pro Asn Gln Leu Tyr Cys Gly Ala Val
                        85                  90                  95

Leu Val His Pro Gln Trp Leu Leu Thr Ala Ala His Cys Arg Lys Lys
                        100                 105                 110

Val Phe Arg Val Arg Leu Gly His Tyr Ser Leu Ser Pro Val Tyr Glu
                        115                 120                 125

Ser Gly Gln Gln Met Phe Gln Gly Val Lys Ser Ile Pro His Pro Gly
                        130                 135                 140

Tyr Ser His Pro Gly His Ser Asn Asp Leu Met Leu Ile Lys Leu Asn
        145                 150                 155                 160

Arg Arg Ile Arg Pro Thr Lys Asp Val Arg Pro Ile Asn Val Ser Ser
                        165                 170                 175

His Cys Pro Ser Ala Gly Thr Lys Cys Leu Val Ser Gly Trp Gly Thr
                        180                 185                 190

Thr Lys Ser Pro Gln Val His Phe Pro Lys Val Leu Gln Cys Leu Asn
                        195                 200                 205

Ile Ser Val Leu Ser Gln Lys Arg Cys Glu Asp Ala Tyr Pro Arg Gln
                        210                 215                 220

Ile Asp Asp Thr Met Phe Cys Ala Gly Asp Lys Ala Gly Arg Asp Ser
        225                 230                 235                 240

Cys Gln Gly Asp Ser Gly Gly Pro Val Val Cys Asn Gly Ser Leu Gln
                        245                 250                 255
```

-continued

```
Gly Leu Val Ser Trp Gly Asp Tyr Pro Cys Ala Arg Pro Asn Arg Pro
            260                 265                 270

Gly Val Tyr Thr Asn Leu Cys Lys Phe Thr Lys Trp Ile Gln Glu Thr
        275                 280                 285

Ile Gln Ala Asn Ser
    290

<210> SEQ ID NO 8
<211> LENGTH: 271
<212> TYPE: PRT
<213> ORGANISM: Homo sapiens

<400> SEQUENCE: 8

Val Thr Glu His Val Leu Ala Asn Asn Asp Val Ser Cys Asp His Pro
1               5                   10                  15

Ser Asn Thr Val Pro Ser Gly Ser Asn Gln Asp Leu Gly Ala Gly Ala
            20                  25                  30

Arg Glu Asp Ala Arg Ser Asp Asp Ser Ser Arg Ile Ile Asn Gly
        35                  40                  45

Ser Asp Cys Asp Met His Thr Gln Pro Trp Gln Ala Ala Leu Leu Leu
    50                  55                  60

Arg Pro Asn Gln Leu Tyr Cys Gly Ala Val Leu Val His Pro Gln Trp
65                  70                  75                  80

Leu Leu Thr Ala Ala His Cys Arg Lys Lys Val Phe Arg Val Arg Leu
                85                  90                  95

Gly His Tyr Ser Leu Ser Pro Val Tyr Glu Ser Gly Gln Gln Met Phe
            100                 105                 110

Gln Gly Val Lys Ser Ile Pro His Pro Gly Tyr Ser His Pro Gly His
        115                 120                 125

Ser Asn Asp Leu Met Leu Ile Lys Leu Asn Arg Arg Ile Arg Pro Thr
    130                 135                 140

Lys Asp Val Arg Pro Ile Asn Val Ser Ser His Cys Pro Ser Ala Gly
145                 150                 155                 160

Thr Lys Cys Leu Val Ser Gly Trp Gly Thr Thr Lys Ser Pro Gln Val
                165                 170                 175

His Phe Pro Lys Val Leu Gln Cys Leu Asn Ile Ser Val Leu Ser Gln
            180                 185                 190

Lys Arg Cys Glu Asp Ala Tyr Pro Arg Gln Ile Asp Asp Thr Met Phe
        195                 200                 205

Cys Ala Gly Asp Lys Ala Gly Arg Asp Ser Cys Gln Gly Asp Ser Gly
    210                 215                 220

Gly Pro Val Val Cys Asn Gly Ser Leu Gln Gly Leu Val Ser Trp Gly
225                 230                 235                 240

Asp Tyr Pro Cys Ala Arg Pro Asn Arg Pro Gly Val Tyr Thr Asn Leu
                245                 250                 255

Cys Lys Phe Thr Lys Trp Ile Gln Glu Thr Ile Gln Ala Asn Ser
            260                 265                 270

<210> SEQ ID NO 9
<211> LENGTH: 1064
<212> TYPE: PRT
<213> ORGANISM: Homo sapiens

<400> SEQUENCE: 9

Met Lys Ile Ala Thr Val Ser Val Leu Leu Pro Leu Ala Leu Cys Leu
1               5                   10                  15
```

```
Ile Gln Asp Ala Ala Ser Lys Asn Glu Asp Gln Met Cys His Glu
             20                  25                  30

Phe Gln Ala Phe Met Lys Asn Gly Lys Leu Phe Cys Pro Gln Asp Lys
         35                  40                  45

Lys Phe Phe Gln Ser Leu Asp Gly Ile Met Phe Ile Asn Lys Cys Ala
 50                  55                  60

Thr Cys Lys Met Ile Leu Glu Lys Glu Ala Lys Ser Gln Lys Arg Ala
 65                  70                  75                  80

Arg His Leu Ala Arg Ala Pro Lys Ala Thr Ala Pro Thr Glu Leu Asn
                 85                  90                  95

Cys Asp Asp Phe Lys Lys Gly Glu Arg Asp Gly Asp Phe Ile Cys Pro
                100                 105                 110

Asp Tyr Tyr Glu Ala Val Cys Gly Thr Asp Gly Lys Thr Tyr Asp Asn
         115                 120                 125

Arg Cys Ala Leu Cys Ala Glu Asn Ala Lys Thr Gly Ser Gln Ile Gly
     130                 135                 140

Val Lys Ser Glu Gly Cys Lys Ser Ser Asn Pro Glu Gln Asp Val
145                 150                 155                 160

Cys Ser Ala Phe Arg Pro Phe Val Arg Asp Gly Arg Leu Gly Cys Thr
                165                 170                 175

Arg Glu Asn Asp Pro Val Leu Gly Pro Asp Gly Lys Thr His Gly Asn
                180                 185                 190

Lys Cys Ala Met Cys Ala Glu Leu Phe Leu Lys Glu Ala Glu Asn Ala
             195                 200                 205

Lys Arg Glu Gly Glu Thr Arg Ile Arg Arg Asn Ala Glu Lys Asp Phe
210                 215                 220

Cys Lys Glu Tyr Glu Lys Gln Val Arg Asn Gly Arg Leu Phe Cys Thr
225                 230                 235                 240

Arg Glu Ser Asp Pro Val Arg Gly Pro Asp Gly Arg Met His Gly Asn
                245                 250                 255

Lys Cys Ala Leu Cys Ala Glu Ile Phe Lys Gln Arg Phe Ser Glu Glu
             260                 265                 270

Asn Ser Lys Thr Asp Gln Asn Leu Gly Lys Ala Glu Glu Lys Thr Lys
             275                 280                 285

Val Lys Arg Glu Ile Val Lys Leu Cys Ser Gln Tyr Gln Asn Gln Ala
290                 295                 300

Lys Asn Gly Ile Leu Phe Cys Thr Arg Glu Asn Asp Pro Ile Arg Gly
305                 310                 315                 320

Pro Asp Gly Lys Met His Gly Asn Leu Cys Ser Met Cys Gln Ala Tyr
             325                 330                 335

Phe Gln Ala Glu Asn Glu Glu Lys Lys Lys Ala Glu Ala Arg Ala Arg
             340                 345                 350

Asn Lys Arg Glu Ser Gly Lys Ala Thr Ser Tyr Ala Glu Leu Cys Ser
         355                 360                 365

Glu Tyr Arg Lys Leu Val Arg Asn Gly Lys Leu Ala Cys Thr Arg Glu
     370                 375                 380

Asn Asp Pro Ile Gln Gly Pro Asp Gly Lys Val His Gly Asn Thr Cys
385                 390                 395                 400

Ser Met Cys Glu Val Phe Phe Gln Ala Glu Glu Glu Lys Lys Lys
                405                 410                 415

Lys Glu Gly Lys Ser Arg Asn Lys Arg Gln Ser Lys Ser Thr Ala Ser
             420                 425                 430

Phe Glu Glu Leu Cys Ser Glu Tyr Arg Lys Ser Arg Lys Asn Gly Arg
```

```
            435                 440                 445
Leu Phe Cys Thr Arg Glu Asn Asp Pro Ile Gln Gly Pro Asp Gly Lys
450                 455                 460

Met His Gly Asn Thr Cys Ser Met Cys Glu Ala Phe Phe Gln Gln Glu
465                 470                 475                 480

Glu Arg Ala Arg Ala Lys Ala Lys Arg Glu Ala Lys Glu Ile Cys
            485                 490                 495

Ser Glu Phe Arg Asp Gln Val Arg Asn Gly Thr Leu Ile Cys Thr Arg
            500                 505                 510

Glu His Asn Pro Val Arg Gly Pro Asp Gly Lys Met His Gly Asn Lys
            515                 520                 525

Cys Ala Met Cys Ala Ser Val Phe Lys Leu Glu Glu Glu Lys Lys
530                 535                 540

Asn Asp Lys Glu Lys Gly Lys Val Glu Ala Glu Lys Val Lys Arg
545                 550                 555                 560

Glu Ala Val Gln Glu Leu Cys Ser Glu Tyr Arg His Tyr Val Arg Asn
            565                 570                 575

Gly Arg Leu Pro Cys Thr Arg Glu Asn Asp Pro Ile Glu Gly Leu Asp
            580                 585                 590

Gly Lys Ile His Gly Asn Thr Cys Ser Met Cys Glu Ala Phe Phe Gln
            595                 600                 605

Gln Glu Ala Lys Glu Lys Glu Arg Ala Glu Pro Arg Ala Lys Val Lys
610                 615                 620

Arg Glu Ala Glu Lys Glu Thr Cys Asp Glu Phe Arg Arg Leu Leu Gln
625                 630                 635                 640

Asn Gly Lys Leu Phe Cys Thr Arg Glu Asn Asp Pro Val Arg Gly Pro
            645                 650                 655

Asp Gly Lys Thr His Gly Asn Lys Cys Ala Met Cys Lys Ala Val Phe
            660                 665                 670

Gln Lys Glu Asn Glu Glu Arg Lys Arg Lys Glu Glu Glu Asp Gln Arg
            675                 680                 685

Asn Ala Ala Gly His Gly Ser Ser Gly Gly Gly Gly Asn Thr Gln
690                 695                 700

Asp Glu Cys Ala Glu Tyr Arg Glu Gln Met Lys Asn Gly Arg Leu Ser
705                 710                 715                 720

Cys Thr Arg Glu Ser Asp Pro Val Arg Asp Ala Asp Gly Lys Ser Tyr
            725                 730                 735

Asn Asn Gln Cys Thr Met Cys Lys Ala Lys Leu Glu Arg Glu Ala Glu
            740                 745                 750

Arg Lys Asn Glu Tyr Ser Arg Ser Arg Ser Asn Gly Thr Gly Ser Glu
            755                 760                 765

Ser Gly Lys Asp Thr Cys Asp Glu Phe Arg Ser Gln Met Lys Asn Gly
            770                 775                 780

Lys Leu Ile Cys Thr Arg Glu Ser Asp Pro Val Arg Gly Pro Asp Gly
785                 790                 795                 800

Lys Thr His Gly Asn Lys Cys Thr Met Cys Lys Glu Lys Leu Glu Arg
            805                 810                 815

Glu Ala Ala Glu Lys Lys Lys Glu Asp Glu Asp Arg Ser Asn Thr
            820                 825                 830

Gly Glu Arg Ser Asn Thr Gly Glu Arg Ser Asn Asp Lys Glu Asp Leu
            835                 840                 845

Cys Arg Glu Phe Arg Ser Met Gln Arg Asn Gly Lys Leu Ile Cys Thr
850                 855                 860
```

```
Arg Glu Asn Asn Pro Val Arg Gly Pro Tyr Gly Lys Met His Ile Asn
865                 870                 875                 880

Lys Cys Ala Met Cys Gln Ser Ile Phe Asp Arg Glu Ala Asn Glu Arg
            885                 890                 895

Lys Lys Lys Asp Glu Glu Lys Ser Ser Ser Lys Pro Ser Asn Asn Ala
        900                 905                 910

Lys Asp Glu Cys Ser Glu Phe Arg Asn Tyr Ile Arg Asn Asn Glu Leu
        915                 920                 925

Ile Cys Pro Arg Glu Asn Asp Pro Val His Gly Ala Asp Gly Lys Phe
930                 935                 940

Tyr Thr Asn Lys Cys Tyr Met Cys Arg Ala Val Phe Leu Thr Glu Ala
945                 950                 955                 960

Leu Glu Arg Ala Lys Leu Gln Glu Lys Pro Ser His Val Arg Ala Ser
            965                 970                 975

Gln Glu Glu Asp Ser Pro Asp Ser Phe Ser Ser Leu Asp Ser Glu Met
            980                 985                 990

Cys Lys Asp Tyr Arg Val Leu Pro Arg Ile Gly Tyr Leu Cys Pro Lys
        995                 1000                1005

Asp Leu Lys Pro Val Cys Gly Asp Asp Gly Gln Thr Tyr Asn Asn
    1010                1015                1020

Pro Cys Met Leu Cys His Glu Asn Leu Ile Arg Gln Thr Asn Thr
    1025                1030                1035

His Ile Arg Ser Thr Gly Lys Cys Glu Glu Ser Ser Thr Pro Gly
    1040                1045                1050

Thr Thr Ala Ala Ser Met Pro Pro Ser Asp Glu
    1055                1060

<210> SEQ ID NO 10
<211> LENGTH: 1042
<212> TYPE: PRT
<213> ORGANISM: Homo sapiens

<400> SEQUENCE: 10

Lys Asn Glu Asp Gln Glu Met Cys His Glu Phe Gln Ala Phe Met Lys
1               5                   10                  15

Asn Gly Lys Leu Phe Cys Pro Gln Asp Lys Lys Phe Phe Gln Ser Leu
            20                  25                  30

Asp Gly Ile Met Phe Ile Asn Lys Cys Ala Thr Cys Lys Met Ile Leu
        35                  40                  45

Glu Lys Glu Ala Lys Ser Gln Lys Arg Ala Arg His Leu Ala Arg Ala
50                  55                  60

Pro Lys Ala Thr Ala Pro Thr Glu Leu Asn Cys Asp Asp Phe Lys Lys
65                  70                  75                  80

Gly Glu Arg Asp Gly Asp Phe Ile Cys Pro Asp Tyr Tyr Glu Ala Val
                85                  90                  95

Cys Gly Thr Asp Gly Lys Thr Tyr Asp Asn Arg Cys Ala Leu Cys Ala
            100                 105                 110

Glu Asn Ala Lys Thr Gly Ser Gln Ile Gly Val Lys Ser Glu Gly Glu
        115                 120                 125

Cys Lys Ser Ser Asn Pro Glu Gln Asp Val Cys Ser Ala Phe Arg Pro
    130                 135                 140

Phe Val Arg Asp Gly Arg Leu Gly Cys Thr Arg Glu Asn Asp Pro Val
145                 150                 155                 160

Leu Gly Pro Asp Gly Lys Thr His Gly Asn Lys Cys Ala Met Cys Ala
```

-continued

```
            165                 170                 175
Glu Leu Phe Leu Lys Glu Ala Glu Asn Ala Lys Arg Glu Gly Glu Thr
            180                 185                 190

Arg Ile Arg Arg Asn Ala Glu Lys Asp Phe Cys Lys Glu Tyr Glu Lys
            195                 200                 205

Gln Val Arg Asn Gly Arg Leu Phe Cys Thr Arg Glu Ser Asp Pro Val
            210                 215                 220

Arg Gly Pro Asp Gly Arg Met His Gly Asn Lys Cys Ala Leu Cys Ala
225                 230                 235                 240

Glu Ile Phe Lys Gln Arg Phe Ser Glu Glu Asn Ser Lys Thr Asp Gln
            245                 250                 255

Asn Leu Gly Lys Ala Glu Lys Thr Lys Val Lys Arg Glu Ile Val
            260                 265                 270

Lys Leu Cys Ser Gln Tyr Gln Asn Gln Ala Lys Asn Gly Ile Leu Phe
            275                 280                 285

Cys Thr Arg Glu Asn Asp Pro Ile Arg Gly Pro Asp Gly Lys Met His
            290                 295                 300

Gly Asn Leu Cys Ser Met Cys Gln Ala Tyr Phe Gln Ala Glu Asn Glu
305                 310                 315                 320

Glu Lys Lys Lys Ala Glu Ala Arg Ala Arg Asn Lys Arg Glu Ser Gly
            325                 330                 335

Lys Ala Thr Ser Tyr Ala Glu Leu Cys Ser Glu Tyr Arg Lys Leu Val
            340                 345                 350

Arg Asn Gly Lys Leu Ala Cys Thr Arg Glu Asn Asp Pro Ile Gln Gly
            355                 360                 365

Pro Asp Gly Lys Val His Gly Asn Thr Cys Ser Met Cys Glu Val Phe
            370                 375                 380

Phe Gln Ala Glu Glu Glu Lys Lys Lys Glu Gly Lys Ser Arg
385                 390                 395                 400

Asn Lys Arg Gln Ser Lys Ser Thr Ala Ser Phe Glu Glu Leu Cys Ser
            405                 410                 415

Glu Tyr Arg Lys Ser Arg Lys Asn Gly Arg Leu Phe Cys Thr Arg Glu
            420                 425                 430

Asn Asp Pro Ile Gln Gly Pro Asp Gly Lys Met His Gly Asn Thr Cys
            435                 440                 445

Ser Met Cys Glu Ala Phe Phe Gln Gln Glu Arg Ala Arg Ala Lys
            450                 455                 460

Ala Lys Arg Glu Ala Ala Lys Glu Ile Cys Ser Glu Phe Arg Asp Gln
465                 470                 475                 480

Val Arg Asn Gly Thr Leu Ile Cys Thr Arg Glu His Asn Pro Val Arg
            485                 490                 495

Gly Pro Asp Gly Lys Met His Gly Asn Lys Cys Ala Met Cys Ala Ser
            500                 505                 510

Val Phe Lys Leu Glu Glu Glu Lys Lys Asn Asp Lys Glu Glu Lys
            515                 520                 525

Gly Lys Val Glu Ala Glu Lys Val Arg Glu Ala Val Gln Glu Leu
            530                 535                 540

Cys Ser Glu Tyr Arg His Tyr Val Arg Asn Gly Arg Leu Pro Cys Thr
545                 550                 555                 560

Arg Glu Asn Asp Pro Ile Glu Gly Leu Asp Gly Lys Ile His Gly Asn
            565                 570                 575

Thr Cys Ser Met Cys Glu Ala Phe Phe Gln Gln Glu Ala Lys Glu Lys
            580                 585                 590
```

```
Glu Arg Ala Glu Pro Arg Ala Lys Val Lys Arg Ala Glu Lys Glu
        595                 600                 605

Thr Cys Asp Glu Phe Arg Arg Leu Leu Gln Asn Gly Lys Leu Phe Cys
    610                 615                 620

Thr Arg Glu Asn Asp Pro Val Arg Gly Pro Asp Gly Lys Thr His Gly
625                 630                 635                 640

Asn Lys Cys Ala Met Cys Lys Ala Val Phe Gln Lys Glu Asn Glu Glu
                645                 650                 655

Arg Lys Arg Lys Glu Glu Asp Gln Arg Asn Ala Ala Gly His Gly
                660                 665                 670

Ser Ser Gly Gly Gly Gly Asn Thr Gln Asp Glu Cys Ala Glu Tyr
                675                 680                 685

Arg Glu Gln Met Lys Asn Gly Arg Leu Ser Cys Thr Arg Glu Ser Asp
                690                 695                 700

Pro Val Arg Asp Ala Asp Gly Lys Ser Tyr Asn Asn Gln Cys Thr Met
705                 710                 715                 720

Cys Lys Ala Lys Leu Glu Arg Glu Ala Glu Arg Lys Asn Glu Tyr Ser
                725                 730                 735

Arg Ser Arg Ser Asn Gly Thr Gly Ser Glu Ser Gly Lys Asp Thr Cys
                740                 745                 750

Asp Glu Phe Arg Ser Gln Met Lys Asn Gly Lys Leu Ile Cys Thr Arg
                755                 760                 765

Glu Ser Asp Pro Val Arg Gly Pro Asp Gly Lys Thr His Gly Asn Lys
770                 775                 780

Cys Thr Met Cys Lys Glu Lys Leu Glu Arg Glu Ala Ala Glu Lys Lys
785                 790                 795                 800

Lys Lys Glu Asp Glu Asp Arg Ser Asn Thr Gly Glu Arg Ser Asn Thr
                805                 810                 815

Gly Glu Arg Ser Asn Asp Lys Glu Asp Leu Cys Arg Glu Phe Arg Ser
                820                 825                 830

Met Gln Arg Asn Gly Lys Leu Ile Cys Thr Arg Glu Asn Asn Pro Val
            835                 840                 845

Arg Gly Pro Tyr Gly Lys Met His Ile Asn Lys Cys Ala Met Cys Gln
        850                 855                 860

Ser Ile Phe Asp Arg Glu Ala Asn Glu Arg Lys Lys Lys Asp Glu Glu
865                 870                 875                 880

Lys Ser Ser Lys Pro Ser Asn Asn Ala Lys Asp Glu Cys Ser Glu
                885                 890                 895

Phe Arg Asn Tyr Ile Arg Asn Asn Glu Leu Ile Cys Pro Arg Glu Asn
                900                 905                 910

Asp Pro Val His Gly Ala Asp Gly Lys Phe Tyr Thr Asn Lys Cys Tyr
            915                 920                 925

Met Cys Arg Ala Val Phe Leu Thr Glu Ala Leu Glu Arg Ala Lys Leu
    930                 935                 940

Gln Glu Lys Pro Ser His Val Arg Ala Ser Gln Glu Asp Ser Pro
945                 950                 955                 960

Asp Ser Phe Ser Ser Leu Asp Ser Glu Met Cys Lys Asp Tyr Arg Val
                965                 970                 975

Leu Pro Arg Ile Gly Tyr Leu Cys Pro Lys Asp Leu Lys Pro Val Cys
                980                 985                 990

Gly Asp Asp Gly Gln Thr Tyr Asn  Asn Pro Cys Met Leu  Cys His Glu
            995                 1000                1005
```

```
Asn Leu Ile Arg Gln Thr Asn Thr His Ile Arg Ser Thr Gly Lys
    1010                1015                1020

Cys Glu Glu Ser Ser Thr Pro Gly Thr Thr Ala Ala Ser Met Pro
    1025                1030                1035

Pro Ser Asp Glu
    1040

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Tyr Asn Met Ala
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Tyr Tyr Met Ala
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Ser Tyr Trp Ile Cys
1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Ser Tyr Trp Ile Cys
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asn Tyr Gly Val Thr
1               5
```

```
<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asn Tyr Gly Val Ser
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Tyr Gly Val Thr
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asn Tyr Gly Val Ser
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Phe Ala Ile Asn
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Tyr Gly Val Ser
1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 21

Asn Tyr Gly Val Thr
1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Tyr Gly Val Ser
1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Tyr Pro Ile Ser
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp Tyr Gly Val Ser
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asn Asn Tyr Val Asn Phe Val Met Cys
1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asp Asn Tyr Val Met Ser
1               5

<210> SEQ ID NO 27
<211> LENGTH: 5
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 27

Gly Gly Gly Ile Tyr
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Asp
<220> FEATURE:
<221> NAME/KEY: MOD_RES
<222> LOCATION: (5)..(5)
<223> OTHER INFORMATION: Thr or Ser

<400> SEQUENCE: 28

Xaa Tyr Gly Val Xaa
1               5

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Thr Ile Ser Tyr Asp Ala Gly Arg Thr Tyr Tyr Arg Asp Ser Val Lys
1               5                   10                  15

Gly

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ser Ile Ser Tyr Asp Gly Asp Thr Thr Tyr Tyr Arg Asp Ser Val Lys
1               5                   10                  15

Gly

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Cys Val Tyr Gly Leu Asp Val Asn Ile Tyr Tyr Ala Ser Trp Thr Lys
1               5                   10                  15

```
<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Cys Val Tyr Gly Leu Asp Val Asn Ile Tyr Tyr Ala Ser Trp Thr Glu
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Phe Ile Gly Ser Gly Gly Ser Ala Tyr Tyr Ala Ser Trp Ala Lys Ser
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Phe Ile Gly Tyr Gly Gly Ser Thr Tyr Tyr Ala Ser Trp Ala Lys Ser
1               5                   10                  15

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Tyr Ile Thr Ser Asn Tyr Gly Val Ser Tyr Tyr Ala Ser Trp Ala Lys
1               5                   10                  15

Ser

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Tyr Ile Thr Ser Asn Tyr Gly Val Ser Tyr Tyr Ala Asn Ser Val Lys
1               5                   10                  15

Gly

<210> SEQ ID NO 37
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 37

Tyr Ile Thr Ser Asn Tyr Gly Val Ser Tyr Tyr Ala Ser Phe Ala Lys
1               5                   10                  15

Ser

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Ser or Asn
<220> FEATURE:
<221> NAME/KEY: MOD_RES
<222> LOCATION: (14)..(14)
<223> OTHER INFORMATION: Trp, Ser or Phe
<220> FEATURE:
<221> NAME/KEY: MOD_RES
<222> LOCATION: (15)..(15)
<223> OTHER INFORMATION: Ala or Val
<220> FEATURE:
<221> NAME/KEY: MOD_RES
<222> LOCATION: (17)..(17)
<223> OTHER INFORMATION: Ser or Gly

<400> SEQUENCE: 38

Tyr Ile Thr Ser Asn Tyr Gly Val Ser Tyr Tyr Ala Xaa Xaa Xaa Lys
1               5                   10                  15

Xaa

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Tyr Ile Gly Ser Ala Gly Ser Thr Tyr Tyr Ala Thr Trp Ala Lys Ser
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Ile Gly Arg Gly Gly Ser Ala Tyr Tyr Ala Ser Trp Ala Lys Ser
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 41

Phe Ile Gly Ser Ser Gly Ser Ala Tyr Tyr Ala Ser Trp Ala Lys Ser
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Phe Ile Gly Ser Gly Gly Phe Ala Tyr Tyr Ala Ser Trp Ala Lys Ser
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Phe Ile Gly Ser Gly Gly Phe Ala Tyr Tyr Ala Asp Ser Val Lys Gly
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Phe Ile Gly Ser Gly Gly Phe Ala Tyr Tyr Ala Ser Phe Ala Lys Ser
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Ser or Asp
<220> FEATURE:
<221> NAME/KEY: MOD_RES
<222> LOCATION: (13)..(13)
<223> OTHER INFORMATION: Trp, Ser or Phe
<220> FEATURE:
<221> NAME/KEY: MOD_RES
<222> LOCATION: (14)..(14)
<223> OTHER INFORMATION: Ala or Val
<220> FEATURE:
<221> NAME/KEY: MOD_RES
<222> LOCATION: (16)..(16)
<223> OTHER INFORMATION: Ser or Gly

<400> SEQUENCE: 45

Phe Ile Gly Ser Gly Gly Phe Ala Tyr Tyr Ala Xaa Xaa Xaa Lys Xaa
1               5                   10                  15

<210> SEQ ID NO 46
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Phe Ile Gly Ser Gly Gly Ser Pro Tyr Tyr Ala Ser Trp Ala Lys Ser
1               5                   10                  15

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Tyr Ile Thr Ser Glu Tyr Gly Val Ala Tyr Tyr Ala Thr Trp Ala Glu
1               5                   10                  15

Ser

<210> SEQ ID NO 48
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ala Ile Gly Ser Ser Gly Val Ala Trp Tyr Ala Asn Trp Ala Lys Gly
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Ile Gly Ser Ser Gly Val Ala Phe Tyr Ala Asn Trp Ala Lys Gly
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ala Ile Gly Ser Ser Gly Val Ala Trp Tyr Ala Asp Ser Val Lys Gly
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 51

Ala Ile Gly Ser Ser Gly Val Ala Phe Tyr Ala Asp Ser Val Lys Gly
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ala Ile Gly Ser Ser Gly Val Ala Trp Tyr Ala Asn Phe Ala Lys Gly
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Ile Gly Ser Ser Gly Val Ala Phe Tyr Ala Asn Phe Ala Lys Gly
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Trp or Phe
<220> FEATURE:
<221> NAME/KEY: MOD_RES
<222> LOCATION: (12)..(12)
<223> OTHER INFORMATION: Asn or Asp
<220> FEATURE:
<221> NAME/KEY: MOD_RES
<222> LOCATION: (13)..(13)
<223> OTHER INFORMATION: Trp, Ser or Phe
<220> FEATURE:
<221> NAME/KEY: MOD_RES
<222> LOCATION: (14)..(14)
<223> OTHER INFORMATION: Ala or Val

<400> SEQUENCE: 54

Ala Ile Gly Ser Ser Gly Val Ala Xaa Tyr Ala Xaa Xaa Xaa Lys Gly
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Ile Asp Pro Gly Asp Asp Ser Thr Asp Tyr Ala Ser Trp Ala Thr
1               5                   10                  15

<210> SEQ ID NO 56
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Cys Ile Asp Pro Gly Asp Asp Ser Thr Tyr Tyr Ala Ser Trp Ala Thr
1               5                   10                  15

<210> SEQ ID NO 57
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ser Ile Tyr Pro Asp His Gly Ser Val Asp Tyr Ala Asn Trp Val Asn
1               5                   10                  15

Gly

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Tyr Ile Tyr Pro Asp His Gly Ser Ala Asp Tyr Ala Thr Trp Val Asn
1               5                   10                  15

Gly

<210> SEQ ID NO 59
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe or Ala
<220> FEATURE:
<221> NAME/KEY: MOD_RES
<222> LOCATION: (5)..(5)
<223> OTHER INFORMATION: Gly or Ser
<220> FEATURE:
<221> NAME/KEY: MOD_RES
<222> LOCATION: (7)..(7)
<223> OTHER INFORMATION: Phe or Val
<220> FEATURE:
<221> NAME/KEY: MOD_RES
<222> LOCATION: (9)..(9)
<223> OTHER INFORMATION: Tyr, Trp or Phe
<220> FEATURE:
<221> NAME/KEY: MOD_RES
<222> LOCATION: (12)..(12)
<223> OTHER INFORMATION: Ser, Asp or Asn
<220> FEATURE:
<221> NAME/KEY: MOD_RES
<222> LOCATION: (13)..(13)
<223> OTHER INFORMATION: Trp, Ser or Phe
<220> FEATURE:
<221> NAME/KEY: MOD_RES
<222> LOCATION: (14)..(14)
```

```
<223> OTHER INFORMATION: Ala or Val
<220> FEATURE:
<221> NAME/KEY: MOD_RES
<222> LOCATION: (16)..(16)
<223> OTHER INFORMATION: Ser or Gly

<400> SEQUENCE: 59

Xaa Ile Gly Ser Xaa Gly Xaa Ala Xaa Tyr Ala Xaa Xaa Xaa Lys Xaa
1               5                   10                  15

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Ile Phe Asn Tyr Gly Thr Asp Tyr Phe Asp Tyr
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Asp Gly Thr Ile Pro Ala Gly Ser Trp Phe Ala Tyr
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Gly Gly Ser Ala Asp Phe Gly Phe Asp Leu
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asp Asp Val Gly Gly Gly Lys Ser Leu Asp Ile
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Leu Cys Gly Val Asp Cys Ala Asp Ala Leu Asp Ser
```

```
<210> SEQ ID NO 65
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Glu Asn Pro Asp Tyr Gly Tyr Ala Tyr Asp Ala
1               5                   10

<210> SEQ ID NO 66
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ala Ala Tyr Ser Ala Gly Ser Ala Asp Ala Glu Asp Ile
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Glu Asn Ala Gly Ser Gly Trp Gly Glu Leu Asp Ile
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asp Asn Val Gly Gly Asp Met Ser Leu Asp Ile
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asp Asp Val Gly Gly Gly Lys Ser Leu Asp Ile
1               5                   10

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
```

```
                                   peptide

<400> SEQUENCE: 70

Asp Asp Val Gly Gly Gly Arg Ser Leu Asp Ile
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Glu Asn Pro Thr Tyr Gly Tyr Ala Tyr Asp Ala
1               5                   10

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Asp Arg Asp Tyr Gly Tyr Arg Ala Asp Ala Thr Ser Gly Met Asp
1               5                   10                  15

Leu

<210> SEQ ID NO 73
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Asp Ala Gly Thr Ser Tyr Ser Phe Asn Phe
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Asp Ala Ala Ala Ser Tyr Ser Phe Asn Phe
1               5                   10

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Glu Ser Gly Gly Ser Tyr Tyr Asp Leu
1               5
```

```
<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Glu Thr Gly Gly Ser Trp Tyr Asp Leu
1               5

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Arg Ala Ser Glu Asp Ile Tyr Ser Gly Leu Ala
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Leu Ala Ser Lys Asn Ile Tyr Arg Asn Leu Ala
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gln Ala Ser Glu Asn Ile Tyr Ser Leu Leu Ala
1               5                   10

<210> SEQ ID NO 80
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gln Ala Ser Gln Asn Ile Gly Asp Tyr Leu Ser
1               5                   10

<210> SEQ ID NO 81
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 81

Gln Ala Ser Glu Asp Ile Gly Ser Tyr Cys Ser
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gln Ala Ser Glu Ser Ile Ser Asn Glu Leu Ser
1               5                   10

<210> SEQ ID NO 83
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gln Ala Ser Gln Ser Ile Ser Asn Tyr Val Ala
1               5                   10

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gln Ala Ser Glu Ser Ile Ser Ser Asp Leu Ala
1               5                   10

<210> SEQ ID NO 85
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gln Ala Ser Gln Asn Ile Asn Asn Tyr Leu Ser
1               5                   10

<210> SEQ ID NO 86
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gln Ala Ser Gln Ser Ile Gly Ser Tyr Leu Ser
1               5                   10

<210> SEQ ID NO 87
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 87

Gln Ala Ser Gln Ser Ile Ser Ser Tyr Leu Ser
1               5                   10

<210> SEQ ID NO 88
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gln Ala Ser Gln Ser Ile Ser Asn Tyr Leu Ser
1               5                   10

<210> SEQ ID NO 89
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gln Ala Ser Gln Ser Ile Ser Thr Tyr Leu Ser
1               5                   10

<210> SEQ ID NO 90
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gln Ala Ser Glu Ser Ile Gly Asn Glu Leu Ser
1               5                   10

<210> SEQ ID NO 91
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gln Ala Ser Glu Ser Ile Gly Asn Ala Leu Ala
1               5                   10

<210> SEQ ID NO 92
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Ala Ser Glu Ser Ile Ser Arg Tyr Leu Ser
1               5                   10
```

```
<210> SEQ ID NO 93
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Ala Ser Glu Ser Ile Ser Thr Tyr Leu Ser
1               5                   10

<210> SEQ ID NO 94
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gln Ala Ser Gln Ser Ile Ser Thr Tyr Leu Ala
1               5                   10

<210> SEQ ID NO 95
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gln Ala Ser Gln Ser Ile Ser Ser Tyr Leu Ala
1               5                   10

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Glu or Gln
<220> FEATURE:
<221> NAME/KEY: MOD_RES
<222> LOCATION: (7)..(7)
<223> OTHER INFORMATION: Ser or Gly
<220> FEATURE:
<221> NAME/KEY: MOD_RES
<222> LOCATION: (8)..(8)
<223> OTHER INFORMATION: Asn or Ser
<220> FEATURE:
<221> NAME/KEY: MOD_RES
<222> LOCATION: (9)..(9)
<223> OTHER INFORMATION: Glu, Tyr or Ala
<220> FEATURE:
<221> NAME/KEY: MOD_RES
<222> LOCATION: (11)..(11)
<223> OTHER INFORMATION: Ser or Ala

<400> SEQUENCE: 96

Gln Ala Ser Xaa Ser Ile Xaa Xaa Xaa Leu Xaa
1               5                   10

<210> SEQ ID NO 97
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Ala Thr Thr Leu His Asp
1               5

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Asp Ala Ser Arg Leu Gln Asp
1               5

<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Asp Ala Ser Asp Leu Ala Ser
1               5

<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ser Ala Ser Thr Leu Ala Ser
1               5

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Tyr Ala Ser Thr Leu Ala Ser
1               5

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102
```

Arg Ala Ser Thr Leu Ala Ser
1               5

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ala Ala Ser Thr Leu Ala Ser
1               5

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Asp Ala Ser Asn Leu Ala Ser
1               5

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ser Ala Ser Thr Leu Ala Ser
1               5

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gln Ala Ser Thr Leu Ala Ser
1               5

<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Lys Thr Ser Thr Leu Ala Ser
1               5

<210> SEQ ID NO 108
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 108

Lys Ala Ser Thr Leu Ala Ser
1               5

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Tyr, Ser or Asp
<220> FEATURE:
<221> NAME/KEY: MOD_RES
<222> LOCATION: (4)..(4)
<223> OTHER INFORMATION: Thr or Asp

<400> SEQUENCE: 109

Xaa Ala Ser Xaa Leu Ala Ser
1               5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

His Gln Gly Leu Ser Phe Pro Tyr Thr
1               5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gln Gln Tyr His Asp Tyr Pro Tyr Thr
1               5

<210> SEQ ID NO 112
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gln Ala Thr Ala Tyr Gly Ser Ser Gly Asn Ala
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Description of Artificial Sequence: Synthetic
```

```
                              peptide

<400> SEQUENCE: 113

His Gln Asp Tyr Thr Ser Asn Asp Val Glu Asn Thr
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Gln Gln Asp Tyr Thr Gly Asn Asn Val Asp Asn Thr
1               5                   10

<210> SEQ ID NO 115
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ala Gln Gly Phe Gly Ser Ser Gly Val Glu Asn Val
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

His Gln Gly Tyr Ser Ser Ser Asn Val Asp Asn Ile
1               5                   10

<210> SEQ ID NO 117
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gln Gln Gly Tyr Thr Trp Asn Asn Val Asp Asn Val
1               5                   10

<210> SEQ ID NO 118
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

His Gln Asp Tyr Thr Ser Asn Asn Val Asp Asn Thr
1               5                   10

<210> SEQ ID NO 119
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

His Gln Asp Tyr Thr Ser Ser Asn Val Asp Asn Thr
1               5                   10

<210> SEQ ID NO 120
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

His Gln Asp Tyr Thr Ser Asn Ser Val Asp Asn Thr
1               5                   10

<210> SEQ ID NO 121
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ala Gln Gly Phe Ser Ser Ser Gly Val Glu Asn Val
1               5                   10

<210> SEQ ID NO 122
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gln Gln Gly Asp Ser His Asn Asn Val Asp Asn Ile
1               5                   10

<210> SEQ ID NO 123
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gln Gln Asp Tyr Ser Arg Ser Asn Ile Val Asn Ser
1               5                   10

<210> SEQ ID NO 124
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124
```

Gln Gln Asp Tyr Ser Ser Ser Asn Ile Val Asn Ser
1               5                   10

<210> SEQ ID NO 125
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gln Gln Gly Tyr Ser Gly Ser Ser Val Glu Asn Thr
1               5                   10

<210> SEQ ID NO 126
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gln Gln Gly Tyr Ser Gly Ser Asn Val Glu Asn Thr
1               5                   10

<210> SEQ ID NO 127
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ala, His or Gln
<220> FEATURE:
<221> NAME/KEY: MOD_RES
<222> LOCATION: (3)..(3)
<223> OTHER INFORMATION: Gly or Asp
<220> FEATURE:
<221> NAME/KEY: MOD_RES
<222> LOCATION: (4)..(4)
<223> OTHER INFORMATION: Phe, Tyr or Asp
<220> FEATURE:
<221> NAME/KEY: MOD_RES
<222> LOCATION: (5)..(5)
<223> OTHER INFORMATION: Gly, Thr or Ser
<220> FEATURE:
<221> NAME/KEY: MOD_RES
<222> LOCATION: (6)..(6)
<223> OTHER INFORMATION: Ser or His
<220> FEATURE:
<221> NAME/KEY: MOD_RES
<222> LOCATION: (7)..(7)
<223> OTHER INFORMATION: Ser or Asn
<220> FEATURE:
<221> NAME/KEY: MOD_RES
<222> LOCATION: (8)..(8)
<223> OTHER INFORMATION: Gly or Asn
<220> FEATURE:
<221> NAME/KEY: MOD_RES
<222> LOCATION: (10)..(10)
<223> OTHER INFORMATION: Glu or Asp
<220> FEATURE:
<221> NAME/KEY: MOD_RES
<222> LOCATION: (12)..(12)
<223> OTHER INFORMATION: Val, Thr or Ile

<400> SEQUENCE: 127

Xaa Gln Xaa Xaa Xaa Xaa Xaa Xaa Val Xaa Asn Xaa

<210> SEQ ID NO 128
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Asp Ile Gln Met Thr Gln Ser Pro Ala Ser Leu Ser Ala Ser Leu Gly
1               5                   10                  15

Glu Thr Val Thr Ile Gln Cys Arg Ala Ser Glu Asp Ile Tyr Ser Gly
                20                  25                  30

Leu Ala Trp Tyr Gln Gln Lys Pro Gly Lys Ser Pro Gln Leu Leu Ile
            35                  40                  45

Tyr Gly Ala Thr Thr Leu His Asp Gly Val Pro Ser Arg Phe Ser Gly
        50                  55                  60

Ser Gly Ser Gly Thr Gln Tyr Ser Leu Lys Ile Ser Ser Met His Ser
65                  70                  75                  80

Glu Asp Glu Gly Ile Tyr Phe Cys His Gln Gly Leu Ser Phe Pro Tyr
                85                  90                  95

Thr Phe Gly Ala Gly Thr Lys Leu Glu Leu Lys
            100                 105

<210> SEQ ID NO 129
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Asp Ile Gln Met Thr Gln Ser Pro Ala Ser Leu Ser Ala Ser Leu Gly
1               5                   10                  15

Glu Thr Val Thr Ile Glu Cys Leu Ala Ser Lys Asn Ile Tyr Arg Asn
                20                  25                  30

Leu Ala Trp Tyr Gln Gln Lys Pro Gly Lys Ser Pro Gln Phe Leu Ile
            35                  40                  45

Ser Asp Ala Ser Arg Leu Gln Asp Gly Val Pro Ser Arg Phe Thr Gly
        50                  55                  60

Ser Asp Ser Gly Ser Gln Tyr Ser Leu Lys Ile Asn Ser Leu Gln Ser
65                  70                  75                  80

Glu Asp Val Ala Thr Tyr Phe Cys Gln Gln Tyr His Asp Tyr Pro Tyr
                85                  90                  95

Thr Phe Gly Ala Gly Thr Lys Leu Glu Leu Lys
            100                 105

<210> SEQ ID NO 130
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Asp Val Val Met Thr Gln Thr Ala Ser Pro Val Ser Ala Ala Val Gly
1               5                   10                  15

Gly Thr Val Thr Ile Lys Cys Gln Ala Ser Glu Asn Ile Tyr Ser Leu
            20                  25                  30

Leu Ala Trp Tyr Gln Gln Lys Pro Gly Gln Pro Pro Lys Val Leu Ile
        35                  40                  45

Tyr Asp Ala Ser Asp Leu Ala Ser Gly Val Pro Ser Arg Phe Lys Gly
 50                  55                  60

Ser Gly Ser Gly Thr Gln Phe Thr Leu Thr Ile Ser Asp Leu Glu Cys
 65                  70                  75                  80

Ala Asp Ala Ala Thr Tyr Tyr Cys Gln Ala Thr Ala Tyr Gly Ser Ser
                85                  90                  95

Gly Asn Ala Phe Gly Gly Gly Thr Glu Val Val Val Lys
                100                 105

<210> SEQ ID NO 131
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Asp Val Val Met Thr Gln Thr Pro Ala Ser Val Ser Glu Pro Val Gly
 1               5                  10                  15

Gly Thr Val Thr Ile Lys Cys Gln Ala Ser Glu Asn Ile Tyr Ser Leu
            20                  25                  30

Leu Ala Trp Tyr Gln Gln Lys Pro Gly Gln Pro Pro Lys Val Leu Ile
        35                  40                  45

Tyr Asp Ala Ser Asp Leu Ala Ser Gly Val Pro Ser Arg Phe Lys Gly
 50                  55                  60

Ser Gly Ser Gly Thr Gln Phe Thr Leu Thr Ile Ser Asp Leu Glu Cys
 65                  70                  75                  80

Ala Asp Ala Ala Thr Tyr Tyr Cys Gln Ala Thr Ala Tyr Gly Ser Ser
                85                  90                  95

Gly Asn Ala Phe Gly Gly Gly Thr Glu Val Val Val Lys
                100                 105

<210> SEQ ID NO 132
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Asn Ile Val Met Thr Gln Thr Pro Ala Ser Val Glu Val Ala Val Gly
 1               5                  10                  15

Gly Thr Val Val Ile Lys Cys Gln Ala Ser Gln Asn Ile Gly Asp Tyr
            20                  25                  30

Leu Ser Trp Tyr Gln Gln Lys Pro Gly Gln Arg Pro Lys Leu Leu Ile
        35                  40                  45

Tyr Ser Ala Ser Thr Leu Ala Ser Gly Val Pro Ser Arg Phe Lys Gly
 50                  55                  60

Ser Gly Ser Gly Thr Gln Phe Thr Leu Thr Ile Ser Asp Leu Glu Cys
 65                  70                  75                  80

Ala Asp Ala Ala Thr Tyr Tyr Cys His Gln Asp Tyr Thr Ser Asn Asp
                85                  90                  95

```
Val Glu Asn Thr Phe Gly Gly Gly Thr Glu Val Val Val Lys
            100                 105                 110
```

<210> SEQ ID NO 133
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

```
Ala Tyr Tyr Met Thr Gln Thr Pro Ala Ser Val Glu Val Ala Val Gly
 1               5                  10                  15

Gly Thr Val Thr Ile Lys Cys Gln Ala Ser Glu Asp Ile Gly Ser Tyr
                20                  25                  30

Cys Ser Trp Tyr Gln Gln Lys Pro Gly Gln Pro Pro Lys Leu Leu Ile
            35                  40                  45

Tyr Asp Ala Ser Asp Leu Ala Ser Gly Val Pro Ser Arg Phe Lys Gly
 50                  55                  60

Ser Gly Ser Gly Thr Asp Phe Thr Leu Thr Ile Ser Gly Val Gln Cys
 65                  70                  75                  80

Asp Asp Ala Ala Thr Tyr Tyr Cys Gln Gln Asp Tyr Thr Gly Asn Asn
                 85                  90                  95

Val Asp Asn Thr Phe Gly Gly Gly Ser Glu Val Val Val Lys
            100                 105                 110
```

<210> SEQ ID NO 134
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

```
Ala Tyr Asp Met Thr Gln Thr Pro Ala Ser Leu Glu Ala Ala Val Gly
 1               5                  10                  15

Gly Thr Val Thr Ile Asn Cys Gln Ala Ser Glu Ser Ile Ser Asn Glu
                20                  25                  30

Leu Ser Trp Tyr Gln Gln Lys Pro Gly Gln Pro Pro Asp Leu Leu Ile
            35                  40                  45

Tyr Tyr Ala Ser Thr Leu Ala Ser Gly Val Pro Ser Arg Phe Lys Gly
 50                  55                  60

Ser Gly Ser Gly Thr Glu Phe Thr Leu Thr Ile Ser Asp Leu Glu Cys
 65                  70                  75                  80

Ala Asp Ala Ala Thr Tyr Tyr Cys Ala Gln Gly Phe Gly Ser Ser Gly
                 85                  90                  95

Val Glu Asn Val Phe Gly Gly Gly Thr Glu Val Val Val Lys
            100                 105                 110
```

<210> SEQ ID NO 135
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Ala Tyr Arg Met Thr Gln Ser Pro Ser Ser Phe Ser Ala Ser Thr Gly
1               5                   10                  15

Asp Arg Val Thr Ile Thr Cys Gln Ala Ser Glu Ser Ile Ser Asn Glu
            20                  25                  30

Leu Ser Trp Tyr Gln Gln Lys Pro Gly Lys Pro Pro Lys Leu Leu Ile
        35                  40                  45

Tyr Tyr Ala Ser Thr Leu Ala Ser Gly Val Pro Ser Arg Phe Ser Gly
    50                  55                  60

Ser Gly Ser Gly Thr Asp Phe Thr Leu Thr Ile Ser Cys Leu Gln Ser
65              70                  75                  80

Glu Asp Phe Ala Thr Tyr Tyr Cys Ala Gln Gly Phe Gly Ser Ser Gly
                85                  90                  95

Val Glu Asn Val Phe Gly Gly Gly Thr Lys Val Glu Ile Lys
            100                 105                 110

<210> SEQ ID NO 136
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Ala Ile Arg Met Thr Gln Ser Pro Ser Ser Phe Ser Ala Ser Thr Gly
1               5                   10                  15

Asp Arg Val Thr Ile Thr Cys Gln Ala Ser Glu Ser Ile Ser Asn Glu
            20                  25                  30

Leu Ser Trp Tyr Gln Gln Lys Pro Gly Lys Pro Pro Lys Leu Leu Ile
        35                  40                  45

Tyr Tyr Ala Ser Thr Leu Ala Ser Gly Val Pro Ser Arg Phe Ser Gly
    50                  55                  60

Ser Gly Ser Gly Thr Asp Phe Thr Leu Thr Ile Ser Cys Leu Gln Ser
65              70                  75                  80

Glu Asp Phe Ala Thr Tyr Tyr Cys Ala Gln Gly Phe Gly Ser Ser Gly
                85                  90                  95

Val Glu Asn Val Phe Gly Gly Gly Thr Lys Val Glu Ile Lys
            100                 105                 110

<210> SEQ ID NO 137
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Ala Tyr Arg Met Thr Gln Ser Pro Ser Ser Phe Ser Ala Ser Thr Gly
1               5                   10                  15

Asp Arg Val Thr Ile Thr Cys Gln Ala Ser Glu Ser Ile Ser Asn Glu
            20                  25                  30

Leu Ser Trp Tyr Gln Gln Lys Pro Gly Lys Ala Pro Lys Leu Leu Ile
        35                  40                  45

Tyr Tyr Ala Ser Thr Leu Ala Ser Gly Val Pro Ser Arg Phe Ser Gly
    50                  55                  60

Ser Gly Ser Gly Thr Asp Phe Thr Leu Thr Ile Ser Cys Leu Gln Ser
65              70                  75                  80

```
Glu Asp Phe Ala Thr Tyr Tyr Cys Ala Gln Gly Phe Gly Ser Ser Gly
            85                  90                  95

Val Glu Asn Val Phe Gly Gly Gly Thr Lys Val Glu Ile Lys
            100                 105                 110

<210> SEQ ID NO 138
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Ala Ile Arg Met Thr Gln Ser Pro Ser Ser Phe Ser Ala Ser Thr Gly
1               5                   10                  15

Asp Arg Val Thr Ile Thr Cys Gln Ala Ser Glu Ser Ile Ser Asn Glu
            20                  25                  30

Leu Ser Trp Tyr Gln Gln Lys Pro Gly Lys Ala Pro Lys Leu Leu Ile
        35                  40                  45

Tyr Tyr Ala Ser Thr Leu Ala Ser Gly Val Pro Ser Arg Phe Ser Gly
50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Ala Gln Gly Phe Gly Ser Ser Gly
            85                  90                  95

Val Glu Asn Val Phe Gly Gly Gly Thr Lys Val Glu Ile Lys
            100                 105                 110

<210> SEQ ID NO 139
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Ala Ile Arg Met Thr Gln Ser Pro Ser Ser Phe Ser Ala Ser Thr Gly
1               5                   10                  15

Asp Arg Val Thr Ile Thr Cys Gln Ala Ser Glu Ser Ile Ser Asn Glu
            20                  25                  30

Leu Ser Trp Tyr Gln Gln Lys Pro Gly Lys Ala Pro Lys Leu Leu Ile
        35                  40                  45

Tyr Tyr Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Gly Phe Gly Ser Ser Gly
            85                  90                  95

Val Glu Asn Val Phe Gly Gly Gly Thr Lys Val Glu Ile Lys
            100                 105                 110

<210> SEQ ID NO 140
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (2)..(2)
<223> OTHER INFORMATION: Tyr or Ile
<220> FEATURE:
<221> NAME/KEY: MOD_RES
<222> LOCATION: (43)..(43)
<223> OTHER INFORMATION: Pro or Ala
<220> FEATURE:
<221> NAME/KEY: MOD_RES
<222> LOCATION: (77)..(77)
<223> OTHER INFORMATION: Cys or Ser
<220> FEATURE:
<221> NAME/KEY: MOD_RES
<222> LOCATION: (80)..(80)
<223> OTHER INFORMATION: Ser or Pro
<220> FEATURE:
<221> NAME/KEY: MOD_RES
<222> LOCATION: (106)..(106)
<223> OTHER INFORMATION: Glu or Lys
<220> FEATURE:
<221> NAME/KEY: MOD_RES
<222> LOCATION: (108)..(108)
<223> OTHER INFORMATION: Glu or Val
<220> FEATURE:
<221> NAME/KEY: MOD_RES
<222> LOCATION: (109)..(109)
<223> OTHER INFORMATION: Ile or Val

<400> SEQUENCE: 140

Ala Xaa Arg Met Thr Gln Ser Pro Ser Ser Phe Ser Ala Ser Thr Gly
1               5                   10                  15

Asp Arg Val Thr Ile Thr Cys Gln Ala Ser Glu Ser Ile Ser Asn Glu
            20                  25                  30

Leu Ser Trp Tyr Gln Gln Lys Pro Gly Lys Xaa Pro Lys Leu Leu Ile
        35                  40                  45

Tyr Tyr Ala Ser Thr Leu Ala Ser Gly Val Pro Ser Arg Phe Ser Gly
    50                  55                  60

Ser Gly Ser Gly Thr Asp Phe Thr Leu Thr Ile Ser Xaa Leu Gln Xaa
65              70                  75                  80

Glu Asp Phe Ala Thr Tyr Tyr Cys Ala Gln Gly Phe Gly Ser Ser Gly
            85                  90                  95

Val Glu Asn Val Phe Gly Gly Gly Thr Xaa Val Xaa Xaa Lys
        100                 105                 110

<210> SEQ ID NO 141
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Ala Tyr Tyr Met Thr Gln Thr Pro Ala Ser Val Glu Ala Val Gly
1               5                   10                  15

Gly Thr Val Thr Ile Lys Cys Gln Ala Ser Gln Ser Ile Ser Asn Tyr
            20                  25                  30

Val Ala Trp Tyr Gln Gln Lys Pro Gly Gln Pro Pro Lys Leu Leu Ile
        35                  40                  45

Tyr Arg Ala Ser Thr Leu Ala Ser Gly Val Ser Ser Arg Phe Ser Gly
    50                  55                  60

Ser Gly Ser Gly Thr Glu Phe Thr Leu Thr Ile Ser Asp Leu Glu Cys
65              70                  75                  80

Ala Asp Ala Ala Thr Tyr Tyr Cys His Gln Gly Tyr Ser Ser Ser Asn
            85                  90                  95
```

Val Asp Asn Ile Phe Gly Gly Gly Thr Glu Val Val Val Lys
                100                 105                 110

<210> SEQ ID NO 142
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Ala Tyr Glu Met Thr Gln Thr Pro Ala Ser Val Glu Val Ala Val Gly
1               5                   10                  15

Gly Thr Val Thr Ile Asn Cys Gln Ala Ser Glu Ser Ile Ser Ser Asp
            20                  25                  30

Leu Ala Trp Tyr Gln Gln Lys Pro Gly Gln Arg Pro Lys Leu Leu Ile
        35                  40                  45

Tyr Ala Ala Ser Thr Leu Ala Ser Gly Val Pro Ser Arg Phe Lys Gly
    50                  55                  60

Ser Gly Ser Gly Thr Glu Phe Thr Leu Ser Ile Ser Gly Val Gln Cys
65                  70                  75                  80

Ala Asp Ala Ala Thr Tyr Tyr Cys Gln Gln Gly Tyr Thr Trp Asn Asn
                85                  90                  95

Val Asp Asn Val Phe Gly Gly Gly Thr Glu Val Val Val Lys
                100                 105                 110

<210> SEQ ID NO 143
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Asp Ile Val Met Thr Gln Thr Pro Ala Ser Val Ser Glu Pro Val Gly
1               5                   10                  15

Gly Thr Val Thr Ile Lys Cys Gln Ala Ser Gln Asn Ile Asn Asn Tyr
            20                  25                  30

Leu Ser Trp Tyr Gln Gln Lys Pro Gly Gln Pro Pro Lys Gln Leu Ile
        35                  40                  45

Tyr Ala Ala Ser Thr Leu Ala Ser Gly Val Pro Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys His Gln Asp Tyr Thr Ser Asn Asn
                85                  90                  95

Val Asp Asn Thr Phe Gly Gly Gly Thr Glu Val Val Val Lys
                100                 105                 110

<210> SEQ ID NO 144
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Asn Ile Val Met Thr Gln Thr Pro Ala Ser Val Glu Val Ala Val Gly
1               5                   10                  15

Gly Thr Val Thr Ile Lys Cys Gln Ala Ser Gln Ser Ile Gly Ser Tyr
            20                  25                  30

Leu Ser Trp Tyr Gln Gln Lys Pro Gly Gln Pro Pro Lys Leu Leu Ile
        35                  40                  45

Tyr Asp Ala Ser Asn Leu Ala Ser Gly Val Pro Ser Arg Phe Lys Gly
    50                  55                  60

Ser Gly Ser Gly Thr Gln Phe Thr Leu Ser Ile Ser Asp Leu Glu Cys
65                  70                  75                  80

Ala Asp Ala Ala Thr Tyr Tyr Cys His Gln Asp Tyr Thr Ser Asn Asn
                85                  90                  95

Val Asp Asn Thr Phe Gly Gly Gly Thr Glu Val Val Ile Lys
            100                 105                 110

<210> SEQ ID NO 145
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Asn Ile Val Met Thr Gln Thr Pro Ala Ser Val Glu Ala Val Gly
1               5                   10                  15

Gly Thr Val Thr Ile Asn Cys Gln Ala Ser Gln Ser Ile Ser Ser Tyr
            20                  25                  30

Leu Ser Trp Tyr Gln Gln Lys Ser Gly Gln Arg Pro Lys Leu Leu Ile
        35                  40                  45

Phe Ser Ala Ser Thr Leu Ala Ser Gly Val Pro Ser Arg Phe Thr Gly
    50                  55                  60

Ser Gly Ser Gly Thr Gln Phe Thr Leu Thr Ile Ser Asp Leu Gln Cys
65                  70                  75                  80

Ala Asp Ala Ala Thr Tyr Tyr Cys His Gln Asp Tyr Thr Ser Ser Asn
                85                  90                  95

Val Asp Asn Thr Phe Gly Gly Gly Thr Glu Val Val Val Lys
            100                 105                 110

<210> SEQ ID NO 146
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Tyr
            20                  25                  30

Leu Ser Trp Tyr Gln Gln Lys Pro Gly Lys Arg Pro Lys Leu Leu Ile
        35                  40                  45

Phe Ser Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys His Gln Asp Tyr Thr Ser Ser Asn
                85                  90                  95

Val Asp Asn Thr Phe Gly Gly Gly Thr Lys Val Glu Ile Lys
            100                 105                 110
```

<210> SEQ ID NO 147
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Tyr
            20                  25                  30

Leu Ser Trp Tyr Gln Gln Lys Pro Gly Lys Ala Pro Lys Leu Leu Ile
        35                  40                  45

Phe Ser Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Asp Tyr Thr Ser Ser Asn
                85                  90                  95

Val Asp Asn Thr Phe Gly Gly Gly Thr Lys Val Glu Ile Lys
            100                 105                 110
```

<210> SEQ ID NO 148
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Tyr
            20                  25                  30

Leu Ser Trp Tyr Gln Gln Lys Pro Gly Lys Arg Pro Lys Leu Leu Ile
        35                  40                  45

Tyr Ser Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Asp Tyr Thr Ser Ser Asn
                85                  90                  95

Val Asp Asn Thr Phe Gly Gly Gly Thr Lys Val Glu Ile Lys
            100                 105                 110
```

<210> SEQ ID NO 149
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Tyr
            20                  25                  30

Leu Ser Trp Tyr Gln Gln Lys Pro Gly Lys Ala Pro Lys Leu Leu Ile
        35                  40                  45

Tyr Ser Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Asp Tyr Thr Ser Ser Asn
                85                  90                  95

Val Asp Asn Thr Phe Gly Gly Gly Thr Lys Val Glu Ile Lys
            100                 105                 110

<210> SEQ ID NO 150
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Tyr
            20                  25                  30

Leu Ser Trp Tyr Gln Gln Lys Pro Gly Lys Ala Pro Lys Leu Leu Ile
        35                  40                  45

Tyr Ser Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Asp Tyr Thr Ser Ser Asn
                85                  90                  95

Val Asp Asn Thr Phe Gly Gly Gly Thr Glu Val Val Val Lys
            100                 105                 110

<210> SEQ ID NO 151
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (43)..(43)
<223> OTHER INFORMATION: Arg or Ala
<220> FEATURE:
<221> NAME/KEY: MOD_RES
<222> LOCATION: (49)..(49)
<223> OTHER INFORMATION: Phe or Tyr
<220> FEATURE:
<221> NAME/KEY: MOD_RES
<222> LOCATION: (106)..(106)
<223> OTHER INFORMATION: Glu or Lys
<220> FEATURE:
<221> NAME/KEY: MOD_RES
<222> LOCATION: (108)..(108)
<223> OTHER INFORMATION: Glu or Val

```
<220> FEATURE:
<221> NAME/KEY: MOD_RES
<222> LOCATION: (109)..(109)
<223> OTHER INFORMATION: Val or Ile

<400> SEQUENCE: 151
```

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Tyr
            20                  25                  30

Leu Ser Trp Tyr Gln Gln Lys Pro Gly Lys Xaa Pro Lys Leu Leu Ile
        35                  40                  45

Xaa Ser Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Asp Tyr Thr Ser Ser Asn
                85                  90                  95

Val Asp Asn Thr Phe Gly Gly Gly Thr Xaa Val Xaa Xaa Lys
                100                 105                 110

```
<210> SEQ ID NO 152
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152
```

Asn Ile Val Met Thr Gln Thr Pro Ala Ser Val Glu Val Ala Val Gly
1               5                   10                  15

Gly Thr Val Ile Ile Lys Cys Gln Ala Ser Gln Ser Ile Ser Asn Tyr
            20                  25                  30

Leu Ser Trp Tyr His Gln Lys Ser Gly Gln Arg Pro Arg Leu Leu Ile
        35                  40                  45

Tyr Ser Ala Ser Thr Leu Ala Ser Gly Val Pro Ser Arg Phe Lys Gly
50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys His Gln Asp Tyr Thr Ser Asn Ser
                85                  90                  95

Val Asp Asn Thr Phe Gly Gly Gly Thr Glu Val Val Val Lys
                100                 105                 110

```
<210> SEQ ID NO 153
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153
```

Asn Ile Val Met Thr Gln Thr Pro Ala Ser Val Glu Val Ala Met Gly
1               5                   10                  15

Gly Thr Val Ile Ile Lys Cys Gln Ala Ser Gln Ser Ile Ser Thr Tyr
            20                  25                  30

Leu Ser Trp Tyr Gln Gln Lys Pro Gly Gln Pro Pro Lys Leu Leu Ile
        35                  40                  45

```
Tyr Ser Ala Ser Thr Leu Ala Ser Gly Val Ser Ser Arg Phe Glu Gly
        50                  55                  60

Ser Gly Ser Gly Thr Gln Phe Thr Leu Thr Ile Ser Gly Val Gln Cys
 65                  70                  75                  80

Ala Asp Ala Ala Thr Tyr Tyr Cys His Gln Asp Tyr Thr Ser Asn Asn
                 85                  90                  95

Val Asp Asn Thr Phe Gly Gly Gly Thr Glu Val Val Val Lys
                100                 105                 110

<210> SEQ ID NO 154
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Ala Tyr Asp Leu Thr Gln Thr Pro Ala Ser Val Glu Ala Ala Val Gly
 1                5                  10                  15

Gly Thr Val Thr Ile Asn Cys Gln Ala Ser Glu Ser Ile Gly Asn Glu
                 20                  25                  30

Leu Ser Trp Tyr Gln Gln Lys Ser Gly Gln Pro Pro Lys Leu Leu Ile
             35                  40                  45

Tyr Gln Ala Ser Thr Leu Ala Ser Gly Val Pro Ser Arg Phe Lys Gly
        50                  55                  60

Ser Gly Ser Gly Thr Asp Phe Thr Leu Thr Ile Ser Asp Leu Glu Cys
 65                  70                  75                  80

Ala Asp Ala Ala Thr Tyr Tyr Cys Ala Gln Gly Phe Ser Ser Ser Gly
                 85                  90                  95

Val Glu Asn Val Phe Gly Gly Gly Thr Glu Val Val Val Lys
                100                 105                 110

<210> SEQ ID NO 155
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Ala Tyr Asp Met Thr Gln Thr Pro Ala Ser Val Glu Ala Ala Val Gly
 1                5                  10                  15

Gly Thr Val Thr Ile Lys Cys Gln Ala Ser Glu Ser Ile Gly Asn Ala
                 20                  25                  30

Leu Ala Trp Tyr Gln Gln Lys Pro Gly Gln Pro Pro Lys Leu Leu Ile
             35                  40                  45

Tyr Asp Ala Ser Asp Leu Ala Ser Gly Val Pro Ser Arg Phe Lys Gly
        50                  55                  60

Ser Gly Ser Gly Thr Gln Phe Thr Leu Thr Ile Ser Gly Val Glu Cys
 65                  70                  75                  80

Ala Asp Ala Ala Thr Tyr Tyr Cys Gln Gln Gly Asp Ser His Asn Asn
                 85                  90                  95

Val Asp Asn Ile Phe Gly Gly Gly Thr Glu Val Val Val Lys
                100                 105                 110

<210> SEQ ID NO 156
```

```
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Ala Tyr Arg Met Thr Gln Ser Pro Ser Ser Phe Ser Ala Ser Thr Gly
1               5                   10                  15

Asp Arg Val Thr Ile Thr Cys Gln Ala Ser Glu Ser Ile Gly Asn Ala
            20                  25                  30

Leu Ala Trp Tyr Gln Gln Lys Pro Gly Lys Pro Pro Lys Leu Leu Ile
        35                  40                  45

Tyr Asp Ala Ser Asp Leu Ala Ser Gly Val Pro Ser Arg Phe Ser Gly
    50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Gly Asp Ser His Asn Asn
                85                  90                  95

Val Asp Asn Ile Phe Gly Gly Gly Thr Lys Val Glu Ile Lys
            100                 105                 110

<210> SEQ ID NO 157
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Ala Ile Arg Met Thr Gln Ser Pro Ser Ser Phe Ser Ala Ser Thr Gly
1               5                   10                  15

Asp Arg Val Thr Ile Thr Cys Gln Ala Ser Glu Ser Ile Gly Asn Ala
            20                  25                  30

Leu Ala Trp Tyr Gln Gln Lys Pro Gly Lys Pro Pro Lys Leu Leu Ile
        35                  40                  45

Tyr Asp Ala Ser Asp Leu Ala Ser Gly Val Pro Ser Arg Phe Ser Gly
    50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Gly Asp Ser His Asn Asn
                85                  90                  95

Val Asp Asn Ile Phe Gly Gly Gly Thr Lys Val Glu Ile Lys
            100                 105                 110

<210> SEQ ID NO 158
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Ala Tyr Arg Met Thr Gln Ser Pro Ser Ser Phe Ser Ala Ser Thr Gly
1               5                   10                  15

Asp Arg Val Thr Ile Thr Cys Gln Ala Ser Glu Ser Ile Gly Asn Ala
            20                  25                  30
```

Leu Ala Trp Tyr Gln Gln Lys Pro Gly Lys Ala Pro Lys Leu Leu Ile
                35                  40                  45

Tyr Asp Ala Ser Asp Leu Ala Ser Gly Val Pro Ser Arg Phe Ser Gly
 50                  55                  60

Ser Gly Ser Gly Thr Asp Phe Thr Leu Thr Ile Ser Cys Leu Gln Ser
 65                  70                  75                  80

Glu Asp Phe Ala Thr Tyr Tyr Cys Gln Gln Gly Asp Ser His Asn Asn
                 85                  90                  95

Val Asp Asn Ile Phe Gly Gly Gly Thr Lys Val Glu Ile Lys
                100                 105                 110

<210> SEQ ID NO 159
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Ala Ile Arg Met Thr Gln Ser Pro Ser Ser Phe Ser Ala Ser Thr Gly
 1               5                  10                  15

Asp Arg Val Thr Ile Thr Cys Gln Ala Ser Glu Ser Ile Gly Asn Ala
                20                  25                  30

Leu Ala Trp Tyr Gln Gln Lys Pro Gly Lys Ala Pro Lys Leu Leu Ile
                35                  40                  45

Tyr Asp Ala Ser Asp Leu Ala Ser Gly Val Pro Ser Arg Phe Ser Gly
 50                  55                  60

Ser Gly Ser Gly Thr Asp Phe Thr Leu Thr Ile Ser Cys Leu Gln Ser
 65                  70                  75                  80

Glu Asp Phe Ala Thr Tyr Tyr Cys Gln Gln Gly Asp Ser His Asn Asn
                 85                  90                  95

Val Asp Asn Ile Phe Gly Gly Gly Thr Lys Val Glu Ile Lys
                100                 105                 110

<210> SEQ ID NO 160
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Ala Ile Arg Met Thr Gln Ser Pro Ser Ser Phe Ser Ala Ser Thr Gly
 1               5                  10                  15

Asp Arg Val Thr Ile Thr Cys Gln Ala Ser Glu Ser Ile Gly Asn Ala
                20                  25                  30

Leu Ala Trp Tyr Gln Gln Lys Pro Gly Lys Ala Pro Lys Leu Leu Ile
                35                  40                  45

Tyr Asp Ala Ser Asp Leu Ala Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Asp Ser His Asn Asn
                 85                  90                  95

Val Asp Asn Ile Phe Gly Gly Gly Thr Lys Val Glu Ile Lys
                100                 105                 110

```
<210> SEQ ID NO 161
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Ala Ile Arg Met Thr Gln Ser Pro Ser Ser Phe Ser Ala Ser Thr Gly
1               5                   10                  15

Asp Arg Val Thr Ile Thr Cys Gln Ala Ser Glu Ser Ile Gly Asn Ala
            20                  25                  30

Leu Ala Trp Tyr Gln Gln Lys Pro Gly Lys Ala Pro Lys Leu Leu Ile
        35                  40                  45

Tyr Asp Ala Ser Asp Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Ser His Asn Asn
                85                  90                  95

Val Asp Asn Ile Phe Gly Gly Gly Thr Glu Val Val Val Lys
            100                 105                 110

<210> SEQ ID NO 162
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Tyr or Ile
<220> FEATURE:
<221> NAME/KEY: MOD_RES
<222> LOCATION: (43)..(43)
<223> OTHER INFORMATION: Pro or Ala
<220> FEATURE:
<221> NAME/KEY: MOD_RES
<222> LOCATION: (77)..(77)
<223> OTHER INFORMATION: Cys or Ser
<220> FEATURE:
<221> NAME/KEY: MOD_RES
<222> LOCATION: (80)..(80)
<223> OTHER INFORMATION: Ser or Pro
<220> FEATURE:
<221> NAME/KEY: MOD_RES
<222> LOCATION: (106)..(106)
<223> OTHER INFORMATION: Glu or Lys
<220> FEATURE:
<221> NAME/KEY: MOD_RES
<222> LOCATION: (108)..(108)
<223> OTHER INFORMATION: Glu or Val
<220> FEATURE:
<221> NAME/KEY: MOD_RES
<222> LOCATION: (109)..(109)
<223> OTHER INFORMATION: Val or Ile

<400> SEQUENCE: 162

Ala Xaa Arg Met Thr Gln Ser Pro Ser Ser Phe Ser Ala Ser Thr Gly
1               5                   10                  15

Asp Arg Val Thr Ile Thr Cys Gln Ala Ser Glu Ser Ile Gly Asn Ala
            20                  25                  30

Leu Ala Trp Tyr Gln Gln Lys Pro Gly Lys Xaa Pro Lys Leu Leu Ile
        35                  40                  45
```

```
Tyr Asp Ala Ser Asp Leu Ala Ser Gly Val Pro Ser Arg Phe Ser Gly
         50                  55                  60

Ser Gly Ser Gly Thr Asp Phe Thr Leu Thr Ile Ser Xaa Leu Gln Xaa
 65                  70                  75                  80

Glu Asp Phe Ala Thr Tyr Tyr Cys Gln Gln Gly Asp Ser His Asn Asn
                 85                  90                  95

Val Asp Asn Ile Phe Gly Gly Gly Thr Xaa Val Xaa Xaa Lys
                100                 105                 110
```

<210> SEQ ID NO 163
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

```
Ala Ile Glu Met Thr Gln Thr Pro Ser Ser Ala Ser Glu Pro Val Gly
 1               5                  10                  15

Gly Thr Val Thr Ile Lys Cys Gln Ala Ser Glu Ser Ile Ser Arg Tyr
                 20                  25                  30

Leu Ser Trp Tyr Gln Gln Lys Pro Gly Gln Pro Pro Lys Leu Leu Ile
             35                  40                  45

Tyr Asp Ala Ser Asp Leu Ala Ser Gly Val Ser Ser Arg Phe Lys Gly
         50                  55                  60

Ser Gly Ser Gly Thr Gln Phe Thr Leu Ile Ile Ser Asp Val Glu Cys
 65                  70                  75                  80

Ala Asp Ala Ala Thr Tyr Tyr Cys Gln Gln Asp Tyr Ser Arg Ser Asn
                 85                  90                  95

Ile Val Asn Ser Phe Gly Gly Gly Thr Glu Val Val Val Lys
                100                 105                 110
```

<210> SEQ ID NO 164
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

```
Ala Tyr Asp Met Thr Gln Thr Pro Ser Ser Ala Ser Glu Pro Val Gly
 1               5                  10                  15

Gly Thr Val Thr Ile Lys Cys Gln Ala Ser Glu Ser Ile Ser Thr Tyr
                 20                  25                  30

Leu Ser Trp Tyr Gln Gln Lys Pro Gly Gln Pro Pro Lys Leu Leu Ile
             35                  40                  45

Tyr Asp Ala Ser Asp Leu Ala Ser Gly Val Ser Ser Arg Phe Lys Gly
         50                  55                  60

Ser Gly Ser Gly Thr Gln Phe Thr Leu Thr Ile Ser Asp Val Glu Cys
 65                  70                  75                  80

Ala Asp Ala Ala Thr Tyr Tyr Cys Gln Gln Asp Tyr Ser Ser Ser Asn
                 85                  90                  95

Ile Val Asn Ser Phe Gly Gly Gly Thr Glu Val Val Val Lys
                100                 105                 110
```

<210> SEQ ID NO 165

<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Ser Thr Tyr
            20                  25                  30

Leu Ala Trp Tyr Gln Gln Lys Pro Gly Gln Arg Pro Asn Leu Leu Ile
        35                  40                  45

Tyr Lys Thr Ser Thr Leu Ala Ser Gly Val Pro Ser Arg Phe Arg Gly
50                  55                  60

Ser Gly Ser Gly Thr Gln Phe Thr Leu Thr Ile Ser Gly Val Glu Cys
65                  70                  75                  80

Ala Asp Ala Ala Thr Tyr Tyr Cys Gln Gln Gly Tyr Ser Gly Ser Ser
                85                  90                  95

Val Glu Asn Thr Phe Gly Gly Gly Thr Glu Val Val Val Lys
            100                 105                 110

<210> SEQ ID NO 166
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Ala Tyr Asp Met Thr Gln Thr Pro Val Ser Val Glu Ala Ala Val Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly Gln Pro Pro Lys Leu Leu Ile
        35                  40                  45

Tyr Lys Ala Ser Thr Leu Ala Ser Gly Val Ser Ser Arg Phe Lys Gly
50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Gln Gly Tyr Ser Gly Ser Asn
                85                  90                  95

Val Glu Asn Thr Phe Gly Gly Gly Thr Glu Val Val Val Lys
            100                 105                 110

<210> SEQ ID NO 167
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Glu Val Gln Leu Val Glu Ser Gly Gly Gly Leu Val Gln Pro Gly Arg
1               5                   10                  15

Ser Leu Lys Leu Ser Cys Thr Ala Ser Gly Phe Thr Phe Ser Asp Tyr
            20                  25                  30

```
Asn Met Ala Trp Val Arg Gln Ala Pro Lys Gly Leu Glu Trp Val
        35                  40                  45

Thr Thr Ile Ser Tyr Asp Ala Gly Arg Thr Tyr Tyr Arg Asp Ser Val
 50                  55                  60

Lys Gly Arg Phe Thr Ile Ser Arg Asp Asn Ala Lys Arg Thr Leu Ser
 65                  70                  75                  80

Leu Gln Met Asp Ser Leu Arg Ser Glu Asp Thr Ala Thr Tyr Tyr Cys
                 85                  90                  95

Ala Thr Gly Ile Phe Asn Tyr Gly Thr Asp Tyr Phe Asp Tyr Trp Gly
            100                 105                 110

Gln Gly Val Met Val Thr Val Ser Ser
        115                 120
```

<210> SEQ ID NO 168
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

```
Glu Val Gln Leu Val Glu Ser Gly Gly Gly Leu Val Arg Pro Gly Arg
 1               5                  10                  15

Ser Leu Arg Leu Ser Cys Ala Ala Ser Gly Phe Thr Phe Ser Asp Tyr
                20                  25                  30

Tyr Met Ala Trp Val Arg Gln Ala Pro Thr Lys Gly Leu Glu Trp Val
            35                  40                  45

Ala Ser Ile Ser Tyr Asp Gly Asp Thr Thr Tyr Tyr Arg Asp Ser Val
 50                  55                  60

Lys Gly Arg Phe Thr Ile Ser Arg Asp Asn Ala Arg Ser Ser Leu Tyr
 65                  70                  75                  80

Leu Gln Met Asp Ser Leu Arg Ser Asp Asp Thr Ala Asn Tyr Phe Cys
                 85                  90                  95

Thr Thr Asp Gly Thr Ile Pro Ala Gly Ser Trp Phe Ala Tyr Trp Gly
            100                 105                 110

Gln Gly Thr Leu Val Thr Val Ser Ser
        115                 120
```

<210> SEQ ID NO 169
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

```
Gln Glu Gln Leu Glu Glu Ser Gly Gly Asp Leu Val Lys Pro Glu Gly
 1               5                  10                  15

Ser Leu Thr Leu Thr Cys Thr Ala Ser Gly Phe Ser Phe Ser Ser Ser
                20                  25                  30

Tyr Trp Ile Cys Trp Val Arg Gln Ala Pro Gly Lys Gly Leu Glu Trp
            35                  40                  45

Ile Ala Cys Val Tyr Gly Leu Asp Val Asn Ile Tyr Tyr Ala Ser Trp
 50                  55                  60

Thr Lys Gly Arg Phe Thr Ile Ser Lys Thr Ser Ser Thr Thr Val Thr
 65                  70                  75                  80
```

Leu Gln Met Thr Ser Leu Thr Ala Ala Asp Thr Ala Thr Tyr Phe Cys
                85                  90                  95

Ala Arg Gly Gly Gly Ser Ala Asp Phe Gly Phe Asp Leu Trp Gly Pro
            100                 105                 110

Gly Thr Leu Val Thr Val Ser Ser
        115                 120

<210> SEQ ID NO 170
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Gln Ser Leu Glu Glu Ser Gly Gly Asp Leu Val Lys Pro Glu Gly Ser
1               5                   10                  15

Leu Thr Leu Thr Cys Thr Ala Ser Gly Phe Ser Phe Ser Thr Ser Tyr
            20                  25                  30

Trp Ile Cys Trp Val Arg Gln Ala Pro Gly Lys Gly Leu Glu Trp Ile
        35                  40                  45

Ala Cys Val Tyr Gly Leu Asp Val Asn Ile Tyr Tyr Ala Ser Trp Thr
    50                  55                  60

Glu Gly Arg Phe Thr Ile Ser Lys Thr Ser Thr Thr Val Thr Leu
65                  70                  75                  80

Gln Val Thr Ser Leu Thr Ala Ala Asp Thr Ala Thr Tyr Phe Cys Ala
                85                  90                  95

Arg Gly Gly Gly Ser Ala Asp Phe Gly Phe Asp Leu Trp Gly Pro Gly
            100                 105                 110

Thr Leu Val Thr Val Ser Ser
        115

<210> SEQ ID NO 171
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Gln Ser Val Lys Glu Ser Glu Gly Gly Leu Phe Lys Pro Thr Asp Asn
1               5                   10                  15

Leu Thr Leu Thr Cys Thr Val Ser Gly Phe Ser Leu Ser Asn Tyr Gly
            20                  25                  30

Val Thr Trp Val Arg Gln Ala Pro Gly Asn Gly Leu Glu Tyr Ile Gly
        35                  40                  45

Phe Ile Gly Ser Gly Gly Ser Ala Tyr Tyr Ala Ser Trp Ala Lys Ser
    50                  55                  60

Arg Ser Thr Ile Thr Arg Asn Thr Asn Leu Asn Val Thr Leu Lys
65                  70                  75                  80

Met Thr Ser Leu Thr Ala Ala Asp Thr Ala Thr Tyr Phe Cys Ala Arg
                85                  90                  95

Asp Asp Val Gly Gly Lys Ser Leu Asp Ile Trp Gly Pro Gly Thr
            100                 105                 110

Leu Val Thr Val Ser Ser
        115

<210> SEQ ID NO 172
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Gln Ser Val Glu Glu Ser Arg Gly Gly Leu Ile Lys Pro Thr Asp Thr
1               5                   10                  15

Leu Thr Leu Thr Cys Thr Ala Ser Gly Phe Ser Leu Ser Asn Tyr Gly
            20                  25                  30

Val Ser Trp Val Arg Gln Ala Pro Gly Asn Gly Leu Glu Tyr Ile Gly
        35                  40                  45

Phe Ile Gly Tyr Gly Gly Ser Thr Tyr Tyr Ala Ser Trp Ala Lys Ser
    50                  55                  60

Arg Ser Thr Ile Thr Arg Asn Thr Asn Leu Asn Thr Val Thr Leu Gln
65                  70                  75                  80

Met Thr Ser Leu Thr Ala Ala Asp Thr Ala Thr Tyr Phe Cys Ala Arg
                85                  90                  95

Leu Cys Gly Val Asp Cys Ala Asp Ala Leu Asp Ser Trp Gly Pro Gly
            100                 105                 110

Thr Leu Val Thr Val Ser Ser
        115

<210> SEQ ID NO 173
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Gln Ser Leu Glu Glu Ser Gly Gly Gly Leu Val Lys Pro Thr Asp Thr
1               5                   10                  15

Leu Thr Leu Thr Cys Thr Val Ser Gly Phe Ser Leu Ser Ser Tyr Gly
            20                  25                  30

Val Thr Trp Val Arg Gln Ala Pro Gly Arg Gly Leu Glu Trp Ile Gly
        35                  40                  45

Tyr Ile Thr Ser Asn Tyr Gly Val Ser Tyr Tyr Ala Ser Trp Ala Lys
    50                  55                  60

Ser Arg Ser Thr Ile Thr Arg Asn Thr Asn Leu Asn Thr Val Thr Leu
65                  70                  75                  80

Lys Met Thr Ser Leu Thr Ala Ala Asp Thr Ala Thr Tyr Phe Cys Ala
                85                  90                  95

Arg Glu Asn Pro Asp Tyr Gly Tyr Ala Tyr Asp Ala Trp Gly Pro Gly
            100                 105                 110

Thr Leu Val Thr Val Ser Val
        115

<210> SEQ ID NO 174
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Val Thr Trp Val Arg Gln Ala Pro Gly Lys Gly Leu Glu Trp Ile
        35                  40                  45

Gly Tyr Ile Thr Ser Asn Tyr Gly Val Ser Tyr Ala Ser Trp Ala
    50                  55                  60

Lys Ser Arg Ser Thr Ile Ser Arg Asp Thr Ser Lys Asn Thr Val Tyr
65                  70                  75                  80

Leu Gln Met Gly Ser Leu Arg Ala Glu Asp Met Ala Val Tyr Phe Cys
                85                  90                  95

Ala Arg Glu Asn Pro Asp Tyr Gly Tyr Ala Tyr Asp Ala Trp Gly Pro
            100                 105                 110

Gly Thr Thr Val Thr Val Ser Ser
        115                 120

<210> SEQ ID NO 175
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Gly Val Thr Trp Val Arg Gln Ala Pro Gly Lys Gly Leu Glu Trp Ile
        35                  40                  45

Gly Tyr Ile Thr Ser Asn Tyr Gly Val Ser Tyr Ala Ser Trp Ala
    50                  55                  60

Lys Ser Arg Ser Thr Ile Ser Arg Asp Thr Ser Lys Asn Thr Val Tyr
65                  70                  75                  80

Leu Gln Met Gly Ser Leu Arg Ala Glu Asp Met Ala Val Tyr Phe Cys
                85                  90                  95

Ala Arg Glu Asn Pro Asp Tyr Gly Tyr Ala Tyr Asp Ala Trp Gly Pro
            100                 105                 110

Gly Thr Thr Val Thr Val Ser Ser
        115                 120

<210> SEQ ID NO 176
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Val Thr Trp Val Arg Gln Ala Pro Gly Lys Gly Leu Glu Tyr Ile

```
                35                  40                  45
Gly Tyr Ile Thr Ser Asn Tyr Gly Val Ser Tyr Tyr Ala Ser Trp Ala
        50                  55                  60
Lys Ser Arg Ser Thr Ile Ser Arg Asp Thr Ser Lys Asn Thr Val Tyr
65                  70                  75                  80
Leu Gln Met Gly Ser Leu Arg Ala Glu Asp Met Ala Val Tyr Phe Cys
                85                  90                  95
Ala Arg Glu Asn Pro Asp Tyr Gly Tyr Ala Tyr Asp Ala Trp Gly Pro
            100                 105                 110
Gly Thr Thr Val Thr Val Ser Ser
        115                 120

<210> SEQ ID NO 177
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Glu Val Gln Leu Val Glu Ser Gly Gly Gly Leu Val Gln Pro Gly Gly
1               5                   10                  15
Ser Leu Arg Leu Ser Cys Ala Val Ser Gly Phe Ser Leu Ser Ser Tyr
            20                  25                  30
Gly Val Thr Trp Val Arg Gln Ala Pro Gly Lys Gly Leu Glu Trp Val
        35                  40                  45
Gly Tyr Ile Thr Ser Asn Tyr Gly Val Ser Tyr Tyr Ala Ser Trp Ala
        50                  55                  60
Lys Ser Arg Ser Thr Ile Ser Arg Asp Thr Ser Lys Asn Thr Val Tyr
65                  70                  75                  80
Leu Gln Met Gly Ser Leu Arg Ala Glu Asp Met Ala Val Tyr Phe Cys
                85                  90                  95
Ala Arg Glu Asn Pro Asp Tyr Gly Tyr Ala Tyr Asp Ala Trp Gly Pro
            100                 105                 110
Gly Thr Thr Val Thr Val Ser Ser
        115                 120

<210> SEQ ID NO 178
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Glu Val Gln Leu Val Glu Ser Gly Gly Gly Leu Val Gln Pro Gly Gly
1               5                   10                  15
Ser Leu Arg Leu Ser Cys Ala Val Ser Gly Phe Ser Leu Ser Ser Tyr
            20                  25                  30
Gly Val Thr Trp Val Arg Gln Ala Pro Gly Lys Gly Leu Glu Trp Ile
        35                  40                  45
Ser Tyr Ile Thr Ser Asn Tyr Gly Val Ser Tyr Tyr Ala Ser Trp Ala
        50                  55                  60
Lys Ser Arg Ser Thr Ile Ser Arg Asp Thr Ser Lys Asn Thr Val Tyr
65                  70                  75                  80
Leu Gln Met Gly Ser Leu Arg Ala Glu Asp Met Ala Val Tyr Phe Cys
```

```
                    85                  90                  95

Ala Arg Glu Asn Pro Asp Tyr Gly Tyr Ala Tyr Asp Ala Trp Gly Pro
                100                 105                 110

Gly Thr Thr Val Thr Val Ser Ser
        115                 120

<210> SEQ ID NO 179
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Val Thr Trp Val Arg Gln Ala Pro Gly Lys Gly Leu Glu Trp Ile
        35                  40                  45

Gly Tyr Ile Thr Ser Asn Tyr Gly Val Ser Tyr Tyr Ala Ser Trp Ala
    50                  55                  60

Lys Ser Arg Phe Thr Ile Ser Arg Asp Thr Ser Lys Asn Thr Val Tyr
65                  70                  75                  80

Leu Gln Met Gly Ser Leu Arg Ala Glu Asp Met Ala Val Tyr Phe Cys
                85                  90                  95

Ala Arg Glu Asn Pro Asp Tyr Gly Tyr Ala Tyr Asp Ala Trp Gly Pro
                100                 105                 110

Gly Thr Thr Val Thr Val Ser Ser
        115                 120

<210> SEQ ID NO 180
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Val Thr Trp Val Arg Gln Ala Pro Gly Lys Gly Leu Glu Trp Ile
        35                  40                  45

Gly Tyr Ile Thr Ser Asn Tyr Gly Val Ser Tyr Tyr Ala Ser Trp Ala
    50                  55                  60

Lys Ser Arg Ser Thr Ile Ser Arg Asp Asn Ser Lys Asn Thr Val Tyr
65                  70                  75                  80

Leu Gln Met Gly Ser Leu Arg Ala Glu Asp Met Ala Val Tyr Phe Cys
                85                  90                  95

Ala Arg Glu Asn Pro Asp Tyr Gly Tyr Ala Tyr Asp Ala Trp Gly Pro
                100                 105                 110

Gly Thr Thr Val Thr Val Ser Ser
        115                 120
```

```
<210> SEQ ID NO 181
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Val Thr Trp Val Arg Gln Ala Pro Gly Lys Gly Leu Glu Trp Ile
        35                  40                  45

Gly Tyr Ile Thr Ser Asn Tyr Gly Val Ser Tyr Ala Ser Trp Ala
    50                  55                      60

Lys Ser Arg Ser Thr Ile Ser Arg Asp Thr Ser Lys Asn Thr Leu Tyr
65                  70                  75                  80

Leu Gln Met Gly Ser Leu Arg Ala Glu Asp Met Ala Val Tyr Phe Cys
                85                  90                  95

Ala Arg Glu Asn Pro Asp Tyr Gly Tyr Ala Tyr Asp Ala Trp Gly Pro
            100                 105                 110

Gly Thr Thr Val Thr Val Ser Ser
        115                 120

<210> SEQ ID NO 182
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Val Thr Trp Val Arg Gln Ala Pro Gly Lys Gly Leu Glu Trp Ile
        35                  40                  45

Gly Tyr Ile Thr Ser Asn Tyr Gly Val Ser Tyr Ala Ser Trp Ala
    50                  55                      60

Lys Ser Arg Ser Thr Ile Ser Arg Asp Thr Ser Lys Asn Thr Val Tyr
65                  70                  75                  80

Leu Gln Met Gly Ser Leu Arg Ala Glu Asp Met Ala Val Tyr Tyr Cys
                85                  90                  95

Ala Arg Glu Asn Pro Asp Tyr Gly Tyr Ala Tyr Asp Ala Trp Gly Pro
            100                 105                 110

Gly Thr Thr Val Thr Val Ser Ser
        115                 120

<210> SEQ ID NO 183
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183
```

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Val Thr Trp Val Arg Gln Ala Pro Gly Lys Gly Leu Glu Trp Ile
            35                  40                  45

Gly Tyr Ile Thr Ser Asn Tyr Gly Val Ser Tyr Ala Ser Trp Ala
50                  55                  60

Lys Ser Arg Ser Thr Ile Ser Arg Asp Thr Ser Lys Asn Thr Val Tyr
65                  70                  75                  80

Leu Gln Met Gly Ser Leu Arg Ala Glu Asp Met Ala Val Tyr Phe Cys
                85                  90                  95

Ala Arg Glu Asn Pro Asp Tyr Gly Tyr Ala Tyr Asp Ala Trp Gly Gln
            100                 105                 110

Gly Thr Thr Val Thr Val Ser Ser
            115                 120

<210> SEQ ID NO 184
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Val Thr Trp Val Arg Gln Ala Pro Gly Lys Gly Leu Glu Trp Ile
            35                  40                  45

Gly Tyr Ile Thr Ser Asn Tyr Gly Val Ser Tyr Ala Asn Ser Val
50                  55                  60

Lys Gly Arg Ser Thr Ile Ser Arg Asp Thr Ser Lys Asn Thr Val Tyr
65                  70                  75                  80

Leu Gln Met Gly Ser Leu Arg Ala Glu Asp Met Ala Val Tyr Phe Cys
                85                  90                  95

Ala Arg Glu Asn Pro Asp Tyr Gly Tyr Ala Tyr Asp Ala Trp Gly Pro
            100                 105                 110

Gly Thr Thr Val Thr Val Ser Ser
            115                 120

<210> SEQ ID NO 185
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Gly Val Thr Trp Val Arg Gln Ala Pro Gly Lys Gly Leu Glu Tyr Val
            35                  40                  45
```

Ser Tyr Ile Thr Ser Asn Tyr Gly Val Ser Tyr Tyr Ala Ser Trp Ala
            50                  55                  60

Lys Ser Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg Glu Asn Pro Asp Tyr Gly Tyr Ala Tyr Asp Ala Trp Gly Gln
            100                 105                 110

Gly Thr Thr Val Thr Val Ser Ser
        115                 120

<210> SEQ ID NO 186
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Gly Val Thr Trp Val Arg Gln Ala Pro Gly Lys Gly Leu Glu Tyr Val
        35                  40                  45

Ser Tyr Ile Thr Ser Asn Tyr Gly Val Ser Tyr Tyr Ala Asn Ser Val
            50                  55                  60

Lys Gly Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg Glu Asn Pro Asp Tyr Gly Tyr Ala Tyr Asp Ala Trp Gly Gln
            100                 105                 110

Gly Thr Thr Val Thr Val Ser Ser
        115                 120

<210> SEQ ID NO 187
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Gly Val Thr Trp Val Arg Gln Ala Pro Gly Lys Gly Leu Glu Trp Val
        35                  40                  45

Gly Tyr Ile Thr Ser Asn Tyr Gly Val Ser Tyr Tyr Ala Ser Trp Ala
            50                  55                  60

Lys Ser Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
                85                  90                  95

```
Ala Arg Glu Asn Pro Asp Tyr Gly Tyr Ala Tyr Asp Ala Trp Gly Gln
            100                 105                 110

Gly Thr Thr Val Thr Val Ser Ser
        115                 120

<210> SEQ ID NO 188
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Glu Gln Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Gly Val Thr Trp Val Arg Gln Ala Pro Gly Lys Gly Leu Glu Trp Val
        35                  40                  45

Gly Tyr Ile Thr Ser Asn Tyr Gly Val Ser Tyr Tyr Ala Ser Trp Ala
    50                  55                  60

Lys Ser Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg Glu Asn Pro Asp Tyr Gly Tyr Ala Tyr Asp Ala Trp Gly Gln
            100                 105                 110

Gly Thr Thr Val Thr Val Ser Ser
        115                 120

<210> SEQ ID NO 189
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Gly Val Thr Trp Val Arg Gln Ala Pro Gly Lys Gly Leu Glu Trp Val
        35                  40                  45

Gly Tyr Ile Thr Ser Asn Tyr Gly Val Ser Tyr Tyr Ala Ser Trp Ala
    50                  55                  60

Lys Ser Arg Phe Thr Ile Ser Arg Asn Leu Asn Thr Asn Thr Leu Tyr
65                  70                  75                  80

Leu Gln Met Gly Ser Leu Arg Ala Glu Asp Met Ala Val Tyr Tyr Cys
                85                  90                  95

Ala Arg Glu Asn Pro Asp Tyr Gly Tyr Ala Tyr Asp Ala Trp Gly Gln
            100                 105                 110

Gly Thr Thr Val Thr Val Ser Ser
        115                 120

<210> SEQ ID NO 190
```

<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Gly Val Thr Trp Val Arg Gln Ala Pro Gly Lys Gly Leu Glu Trp Val
        35                  40                  45

Gly Tyr Ile Thr Ser Asn Tyr Gly Val Ser Tyr Tyr Ala Ser Phe Ala
    50                  55                  60

Lys Ser Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg Glu Asn Pro Asp Tyr Gly Tyr Ala Tyr Asp Ala Trp Gly Gln
            100                 105                 110

Gly Thr Thr Val Thr Val Ser Ser
        115                 120

<210> SEQ ID NO 191
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Gly Val Thr Trp Val Arg Gln Ala Pro Gly Lys Gly Leu Glu Trp Val
        35                  40                  45

Gly Tyr Ile Thr Ser Asn Tyr Gly Val Ser Tyr Tyr Ala Ser Trp Ala
    50                  55                  60

Lys Ser Arg Phe Thr Ile Ser Arg Asn Thr Asn Leu Asn Thr Leu Tyr
65                  70                  75                  80

Leu Gln Met Gly Ser Leu Arg Ala Glu Asp Met Ala Val Tyr Tyr Cys
                85                  90                  95

Ala Arg Glu Asn Pro Asp Tyr Gly Tyr Ala Tyr Asp Ala Trp Gly Gln
            100                 105                 110

Gly Thr Thr Val Thr Val Ser Ser
        115                 120

<210> SEQ ID NO 192
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Gly Val Thr Trp Val Arg Gln Ala Pro Gly Lys Gly Leu Glu Trp Val
        35                  40                  45

Gly Tyr Ile Thr Ser Asn Tyr Gly Val Ser Tyr Ala Ser Trp Ala
    50                  55                  60

Lys Ser Arg Phe Thr Ile Ser Arg Asn Asn Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg Glu Asn Pro Asp Tyr Gly Tyr Ala Tyr Asp Ala Trp Gly Gln
            100                 105                 110

Gly Thr Thr Val Thr Val Ser Ser
        115                 120

<210> SEQ ID NO 193
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Gly Val Thr Trp Val Arg Gln Ala Pro Gly Lys Gly Leu Glu Trp Val
        35                  40                  45

Gly Tyr Ile Thr Ser Asn Tyr Gly Val Ser Tyr Ala Ser Trp Ala
    50                  55                  60

Lys Ser Arg Phe Thr Ile Ser Arg Asp Asn Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg Glu Asn Pro Asp Tyr Gly Tyr Ala Tyr Asp Ala Trp Gly Gln
            100                 105                 110

Gly Thr Thr Val Thr Val Ser Ser
        115                 120

<210> SEQ ID NO 194
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Gly Val Thr Trp Val Arg Gln Ala Pro Gly Lys Gly Leu Glu Trp Val
        35                  40                  45

Gly Tyr Ile Thr Ser Asn Tyr Gly Val Ser Tyr Tyr Ala Ser Trp Ala
            50                  55                  60

Lys Ser Arg Phe Thr Ile Ser Arg Asn Asn Lys Asn Thr Leu Tyr
 65                  70                  75                  80

Leu Gln Met Gly Ser Leu Arg Ala Glu Asp Met Ala Val Tyr Tyr Cys
                85                  90                  95

Ala Arg Glu Asn Pro Asp Tyr Gly Tyr Ala Tyr Asp Ala Trp Gly Gln
                100                 105                 110

Gly Thr Thr Val Thr Val Ser Ser
            115                 120

<210> SEQ ID NO 195
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
                20                  25                  30

Gly Val Thr Trp Val Arg Gln Ala Pro Gly Lys Gly Leu Glu Trp Ile
            35                  40                  45

Gly Tyr Ile Thr Ser Asn Tyr Gly Val Ser Tyr Tyr Ala Ser Trp Ala
            50                  55                  60

Lys Ser Arg Phe Thr Ile Ser Arg Asp Asn Ser Lys Asn Thr Leu Tyr
 65                  70                  75                  80

Leu Gln Met Gly Ser Leu Arg Ala Glu Asp Met Ala Val Tyr Tyr Cys
                85                  90                  95

Ala Arg Glu Asn Pro Asp Tyr Gly Tyr Ala Tyr Asp Ala Trp Gly Gln
                100                 105                 110

Gly Thr Thr Val Thr Val Ser Ser
            115                 120

<210> SEQ ID NO 196
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
                20                  25                  30

Gly Val Thr Trp Val Arg Gln Ala Pro Gly Lys Gly Leu Glu Trp Val
            35                  40                  45

Gly Tyr Ile Thr Ser Asn Tyr Gly Val Ser Tyr Tyr Ala Ser Trp Ala
            50                  55                  60

Lys Ser Arg Ser Thr Ile Ser Arg Asp Asn Ser Lys Asn Thr Leu Tyr
 65                  70                  75                  80

Leu Gln Met Gly Ser Leu Arg Ala Glu Asp Met Ala Val Tyr Tyr Cys
                85                  90                  95

-continued

Ala Arg Glu Asn Pro Asp Tyr Gly Tyr Ala Tyr Asp Ala Trp Gly Gln
                100                 105                 110

Gly Thr Thr Val Thr Val Ser Ser
        115                 120

<210> SEQ ID NO 197
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Gly Val Thr Trp Val Arg Gln Ala Pro Gly Lys Gly Leu Glu Trp Ile
        35                  40                  45

Gly Tyr Ile Thr Ser Asn Tyr Gly Val Ser Tyr Tyr Ala Ser Trp Ala
    50                  55                  60

Lys Ser Arg Ser Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg Glu Asn Pro Asp Tyr Gly Tyr Ala Tyr Asp Ala Trp Gly Gln
                100                 105                 110

Gly Thr Thr Val Thr Val Ser Ser
        115                 120

<210> SEQ ID NO 198
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Gly Val Thr Trp Val Arg Gln Ala Pro Gly Lys Gly Leu Glu Trp Val
        35                  40                  45

Gly Tyr Ile Thr Ser Asn Tyr Gly Val Ser Tyr Tyr Ala Ser Trp Ala
    50                  55                  60

Lys Ser Arg Phe Thr Ile Ser Arg Asp Thr Ser Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg Glu Asn Pro Asp Tyr Gly Tyr Ala Tyr Asp Ala Trp Gly Gln
                100                 105                 110

Gly Thr Thr Val Thr Val Ser Ser
        115                 120

<210> SEQ ID NO 199
<211> LENGTH: 120

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Gly Val Thr Trp Val Arg Gln Ala Pro Gly Lys Gly Leu Glu Trp Val
        35                  40                  45

Gly Tyr Ile Thr Ser Asn Tyr Gly Val Ser Tyr Tyr Ala Ser Trp Ala
    50                  55                  60

Lys Ser Arg Phe Thr Ile Ser Arg Asp Asn Ser Lys Asn Thr Val Tyr
65                  70                  75                  80

Leu Gln Met Gly Ser Leu Arg Ala Glu Asp Met Ala Val Tyr Tyr Cys
                85                  90                  95

Ala Arg Glu Asn Pro Asp Tyr Gly Tyr Ala Tyr Asp Ala Trp Gly Gln
            100                 105                 110

Gly Thr Thr Val Thr Val Ser Ser
        115                 120

<210> SEQ ID NO 200
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Gly Val Thr Trp Val Arg Gln Ala Pro Gly Lys Gly Leu Glu Trp Ile
        35                  40                  45

Gly Tyr Ile Thr Ser Asn Tyr Gly Val Ser Tyr Tyr Ala Ser Trp Ala
    50                  55                  60

Lys Ser Arg Ser Thr Ile Ser Arg Asp Asn Ser Lys Asn Thr Val Tyr
65                  70                  75                  80

Leu Gln Met Gly Ser Leu Arg Ala Glu Asp Met Ala Val Tyr Tyr Cys
                85                  90                  95

Ala Arg Glu Asn Pro Asp Tyr Gly Tyr Ala Tyr Asp Ala Trp Gly Gln
            100                 105                 110

Gly Thr Thr Val Thr Val Ser Ser
        115                 120

<210> SEQ ID NO 201
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Glu Val Gln Leu Val Glu Ser Gly Gly Gly Leu Val Gln Pro Gly Gly
```

-continued

```
               1               5                    10                       15
           Ser Leu Arg Leu Ser Cys Ala Ala Ser Gly Phe Ser Leu Ser Ser Tyr
                           20                  25                  30
           Gly Val Thr Trp Val Arg Gln Ala Pro Gly Lys Gly Leu Glu Trp Ile
                           35                  40                  45
           Gly Tyr Ile Thr Ser Asn Tyr Gly Val Ser Tyr Tyr Ala Ser Trp Ala
                   50                  55                  60
           Lys Ser Arg Ser Thr Ile Ser Arg Asp Thr Ser Lys Asn Thr Val Tyr
           65                  70                  75                  80
           Leu Gln Met Gly Ser Leu Arg Ala Glu Asp Met Ala Val Tyr Tyr Cys
                           85                  90                  95
           Ala Arg Glu Asn Pro Asp Tyr Gly Tyr Ala Tyr Asp Ala Trp Gly Gln
                           100                 105                 110
           Gly Thr Thr Val Thr Val Ser Ser
                           115                 120

<210> SEQ ID NO 202
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Val or Gln
<220> FEATURE:
<221> NAME/KEY: MOD_RES
<222> LOCATION: (24)..(24)
<223> OTHER INFORMATION: Val or Ala
<220> FEATURE:
<221> NAME/KEY: MOD_RES
<222> LOCATION: (47)..(47)
<223> OTHER INFORMATION: Trp or Tyr
<220> FEATURE:
<221> NAME/KEY: MOD_RES
<222> LOCATION: (48)..(48)
<223> OTHER INFORMATION: Ile or Val
<220> FEATURE:
<221> NAME/KEY: MOD_RES
<222> LOCATION: (49)..(49)
<223> OTHER INFORMATION: Gly or Ser
<220> FEATURE:
<221> NAME/KEY: MOD_RES
<222> LOCATION: (62)..(62)
<223> OTHER INFORMATION: Ser or Asn
<220> FEATURE:
<221> NAME/KEY: MOD_RES
<222> LOCATION: (63)..(63)
<223> OTHER INFORMATION: Trp, Ser or Phe
<220> FEATURE:
<221> NAME/KEY: MOD_RES
<222> LOCATION: (64)..(64)
<223> OTHER INFORMATION: Ala or Val
<220> FEATURE:
<221> NAME/KEY: MOD_RES
<222> LOCATION: (66)..(66)
<223> OTHER INFORMATION: Ser or Gly
<220> FEATURE:
<221> NAME/KEY: MOD_RES
<222> LOCATION: (68)..(68)
<223> OTHER INFORMATION: Ser or Phe
<220> FEATURE:
<221> NAME/KEY: MOD_RES
<222> LOCATION: (73)..(73)
<223> OTHER INFORMATION: Asp or Asn
<220> FEATURE:
<221> NAME/KEY: MOD_RES
<222> LOCATION: (74)..(74)
<223> OTHER INFORMATION: Thr, Leu or Asn
```

```
<220> FEATURE:
<221> NAME/KEY: MOD_RES
<222> LOCATION: (75)..(75)
<223> OTHER INFORMATION: Ser or Asn
<220> FEATURE:
<221> NAME/KEY: MOD_RES
<222> LOCATION: (76)..(76)
<223> OTHER INFORMATION: Lys, Thr or Leu
<220> FEATURE:
<221> NAME/KEY: MOD_RES
<222> LOCATION: (79)..(79)
<223> OTHER INFORMATION: Val or Leu
<220> FEATURE:
<221> NAME/KEY: MOD_RES
<222> LOCATION: (95)..(95)
<223> OTHER INFORMATION: Phe or Tyr
<220> FEATURE:
<221> NAME/KEY: MOD_RES
<222> LOCATION: (112)..(112)
<223> OTHER INFORMATION: Pro or Gln

<400> SEQUENCE: 202

Glu Xaa Gln Leu Val Glu Ser Gly Gly Gly Leu Val Gln Pro Gly Gly
1               5                   10                  15

Ser Leu Arg Leu Ser Cys Ala Xaa Ser Gly Phe Ser Leu Ser Ser Tyr
            20                  25                  30

Gly Val Thr Trp Val Arg Gln Ala Pro Gly Lys Gly Leu Glu Xaa Xaa
        35                  40                  45

Xaa Tyr Ile Thr Ser Asn Tyr Gly Val Ser Tyr Ala Xaa Xaa Xaa
50                  55                  60

Lys Xaa Arg Xaa Thr Ile Ser Arg Xaa Xaa Xaa Asn Thr Xaa Tyr
65                  70                  75                  80

Leu Gln Met Gly Ser Leu Arg Ala Glu Asp Met Ala Val Tyr Xaa Cys
            85                  90                  95

Ala Arg Glu Asn Pro Asp Tyr Gly Tyr Ala Tyr Asp Ala Trp Gly Xaa
            100                 105                 110

Gly Thr Thr Val Thr Val Ser Ser
        115                 120

<210> SEQ ID NO 203
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Gln Ser Val Lys Glu Ser Glu Gly Gly Leu Phe Lys Pro Thr Asp Thr
1               5                   10                  15

Leu Thr Leu Thr Cys Thr Val Ser Gly Phe Ser Leu Ile Asn Tyr Gly
            20                  25                  30

Val Ser Trp Val Arg Gln Ala Pro Gly Lys Gly Leu Glu Trp Ile Gly
        35                  40                  45

Tyr Ile Gly Ser Ala Gly Ser Thr Tyr Tyr Ala Thr Trp Ala Lys Ser
50                  55                  60

Arg Ala Thr Ile Thr Arg Asn Thr Asn Leu Asn Thr Val Thr Leu Lys
65                  70                  75                  80

Met Thr Ser Leu Thr Ala Ala Asp Thr Ala Thr Tyr Phe Cys Ala Arg
            85                  90                  95

Ala Ala Tyr Ser Ala Gly Ser Ala Asp Ala Glu Asp Ile Trp Gly Pro
            100                 105                 110
```

Gly Thr Leu Val Thr Val Ser Ser
        115                 120

<210> SEQ ID NO 204
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Gln Ser Val Lys Glu Ser Glu Gly Gly Leu Ile Lys Pro Thr Asp Thr
1               5                   10                  15

Leu Thr Leu Thr Cys Thr Val Ser Gly Phe Ser Leu Ser Thr Phe Ala
            20                  25                  30

Ile Asn Trp Val Arg Gln Ala Pro Gly Asn Gly Leu Glu Trp Ile Gly
        35                  40                  45

Ala Ile Gly Arg Gly Gly Ser Ala Tyr Tyr Ala Ser Trp Ala Lys Ser
    50                  55                  60

Arg Ser Thr Ile Thr Lys Asn Thr Asn Leu Asn Thr Val Thr Leu Lys
65                  70                  75                  80

Met Thr Arg Pro Thr Ala Ala Asp Thr Ala Thr Tyr Phe Cys Ala Arg
                85                  90                  95

Glu Asn Ala Gly Ser Gly Trp Gly Glu Leu Asp Ile Trp Gly Pro Gly
            100                 105                 110

Thr Leu Val Thr Val Ser Ser
        115

<210> SEQ ID NO 205
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Gln Ser Val Lys Glu Ser Glu Gly Gly Leu Phe Lys Pro Thr Asp Thr
1               5                   10                  15

Leu Thr Leu Thr Cys Thr Val Ser Gly Phe Ser Leu Ser Gly Tyr Gly
            20                  25                  30

Val Ser Trp Val Arg Gln Ala Pro Gly Lys Gly Leu Glu Tyr Ile Gly
        35                  40                  45

Phe Ile Gly Ser Gly Gly Ser Ala Tyr Tyr Ala Ser Trp Ala Lys Ser
    50                  55                  60

Arg Ser Thr Ile Thr Arg Asn Thr Asn Leu Asn Thr Val Thr Leu Lys
65                  70                  75                  80

Met Thr Arg Leu Thr Ala Ala Asp Thr Ala Thr Tyr Phe Cys Ala Arg
                85                  90                  95

Asp Asn Val Gly Gly Asp Met Ser Leu Asp Ile Trp Gly Pro Gly Thr
            100                 105                 110

Leu Val Thr Val Ser Ser
        115

<210> SEQ ID NO 206
<211> LENGTH: 118
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 206

Gln Ser Val Lys Glu Ser Glu Gly Gly Leu Phe Lys Pro Thr Asp Asn
1               5                   10                  15

Leu Thr Leu Thr Cys Thr Val Ser Gly Phe Ser Leu Ser Asn Tyr Gly
            20                  25                  30

Val Thr Trp Val Arg Gln Ala Pro Gly Asn Gly Leu Glu Tyr Ile Gly
        35                  40                  45

Phe Ile Gly Ser Ser Gly Ser Ala Tyr Tyr Ala Ser Trp Ala Lys Ser
    50                  55                  60

Arg Ser Thr Ile Thr Arg Asn Thr Asn Leu Asn Val Thr Leu Lys
65                  70                  75                  80

Met Thr Ser Leu Thr Ala Ala Asp Thr Ala Thr Tyr Phe Cys Ala Arg
                85                  90                  95

Asp Asp Val Gly Gly Gly Lys Ser Leu Asp Ile Trp Gly Pro Gly Thr
            100                 105                 110

Leu Val Thr Val Ser Ser
        115

<210> SEQ ID NO 207
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Gln Ser Val Lys Glu Ser Glu Gly Gly Leu Phe Lys Pro Thr Asp Asn
1               5                   10                  15

Leu Thr Leu Thr Cys Thr Val Ser Gly Phe Ser Leu Ser Ser Tyr Gly
            20                  25                  30

Val Ser Trp Val Arg Gln Ala Pro Gly Asn Gly Leu Glu Tyr Ile Gly
        35                  40                  45

Phe Ile Gly Ser Gly Gly Phe Ala Tyr Tyr Ala Ser Trp Ala Lys Ser
    50                  55                  60

Arg Ser Thr Ile Thr Arg Asn Thr Asn Leu Asn Val Thr Leu Lys
65                  70                  75                  80

Met Thr Ser Leu Thr Ala Ala Asp Thr Ala Thr Tyr Phe Cys Ala Arg
                85                  90                  95

Asp Asp Val Gly Gly Gly Lys Ser Leu Asp Ile Trp Gly Pro Gly Thr
            100                 105                 110

Val Val Thr Val Ser Val
        115

<210> SEQ ID NO 208
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Glu Val Gln Leu Val Glu Ser Gly Gly Gly Leu Ile Gln Pro Gly Gly
1               5                   10                  15

Ser Leu Arg Leu Ser Cys Ala Val Ser Gly Phe Ser Leu Ser Ser Tyr

```
            20                  25                  30

Gly Val Ser Trp Val Arg Gln Ala Pro Gly Lys Gly Leu Glu Tyr Ile
            35                  40                  45

Gly Phe Ile Gly Ser Gly Gly Phe Ala Tyr Tyr Ala Ser Trp Ala Lys
        50                  55                  60

Ser Arg Ser Thr Ile Ser Arg Asp Thr Ser Lys Asn Thr Val Tyr Leu
 65                 70                  75                  80

Gln Met Asn Ser Leu Arg Ala Glu Asp Thr Ala Val Tyr Phe Cys Ala
                85                  90                  95

Arg Asp Asp Val Gly Gly Gly Lys Ser Leu Asp Ile Trp Gly Pro Gly
            100                 105                 110

Thr Leu Val Thr Val Ser Ser
        115

<210> SEQ ID NO 209
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Glu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Ser Leu Ser Ser Tyr
            20                  25                  30

Gly Val Ser Trp Val Arg Gln Ala Pro Gly Lys Gly Leu Glu Tyr Ile
            35                  40                  45

Gly Phe Ile Gly Ser Gly Gly Phe Ala Tyr Tyr Ala Ser Trp Ala Lys
        50                  55                  60

Ser Arg Ser Thr Ile Ser Arg Asp Thr Ser Lys Asn Thr Val Tyr Leu
 65                 70                  75                  80

Gln Met Asn Ser Leu Arg Ala Glu Asp Thr Ala Val Tyr Phe Cys Ala
                85                  90                  95

Arg Asp Asp Val Gly Gly Gly Lys Ser Leu Asp Ile Trp Gly Pro Gly
            100                 105                 110

Thr Leu Val Thr Val Ser Ser
        115

<210> SEQ ID NO 210
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Glu Val Gln Leu Val Glu Ser Gly Gly Gly Leu Ile Gln Pro Gly Gly
 1               5                  10                  15

Ser Leu Arg Leu Ser Cys Ala Val Ser Gly Phe Ser Leu Ser Ser Tyr
            20                  25                  30

Gly Val Ser Trp Val Arg Gln Ala Pro Gly Lys Gly Leu Glu Trp Ile
            35                  40                  45

Gly Phe Ile Gly Ser Gly Gly Phe Ala Tyr Tyr Ala Ser Trp Ala Lys
        50                  55                  60

Ser Arg Ser Thr Ile Ser Arg Asp Thr Ser Lys Asn Thr Val Tyr Leu
```

```
                65                  70                  75                  80
Gln Met Asn Ser Leu Arg Ala Glu Asp Thr Ala Val Tyr Phe Cys Ala
                    85                  90                  95
Arg Asp Asp Val Gly Gly Gly Lys Ser Leu Asp Ile Trp Gly Pro Gly
                100                 105                 110
Thr Leu Val Thr Val Ser Ser
            115
```

<210> SEQ ID NO 211
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

```
Glu Val Gln Leu Val Glu Ser Gly Gly Gly Leu Ile Gln Pro Gly Gly
1               5                   10                  15
Ser Leu Arg Leu Ser Cys Ala Val Ser Gly Phe Ser Leu Ser Ser Tyr
            20                  25                  30
Gly Val Ser Trp Val Arg Gln Ala Pro Gly Lys Gly Leu Glu Tyr Val
        35                  40                  45
Gly Phe Ile Gly Ser Gly Gly Phe Ala Tyr Tyr Ala Ser Trp Ala Lys
    50                  55                  60
Ser Arg Ser Thr Ile Ser Arg Asp Thr Ser Lys Asn Thr Val Tyr Leu
65                  70                  75                  80
Gln Met Asn Ser Leu Arg Ala Glu Asp Thr Ala Val Tyr Phe Cys Ala
                85                  90                  95
Arg Asp Asp Val Gly Gly Gly Lys Ser Leu Asp Ile Trp Gly Pro Gly
            100                 105                 110
Thr Leu Val Thr Val Ser Ser
        115
```

<210> SEQ ID NO 212
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

```
Glu Val Gln Leu Val Glu Ser Gly Gly Gly Leu Ile Gln Pro Gly Gly
1               5                   10                  15
Ser Leu Arg Leu Ser Cys Ala Val Ser Gly Phe Ser Leu Ser Ser Tyr
            20                  25                  30
Gly Val Ser Trp Val Arg Gln Ala Pro Gly Lys Gly Leu Glu Tyr Ile
        35                  40                  45
Ser Phe Ile Gly Ser Gly Gly Phe Ala Tyr Tyr Ala Ser Trp Ala Lys
    50                  55                  60
Ser Arg Ser Thr Ile Ser Arg Asp Thr Ser Lys Asn Thr Val Tyr Leu
65                  70                  75                  80
Gln Met Asn Ser Leu Arg Ala Glu Asp Thr Ala Val Tyr Phe Cys Ala
                85                  90                  95
Arg Asp Asp Val Gly Gly Gly Lys Ser Leu Asp Ile Trp Gly Pro Gly
            100                 105                 110
Thr Leu Val Thr Val Ser Ser
```

<210> SEQ ID NO 213
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Glu Val Gln Leu Val Glu Ser Gly Gly Gly Leu Ile Gln Pro Gly Gly
1               5                   10                  15

Ser Leu Arg Leu Ser Cys Ala Val Ser Gly Phe Ser Leu Ser Ser Tyr
            20                  25                  30

Gly Val Ser Trp Val Arg Gln Ala Pro Gly Lys Gly Leu Glu Tyr Ile
        35                  40                  45

Gly Phe Ile Gly Ser Gly Gly Phe Ala Tyr Tyr Ala Ser Trp Ala Lys
    50                  55                  60

Ser Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Phe Cys Ala
                85                  90                  95

Arg Asp Asp Val Gly Gly Gly Lys Ser Leu Asp Ile Trp Gly Pro Gly
            100                 105                 110

Thr Leu Val Thr Val Ser Ser
        115

<210> SEQ ID NO 214
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Glu Val Gln Leu Val Glu Ser Gly Gly Gly Leu Ile Gln Pro Gly Gly
1               5                   10                  15

Ser Leu Arg Leu Ser Cys Ala Val Ser Gly Phe Ser Leu Ser Ser Tyr
            20                  25                  30

Gly Val Ser Trp Val Arg Gln Ala Pro Gly Lys Gly Leu Glu Tyr Ile
        35                  40                  45

Gly Phe Ile Gly Ser Gly Gly Phe Ala Tyr Tyr Ala Ser Trp Ala Lys
    50                  55                  60

Ser Arg Ser Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Phe Cys Ala
                85                  90                  95

Arg Asp Asp Val Gly Gly Gly Lys Ser Leu Asp Ile Trp Gly Pro Gly
            100                 105                 110

Thr Leu Val Thr Val Ser Ser
        115

<210> SEQ ID NO 215
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 215

Glu Val Gln Leu Val Glu Ser Gly Gly Gly Leu Ile Gln Pro Gly Gly
1               5                   10                  15

Ser Leu Arg Leu Ser Cys Ala Val Ser Gly Phe Ser Leu Ser Ser Tyr
            20                  25                  30

Gly Val Ser Trp Val Arg Gln Ala Pro Gly Lys Gly Leu Glu Tyr Ile
        35                  40                  45

Gly Phe Ile Gly Ser Gly Gly Phe Ala Tyr Tyr Ala Ser Trp Ala Lys
    50                  55                  60

Ser Arg Ser Thr Ile Ser Arg Asp Thr Ser Lys Asn Thr Leu Tyr Leu
65                  70                  75                  80

Gln Met Asn Ser Leu Arg Ala Glu Asp Thr Ala Val Tyr Phe Cys Ala
                85                  90                  95

Arg Asp Asp Val Gly Gly Gly Lys Ser Leu Asp Ile Trp Gly Pro Gly
            100                 105                 110

Thr Leu Val Thr Val Ser Ser
        115

<210> SEQ ID NO 216
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Glu Val Gln Leu Val Glu Ser Gly Gly Gly Leu Ile Gln Pro Gly Gly
1               5                   10                  15

Ser Leu Arg Leu Ser Cys Ala Val Ser Gly Phe Ser Leu Ser Ser Tyr
            20                  25                  30

Gly Val Ser Trp Val Arg Gln Ala Pro Gly Lys Gly Leu Glu Tyr Ile
        35                  40                  45

Gly Phe Ile Gly Ser Gly Gly Phe Ala Tyr Tyr Ala Ser Trp Ala Lys
    50                  55                  60

Ser Arg Ser Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Asp Val Gly Gly Gly Lys Ser Leu Asp Ile Trp Gly Pro Gly
            100                 105                 110

Thr Leu Val Thr Val Ser Ser
        115

<210> SEQ ID NO 217
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Glu Val Gln Leu Val Glu Ser Gly Gly Gly Leu Ile Gln Pro Gly Gly
1               5                   10                  15

Ser Leu Arg Leu Ser Cys Ala Val Ser Gly Phe Ser Leu Ser Ser Tyr
            20                  25                  30

Gly Val Ser Trp Val Arg Gln Ala Pro Gly Lys Gly Leu Glu Tyr Ile
            35                  40                  45

Gly Phe Ile Gly Ser Gly Gly Phe Ala Tyr Tyr Ala Ser Trp Ala Lys
        50                  55                  60

Ser Arg Ser Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Phe Cys Ala
                85                  90                  95

Arg Asp Asp Val Gly Gly Lys Ser Leu Asp Ile Trp Gly Gln Gly
            100                 105                 110

Thr Leu Val Thr Val Ser Ser
        115

<210> SEQ ID NO 218
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Glu Val Gln Leu Val Glu Ser Gly Gly Gly Leu Ile Gln Pro Gly Gly
1               5                   10                  15

Ser Leu Arg Leu Ser Cys Ala Val Ser Gly Phe Ser Leu Ser Ser Tyr
            20                  25                  30

Gly Val Ser Trp Val Arg Gln Ala Pro Gly Lys Gly Leu Glu Tyr Ile
            35                  40                  45

Gly Phe Ile Gly Ser Gly Gly Phe Ala Tyr Tyr Ala Asp Ser Val Lys
        50                  55                  60

Gly Arg Ser Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Phe Cys Ala
                85                  90                  95

Arg Asp Asp Val Gly Gly Lys Ser Leu Asp Ile Trp Gly Pro Gly
            100                 105                 110

Thr Leu Val Thr Val Ser Ser
        115

<210> SEQ ID NO 219
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ser Leu Ser Ser Tyr
            20                  25                  30

Gly Val Ser Trp Val Arg Gln Ala Pro Gly Lys Gly Leu Glu Trp Val
            35                  40                  45

Ser Phe Ile Gly Ser Gly Gly Phe Ala Tyr Tyr Ala Ser Trp Ala Lys
        50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Asp Val Gly Gly Gly Lys Ser Leu Asp Ile Trp Gly Gln Gly
            100                 105                 110

Thr Leu Val Thr Val Ser Ser
        115

<210> SEQ ID NO 220
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ser Leu Ser Ser Tyr
            20                  25                  30

Gly Val Ser Trp Val Arg Gln Ala Pro Gly Lys Gly Leu Glu Trp Val
        35                  40                  45

Ser Phe Ile Gly Ser Gly Gly Phe Ala Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Asp Val Gly Gly Gly Lys Ser Leu Asp Ile Trp Gly Gln Gly
            100                 105                 110

Thr Leu Val Thr Val Ser Ser
        115

<210> SEQ ID NO 221
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ser Leu Ser Ser Tyr
            20                  25                  30

Gly Val Ser Trp Val Arg Gln Ala Pro Gly Lys Gly Leu Glu Tyr Val
        35                  40                  45

Gly Phe Ile Gly Ser Gly Gly Phe Ala Tyr Tyr Ala Ser Trp Ala Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Asp Val Gly Gly Gly Lys Ser Leu Asp Ile Trp Gly Gln Gly
            100                 105                 110

Thr Leu Val Thr Val Ser Ser
        115

<210> SEQ ID NO 222
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Glu Gln Gln Leu Val Glu Ser Gly Gly Gly Leu Ile Gln Pro Gly Gly
1               5                   10                  15

Ser Leu Arg Leu Ser Cys Ala Ala Ser Gly Phe Ser Leu Ser Ser Tyr
            20                  25                  30

Gly Val Ser Trp Val Arg Gln Ala Pro Gly Lys Gly Leu Glu Tyr Val
        35                  40                  45

Gly Phe Ile Gly Ser Gly Gly Phe Ala Tyr Tyr Ala Ser Trp Ala Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Asp Val Gly Gly Gly Lys Ser Leu Asp Ile Trp Gly Gln Gly
            100                 105                 110

Thr Leu Val Thr Val Ser Ser
        115

<210> SEQ ID NO 223
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ser Leu Ser Ser Tyr
            20                  25                  30

Gly Val Ser Trp Val Arg Gln Ala Pro Gly Lys Gly Leu Glu Tyr Val
        35                  40                  45

Gly Phe Ile Gly Ser Gly Gly Phe Ala Tyr Tyr Ala Ser Trp Ala Lys
    50                  55                  60

Ser Arg Phe Thr Ile Ser Arg Asn Thr Asn Leu Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Asp Val Gly Gly Gly Lys Ser Leu Asp Ile Trp Gly Gln Gly
            100                 105                 110

Thr Leu Val Thr Val Ser Ser
        115

<210> SEQ ID NO 224
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ser Leu Ser Ser Tyr
            20                  25                  30

Gly Val Ser Trp Val Arg Gln Ala Pro Gly Lys Gly Leu Glu Tyr Val
        35                  40                  45

Gly Phe Ile Gly Ser Gly Gly Phe Ala Tyr Tyr Ala Ser Phe Ala Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Asp Val Gly Gly Gly Lys Ser Leu Asp Ile Trp Gly Gln Gly
            100                 105                 110

Thr Leu Val Thr Val Ser Ser
        115

<210> SEQ ID NO 225
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Val or Gln
<220> FEATURE:
<221> NAME/KEY: MOD_RES
<222> LOCATION: (24)..(24)
<223> OTHER INFORMATION: Val or Ala
<220> FEATURE:
<221> NAME/KEY: MOD_RES
<222> LOCATION: (47)..(47)
<223> OTHER INFORMATION: Tyr or Trp
<220> FEATURE:
<221> NAME/KEY: MOD_RES
<222> LOCATION: (48)..(48)
<223> OTHER INFORMATION: Ile or Val
<220> FEATURE:
<221> NAME/KEY: MOD_RES
<222> LOCATION: (49)..(49)
<223> OTHER INFORMATION: Gly or Ser
<220> FEATURE:
<221> NAME/KEY: MOD_RES
<222> LOCATION: (61)..(61)
<223> OTHER INFORMATION: Ser or Asp
<220> FEATURE:
<221> NAME/KEY: MOD_RES
<222> LOCATION: (62)..(62)
<223> OTHER INFORMATION: Trp, Ser or Phe
<220> FEATURE:
<221> NAME/KEY: MOD_RES
<222> LOCATION: (63)..(63)
<223> OTHER INFORMATION: Ala or Val
<220> FEATURE:
<221> NAME/KEY: MOD_RES
<222> LOCATION: (65)..(65)
<223> OTHER INFORMATION: Ser or Gly
<220> FEATURE:
<221> NAME/KEY: MOD_RES
<222> LOCATION: (67)..(67)
<223> OTHER INFORMATION: Ser or Phe
<220> FEATURE:
<221> NAME/KEY: MOD_RES
<222> LOCATION: (72)..(72)
<223> OTHER INFORMATION: Asp or Asn

```
<220> FEATURE:
<221> NAME/KEY: MOD_RES
<222> LOCATION: (73)..(73)
<223> OTHER INFORMATION: Thr or Asn
<220> FEATURE:
<221> NAME/KEY: MOD_RES
<222> LOCATION: (74)..(74)
<223> OTHER INFORMATION: Ser or Asn
<220> FEATURE:
<221> NAME/KEY: MOD_RES
<222> LOCATION: (75)..(75)
<223> OTHER INFORMATION: Lys or Leu
<220> FEATURE:
<221> NAME/KEY: MOD_RES
<222> LOCATION: (78)..(78)
<223> OTHER INFORMATION: Val or Leu
<220> FEATURE:
<221> NAME/KEY: MOD_RES
<222> LOCATION: (94)..(94)
<223> OTHER INFORMATION: Phe or Tyr
<220> FEATURE:
<221> NAME/KEY: MOD_RES
<222> LOCATION: (111)..(111)
<223> OTHER INFORMATION: Pro or Gln

<400> SEQUENCE: 225

Glu Xaa Gln Leu Val Glu Ser Gly Gly Gly Leu Ile Gln Pro Gly Gly
1               5                   10                  15

Ser Leu Arg Leu Ser Cys Ala Xaa Ser Gly Phe Ser Leu Ser Ser Tyr
            20                  25                  30

Gly Val Ser Trp Val Arg Gln Ala Pro Gly Lys Gly Leu Glu Xaa Xaa
        35                  40                  45

Xaa Phe Ile Gly Ser Gly Gly Phe Ala Tyr Tyr Ala Xaa Xaa Xaa Lys
50                  55                  60

Xaa Arg Xaa Thr Ile Ser Arg Xaa Xaa Xaa Xaa Asn Thr Xaa Tyr Leu
65                  70                  75                  80

Gln Met Asn Ser Leu Arg Ala Glu Asp Thr Ala Val Tyr Xaa Cys Ala
                85                  90                  95

Arg Asp Asp Val Gly Gly Gly Lys Ser Leu Asp Ile Trp Gly Xaa Gly
            100                 105                 110

Thr Leu Val Thr Val Ser Ser
        115

<210> SEQ ID NO 226
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Gln Ser Val Lys Glu Ser Glu Gly Gly Leu Phe Lys Pro Thr Asp Asn
1               5                   10                  15

Leu Thr Leu Thr Cys Thr Val Ser Gly Phe Ser Leu Ser Ser Tyr Gly
            20                  25                  30

Val Ser Trp Val Arg Gln Ala Pro Gly Asn Gly Leu Glu Tyr Ile Gly
        35                  40                  45

Phe Ile Gly Ser Gly Gly Ser Pro Tyr Tyr Ala Ser Trp Ala Lys Ser
50                  55                  60

Arg Ser Thr Ile Thr Arg Asn Thr Asn Leu Asn Thr Val Thr Leu Lys
65                  70                  75                  80

Met Thr Ser Leu Thr Ala Ala Asp Thr Ala Thr Tyr Phe Cys Ala Arg
                85                  90                  95
```

```
Asp Asp Val Gly Gly Gly Lys Ser Leu Asp Ile Trp Gly Pro Gly Thr
            100                 105                 110

Leu Val Thr Val Ser Ser
        115

<210> SEQ ID NO 227
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Gln Ser Val Lys Glu Ser Glu Gly Gly Leu Phe Lys Pro Thr Asp Asn
1               5                   10                  15

Leu Thr Leu Thr Cys Thr Val Ser Gly Phe Ser Leu Ser Ser Tyr Gly
            20                  25                  30

Val Ser Trp Val Arg Gln Ala Pro Gly Asn Gly Leu Glu Tyr Ile Gly
        35                  40                  45

Phe Ile Gly Ser Gly Gly Phe Ala Tyr Tyr Ala Ser Trp Ala Lys Ser
    50                  55                  60

Arg Ser Thr Ile Thr Arg Asn Thr Asn Leu Asn Thr Val Thr Leu Lys
65                  70                  75                  80

Met Thr Ser Leu Thr Ala Ala Asp Thr Ala Thr Tyr Phe Cys Ala Arg
                85                  90                  95

Asp Asp Val Gly Gly Gly Arg Ser Leu Asp Ile Trp Gly Pro Gly Thr
            100                 105                 110

Val Val Thr Val Ser Ser
        115

<210> SEQ ID NO 228
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Gln Ser Val Lys Glu Ser Glu Gly Gly Leu Phe Lys Pro Thr Asp Thr
1               5                   10                  15

Leu Thr Leu Thr Cys Thr Val Ser Gly Phe Ser Leu Ser Ser Tyr Pro
            20                  25                  30

Ile Ser Trp Val Arg Gln Ala Pro Gly Asn Gly Leu Glu Trp Ile Gly
        35                  40                  45

Tyr Ile Thr Ser Glu Tyr Gly Val Ala Tyr Tyr Ala Thr Trp Ala Glu
    50                  55                  60

Ser Arg Ser Thr Ile Thr Arg Asn Thr Asn Leu Asn Thr Val Thr Leu
65                  70                  75                  80

Lys Met Thr Ser Leu Thr Ala Ala Asp Thr Ala Thr Tyr Phe Cys Val
                85                  90                  95

Arg Glu Asn Pro Thr Tyr Gly Tyr Ala Tyr Asp Ala Trp Gly Pro Gly
            100                 105                 110

Thr Leu Val Thr Val Ser Ser
        115

<210> SEQ ID NO 229
```

<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 229

Gln Ser Val Lys Glu Ser Glu Gly Gly Leu Phe Lys Pro Thr Asp Thr
1               5                   10                  15

Leu Thr Leu Thr Cys Thr Val Ser Gly Phe Ser Leu Asn Asp Tyr Gly
            20                  25                  30

Val Ser Trp Val Arg Gln Ala Pro Gly Asn Gly Leu Glu Trp Ile Gly
        35                  40                  45

Ala Ile Gly Ser Ser Gly Val Ala Trp Tyr Ala Asn Trp Ala Lys Gly
    50                  55                  60

Arg Ser Thr Ile Thr Arg Asn Thr Asn Leu Asn Val Thr Leu Lys
65                  70                  75                  80

Met Ala Ser Leu Thr Ala Ala Asp Thr Ala Thr Tyr Phe Cys Ala Arg
                85                  90                  95

Asp Arg Asp Tyr Gly Tyr Arg Ala Asp Asp Ala Thr Ser Gly Met Asp
            100                 105                 110

Leu Trp Gly Pro Gly Thr Leu Val Thr Val Ser Ser
        115                 120

<210> SEQ ID NO 230
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 230

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Asn Asp Tyr
            20                  25                  30

Gly Val Ser Trp Val Arg Gln Ala Pro Gly Lys Gly Leu Glu Trp Ile
        35                  40                  45

Gly Ala Ile Gly Ser Ser Gly Val Ala Trp Tyr Ala Asn Trp Ala Lys
    50                  55                  60

Gly Arg Ser Thr Ile Ser Arg His Thr Ser Lys Asn Thr Val Tyr Leu
65                  70                  75                  80

Gln Met Asn Ser Leu Arg Ala Glu Asp Thr Ala Val Tyr Phe Cys Ala
                85                  90                  95

Arg Asp Arg Asp Tyr Gly Tyr Arg Ala Asp Asp Ala Thr Ser Gly Met
            100                 105                 110

Asp Leu Trp Gly Pro Gly Thr Leu Val Thr Val Ser Ser
        115                 120                 125

<210> SEQ ID NO 231
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 231

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asn Asp Tyr
            20                  25                  30

Gly Val Ser Trp Val Arg Gln Ala Pro Gly Lys Gly Leu Glu Trp Ile
        35                  40                  45

Gly Ala Ile Gly Ser Ser Gly Val Ala Trp Tyr Ala Asn Trp Ala Lys
    50                  55                  60

Gly Arg Ser Thr Ile Ser Arg His Thr Ser Lys Asn Thr Val Tyr Leu
65                  70                  75                  80

Gln Met Asn Ser Leu Arg Ala Glu Asp Thr Ala Val Tyr Phe Cys Ala
                85                  90                  95

Arg Asp Arg Asp Tyr Gly Tyr Arg Ala Asp Ala Thr Ser Gly Met
            100                 105                 110

Asp Leu Trp Gly Pro Gly Thr Leu Val Thr Val Ser Ser
            115                 120                 125
```

<210> SEQ ID NO 232
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 232

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Asn Asp Tyr
            20                  25                  30

Gly Val Ser Trp Val Arg Gln Ala Pro Gly Lys Gly Leu Glu Trp Val
        35                  40                  45

Gly Ala Ile Gly Ser Ser Gly Val Ala Trp Tyr Ala Asn Trp Ala Lys
    50                  55                  60

Gly Arg Ser Thr Ile Ser Arg His Thr Ser Lys Asn Thr Val Tyr Leu
65                  70                  75                  80

Gln Met Asn Ser Leu Arg Ala Glu Asp Thr Ala Val Tyr Phe Cys Ala
                85                  90                  95

Arg Asp Arg Asp Tyr Gly Tyr Arg Ala Asp Ala Thr Ser Gly Met
            100                 105                 110

Asp Leu Trp Gly Pro Gly Thr Leu Val Thr Val Ser Ser
            115                 120                 125
```

<210> SEQ ID NO 233
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 233

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Asn Asp Tyr
            20                  25                  30

Gly Val Ser Trp Val Arg Gln Ala Pro Gly Lys Gly Leu Glu Trp Ile
        35                  40                  45
```

Ser Ala Ile Gly Ser Ser Gly Val Ala Trp Tyr Ala Asn Trp Ala Lys
            50                  55                  60

Gly Arg Ser Thr Ile Ser Arg His Thr Ser Lys Asn Thr Val Tyr Leu
 65                  70                  75                  80

Gln Met Asn Ser Leu Arg Ala Glu Asp Thr Ala Val Tyr Phe Cys Ala
                 85                  90                  95

Arg Asp Arg Asp Tyr Gly Tyr Arg Ala Asp Asp Ala Thr Ser Gly Met
            100                 105                 110

Asp Leu Trp Gly Pro Gly Thr Leu Val Thr Val Ser Ser
            115                 120                 125

<210> SEQ ID NO 234
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Glu Val Gln Leu Val Glu Ser Gly Gly Gly Leu Val Gln Pro Gly Gly
 1               5                  10                  15

Ser Leu Arg Leu Ser Cys Ala Val Ser Gly Phe Ser Leu Asn Asp Tyr
                 20                  25                  30

Gly Val Ser Trp Val Arg Gln Ala Pro Gly Lys Gly Leu Glu Trp Ile
             35                  40                  45

Gly Ala Ile Gly Ser Ser Gly Val Ala Trp Tyr Ala Asn Trp Ala Lys
         50                  55                  60

Gly Arg Phe Thr Ile Ser Arg His Thr Ser Lys Asn Thr Val Tyr Leu
 65                  70                  75                  80

Gln Met Asn Ser Leu Arg Ala Glu Asp Thr Ala Val Tyr Phe Cys Ala
                 85                  90                  95

Arg Asp Arg Asp Tyr Gly Tyr Arg Ala Asp Asp Ala Thr Ser Gly Met
            100                 105                 110

Asp Leu Trp Gly Pro Gly Thr Leu Val Thr Val Ser Ser
            115                 120                 125

<210> SEQ ID NO 235
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Glu Val Gln Leu Val Glu Ser Gly Gly Gly Leu Val Gln Pro Gly Gly
 1               5                  10                  15

Ser Leu Arg Leu Ser Cys Ala Val Ser Gly Phe Ser Leu Asn Asp Tyr
                 20                  25                  30

Gly Val Ser Trp Val Arg Gln Ala Pro Gly Lys Gly Leu Glu Trp Ile
             35                  40                  45

Gly Ala Ile Gly Ser Ser Gly Val Ala Trp Tyr Ala Asn Trp Ala Lys
         50                  55                  60

Gly Arg Ser Thr Ile Ser Arg His Asn Ser Lys Asn Thr Val Tyr Leu
 65                  70                  75                  80

Gln Met Asn Ser Leu Arg Ala Glu Asp Thr Ala Val Tyr Phe Cys Ala
                 85                  90                  95

Arg Asp Arg Asp Tyr Gly Tyr Arg Ala Asp Asp Ala Thr Ser Gly Met
            100                 105                 110

Asp Leu Trp Gly Pro Gly Thr Leu Val Thr Val Ser Ser
        115                 120                 125

<210> SEQ ID NO 236
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Asn Asp Tyr
            20                  25                  30

Gly Val Ser Trp Val Arg Gln Ala Pro Gly Lys Gly Leu Glu Trp Ile
        35                  40                  45

Gly Ala Ile Gly Ser Ser Gly Val Ala Trp Tyr Ala Asn Trp Ala Lys
    50                  55                  60

Gly Arg Ser Thr Ile Ser Arg His Thr Ser Lys Asn Thr Leu Tyr Leu
65                  70                  75                  80

Gln Met Asn Ser Leu Arg Ala Glu Asp Thr Ala Val Tyr Phe Cys Ala
                85                  90                  95

Arg Asp Arg Asp Tyr Gly Tyr Arg Ala Asp Asp Ala Thr Ser Gly Met
            100                 105                 110

Asp Leu Trp Gly Pro Gly Thr Leu Val Thr Val Ser Ser
        115                 120                 125

<210> SEQ ID NO 237
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Asn Asp Tyr
            20                  25                  30

Gly Val Ser Trp Val Arg Gln Ala Pro Gly Lys Gly Leu Glu Trp Ile
        35                  40                  45

Gly Ala Ile Gly Ser Ser Gly Val Ala Trp Tyr Ala Asn Trp Ala Lys
    50                  55                  60

Gly Arg Ser Thr Ile Ser Arg His Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Arg Asp Tyr Gly Tyr Arg Ala Asp Asp Ala Thr Ser Gly Met
            100                 105                 110

Asp Leu Trp Gly Pro Gly Thr Leu Val Thr Val Ser Ser
        115                 120                 125

<210> SEQ ID NO 238
<211> LENGTH: 125

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Asn Asp Tyr
            20                  25                  30

Gly Val Ser Trp Val Arg Gln Ala Pro Gly Lys Gly Leu Glu Trp Ile
        35                  40                  45

Gly Ala Ile Gly Ser Ser Gly Val Ala Trp Tyr Ala Asn Trp Ala Lys
    50                  55                  60

Gly Arg Ser Thr Ile Ser Arg His Thr Ser Lys Asn Thr Val Tyr Leu
65                  70                  75                  80

Gln Met Asn Ser Leu Arg Ala Glu Asp Thr Ala Val Tyr Phe Cys Ala
                85                  90                  95

Arg Asp Arg Asp Tyr Gly Tyr Arg Ala Asp Asp Ala Thr Ser Gly Met
            100                 105                 110

Asp Leu Trp Gly Arg Gly Thr Leu Val Thr Val Ser Ser
        115                 120                 125

<210> SEQ ID NO 239
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Asn Asp Tyr
            20                  25                  30

Gly Val Ser Trp Val Arg Gln Ala Pro Gly Lys Gly Leu Glu Trp Ile
        35                  40                  45

Gly Ala Ile Gly Ser Ser Gly Val Ala Phe Tyr Ala Asn Trp Ala Lys
    50                  55                  60

Gly Arg Ser Thr Ile Ser Arg His Thr Ser Lys Asn Thr Val Tyr Leu
65                  70                  75                  80

Gln Met Asn Ser Leu Arg Ala Glu Asp Thr Ala Val Tyr Phe Cys Ala
                85                  90                  95

Arg Asp Arg Asp Tyr Gly Tyr Arg Ala Asp Asp Ala Thr Ser Gly Met
            100                 105                 110

Asp Leu Trp Gly Pro Gly Thr Leu Val Thr Val Ser Ser
        115                 120                 125

<210> SEQ ID NO 240
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Glu Val Gln Leu Val Glu Ser Gly Gly Gly Leu Val Gln Pro Gly Gly
```

```
              1               5                  10                 15
Ser Leu Arg Leu Ser Cys Ala Val Ser Gly Phe Ser Leu Asn Asp Tyr
                20                  25                  30
Gly Val Ser Trp Val Arg Gln Ala Pro Gly Lys Gly Leu Glu Trp Ile
                35                  40                  45
Gly Ala Ile Gly Ser Ser Gly Val Ala Trp Tyr Ala Asp Ser Val Lys
            50                  55                  60
Gly Arg Ser Thr Ile Ser Arg His Thr Ser Lys Asn Thr Val Tyr Leu
65                  70                  75                  80
Gln Met Asn Ser Leu Arg Ala Glu Asp Thr Ala Val Tyr Phe Cys Ala
                85                  90                  95
Arg Asp Arg Asp Tyr Gly Tyr Arg Ala Asp Ala Thr Ser Gly Met
                100                 105                 110
Asp Leu Trp Gly Pro Gly Thr Leu Val Thr Val Ser Ser
            115                 120                 125
```

<210> SEQ ID NO 241
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Ser Leu Asn Asp Tyr
                20                  25                  30
Gly Val Ser Trp Val Arg Gln Ala Pro Gly Lys Gly Leu Glu Trp Val
                35                  40                  45
Ser Ala Ile Gly Ser Ser Gly Val Ala Phe Tyr Ala Asn Trp Ala Lys
            50                  55                  60
Gly Arg Phe Thr Ile Ser Arg His Asn Ser Lys Asn Thr Leu Tyr Leu
65                  70                  75                  80
Gln Met Asn Ser Leu Arg Ala Glu Asp Thr Ala Val Tyr Tyr Cys Ala
                85                  90                  95
Arg Asp Arg Asp Tyr Gly Tyr Arg Ala Asp Asp Ala Thr Ser Gly Met
                100                 105                 110
Asp Leu Trp Gly Arg Gly Thr Leu Val Thr Val Ser Ser
            115                 120                 125
```

<210> SEQ ID NO 242
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Ser Leu Asn Asp Tyr
                20                  25                  30
Gly Val Ser Trp Val Arg Gln Ala Pro Gly Lys Gly Leu Glu Trp Val
                35                  40                  45
Ser Ala Ile Gly Ser Ser Gly Val Ala Phe Tyr Ala Asp Ser Val Lys
```

```
                    50                  55                  60
Gly Arg Phe Thr Ile Ser Arg His Asn Ser Lys Asn Thr Leu Tyr Leu
 65                  70                  75                  80

Gln Met Asn Ser Leu Arg Ala Glu Asp Thr Ala Val Tyr Tyr Cys Ala
                    85                  90                  95

Arg Asp Arg Asp Tyr Gly Tyr Arg Ala Asp Asp Ala Thr Ser Gly Met
                    100                 105                 110

Asp Leu Trp Gly Arg Gly Thr Leu Val Thr Val Ser Ser
                    115                 120                 125

<210> SEQ ID NO 243
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Glu Val Gln Leu Leu Glu Ser Gly Gly Gly Leu Val Gln Pro Gly Gly
 1                   5                  10                  15

Ser Leu Arg Leu Ser Cys Ala Ala Ser Gly Phe Ser Leu Asn Asp Tyr
                    20                  25                  30

Gly Val Ser Trp Val Arg Gln Ala Pro Gly Lys Gly Leu Glu Trp Val
                    35                  40                  45

Gly Ala Ile Gly Ser Ser Gly Val Ala Trp Tyr Ala Asn Trp Ala Lys
                    50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                    85                  90                  95

Arg Asp Arg Asp Tyr Gly Tyr Arg Ala Asp Asp Ala Thr Ser Gly Met
                    100                 105                 110

Asp Leu Trp Gly Arg Gly Thr Leu Val Thr Val Ser Ser
                    115                 120                 125

<210> SEQ ID NO 244
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Glu Val Gln Leu Leu Glu Ser Gly Gly Gly Leu Val Gln Pro Gly Gly
 1                   5                  10                  15

Ser Leu Arg Leu Ser Cys Ala Ala Ser Gly Phe Ser Leu Asn Asp Tyr
                    20                  25                  30

Gly Val Ser Trp Val Arg Gln Ala Pro Gly Lys Gly Leu Glu Trp Val
                    35                  40                  45

Gly Ala Ile Gly Ser Ser Gly Val Ala Phe Tyr Ala Asn Trp Ala Lys
                    50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                    85                  90                  95

Arg Asp Arg Asp Tyr Gly Tyr Arg Ala Asp Asp Ala Thr Ser Gly Met
```

```
                   100                 105                 110

Asp Leu Trp Gly Arg Gly Thr Leu Val Thr Val Ser Ser
        115                 120                 125

<210> SEQ ID NO 245
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Glu Gln Gln Leu Leu Glu Ser Gly Gly Gly Leu Val Gln Pro Gly Gly
1               5                   10                  15

Ser Leu Arg Leu Ser Cys Ala Ala Ser Gly Phe Ser Leu Asn Asp Tyr
            20                  25                  30

Gly Val Ser Trp Val Arg Gln Ala Pro Gly Lys Gly Leu Glu Trp Val
        35                  40                  45

Gly Ala Ile Gly Ser Ser Gly Val Ala Trp Tyr Ala Asn Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Arg Asp Tyr Gly Tyr Arg Ala Asp Asp Ala Thr Ser Gly Met
            100                 105                 110

Asp Leu Trp Gly Arg Gly Thr Leu Val Thr Val Ser Ser
        115                 120                 125

<210> SEQ ID NO 246
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Leu Asn Asp Tyr
            20                  25                  30

Gly Val Ser Trp Val Arg Gln Ala Pro Gly Lys Gly Leu Glu Trp Val
        35                  40                  45

Gly Ala Ile Gly Ser Ser Gly Val Ala Trp Tyr Ala Asn Trp Ala Lys
    50                  55                  60

Gly Arg Phe Thr Ile Ser Arg Asn Thr Asn Leu Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Arg Asp Tyr Gly Tyr Arg Ala Asp Asp Ala Thr Ser Gly Met
            100                 105                 110

Asp Leu Trp Gly Arg Gly Thr Leu Val Thr Val Ser Ser
        115                 120                 125

<210> SEQ ID NO 247
<211> LENGTH: 125
<212> TYPE: PRT
```

<213> ORGANISM: Artificial Sequence
<220> FEATURE:
<223> OTHER INFORMATION: Description of Artificial Sequence: Synthetic
     polypeptide

<400> SEQUENCE: 247

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Leu Asn Asp Tyr
            20                  25                  30

Gly Val Ser Trp Val Arg Gln Ala Pro Gly Lys Gly Leu Glu Trp Val
        35                  40                  45

Gly Ala Ile Gly Ser Ser Gly Val Ala Trp Tyr Ala Asn Phe Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Arg Asp Tyr Gly Tyr Arg Ala Asp Asp Ala Thr Ser Gly Met
            100                 105                 110

Asp Leu Trp Gly Arg Gly Thr Leu Val Thr Val Ser Ser
        115                 120                 125

<210> SEQ ID NO 248
<211> LENGTH: 125
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 248

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Ser Leu Asn Asp Tyr
            20                  25                  30

Gly Val Ser Trp Val Arg Gln Ala Pro Gly Lys Gly Leu Glu Trp Val
        35                  40                  45

Gly Ala Ile Gly Ser Ser Gly Val Ala Trp Tyr Ala Asn Phe Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Arg Asp Tyr Gly Tyr Arg Ala Asp Asp Ala Thr Ser Gly Met
            100                 105                 110

Asp Leu Trp Gly Arg Gly Thr Leu Val Thr Val Ser Ser
        115                 120                 125

<210> SEQ ID NO 249
<211> LENGTH: 125
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 249

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Ser Leu Asn Asp Tyr
            20                  25                  30

Gly Val Ser Trp Val Arg Gln Ala Pro Gly Lys Gly Leu Glu Trp Ile
        35                  40                  45

Gly Ala Ile Gly Ser Ser Gly Val Ala Trp Tyr Ala Asn Phe Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Arg Asp Tyr Gly Tyr Arg Ala Asp Ala Thr Ser Gly Met
                100                 105                 110

Asp Leu Trp Gly Arg Gly Thr Leu Val Thr Val Ser Ser
            115                 120                 125

<210> SEQ ID NO 250
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Leu Asn Asp Tyr
            20                  25                  30

Gly Val Ser Trp Val Arg Gln Ala Pro Gly Lys Gly Leu Glu Trp Val
        35                  40                  45

Gly Ala Ile Gly Ser Ser Gly Val Ala Trp Tyr Ala Asn Phe Ala Lys
    50                  55                  60

Gly Arg Ser Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Arg Asp Tyr Gly Tyr Arg Ala Asp Ala Thr Ser Gly Met
                100                 105                 110

Asp Leu Trp Gly Arg Gly Thr Leu Val Thr Val Ser Ser
            115                 120                 125

<210> SEQ ID NO 251
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Leu Asn Asp Tyr
            20                  25                  30

Gly Val Ser Trp Val Arg Gln Ala Pro Gly Lys Gly Leu Glu Trp Ile
        35                  40                  45

Gly Ala Ile Gly Ser Ser Gly Val Ala Trp Tyr Ala Asn Phe Ala Lys
    50                  55                  60
```

Gly Arg Ser Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Arg Asp Tyr Gly Tyr Arg Ala Asp Asp Ala Thr Ser Gly Met
            100                 105                 110

Asp Leu Trp Gly Arg Gly Thr Leu Val Thr Val Ser Ser
        115                 120                 125

<210> SEQ ID NO 252
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Leu Asn Asp Tyr
            20                  25                  30

Gly Val Ser Trp Val Arg Gln Ala Pro Gly Lys Gly Leu Glu Trp Val
        35                  40                  45

Gly Ala Ile Gly Ser Ser Gly Val Ala Trp Tyr Ala Asn Phe Ala Lys
    50                  55                  60

Gly Arg Phe Thr Ile Ser Arg Asp Thr Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Arg Asp Tyr Gly Tyr Arg Ala Asp Asp Ala Thr Ser Gly Met
            100                 105                 110

Asp Leu Trp Gly Arg Gly Thr Leu Val Thr Val Ser Ser
        115                 120                 125

<210> SEQ ID NO 253
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Leu Asn Asp Tyr
            20                  25                  30

Gly Val Ser Trp Val Arg Gln Ala Pro Gly Lys Gly Leu Glu Trp Val
        35                  40                  45

Gly Ala Ile Gly Ser Ser Gly Val Ala Trp Tyr Ala Asn Phe Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Arg Asp Tyr Gly Tyr Arg Ala Asp Asp Ala Thr Ser Gly Met
            100                 105                 110

Asp Leu Trp Gly Arg Gly Thr Leu Val Thr Val Ser Ser
            115                 120                 125

<210> SEQ ID NO 254
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Leu Asn Asp Tyr
            20                  25                  30

Gly Val Ser Trp Val Arg Gln Ala Pro Gly Lys Gly Leu Glu Trp Val
        35                  40                  45

Gly Ala Ile Gly Ser Ser Gly Val Ala Trp Tyr Ala Asn Phe Ala Lys
    50                  55                  60

Gly Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Arg Asp Tyr Gly Tyr Arg Ala Asp Asp Ala Thr Ser Gly Met
            100                 105                 110

Asp Leu Trp Gly Arg Gly Thr Leu Val Thr Val Ser Ser
            115                 120                 125

<210> SEQ ID NO 255
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Leu Asn Asp Tyr
            20                  25                  30

Gly Val Ser Trp Val Arg Gln Ala Pro Gly Lys Gly Leu Glu Trp Ile
        35                  40                  45

Gly Ala Ile Gly Ser Ser Gly Val Ala Trp Tyr Ala Asn Phe Ala Lys
    50                  55                  60

Gly Arg Ser Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Arg Asp Tyr Gly Tyr Arg Ala Asp Asp Ala Thr Ser Gly Met
            100                 105                 110

Asp Leu Trp Gly Arg Gly Thr Leu Val Thr Val Ser Ser
            115                 120                 125

<210> SEQ ID NO 256
<211> LENGTH: 125
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 256

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Leu Asn Asp Tyr
            20                  25                  30

Gly Val Ser Trp Val Arg Gln Ala Pro Gly Lys Gly Leu Glu Trp Ile
        35                  40                  45

Gly Ala Ile Gly Ser Ser Gly Val Ala Phe Tyr Ala Asn Phe Ala Lys
    50                  55                  60

Gly Arg Ser Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Arg Asp Tyr Gly Tyr Arg Ala Asp Asp Ala Thr Ser Gly Met
            100                 105                 110

Asp Leu Trp Gly Arg Gly Thr Leu Val Thr Val Ser Ser
        115                 120                 125

<210> SEQ ID NO 257
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Val or Gln
<220> FEATURE:
<221> NAME/KEY: MOD_RES
<222> LOCATION: (5)..(5)
<223> OTHER INFORMATION: Val or Leu
<220> FEATURE:
<221> NAME/KEY: MOD_RES
<222> LOCATION: (24)..(24)
<223> OTHER INFORMATION: Val or Ala
<220> FEATURE:
<221> NAME/KEY: MOD_RES
<222> LOCATION: (48)..(48)
<223> OTHER INFORMATION: Ile or Val
<220> FEATURE:
<221> NAME/KEY: MOD_RES
<222> LOCATION: (49)..(49)
<223> OTHER INFORMATION: Gly or Ser
<220> FEATURE:
<221> NAME/KEY: MOD_RES
<222> LOCATION: (58)..(58)
<223> OTHER INFORMATION: Trp or Phe
<220> FEATURE:
<221> NAME/KEY: MOD_RES
<222> LOCATION: (61)..(61)
<223> OTHER INFORMATION: Asp or Asn
<220> FEATURE:
<221> NAME/KEY: MOD_RES
<222> LOCATION: (62)..(62)
<223> OTHER INFORMATION: Trp, Ser or Phe
<220> FEATURE:
<221> NAME/KEY: MOD_RES
<222> LOCATION: (63)..(63)
<223> OTHER INFORMATION: Ala or Val
<220> FEATURE:
<221> NAME/KEY: MOD_RES
<222> LOCATION: (67)..(67)
<223> OTHER INFORMATION: Ser or Phe
<220> FEATURE:
```

```
<221> NAME/KEY: MOD_RES
<222> LOCATION: (72)..(72)
<223> OTHER INFORMATION: His, Asn or Asp
<220> FEATURE:
<221> NAME/KEY: MOD_RES
<222> LOCATION: (73)..(73)
<223> OTHER INFORMATION: Thr or Asn
<220> FEATURE:
<221> NAME/KEY: MOD_RES
<222> LOCATION: (74)..(74)
<223> OTHER INFORMATION: Ser or Asn
<220> FEATURE:
<221> NAME/KEY: MOD_RES
<222> LOCATION: (75)..(75)
<223> OTHER INFORMATION: Lys or Leu
<220> FEATURE:
<221> NAME/KEY: MOD_RES
<222> LOCATION: (78)..(78)
<223> OTHER INFORMATION: Val or Leu
<220> FEATURE:
<221> NAME/KEY: MOD_RES
<222> LOCATION: (94)..(94)
<223> OTHER INFORMATION: Phe or Tyr
<220> FEATURE:
<221> NAME/KEY: MOD_RES
<222> LOCATION: (117)..(117)
<223> OTHER INFORMATION: Pro or Arg

<400> SEQUENCE: 257

Glu Xaa Gln Leu Xaa Glu Ser Gly Gly Gly Leu Val Gln Pro Gly Gly
1               5                   10                  15

Ser Leu Arg Leu Ser Cys Ala Xaa Ser Gly Phe Ser Leu Asn Asp Tyr
            20                  25                  30

Gly Val Ser Trp Val Arg Gln Ala Pro Gly Lys Gly Leu Glu Trp Xaa
        35                  40                  45

Xaa Ala Ile Gly Ser Ser Gly Val Ala Xaa Tyr Ala Xaa Xaa Xaa Lys
    50                  55                  60

Gly Arg Xaa Thr Ile Ser Arg Xaa Xaa Xaa Xaa Asn Thr Xaa Tyr Leu
65                  70                  75                  80

Gln Met Asn Ser Leu Arg Ala Glu Asp Thr Ala Val Tyr Xaa Cys Ala
                85                  90                  95

Arg Asp Arg Asp Tyr Gly Tyr Arg Ala Asp Asp Ala Thr Ser Gly Met
            100                 105                 110

Asp Leu Trp Gly Xaa Gly Thr Leu Val Thr Val Ser Ser
        115                 120                 125

<210> SEQ ID NO 258
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Gln Glu Gln Leu Glu Glu Ser Gly Gly Gly Leu Val Lys Pro Gly Ala
1               5                   10                  15

Ser Leu Thr Leu Thr Cys Thr Val Ser Gly Phe Ser Leu Thr Asn Asn
            20                  25                  30

Tyr Val Asn Phe Val Met Cys Trp Val Arg Gln Ala Pro Gly Lys Gly
        35                  40                  45

Leu Glu Trp Ile Ala Ser Ile Asp Pro Gly Asp Asp Ser Thr Asp Tyr
    50                  55                  60

Ala Ser Trp Ala Thr Gly Arg Phe Thr Ile Ser Lys Ala Ser Ser Thr
65                  70                  75                  80
```

```
Thr Val Thr Leu Gln Val Thr Ser Leu Thr Ala Ala Asp Thr Ala Thr
                85                  90                  95

Tyr Phe Cys Ala Arg Gly Asp Ala Gly Thr Ser Tyr Ser Phe Asn Phe
            100                 105                 110

Trp Gly Pro Gly Thr Leu Val Thr Val Ser
        115                 120

<210> SEQ ID NO 259
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Gln Glu Gln Leu Val Glu Ser Gly Gly Gly Leu Val Lys Pro Gly Ala
1               5                   10                  15

Ser Leu Thr Leu Thr Cys Thr Ala Ser Gly Phe Ser Leu Thr Asp Asn
            20                  25                  30

Tyr Val Met Ser Trp Val Arg Gln Ala Pro Gly Lys Gly Leu Glu Trp
        35                  40                  45

Ile Ala Cys Ile Asp Pro Gly Asp Ser Thr Tyr Tyr Ala Ser Trp
    50                  55                  60

Ala Thr Gly Arg Phe Thr Ile Ser Arg Ala Ser Ser Thr Thr Val Thr
65                  70                  75                  80

Leu Gln Val Thr Ser Leu Thr Ala Ala Asp Thr Ala Thr Tyr Phe Cys
                85                  90                  95

Ala Arg Gly Asp Ala Ala Ala Ser Tyr Ser Phe Asn Phe Trp Gly Pro
            100                 105                 110

Gly Thr Leu Val Thr Val Ser Ser
        115                 120

<210> SEQ ID NO 260
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Gln Ser Leu Glu Glu Ser Gly Gly Gly Leu Val Lys Pro Gly Gly Thr
1               5                   10                  15

Leu Thr Leu Thr Cys Lys Ala Ser Gly Ile Asp Phe Asn Gly Gly Gly
            20                  25                  30

Ile Tyr Trp Val Arg Gln Ala Pro Gly Lys Gly Leu Glu Trp Ile Ala
        35                  40                  45

Ser Ile Tyr Pro Asp His Gly Ser Val Asp Tyr Ala Asn Trp Val Asn
    50                  55                  60

Gly Arg Phe Thr Ile Ser Leu Asp Asn Ala Gln Asn Thr Val Phe Leu
65                  70                  75                  80

Gln Leu Thr Ser Leu Thr Val Ala Asp Thr Ala Thr Tyr Phe Cys Ala
                85                  90                  95

Arg Glu Ser Gly Gly Ser Tyr Tyr Asp Leu Trp Gly Pro Gly Thr Leu
            100                 105                 110

Val Thr Val Ser Ser
        115
```

<210> SEQ ID NO 261
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Gln Ser Leu Glu Glu Ser Gly Gly Gly Leu Val Lys Pro Gly Gly Thr
1               5                   10                  15

Leu Thr Leu Thr Cys Thr Ala Ser Gly Phe Asp Phe Asn Gly Gly Gly
            20                  25                  30

Ile Tyr Trp Val Arg Gln Ala Pro Gly Lys Gly Leu Glu Trp Ile Ala
        35                  40                  45

Tyr Ile Tyr Pro Asp His Gly Ser Ala Asp Tyr Ala Thr Trp Val Asn
    50                  55                  60

Gly Arg Phe Thr Ile Ser Leu Asp Asn Ala Gln Asn Thr Val Phe Leu
65                  70                  75                  80

Gln Met Thr Ser Leu Thr Val Ala Asp Thr Ala Thr Tyr Phe Cys Ala
                85                  90                  95

Arg Glu Thr Gly Gly Ser Trp Tyr Asp Leu Trp Gly Pro Gly Thr Leu
            100                 105                 110

Val Thr Val Ser Ser
        115

<210> SEQ ID NO 262
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Asp Ile Gln Met Thr Gln Ser Pro Ala Ser Leu Ser Ala Ser Leu Gly
1               5                   10                  15

Glu Thr Val Thr Ile Gln Cys Arg Ala Ser Glu Asp Ile Tyr Ser Gly
            20                  25                  30

Leu Ala Trp Tyr Gln Gln Lys Pro Gly Lys Ser Pro Gln Leu Leu Ile
        35                  40                  45

Tyr Gly Ala Thr Thr Leu His Asp Gly Val Pro Ser Arg Phe Ser Gly
    50                  55                  60

Ser Gly Ser Gly Thr Gln Tyr Ser Leu Lys Ile Ser Ser Met His Ser
65                  70                  75                  80

Glu Asp Glu Gly Ile Tyr Phe Cys His Gln Gly Leu Ser Phe Pro Tyr
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 263
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Asp Ile Gln Met Thr Gln Ser Pro Ala Ser Leu Ser Ala Ser Leu Gly
1               5                   10                  15

Glu Thr Val Thr Ile Glu Cys Leu Ala Ser Lys Asn Ile Tyr Arg Asn
            20                  25                  30

Leu Ala Trp Tyr Gln Gln Lys Pro Gly Lys Ser Pro Gln Phe Leu Ile
        35                  40                  45

Ser Asp Ala Ser Arg Leu Gln Asp Gly Val Pro Ser Arg Phe Thr Gly
    50                  55                  60

Ser Asp Ser Gly Ser Gln Tyr Ser Leu Lys Ile Asn Ser Leu Gln Ser
65                  70                  75                  80

Glu Asp Val Ala Thr Tyr Phe Cys Gln Gln Tyr His Asp Tyr Pro Tyr
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 264
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Asp Val Val Met Thr Gln Thr Ala Ser Pro Val Ser Ala Ala Val Gly
1               5                   10                  15

Gly Thr Val Thr Ile Lys Cys Gln Ala Ser Glu Asn Ile Tyr Ser Leu
            20                  25                  30

```
Leu Ala Trp Tyr Gln Gln Lys Pro Gly Gln Pro Pro Lys Val Leu Ile
                35                  40                  45

Tyr Asp Ala Ser Asp Leu Ala Ser Gly Val Pro Ser Arg Phe Lys Gly
 50                  55                  60

Ser Gly Ser Gly Thr Gln Phe Thr Leu Thr Ile Ser Asp Leu Glu Cys
 65                  70                  75                  80

Ala Asp Ala Ala Thr Tyr Tyr Cys Gln Ala Thr Ala Tyr Gly Ser Ser
                 85                  90                  95

Gly Asn Ala Phe Gly Gly Gly Thr Glu Val Val Lys Arg Ala Asp
                100                 105                 110

Ala Ala Pro Thr Val Ser Ile Phe Pro Pro Ser Ser Glu Gln Leu Thr
                115                 120                 125

Ser Gly Gly Ala Ser Val Val Cys Phe Leu Asn Asn Phe Tyr Pro Lys
        130                 135                 140

Asp Ile Asn Val Lys Trp Lys Ile Asp Gly Ser Glu Arg Gln Asn Gly
145                 150                 155                 160

Val Leu Asn Ser Trp Thr Asp Gln Asp Ser Lys Asp Ser Thr Tyr Ser
                165                 170                 175

Met Ser Ser Thr Leu Thr Leu Thr Lys Asp Glu Tyr Glu Arg His Asn
                180                 185                 190

Ser Tyr Thr Cys Glu Ala Thr His Lys Thr Ser Thr Ser Pro Ile Val
                195                 200                 205

Lys Ser Phe Asn Arg Asn Glu Cys
210                 215

<210> SEQ ID NO 265
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Asp Val Val Met Thr Gln Thr Pro Ala Ser Val Ser Glu Pro Val Gly
 1               5                  10                  15

Gly Thr Val Thr Ile Lys Cys Gln Ala Ser Glu Asn Ile Tyr Ser Leu
                20                  25                  30

Leu Ala Trp Tyr Gln Gln Lys Pro Gly Gln Pro Pro Lys Val Leu Ile
                35                  40                  45

Tyr Asp Ala Ser Asp Leu Ala Ser Gly Val Pro Ser Arg Phe Lys Gly
 50                  55                  60

Ser Gly Ser Gly Thr Gln Phe Thr Leu Thr Ile Ser Asp Leu Glu Cys
 65                  70                  75                  80

Ala Asp Ala Ala Thr Tyr Tyr Cys Gln Ala Thr Ala Tyr Gly Ser Ser
                 85                  90                  95

Gly Asn Ala Phe Gly Gly Gly Thr Glu Val Val Lys Arg Ala Asp
                100                 105                 110

Ala Ala Pro Thr Val Ser Ile Phe Pro Pro Ser Ser Glu Gln Leu Thr
                115                 120                 125

Ser Gly Gly Ala Ser Val Val Cys Phe Leu Asn Asn Phe Tyr Pro Lys
        130                 135                 140

Asp Ile Asn Val Lys Trp Lys Ile Asp Gly Ser Glu Arg Gln Asn Gly
145                 150                 155                 160

Val Leu Asn Ser Trp Thr Asp Gln Asp Ser Lys Asp Ser Thr Tyr Ser
```

```
                    165                 170                 175
Met Ser Ser Thr Leu Thr Leu Thr Lys Asp Glu Tyr Glu Arg His Asn
            180                 185                 190

Ser Tyr Thr Cys Glu Ala Thr His Lys Thr Ser Thr Ser Pro Ile Val
        195                 200                 205

Lys Ser Phe Asn Arg Asn Glu Cys
    210                 215

<210> SEQ ID NO 266
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Asn Ile Val Met Thr Gln Thr Pro Ala Ser Val Glu Val Ala Val Gly
1               5                   10                  15

Gly Thr Val Val Ile Lys Cys Gln Ala Ser Gln Asn Ile Gly Asp Tyr
            20                  25                  30

Leu Ser Trp Tyr Gln Gln Lys Pro Gly Gln Arg Pro Lys Leu Leu Ile
        35                  40                  45

Tyr Ser Ala Ser Thr Leu Ala Ser Gly Val Pro Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys His Gln Asp Tyr Thr Ser Asn Asp
                85                  90                  95

Val Glu Asn Thr Phe Gly Gly Gly Thr Glu Val Val Val Lys Arg Ala
            100                 105                 110

Asp Ala Ala Pro Thr Val Ser Ile Phe Pro Pro Ser Ser Glu Gln Leu
        115                 120                 125

Thr Ser Gly Gly Ala Ser Val Val Cys Phe Leu Asn Asn Phe Tyr Pro
    130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Ile
        195                 200                 205

Val Lys Ser Phe Asn Arg Asn Glu Cys
    210                 215

<210> SEQ ID NO 267
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Ala Tyr Tyr Met Thr Gln Thr Pro Ala Ser Val Glu Val Ala Val Gly
1               5                   10                  15

Gly Thr Val Thr Ile Lys Cys Gln Ala Ser Glu Asp Ile Gly Ser Tyr
```

```
            20                  25                  30
Cys Ser Trp Tyr Gln Gln Lys Pro Gly Gln Pro Pro Lys Leu Leu Ile
        35                  40                  45
Tyr Asp Ala Ser Asp Leu Ala Ser Gly Val Pro Ser Arg Phe Lys Gly
    50                  55                  60
Ser Gly Ser Gly Thr Asp Phe Thr Leu Thr Ile Ser Gly Val Gln Cys
65                  70                  75                  80
Asp Asp Ala Ala Thr Tyr Tyr Cys Gln Gln Asp Tyr Thr Gly Asn Asn
                85                  90                  95
Val Asp Asn Thr Phe Gly Gly Gly Ser Glu Val Val Lys Arg Ala
            100                 105                 110
Asp Ala Ala Pro Thr Val Ser Ile Phe Pro Pro Ser Ser Glu Gln Leu
        115                 120                 125
Thr Ser Gly Gly Ala Ser Val Val Cys Phe Leu Asn Asn Phe Tyr Pro
    130                 135                 140
Lys Asp Ile Asn Val Lys Trp Lys Ile Asp Gly Ser Glu Arg Gln Asn
145                 150                 155                 160
Gly Val Leu Asn Ser Trp Thr Asp Gln Asp Ser Lys Asp Ser Thr Tyr
                165                 170                 175
Ser Met Ser Ser Thr Leu Thr Leu Thr Lys Asp Glu Tyr Glu Arg His
            180                 185                 190
Asn Ser Tyr Thr Cys Glu Ala Thr His Lys Thr Ser Thr Ser Pro Ile
        195                 200                 205
Val Lys Ser Phe Asn Arg Asn Glu Cys
    210                 215

<210> SEQ ID NO 268
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Ala Tyr Asp Met Thr Gln Thr Pro Ala Ser Leu Glu Ala Ala Val Gly
1               5                   10                  15
Gly Thr Val Thr Ile Asn Cys Gln Ala Ser Glu Ser Ile Ser Asn Glu
            20                  25                  30
Leu Ser Trp Tyr Gln Gln Lys Pro Gly Gln Pro Pro Asp Leu Leu Ile
        35                  40                  45
Tyr Tyr Ala Ser Thr Leu Ala Ser Gly Val Pro Ser Arg Phe Lys Gly
    50                  55                  60
Ser Gly Ser Gly Thr Glu Phe Thr Leu Thr Ile Ser Asp Leu Glu Cys
65                  70                  75                  80
Ala Asp Ala Ala Thr Tyr Tyr Cys Ala Gln Gly Phe Gly Ser Ser Gly
                85                  90                  95
Val Glu Asn Val Phe Gly Gly Gly Thr Glu Val Val Val Lys Arg Ala
            100                 105                 110
Asp Ala Ala Pro Thr Val Ser Ile Phe Pro Pro Ser Ser Glu Gln Leu
        115                 120                 125
Thr Ser Gly Gly Ala Ser Val Val Cys Phe Leu Asn Asn Phe Tyr Pro
    130                 135                 140
Lys Asp Ile Asn Val Lys Trp Lys Ile Asp Gly Ser Glu Arg Gln Asn
145                 150                 155                 160
```

```
Gly Val Leu Asn Ser Trp Thr Asp Gln Asp Ser Lys Asp Ser Thr Tyr
            165                 170                 175

Ser Met Ser Ser Thr Leu Thr Leu Thr Lys Asp Glu Tyr Glu Arg His
        180                 185                 190

Asn Ser Tyr Thr Cys Glu Ala Thr His Lys Thr Ser Thr Ser Pro Ile
        195                 200                 205

Val Lys Ser Phe Asn Arg Asn Glu Cys
    210                 215

<210> SEQ ID NO 269
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Ala Ile Arg Met Thr Gln Ser Pro Ser Ser Phe Ser Ala Ser Thr Gly
1               5                   10                  15

Asp Arg Val Thr Ile Thr Cys Gln Ala Ser Glu Ser Ile Ser Asn Glu
            20                  25                  30

Leu Ser Trp Tyr Gln Gln Lys Pro Gly Lys Ala Pro Lys Leu Leu Ile
        35                  40                  45

Tyr Tyr Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Gly Phe Gly Ser Ser Gly
                85                  90                  95

Val Glu Asn Val Phe Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 270
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

Ala Tyr Tyr Met Thr Gln Thr Pro Ala Ser Val Glu Ala Ala Val Gly
1               5                   10                  15
```

```
Gly Thr Val Thr Ile Lys Cys Gln Ala Ser Gln Ser Ile Ser Asn Tyr
            20                  25                  30

Val Ala Trp Tyr Gln Gln Lys Pro Gly Gln Pro Pro Lys Leu Leu Ile
        35                  40                  45

Tyr Arg Ala Ser Thr Leu Ala Ser Gly Val Ser Ser Arg Phe Ser Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys His Gln Gly Tyr Ser Ser Ser Asn
                85                  90                  95

Val Asp Asn Ile Phe Gly Gly Gly Thr Glu Val Val Val Lys Arg Ala
            100                 105                 110

Asp Ala Ala Pro Thr Val Ser Ile Phe Pro Pro Ser Ser Glu Gln Leu
        115                 120                 125

Thr Ser Gly Gly Ala Ser Val Val Cys Phe Leu Asn Asn Phe Tyr Pro
    130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Ile
        195                 200                 205

Val Lys Ser Phe Asn Arg Asn Glu Cys
    210                 215

<210> SEQ ID NO 271
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Ala Tyr Glu Met Thr Gln Thr Pro Ala Ser Val Glu Val Ala Val Gly
1               5                   10                  15

Gly Thr Val Thr Ile Asn Cys Gln Ala Ser Glu Ser Ile Ser Ser Asp
            20                  25                  30

Leu Ala Trp Tyr Gln Gln Lys Pro Gly Gln Arg Pro Lys Leu Leu Ile
        35                  40                  45

Tyr Ala Ala Ser Thr Leu Ala Ser Gly Val Pro Ser Arg Phe Lys Gly
    50                  55                  60

Ser Gly Ser Gly Thr Glu Phe Thr Leu Ser Ile Ser Gly Val Gln Cys
65                  70                  75                  80

Ala Asp Ala Ala Thr Tyr Tyr Cys Gln Gln Gly Tyr Thr Trp Asn Asn
                85                  90                  95

Val Asp Asn Val Phe Gly Gly Gly Thr Glu Val Val Val Lys Arg Ala
            100                 105                 110

Asp Ala Ala Pro Thr Val Ser Ile Phe Pro Pro Ser Ser Glu Gln Leu
        115                 120                 125

Thr Ser Gly Gly Ala Ser Val Val Cys Phe Leu Asn Asn Phe Tyr Pro
    130                 135                 140

Lys Asp Ile Asn Val Lys Trp Lys Ile Asp Gly Ser Glu Arg Gln Asn
145                 150                 155                 160
```

```
Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Ser Thr Ser Pro Ile
        195                 200                 205

Val Lys Ser Phe Asn Arg Asn Glu Cys
    210                 215

<210> SEQ ID NO 272
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Asp Ile Val Met Thr Gln Thr Pro Ala Ser Val Ser Glu Pro Val Gly
1               5                   10                  15

Gly Thr Val Thr Ile Lys Cys Gln Ala Ser Gln Asn Ile Asn Asn Tyr
            20                  25                  30

Leu Ser Trp Tyr Gln Gln Lys Pro Gly Gln Pro Lys Gln Leu Ile
        35                  40                  45

Tyr Ala Ala Ser Thr Leu Ala Ser Gly Val Pro Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys His Gln Asp Tyr Thr Ser Asn Asn
                85                  90                  95

Val Asp Asn Thr Phe Gly Gly Gly Thr Glu Val Val Lys Arg Ala
            100                 105                 110

Asp Ala Ala Pro Thr Val Ser Ile Phe Pro Pro Ser Ser Glu Gln Leu
        115                 120                 125

Thr Ser Gly Gly Ala Ser Val Val Cys Phe Leu Asn Asn Phe Tyr Pro
130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Ser Thr Ser Pro Ile
        195                 200                 205

Val Lys Ser Phe Asn Arg Asn Glu Cys
    210                 215

<210> SEQ ID NO 273
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 273

Asn Ile Val Met Thr Gln Thr Pro Ala Ser Val Glu Val Ala Val Gly
1               5                   10                  15
```

Gly Thr Val Thr Ile Lys Cys Gln Ala Ser Gln Ser Ile Gly Ser Tyr
            20                  25                  30

Leu Ser Trp Tyr Gln Gln Lys Pro Gly Gln Pro Lys Leu Leu Ile
        35                  40                  45

Tyr Asp Ala Ser Asn Leu Ala Ser Gly Val Pro Ser Arg Phe Lys Gly
 50                  55                  60

Ser Gly Ser Gly Thr Gln Phe Thr Leu Ser Ile Ser Asp Leu Glu Cys
65                  70                  75                  80

Ala Asp Ala Ala Thr Tyr Tyr Cys His Gln Asp Tyr Ser Ser Asn Asn
                85                  90                  95

Val Asp Asn Thr Phe Gly Gly Thr Glu Val Val Ile Lys Arg Ala
            100                 105                 110

Asp Ala Ala Pro Thr Val Ser Ile Phe Pro Pro Ser Ser Glu Gln Leu
            115                 120                 125

Thr Ser Gly Gly Ala Ser Val Val Cys Phe Leu Asn Asn Phe Tyr Pro
130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Ile
        195                 200                 205

Val Lys Ser Phe Asn Arg Asn Glu Cys
        210                 215

<210> SEQ ID NO 274
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

Asn Ile Val Met Thr Gln Thr Pro Ala Ser Val Glu Ala Ala Val Gly
1               5                   10                  15

Gly Thr Val Thr Ile Asn Cys Gln Ala Ser Gln Ser Ile Ser Ser Tyr
            20                  25                  30

Leu Ser Trp Tyr Gln Gln Lys Ser Gly Gln Arg Pro Lys Leu Leu Ile
        35                  40                  45

Phe Ser Ala Ser Thr Leu Ala Ser Gly Val Pro Ser Arg Phe Thr Gly
 50                  55                  60

Ser Gly Ser Gly Thr Gln Phe Thr Leu Thr Ile Ser Asp Leu Gln Cys
65                  70                  75                  80

Ala Asp Ala Ala Thr Tyr Tyr Cys His Gln Asp Tyr Thr Ser Ser Asn
                85                  90                  95

Val Asp Asn Thr Phe Gly Gly Gly Thr Glu Val Val Val Lys Arg Ala
            100                 105                 110

Asp Ala Ala Pro Thr Val Ser Ile Phe Pro Pro Ser Ser Glu Gln Leu
            115                 120                 125

Thr Ser Gly Gly Ala Ser Val Val Cys Phe Leu Asn Asn Phe Tyr Pro
130                 135                 140

Lys Asp Ile Asn Val Lys Trp Lys Ile Asp Gly Ser Glu Arg Gln Asn 145                 150                 155                 160
Gly Val Leu Asn Ser Trp Thr Asp Gln Asp Ser Lys Asp Ser Thr Tyr
                    165                 170                 175

Ser Met Ser Ser Thr Leu Thr Leu Thr Lys Asp Glu Tyr Glu Arg His
                180                 185                 190

Asn Ser Tyr Thr Cys Glu Ala Thr His Lys Thr Ser Thr Ser Pro Ile
            195                 200                 205

Val Lys Ser Phe Asn Arg Asn Glu Cys
        210                 215

<210> SEQ ID NO 275
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Tyr
            20                  25                  30

Leu Ser Trp Tyr Gln Gln Lys Pro Gly Lys Ala Pro Lys Leu Leu Ile
        35                  40                  45

Tyr Ser Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Asp Tyr Thr Ser Ser Asn
                85                  90                  95

Val Asp Asn Thr Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 276
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Asn Ile Val Met Thr Gln Thr Pro Ala Ser Val Glu Val Ala Val Gly

```
                1               5                   10                  15
Gly Thr Val Ile Ile Lys Cys Gln Ala Ser Gln Ser Ile Ser Asn Tyr
                20                  25                  30

Leu Ser Trp Tyr His Gln Lys Ser Gly Gln Arg Pro Arg Leu Leu Ile
            35                  40                  45

Tyr Ser Ala Ser Thr Leu Ala Ser Gly Val Pro Ser Arg Phe Lys Gly
        50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys His Gln Asp Tyr Thr Ser Asn Ser
                85                  90                  95

Val Asp Asn Thr Phe Gly Gly Gly Thr Glu Val Val Lys Arg Ala
            100                 105                 110

Asp Ala Ala Pro Thr Val Ser Ile Phe Pro Pro Ser Ser Glu Gln Leu
        115                 120                 125

Thr Ser Gly Gly Ala Ser Val Val Cys Phe Leu Asn Asn Phe Tyr Pro
    130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Ile
        195                 200                 205

Val Lys Ser Phe Asn Arg Asn Glu Cys
    210                 215
```

<210> SEQ ID NO 277
<211> LENGTH: 217
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 277

```
Asn Ile Val Met Thr Gln Thr Pro Ala Ser Val Glu Val Ala Met Gly
1               5                   10                  15

Gly Thr Val Ile Ile Lys Cys Gln Ala Ser Gln Ser Ile Ser Thr Tyr
                20                  25                  30

Leu Ser Trp Tyr Gln Gln Lys Pro Gly Gln Pro Pro Lys Leu Leu Ile
            35                  40                  45

Tyr Ser Ala Ser Thr Leu Ala Ser Gly Val Ser Ser Arg Phe Glu Gly
        50                  55                  60

Ser Gly Ser Gly Thr Gln Phe Thr Leu Thr Ile Ser Gly Val Gln Cys
65                  70                  75                  80

Ala Asp Ala Ala Thr Tyr Tyr Cys His Gln Asp Tyr Thr Ser Asn Asn
                85                  90                  95

Val Asp Asn Thr Phe Gly Gly Gly Thr Glu Val Val Val Lys Arg Ala
            100                 105                 110

Asp Ala Ala Pro Thr Val Ser Ile Phe Pro Pro Ser Ser Glu Gln Leu
        115                 120                 125

Thr Ser Gly Gly Ala Ser Val Val Cys Phe Leu Asn Asn Phe Tyr Pro
    130                 135                 140
```

```
Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Ile
        195                 200                 205

Val Lys Ser Phe Asn Arg Asn Glu Cys
    210                 215

<210> SEQ ID NO 278
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

Ala Tyr Asp Leu Thr Gln Thr Pro Ala Ser Val Glu Ala Ala Val Gly
1               5                   10                  15

Gly Thr Val Thr Ile Asn Cys Gln Ala Ser Glu Ser Ile Gly Asn Glu
                20                  25                  30

Leu Ser Trp Tyr Gln Lys Ser Gly Gln Pro Pro Lys Leu Leu Ile
            35                  40                  45

Tyr Gln Ala Ser Thr Leu Ala Ser Gly Val Pro Ser Arg Phe Lys Gly
    50                  55                  60

Ser Gly Ser Gly Thr Asp Phe Thr Leu Thr Ile Ser Asp Leu Glu Cys
65                  70                  75                  80

Ala Asp Ala Ala Thr Tyr Tyr Cys Ala Gln Gly Phe Ser Ser Ser Gly
                85                  90                  95

Val Glu Asn Val Phe Gly Gly Gly Thr Glu Val Val Val Lys Arg Ala
            100                 105                 110

Asp Ala Ala Pro Thr Val Ser Ile Phe Pro Pro Ser Ser Glu Gln Leu
        115                 120                 125

Thr Ser Gly Gly Ala Ser Val Val Cys Phe Leu Asn Asn Phe Tyr Pro
130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Ile
        195                 200                 205

Val Lys Ser Phe Asn Arg Asn Glu Cys
    210                 215

<210> SEQ ID NO 279
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 279
```

-continued

Ala Tyr Asp Met Thr Gln Thr Pro Ala Ser Val Glu Ala Val Gly
1               5                   10                  15

Gly Thr Val Thr Ile Lys Cys Gln Ala Ser Glu Ser Ile Gly Asn Ala
            20                  25                  30

Leu Ala Trp Tyr Gln Gln Lys Pro Gly Gln Pro Pro Lys Leu Leu Ile
        35                  40                  45

Tyr Asp Ala Ser Asp Leu Ala Ser Gly Val Pro Ser Arg Phe Lys Gly
    50                  55                  60

Ser Gly Ser Gly Thr Gln Phe Thr Leu Thr Ile Ser Gly Val Glu Cys
65                  70                  75                  80

Ala Asp Ala Ala Thr Tyr Tyr Cys Gln Gln Gly Asp Ser His Asn Asn
            85                  90                  95

Val Asp Asn Ile Phe Gly Gly Gly Thr Glu Val Val Val Lys Arg Ala
            100                 105                 110

Asp Ala Ala Pro Thr Val Ser Ile Phe Pro Pro Ser Glu Gln Leu
            115                 120                 125

Thr Ser Gly Gly Ala Ser Val Val Cys Phe Leu Asn Asn Phe Tyr Pro
    130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Ile
        195                 200                 205

Val Lys Ser Phe Asn Arg Asn Glu Cys
    210                 215

<210> SEQ ID NO 280
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 280

Ala Ile Arg Met Thr Gln Ser Pro Ser Ser Phe Ser Ala Ser Thr Gly
1               5                   10                  15

Asp Arg Val Thr Ile Thr Cys Gln Ala Ser Glu Ser Ile Gly Asn Ala
            20                  25                  30

Leu Ala Trp Tyr Gln Gln Lys Pro Gly Lys Ala Pro Lys Leu Leu Ile
        35                  40                  45

Tyr Asp Ala Ser Asp Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Ser His Asn Asn
            85                  90                  95

Val Asp Asn Ile Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 281
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 281

Ala Ile Glu Met Thr Gln Thr Pro Ser Ser Ala Ser Glu Pro Val Gly
1               5                   10                  15

Gly Thr Val Thr Ile Lys Cys Gln Ala Ser Glu Ser Ile Ser Arg Tyr
            20                  25                  30

Leu Ser Trp Tyr Gln Gln Lys Pro Gly Gln Pro Lys Leu Leu Ile
        35                  40                  45

Tyr Asp Ala Ser Asp Leu Ala Ser Gly Val Ser Ser Arg Phe Lys Gly
    50                  55                  60

Ser Gly Ser Gly Thr Gln Phe Thr Leu Ile Ile Ser Asp Val Glu Cys
65                  70                  75                  80

Ala Asp Ala Ala Thr Tyr Tyr Cys Gln Gln Asp Tyr Ser Arg Ser Asn
                85                  90                  95

Ile Val Asn Ser Phe Gly Gly Thr Glu Val Val Val Lys Arg Ala
            100                 105                 110

Asp Ala Ala Pro Thr Val Ser Ile Phe Pro Pro Ser Ser Glu Gln Leu
        115                 120                 125

Thr Ser Gly Gly Ala Ser Val Val Cys Phe Leu Asn Asn Phe Tyr Pro
130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Ile
        195                 200                 205

Val Lys Ser Phe Asn Arg Asn Glu Cys
    210                 215

<210> SEQ ID NO 282
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

```
Ala Tyr Asp Met Thr Gln Thr Pro Ser Ser Ala Ser Glu Pro Val Gly
1               5                   10                  15

Gly Thr Val Thr Ile Lys Cys Gln Ala Ser Glu Ser Ile Ser Thr Tyr
            20                  25                  30

Leu Ser Trp Tyr Gln Gln Lys Pro Gly Gln Pro Pro Lys Leu Leu Ile
        35                  40                  45

Tyr Asp Ala Ser Asp Leu Ala Ser Gly Val Ser Ser Arg Phe Lys Gly
50                  55                  60

Ser Gly Ser Gly Thr Gln Phe Thr Leu Thr Ile Ser Asp Val Glu Cys
65                  70                  75                  80

Ala Asp Ala Ala Thr Tyr Tyr Cys Gln Gln Asp Tyr Ser Ser Ser Asn
                85                  90                  95

Ile Val Asn Ser Phe Gly Gly Gly Thr Glu Val Val Lys Arg Ala
                100                 105                 110

Asp Ala Ala Pro Thr Val Ser Ile Phe Pro Pro Ser Ser Glu Gln Leu
            115                 120                 125

Thr Ser Gly Gly Ala Ser Val Val Cys Phe Leu Asn Asn Phe Tyr Pro
    130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
                180                 185                 190

Asn Ser Tyr Thr Cys Glu Ala Thr His Lys Thr Ser Thr Ser Pro Ile
            195                 200                 205

Val Lys Ser Phe Asn Arg Asn Glu Cys
        210                 215

<210> SEQ ID NO 283
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 283

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Ser Thr Tyr
            20                  25                  30

Leu Ala Trp Tyr Gln Gln Lys Pro Gly Gln Arg Pro Asn Leu Leu Ile
        35                  40                  45

Tyr Lys Thr Ser Thr Leu Ala Ser Gly Val Pro Ser Arg Phe Arg Gly
50                  55                  60

Ser Gly Ser Gly Thr Gln Phe Thr Leu Thr Ile Ser Gly Val Glu Cys
65                  70                  75                  80

Ala Asp Ala Ala Thr Tyr Tyr Cys Gln Gln Gly Tyr Ser Gly Ser Ser
                85                  90                  95

Val Glu Asn Thr Phe Gly Gly Gly Thr Glu Val Val Lys Arg Ala
                100                 105                 110

Asp Ala Ala Pro Thr Val Ser Ile Phe Pro Pro Ser Ser Glu Gln Leu
            115                 120                 125

Thr Ser Gly Gly Ala Ser Val Val Cys Phe Leu Asn Asn Phe Tyr Pro
```

```
            130                 135                 140
Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
                180                 185                 190

Asn Ser Tyr Thr Cys Glu Ala Thr His Lys Thr Ser Thr Ser Pro Ile
                195                 200                 205

Val Lys Ser Phe Asn Arg Asn Glu Cys
            210                 215

<210> SEQ ID NO 284
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

Ala Tyr Asp Met Thr Gln Thr Pro Val Ser Val Glu Ala Ala Val Gly
1               5                   10                  15

Gly Thr Val Thr Ile Lys Cys Gln Ala Ser Gln Ser Ile Ser Ser Tyr
                20                  25                  30

Leu Ala Trp Tyr Gln Gln Lys Pro Gly Gln Pro Pro Lys Leu Leu Ile
            35                  40                  45

Tyr Lys Ala Ser Thr Leu Ala Ser Gly Val Ser Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Gln Gly Tyr Ser Gly Ser Asn
                85                  90                  95

Val Glu Asn Thr Phe Gly Gly Gly Thr Glu Val Val Val Lys Arg Ala
                100                 105                 110

Asp Ala Ala Pro Thr Val Ser Ile Phe Pro Pro Ser Ser Glu Gln Leu
            115                 120                 125

Thr Ser Gly Gly Ala Ser Val Val Cys Phe Leu Asn Asn Phe Tyr Pro
        130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
                180                 185                 190

Asn Ser Tyr Thr Cys Glu Ala Thr His Lys Thr Ser Thr Ser Pro Ile
                195                 200                 205

Val Lys Ser Phe Asn Arg Asn Glu Cys
            210                 215

<210> SEQ ID NO 285
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 285

Glu Val Gln Leu Val Glu Ser Gly Gly Gly Leu Val Gln Pro Gly Arg
1               5                   10                  15

Ser Leu Lys Leu Ser Cys Thr Ala Ser Gly Phe Thr Phe Ser Asp Tyr
            20                  25                  30

Asn Met Ala Trp Val Arg Gln Ala Pro Lys Gly Gly Leu Glu Trp Val
        35                  40                  45

Thr Thr Ile Ser Tyr Asp Ala Gly Arg Thr Tyr Tyr Arg Asp Ser Val
    50                  55                  60

Lys Gly Arg Phe Thr Ile Ser Arg Asp Asn Ala Lys Arg Thr Leu Ser
65                  70                  75                  80

Leu Gln Met Asp Ser Leu Arg Ser Glu Asp Thr Ala Thr Tyr Tyr Cys
                85                  90                  95

Ala Thr Gly Ile Phe Asn Tyr Gly Thr Asp Tyr Phe Asp Tyr Trp Gly
            100                 105                 110

Gln Gly Val Met Val Thr Val Ser Ser Ala Ser Thr Lys Gly Pro Ser
        115                 120                 125

Val Tyr Pro Leu Ala Pro Val Cys Gly Asp Thr Thr Gly Ser Ser Val
    130                 135                 140

Thr Leu Gly Cys Leu Val Lys Gly Tyr Phe Pro Glu Pro Val Thr Leu
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Thr
            180                 185                 190

Ser Ser Thr Trp Pro Ser Gln Ser Ile Thr Cys Asn Val Ala His Pro
        195                 200                 205

Ala Ser Ser Thr Lys Val Asp Lys Lys Ile Glu Pro Arg Gly Pro Thr
    210                 215                 220

Ile Lys Pro Cys Pro Pro Cys Lys Cys Pro Ala Pro Asn Leu Leu Gly
225                 230                 235                 240

Gly Pro Ser Val Phe Ile Phe Pro Pro Lys Ile Lys Asp Val Leu Met
                245                 250                 255

Ile Ser Leu Ser Pro Ile Val Thr Cys Val Val Asp Val Ser Glu
            260                 265                 270

Asp Asp Pro Asp Val Gln Ile Ser Trp Phe Val Asn Asn Val Glu Val
        275                 280                 285

His Thr Ala Gln Thr Gln Thr His Arg Glu Asp Tyr Asn Ser Thr Leu
    290                 295                 300

Arg Val Val Ser Ala Leu Pro Ile Gln His Gln Asp Trp Met Ser Gly
305                 310                 315                 320

Lys Glu Phe Lys Cys Lys Val Asn Asn Lys Asp Leu Pro Ala Pro Ile
                325                 330                 335

Glu Arg Thr Ile Ser Lys Pro Lys Gly Ser Val Arg Ala Pro Gln Val
            340                 345                 350

Tyr Val Leu Pro Pro Pro Glu Glu Glu Met Thr Lys Lys Gln Val Thr
        355                 360                 365

Leu Thr Cys Met Val Thr Asp Phe Met Pro Glu Asp Ile Tyr Val Glu
    370                 375                 380

Trp Thr Asn Asn Gly Lys Thr Glu Leu Asn Tyr Lys Asn Thr Glu Pro
385                 390                 395                 400

Val Leu Asp Ser Asp Gly Ser Tyr Phe Met Tyr Ser Lys Leu Arg Val
                405                 410                 415
```

```
Glu Lys Lys Asn Trp Val Glu Arg Asn Ser Tyr Ser Cys Ser Val Val
                420                 425                 430

His Glu Gly Leu His Asn His Thr Thr Lys Ser Phe Ser Arg Thr
            435                 440                 445

Pro Gly Lys
    450

<210> SEQ ID NO 286
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 286

Glu Val Gln Leu Val Glu Ser Gly Gly Gly Leu Val Arg Pro Gly Arg
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Thr Lys Gly Leu Glu Trp Val
        35                  40                  45

Ala Ser Ile Ser Tyr Asp Gly Asp Thr Thr Tyr Tyr Arg Asp Ser Val
    50                  55                  60

Lys Gly Arg Phe Thr Ile Ser Arg Asp Asn Ala Arg Ser Ser Leu Tyr
65                  70                  75                  80

Leu Gln Met Asp Ser Leu Arg Ser Asp Asp Thr Ala Asn Tyr Phe Cys
                85                  90                  95

Thr Thr Asp Gly Thr Ile Pro Ala Gly Ser Trp Phe Ala Tyr Trp Gly
            100                 105                 110

Gln Gly Thr Leu Val Thr Val Ser Ser Ala Ser Thr Lys Gly Pro Ser
        115                 120                 125

Val Tyr Pro Leu Ala Pro Val Cys Gly Asp Thr Thr Gly Ser Ser Val
    130                 135                 140

Thr Leu Gly Cys Leu Val Lys Gly Tyr Phe Pro Glu Pro Val Thr Leu
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Thr
            180                 185                 190

Ser Ser Thr Trp Pro Ser Gln Ser Ile Thr Cys Asn Val Ala His Pro
        195                 200                 205

Ala Ser Ser Thr Lys Val Asp Lys Lys Ile Glu Pro Arg Gly Pro Thr
    210                 215                 220

Ile Lys Pro Cys Pro Pro Cys Lys Cys Pro Ala Pro Asn Leu Leu Gly
225                 230                 235                 240

Gly Pro Ser Val Phe Ile Phe Pro Pro Lys Ile Lys Asp Val Leu Met
                245                 250                 255

Ile Ser Leu Ser Pro Ile Val Thr Cys Val Val Val Asp Val Ser Glu
            260                 265                 270

Asp Asp Pro Asp Val Gln Ile Ser Trp Phe Val Asn Asn Val Glu Val
        275                 280                 285

His Thr Ala Gln Thr Gln Thr His Arg Glu Asp Tyr Asn Ser Thr Leu
    290                 295                 300

Arg Val Val Ser Ala Leu Pro Ile Gln His Gln Asp Trp Met Ser Gly
```

```
            305                 310                 315                 320
Lys Glu Phe Lys Cys Lys Val Asn Asn Lys Asp Leu Pro Ala Pro Ile
                325                 330                 335

Glu Arg Thr Ile Ser Lys Pro Lys Gly Ser Val Arg Ala Pro Gln Val
                340                 345                 350

Tyr Val Leu Pro Pro Glu Glu Met Thr Lys Lys Gln Val Thr
                355                 360                 365

Leu Thr Cys Met Val Thr Asp Phe Met Pro Glu Asp Ile Tyr Val Glu
                370                 375                 380

Trp Thr Asn Asn Gly Lys Thr Glu Leu Asn Tyr Lys Asn Thr Glu Pro
385                 390                 395                 400

Val Leu Asp Ser Asp Gly Ser Tyr Phe Met Tyr Ser Lys Leu Arg Val
                405                 410                 415

Glu Lys Lys Asn Trp Val Glu Arg Asn Ser Tyr Ser Cys Ser Val Val
                420                 425                 430

His Glu Gly Leu His Asn His His Thr Thr Lys Ser Phe Ser Arg Thr
                435                 440                 445

Pro Gly Lys
      450

<210> SEQ ID NO 287
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 287

Gln Glu Gln Leu Glu Glu Ser Gly Gly Asp Leu Val Lys Pro Glu Gly
1               5                   10                  15

Ser Leu Thr Leu Thr Cys Thr Ala Ser Gly Phe Ser Phe Ser Ser Ser
                20                  25                  30

Tyr Trp Ile Cys Trp Val Arg Gln Ala Pro Gly Lys Gly Leu Glu Trp
                35                  40                  45

Ile Ala Cys Val Tyr Gly Leu Asp Val Asn Ile Tyr Tyr Ala Ser Trp
50                  55                  60

Thr Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Gly Gly Gly Ser Ala Asp Phe Gly Phe Asp Leu Trp Gly Pro
                100                 105                 110

Gly Thr Leu Val Thr Val Ser Ser Ala Ser Thr Lys Gly Pro Ser Val
                115                 120                 125

Tyr Pro Leu Ala Pro Val Cys Gly Asp Thr Thr Gly Ser Ser Val Thr
130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
                180                 185                 190

Ser Thr Trp Pro Ser Gln Ser Ile Thr Cys Asn Val Ala His Pro Ala
                195                 200                 205
```

```
Ser Ser Thr Lys Val Asp Lys Lys Ile Glu Pro Arg Gly Pro Thr Ile
    210                 215                 220

Lys Pro Cys Pro Pro Cys Lys Cys Pro Ala Pro Asn Leu Leu Gly Gly
225                 230                 235                 240

Pro Ser Val Phe Ile Phe Pro Pro Lys Ile Lys Asp Val Leu Met Ile
                245                 250                 255

Ser Leu Ser Pro Ile Val Thr Cys Val Val Asp Val Ser Glu Asp
    260                 265                 270

Asp Pro Asp Val Gln Ile Ser Trp Phe Val Asn Asn Val Glu Val His
        275                 280                 285

Thr Ala Gln Thr Gln Thr His Arg Glu Asp Tyr Asn Ser Thr Leu Arg
    290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Asp Leu Pro Ala Pro Ile Glu
                325                 330                 335

Arg Thr Ile Ser Lys Pro Lys Gly Ser Val Arg Ala Pro Gln Val Tyr
            340                 345                 350

Val Leu Pro Pro Pro Glu Glu Glu Met Thr Lys Lys Gln Val Thr Leu
        355                 360                 365

Thr Cys Met Val Thr Asp Phe Met Pro Glu Asp Ile Tyr Val Glu Trp
370                 375                 380

Thr Asn Asn Gly Lys Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
        435                 440                 445

Gly Lys
    450

<210> SEQ ID NO 288
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 288

Gln Ser Leu Glu Glu Ser Gly Gly Asp Leu Val Lys Pro Glu Gly Ser
1               5                   10                  15

Leu Thr Leu Thr Cys Thr Ala Ser Gly Phe Ser Phe Ser Thr Ser Tyr
            20                  25                  30

Trp Ile Cys Trp Val Arg Gln Ala Pro Gly Lys Gly Leu Glu Trp Ile
        35                  40                  45

Ala Cys Val Tyr Gly Leu Asp Val Asn Ile Tyr Tyr Ala Ser Trp Thr
    50                  55                  60

Glu Gly Arg Phe Thr Ile Ser Lys Thr Ser Thr Thr Val Thr Leu
65                  70                  75                  80

Gln Val Thr Ser Leu Thr Ala Ala Asp Thr Ala Thr Tyr Phe Cys Ala
                85                  90                  95

Arg Gly Gly Gly Ser Ala Asp Phe Gly Phe Asp Leu Trp Gly Pro Gly
            100                 105                 110
```

```
Thr Leu Val Thr Val Ser Ser Ala Ser Thr Lys Gly Pro Ser Val Tyr
            115                 120                 125

Pro Leu Ala Pro Val Cys Gly Asp Thr Thr Gly Ser Ser Val Thr Leu
        130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Val Thr Val Thr Ser Ser
            180                 185                 190

Thr Trp Pro Ser Gln Ser Ile Thr Cys Asn Val Ala His Pro Ala Ser
            195                 200                 205

Ser Thr Lys Val Asp Lys Lys Ile Glu Pro Arg Gly Pro Thr Ile Lys
        210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
        275                 280                 285

Ala Gln Thr Gln Thr His Arg Glu Asp Tyr Asn Ser Thr Leu Arg Val
        290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Tyr Val
            340                 345                 350

Leu Pro Pro Pro Glu Glu Met Thr Lys Lys Gln Val Thr Leu Thr
        355                 360                 365

Cys Met Val Thr Asp Phe Met Pro Glu Asp Ile Tyr Val Glu Trp Thr
    370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val Val His Glu
            420                 425                 430

Gly Leu His Asn His His Thr Thr Lys Ser Phe Ser Arg Thr Pro Gly
        435                 440                 445

Lys

<210> SEQ ID NO 289
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

Gln Ser Val Lys Glu Ser Glu Gly Gly Leu Phe Lys Pro Thr Asp Asn
1               5                   10                  15
```

-continued

```
Leu Thr Leu Thr Cys Thr Val Ser Gly Phe Ser Leu Ser Asn Tyr Gly
            20                  25                  30

Val Thr Trp Val Arg Gln Ala Pro Gly Asn Gly Leu Glu Tyr Ile Gly
        35                  40                  45

Phe Ile Gly Ser Gly Gly Ser Ala Tyr Tyr Ala Ser Trp Ala Lys Ser
 50                  55                  60

Arg Ser Thr Ile Thr Arg Asn Thr Asn Leu Asn Thr Val Thr Leu Lys
 65                  70                  75                  80

Met Thr Ser Leu Thr Ala Ala Asp Thr Ala Thr Tyr Phe Cys Ala Arg
                 85                  90                  95

Asp Asp Val Gly Gly Lys Ser Leu Asp Ile Trp Gly Pro Gly Thr
            100                 105                 110

Leu Val Thr Val Ser Ser Ala Ser Thr Lys Gly Pro Ser Val Tyr Pro
        115                 120                 125

Leu Ala Pro Val Cys Gly Asp Thr Thr Gly Ser Ser Val Thr Leu Gly
130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Thr Ser Ser Thr
            180                 185                 190

Trp Pro Ser Gln Ser Ile Thr Cys Asn Val Ala His Pro Ala Ser Ser
        195                 200                 205

Thr Lys Val Asp Lys Lys Ile Glu Pro Arg Gly Pro Thr Ile Lys Pro
210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Asp Val Ser Glu Asp Asp Pro
            260                 265                 270

Asp Val Gln Ile Ser Trp Phe Val Asn Asn Val Glu Val His Thr Ala
        275                 280                 285

Gln Thr Gln Thr His Arg Glu Asp Tyr Asn Ser Thr Leu Arg Val Val
290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
            340                 345                 350

Pro Pro Pro Glu Glu Glu Met Thr Lys Lys Gln Val Thr Leu Thr Cys
        355                 360                 365

Met Val Thr Asp Phe Met Pro Glu Asp Ile Tyr Val Glu Trp Thr Asn
370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
            420                 425                 430
```

Leu His Asn His His Thr Thr Lys Ser Phe Ser Arg Thr Pro Gly Lys
         435                 440                 445

<210> SEQ ID NO 290
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 290

Gln Ser Val Glu Glu Ser Arg Gly Gly Leu Ile Lys Pro Thr Asp Thr
1               5                   10                  15

Leu Thr Leu Thr Cys Thr Ala Ser Gly Phe Ser Leu Ser Asn Tyr Gly
            20                  25                  30

Val Ser Trp Val Arg Gln Ala Pro Gly Asn Gly Leu Glu Tyr Ile Gly
        35                  40                  45

Phe Ile Gly Tyr Gly Gly Ser Thr Tyr Tyr Ala Ser Trp Ala Lys Ser
    50                  55                  60

Arg Ser Thr Ile Thr Arg Asn Thr Asn Leu Asn Thr Val Thr Leu Gln
65                  70                  75                  80

Met Thr Ser Leu Thr Ala Ala Asp Thr Ala Thr Tyr Phe Cys Ala Arg
                85                  90                  95

Leu Cys Gly Val Asp Cys Ala Asp Ala Leu Asp Ser Trp Gly Pro Gly
            100                 105                 110

Thr Leu Val Thr Val Ser Ser Ala Ser Thr Lys Gly Pro Ser Val Tyr
        115                 120                 125

Pro Leu Ala Pro Val Cys Gly Asp Thr Thr Gly Ser Ser Val Thr Leu
130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Gly Pro Thr Ile Lys
210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Asp Val Ser Glu Asp Asp
            260                 265                 270

Pro Asp Val Gln Ile Ser Trp Phe Val Asn Asn Val Glu Val His Thr
        275                 280                 285

Ala Gln Thr Gln Thr His Arg Glu Asp Tyr Asn Ser Thr Leu Arg Val
    290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Tyr Val
            340                 345                 350

```
Leu Pro Pro Pro Glu Glu Glu Met Thr Lys Lys Gln Val Thr Leu Thr
            355                 360                 365

Cys Met Val Thr Asp Phe Met Pro Glu Asp Ile Tyr Val Glu Trp Thr
        370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val Val His Glu
            420                 425                 430

Gly Leu His Asn His His Thr Thr Lys Ser Phe Ser Arg Thr Pro Gly
        435                 440                 445

Lys

<210> SEQ ID NO 291
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Gln Ser Leu Glu Glu Ser Gly Gly Gly Leu Val Lys Pro Thr Asp Thr
1               5                   10                  15

Leu Thr Leu Thr Cys Thr Val Ser Gly Phe Ser Leu Ser Ser Tyr Gly
            20                  25                  30

Val Thr Trp Val Arg Gln Ala Pro Gly Arg Gly Leu Glu Trp Ile Gly
        35                  40                  45

Tyr Ile Thr Ser Asn Tyr Gly Val Ser Tyr Tyr Ala Ser Trp Ala Lys
    50                  55                  60

Ser Arg Ser Thr Ile Thr Arg Asn Thr Asn Leu Asn Thr Val Thr Leu
65                  70                  75                  80

Lys Met Thr Ser Leu Thr Ala Ala Asp Thr Ala Thr Tyr Phe Cys Ala
                85                  90                  95

Arg Glu Asn Pro Asp Tyr Gly Tyr Ala Tyr Asp Ala Trp Gly Pro Gly
            100                 105                 110

Thr Leu Val Thr Val Ser Ser Ala Ser Thr Lys Gly Pro Ser Val Tyr
        115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Gly Pro Thr Ile Lys
    210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255
```

Leu Ser Pro Ile Val Thr Cys Val Val Val Asp Val Ser Glu Asp Asp
             260                 265                 270

Pro Asp Val Gln Ile Ser Trp Phe Val Asn Asn Val Glu Val His Thr
             275                 280                 285

Ala Gln Thr Gln Thr His Arg Glu Asp Tyr Asn Ser Thr Leu Arg Val
         290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                 325                 330                 335

Thr Ile Ser Lys Pro Lys Gly Ser Val Arg Ala Pro Gln Val Tyr Val
             340                 345                 350

Leu Pro Pro Pro Glu Glu Glu Met Thr Lys Lys Gln Val Thr Leu Thr
             355                 360                 365

Cys Met Val Thr Asp Phe Met Pro Glu Asp Ile Tyr Val Glu Trp Thr
370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                 405                 410                 415

Lys Asn Trp Val Glu Arg Asn Ser Tyr Ser Cys Ser Val Val His Glu
             420                 425                 430

Gly Leu His Asn His His Thr Thr Lys Ser Phe Ser Arg Thr Pro Gly
             435                 440                 445

Lys

<210> SEQ ID NO 292
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Gly Val Thr Trp Val Arg Gln Ala Pro Gly Lys Gly Leu Glu Trp Ile
        35                  40                  45

Gly Tyr Ile Thr Ser Asn Tyr Gly Val Ser Tyr Tyr Ala Ser Trp Ala
    50                  55                  60

Lys Ser Arg Ser Thr Ile Ser Arg Asp Thr Ser Lys Asn Thr Val Tyr
65                  70                  75                  80

Leu Gln Met Gly Ser Leu Arg Ala Glu Asp Met Ala Val Tyr Tyr Cys
                85                  90                  95

Ala Arg Glu Asn Pro Asp Tyr Gly Tyr Ala Tyr Asp Ala Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

-continued

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Gly Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 293
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 293

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Gly Val Thr Trp Val Arg Gln Ala Pro Gly Lys Gly Leu Glu Trp Ile
        35                  40                  45

Gly Tyr Ile Thr Ser Asn Tyr Gly Val Ser Tyr Tyr Ala Ser Trp Ala
```

```
            50                  55                  60
Lys Ser Arg Ser Thr Ile Ser Arg Asp Thr Ser Lys Asn Thr Val Tyr
 65                  70                  75                  80

Leu Gln Met Gly Ser Leu Arg Ala Glu Asp Met Ala Val Tyr Tyr Cys
                 85                  90                  95

Ala Arg Glu Asn Pro Asp Tyr Gly Tyr Ala Tyr Asp Ala Trp Gly Gln
                100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 294
<211> LENGTH: 450
<212> TYPE: PRT
<213> ORGANISM: Artificial Sequence
```

-continued

```
<220> FEATURE:
<223> OTHER INFORMATION: Description of Artificial Sequence: Synthetic
      polypeptide

<400> SEQUENCE: 294

Gln Ser Val Lys Glu Ser Glu Gly Gly Leu Phe Lys Pro Thr Asp Thr
1               5                   10                  15

Leu Thr Leu Thr Cys Thr Val Ser Gly Phe Ser Leu Ile Asn Tyr Gly
            20                  25                  30

Val Ser Trp Val Arg Gln Ala Pro Gly Lys Gly Leu Glu Trp Ile Gly
        35                  40                  45

Tyr Ile Gly Ser Ala Gly Ser Thr Tyr Tyr Ala Thr Trp Ala Lys Ser
    50                  55                  60

Arg Ala Thr Ile Thr Arg Asn Thr Asn Leu Asn Thr Val Thr Leu Lys
65                  70                  75                  80

Met Thr Ser Leu Thr Ala Ala Asp Thr Ala Thr Tyr Phe Cys Ala Arg
                85                  90                  95

Ala Ala Tyr Ser Ala Gly Ser Ala Asp Ala Glu Asp Ile Trp Gly Pro
            100                 105                 110

Gly Thr Leu Val Thr Val Ser Ser Ala Ser Thr Lys Gly Pro Ser Val
        115                 120                 125

Tyr Pro Leu Ala Pro Val Cys Gly Asp Thr Thr Gly Ser Ser Val Thr
    130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
            180                 185                 190

Ser Thr Trp Pro Ser Gln Ser Ile Thr Cys Asn Val Ala His Pro Ala
        195                 200                 205

Ser Ser Thr Lys Val Asp Lys Lys Ile Glu Pro Arg Gly Pro Thr Ile
    210                 215                 220

Lys Pro Cys Pro Pro Cys Lys Cys Pro Ala Pro Asn Leu Leu Gly Gly
225                 230                 235                 240

Pro Ser Val Phe Ile Phe Pro Pro Lys Ile Lys Asp Val Leu Met Ile
                245                 250                 255

Ser Leu Ser Pro Ile Val Thr Cys Val Val Asp Val Ser Glu Asp
            260                 265                 270

Asp Pro Asp Val Gln Ile Ser Trp Phe Val Asn Asn Val Glu Val His
        275                 280                 285

Thr Ala Gln Thr Gln Thr His Arg Glu Asp Tyr Asn Ser Thr Leu Arg
    290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Asp Leu Pro Ala Pro Ile Glu
                325                 330                 335

Arg Thr Ile Ser Lys Pro Lys Gly Ser Val Arg Ala Pro Gln Val Tyr
            340                 345                 350

Val Leu Pro Pro Pro Glu Glu Glu Met Thr Lys Lys Gln Val Thr Leu
        355                 360                 365

Thr Cys Met Val Thr Asp Phe Met Pro Glu Asp Ile Tyr Val Glu Trp
    370                 375                 380

Thr Asn Asn Gly Lys Thr Glu Leu Asn Tyr Lys Asn Thr Glu Pro Val
```

```
                385                 390                 395                 400
Leu Asp Ser Asp Gly Ser Tyr Phe Met Tyr Ser Lys Leu Arg Val Glu
                    405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
        435                 440                 445

Gly Lys
    450

<210> SEQ ID NO 295
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 295

Gln Ser Val Lys Glu Ser Glu Gly Gly Leu Ile Lys Pro Thr Asp Thr
1               5                   10                  15

Leu Thr Leu Thr Cys Thr Val Ser Gly Phe Ser Leu Ser Thr Phe Ala
            20                  25                  30

Ile Asn Trp Val Arg Gln Ala Pro Gly Asn Gly Leu Glu Trp Ile Gly
        35                  40                  45

Ala Ile Gly Arg Gly Gly Ser Ala Tyr Tyr Ala Ser Trp Ala Lys Ser
    50                  55                  60

Arg Ser Thr Ile Thr Lys Asn Thr Asn Leu Asn Thr Val Thr Leu Lys
65                  70                  75                  80

Met Thr Arg Pro Thr Ala Ala Asp Thr Ala Thr Tyr Phe Cys Ala Arg
                85                  90                  95

Glu Asn Ala Gly Ser Gly Trp Gly Glu Leu Asp Ile Trp Gly Pro Gly
            100                 105                 110

Thr Leu Val Thr Val Ser Ser Ala Ser Thr Lys Gly Pro Ser Val Tyr
        115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Gly Pro Thr Ile Lys
    210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
        275                 280                 285
```

```
Ala Gln Thr Gln Thr His Arg Glu Asp Tyr Asn Ser Thr Leu Arg Val
    290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Tyr Val
            340                 345                 350

Leu Pro Pro Pro Glu Glu Glu Met Thr Lys Lys Gln Val Thr Leu Thr
        355                 360                 365

Cys Met Val Thr Asp Phe Met Pro Glu Asp Ile Tyr Val Glu Trp Thr
370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val Val His Glu
            420                 425                 430

Gly Leu His Asn His His Thr Thr Lys Ser Phe Ser Arg Thr Pro Gly
        435                 440                 445

Lys

<210> SEQ ID NO 296
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 296

Gln Ser Val Lys Glu Ser Glu Gly Gly Leu Phe Lys Pro Thr Asp Thr
1               5                   10                  15

Leu Thr Leu Thr Cys Thr Val Ser Gly Phe Ser Leu Ser Gly Tyr Gly
                20                  25                  30

Val Ser Trp Val Arg Gln Ala Pro Gly Lys Gly Leu Glu Tyr Ile Gly
            35                  40                  45

Phe Ile Gly Ser Gly Gly Ser Ala Tyr Tyr Ala Ser Trp Ala Lys Ser
        50                  55                  60

Arg Ser Thr Ile Thr Arg Asn Thr Asn Leu Asn Thr Val Thr Leu Lys
65                  70                  75                  80

Met Thr Arg Leu Thr Ala Ala Asp Thr Ala Thr Tyr Phe Cys Ala Arg
                85                  90                  95

Asp Asn Val Gly Gly Asp Met Ser Leu Asp Ile Trp Gly Pro Gly Thr
            100                 105                 110

Leu Val Thr Val Ser Ser Ala Ser Thr Lys Gly Pro Ser Val Tyr Pro
        115                 120                 125

Leu Ala Pro Val Cys Gly Asp Thr Thr Gly Ser Ser Val Thr Leu Gly
    130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Val Thr Val Thr Ser Ser Thr
            180                 185                 190
```

Trp Pro Ser Gln Ser Ile Thr Cys Asn Val Ala His Pro Ala Ser Ser
            195                 200                 205

Thr Lys Val Asp Lys Lys Ile Glu Pro Arg Gly Pro Thr Ile Lys Pro
        210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Asp Val Ser Glu Asp Asp Pro
            260                 265                 270

Asp Val Gln Ile Ser Trp Phe Val Asn Asn Val Glu Val His Thr Ala
        275                 280                 285

Gln Thr Gln Thr His Arg Glu Asp Tyr Asn Ser Thr Leu Arg Val Val
    290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
            340                 345                 350

Pro Pro Pro Glu Glu Glu Met Thr Lys Lys Gln Val Thr Leu Thr Cys
        355                 360                 365

Met Val Thr Asp Phe Met Pro Glu Asp Ile Tyr Val Glu Trp Thr Asn
    370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
            420                 425                 430

Leu His Asn His His Thr Thr Lys Ser Phe Ser Arg Thr Pro Gly Lys
        435                 440                 445

<210> SEQ ID NO 297
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297

Gln Ser Val Lys Glu Ser Glu Gly Gly Leu Phe Lys Pro Thr Asp Asn
1               5                   10                  15

Leu Thr Leu Thr Cys Thr Val Ser Gly Phe Ser Leu Ser Asn Tyr Gly
            20                  25                  30

Val Thr Trp Val Arg Gln Ala Pro Gly Asn Gly Leu Glu Tyr Ile Gly
        35                  40                  45

Phe Ile Gly Ser Ser Gly Ser Ala Tyr Tyr Ala Ser Trp Ala Lys Ser
    50                  55                  60

Arg Ser Thr Ile Thr Arg Asn Thr Asn Leu Asn Thr Val Thr Leu Lys
65                  70                  75                  80

Met Thr Ser Leu Thr Ala Ala Asp Thr Ala Thr Tyr Phe Cys Ala Arg
                85                  90                  95

Asp Asp Val Gly Gly Gly Lys Ser Leu Asp Ile Trp Gly Pro Gly Thr
            100                 105                 110

Leu Val Thr Val Ser Ser Ala Ser Thr Lys Gly Pro Ser Val Tyr Pro
            115                 120                 125

Leu Ala Pro Val Cys Gly Asp Thr Thr Gly Ser Ser Val Thr Leu Gly
        130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Val Thr Val Thr Ser Ser Thr
            180                 185                 190

Trp Pro Ser Gln Ser Ile Thr Cys Asn Val Ala His Pro Ala Ser Ser
        195                 200                 205

Thr Lys Val Asp Lys Lys Ile Glu Pro Arg Gly Pro Thr Ile Lys Pro
    210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Asp Val Ser Glu Asp Asp Pro
            260                 265                 270

Asp Val Gln Ile Ser Trp Phe Val Asn Asn Val Glu Val His Thr Ala
        275                 280                 285

Gln Thr Gln Thr His Arg Glu Asp Tyr Asn Ser Thr Leu Arg Val Val
    290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
            340                 345                 350

Pro Pro Pro Glu Glu Glu Met Thr Lys Lys Gln Val Thr Leu Thr Cys
        355                 360                 365

Met Val Thr Asp Phe Met Pro Glu Asp Ile Tyr Val Glu Trp Thr Asn
    370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
            420                 425                 430

Leu His Asn His His Thr Thr Lys Ser Phe Ser Arg Thr Pro Gly Lys
        435                 440                 445

<210> SEQ ID NO 298
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

Gln Ser Val Lys Glu Ser Glu Gly Gly Leu Phe Lys Pro Thr Asp Asn
1               5                   10                  15

Leu Thr Leu Thr Cys Thr Val Ser Gly Phe Ser Leu Ser Ser Tyr Gly

```
            20                  25                  30
Val Ser Trp Val Arg Gln Ala Pro Gly Asn Gly Leu Glu Tyr Ile Gly
            35                  40                  45
Phe Ile Gly Ser Gly Gly Phe Ala Tyr Tyr Ala Ser Trp Ala Lys Ser
            50                  55                  60
Arg Ser Thr Ile Thr Arg Asn Thr Asn Leu Asn Thr Val Thr Leu Lys
 65                  70                  75                  80
Met Thr Ser Leu Thr Ala Ala Asp Thr Ala Thr Tyr Phe Cys Ala Arg
                85                  90                  95
Asp Asp Val Gly Gly Gly Lys Ser Leu Asp Ile Trp Gly Pro Gly Thr
                100                 105                 110
Val Val Thr Val Ser Ser Ala Ser Thr Lys Gly Pro Ser Val Tyr Pro
                115                 120                 125
Leu Ala Pro Val Cys Gly Asp Thr Thr Gly Ser Ser Val Thr Leu Gly
            130                 135                 140
Cys Leu Val Lys Gly Tyr Phe Pro Glu Pro Val Thr Leu Thr Trp Asn
145                 150                 155                 160
Ser Gly Ser Leu Ser Ser Gly Val His Thr Phe Pro Ala Val Leu Gln
                165                 170                 175
Ser Asp Leu Tyr Thr Leu Ser Ser Ser Val Thr Val Thr Ser Ser Thr
                180                 185                 190
Trp Pro Ser Gln Ser Ile Thr Cys Asn Val Ala His Pro Ala Ser Ser
            195                 200                 205
Thr Lys Val Asp Lys Lys Ile Glu Pro Arg Gly Pro Thr Ile Lys Pro
            210                 215                 220
Cys Pro Pro Cys Lys Cys Pro Ala Pro Asn Leu Leu Gly Gly Pro Ser
225                 230                 235                 240
Val Phe Ile Phe Pro Pro Lys Ile Lys Asp Val Leu Met Ile Ser Leu
                245                 250                 255
Ser Pro Ile Val Thr Cys Val Val Val Asp Val Ser Glu Asp Asp Pro
                260                 265                 270
Asp Val Gln Ile Ser Trp Phe Val Asn Asn Val Glu Val His Thr Ala
            275                 280                 285
Gln Thr Gln Thr His Arg Glu Asp Tyr Asn Ser Thr Leu Arg Val Val
            290                 295                 300
Ser Ala Leu Pro Ile Gln His Gln Asp Trp Met Ser Gly Lys Glu Phe
305                 310                 315                 320
Lys Cys Lys Val Asn Asn Lys Asp Leu Pro Ala Pro Ile Glu Arg Thr
                325                 330                 335
Ile Ser Lys Pro Lys Gly Ser Val Arg Ala Pro Gln Val Tyr Val Leu
                340                 345                 350
Pro Pro Pro Glu Glu Met Thr Lys Lys Gln Val Thr Leu Thr Cys
            355                 360                 365
Met Val Thr Asp Phe Met Pro Glu Asp Ile Tyr Val Glu Trp Thr Asn
            370                 375                 380
Asn Gly Lys Thr Glu Leu Asn Tyr Lys Asn Thr Glu Pro Val Leu Asp
385                 390                 395                 400
Ser Asp Gly Ser Tyr Phe Met Tyr Ser Lys Leu Arg Val Glu Lys Lys
                405                 410                 415
Asn Trp Val Glu Arg Asn Ser Tyr Ser Cys Ser Val Val His Glu Gly
            420                 425                 430
Leu His Asn His His Thr Thr Lys Ser Phe Ser Arg Thr Pro Gly Lys
            435                 440                 445
```

<210> SEQ ID NO 299
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ser Leu Ser Ser Tyr
            20                  25                  30

Gly Val Ser Trp Val Arg Gln Ala Pro Gly Lys Gly Leu Glu Tyr Val
        35                  40                  45

Gly Phe Ile Gly Ser Gly Gly Phe Ala Tyr Tyr Ala Ser Trp Ala Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Asp Val Gly Gly Lys Ser Leu Asp Ile Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr

```
                355                 360                 365
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 300
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ser Leu Ser Ser Tyr
            20                  25                  30

Gly Val Ser Trp Val Arg Gln Ala Pro Gly Lys Gly Leu Glu Tyr Val
        35                  40                  45

Gly Phe Ile Gly Ser Gly Gly Phe Ala Tyr Tyr Ala Ser Trp Ala Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Asp Val Gly Gly Gly Lys Ser Leu Asp Ile Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
```

```
                260                 265                 270
Gln Phe Asn Trp Tyr Val Asp Gly Val Glu Val His Asn Ala Lys Thr
            275                 280                 285
Lys Pro Arg Glu Glu Gln Phe Asn Ser Thr Tyr Arg Val Val Ser Val
        290                 295                 300
Leu Thr Val Leu His Gln Asp Trp Leu Asn Gly Lys Glu Tyr Lys Cys
305                 310                 315                 320
Lys Val Ser Asn Lys Gly Leu Pro Ser Ser Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Gln Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Arg Leu Thr Val Asp Lys Ser Arg Trp
                405                 410                 415
Gln Glu Gly Asn Val Phe Ser Cys Ser Val Met His Glu Ala Leu His
            420                 425                 430
Asn His Tyr Thr Gln Lys Ser Leu Ser Leu Ser Leu Gly Lys
        435                 440                 445

<210> SEQ ID NO 301
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 301

Gln Ser Val Lys Glu Ser Glu Gly Gly Leu Phe Lys Pro Thr Asp Asn
1               5                   10                  15
Leu Thr Leu Thr Cys Thr Val Ser Gly Phe Ser Leu Ser Ser Tyr Gly
            20                  25                  30
Val Ser Trp Val Arg Gln Ala Pro Gly Asn Gly Leu Glu Tyr Ile Gly
        35                  40                  45
Phe Ile Gly Ser Gly Gly Ser Pro Tyr Tyr Ala Ser Trp Ala Lys Ser
    50                  55                  60
Arg Ser Thr Ile Thr Arg Asn Thr Asn Leu Asn Thr Val Thr Leu Lys
65                  70                  75                  80
Met Thr Ser Leu Thr Ala Ala Asp Thr Ala Thr Tyr Phe Cys Ala Arg
                85                  90                  95
Asp Asp Val Gly Gly Gly Lys Ser Leu Asp Ile Trp Gly Pro Gly Thr
            100                 105                 110
Leu Val Thr Val Ser Ser Ala Ser Thr Lys Gly Pro Ser Val Tyr Pro
        115                 120                 125
Leu Ala Pro Val Cys Gly Asp Thr Thr Gly Ser Ser Val Thr Leu Gly
    130                 135                 140
Cys Leu Val Lys Gly Tyr Phe Pro Glu Pro Val Thr Leu Thr Trp Asn
145                 150                 155                 160
Ser Gly Ser Leu Ser Ser Gly Val His Thr Phe Pro Ala Val Leu Gln
                165                 170                 175
```

Ser Asp Leu Tyr Thr Leu Ser Ser Val Thr Val Thr Ser Ser Thr
            180                 185                 190

Trp Pro Ser Gln Ser Ile Thr Cys Asn Val Ala His Pro Ala Ser Ser
        195                 200                 205

Thr Lys Val Asp Lys Lys Ile Glu Pro Arg Gly Pro Thr Ile Lys Pro
    210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Asp Val Ser Glu Asp Asp Pro
            260                 265                 270

Asp Val Gln Ile Ser Trp Phe Val Asn Asn Val Glu Val His Thr Ala
        275                 280                 285

Gln Thr Gln Thr His Arg Glu Asp Tyr Asn Ser Thr Leu Arg Val Val
    290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
            340                 345                 350

Pro Pro Pro Glu Glu Met Thr Lys Lys Gln Val Thr Leu Thr Cys
        355                 360                 365

Met Val Thr Asp Phe Met Pro Glu Asp Ile Tyr Val Glu Trp Thr Asn
370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
            420                 425                 430

Leu His Asn His His Thr Thr Lys Ser Phe Ser Arg Thr Pro Gly Lys
        435                 440                 445

<210> SEQ ID NO 302
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 302

Gln Ser Val Lys Glu Ser Glu Gly Gly Leu Phe Lys Pro Thr Asp Asn
1               5                   10                  15

Leu Thr Leu Thr Cys Thr Val Ser Gly Phe Ser Leu Ser Ser Tyr Gly
            20                  25                  30

Val Ser Trp Val Arg Gln Ala Pro Gly Asn Gly Leu Glu Tyr Ile Gly
        35                  40                  45

Phe Ile Gly Ser Gly Gly Phe Ala Tyr Tyr Ala Ser Trp Ala Lys Ser
    50                  55                  60

Arg Ser Thr Ile Thr Arg Asn Thr Asn Leu Asn Thr Val Thr Leu Lys
65                  70                  75                  80

Met Thr Ser Leu Thr Ala Ala Asp Thr Ala Thr Tyr Phe Cys Ala Arg
                85                  90                  95

```
Asp Asp Val Gly Gly Gly Arg Ser Leu Asp Ile Trp Gly Pro Gly Thr
                100                 105                 110

Val Val Thr Val Ser Ser Ala Ser Thr Lys Gly Pro Ser Val Tyr Pro
            115                 120                 125

Leu Ala Pro Val Cys Gly Asp Thr Thr Gly Ser Ser Val Thr Leu Gly
130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Val Thr Val Thr Ser Ser Thr
            180                 185                 190

Trp Pro Ser Gln Ser Ile Thr Cys Asn Val Ala His Pro Ala Ser Ser
            195                 200                 205

Thr Lys Val Asp Lys Lys Ile Glu Pro Arg Gly Pro Thr Ile Lys Pro
210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Asp Val Ser Glu Asp Asp Pro
            260                 265                 270

Asp Val Gln Ile Ser Trp Phe Val Asn Asn Val Glu Val His Thr Ala
            275                 280                 285

Gln Thr Gln Thr His Arg Glu Asp Tyr Asn Ser Thr Leu Arg Val Val
            290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
            340                 345                 350

Pro Pro Pro Glu Glu Glu Met Thr Lys Lys Gln Val Thr Leu Thr Cys
            355                 360                 365

Met Val Thr Asp Phe Met Pro Glu Asp Ile Tyr Val Glu Trp Thr Asn
370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
            420                 425                 430

Leu His Asn His His Thr Thr Lys Ser Phe Ser Arg Thr Pro Gly Lys
            435                 440                 445

<210> SEQ ID NO 303
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 303

Gln Ser Val Lys Glu Ser Glu Gly Gly Leu Phe Lys Pro Thr Asp Thr
```

-continued

```
1               5                   10                  15
Leu Thr Leu Thr Cys Thr Val Ser Gly Phe Ser Leu Ser Ser Tyr Pro
                20                  25                  30
Ile Ser Trp Val Arg Gln Ala Pro Gly Asn Gly Leu Glu Trp Ile Gly
                35                  40                  45
Tyr Ile Thr Ser Glu Tyr Gly Val Ala Tyr Ala Thr Trp Ala Glu
                50                  55                  60
Ser Arg Ser Thr Ile Thr Arg Asn Thr Asn Leu Asn Thr Val Thr Leu
65                  70                  75                  80
Lys Met Thr Ser Leu Thr Ala Ala Asp Thr Ala Thr Tyr Phe Cys Val
                85                  90                  95
Arg Glu Asn Pro Thr Tyr Gly Tyr Ala Tyr Asp Ala Trp Gly Pro Gly
                100                 105                 110
Thr Leu Val Thr Val Ser Ser Ala Ser Thr Lys Gly Pro Ser Val Tyr
                115                 120                 125
Pro Leu Ala Pro Val Cys Gly Asp Thr Thr Gly Ser Ser Val Thr Leu
                130                 135                 140
Gly Cys Leu Val Lys Gly Tyr Phe Pro Glu Pro Val Thr Leu Thr Trp
145                 150                 155                 160
Asn Ser Gly Ser Leu Ser Ser Gly Val His Thr Phe Pro Ala Val Leu
                165                 170                 175
Gln Ser Asp Leu Tyr Thr Leu Ser Ser Val Thr Val Thr Ser Ser
                180                 185                 190
Thr Trp Pro Ser Gln Ser Ile Thr Cys Asn Val Ala His Pro Ala Ser
                195                 200                 205
Ser Thr Lys Val Asp Lys Lys Ile Glu Pro Arg Gly Pro Thr Ile Lys
210                 215                 220
Pro Cys Pro Pro Cys Lys Cys Pro Ala Pro Asn Leu Leu Gly Gly Pro
225                 230                 235                 240
Ser Val Phe Ile Phe Pro Pro Lys Ile Lys Asp Val Leu Met Ile Ser
                245                 250                 255
Leu Ser Pro Ile Val Thr Cys Val Val Val Asp Val Ser Glu Asp Asp
                260                 265                 270
Pro Asp Val Gln Ile Ser Trp Phe Val Asn Asn Val Glu Val His Thr
                275                 280                 285
Ala Gln Thr Gln Thr His Arg Glu Asp Tyr Asn Ser Thr Leu Arg Val
                290                 295                 300
Val Ser Ala Leu Pro Ile Gln His Gln Asp Trp Met Ser Gly Lys Glu
305                 310                 315                 320
Phe Lys Cys Lys Val Asn Asn Lys Asp Leu Pro Ala Pro Ile Glu Arg
                325                 330                 335
Thr Ile Ser Lys Pro Lys Gly Ser Val Arg Ala Pro Gln Val Tyr Val
                340                 345                 350
Leu Pro Pro Pro Glu Glu Glu Met Thr Lys Lys Gln Val Thr Leu Thr
                355                 360                 365
Cys Met Val Thr Asp Phe Met Pro Glu Asp Ile Tyr Val Glu Trp Thr
370                 375                 380
Asn Asn Gly Lys Thr Glu Leu Asn Tyr Lys Asn Thr Glu Pro Val Leu
385                 390                 395                 400
Asp Ser Asp Gly Ser Tyr Phe Met Tyr Ser Lys Leu Arg Val Glu Lys
                405                 410                 415
Lys Asn Trp Val Glu Arg Asn Ser Tyr Ser Cys Ser Val Val His Glu
                420                 425                 430
```

Gly Leu His Asn His His Thr Thr Lys Ser Phe Ser Arg Thr Pro Gly
            435                 440                 445

Lys

<210> SEQ ID NO 304
<211> LENGTH: 454
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 304

Gln Ser Val Lys Glu Ser Glu Gly Gly Leu Phe Lys Pro Thr Asp Thr
1               5                   10                  15

Leu Thr Leu Thr Cys Thr Val Ser Gly Phe Ser Leu Asn Asp Tyr Gly
            20                  25                  30

Val Ser Trp Val Arg Gln Ala Pro Gly Asn Gly Leu Glu Trp Ile Gly
        35                  40                  45

Ala Ile Gly Ser Ser Gly Val Ala Trp Tyr Ala Asn Trp Ala Lys Gly
    50                  55                  60

Arg Ser Thr Ile Thr Arg Asn Thr Asn Leu Asn Thr Val Thr Leu Lys
65                  70                  75                  80

Met Ala Ser Leu Thr Ala Ala Asp Thr Ala Thr Tyr Phe Cys Ala Arg
                85                  90                  95

Asp Arg Asp Tyr Gly Tyr Arg Ala Asp Asp Ala Thr Ser Gly Met Asp
            100                 105                 110

Leu Trp Gly Pro Gly Thr Leu Val Thr Val Ser Ser Ala Ser Thr Lys
        115                 120                 125

Gly Pro Ser Val Tyr Pro Leu Ala Pro Val Cys Gly Asp Thr Thr Gly
    130                 135                 140

Ser Ser Val Thr Leu Gly Cys Leu Val Lys Gly Tyr Phe Pro Glu Pro
145                 150                 155                 160

Val Thr Leu Thr Trp Asn Ser Gly Ser Leu Ser Ser Gly Val His Thr
                165                 170                 175

Phe Pro Ala Val Leu Gln Ser Asp Leu Tyr Thr Leu Ser Ser Ser Val
            180                 185                 190

Thr Val Thr Ser Ser Thr Trp Pro Ser Gln Ser Ile Thr Cys Asn Val
        195                 200                 205

Ala His Pro Ala Ser Ser Thr Lys Val Asp Lys Lys Ile Glu Pro Arg
    210                 215                 220

Gly Pro Thr Ile Lys Pro Cys Pro Pro Cys Lys Cys Pro Ala Pro Asn
225                 230                 235                 240

Leu Leu Gly Gly Pro Ser Val Phe Ile Phe Pro Pro Lys Ile Lys Asp
                245                 250                 255

Val Leu Met Ile Ser Leu Ser Pro Ile Val Thr Cys Val Val Val Asp
            260                 265                 270

Val Ser Glu Asp Asp Pro Asp Val Gln Ile Ser Trp Phe Val Asn Asn
        275                 280                 285

Val Glu Val His Thr Ala Gln Thr Gln Thr His Arg Glu Asp Tyr Asn
    290                 295                 300

Ser Thr Leu Arg Val Val Ser Ala Leu Pro Ile Gln His Gln Asp Trp
305                 310                 315                 320

Met Ser Gly Lys Glu Phe Lys Cys Lys Val Asn Asn Lys Asp Leu Pro
                325                 330                 335

```
Ala Pro Ile Glu Arg Thr Ile Ser Lys Pro Lys Gly Ser Val Arg Ala
            340                 345                 350

Pro Gln Val Tyr Val Leu Pro Pro Glu Glu Met Thr Lys Lys
        355                 360                 365

Gln Val Thr Leu Thr Cys Met Val Thr Asp Phe Met Pro Glu Asp Ile
    370                 375                 380

Tyr Val Glu Trp Thr Asn Asn Gly Lys Thr Glu Leu Asn Tyr Lys Asn
385                 390                 395                 400

Thr Glu Pro Val Leu Asp Ser Asp Gly Ser Tyr Phe Met Tyr Ser Lys
                405                 410                 415

Leu Arg Val Glu Lys Lys Asn Trp Val Glu Arg Asn Ser Tyr Ser Cys
            420                 425                 430

Ser Val Val His Glu Gly Leu His Asn His His Thr Thr Lys Ser Phe
            435                 440                 445

Ser Arg Thr Pro Gly Lys
    450

<210> SEQ ID NO 305
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 305

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Ser Leu Asn Asp Tyr
            20                  25                  30

Gly Val Ser Trp Val Arg Gln Ala Pro Gly Lys Gly Leu Glu Trp Val
        35                  40                  45

Gly Ala Ile Gly Ser Ser Gly Val Ala Trp Tyr Ala Asn Phe Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Asp Arg Asp Tyr Gly Tyr Arg Ala Asp Ala Thr Ser Gly Met
            100                 105                 110

Asp Leu Trp Gly Arg Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
```

```
                225                 230                 235                 240
Glu Leu Leu Gly Gly Pro Ser Val Phe Leu Phe Pro Pro Lys Pro Lys
                    245                 250                 255

Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
        290                 295                 300

Gly Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 306
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Ser Leu Asn Asp Tyr
                20                  25                  30

Gly Val Ser Trp Val Arg Gln Ala Pro Gly Lys Gly Leu Glu Trp Val
            35                  40                  45

Gly Ala Ile Gly Ser Ser Gly Val Ala Trp Tyr Ala Asn Phe Ala Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Arg Asp Tyr Gly Tyr Arg Ala Asp Ala Thr Ser Gly Met
            100                 105                 110

Asp Leu Trp Gly Arg Gly Thr Leu Val Thr Val Ser Ser Ala Ser Thr
        115                 120                 125
```

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450

<210> SEQ ID NO 307
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 307

Gln Glu Gln Leu Glu Glu Ser Gly Gly Gly Leu Val Lys Pro Gly Ala
1               5                   10                  15

Ser Leu Thr Leu Thr Cys Thr Val Ser Gly Phe Ser Leu Thr Asn Asn
            20                  25                  30

-continued

```
Tyr Val Asn Phe Val Met Cys Trp Val Arg Gln Ala Pro Gly Lys Gly
             35                  40                  45

Leu Glu Trp Ile Ala Ser Ile Asp Pro Gly Asp Ser Thr Asp Tyr
 50              55                  60

Ala Ser Trp Ala Thr Gly Arg Phe Thr Ile Ser Lys Ala Ser Ser Thr
 65                  70                  75                  80

Thr Val Thr Leu Gln Val Thr Ser Leu Thr Ala Ala Asp Thr Ala Thr
                     85                  90                  95

Tyr Phe Cys Ala Arg Gly Asp Ala Gly Thr Ser Tyr Ser Phe Asn Phe
                100                 105                 110

Trp Gly Pro Gly Thr Leu Val Thr Val Ser Ser Ala Ser Thr Lys Gly
            115                 120                 125

Pro Ser Val Tyr Pro Leu Ala Pro Val Cys Gly Asp Thr Thr Gly Ser
130                 135                 140

Ser Val Thr Leu Gly Cys Leu Val Lys Gly Tyr Phe Pro Glu Pro Val
145                 150                 155                 160

Thr Leu Thr Trp Asn Ser Gly Ser Leu Ser Ser Gly Val His Thr Phe
                165                 170                 175

Pro Ala Val Leu Gln Ser Asp Leu Tyr Thr Leu Ser Ser Ser Val Thr
            180                 185                 190

Val Thr Ser Ser Thr Trp Pro Ser Gln Ser Ile Thr Cys Asn Val Ala
        195                 200                 205

His Pro Ala Ser Ser Thr Lys Val Asp Lys Lys Ile Glu Pro Arg Gly
    210                 215                 220

Pro Thr Ile Lys Pro Cys Pro Pro Cys Lys Cys Pro Ala Pro Asn Leu
225                 230                 235                 240

Leu Gly Gly Pro Ser Val Phe Ile Phe Pro Pro Lys Ile Lys Asp Val
                245                 250                 255

Leu Met Ile Ser Leu Ser Pro Ile Val Thr Cys Val Val Val Asp Val
            260                 265                 270

Ser Glu Asp Asp Pro Asp Val Gln Ile Ser Trp Phe Val Asn Asn Val
        275                 280                 285

Glu Val His Thr Ala Gln Thr Gln Thr His Arg Glu Asp Tyr Asn Ser
    290                 295                 300

Thr Leu Arg Val Val Ser Ala Leu Pro Ile Gln His Gln Asp Trp Met
305                 310                 315                 320

Ser Gly Lys Glu Phe Lys Cys Lys Val Asn Asn Lys Asp Leu Pro Ala
                325                 330                 335

Pro Ile Glu Arg Thr Ile Ser Lys Pro Lys Gly Ser Val Arg Ala Pro
            340                 345                 350

Gln Val Tyr Val Leu Pro Pro Glu Glu Glu Met Thr Lys Lys Gln
        355                 360                 365

Val Thr Leu Thr Cys Met Val Thr Asp Phe Met Pro Glu Asp Ile Tyr
370                 375                 380

Val Glu Trp Thr Asn Asn Gly Lys Thr Glu Leu Asn Tyr Lys Asn Thr
385                 390                 395                 400

Glu Pro Val Leu Asp Ser Asp Gly Ser Tyr Phe Met Tyr Ser Lys Leu
                405                 410                 415

Arg Val Glu Lys Lys Asn Trp Val Glu Arg Asn Ser Tyr Ser Cys Ser
            420                 425                 430

Val Val His Glu Gly Leu His Asn His His Thr Thr Lys Ser Phe Ser
        435                 440                 445
```

```
Arg Thr Pro Gly Lys
            450

<210> SEQ ID NO 308
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 308

Gln Glu Gln Leu Val Glu Ser Gly Gly Gly Leu Val Lys Pro Gly Ala
1               5                   10                  15

Ser Leu Thr Leu Thr Cys Thr Ala Ser Gly Phe Ser Leu Thr Asp Asn
            20                  25                  30

Tyr Val Met Ser Trp Val Arg Gln Ala Pro Gly Lys Gly Leu Glu Trp
        35                  40                  45

Ile Ala Cys Ile Asp Pro Gly Asp Ser Thr Tyr Tyr Ala Ser Trp
    50                  55                  60

Ala Thr Gly Arg Phe Thr Ile Ser Arg Ala Ser Ser Thr Val Thr
65              70                  75                  80

Leu Gln Val Thr Ser Leu Thr Ala Ala Asp Thr Ala Thr Tyr Phe Cys
                85                  90                  95

Ala Arg Gly Asp Ala Ala Ser Tyr Ser Phe Asn Phe Trp Gly Pro
            100                 105                 110

Gly Thr Leu Val Thr Val Ser Ser Ala Ser Lys Gly Pro Ser Val
        115                 120                 125

Tyr Pro Leu Ala Pro Val Cys Gly Asp Thr Thr Gly Ser Ser Val Thr
    130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
            180                 185                 190

Ser Thr Trp Pro Ser Gln Ser Ile Thr Cys Asn Val Ala His Pro Ala
        195                 200                 205

Ser Ser Thr Lys Val Asp Lys Lys Ile Glu Pro Arg Gly Pro Thr Ile
    210                 215                 220

Lys Pro Cys Pro Pro Cys Lys Cys Pro Ala Pro Asn Leu Leu Gly Gly
225                 230                 235                 240

Pro Ser Val Phe Ile Phe Pro Pro Lys Ile Lys Asp Val Leu Met Ile
                245                 250                 255

Ser Leu Ser Pro Ile Val Thr Cys Val Val Asp Val Ser Glu Asp
            260                 265                 270

Asp Pro Asp Val Gln Ile Ser Trp Phe Val Asn Asn Val Glu Val His
        275                 280                 285

Thr Ala Gln Thr Gln Thr His Arg Glu Asp Tyr Asn Ser Thr Leu Arg
    290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Asp Leu Pro Ala Pro Ile Glu
                325                 330                 335

Arg Thr Ile Ser Lys Pro Lys Gly Ser Val Arg Ala Pro Gln Val Tyr
            340                 345                 350
```

Val Leu Pro Pro Glu Glu Glu Met Thr Lys Lys Gln Val Thr Leu
            355                 360                 365

Thr Cys Met Val Thr Asp Phe Met Pro Glu Asp Ile Tyr Val Glu Trp
        370                 375                 380

Thr Asn Asn Gly Lys Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
        435                 440                 445

Gly Lys
    450

<210> SEQ ID NO 309
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 309

Gln Ser Leu Glu Glu Ser Gly Gly Gly Leu Val Lys Pro Gly Gly Thr
1               5                   10                  15

Leu Thr Leu Thr Cys Lys Ala Ser Gly Ile Asp Phe Asn Gly Gly Gly
            20                  25                  30

Ile Tyr Trp Val Arg Gln Ala Pro Gly Lys Gly Leu Glu Trp Ile Ala
        35                  40                  45

Ser Ile Tyr Pro Asp His Gly Ser Val Asp Tyr Ala Asn Trp Val Asn
    50                  55                  60

Gly Arg Phe Thr Ile Ser Leu Asp Asn Ala Gln Asn Thr Val Phe Leu
65                  70                  75                  80

Gln Leu Thr Ser Leu Thr Val Ala Asp Thr Ala Thr Tyr Phe Cys Ala
            85                  90                  95

Arg Glu Ser Gly Gly Ser Tyr Tyr Asp Leu Trp Gly Pro Gly Thr Leu
            100                 105                 110

Val Thr Val Ser Ser Ala Ser Thr Lys Gly Pro Ser Val Tyr Pro Leu
        115                 120                 125

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

Lys Val Asp Lys Lys Ile Glu Pro Arg Gly Pro Thr Ile Lys Pro Cys
    210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser

-continued

```
                245                 250                 255
Pro Ile Val Thr Cys Val Val Asp Val Ser Glu Asp Pro Asp
            260                 265                 270

Val Gln Ile Ser Trp Phe Val Asn Asn Val Glu Val His Thr Ala Gln
        275                 280                 285

Thr Gln Thr His Arg Glu Asp Tyr Asn Ser Thr Leu Arg Val Val Ser
    290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
                325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
        355                 360                 365

Val Thr Asp Phe Met Pro Glu Asp Ile Tyr Val Glu Trp Thr Asn Asn
    370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val Val His Glu Gly Leu
            420                 425                 430

His Asn His His Thr Thr Lys Ser Phe Ser Arg Thr Pro Gly Lys
        435                 440                 445

<210> SEQ ID NO 310
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 310

Gln Ser Leu Glu Glu Ser Gly Gly Gly Leu Val Lys Pro Gly Gly Thr
1               5                   10                  15

Leu Thr Leu Thr Cys Thr Ala Ser Gly Phe Asp Phe Asn Gly Gly Gly
            20                  25                  30

Ile Tyr Trp Val Arg Gln Ala Pro Gly Lys Gly Leu Glu Trp Ile Ala
        35                  40                  45

Tyr Ile Tyr Pro Asp His Gly Ser Ala Asp Tyr Ala Thr Trp Val Asn
    50                  55                  60

Gly Arg Phe Thr Ile Ser Leu Asp Asn Ala Gln Asn Thr Val Phe Leu
65                  70                  75                  80

Gln Met Thr Ser Leu Thr Val Ala Asp Thr Ala Thr Tyr Phe Cys Ala
                85                  90                  95

Arg Glu Thr Gly Gly Ser Trp Tyr Asp Leu Trp Gly Pro Gly Thr Leu
            100                 105                 110

Val Thr Val Ser Ser Ala Ser Thr Lys Gly Pro Ser Val Tyr Pro Leu
        115                 120                 125

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160
```

Gly Ser Leu Ser Ser Gly Val His Thr Phe Pro Ala Val Leu Gln Ser
              165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

Lys Val Asp Lys Lys Ile Glu Pro Arg Gly Pro Thr Ile Lys Pro Cys
    210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Val Asp Val Ser Glu Asp Asp Pro Asp
            260                 265                 270

Val Gln Ile Ser Trp Phe Val Asn Asn Val Glu Val His Thr Ala Gln
        275                 280                 285

Thr Gln Thr His Arg Glu Asp Tyr Asn Ser Thr Leu Arg Val Val Ser
    290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
                325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
        355                 360                 365

Val Thr Asp Phe Met Pro Glu Asp Ile Tyr Val Glu Trp Thr Asn Asn
    370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val Val His Glu Gly Leu
            420                 425                 430

His Asn His His Thr Thr Lys Ser Phe Ser Arg Thr Pro Gly Lys
        435                 440                 445

<210> SEQ ID NO 311
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 311

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

```
Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 312
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 312

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 313
<211> LENGTH: 330
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 313

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gly Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 314
<211> LENGTH: 327

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 314

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 315
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 315

```
Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Pro Cys Pro Ala Pro
            100                 105                 110
Glu Phe Leu Gly Gly Pro Ser Val Phe Leu Phe Pro Pro Lys Pro Lys
            115                 120                 125
Asp Thr Leu Met Ile Ser Arg Thr Pro Glu Val Thr Cys Val Val Val
130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
            275                 280                 285
Arg Leu Thr Val Asp Lys Ser Arg Trp Gln Gly Asn Val Phe Ser
290                 295                 300
Cys Ser Val Met His Glu Ala Leu His Asn His Tyr Thr Gln Lys Ser
305                 310                 315                 320
Leu Ser Leu Ser Leu Gly Lys
                325
```

<210> SEQ ID NO 316
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 316

```
Leu Arg Pro Asn Gln Leu
1               5
```

<210> SEQ ID NO 317
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Gln Gly Val Lys Ser Ile
1               5

<210> SEQ ID NO 318
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Lys Arg Cys Glu Asp Ala Tyr Pro Arg Gln Ile Asp Asp Thr
1               5                   10

<210> SEQ ID NO 319
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Asp Tyr Pro Cys Ala Arg Pro Asn Arg Pro Gly Val Tyr
1               5                   10

<210> SEQ ID NO 320
<211> LENGTH: 299
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 320

Ile Glu Ser Ala Lys Gln Thr Lys Gln Met Val Asp Cys Ser His Tyr
1               5                   10                  15

Lys Lys Leu Pro Pro Gly Gln Gln Arg Phe Cys His Arg Glu Tyr Asp
            20                  25                  30

Pro Ile Cys Gly Ser Asp Gly Lys Thr Tyr Lys Asn Asp Cys Phe Phe
        35                  40                  45

Cys Ser Lys Val Lys Lys Thr Asp Gly Thr Leu Lys Phe Val His Phe
    50                  55                  60

Gly Lys Cys Gly Asn Ser Val Thr Asp Lys Thr His Thr Cys Pro Pro
65                  70                  75                  80

Cys Pro Ala Pro Glu Leu Leu Gly Gly Pro Ser Val Phe Leu Phe Pro
                85                  90                  95

Pro Lys Pro Lys Asp Thr Leu Met Ile Ser Arg Thr Pro Glu Val Thr
                100                 105                 110

Cys Val Val Val Asp Val Ser His Glu Asp Pro Glu Val Lys Phe Asn
            115                 120                 125

Trp Tyr Val Asp Gly Val Glu Val His Asn Ala Lys Thr Lys Pro Arg

```
                130                 135                 140
Glu Glu Gln Tyr Asn Ser Thr Tyr Arg Val Val Ser Val Leu Thr Val
145                 150                 155                 160

Leu His Gln Asp Trp Leu Asn Gly Lys Glu Tyr Lys Cys Lys Val Ser
                165                 170                 175

Asn Lys Ala Leu Pro Ala Pro Ile Glu Lys Thr Ile Ser Lys Ala Lys
            180                 185                 190

Gly Gln Pro Arg Glu Pro Gln Val Tyr Thr Leu Pro Pro Ser Arg Glu
        195                 200                 205

Glu Met Thr Lys Asn Gln Val Ser Leu Thr Cys Leu Val Lys Gly Phe
    210                 215                 220

Tyr Pro Ser Asp Ile Ala Val Glu Trp Glu Ser Asn Gly Gln Pro Glu
225                 230                 235                 240

Asn Asn Tyr Lys Thr Thr Pro Pro Val Leu Asp Ser Asp Gly Ser Phe
                245                 250                 255

Phe Leu Tyr Ser Lys Leu Thr Val Asp Lys Ser Arg Trp Gln Gln Gly
            260                 265                 270

Asn Val Phe Ser Cys Ser Val Met His Glu Ala Leu His Asn His Tyr
        275                 280                 285

Thr Gln Lys Ser Leu Ser Leu Ser Pro Gly Lys
    290                 295

<210> SEQ ID NO 321
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 321

Ala Ile Arg Met Thr Gln Ser Pro Ser Phe Ser Ala Ser Thr Gly
1               5                   10                  15

Asp Arg Val Thr Ile Thr Cys Gln Ala Ser Glu Ser Ile Ser Asn Glu
                20                  25                  30

Leu Ser Trp Tyr Gln Gln Lys Pro Gly Lys Ala Pro Lys Leu Leu Ile
            35                  40                  45

Tyr Tyr Ala Ser Thr Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Gly Phe Gly Ser Ser Gly
                85                  90                  95

Val Glu Asn Val Phe Gly Gly Thr Glu Val Val Val Lys
            100                 105                 110

<210> SEQ ID NO 322
<211> LENGTH: 224
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 322

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
```

```
            20                  25                  30
Gly Val Thr Trp Val Arg Gln Ala Pro Gly Lys Gly Leu Glu Trp Ile
                35                  40                  45
Gly Tyr Ile Thr Ser Asn Tyr Gly Val Ser Tyr Tyr Ala Ser Trp Ala
            50                  55                  60
Lys Ser Arg Ser Thr Ile Ser Arg Asp Thr Ser Lys Asn Thr Val Tyr
65                  70                  75                  80
Leu Gln Met Gly Ser Leu Arg Ala Glu Asp Met Ala Val Tyr Tyr Cys
                85                  90                  95
Ala Arg Glu Asn Pro Asp Tyr Gly Tyr Ala Tyr Asp Ala Trp Gly Gln
                100                 105                 110
Gly Thr Thr Val Thr Val Ser Ser Ala Ser Thr Lys Gly Pro Ser Val
                115                 120                 125
Phe Pro Leu Ala Pro Ser Ser Lys Ser Thr Ser Gly Gly Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Lys Val Glu Pro Lys Ser Cys Asp
            210                 215                 220

<210> SEQ ID NO 323
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 323

Ala Ile Arg Met Thr Gln Ser Pro Ser Ser Phe Ser Ala Ser Thr Gly
1               5                   10                  15
Asp Arg Val Thr Ile Thr Cys Gln Ala Ser Glu Ser Ile Ser Asn Glu
                20                  25                  30
Leu Ser Trp Tyr Gln Gln Lys Pro Gly Lys Ala Pro Lys Leu Leu Ile
                35                  40                  45
Tyr Tyr Ala Ser Thr Leu Ala Ser Gly Val Pro Ser Arg Phe Ser Gly
            50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Ala Gln Gly Phe Gly Ser Ser Gly
                85                  90                  95
Val Glu Asn Val Phe Gly Gly Gly Thr Lys Val Glu Ile Lys Arg Thr
                100                 105                 110
Val Ala Ala Pro Ser Val Phe Ile Phe Pro Pro Ser Asp Glu Gln Leu
                115                 120                 125
Lys Ser Gly Thr Ala Ser Val Val Cys Leu Leu Asn Asn Phe Tyr Pro
            130                 135                 140
Arg Glu Ala Lys Val Gln Trp Lys Val Asp Asn Ala Leu Gln Ser Gly
145                 150                 155                 160
```

```
Asn Ser Gln Glu Ser Val Thr Glu Gln Asp Ser Lys Asp Ser Thr Tyr
            165                 170                 175

Ser Leu Ser Ser Thr Leu Thr Leu Ser Lys Ala Asp Tyr Glu Lys His
        180                 185                 190

Lys Val Tyr Ala Cys Glu Val Thr His Gln Gly Leu Ser Ser Pro Val
    195                 200                 205

Thr Lys Ser Phe Asn Arg Gly Glu Cys
    210                 215

<210> SEQ ID NO 324
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 324

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ser Leu Ser Ser Tyr
            20                  25                  30

Gly Val Ser Trp Val Arg Gln Ala Pro Gly Lys Gly Leu Glu Tyr Val
        35                  40                  45

Gly Phe Ile Gly Ser Gly Gly Phe Ala Tyr Tyr Ala Ser Trp Ala Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Asp Asp Val Gly Gly Lys Ser Leu Asp Ile Trp Gly Gln Gly
        100                 105                 110

Thr Leu Val Thr Val Ser Ser Ala Ser Thr Lys Gly Pro Ser Val Phe
    115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp
    210                 215                 220

<210> SEQ ID NO 325
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Asp Ile Gln Met Thr Gln Ser Pro Ser Ser Leu Ser Ala Ser Val Gly
1               5                   10                  15
```

```
Asp Arg Val Thr Ile Thr Cys Gln Ala Ser Gln Ser Ile Ser Ser Tyr
             20                  25                  30

Leu Ser Trp Tyr Gln Gln Lys Pro Gly Lys Ala Pro Lys Leu Leu Ile
         35                  40                  45

Tyr Ser Ala Ser Thr Leu Ala Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys His Gln Asp Tyr Thr Ser Ser Asn
                 85                  90                  95

Val Asp Asn Thr Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
        130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 326
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Ser Leu Asn Asp Tyr
             20                  25                  30

Gly Val Ser Trp Val Arg Gln Ala Pro Gly Lys Gly Leu Glu Trp Val
         35                  40                  45

Gly Ala Ile Gly Ser Ser Gly Val Ala Trp Tyr Ala Asn Phe Ala Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Asp Arg Asp Tyr Gly Tyr Arg Ala Asp Ala Thr Ser Gly Met
            100                 105                 110

Asp Leu Trp Gly Arg Gly Thr Leu Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160
```

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
            195                 200                 205

Asn Val Asn His Lys Pro Ser Asn Thr Lys Val Asp Lys Lys Val Glu
        210                 215                 220

Pro Lys Ser Cys Asp
225

<210> SEQ ID NO 327
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

Ala Ile Arg Met Thr Gln Ser Pro Ser Ser Phe Ser Ala Ser Thr Gly
1               5                   10                  15

Asp Arg Val Thr Ile Thr Cys Gln Ala Ser Glu Ser Ile Gly Asn Ala
            20                  25                  30

Leu Ala Trp Tyr Gln Gln Lys Pro Gly Lys Ala Pro Lys Leu Leu Ile
        35                  40                  45

Tyr Asp Ala Ser Asp Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Ser His Asn Asn
                85                  90                  95

Val Asp Asn Ile Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 328
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 328

```
Ile Ile Asn Gly Ser Asp Cys Asp Met His Thr Gln Pro Trp Gln Ala
1               5                   10                  15

Ala Leu Leu Leu Arg Pro Asn Gln Leu Tyr Cys Gly Ala Val Leu Val
            20                  25                  30

His Pro Gln Trp Leu Leu Thr Ala Ala His Cys Arg Lys Lys Val Phe
        35                  40                  45

Arg Val Arg Leu Gly His Tyr Ser Leu Ser Pro Val Tyr Glu Ser Gly
    50                  55                  60

Gln Gln Met Phe Gln Gly Val Lys Ser Ile Pro His Pro Gly Tyr Ser
65                  70                  75                  80

His Pro Gly His Ser Asn Asp Leu Met Leu Ile Lys Leu Asn Arg Arg
            85                  90                  95

Ile Arg Pro Thr Lys Asp Val Arg Pro Ile Asn Val Ser Ser His Cys
            100                 105                 110

Pro Ser Ala Gly Thr Lys Cys Leu Val Ser Gly Trp Gly Thr Thr Lys
            115                 120                 125

Ser Pro Gln Val His Phe Pro Lys Val Leu Gln Cys Leu Asn Ile Ser
130                 135                 140

Val Leu Ser Gln Lys Arg Cys Glu Asp Ala Tyr Pro Arg Gln Ile Asp
145                 150                 155                 160

Asp Thr Met Phe Cys Ala Gly Asp Lys Ala Gly Arg Asp Ser Cys Gln
            165                 170                 175

Gly Asp Ser Gly Gly Pro Val Val Cys Asn Gly Ser Leu Gln Gly Leu
            180                 185                 190

Val Ser Trp Gly Asp Tyr Pro Cys Ala Arg Pro Asn Arg Pro Gly Val
            195                 200                 205

Tyr Thr Asn Leu Cys Lys Phe Thr Lys Trp Ile Gln Glu Thr Ile Gln
210                 215                 220

Ala Asn Ser
225

<210> SEQ ID NO 329
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Tyr or Ile

<400> SEQUENCE: 329

Ala Xaa Arg Met Thr Gln Ser Pro Ser Ser Phe Ser Ala Ser Thr Gly
1               5                   10                  15

Asp Arg Val Thr Ile Thr Cys
            20

<210> SEQ ID NO 330
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Pro or Ala
```

```
<400> SEQUENCE: 330

Trp Tyr Gln Gln Lys Pro Gly Lys Xaa Pro Lys Leu Leu Ile Tyr
1               5                   10                  15

<210> SEQ ID NO 331
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Cys or Ser
<220> FEATURE:
<221> NAME/KEY: MOD_RES
<222> LOCATION: (24)..(24)
<223> OTHER INFORMATION: Ser or Pro

<400> SEQUENCE: 331

Gly Val Pro Ser Arg Phe Ser Gly Ser Gly Ser Gly Thr Asp Phe Thr
1               5                   10                  15

Leu Thr Ile Ser Xaa Leu Gln Xaa Glu Asp Phe Ala Thr Tyr Tyr Cys
            20                  25                  30

<210> SEQ ID NO 332
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Glu or Lys
<220> FEATURE:
<221> NAME/KEY: MOD_RES
<222> LOCATION: (8)..(8)
<223> OTHER INFORMATION: Glu or Val
<220> FEATURE:
<221> NAME/KEY: MOD_RES
<222> LOCATION: (9)..(9)
<223> OTHER INFORMATION: Ile or Val

<400> SEQUENCE: 332

Phe Gly Gly Gly Thr Xaa Val Xaa Xaa Lys
1               5                   10

<210> SEQ ID NO 333
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Val or Gln
<220> FEATURE:
<221> NAME/KEY: MOD_RES
<222> LOCATION: (24)..(24)
<223> OTHER INFORMATION: Val or Ala

<400> SEQUENCE: 333

Glu Xaa Gln Leu Val Glu Ser Gly Gly Gly Leu Val Gln Pro Gly Gly
1               5                   10                  15
```

```
Ser Leu Arg Leu Ser Cys Ala Xaa Ser Gly Phe Ser Leu Ser
            20                  25                  30
```

<210> SEQ ID NO 334
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Trp or Tyr
<220> FEATURE:
<221> NAME/KEY: MOD_RES
<222> LOCATION: (13)..(13)
<223> OTHER INFORMATION: Ile or Val
<220> FEATURE:
<221> NAME/KEY: MOD_RES
<222> LOCATION: (14)..(14)
<223> OTHER INFORMATION: Gly or Ser

<400> SEQUENCE: 334

```
Trp Val Arg Gln Ala Pro Gly Lys Gly Leu Glu Xaa Xaa Xaa
1               5                   10
```

<210> SEQ ID NO 335
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Ser or Phe
<220> FEATURE:
<221> NAME/KEY: MOD_RES
<222> LOCATION: (7)..(7)
<223> OTHER INFORMATION: Asp or Asn
<220> FEATURE:
<221> NAME/KEY: MOD_RES
<222> LOCATION: (8)..(8)
<223> OTHER INFORMATION: Thr, Leu or Asn
<220> FEATURE:
<221> NAME/KEY: MOD_RES
<222> LOCATION: (9)..(9)
<223> OTHER INFORMATION: Ser or Asn
<220> FEATURE:
<221> NAME/KEY: MOD_RES
<222> LOCATION: (10)..(10)
<223> OTHER INFORMATION: Lys, Thr or Leu
<220> FEATURE:
<221> NAME/KEY: MOD_RES
<222> LOCATION: (13)..(13)
<223> OTHER INFORMATION: Val or Leu
<220> FEATURE:
<221> NAME/KEY: MOD_RES
<222> LOCATION: (29)..(29)
<223> OTHER INFORMATION: Phe or Tyr

<400> SEQUENCE: 335

```
Arg Xaa Thr Ile Ser Arg Xaa Xaa Xaa Xaa Asn Thr Xaa Tyr Leu Gln
1               5                   10                  15

Met Gly Ser Leu Arg Ala Glu Asp Met Ala Val Tyr Xaa Cys Ala Arg
            20                  25                  30
```

<210> SEQ ID NO 336
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pro or Gln

<400> SEQUENCE: 336

Trp Gly Xaa Gly Thr Thr Val Thr Val Ser Ser
1               5                   10

<210> SEQ ID NO 337
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 338
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Arg or Ala
<220> FEATURE:
<221> NAME/KEY: MOD_RES
<222> LOCATION: (15)..(15)
<223> OTHER INFORMATION: Phe or Tyr

<400> SEQUENCE: 338

Trp Tyr Gln Gln Lys Pro Gly Lys Xaa Pro Lys Leu Leu Ile Xaa
1               5                   10                  15

<210> SEQ ID NO 339
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 339

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
                20                  25                  30

<210> SEQ ID NO 340
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (6)..(6)
<223> OTHER INFORMATION: Glu or Lys
<220> FEATURE:
<221> NAME/KEY: MOD_RES
<222> LOCATION: (8)..(8)
<223> OTHER INFORMATION: Glu or Val
<220> FEATURE:
<221> NAME/KEY: MOD_RES
<222> LOCATION: (9)..(9)
<223> OTHER INFORMATION: Val or Ile

<400> SEQUENCE: 340

Phe Gly Gly Gly Thr Xaa Val Xaa Xaa Lys
1               5                   10

<210> SEQ ID NO 341
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Val or Gln
<220> FEATURE:
<221> NAME/KEY: MOD_RES
<222> LOCATION: (24)..(24)
<223> OTHER INFORMATION: Val or Ala

<400> SEQUENCE: 341

Glu Xaa Gln Leu Val Glu Ser Gly Gly Gly Leu Ile Gln Pro Gly Gly
1               5                   10                  15

Ser Leu Arg Leu Ser Cys Ala Xaa Ser Gly Phe Ser Leu Ser
            20                  25                  30

<210> SEQ ID NO 342
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Tyr or Trp
<220> FEATURE:
<221> NAME/KEY: MOD_RES
<222> LOCATION: (13)..(13)
<223> OTHER INFORMATION: Ile or Val
<220> FEATURE:
<221> NAME/KEY: MOD_RES
<222> LOCATION: (14)..(14)
<223> OTHER INFORMATION: Gly or Ser

<400> SEQUENCE: 342

Trp Val Arg Gln Ala Pro Gly Lys Gly Leu Glu Xaa Xaa Xaa
1               5                   10

<210> SEQ ID NO 343
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Ser or Phe
```

```
<220> FEATURE:
<221> NAME/KEY: MOD_RES
<222> LOCATION: (7)..(7)
<223> OTHER INFORMATION: Asp or Asn
<220> FEATURE:
<221> NAME/KEY: MOD_RES
<222> LOCATION: (8)..(8)
<223> OTHER INFORMATION: Thr or Asn
<220> FEATURE:
<221> NAME/KEY: MOD_RES
<222> LOCATION: (9)..(9)
<223> OTHER INFORMATION: Ser or Asn
<220> FEATURE:
<221> NAME/KEY: MOD_RES
<222> LOCATION: (10)..(10)
<223> OTHER INFORMATION: Lys or Leu
<220> FEATURE:
<221> NAME/KEY: MOD_RES
<222> LOCATION: (13)..(13)
<223> OTHER INFORMATION: Val or Leu
<220> FEATURE:
<221> NAME/KEY: MOD_RES
<222> LOCATION: (29)..(29)
<223> OTHER INFORMATION: Phe or Tyr

<400> SEQUENCE: 343

Arg Xaa Thr Ile Ser Arg Xaa Xaa Xaa Asn Thr Xaa Tyr Leu Gln
1               5                   10                  15

Met Asn Ser Leu Arg Ala Glu Asp Thr Ala Val Tyr Xaa Cys Ala Arg
            20                  25                  30

<210> SEQ ID NO 344
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pro or Gln

<400> SEQUENCE: 344

Trp Gly Xaa Gly Thr Leu Val Thr Val Ser Ser
1               5                   10

<210> SEQ ID NO 345
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Tyr or Ile

<400> SEQUENCE: 345

Ala Xaa Arg Met Thr Gln Ser Pro Ser Ser Phe Ser Ala Ser Thr Gly
1               5                   10                  15

Asp Arg Val Thr Ile Thr Cys
            20

<210> SEQ ID NO 346
<211> LENGTH: 15
<212> TYPE: PRT
<213> ORGANISM: Artificial Sequence
<220> FEATURE:
<223> OTHER INFORMATION: Description of Artificial Sequence: Synthetic
```

```
          peptide
<220> FEATURE:
<221> NAME/KEY: MOD_RES
<222> LOCATION: (9)..(9)
<223> OTHER INFORMATION: Pro or Ala

<400> SEQUENCE: 346

Trp Tyr Gln Gln Lys Pro Gly Lys Xaa Pro Lys Leu Leu Ile Tyr
1               5                  10                  15

<210> SEQ ID NO 347
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Cys or Ser
<220> FEATURE:
<221> NAME/KEY: MOD_RES
<222> LOCATION: (24)..(24)
<223> OTHER INFORMATION: Ser or Pro

<400> SEQUENCE: 347

Gly Val Pro Ser Arg Phe Ser Gly Ser Gly Ser Gly Thr Asp Phe Thr
1               5                  10                  15

Leu Thr Ile Ser Xaa Leu Gln Xaa Glu Asp Phe Ala Thr Tyr Tyr Cys
            20                  25                  30

<210> SEQ ID NO 348
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Glu or Lys
<220> FEATURE:
<221> NAME/KEY: MOD_RES
<222> LOCATION: (8)..(8)
<223> OTHER INFORMATION: Glu or Val
<220> FEATURE:
<221> NAME/KEY: MOD_RES
<222> LOCATION: (9)..(9)
<223> OTHER INFORMATION: Val or Ile

<400> SEQUENCE: 348

Phe Gly Gly Gly Thr Xaa Val Xaa Xaa Lys
1               5                  10

<210> SEQ ID NO 349
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Val or Gln
<220> FEATURE:
<221> NAME/KEY: MOD_RES
<222> LOCATION: (5)..(5)
<223> OTHER INFORMATION: Val or Leu
<220> FEATURE:
```

```
<221> NAME/KEY: MOD_RES
<222> LOCATION: (24)..(24)
<223> OTHER INFORMATION: Val or Ala

<400> SEQUENCE: 349

Glu Xaa Gln Leu Xaa Glu Ser Gly Gly Gly Leu Val Gln Pro Gly Gly
1               5                   10                  15

Ser Leu Arg Leu Ser Cys Ala Xaa Ser Gly Phe Ser Leu Asn
            20                  25                  30

<210> SEQ ID NO 350
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Ile or Val
<220> FEATURE:
<221> NAME/KEY: MOD_RES
<222> LOCATION: (14)..(14)
<223> OTHER INFORMATION: Gly or Ser

<400> SEQUENCE: 350

Trp Val Arg Gln Ala Pro Gly Lys Gly Leu Glu Trp Xaa Xaa
1               5                   10

<210> SEQ ID NO 351
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Ser or Phe
<220> FEATURE:
<221> NAME/KEY: MOD_RES
<222> LOCATION: (7)..(7)
<223> OTHER INFORMATION: His, Asn or Asp
<220> FEATURE:
<221> NAME/KEY: MOD_RES
<222> LOCATION: (8)..(8)
<223> OTHER INFORMATION: Thr or Asn
<220> FEATURE:
<221> NAME/KEY: MOD_RES
<222> LOCATION: (9)..(9)
<223> OTHER INFORMATION: Ser or Asn
<220> FEATURE:
<221> NAME/KEY: MOD_RES
<222> LOCATION: (10)..(10)
<223> OTHER INFORMATION: Lys or Leu
<220> FEATURE:
<221> NAME/KEY: MOD_RES
<222> LOCATION: (13)..(13)
<223> OTHER INFORMATION: Val or Leu
<220> FEATURE:
<221> NAME/KEY: MOD_RES
<222> LOCATION: (29)..(29)
<223> OTHER INFORMATION: Phe or Tyr

<400> SEQUENCE: 351

Arg Xaa Thr Ile Ser Arg Xaa Xaa Xaa Xaa Asn Thr Xaa Tyr Leu Gln
1               5                   10                  15

Met Asn Ser Leu Arg Ala Glu Asp Thr Ala Val Tyr Xaa Cys Ala Arg
            20                  25                  30
```

<210> SEQ ID NO 352
<211> LENGTH: 11
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<221> NAME/KEY: MOD_RES
<222> LOCATION: (3)..(3)
<223> OTHER INFORMATION: Pro or Arg

<400> SEQUENCE: 352

Trp Gly Xaa Gly Thr Leu Val Thr Val Ser Ser
1               5                   10

<210> SEQ ID NO 353
<211> LENGTH: 275
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 353

Asn Asn Asp Val Ser Cys Asp His Pro Ser Asn Thr Val Pro Ser Gly
1               5                   10                  15

Ser Asn Gln Asp Leu Gly Ala Gly Ala Gly Glu Asp Ala Arg Ser Asp
            20                  25                  30

Asp Ser Ser Arg Ile Ile Asn Gly Ser Asp Cys Asp Met His Thr
        35                  40                  45

Gln Pro Trp Gln Ala Ala Leu Leu Leu Arg Pro Asn Gln Leu Tyr Cys
    50                  55                  60

Gly Ala Val Leu Val His Pro Gln Trp Leu Leu Thr Ala Ala His Cys
65                  70                  75                  80

Arg Lys Lys Val Phe Arg Val Arg Leu Gly His Tyr Ser Leu Ser Pro
                85                  90                  95

Val Tyr Glu Ser Gly Gln Gln Met Phe Gln Gly Val Lys Ser Ile Pro
            100                 105                 110

His Pro Gly Tyr Ser His Pro Gly His Ser Asn Asp Leu Met Leu Ile
        115                 120                 125

Lys Leu Asn Arg Arg Ile Arg Pro Thr Lys Asp Val Arg Pro Ile Asn
    130                 135                 140

Val Ser Ser His Cys Pro Ser Ala Gly Thr Lys Cys Leu Val Ser Gly
145                 150                 155                 160

Trp Gly Thr Thr Lys Ser Pro Gln Val His Phe Pro Lys Val Leu Gln
                165                 170                 175

Cys Leu Asn Ile Ser Val Leu Ser Gln Lys Arg Cys Glu Asp Ala Tyr
            180                 185                 190

Pro Arg Gln Ile Asp Asp Thr Met Phe Cys Ala Gly Asp Lys Ala Gly
        195                 200                 205

Arg Asp Ser Cys Gln Gly Asp Ser Gly Gly Pro Val Val Cys Asn Gly
    210                 215                 220

Ser Leu Gln Gly Leu Val Ser Trp Gly Asp Tyr Pro Cys Ala Arg Pro
225                 230                 235                 240

Asn Arg Pro Gly Val Tyr Thr Asn Leu Cys Lys Phe Thr Lys Trp Ile
                245                 250                 255

Gln Glu Thr Ile Gln Ala Asn Ser Gly Asn Ser Asp Tyr Lys Asp Asp
            260                 265                 270

```
Asp Asp Lys
        275

<210> SEQ ID NO 354
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Leu Leu Val Tyr
1

<210> SEQ ID NO 355
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Glu Glu Ala Gln Gly Asp Lys
1               5

<210> SEQ ID NO 356
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: NorVal
<220> FEATURE:
<221> NAME/KEY: MOD_RES
<222> LOCATION: (10)..(10)
<223> OTHER INFORMATION: Lys(Dnp)

<400> SEQUENCE: 356

Arg Pro Lys Pro Val Glu Xaa Trp Arg Lys
1               5                   10
```